US010273474B2

(12) United States Patent
Miller et al.

(10) Patent No.: US 10,273,474 B2
(45) Date of Patent: Apr. 30, 2019

(54) METHODS FOR MODULATING TAU EXPRESSION FOR REDUCING SEIZURE AND MODIFYING A NEURODEGENERATIVE SYNDROME

(71) Applicants: WASHINGTON UNIVERSITY, St. Louis, MO (US); ISIS PHARMACEUTICALS, INC., Carlsbad, CA (US)

(72) Inventors: Timothy M. Miller, St. Louis, MO (US); Sarah Devos, St. Louis, MO (US); C. Frank Bennett, Carlsbad, CA (US); Frank Rigo, Carlsbad, CA (US)

(73) Assignees: WASHINGTON UNIVERSITY, St. Louis, MO (US); ISIS PHARMACEUTICALS, INC., Carlsbad, CA (US)

( * ) Notice: Subject to any disclaimer, the term of this patent is extended or adjusted under 35 U.S.C. 154(b) by 0 days.

(21) Appl. No.: 14/387,853

(22) PCT Filed: Mar. 14, 2013

(86) PCT No.: PCT/US2013/031500
§ 371 (c)(1),
(2) Date: Sep. 25, 2014

(87) PCT Pub. No.: WO2013/148260
PCT Pub. Date: Oct. 3, 2013

(65) Prior Publication Data

US 2015/0275205 A1 Oct. 1, 2015

(51) Int. Cl.
*C12N 15/113* (2010.01)
*C07H 21/02* (2006.01)
*C07H 21/04* (2006.01)

(52) U.S. Cl.
CPC ........... *C12N 15/113* (2013.01); *C07H 21/02* (2013.01); *C07H 21/04* (2013.01); *C12N 2310/11* (2013.01); *C12N 2310/315* (2013.01); *C12N 2310/321* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 4,845,205 | A | 7/1989 | Huynh Dinh et al. |
| 4,880,635 | A | 11/1989 | Janoff et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 5,034,506 | A | 7/1991 | Summerton et al. |
| 5,130,302 | A | 7/1992 | Spielvogel et al. |
| 5,134,066 | A | 7/1992 | Rogers et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,185,444 | A | 2/1993 | Summerton et al. |
| 5,367,066 | A | 11/1994 | Urdea et al. |
| 5,432,272 | A | 7/1995 | Benner |
| 5,457,187 | A | 10/1995 | Gmelner et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Haralambidis |
| 5,587,469 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,645,985 | A | 7/1997 | Froehler et al. |
| 5,681,941 | A | 10/1997 | Cook et al. |

(Continued)

FOREIGN PATENT DOCUMENTS

| | | |
|---|---|---|
| CN | 1696294 | 11/2005 |
| WO | WO 98/39352 | 9/1998 |

(Continued)

OTHER PUBLICATIONS

Boiziau et al., “Antisense 2'-0-alkyl oligoribonucleotides are efficient inhibitors of reverse transcription,” Nucleic Acids Research, 1995, vol. 23, No. 1, pp. 64-71.
Usman et al., “Exploiting the chemical synthesis of RNA,” Trends in Biochecmical Sciences, Elsevier, Haywards, GB, vol. 17, No. 9., Sep. 1, 1992, pp. 334-339.
Hatta et al., “Mechanisms of the inhibition of reverse transcription by unmodified and modified antisense oligonucleotides,” vol. 330, No. 2, 1993, pp. 161-164.
Extended European Examination Report for Application No. 13770075.3 dated Oct. 2, 2015 (8 pages).
U.S. Appl. No. 60/130,377, filed Apr. 21, 1999, Pachuk et al.

(Continued)

*Primary Examiner* — J. E. Angell
(74) *Attorney, Agent, or Firm* — Michael Best & Friedrich LLP

(57) ABSTRACT

Disclosed herein are methods for reducing expression of Tau mRNA and protein in an animal with Tau antisense compounds. Also disclosed are methods for modulating splicing of Tau mRNA in an animal with Tau antisense compounds. Such methods are useful to treat, prevent, or ameliorate neurodegenerative diseases in an individual in need thereof. Examples of neurodegenerative diseases that can be treated, prevented, and ameliorated with the administration Tau antisense oligonucleotides include Alzheimer’s Disease, Fronto-temporal Dementia (FTD), FTDP-17, Progressive Supranuclear Palsy, Chronic Traumatic Encephalopathy, Epilepsy, and Dravet’s Syndrome.

17 Claims, 46 Drawing Sheets

Specification includes a Sequence Listing.

(56) References Cited

U.S. PATENT DOCUMENTS

| | | | |
|---|---|---|---|
| 5,698,685 A | 12/1997 | Summerton et al. | |
| 5,750,692 A | 5/1998 | Cook et al. | |
| 5,763,588 A | 6/1998 | Matteucci et al. | |
| 5,801,154 A | 9/1998 | Baracchini et al. | |
| 5,830,653 A | 11/1998 | Froehler et al. | |
| 5,837,853 A | 11/1998 | Takashima et al. | |
| 6,005,096 A | 12/1999 | Matteucci et al. | |
| 6,268,490 B1 | 7/2001 | Imanishi et al. | |
| 6,525,191 B1 | 2/2003 | Ramasamy | |
| 6,582,908 B2 | 6/2003 | Fodor et al. | |
| 6,670,461 B1 | 12/2003 | Wengel et al. | |
| 6,673,661 B1 | 1/2004 | Liu et al. | |
| 6,770,748 B2 | 8/2004 | Imanishi et al. | |
| 6,794,499 B2 | 9/2004 | Wegel et al. | |
| 7,034,133 B2 | 4/2006 | Wengel et al. | |
| 7,053,207 B2 | 5/2006 | Wengel | |
| 7,084,125 B2 | 8/2006 | Wengel | |
| 7,217,805 B2 | 5/2007 | Imanishi et al. | |
| 7,314,923 B2 | 1/2008 | Kaneko et al. | |
| 7,399,845 B2 | 7/2008 | Seth et al. | |
| 7,427,672 B2 | 9/2008 | Imanishi et al. | |
| 7,547,684 B2 | 6/2009 | Seth et al. | |
| 7,569,575 B2 | 8/2009 | Sorensen et al. | |
| 7,696,345 B2 | 4/2010 | Allerson et al. | |
| 7,741,457 B2 | 6/2010 | Seth et al. | |
| 7,858,747 B2 | 12/2010 | Woldike et al. | |
| 8,178,503 B2 | 5/2012 | Rigoutsos et al. | |
| 8,329,890 B2 | 12/2012 | Davidson et al. | |
| 8,871,729 B2 | 10/2014 | Yague et al. | |
| 9,084,813 B2 | 7/2015 | Roberson et al. | |
| 9,198,982 B2 | 12/2015 | Roberson et al. | |
| 9,644,207 B2 | 5/2017 | Rigo et al. | |
| 9,683,235 B2 | 6/2017 | Freier | |
| 2001/0053519 A1 | 12/2001 | Fodor et al. | |
| 2002/0018995 A1 | 2/2002 | Ghetti et al. | |
| 2003/0219770 A1 | 11/2003 | Eshleman et al. | |
| 2003/0228597 A1 | 12/2003 | Cowsert et al. | |
| 2004/0054156 A1 | 3/2004 | Draper et al. | |
| 2004/0171570 A1 | 9/2004 | Allerson et al. | |
| 2004/0241651 A1 | 12/2004 | Olek et al. | |
| 2005/0108783 A1 | 5/2005 | Koike et al. | |
| 2005/0130923 A1 | 6/2005 | Bhat et al. | |
| 2005/0153336 A1 | 7/2005 | Bennett et al. | |
| 2005/0244851 A1 | 11/2005 | Blume et al. | |
| 2005/0255487 A1 | 11/2005 | Khvorova et al. | |
| 2006/0216722 A1 | 9/2006 | Betsholtz et al. | |
| 2007/0031844 A1 | 2/2007 | Khvorova et al. | |
| 2007/0203333 A1 | 8/2007 | McSwiggen et al. | |
| 2007/0287831 A1 | 12/2007 | Seth et al. | |
| 2008/0003570 A1 | 1/2008 | Rogers et al. | |
| 2008/0039618 A1 | 2/2008 | Allerson et al. | |
| 2008/0249058 A1 | 10/2008 | Roberson et al. | |
| 2008/0318210 A1 | 12/2008 | Bentwich | |
| 2009/0012281 A1 | 1/2009 | Swayze et al. | |
| 2009/0076725 A1 | 3/2009 | Bhogal et al. | |
| 2009/0176728 A1 | 7/2009 | Yague et al. | |
| 2010/0261175 A1 | 10/2010 | Rasmussen et al. | |
| 2011/0054005 A1 | 3/2011 | Naito et al. | |
| 2011/0150897 A1 | 6/2011 | Meyer et al. | |
| 2011/0244561 A1 | 10/2011 | Davidson et al. | |
| 2011/0263687 A1 | 10/2011 | Mattick et al. | |
| 2013/0046007 A1* | 2/2013 | Bennett ................ | C12N 15/113<br>514/44 A |
| 2013/0123133 A1 | 5/2013 | Ward et al. | |
| 2014/0155462 A1 | 6/2014 | Brown et al. | |
| 2014/0315983 A1 | 10/2014 | Brown et al. | |
| 2015/0057329 A1 | 2/2015 | Bhanot et al. | |
| 2016/0032285 A1 | 2/2016 | Rigo et al. | |
| 2016/0145617 A1 | 5/2016 | Kordasiewicz et al. | |
| 2017/0211064 A1 | 7/2017 | Rigo | |
| 2018/0051283 A1 | 2/2018 | Rigo | |
| 2018/0094261 A1 | 4/2018 | Kordasiewicz et al. | |
| 2018/0119145 A1 | 5/2018 | Kordasiewicz et al. | |

FOREIGN PATENT DOCUMENTS

| | | |
|---|---|---|
| WO | WO 99/14226 | 3/1999 |
| WO | WO 1999/062548 | 12/1999 |
| WO | WO 00/63364 | 10/2000 |
| WO | WO 2001/032703 | 5/2001 |
| WO | 01/72765 | 10/2001 |
| WO | WO 02/081494 | 10/2002 |
| WO | WO 03/004602 | 1/2003 |
| WO | WO 2004/017072 | 2/2004 |
| WO | WO 2004/035765 | 4/2004 |
| WO | WO 2004/058940 | 7/2004 |
| WO | WO 2004/106356 | 12/2004 |
| WO | WO 2005/017143 | 2/2005 |
| WO | WO 2005/021570 | 3/2005 |
| WO | WO 2005/040180 | 5/2005 |
| WO | 2006047673 | 5/2006 |
| WO | 2007/027775 | 3/2007 |
| WO | 2007/107789 | 9/2007 |
| WO | WO 2007/134181 | 11/2007 |
| WO | WO 2008/101157 | 8/2008 |
| WO | 2008/124066 A1 | 10/2008 |
| WO | 2008/131807 | 11/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036698 | 4/2010 |
| WO | WO 2010/148249 | 12/2010 |
| WO | WO 2011/017521 | 5/2011 |
| WO | WO 2011/131693 | 10/2011 |
| WO | WO 2011/139702 | 11/2011 |
| WO | WO 2013/148260 | 10/2013 |
| WO | WO 2013/148283 | 10/2013 |
| WO | WO 2013/173647 | 11/2013 |
| WO | 2014/012081 | 1/2014 |
| WO | WO 2014/114937 | 7/2014 |
| WO | 2014/153236 | 9/2014 |
| WO | WO 2015/010135 | 1/2015 |
| WO | 2016/019063 | 2/2016 |
| WO | 20160151523 | 9/2016 |
| WO | 2018/064593 | 4/2018 |

OTHER PUBLICATIONS

U.S. Appl. No. 60/399,998, filed Jul. 31, 2002, Pachuk et al.
U.S. Appl. No. 60/419,532, filed Oct. 18, 2002, Pachuk et al.
Agrawal, S. et al., Proc. Natl. Acad. Sci. USA 87, 1401-1405 (1990).
Albaek et al., J. Org. Chem., 2006, 71, 7731-7740.
Allshire, 2002, Science 297, 1818-1819.
Altmann et al., Biochem. Soc. Trans., 1996, 24, 630-637.
Altmann et al., Chimia, 1996, 50, 168-176.
Altmann et al., Nucleosides Nucleotides, 1997, 16, 917-926.
Altschul et al., J. Mol. Biol., 1990, 215, 403-410.
Andorfer et al., "Hyperphosphorylation and aggregation of tau in mice expressing normal human tau isoforms" Journal of Neurochemistry (2003) 86: 582-590.
Australian Patent Examination Report for Application No. 2013202595 dated Jul. 4, 2014 (15 pages).
Badiola et al., "Tau phosphorylation and aggregation as a therapeutic target in tauopathies," CNS Neurol. Disord. Drug Targets, Dec. 2010, vol. 9, No. 6, pp. 727-740.
Baker et al., J. Biol. Chem., 1997, 272, 11944-12000.
Baker, C. et al., Nucleic Acids Res. 18, 3537-3543 (1990).
Bevins, R.A. and Besheer, J., J. Nature Protocols, 2006, 1: 1306-1311.
Braasch et al., Chem. Biol., 2001, 8, 1-7.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.

(56) References Cited

OTHER PUBLICATIONS

Dawson, H.N. et al., J. Neurosci. 27: 9155-9168, 2007.
Deacon, R. M., Nat. Protocol. 2006, 1:1117-9.
DeVos et al., "Antisense oligonucleotides: treating neurodegeneration at the level of RNA" Neurotherapeutics (2013) 10(3): 486-497.
Elayadi et al., Curr. Opinion Inves. Drugs, 2001, 2, 558-561.
Freier et al., Nucleic Acids Research, 1997, 25(22), 4429-4443.
Frieden et al., Nucleic Acids Research, 2003, 21, 6365-6372.
Frost, S. Digital Telerential Screen, 2012, 91-100.
Furdon, P. et al., Nucleic Acids Res. 17, 9193-9204 (1989).
Gautschi et al., J. Natl. Cancer Inst., 93:463-471, 2001.
GenBank Accession No. AK226139.1 (2007).
GenBank Accession No. NM_001123066.3 (2015).
GenBank Accession No. NM_001123067.3 (2015).
GenBank Accession No. NM_001203251.1 (2015).
GenBank Accession No. NM_001203252.1 (2015).
GenBank Accession No. NM_005910.5 (2015).
GenBank Accession No. NM_016834.4 (2015).
GenBank Accession No. NM_016835.4 (2015).
GenBank Accession NT_010783.15 (2013).
GenBank Accession NT010783.14 (2008).
GenkBank Accession No. NM_16841.4 (2015).
Goedert, M. et al., Neurosci. Lett. 1995, 167-9.
Gupta, N. et al., Can. J. Ophtalmol., 2008, 43:53-60.
Hall et al., 2002, Science, 297, 2232-2237.
Ho, W. L. et al., Molecular Vision, 2012, 18:2700-2710.
International Search Report and Written Opinion for Application No. PCT/US2013/31500 dated Jun. 5, 2013 (12 pages).
Jenuwein, 2002, Science, 297, 2215-2218.
Jones et al., "Targeting hyperphosphorylated tau with sodium selenate suppresses seizures in rodent models" Neurobiology of Disease (2012) 897-901.
Jones, L.J. et al., Analytical Biochemistry, 1998, 265, 368-374.
Kalbfuss, B. et al., "Correction of Alternative Splicing of Tau in Frontotemporal Dementia and Parkinsonism Linked to Chromosome 17," Journal of Biological Chemistry, 2001, vol. 276, pp. 42986-42993.
Koshkin et al., Tetrahedron, 1998, 54, 3607-3630.
Kumar et al., Bioorg. Med. Chem. Lett., 1998, 8, 2219-2222.
Leumann, J. C., Bioorganic & Medicinal Chemistry, 2002, 10, 841-854.
Maher and Dolnick, Nuc. Acid. Res. 16:3341-3358, 1988.
Martin, P., Helv. Chim. Acta, 1995, 78, 486-504.
Morita et al., Bioorganic Medicinal Chemistry, 2003, 11, 2211-2226.
New England Biolabs 1998/1999 Catalog (cover page and pp. 121 and 284).
Orum et al., Curr. Opinion Mol. Ther., 2001, 3, 239-243.
Pal-Bhadra et al., 2004, Science, 303, 669-672.
Reynolds et al., "Rational siRNA design for RNA interference" Nature Biotechnology (2004) 22(3):326-330.
Rodriguez-Martin, T. et al., Reprograming of tau alternative splicing by spliceosome-mediated RNA trans-splicing: Implications for taupathies, Proceedings of the National Academy of Sciences, 2005, Vo. 102, No. 43, pp. 15659-15664.
Sanghvi et al., "Heterocyclic Base Modifications in Nucleic Acids and Their Applications in Antisense Oligonucleotides" Antisense Research and Applications (1993) pp. 273-288.
Singh et al., Chem. Commun., 1998, 4, 455-456.
Singh et al., J. Org. Chem., 1998, 63, 10035-10039.
Smith and Waterman, Adv. Appl. Math., 1981, 2, 482-489.
Sproat, B. et al., Nucleic Acids Res. 17, 3373-3386 (1989).
Srivastava et al., J. Am. Chem. Soc., 2007, 129(26), 8362-8379.
Verdel et al., 2004, Science, 303, 672-676.
Volpe et al., 2002, Science, 297, 1833-1837.
Wahlestedt et al., Proc. Natl. Acad. Sci. U.S.A., 2000, 97, 5633-5638.
Walder, R. and Walder, J., Proc. Natl. Acad. Sci. USA 85, 5011-5015 (1988).
Woolf et al., Proc. Natl. Acad. Sci. USA 89:7305-7309, 1992.
Yamada et al., Neurosci. 2011, 31: 13110-117.
Yoshiyama, Y. et al., Neuron 53: 337-351, 2007.
Zhang and Madden, Genome Res., 1997, 7, 649-656.
Australian Patent Examination Report for Application No. 2013202595 dated Mar. 17, 2016 (3 pages).
Andorfer et al., "Hyperphosphorylation and aggregation of tau in mice expressing normal human tau isoforms", Journal of Neurochemistry, 86: 582-590 (2003).
Duff et al.,"Characterization of Pathology in Transgenic Mice Over-Expressing Human Genomic and cDNA Tau Transgenes", Neurobiology of Disease, 7: 87-98 (2000).
Wolfe, "Tau Mutations in Neurodegenerative Diseases", J. Biol. Chem., 284(10): 6021-6025 (2009).
Australian Patent Examination Report for Application No. 2016202220 dated Jan. 12, 2017 (4 pages).
Japanese Patent Office Action for Application No. 2015-503306 dated Nov. 22, 2016 (5 pages, English translation included).
International Search Report and Written Opinion for Application No. PCT/US2015/042740 dated Dec. 15, 2015 (13 pages).
International Search Report and Written Opinion for Application No. PCT/US2014/047486 dated Feb. 9, 2015 (12 pages).
Extended European Search Report for Application No. 14767904.7 dated Sep. 19, 2016 (10 pages).
Spicakova et al.: "Expression and silencing of the Microtubule-Associated Protein Tau in breast cancer cells", Molecular Cancer Therapeutics, vol. 9, No. 11, Nov. 1, 2010, pp. 2970-2981.
Gordon et al.: "Antisense suppression of tau in cultured rat oligodendrocytes inhibits process formation", Journal of Neuroscience Research, vol. 86, No. 12, May 23, 2008, pp. 2591-2601.
International Search Report and Written Opinion for Application No. PCT/US2017/054540 dated Jan. 18, 2018 (11 pages).
Sazani et al., "Therapeutic potential of antisense oligonucleotides as modulators of alternative splicing," J. Clinical Invest (2003) 112 481-486.
Canadian Patent Office Action for Application No. 2,866,392 dated Feb. 5, 2018 (6 pages).
European Patent Office Action for Application No. 13770075.3 dated Feb. 8, 2018 (5 pages).
Japanese Patent Office Action for Application No. 2015-503306 dated Jun. 12, 2018 (13 pages, English translation included).
Bi et al., Tau-Targeted Immunization Impedes Progression fo Neurofibrillary Histopathology in Aged P301L Tau Transgenic Mice Plos ONE (2011) 6(12):e26860.
Braasch et al., "Novel antisense and peptide nucleic acid strategies for controlling gene expression" Biochemistry (2002) 41(14):4503-4510.
Caceres et al., "Inhibition of neurite polarity by tau antisense oligonucleotides in primary cerebellar neurons" Nature (1990) 343:461-463.
Caceres et al., "The Effect of Tau antisense Oligonucleotides on Neurite Formation of Cultured Cerebellar Macroneurons" J. Neuroscience (1991) 11(6):1515-1523.
Craig et al., "Towards a small molecule inhibitor of tau exon 10 splicing: Identification of compounds that stabilise the 5'-splice site stem-loop" Alzheimer's & Dementia: The Journal of the Alzheimer's Association (2012) 8(4): P636.
Crooke et al., "Pharmacokinetic Properties of Several Novel Oligonucleotide Analogs in mice" J. Pharmacol. Exp. Ther. (1996) 277(2):923-937.
Dawson, "Tau Exon 10 Splicing Tauopathy", presentation given at CurePSP 2010 International Research Symposium, Nov. 18, 2010, San Diego, CA.
Dawson, "The Effects of the CBD-Associated Tau Gene H1 Haplotype on Tau Expression," Abstract presented at CurePSP 2010 International Research Symposium, Nov. 18, 2010, San Diego, CA (retrieved online Jan. 13, 2016).
Devos et al., "Antisense Reduction of Human Tau in the CNS of P301S mice both Prevents and Reverses Hyperphosphorylated Tau Deposition" abstract presented at Keystone Symposium: Long Noncoding RNAs: Marching toward Mechanism, Feb. 27-Mar. 4, 2014, Santa Fe, NM.
Devos et al., "Antisense Reduction of Tau in Adult Mice Protects against Seizures" J. Neuroscience (2013) 33(31): 12887-12897.

(56) References Cited

OTHER PUBLICATIONS

Devos et al., "Antisense Reduction of the Human Tau Transgene in the CNS of P301S mice Robustly Decreases Tau Deposition" abstract presented at Keystone Symposia: New Frontiers in Neurodegenerative Disease Research, Feb. 3-8, 2013, Santa Fe, NM.
Devos et al., "Reducing Human Tau in the CNS of P301S mice Dramatically Reverses Tau Pathology" abstract presented at14th International Conference on Alzheimer's Drug Discovery, Sep. 9-10, 2013, Jersey City, NJ.
Devos et al., "Using antisense oligonucleotides to knockdown endogenous brain tau in vivo" Alzheimer's & Dementia: The Journal of the Alzheimer's Association (2012) 8(4): P205.
Devos et al., "Using antisense oligonucleotides to knockdown endogenous brain tau in vivo" poster presentation at AAIC 2012; Jul. 14-19, 2012.
Donahue et al., "Stabilization of the Tau Exon 10 Stem Loop Alters Pre-mRNA Splicing" J. Biol. Chem. (2006) 281(33):23302-23306.
Englisch et al., "Chemically Modified Oligonucleotides as Probes and Inhibitors" Angewandte Chemie, International Edition (1991) 30(6): 613-629.
Goedert et al., "Cloning and Sequencing of the cDNA Encoding a Core Protein of the Paired Helical Filament of Alzheimers Disease: Identification as the Microtubule-Associated Protein Tau" PNAS (1988) 85(11):4051-4055.
International Search Report for application PCT/US2014/029752 dated Sep. 18, 2014.
Jiang et al., "Aberrant Splicing of tau Pre-mRNA Caused by Intronic Mutations Associated with the Inherited Dementia Frontotemporal Dementia with Parkinsonsism Linked to Chromosome 17" Mol. Cell Biol. (2000) 20(11):4036-4048.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.
Kroschwitz, The Concise Encyclopedia of Polymer Science and Engineering, John Wiley & Sons, 1990, 858-859.
Letsinger et al., "Cholesteryl-conjugated oligonucleotides: Synthesis, properties, and activity as inhibitors of replication of human immunodeficiency virus in cell culture" PNAS (1989) 86:6553-6556.
Manoharan et al., "Chemical Modifications to Improve Uptake and Bioavailability of Antisense Oligonucleotides" Ann. N.Y. Acad. Sci. (1992) 660:306.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Mishra et al., "Improved leishmanicidal effect of phosphorotioate antisense oligonucleotides by LDL-mediated delivery" Biochim. Biophys. Acta (1995) 1264:229-237.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Peacey et al., "Targeting a pre-mRNA structure with bipartite antisense molecules modulates tau alternative splicing" Nucleic Acids Research (2012) 40(19):9836-9849.
Pizzi et al., "Antisense Strategy Unravels Tau Proteins as Molecular Risk Factors for Glutamate-Induced Neurodegeneration" Cellular and Molecular Neurobiology (1994) 14(5):569-578.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sapir et al., "Tau's role in the developing brain: implications for intellectual disability" Human Molecular Genetics (2012) 21(8):1681-1692.
Schoch et al., "Antisense oligonucleotide-mediated tau splicing reduces behavioral deficits and tau pathology in a tauopathy model" abstract presented at Keystone Symposium: Alzheimer's Disease, Mar. 2-7, 2014, Keystone, CO.
Schoch et al., "Antisense oligonucleotide-mediated tau splicing reduces behavioral deficits and tau pathology in a tauopathy model" poster presented at Keystone Symposium: Alzheimer's Disease, Mar. 2-7, 2014, Keystone, CO.
Shea et al., "Synthesis, hybridization properties and antiviral activity of lipid-oligodeoxynucleotide conjugates" Nucl. Acids Res. (1990) 18(13):3777-3783.
Svinarchuk et al., "Inhibition of HIV proliferation in MT-4 cells by antisense oligonucleotide conjugated to lipophilic groups" Biochimie (1993) 75:49-54.
Wang et al., "A Novel Tau Transcript in Cultured Human Neuroblastoma Cells Expression Nuclear Tau" J. Cell Biol. (1993) 121(2):257-267.
Wolfe M.S., "The Roll of Tau in Neurodegenerative Diseases and Its Potential as a Therapeutic Target" Scientifica (2012) 1-20.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
European Patent Office Action for Application No. 13770075.3 dated Aug. 16, 2018 (8 pages).
GenBank Accession No. NM_001285455.1 (2013).
Buck et al., "Design strategies and performance of custom DNA sequencing primers" Biotechniques (1999) 27(3): 528-536.

* cited by examiner

No significant effects involving Genotype.

No significant effects involving Genotype.
Block 1 vs Block 5: NTG CON - * p = 0.023;
N279K p = 0.071.

No significant effects involving Genotype.
Block 1 vs Block 5: NTG CON - *p=0.046.

No significant effects involving Genotype.

No significant effects involving Genotype.
Genotype effect: $p = 0.086$
Block 1 vs Block 5 (NTG CON): *$p = 0.002$.

Significant main effect of Genotype; **p = 0.034.
Block 1 vs Block 5 (NTG CON): *p = 0.004.

No significant effects involving Genotype.

SEQUENCE LISTING

```
<160> NUMBER OF SEQ ID NOS: 32

<210> SEQ ID NO 1
<211> LENGTH: 137001
<212> TYPE: DNA
<213> ORGANISM: homo sapiens

<400> SEQUENCE: 1

caaaaattag ccgggagtgg tggcatatgc ctgtaatccc agtagctggg aggctgagac     60

aggaaaatcg cttgaacccg ggaaacaggt tgcagtgagc cgagatcgtg ccactgcact    120

ccagcctggg caacagagcg agactccatc tcaaaaaaac aaaacaaaca cacacaaaaa    180

accaaaaata aataaataaa atgatcactt ctgaatactg atctaactag gggttgcagg    240

gtgggctgat atagggagaa actggagagc aaggagatca ctaaggtccc tacatgtcca    300
```

-continued

```
gaaccaagat agaggtcttg aactaggatg gtggcagtta gaacaacaac aacaaaaagt    360
caattccagg ctgagtgcag tggctcatgc ttgtaatccc aacgctttgg gaggctgagg    420
tgggagttag aaagcagcct gggcaacact gcaagacctc ctctctaaaa aaaaaaaaaa    480
aaaaaagtta gccaggtgtg gtggtgccca cctgtagtcc cagcaactca gaaggctgag    540
gtgggaagat tgcttgagcc ccaggagttc aagcttgccg tgagctacga ttgtgccact    600
gcactccagc ctgagcaaga ccttgtctcc aaaaaaaggt caattccact gacttttcta    660
aggtgtacac catcaagggg cagctccatc tccaggccat tggctcatga gacattctgt    720
agtcagaagg ctagggcaga ttgctttgag caagccccca tggtggttct cactcctact    780
tctttgggta tatgcccctc tgtttaaaaa taaagttaat atgcatttaa aaaaaaaaag    840
gagaaaaagg tcagttccag aaactgtgtg aataaagcat tttacttgct ttttctatta    900
atctataaca tatgttgatt ttttaaaaag aatataagag ctatgcaaat tggagcttca    960
agacaacttc ccatctccct aggaggagat ggctgcccta aaccccccta catagaaatc   1020
atcccactgc ttgggcttaa acttgatgtt ggggaaatga aaaatccaag ctaaggccga   1080
agcctggggc ctgggcgacc agcagaatga ggaccactgg tcagtttcag gctgaggtgc   1140
gtcttccagg ggacaatctc tagctggccc ttaaacattc agacttcaag ctctatttac   1200
agcataaagg tgtttcaaaa gacgtgatac aaataactgc aaatgctctg cgatgtgtta   1260
agcactgttt gaaattcgtc taatttaaga tttttttttc tgacgtaacg gttagattca   1320
cgtttctttt tttttaagta cagttctact gtattgtaac tgagttagct tgctttaagc   1380
cgatttgtta aggaaaggat tcaccttggt cagtaacaaa aaaggtggga aaaaagcaag   1440
gagaaaggaa gcagcctggg ggaaagagac cttagccagg ggggcggttt cgggactacg   1500
aagggtcggg gcggacggac tcgagggccg gccacgtgga aggccgctca ggacttctgt   1560
aggagaggac accgccccag gctgactgaa agtaaagggc agcggaccca gcggcggagc   1620
cactggcctt gccccgaccc cgcatggccc gaaggaggac acccaccccc acaacgacac   1680
aaagactcca actacaggag gtggagaaag cgcgtgcgcc acggaacgcg cgtgcgcgct   1740
gcggtcagcg ccgcggcctg aggcgtagcg ggagggggac cgcgaaaggg cagcgccgag   1800
aggaacgagc cgggagacgc cggacggccg agcggcaggg cgctcgcgcg cgcccactag   1860
tggccggagg agaaggctcc cgcggaggcc gcgctgcccg ccccctcccc tggggaggct   1920
cgcgttcccg ctgctcgcgc ctgcgccgcc cgccggcctc aggaacgcgc cctcttcgcc   1980
ggcgcgcgcc ctcgcagtca ccgccaccca ccagctccgg caccaacagc agcgccgctg   2040
ccaccgccca ccttctgccg ccgccaccac agccaccttc tcctcctccg ctgtcctctc   2100
ccgtcctcgc ctctgtcgac tatcaggtaa gcgccgcggc tccgaaatct gcctcgccgt   2160
ccgcctctgt gcacccctgc gccgccgccc ctcgccctcc ctctccgcag actggggctt   2220
cgtgcgccgg gcatcggtcg gggccaccgc agggcccctc cctgcctccc ctgctcgggg   2280
gctggggcca gggcggcctg gaaagggacc tgagcaaggg atgcacgcac gcgtgagtgc   2340
gcgcgtgtgt gtgtgctgga gggtcttcac caccagattc gcgcagaccc caggtggagg   2400
ctgtgccggc agggtggggc gcggcggcgg tgacttgggg gagggggctg cccttcactc   2460
tcgactgcag ccttttgccg caatgggcgt gtgtgtgtgt gtgtgtgtgt gtgtgtgtgt   2520
gtgtgtgtgt gtggaggggt ccgataacga cccccgaaac cgaatctgaa atccgctgtc   2580
cctgccgctg ttcgccatca gctctaagaa agacgtggat cgggttctag aaaagatgac   2640
tccctgcacg cccctccctg cacctcccga gcagtgattc cgacagggcc ttcactgccc   2700
```

-continued

```
ctgattttag gcgggggccg gccccctccc cttttcctcc ttcagaaacc cgtaggggac   2760
atttgggggc tgggagaaat cgaggagatg gggaggggtc cacgcgctgt cactttagtt   2820
gcccttcccc ctgcgcacgc ctggcacaga gacgcgagca gcgccgtgcc tgagaacagt   2880
gcgcggatcc cactgtgcac gctcgcaaag gcagggttca cctggcctgg cgatgtggac   2940
ggactcggcg gccgctggtc cccgttcgcg ggcacgcaca gccgcagcca cgcacggatg   3000
ggcgcggggc tgcaggtgca tctcggggcg gatttctttc tcagcgctcg gagcgcaggg   3060
cgccccggcgt gtgcgctccc tgccggaggc gcggggctgg cgcgcagggc tcgcccctca   3120
ctgcggcagt gggtgtggac cctggtgggc gaggaagggg gaggataggc tgtgcctcct   3180
cccactcccg cccccagccc ccctttttt cccccctcgga acgcgaggtg ccatcttttt   3240
tcggcgtgtc acgtctttac ggtgccatgc caaaccgggt ggccgggctt cataggacag   3300
ggcggggcct ggcattaaag ggagggggac aatcagcgct gaaatcttgg cgttttgctg   3360
ctgcgggcgt gagcactggg ggcgttcgcc cagcaccttc ttcgggggct ctttgctttg   3420
tctgtagagg ttacgtgatc tgcgctccca gccctggttt ctggctttta ttctgagggt   3480
gttcagtcaa cctcccccct acgcccatgc gcctctcttt cctttttcgc tcctcatttc   3540
cgagcccatt gttggatctc gaggcttgct gggttcgatg aactcgagtc aaccccccga   3600
cccccggcac gcatggaacg ggcgtgaccg cgcgcagcct cgtctcggag tctgccggcg   3660
ccgggaagct tctgaaggga tgggattcga gtctccgtgc gcgctgcggg cggcggcaga   3720
gggatctcgc ccctccctac accccaagtg tcctgagggc cacgccacac caggttgccc   3780
agcgagggac gctggctacc catccgggga tgggtgggga gccctggcgg ggcctctccg   3840
gctttacgcc ctgttgcttc gcctggccgg agaatgtgag gaaggggcat aaggttactg   3900
gtgcttcggc cacacccatc tttctgagcc cactggactg ggcgcagagg ggggattgcc   3960
atggaaacca caggtgtccg gagaggggat cttggggctg gcctcacccc ttccctgcgg   4020
agattgggga ccctggggta gggggagccg cgcccagtcg gcctcctgga ggacacggga   4080
ggaagccccg aacccccgcg cctgaggctg tttctgattg gcccctggag gccgcagaca   4140
cgcagatagg cggccctggg tgtattttta ttaatattat gtccgtactg attaatatta   4200
tttatcttaa ataaatttca cccgtgtcca agttcaccgc gcccccaaaa ccgagtctgg   4260
ggcggcaggg ggaactcctg gccaacgaat ccatgcctcg ccctcctgtg atgaacctgg   4320
tacgcacggt tttctggtta attctatcgc tgaaaactgg tgcggggggc gcacttctga   4380
gacggaagag catctaggag ctgaatcctc cacgcgggtc gcccaggttg atctgaattt   4440
ctggggaatg gcttggctgc ccgcccggga ccaggccgac cctccttgac ggtggcgtag   4500
agggctggag cctgggtact gcgaggctcc tcgcatggct gggcccgccg cgaggggttg   4560
cagagcggct cagggatcga ttcaagcatc gtctctcctc cctcgccccc agacagagct   4620
gggcgcgggg ttccccttcc agatggagcg agggtctcgg ggtggccccg gaaaagggga   4680
gcccgcggcc acggctacgt attgccatct cgcgagcaga gatgtcacct cctgcctttg   4740
gaggaaaggg agcccggtgg ggatgagcgc atttagccca atgctgggaa caaagcgcac   4800
tccgcgcttc tgcgatttcg ctccattttg aaatgtgttg gcgctttggt ggggccgctg   4860
cggtgggcaa ggccgggggc gctgttaatg gaggaacctc agggggacgg tccttcgtag   4920
gaaactctat cctggctctg cgcgcgcttt aaggaaatgg cttccctcca ggacctcgag   4980
ggatgcagct tttgcgcgga tgacggtggg gtgctgaacc agccggtgcg cctctggaaa   5040
```

-continued

```
tgtctgggca cggatcctgg ggccatcgac gactcctccc cattcccagc aggcgggagc   5100
tcttacattc cgagcgagtg acccctctca ccctctggcg ctcacacacc tgtaactcca   5160
aacctccgtc tcagaatggt ccaggctgga agggatgatg ggggctccga cagcgactgc   5220
ctagctcacc cctctgcgtg ctcaggctcc aggctcagca ggaccaattt gagttctatc   5280
tgatccccct cggcccctta actgacccat cctacaggag acagggaaat gtctttccta   5340
ccgcggttga ttctggggtg tcattttgtg ttttgtgatg gctgcttata tttactgtat   5400
aagcattgta tttactgtat aagcattgta ttataattac tgtataagct gcttatattt   5460
actgtataag catctccaaa tcctccctct acgtaaacaa attaatggat aaacagataa   5520
gtgtatcccc tgcccccacc cctgctacgc aggtccggag tgactcttga agctcataca   5580
ttccttggcc aagtttgctt ctctaacaga tgtttatata gcaataacct ggcttggctc   5640
ttgggttcac ctttggacga tttggggaag ggcttgttg gctttgctgg gttttggatg    5700
agtgacagtc catgactgtt cctgctggaa gggcgtgact tttaagtggt ttctaatatc   5760
aggcattgct cctccgacag gaacaaaaga aatggatact gcccataaat tgttagaaaa   5820
cttagaatcg ctttgattga ggaaaggtta gatttattcc ggttggaaaa agtggccttt   5880
ctattaaacg tgccctttga ccctcatgcc cttggaggtc ggtgccagcc tggagatggg   5940
ataagattgt ggttttcctt ctgccttttt aacatctgtt gttacagtcc atttgttgaa   6000
aatttaaaga aactgtttta ttccactttc cctcagcatt tatgtgtgtg gtttcagtag   6060
ctctgtggct atatgtacga acacgtgtta tttttccaat tggacatgtg ataattttcc   6120
aactggacct tgccttctat tgatgtattt atttagcatc ttccttactc cctccttgaa   6180
aaagaatcac tcaaaaacaa ataaaaacag ccgtaggggc ctaatacagt gctagacata   6240
caagaggtat tcggtccata ccaaatggat tttatccatg aaggataaat ggggaaatac   6300
agtgggaagc aggtgggaaa ctgcgtttga ctctgctctt tcctccacca ccactttcct   6360
catcaccgtg ttcagagacc cccaaagccc cctcacactc ccagaaacac ccccctggcc   6420
actcctaact tgccatgccc aggagttagg tgcttccact agtgacatgg agctggcgtt   6480
tggggggcac ctcagcaggt gacgggaaga gaagacccca gcctcaccag ctgggctgca   6540
gcagggagag gagtcctcat gttccagcag ggactctcag ctgttttcct gtaaaaccat   6600
ggttctcaac tgggggccac tgagatgtct agagagatgt ttttgttttc acaactcggg   6660
gagggtgcta ctgacatctt gtgggtagag gccaggaatg ctgttaaaca tcctacaagg   6720
aaggcacagg acagtctcct acatcaaaat atgacccagt cccaatgtca ccactgctgg   6780
ggttgacact ggcactgcta tcttaattac attcattgag tgtcttttag gaggccctat   6840
tctaagtgct tgctaagatt atctcattta atcctcacaa cacttccgct atgtagcagg   6900
tgctgttatt atctccgtga tggggaaact gaagcacaga gagggttagt aacttgctaa   6960
aggtcacaga gccagtgggt ggtggagctg gttgcctgac actagttccc tcccctctca   7020
gccacatgtg ggtttacttg gccattgtgg actagtctgg gaacccagat atgatctata   7080
acattgaccc agtagaatat tgattccaaa accactgtct cacaaatgaa tttttacaag   7140
agtctgtaat cggagcatga cccagaataa ggttagggag atgtggagtt aaagctctca   7200
atttcttatc tggccccgac acagagagca aggcatttca ctctacattg gtgctctgtt   7260
tataaaacaa agagcaaata tctcttccta aggtccttaa acctcttccc ccaatccagg   7320
gtttctggac tgctctgcca tatgacgggg cagctggttt gattgaccca gggaaggctg   7380
gaaatcaaga ctgggggatc aagacgtaga ttcagtgtgg ccaaggtcaa gtctctgagg   7440
```

tttagggaca tcagatcccc agcttaggtt ctgtacctcg gcaaggtgaa agcgttggcg 7500
cccactgatg aggcctgctc tgagattgtg ggtgtgggtt gagttgggtg ggcataggca 7560
agtcctcttg taagaatctt ttggcaaaga tgggcctggg aggcttttct cacttcctgg 7620
ggcccaggct ttgcaataag tattccatta tactgtggta ccttggggct acctgagaat 7680
cctctgtctc gcccctgttg ccttgccaaa gagtttgctg tccaagaatt cctttcctgt 7740
ctccaggtgc catgctcctg ccacctctgc caggttccct gcctgcccag atggctccca 7800
actgagtgtg aggaggaatt tgagacaggt tttgagcttt ctgggttctc cagttaggaa 7860
actttctgta agcatgcaga tagaatgggc ttcagcaaaa tacaaactcg aacaacttcc 7920
atgtatagtc ccttaatttt ctttgctttt ttcatatttc atcaggctcc atgctgagcc 7980
caatcaggga cccgatagaa atccaaacac catgtcagcg agtccccaag aaatgcattt 8040
tgtgccaagg ctattcaagg aaggtttggg agcagctcaa gggcagacac tgttaccctc 8100
ccccaggtcc ccagtgcagg gcagtgttct gcatgtggag gcagtttggc ctaatggtta 8160
aggaggtagg ctctgatcgg gcctcctggg cacaaatccc agctccctgc tcactgtgag 8220
acctaagcca tattgtttag ctgcttggag agtttttttgt catccacaac ttggagtatg 8280
atggtacctg tctcacgggt tgccatgggg ttcacacaag ctaacccggt actcactagg 8340
gccaagcaca tagtaactgc tcagtaaatg gcatcatcgg cggtgtcctg tggatgagtg 8400
cttgtgattg gctgaatgac cagaggggtc taaagatcct ggtgatggaa tcagttgtac 8460
agataaattg ttacactgag tagggatcaa gataggaaaa gtcggcaact acccagctcc 8520
cctgcaccaa actgggcaga agtggatcct ctgaaaattg cacacaccca tgtttaaatg 8580
tacacacaga actcttgcca caggcaagcg gagatttgtc atctgctgtc cctgcctcat 8640
cttcttcctg aaatccactc catgccagga ataaactgca tgctctccac cagcccaaac 8700
tgacctgcct tcccgccagc catcccgggc agggtgacct ggcttagtac atcgggttca 8760
gagatctttc cagtttactc gttgaataaa aagtgagggc tgatcgagaa agtaatggca 8820
gtcagggaag gcgaaggagg taaagaagag attttacaaa tgaagtaatt caacagagtg 8880
ctgacattgg taaactggca aacagatttc agggtggttg gttgagagta gagtagaaaa 8940
ggattaaata aagcaaactt gtggtgtact gaatcttagg aattccatgt atccaataag 9000
tatagtcatt tatgaattaa taaattcggc ctaagaagcc ttcttatcgc ttaaatcaag 9060
actaagtaac aatatatcag ttttaaaaag tcattatatc agaaaatcat ttaaatgata 9120
cacatagatt tccaagattt tactttaacc gaaactatat aaatgtgaat ttgttcaccc 9180
atcttttgac acagggctca ggtcttctct tggtgtctgg atcagccagt tgaaatttct 9240
tgtctgtttt gcctatgcca cattaataat gcactgtctg ggtcctccga tttcagtttg 9300
gattttgggt ttacattgtg gagtcatctg aatgcagaat ccttcaggga ttttactttt 9360
tttttttttt ttcatggtct ttaccatccc atttgatagt aaatattact cacctttatg 9420
aagtctttcc aaaacattca actaaatttt cttaaaatca ttgaatgatt tgaagagctt 9480
attcctcagc acttttactc catcagcttg caccttattt tttaatcttt ttttgagacg 9540
gagtctcgct ctatcgccca ggcttaagtg caatggcgcg atcttggctc actgcgacct 9600
ccacctcctg ggttcaagca attccgcctc agcctccgcc gtagccggga ctacaggtac 9660
acaccataat gctcggctga tttttgtatt tttgtaggga tggggtatcg ccatgttggc 9720
caggctggtc ccgaacttct gacccaagtg atccacccac ctcggcctcc caaagtgctg 9780

-continued

```
ggattacagg tgtgagccac cgcgcccggc cagcttgcac cttatttagg atatgtgatt   9840
attatagcaa gtctggtgta catacaagat tttgaatggg cacagatgac ctttagtaag   9900
tgcttggctg tgataagagg cagtcctgac tgcagatcag gctgtgtgga ccccagcctt   9960
gcatgtttac agaccttcat gtcttattct tacagggtat cagaagaaca cctactgggg  10020
aaacttataa attagtaaaa ggtgggcatt ctccccgccc atcttctgtc tgtctgccag  10080
gactagcaca gcactttgaa gtcattcaca tagaatccca acttaagagg gtaaaatcct  10140
cctcaacaga ctgaaaataa gtttaaattc cctttgctat attaactccc ctgaggaaag  10200
agtcttagat caatgtccaa cactaaaaac agttttaaat cagcaagtga gaattaaatc  10260
tgaagcaatt gataataatg tttcattcat tcctctcctt tggccccgtc caccctactg  10320
ctaaatccag gcatcaaaga gaagagggac ataattatct ctagtcccag ctgctggttt  10380
tccttccagc ctatggccca gttttctgtt ttactgagaa ggctggtgat gttatcttgg  10440
gatctaagtc tgcagtttca ccacaaaaag tccagggatg cactttcatg cttgtgtcct  10500
cctccctggg atagcaagga tattagaaga cccctggctc tgtaattgct tgtcatgtgc  10560
tctacagacg ccacagaatg ccaagaacga agtgctggga aggacaaatt catggaaccg  10620
tgggacggtg ctcctccccc agcgtaaagg acagctcctc ctcctgaatt ggagccagcg  10680
ttctaaatca tgtgtcaaca gagttgtcct ggatcggatc cagttctgcc attgatttgc  10740
aggtcatttc agtggtacct gtttccagtt gttcttaatt gaacagtggc accaaactat  10800
tgtcttgcct catccccctc ccatggcctg tcccccaaaa agagacttct tgggtaatta  10860
atcagggcaa catcaggcag tctgggcgcg gtggctcacg cctgtaatcc cagcactttg  10920
ggaggccgag gcgggcagat catgaggtta ggagattgag accatcctgg ctttgtgaaa  10980
ccccgtctct actaaaaata caaaaaatta gccgggcgtg gtggcgggcg cctgtagtcc  11040
cagctactcg agaggctgag gcaggggaat ggcgtgaacc cgggaggtgg aggttgcagt  11100
gagccgagat cgcaccactg cactctagcc tgggcgacag agctagactt cttctcaaaa  11160
aaaaaaaaaa aaaggaatct ctttggtttt atatattttt ttttatatat ataatatata  11220
ttaaaatata atatatatat ttatataata taatatataa atatattata tattatatat  11280
ttttatatat tatatattat atatattata tattatatat ttatatattt atatattata  11340
tatatttata tattatatat ttatatatat tatatattta tatataatat atattatata  11400
ttatatatta tatattatat attatatatt tatatatatt atatattata tatattatat  11460
attatatatt tatatattat atatttatat atattatata ttatatatta tatatttata  11520
tattatatat ttatatatta tatatattta tatatattat atattatata ttatatatgt  11580
atatattata tatgttatat attatatata tttatatata taatatattg tatatattat  11640
atatctaata tattatatat attatatata ttatatatta taatatatat tatatattat  11700
atatattttt atatatataa tatgtataat atataatata tataaaaaca tatataatat  11760
atattatata ttatatatat attatatata ttatatatat taaatatatt ttatatatat  11820
tatatatatt atatatatta aatatatttt atatatatta tatatatata cacatatata  11880
tatataaatg aggccaggct cggtggctca cacttgtaat cccagcactg tgggaggatc  11940
acttgaagcc aggagtctga gactagcctg ggcaacaaaa caagatcctg tctctacaaa  12000
aggaaactgt aaaaattagc tgggcatgat ggcatgtgtc tgtagcccta gctacttggg  12060
aggccgaagc aggaggatcg cttgagccca ggagttcaag gctacagtga gctatgattg  12120
tcccatagca ctccagcctg ggtaacacag caaggccctg tctctaaact tttttttttt  12180
```

-continued aattctattt atatttacat gtatttaaat gtgaatattc actacctatt tgttgcatgc 12240
ctgcattttt tatactgggc ttgccaaaaa cccgaacagc tttctacttt gacaatgtat 12300
cagaatttaa atcagcaata tgttaataag ccaagcaaag gttatatatg caaataaaac 12360
tgttgtctat aacctcctgt tacactgggg cacagcaaaa gtcatggtgt agtcgcatgt 12420
gaacctgtcc ctttcatagc tgctcattgc caggaaacat caggaatagc catttggaag 12480
agtcatcagc cctcccacca tccgttttct gtcttgtctt ttccctatga gcaggggaaa 12540
ttccacgctg gccccaatcc ccagtgcagc ggctcagcct ctgcctctgc tgctggtccc 12600
catgaggcca gcttagaaac ggaggatttt gcagaacatc cctaaatccg cttgaataat 12660
gaagtgatca ttcataaact cacctgaacc ttattaaaac ctatttaata tttttcctgg 12720
ataatcctat agggataact tgcctcctgg gcttctctcc accgggttca gttcttcctt 12780
tagtggtgaa gttcctccct tcttagcatc tcaactgtgc ctgagaaaag gccagtggcg 12840
gctgcactct gttccctgtg gagtgttaat aaagactgaa taaattgaaa taaatccctt 12900
tcaatgtcat taagtgctat aaataatcat gaaccaatgt tcgatggctg atgagaaatg 12960
caagaaaaaa tttttaatca gtaggattca taagttgaca atctgggcca agttaaaaaa 13020
aataaaaata aaaagacttt taaaaagatc ttatcgtttg ttaccagtaa gactgaattc 13080
cagaagcaag ctactccctc atttgtgggc ccctgttatc actggctgct tagggttgcc 13140
aagccctgaa ttcatttgtc aactaagaga tttttggcca agattaagat ttcccatgcc 13200
tccatatttc catctgagaa atggagatta tactgtcttc cccctcagaa tggatgataa 13260
tgtggtctct cttctgttcg catagtcata gaactgaaat aaaacaactt aagagaattc 13320
ctttgagctt ctcagaagtg ctgcagggct gggggatgcc tcccaggagc cgcagtcagg 13380
tgctgatctg aagtctttgg tgggctgact ttagcctgac ctgaaatagt atagctgctg 13440
ccacctggct cccttagcgt cagtcagacg gtgcagctgg ttcctagggg tgagggctga 13500
gccagcaggg tccgtgccca ggagggatgc atgggtggcc acagcccagc ctgcactgat 13560
cttgtctgtc cccttctttg gaaggaagga gccccaaacc agggtgcaag acagtgggtg 13620
ggggtgcctt gagcatgacc tcaagtgatt tccagcccct gccagtgctg acttctctgg 13680
ggaagggctg ggacttcctt ctgggctcaa gtcacgaccc ttggatggaa tttcctggga 13740
gcttttctgt tttttctgga gttttcagtt ttttcctaac cagacaggga cttggtacag 13800
aatctcatat tctaattatg cctaggagca gcctctcccc accactcaca gtgtttagca 13860
tgtgacagga atcgattaag gcatgagtga ttaaattaaa gccaggcatt gacttggatg 13920
gtgtaatatt ctgacatctg tttggtgtca aaggcacggg gcaggcgcgt taattgaact 13980
gcttgcacct ggcatttgaa ttgagccaga gcggggctaa agtcagtttg ccttcaccct 14040
gtaaatggag ggtttctccg gagcgtggat ggtgggaggt atttcagggt gtatgcataa 14100
cccccaccct gacaatggcc catctcttct ccagcgtggc caggtttgag tgccagtcct 14160
gggtgtccag tggccccata gccttgcgtt ttagtaaaat gctgccccca ttaccacctg 14220
gtctgtgcac ttcggtcact ggaatttgcc atcttccagt cccgaatgtg gcaagccatg 14280
gagccttaag ctcttctccc tccacatcct ggaacagacc cgccagtttc ttccaggcat 14340
tgcctcagtt tgcccctctg tttccagtca cactctcacc agcgataaaa tgattttaga 14400
ccttatcatc tcaccctcgg atccttatgg aaacaataat gagttgttcc ctgtttcaat 14460
tccaaaattc atatccaatc cgttttgcat gccattgcca aattcctccc agagcaaccc 14520

-continued cgtcacctgc cctggccctc tccaagtgtg gtcctgccat gggcatcgcc tgctaagcca 14580
agctggcctc gagctgcctg cccgggtccc cacaccttgg ctcacctccc tgcccagtcc 14640
cgcctcctgc cagcctgccc tgtggctcct tcatagatgc cgtgctcttt ctgccccttg 14700
ctcacccatg gcagccttgc ccctctctcc ctgccccacc ccctatttaa attgacctga 14760
ccttcctcag tgtccatctt ccccgaagct ttccccagcc ttggcactca aggtccagag 14820
gctacgcgtt tcctctcacc tgtggcagcg ccgtgctccc cagtgcctca cagtttcctt 14880 cttgccccccg cttcctgtgt aggactcatc tgcccacagg ttgcacgtcc tgtgagggca 14940
aggactgtgt cttatgtgac tttccttctc cagtcacaga gctgggcaca tagatagctc 15000
aaaaccctct ttattaacac agttggatgt tgagaaatca aacaggccaa tgtcaaatga 15060
gctctcctta tttaaatcaa gtcagttctc cacctcctag cactcagttc cagtactcta 15120
tatacatgga aataataaaa aacacatttc ctttgaaaca ttctataatc gttcctttgc 15180
cctacttcag accaacttaa cgcactcccc attggtccaa atgagttttg ctatacgaag 15240
atgctgataa taatagcagc agtggattat tctgctaaaa ccattgcctc gttaatcctc 15300
agtcccgagg tggggattat tatcctcatt ttgcagagaa gcaaactgag actcagagat 15360
ttcacagctg gggagggagc cagctcatcc ctctgtccag gcccaagctc tctcccgctt 15420
gccttcctgc ctctgcaacc tcagagcatc ccccatctgg ttctactgcc tgtgctagtc 15480
gtgcaggagc caaaagacac gtctttagtg ctaaggactg gagaagccat gccctccagc 15540
ctctgtgaat gggtcatatg taacatgagc ctggagaaat tatttgaaac caaaggcaag 15600
cctctaaacc aggctgctgc ttcatggcgc cggtgacggc agaaccaaat ttagtgctgt 15660
gggcaggtcc acacttatca aatagagaag ctcatttttc ttccggctca catcaagcat 15720
gaaaaatgtt cacacatacc ccccacacac acatgctttc cggaggggtc catgtggcta 15780
gaggctggaa gatgtggatg agaggagcct ggcaggtaag cccagggaag atgacattca 15840
gcttcccaga cagcatctac agggagaaat ttaattaaaa gtggggcggt ttccctgagc 15900
aaggcagaca aagtcagccc tctactgtta agaaaaaggg tcacagtgag aggggaggtg 15960
aggagactga gtctgtattt tctagtctgt tgggctacac tacctgatcc cccttcctca 16020
aaaatccact ttactttccc catgtctaca ccaatgtggt tcacactctg ggaccaggaa 16080
aagggggagt gatggggaac agagaaggga ggagctcaca cagctgaggc tggggttatg 16140
catatcgaat tacttagaat ttgcaacctc acagggtact ttcatggcgt tgaaatacac 16200
ttcccacagc caccctccct ctaactaaaa gcaagagtca tttctcagtt ctggtcttgc 16260
ctcccacgtt ctcctccaca tttaagaaaa tccaccagct acaaagtgaa gataccatat 16320
gtgatatccc accctagttt ctgttttatc agggtttgga gcaggtggag caggcagagg 16380
gatcatttca gcctataaat tgtattaagg gtgagtactg agtcattctt caagaaaagt 16440
tttagaagca tccaaaactg aagggtggag ccacctggag acagtatcat cagtcctggc 16500
cccgagcatg gcctgcatag gcccccatgg atcccagcgg gagctgcaga gtgcgggcac 16560
cttggcacac agccctgagt gcaaaattag gagctgggca gagggcatct ctctgtcgcc 16620
attgggcagc ccagggcaca ctggtcatag ccttagacca cgaacaccct gtgcccgggg 16680
gacagatgca accagtgtgc cctgggctgc ccaatggcaa cagagagatc gacacctgga 16740
ccccatgtca cggggactcc actactaagg ctcctaagac tgccaccttc cagtgggata 16800
agccctgcct cctactgggc ccacaatgtg cagagaacac ttgggactac ctggctttct 16860
ggatacacaa atattgatcc aatctggact aattagaagg tcagtcccaa taacaaatcg 16920

-continued aagtcagctg ggcgtgatgg ctcactccta taatcccagc actttgggag gctgaggtgg 16980
gcagatcatt tgaagccaga agttcaagac cagcctgggc aacatagcaa aaccctgtct 17040
ctactaaaaa tacaaataat taggctgggt gtggtggctc atgcctgtaa tcccaacagt 17100
ttgggaggct gaggcaggtg gtcacctgag gtcaggagtt tgagaccagc ctggccaaca 17160
gggtgaaacc ccgtgtctac taaaaacata aaaattagcc aagcatgatg gcatgtgcct 17220
ataatcctgg ctactaggga ggctgagaca ggagagaatc gcttgaatcc aggaggtggt 17280
tgcagtgagc tgagatggtg ccactgcact ccagcctggt tgacagagca agactctgtc 17340
tcaaaaaaaa aaaaaaaaaa aaaaaaagcc atgcctggtg gagcactacg tgtaatctca 17400
gctatttggg aggctgaggc acgagaatca cttgaacctg ggaggcagtg gttgcagtga 17460
gctgagatcg cgccactgca ctccagcctg ggcgacagag tgagtgagac tccatttcaa 17520
aaaaataata aatctgagtc actttaatat tgttatttgg atgtcaacct ctaggtgttt 17580
gagacaggag agtgatatgg gggcactgga aacacacagg cacggggtgt cctcacactt 17640
gggtagccca cacgatgtga tttcagggtg ctgggaggtc cccccactcc ccaaattact 17700
aacaagtgga tagtacttta cagtttatat gatctcattt gattcttaac atgagcctgt 17760
gagtgaaaaa ttccttcccc tcttctacag attaggacgt tgagattcag ggaggttcag 17820
agggattcag ggaagtcaag tggcacctgg agtcccgtgg ctaatttgag gccggtaggg 17880
gattcgaacc caggatttgt gcttcttatg cctgggcttc tgctccctgg ggcatggtct 17940
tccccctagc tttcccattc actgctttag cctaggggtc ctaccctttta ttaaactgcc 18000
agtgcctcac tgcttttctc ccccaaagac aaaaaaaaag tgtttttgct tttgttttgt 18060
ttttcatggg cagagacctg gaatttcagc ttgagaattt gtgccatatg ataaataaat 18120
caacagatgg ctttttcctt aaaaaaaaaa aaaaaaaaaa ctaagatgta tttgcagtga 18180
ggcataattt gtaccaaaaa gtgctcacca cactgtagtc atgggggcag gaggcagccg 18240
cgggtgaagg gagaaatctt ggagtccagg cagccccctt ctgggctgaa ctggggagct 18300
gggggtgctg ccagccctgc caggttctcc taggaggcgg cagctcatat ggctgtggga 18360
ggaggcagag ggagcctcat atgcacccac atttccaggg atctagaaga cagaaggagg 18420
aaaaccacca tcatgttaaa gcagacagtt aggtaacaca tcctgtaata caagttattt 18480
tttccacatc taaaggctaa aaatagttgt tagaatttaa agataattgg taaatgagtt 18540
tctatccttc tagtttcaca tcaaatggaa tcatgctgcc ttcacatcac tagtgcccgt 18600
tatttgtgtt taatttccac aatgttgtct aattccactc tttgggcttc cccagggatc 18660
cagcctccct cactcgccca tcgcagggag atgctttatt catctttgtg tcttctgtgc 18720
cgggcatagc gcatggcaca gaataagcac tcagtaattg attcacgagt gaataaatgg 18780
atgagtgggt gagttcaata ttgactacaa aaaccctaag gccacactgg tgagtggctg 18840
cgcctgtagt cccagctgct ggggaatctg aggcaggagg atctcttgag cccaggagtt 18900
tgaaactagc ctgggcgata tagcgagaac ctgtctcaaa tgacaaaaac agggccaggt 18960
gcagtggctc acgcctggaa tcccagcact ttaggaggcc aagatgggag gatcacttga 19020
ggccaggagt ccgagaccag cctgggcaac atagggagac cctgtctcta caaaaaattt 19080
tttaaaaatt agctgggcat ggcggtgtgc gcttgtagtc ccagctactc aggaggctga 19140
ggcaggagga tcacttgagc ccaggaaatt gaggctgcag cgagccatga tggcaccact 19200
gcactgcagc ctgggcgtca gaacgagacc tgctctcaaa aaaacaaaca aacaacaaaa 19260
aaaaaggctt tcttaaagag acttgagaac agaaagggga acagatacat aacttatata 19320
tttatttgtt catctttcca ccttcctgga gggtggaggg gaacaggtct gtatttggag 19380
ttttgaatgc taaaagtggg aatacatgta ctgtttgcca tgatctgttc aaaagttaag 19440
ccaaatgcct tagattctcc tgaaaactgg aatgccactg taaactataa gccccacttc 19500
aaagataaaa gatcttgatg aacagggctg ggtctgtgga ctgggcctct ccccaccaca 19560
caaggaaggg tggtgccagt tgaaggaaaa tcacttaaat ccttgctgtc tcctaataag 19620
gtgtggtccc aggtagggct gtcagaatta gcaaattaaa acacagggca tctgtgaaaa 19680
ttagaatttc agataacaac aaataattgg cataggctgc ataatgtccc tcaaagatat 19740
caggtcctaa tctccagaac ctgtaaatgt gatcttattt ggaaaagggg tctttgtaga 19800
tgtggttaaa ttaaggattt tgagatgggg ggattatcct gtattatcta ggtaggtcct 19860
aaatgcagtc acactcatcc ttgtaagagg aaggaagaga gagatggaaa acacagaaga 19920
gaagacaatg tggtgatgga ggcagagatt ggagtgaggt ggccacaagc caaggactgc 19980
tggcagctac cagcagccag aaaagtccag gaaccaattc tctcttggag ctccagaggg 20040
agtgtggccc tgctgacacc ttagcttcaa cctagtgatc ctgattttgg actttggcct 20100
tcagaagtgt gagggaatga atatctgttg ttttaagcca ccaagtttat ggtcatttcc 20160
tacagcagcc acaggaatca aaaacagtaa gtatgtccca tgcaatgttt gtgacacaca 20220
ccaaaaatat tacttgttgt tcacctgaaa ttcaaattta actgggtctc ctgtatttta 20280
tttggccaac ctagttccca ggcccaaaga aagaggcttt tgaaatttgc aagaaagctg 20340
gttggagctg tcagaaagtg gactttgtaa acacagtacc accgaaccaa tttgaactgt 20400
actacctcta gacaaaagag agggcagtca gacagttgtt cgtgatttct tctttcaaca 20460
gtcatttgag cacttactac aaaacagaag ctatgtgtaa gggtggaggc gttagctgtt 20520
aatcaggacc tccaggctaa gtttctgtat tagtccgttt tcacgctgct gataaagaca 20580
tacccgagac tggggaattt acaaaagaaa gaggtttaat tggacttaca gttccaagtg 20640
gctggggaag cctcacaatc atggcagaag gcaaggagga gcaagccaca tcttacatgg 20700
atggcagcag acagacaggg agagagagct tgtgcagggg aactcctctt tttaaaacca 20760
tcagatctcg ttagacttat tcactatcaa gagaacagca cagaaaagac ctgcccccat 20820
gattcagtta cttcccacca gatccctccc acaacatgtg ggaattcaag atgagatttg 20880
ttaccatatc agttaccaac ccttccagat aaatcacgtg aaatatcgcc attaacagag 20940
tgagctcagg tggttcttca gtgcatttct gatacctgaa ccttccctgg gaatttcaca 21000
gaccatcagg ctctccaccc tttgatagca ggatagcagg gcccaggttc tgcaggagga 21060
gatgttacca caggcctgaa agggagggag gggcagatgc tacaggaaga tgctggctct 21120
ggattcgctg gaggagcttt caagggaagt agatacacac tgtctccatc atttcatgtc 21180
catcacactc taaaatgctt tggacaagaa gcaaatgtta aagacaaatg tggcccattt 21240
tcctgtacaa agagggctgc tcccatgcca ggctattggc actggtgggc atgaggcttc 21300
tctgctgccc tggccggggg gttctctcac tcaccattgg ctctctgaca cctggagaga 21360
ccaccaccct tgggctttca tgatgctcac agaatccaca ctgttggagc tttaaggagc 21420
ctggatcaac tggaacaggc agggagtact aggacagccc agcattgccc caaaatatcc 21480
aggcctgata aaagagaaaa acaggtagct cacaggaaaa ggataaaaaa aggaggaggg 21540
atttaacatg aaaaggtgct tgatctccct cataataaaa agactgctga ttccatccag 21600
gcaagtgaca gaaaaaaaaa atttaattta aaaagactgc tgataaaacc acagcgagac 21660
actgctgctc agggatctga gggtgtgggc agccaggctg ccacgcatca tgggtcggag 21720
aggaagacca cacccctgga gcagagggcg gctgatctgt cagatgccct ttgacagcac 21780
ctcagcttcc aagaattaac cctttctatg tgagcagagg catccatggg gggacacact 21840
ggtgaatcat ctgttatgta gaagtctgga aaacatcagg atggaactgg tgaaataagt 21900
gtggcctctg acggaatgga gcggtccgtc tgcactgctg cgggtgcccc tcagatcctg 21960
tgggtcagtg agaaaagcag tgaggaacaa ggcaggtact gtgtactgtc ctctgcgtgc 22020
aaggaaggcc agcgcatgca acagagtcca cacagacata gcctaactct ggaaggaaga 22080
atgagaatgc agtttcagtg gtggcctctg gtggggagaa actgggtgaa gggagatgtc 22140
atttccattt ctctactatt aattttgtat taccatgctt aaatgttact ttttaccttt 22200
ttttttttt ttgagacagg gtctctctct gttgcccagg caggagtgca gtggtacaat 22260
catggttcac tgcagcctga acctcccagg ctcaagcaat cctcccacct cagcctcctg 22320
agtagctggg actataggca cgcataccac cgtgcccagc tattttttt aatcaagatg 22380
gagtttttct atgttgccca ggctggtctc aagctcctgg actcaagcaa tcctcctgcc 22440
tcagcctccc aaagggctga gattaaaacg tgagtcaccc tgcccagcca attgcttttt 22500
aaaaaagatt aaatgcatgt atacgctcag gcatcagcac acttggaaag gatgaaaata 22560
tccggaagaa gggttctttt aaaaggctcc tcaagtgatg ctggcaggca tgacgaatgt 22620
ccctggtcac aaaagctctg atctggccta accctgtcat gttagagact ggagtgcgtg 22680
tgtgtgcgcg caaagtgtgg ggggatgggg gtgagtgtgt gtggtgtgta agcatgagtg 22740
tgtatgtgtg tggtgtgggg gtgtgtgctg tgtgagcgtg tgtgagtctg tgtgtgtagt 22800
gtgtgtgtga agtatgtggt gtgtatgtgt gacgtgaggt gtgtgtggtg tgtgagttgt 22860
gtatggtgtg tgcatgagca tgtgtgtggg catgtgatgt gtgtgtggtg tgtaagcatg 22920
tgtgagtgtg tatgtttgag catgtgtggt gtgttgtgat atgtgtgtgg tgtgtgagca 22980
tgtgtgtgtg atgtgtctgt gtgtggtgtg tgtgagcatg tgtgttgtgt gtgtggtgca 23040
tgtgtgtggc gtgtgagcgt gtgtgtgcat tgtgtctgtg agcatgtgtg agtgtgtgtg 23100
tgttcagcat atataaggca tgtaactgaa cacagcactt tagagggctc tcctggagtc 23160
agagggggtg ggtaggagga gaagggaggt gggctagtgt gctgaagtat ctactccttg 23220
tcatagtctg tgacaaccca gactagccca tgagccaccc tgttccctgc atttccaatg 23280
agacctcggt ggacatgttc cctgaggtga ggctgactga tgtcatttga cgatcttgat 23340
gccaaatcct tttatatcaa aaacaaccag aacactctct tttctcttag tgctttcacc 23400
cagatgacca catttcatcc tcccagccac tctgggccag gtggcactgc tggtttgaaa 23460
gggaggtctc ccctggagta acttccgtgg gcggattcac accctgccca cagtcctgtc 23520
ccagtcagcc caccatggtg gtctccggtt cctccagaat tcccgctttt cagctcatcc 23580
ccacattccc ggagggactg agagcgcagc cccagggccc tgctctttgg gggccgtctc 23640
tacacccaga gaagcagcaa ggcattccta ggtttctctt tcagatgcag aacttcagtg 23700
ttcagagatg ttcccactgg tcctgagagg gctcagttca gctttaatga ctgcgctgtt 23760
gcgtgtgctc tgcagagggc gggtggccca gcgtggctga ctgcagtttt cctgacgtgg 23820
agcccgagcc tgccccgctg tttattaatt aaggatcact ctgcttgcag aaccctgaac 23880
tccccagaac tgtgaggtgg gagaaccccg agaggccacc tggccccact tcccacctgc 23940
tgcccaaacc ccctctctgc cttcctgaca gtcaccccaa ctcccagtga tccccatcaa 24000

-continued

```
ccatctgaca aggggactga gagggaagag aaaggagggg cccaaagagg aaggtaaaac  24060
tgtcgggaac agcccccaaa tgtgtgacag ccttcagtgg agttgcccac tttccctttt  24120
ctcctccctg caggacctcc cttctcccca gtcctcccca acttctgagg ttacattgag  24180
aaaagtctgc agagaggtgc cagcatcaca aggtgttaag gaccacgagt ttggcatttt  24240
aacagatgcc agagccactt gagaaatgtg gtaactaagc ccagagaggt acagttaacc  24300
tccccagagt cacacagcag gttcatggca aagctggact agcacaggtg tccttcccct  24360
gcagatcccc ttctgtgccc cacatcacct ccctccagtg tctgggccac ctggagatgg  24420
gccctcagac tcacccggcc agaggtgcca tctcatggga gaggtctggc caggaagcat  24480
cgatatttga gatcccaaga aatgaagact tggcctgtca gatgacagac ttcggtcatg  24540
ggaacacgtg atctgtttta cacatgcgtc ccctcagcag cagctttcca gaacattccc  24600
actttcttct gtagtgagaa gaactctttc cctgcagcct cctgcccaac tcctccttca  24660
gtgtctttgc ttcagtgtct ttgataaacc attctgcttt gcagagtgcg agctctgcct  24720
tgcagggttc gcatctgcct gtgctgagta accaacgcta aggtcgagtg gtcggtcacc  24780
tctcataaga gctagggttg tctcatgctg atgactagga cttgccctca aggagaaaaa  24840
taaatcaaaa caaaagcaaa aacagcaaac atgcatctct taaagaaggc tctgagtcca  24900
ggtaaatttc cttccactga agcagccagg ctgaattcga attatctttg cccctgctta  24960
aaaactaatg caaattttcc tagagaatat ccactaattc ctggaggggg catgggcatt  25020
cctgatgccc atgagaggac catttgctct tccctcagta tgctaaataa cagaagcgac  25080
atttgttgct ggaaagtatc agtgaagtta ataaggtttt tcttgcccag ggtgagggaa  25140
cagttcccaa tgacaaatgc tgtatgggaa ggggctgtag aactgccagc cccttttggtc  25200
catccgtaaa gtgaactctg tggatcctgg aggattccag cgtctttttt ttttttttctt  25260
tttttttaag acagagcctt gctgtcaccc aggctggagt gcagtggcac gatctcagtt  25320
cactgcaacc tccgcctccc gggttcaagc gattctcatg tctcggcctc ccgagcagca  25380
agactacagg tgcgcaccac catgcccgac taatttttgt attattagta gagacggggg  25440
tttcactctg ttggccaggc tggtctcaaa ctcctgacct caggtgatcc acccgcctca  25500
gcctcccaaa gtgctgggat tacaggcatg agccaccatg cccagccagc atctttcatt  25560
tttctgtctg ctttggccct ttcctctctc actgtcttcc ttttccattt ccaaagtcag  25620
tccatctcac tattagcaca aaaactgcta gagcgcttgt cattggtcat ctctccctgc  25680
acctggctgg tctgttcttg gccactgaag cgtttccccc agctgttgct ttaatcattt  25740
tattgttatt atgccttact taagaaatgg atatgagatg catttacctg tctcttcctg  25800
ccactctgca gagccagtaa gatgtggtgg aaagggccca ggctttggag gagggctggc  25860
tggggttgga tcttggctgc cccctactag ctgtgtgacc ttgggtaagt agctggacct  25920
ctctgagcct ggttcggaat catagcacct ctctttcagg gctgctgtaa ggaatagcag  25980
tggtgtgtat aaagcagagc gcacagccag caactggccc ctagccacac tgctgagcac  26040
ctactgtgat aagctgccat tgtggtgtgt gaagcaaagg ggaaacatgc ctgctgtagt  26100
gagcttcctg tagggcaggt tgtagaacca gaggtgggtt ccaaggttac aaagggactc  26160
ttagtgtatt agtctgttct cacattacta taaagaccta cctgagactg gatcatttat  26220
aaagaaaaga ggtttaattg gctcacattg gctgggtgcg gtggctcacg cctgtaatcc  26280
cagcattttg ggaggccaag gccggcggat cacttgaggt caggaatttg agaccagcct  26340
ggccaacatg gtgaaaccct gtctcttcta aaataaaata caaaaattag ctggccatgg  26400
```

tggtgtgcgc ctggaatccc agctactcag gaggctgagg tggaagaatt gcttgagccc 26460
gggaggtgga ggttgcagtg agccaagatc gccccactgc actctagcct gggcagcaga 26520
ctgagactct gtctcaataa aaaaaaaaaa aaagaaaaga aaaagaattg caagaaataa 26580
attattgttt atgagctata tggtctgtgg taccttgttg tgggactggg agtcttggcg 26640
tctccctgac cctgcctgtt gctgcagcac cgctcagccc tgcctgctcc ctacctgcct 26700
cccctcggcc tctcctgcct ccaccgggcc cctggtgcct cctctagaga cagtcctcct 26760
gggaccgatt gtgttctcac ttacacgagg catccaggac tacagataac cagaggaagg 26820
ggcgcccccc ccgcctgccc tcctccctgg catcctcacg ctgcagaggt cagagcctca 26880
tcccagcccc ttacctgccc ctactctgtg gagaaccgtg gtcagttcgc caggccggat 26940
ccacgaacgg ccttgtggaa gatggtgagc tcacacccag agctggctcc gatgaccctg 27000
tctcctttac atgtttctac cttcccctcc ctaccttccc ccactgctgg gcgcagagtg 27060
gaggcagatg aggtttaaag ctcagaaggg cttaaacggg ttggggcgca gtggctcatg 27120
cctgtaatcc cggcactttg ggaggccaag gcagaggatc acttgagccc aggagttcga 27180
gaccaacctg agcaacatag tgagaccgcg tctctacaaa aaataaaata aataaaatta 27240
gctttgcagg gtggcatgca cctgcagtcc ctgctactca gaaggctgag gtgggaggat 27300
cgcttgtgcc caggagtttg aggctgcagt gagctatgct ggcaccacag cactccagcc 27360
tgagtaacag aatgagatcc tgtctcaaaa caaacaaaca aacaaacaaa agaaggctta 27420
aagggggctc caggtgggct tggcagcaca aagctatgaa gttctatctt agacacaagt 27480
tctgttactg ggcctttgca ggctggcctg ggtacctggc tgccatagac agggaacctt 27540
ccagatgagc tgcaggcgtg gagcacagga gccagggtgc tcttcctggg ctctgtccac 27600
aggcagaacg tacacagtct ttgtacacgt ccggcggctc tggtgcctat ttttgtttgt 27660
gtttttcttt tgtttggggg gatggatttg gtttccccccg agccctctgt cctcctgtca 27720
cctggctggt gctcggcaat gttgaccagc tgcctggctg gagttggcag tggctaaggc 27780
tgtgacagct aacatgttcc tgagtcctct catttcttca ccataatgcc ctgttgagtt 27840
tgcagatact gtctctgttt ttatctcccg gggaaactga ggctcagagt ggctaggcca 27900
ccttcccatg gtccctcagc tcatgagggc cacacagggc attgcggtgg ccttctcctc 27960
agccttgacc ctccggcccc agcattgctg cctcaagggg tctcctctgc tgagccgtgc 28020
accttctgcc tggcagctcc aactctgtgg ctgtgttcag tggctcagca ctgccccttg 28080
accctccctg gccttctgcg gatgccagac tggagcactc tgacaaggtc tggggtggtt 28140
gtatgggtcc tgtgacctct atacacctcc cagtgcctgg gaatcctgca gatacaccct 28200
ccttagccgt ccctaaccat agaggacatt tctgaggtcc ccgagagagt ggggcacccc 28260
tgcaggatcc aactgctggg cccaggaagg atagcagcag catgaggggt tccattagcc 28320
acaaactcac ggcatggaac cttcacccac ctcgcccctc atctgctgtt tagcacctgg 28380
cacgccgtgt atacttactg attattacat tttaatggca aattatagtg gcaaacgtat 28440
gcatctttgc acaattgttg tacagcatga tgaacaagtc attaatagta aagaataaat 28500
gtgaaagtga gaaaaatctg actgccaaag tttttactcc ttccttccct ccccagactt 28560
ttaaatgaaa gtttagggat aatcccttag ttgtcctgct agtaggactt gcaattaaaa 28620
gaattgggcc aagaacactt ctacgcttct ccttttaggt ttgggtgtaa attcggggta 28680
tttctcactg atgaaagcct ggtgcagggc agaccgtggg aagctttcat ttccggaatg 28740

```
gaccatcaac atcccttgga gaagaattct cttctccaga cccagacctg gtgtcctggc  28800
acccattggg caagtgggtc ctagaagaca aacctggtca gagcctggag gctgcttagc  28860
attccccacg cacattagca gctcggagag ctcaggaagc cgcagcccct ccttgcctca  28920
ccagcctgga tcaggacagc atcccctgga agacacacag ggcctggcct ctgattaccc  28980
agcctggagg gaaagctcaa tcgagcatca tgtcacccgg tgccccatg cagggtggca  29040
ctggtgagac cccaagcca atgataccac ctcacaggag tgcaggccca ttgtggccag  29100
atcatcttga cttttcaaga taaatcagaa atcgtatttc catgagatat ccctatttgc  29160
aagtgatggt gactaaatta gaagtttttg aatattgtaa catgttcgta ggctgtttgt  29220
ctggtttaaa ctctatctgg aggaattcaa gctagacttc aggaataact tcttgaggca  29280
aggattttga gaccttaggg aaagaaggac gtcttggggg tattctgact gttgtcctcc  29340
tggaagggaa gaacagagaa ctagaagact gcccttagcg aagttcaaag cacctaagcc  29400
cgggaccctc agcaagtgtt cttgagtcac agattctccc tgaggcgcct ctttctggct  29460
ccatagaatg gctgattctg taactcggtg agtttgcttt tttttttcc tccatcaccc  29520
aggctggagt gcagtgaagc tggagtgccg tggagcgatc actgcaacct ctgtctccca  29580
ggttcaagca attctccttc ctcagcctcc caagtagctg ggattacaag catgcagcac  29640
cacacctggc taatttttgt gtttttaata gagacggccc gaagtgctag gattacaggc  29700
atgagccacc gcggccagcc ataactctgt gactcttgtt acaaaggcct tatattttgc  29760
tctttgaggg tggttttggt ttgatgcctg ttggttgcca tcttttaact agggatgttt  29820
tatcaaaatg cccagccaaa gtgtccaaac aaattatacc ttaaagtttg aaaatgtctg  29880
gcacttctaa ttcaatgcct gttgtgccag gcactgggct gctgaggaac tgagtcccgt  29940
ccctgcaggc tagctagaga acacacacac acacacacac acacacacac acagagtggt  30000
cttacaagtc agttttatat tctacctata tgcaataaag gtattattat gttgaggtgc  30060
cttgatataa aaatttttct taaaggagag gatgcctaaa acaggcatta cctgaaacct  30120
cctctctcca gcattggttg tcttctgtca tgactcaggg ttttcactga gaatgggatg  30180
gaaatgtggt ctaaagatag ggccaatgtt gggactggat cccctctggg aagtcagacc  30240
aggctagggc aggtccttga agccatcagg aaaagcctct ggagccagaa acaaaacaaa  30300
aaaaaaatgg tgttaactaa actcagtctc aaatcctgaa taggactcaa gtcaagcaaa  30360
ataattaaag gagttagcaa agggcaagtc agagagaccg agcaacacca atgtcttccg  30420
ggagccctgt ggcgagtgac agagcctgga ctctggagta gaactcatct tgtgtcttct  30480
tctgccactc gttagctggg tgaccttgag ccaagcccct taacctcttg gaccctatgt  30540
tcttatctct aagtaggggc tggtaatatc ttcccctttg aggaatgccc tctaaggggt  30600
gttgtgaaga ttcggtaagg tggcaggggt aggactcctg gccagaaaca ggcacataat  30660
aaatgctaag tctctccttc tctccacctg ctggatgctg tagatactaa ggatttcgat  30720
gtgaatgaga caaaacccct gccttccagg agcctttgag aatcagagaa ctagacccat  30780
ttccagaaca aggggatgca gggtctggat aaagttttgg ggatcaatag agcagagggc  30840
tcccagagga tcccataggg ttgactccta actcaagggc atgagacaac ccccaggaag  30900
ggcaccctgg aaggggtccg gctgtccctg atttacttgt gggcactggg ggaatgcccg  30960
gagccatcca gccctcaggg ctctgtgtga ttctgggttc ctcccataaa agataatcag  31020
attctttcac gttaatgtct ttctccacct cattgcacat catgcagcta ttcattgact  31080
cagcaagtat cagctttgca tgcgaccttg gcctacccac tttagctttt agtaatagct  31140
```

```
ccccttcttga ataatacaac cagtggggaa acagaaccta actcttacct ctgggaggct  31200
tatttgcttt gagaacatat gtcctgcagt tttgttcata tggcagtgaa gtttcgtgca  31260
cacactctag agccaggcag cctgggttca aagcgcagct ctgccaggtc ctaactgcat  31320
gaatttgggc aagtcgctca acctctccat gcctgagttt cctcatctgt aagattggag  31380
caatggtaat acctgctttt tagggttgag aagagaatta aatgaattaa gatgggtaaa  31440
gtgcttagag tggagctttg caagtagtaa gtgctatgta agtgttcgat ttaaaatgaa  31500
agacccttaa atacattctt tgttcatttc acaagccctt catttcacaa ccttacattt  31560
cacaaccaag ctctgtctcc cctggaatcc agccataact ctgctcacaa gtgtgagaca  31620
ggccccagca gagctgcacg aagaggagag aaggcagccc cccagactcc caaccccctg  31680
tccaagatgg caaaaccaga acacagcctc tgtaccaccc cagcaggtat tcagaatctg  31740
caatctccaa agcccacttc aattgtaaat gtagagccac gtgcgcttta agtcacctgt  31800
cactctggag gctcttttgc tcagttcctc accattagca gggatgacag ggagtgcagg  31860
agtgcggtcg actcccagat attggagagc gctgggctag ctgcccattc tcccggcctc  31920
cactcctctt tgctgtccag ccatcacttg ctctttgaag gcaaacaaaa cagaaaacag  31980
tgccaaaagt atgggaagaa agccagcttc tcccctgggg tgcctgtgat gccatgccca  32040
ccctccctga ccacgcagcc cctgtggacc ctcagggccc caagccccca tttccatcac  32100
atgcgtacac ccatgtgtgt ccatagccgc ccatctcagt caataaggct gctcctgccc  32160
acttggaata gtggtgacaa ccaggagtgg cttatgggaa ctatcccaat ggcctgacag  32220
catgtccgct gcaaaccgct gaggtaggac actgccctca tgtctagctg atcagcaaga  32280
ggcgcagttg ctttcttagg taacattgct gctgtgtcct ggccattgct ggggggtggc  32340
acttaatcta caccagattt ttccctcctg tatcttccaa gctgcttgga tcttggtgct  32400
gaattaggtt ggactttgtc ttgtggggaa gggaggacta tagaccctca acgtaagcaa  32460
tggtcagact attctaagaa aactcgccga attaaagcat gaggtaaatt tagttctgac  32520
ttctgtccac cccactgcca ctgtcccctt ttatcccatg atcccttgct tttcttttcc  32580
tcctctctcc ctatctcttg tgtttgacgc atgataggaa ttcagaaata tatgtttgtg  32640
gatttgttta ttcacgtagc aaaccatttc ttgagtgcct accatgggcc aggtagaatg  32700
ggcggccccg ggctgcagtg gtttcttcag cccctctcca gggtttacac tgtgcaagac  32760
ggtttgtgat gggtcctccc atcgaggacc acactcttct ttctctgtgc cccttggtcc  32820
tcagtctctg accccacttc aaaggcagca ttcactcagg gaagctccca tacaatgcta  32880
gtcagagtaa aagtttggac aaattgccag gaagcagctt gtcagtatgc ataaacagcc  32940
tttaaaatat tactactctt tgacccagaa tttcacttct aggaatctgt cctaaggaag  33000
tagtcacatg caaaagattt atgtaccaag atgttcatca aagtgttgtt ttataacagg  33060
aagtctcaga agctggataa atatccaacc tctggaaatg gttagataga atagtatgta  33120
gccattagaa aattatgtct atggggttta aaatgtcatg ggaaaacact tctgacataa  33180
aagagcatga gaactgtata tttagcataa tcttaactat gttttagaat gcacaggaaa  33240
aaaatgtaca aacatattca tagtgatgtc tctggtggta ggattatgat cagtaagtac  33300
ttctgtctct tcatattttc ctgtatttga taatacatgc atatgttgtt tttaaaataa  33360
gaaaaatttt aagtttaaaa ttggagctga aaagtgtttt taggtcaggc gaggtggctc  33420
acacctgtaa tagcaccact ttgggaggct gaggcagtca gatcacttga gcccaggagt  33480
```

-continued

```
tcgagaccag cctggccaac atggtgaaac cccatctcta ctaaaaataa aaaaattagc  33540
catgtgtggt ggcacacatc tgtaatccca gctacttggg aggctgaggc atgagaattg  33600
cttgaaccca ggaggtggag gttgcagtga gccaagatcg tgccactgca ctctagtctg  33660
ggcaacagag taagactcta tgtcaaagaa aaaaaaaaaa gaaaagcctt tttaaacagt  33720
agcagacata actatataat ccttactaag ctgtcggtca aatttttatt tatatattta  33780
ttttattcat ttattatttt tagacagggt ctcactctgt tgcccaggct ggagtacagt  33840
ggcgtgatca tggctctctt caaacttgac ctcccgggct caagtgatcc tcccatctta  33900
gcctcccaag tagatgggac cacaggtgca taccaccaca cctggctaat ttttttattt  33960
ttttattttt agagatggtg tttactatgt tgcccaggct agtctcaaac tcctgggctc  34020
aagctatcct cccacctcgg cctcccgaag tgctggggtt accagcatga gccactgtac  34080
ccagccctca aatttttaaa aatctataag agacattatt ggacaattag agaaattcac  34140
atatggactt ataatagtat cagagtgtgt ggtgtgatgg ttctggaggg aatggacttt  34200
ttctttggag acaggctttt ctatgcccac ccttttatct tgctaactta tcatcatcca  34260
ggttccagca gaaacattac ttcccccagg aaatttctta agggtgcagt atcatgatgt  34320
ctgcagcaaa ttctcaaata gctcaggaaa aaagtacgtg tgtggtatga gtgtgtgtat  34380
gtatgtgtgt atatatatac acatatatac acatatatat acatatatgt gtatatatat  34440
acatatatgt gtatatatat acacacacat acacatatat atacacacac acatacatac  34500
atgtattttt atataattat atatgcagag agtgcaaatg ttgccaagtt aaagattggt  34560
gagtctaggt gaagggaata tggtatttat tgtattattt gtgcaacttt tcttaagttt  34620
gaaaattttc aaaacaaaaa attggaggaa gaaggcatgc cagtctaccc caagccctcc  34680
attggaatgc tgaaaatcta aacaatgtga tttggcaatt tcatttcttt tctgttgtgg  34740
gccagtagtc cttagatgtt ggggaagggg gtagtcgctg aggtgtggtt gacttaggat  34800
ggaagaagca gaagtcaaga ctcccagggt caaagtggtt tgctctgctg acccaagtgt  34860
gggaggccca gagtcagcgt ttcaggtgtg ctaattcagc atggttctat tcacggccaa  34920
agtccaccct gggcacctct ctggcagcaa tcttgggtga ctctactaag gccaggcctc  34980
catgacccta tgtctggatc ccatatctcc acctctccca ctgtctcagg aacggtgctt  35040
agctttttct tttccctctc ctgtcttctt tgccagcatg tagaaagttt aaataattcc  35100
cctctttaca acaaaacaaa acatacccccc ttcagtcaac caccctagct ctcttctcct  35160
tttcccagcc agattttttt aaaagcatcc taggccaggc gcggtgactc acgcctgtaa  35220
ttccagcact ttgggaggcc aaggtgggtg gatcacaagg tcaggagatc gagaccatcc  35280
tggctaacat ggtgaaaccc catctctact aaaaatacaa aaaagtagcc gggagtggtg  35340
gcaggtgcct gtagtcccag ctactcggga ggctgaggca ggagaatggc gtgaacctgg  35400
taggcggagg ttgcagtgag ccgagatggc gccactgcac tccagcctgg gtgacagagt  35460
gagactccgt ctcaggaaaa aaaaaaaaaa aaaaaaaaaa agcatcctca gcactttggc  35520
aactccatct cctcccaaca tgtccctgtt actggaatcc agccaggact cagccccgat  35580
ctttctactc taaccagttg tctcagttaa caaggacagg tttatgctgc agtgacaaac  35640
aagatcccaa attcttgtgg cttcacacat ctggcaccac ctcatcttcc agccttagga  35700
gtcatctttt agttccttga aaactcttta cagttttctg ttggggcctt gtcatatact  35760
attcccctgg aatgttcttt cctatcccct ccctttcacc ttgctaactt gtgcccatcc  35820
ttcaggtctc agcagaaaca tcacttcctt ggggaagttt tctccaacac ccacactaca  35880
```

caggtgtccc atctacactc ctatgacttt gtggtacttg tctcacttca ttttccactg 35940
ccttccccac aaggcacctg cacaagggca aggaccgtac cactgtacct atgtcactca 36000
ttgctgtggt cacctgcact ctggctgcct accttaacta cacattagaa tcacctgagg 36060
agcttttaaa gccacaatgc aagactccac cctaggccaa ttggatccaa atccctgggg 36120
tagggccaga catcagtgga gttatatata catatatata ttttgtttgt ttgtttgttt 36180
gttttttgag acagagtttt gctctgtcac ccaggctgga gtgcagtggc gcgatcttgg 36240
ctcactgcaa gctccgcctc tcgggttcac accattctcc tgcctcagcc tcctgagtgg 36300
ctggaactac aagtgctcgc caccacgccc agctaatttt tttgtgtttt tagtagagat 36360
ggggtttcac cgtgttagcc aggatggtct cgatctcctg acctcatgat ctgcctgcct 36420
catcagcctc ccagagtgct gggattacag gcatgagcca ctgcacccgg ccatcagtgg 36480
atatattttt aaagcactgc agagaattct gttgcatcag cttgagaacc actgatctgc 36540
cttgtgcttc acatttaaaa ctttttttta atgaataaat aaaccccaaa aaattaatct 36600
ccctaagcct ccctagaaga taggatggta aggatatttt cctaggtaaa aatatgttaa 36660
tttcatattt catgaaattt catgtttcat ttcaatcaag ctctgtcata caccttacat 36720
ggggcaagcc cagtgcctgg gcagggtgta attatactca ttacacaggc aaggaaaagt 36780
cacattaggt gatggagcac aaataggcag ttaatggttt cagggctagt taggatatgt 36840
ttgtctttca attgcaagta atagaagccc aaagaaattg gttatttata taatataatt 36900
gattggttcc caaatttgaa aaattcagga atagacccag cttaggtaca gctggatcca 36960
gtcactcaaa caatgtcaca aagaaccctt tgacaggaat gtatcctgtg ttgactctac 37020
tttgctctga gtagtctttc cccaggtgat gataaaaatg gtcatcatcg ccaggcttgt 37080
gtcctgttta gtaggaatat acaagaagag ctcagtaaat gctggcccca ccactaagca 37140
aaaacaaaac ttttgttgtt gttattgttg ttttaaataa cagcttagac ctttcttctt 37200
tccttgttat tctctttcat ctgtaatcca gttttctact tctgaagtat agaatgttct 37260
gatgatttat tcttcattac ccacaacttg cacatgttta tttaaaaatg ccaggattgc 37320
ctggccgttg tgtgctgtta acctttgttt gctgttagtg gatccctgaa gttcaggctc 37380
ccaggggagc agataatggg tatccagttc ctgcaatatc caccctctgg caagccaagt 37440
tccttcctgg gtaaggtttt gcctacctgc attcctaggg aagtttctgg gcctgaccac 37500
caagccagct ctgagaaggg gtgcataagc ccccaccatgc tttggctctg tccctataga 37560
atattttatg ttgttactga aaactaaagg aagatgggtg cggtggctca tgcctgtaat 37620
cccagcactt tgggaggcca agacagattg atcactcgat gccaggagtt caagaccagc 37680
ctggccaaca tggtgaaacc ttgtctctac aaaaacaaaa caaaacaaaa attagccggg 37740
tatggtggca tgcacctgtg gtaccagcta ctcaagaggc tgaggcacaa gaatctcttg 37800
aacctgggag gtagaggttg cagtgagccg agatcgcact actgcattcc agcctgggtg 37860
acagagcaag attctgtctc caaaaaaaaa aaaaaaaaga aaaggaaagc taaaggagag 37920
agactaaaat gatatcaggt tcctggagaa caaacagaca tgattttgct tcatggcagg 37980
acagccggaa gaagtgggat tatatcctca cattacaaat aagaaaactg agactcagaa 38040
tggttaagtc acttgtccca ggccacacag ccagtaaatt acagaaacag aatttgaacc 38100
caaatcttcc agctccaaag cttgtgttct tttcactacc tcctgcttaa ttttttaatt 38160
tctaagatta gacccttcat ctatccatga cacctgcctg tcatcccctg aaaaaaggtg 38220
aacgccgttc agaaattttt ctagcctgag ctcactccca gttcacttat ttttgctttg 38280
tcatggctgc ccagtcccca cttgtagacc aggaataggt catggctgcg gggactacac 38340
gctgtcgctg ctgcaagggc cggcctctgt ttccggggct gagtgggggc cagacctgcc 38400
aggagcacca tcttctgtgg gtcctgcctg gatgtcacat cccggcccca agaagtcact 38460
gcaaaccttc gtattattga gcttcacatc ctagaatttg ctgtcactgt ggctgctgca 38520
tgaagttgtc ctgagagaaa cggcattgt cattaacagg gaaattgatg gtctgggga 38580
aaagtcatcc tcattctctt gcagatctat gggtgattga gactggctga tgttgaaggg 38640
gtttctcagc catcgtgtgc catgttatgg aacagtggtg tagccagcca tttgacaccc 38700
agcgctgacc tttgtttaac aacctcacct atatatgaca aaatgattgt cagaaataat 38760
cgtgtaatga aatgactgta ataatggcca gaaaagaaac gcagatagta aaatgtttct 38820
cttgttgaac tctgtacata taattgcacc aggatttttt tcaaataaaa agtaaatatt 38880
atactacaaa aaagggaaaa agcacaagca tttattaaat agctttctat atctttctga 38940
gttttgatcc tttgattgca gactgatgta atattttatg taaatcattg cttggttact 39000
aagtgaactt taagaaaagt gagacgtctg cagaagttgc ccataattta gcagctactg 39060
tattgtacca ttgatgtacg gctttatttt cttgattaat tatttaaaca atataattca 39120
caattttaaa ataataaatt tccacttaaa atggtattta aactcagcaa aatatatcat 39180
ctatgagtaa aatttgtatt taccaagcaa aaatattaca gtttgtggtt cacatgctgt 39240
ctcactgttt taaattttaa atacaaaaac tccaagtagg ctgggtgtgg tggctcacac 39300
ctgtaatccc agtactttgg gaggctgagg caggcatatc gcttgagttc aggagttcaa 39360
gatttgcctg ggcaacatag tgagatcctg tctctactga aaacaattag ctgggtgtgg 39420
tggcacatgc ctgcggtccc agctactcag gaggctgaga taggaggatc acttgaaccc 39480
tgggggacag aggttgcagt gaggcaagat tgcaccactg cactccagcc tgggtgacag 39540
attgagaccc tgtctcaaaa aaagaaaaaa aaaaaagaaa cacaaaaact ccaggtggtc 39600
gcacagaatg acaggactga agtaacttag ctccaatttc tgtcttcata atcactgtcc 39660
taccattgtc tgtgcttaga atctacttgc ttaatgcagg aacatgtgtt ctcacagaga 39720
tggaaaatgc aaatggcgcc agaagcaagc tggaaattct gaaccattaa gaatttactc 39780
tctgccaggc acggtggctc acgcctgtaa tcccaggact ttgggaggct gaggcaggca 39840
gatcatctga ggtcaggagt tcaagaccag cctggccaac atggtgaaac ttcatctcta 39900
caaaaataca aaaattagcc aggcatgatg gtgggtgcct gtaatcccag ctactcggga 39960
ggctgaggca ggagaatcgc ttgcacctga gaggtggagg ttgcagtgag ccgagatcta 40020
tctgcaccat tgcacttcag cctgggagac agagtaagac tccatctcaa aaaaaaaaaa 40080
aaaaaaaaag aacttactct caaaataaat acgtgtggct gactccacat atggtagggc 40140
caactgtata actagaagtt ctccaaataa cttctgtgga gaaaaaaaag tttattaaag 40200
gttaactttt ttaaagtgct aactagaacc ttactaacac tgagatcgca ccaattgttt 40260
ataacttaga cagggccggg tgcagtggct catgcctata atcccaacac tttgggaggc 40320
cgaggcaggt ggatcacttg atgtcaggag ttcgagacca gcctaaccaa catgatgaaa 40380
ccccatctct actaaaaata caaaaattag ccaggcacgg tggtacacgc ctgtaatccc 40440
agctactggg gagggtgagg caggagaatc tcttgaaccc aggaggcgga gattgcagtg 40500
ggccaagatc gcaccattgc actctagccc cagcaacaag agtgaaactc tgtttcaaac 40560
aaacaaacaa aaaaaaaaac ctcttggacc aggaaaatat tttttaaggg aggagtattt 40620

```
tatcactggc attgtttagg attgcaggca catgatgcta atgaaaagca gactaactat  40680
tagttggttt tattactgtt tttgaactct ctctctccct tttttttttt tttgagacag  40740
agtctctctc tctgtcaccc aggctggaat gcagtgactg cagtctcagc tcactacatc  40800
ctctgcctcc tcagttcaag tgattctcgt gcctcagcct cccgagtagc tgggattaca  40860
gggcaccaca ccaggctaag tttttgtatt tttagtagag gcagggtttc accatgttgc  40920
ccaggctggt ctcaaactcc tggcctcaag cgatctgccc atcttgacct cccaaagtgt  40980
tgggattaca ggcgtgagcc accgtgccta gccctgtttt tgaactctct agagacagtc  41040
cagcccctta ttacttgtcc tgaggcagct gctcccttca cctggccccc cgcattgtgt  41100
tccggaccct tgtcctggtg gtgctaaaga atatctctgt cgatcctttg gggactgggg  41160
aaactgaggc ccagtgccac gcgatgccat ttgttcaggg aagattaggt catctgctag  41220
gtccccagtc acttgacctt cttcccagac aggaagaagc tgctctgggt ctctcagtgc  41280
tccacgtgtc tttgcacatt gaaatgtttt ctgatttttt tttttttttt tttgctgtta  41340
catttacttt taaaaaataa caagcaataa aatgttacat ttgagaaggt tgaaatgaga  41400
attgatttga gttaaattct agcagatttt tcttagaaga atgatatcat catctccagc  41460
tacctgcaat tgatctactc tgaattaaga aagagacttc catttgttgt ttatattttg  41520
cactcttgat gtgtttcttt aaattatggt catgggccag gtgtaggagc tcacacctgt  41580
aatcccagca ccttgggact ctgaggaggg aggatcactg gaggccagga gttcaagacc  41640
tcgtctgtac agtaaatttt aaaaattagc caggcatggt agcattcacc tgtagtctta  41700
gctacttggg aggctgagat gggaggattg cttgagccag aactttgagg ctacagtgag  41760
ttattttcac gccactgccc tctagcctgg ctgacagagc aagacctgcc tcaaaaaaat  41820
aagtaaaaaa taaattaaat ttcaatcatt agcagtcatt aggatattta aatacagtat  41880
gttgaatcaa agttacgcat gtgtgtattt ttttttccag agagttgttt atcatgtggg  41940
ttttaattta actttaaaaa aatgttggct ggacagttgc ccaaatggta tcatcagcca  42000
tttggttgag aacgtatgtc ctgcgggctc ctctgtcact ggagttttgc tagctgacag  42060
ccactggcta gttagagact gcagtcagca cagatgcagg cgtggacttg cgcacgtaac  42120
catgtcaatg caaagccatc acttcttaaa aattctgaac cctgctgtct gagatggtgg  42180
tgcagcggat agaactctgc tctaagaggc agtagctaat tccatgtctt ctttgccctt  42240
gactagctga gtgactttgc acatggggct tgcctctctg ttgccttgtc tgcaaagtgg  42300
aatcatcttt tccttgctag acagaaggtg gaccctggac ctatggcctt tttgagtttc  42360
ccccccgctt cttagaagga cctctgatcc tactgagttt aatacccacg ggttaataat  42420
tgggaaaagc aaaggaagcg cttctgttta ggtaattata tgcatgtttt tgtctttttc  42480
tggctggaaa gatatccaag ccactgggaa ggtccgtggc tacccagggt agccctctct  42540
ggggagggct gctatatcca agagcccctc atgagaattt gaaaatcgac catggtaggg  42600
cctgctgact tttgacagct aatggtgtgc tgagaattgt ccctccaaag atgcctttcc  42660
attccctcgg gagagtctgg gcagccccta ctgggggctg ggatgctggc tcttccctca  42720
gcctccaccc caactgctct cttccctcct cccctcccca gccccctaat ttctctcaca  42780
aggctttgtt ctgcagcaac ctttcctaat gcagtcctgg cctcttcgca gcttcattac  42840
ataaccttcc gtggactcct ggtccaagga tcaccccaga aagccagtca gaggtaggca  42900
cgcagctggg gtccatttac ttaccttccc caccccctcg gaactcagag gtggtgcagg  42960
```

-continued

```
aatttggact ccaagaatta acagctccac caccatcacc agagccaaaa ctcaggatgc  43020
atgtgcttca tctgctgctt atttccagct gagagccagt ggtgccatgg ttccttaggg  43080
agccggtccc ctgatgccgg ctcctggccc caaatctctc tgatccgggc tcttccagaa  43140
tgtcttgtct ccaccatcgc ctttgaccaa tggtgtccct ttgcctggta atgtcccctt  43200
tgcctgatga tggccctgtc actcctctct ttagcacaga ggaggctgtt tcatcccttc  43260
aagcctgccc tcccttcaag tcttagctca agttcacctt ctccgcagag ccttctccaa  43320
tcttcttgac tacgtctcct ctcagctcca gcaacctctg tctctggcac tgattcctta  43380
cttagctaag agaatcacag acacttgggg ctcaggacaa tctgctttct ctcttcttac  43440
ccatggcctt ggactgtgtg tacctctttg tctccactcc caaacccaac ccccagaggg  43500
cagagagcat gttgtctgtc cctttgctca gcatgaagcc atgcgtgtgg tagatcggca  43560
gagttccata acttgtgttg accgaggggt cactttgctc tgaaattacc cctgtgtcct  43620
tcagtatttg cacagatagc ttcctggcca gaccgaatat atccaagggc atggcccacc  43680
tctgctcctg tttccaggtc cctggtgggg gttagttcat gccttcctca taatctgccc  43740
actggcctgg tcctcaaggt cttcccaact gctcagccag agttgagaaa atgggtcgct  43800
ccatcctgtt tgtgtcgttc tctccttcct ggcccactct cctgcccaca ggtatccagg  43860
ggctgcctgt agcattagag gacatacatg cacatgcgtg ggcatgggac actcacgtag  43920
cctccaagca cagcatcaat aatgcattct gtgctttata gcatggaaag ctgctctaaa  43980
ctttattaca cagtggacat gtctgaagca gctcccaaat ccacccctga gtgtgttgga  44040
attggcaagc ctatcacttg ggagtctagt ttttttgttc gttaataata gatgcttcct  44100
gtggccccag cttggcaatt ttgatttaaa gtgatcttaa ctgaagagac taatggacgg  44160
gtctgaattt gtgcctttta agcacaaagt attgctctta attaactgga ttctatcctt  44220
tgagcaggca gaggccttcc cccaagggcg tcattaacga tccacatctg gacatcttcc  44280
aaagccttct tctgtttcag gccaaccgca ggtgtgttcc tgaacaccca ggaggctatg  44340
agagccacat atgcctccca aatacacaca gtgtgcatgc ccagggacat agagcagtgt  44400
gcaaagtccc attccatctc tctccacctg ggagaggatg gctcttctgt ctgattcatg  44460
gctcaaagtg gtaaaggagc tccccactcc ccgtcccacg cctactcaga gtctgcaaat  44520
atgtatgcga tatgagagct cgtcagttag ctgtcttcag tgtggcgcac atttgaggag  44580
tctgactccc ctccagcaca ggccaatgtg cactgctctc ctatctttgt acccccactg  44640
ttgcactgtg cagaggttgg agccatagaa gtaccagagc tgtgaaagga gaggccccct  44700
ctcacctctg ccctggtctc catccccact ttctctagga agctagtagg tgctgacagg  44760
ggagagaagg gaggggaggg gtccagaaac agtggctcat gcctgcaatc ctagcacttt  44820
gggaggctga ggcaggagga tcatttgagg tcaggagttt gagaccagcc tgggcaatgt  44880
agcaagaccc tatctctaca aaaagaaaaa atgtaattag ctgggtgtgg tggtgggcac  44940
ctgtagtcct agctacttgg gaggatgagg tgggaggatt gcttgagccc aagagtttga  45000
ggttacagta agctgtgatt gcaccactgc actccagcct gggcaacaga gctgagaccc  45060
tatctcaaaa aaagaaaaaa aaaaagaaag gagagagaga gaaagaaaag aaaagaaaaa  45120
aaaaaaagaa gggaagggaa agcccagaag agtgtgggga gaggaggcgg ccgtcattct  45180
ggggccctca gtgtgcacaa ccagataaca catgctctgt gggcttttgt accattttgc  45240
ttgagcataa agaaaggaag gctgccccta aatagaaagc actctggagg caaacaaatc  45300
tgactccaat cctggccctg ccactttccc agctgaggac ttagacaagc accctagcct  45360
```

cttggacatt ctcagagcca tctgctgcaa gtgggtgctg ccatacccac cttactgggc 45420
aggcttgggg gaccaagggt ggtaaatggc tcagtctttc atgatgcggc cacacagcag 45480
gtgcgccatc caggtccatt tctttccttc ctttccccca aatcaagttg tcattaaagt 45540
actagtccac attaatgaaa tcaactgtat taattttcta tttgctgcta taataaatca 45600
tcagaaattt agtggcttaa accaacacaa atgtattacc ttacagttct ggaggccaga 45660
agccctccat aggtgtcact gggctgaaat caaggttttg gcaaggttgc ggtcctttct 45720
ggagggtcca ggggagaatc cattttcttc ctttttccag cttctaaagg tttcatgcat 45780
tccttggctc atgatcttct atagctatag tcagaaaaat tttccatcaa tcatcttcaa 45840
agccagcaat ggcaggatga gtcctcacat caccttgctc tgacaccagt tctctgcctc 45900
cctcttccac atgtcaggac cctcatgatt actttgggct cactctgata atctgggatg 45960
atctctctat tttagagtca gctgactggg aaccttaatt ccatctacaa ccccaattcc 46020
tctttgccat gtacagtgac atattcacag gttctgggga ttaggacgag cctgtctctg 46080
aaaggctact ttacatgaaa attcattttt ttaattaaga tttttttttc ctcttgagac 46140
aaggtctcac tctatggttc aggctggagt gcagtggtat gatcacagct cactgcagcc 46200
tcgacgtctc tgggctcagg tgatcctccc acctcagctt ccctagtagc tggaactaca 46260
ggggtgagcc cccatgccca gctaattttt tttttttttt ttttttgaga cagagtctca 46320
ctcagtcacc caggctggtg tgcagtggtg caatctcagc tcacagcaac ctccgcctcc 46380
tgggttcaag tgattcttgt gcctcagcct cccaaggagc tgggactaca ggtgtgcacc 46440
accacgcccg actaattttt gtatttttag taaagatggg gtttcaccat gttggccagg 46500
ctggtctcaa actcctgatc tcaagtgatc caccaacctc agcctctcaa agtgctggga 46560
ttacaggtgt aagccaacat gcccggcccc agctaatttt taaatatttt ttttgtagag 46620
atggggtttt accattttgt ctaggctggt cttgaactcc tgggctcaag caaacctccc 46680
accttggtct cccaaagtgc tgggattaca gcatgagcca ctgcactcgg ccttaagaga 46740
agatttaata attaatactt tacaacaaga tctggaagag gtgggatgag taactaaatg 46800
aggatacaag taacccgggt catatttgct aatacccttg gtcacattga acttgatatc 46860
ttatcagatt ttcctaatca gctcctttag cagcagtgtt gcagcatctt atctcatttt 46920 gtttttgtt tttttgccta gcacatgcct gtaaatcact ggattgaggt gtttagatgt 46980
ttgttgtcct ttggatgctt cttataaatc catatttcat ggctccctgg aaagtgctat 47040
gcaaatgata agctgcaagg atggaaagga aattgcagtg ctcctgaatt gtaaatgggc 47100
ttttacgagg aggtttctaa ttactcgctc tttctcttga actgaggagt tgaagtgtag 47160
gtggcagatc cataacagat aatcatgtgt gtgatgtgac ttcagcctga gcgtcgagga 47220
ccaagtcaca gagcaggaac agccactctc cagtgtcctt ggggctacgt ctgaggagaa 47280
cctgggattt catatatgac ctgcactggc tggggggctc tcttgacgta acgtgttccc 47340
tctgagcatg ttacagattc tgacattctt atgttccttc tgtggagaga catgtactta 47400
gtgacctaac tcactttagc atatttttgc tcatcgtttg tgtagcttaa aggaatcaga 47460
taattacccc ctccccacta ctttcggaag cacaaatgca atgccctaga attgtactgg 47520
ggactcaaaa agaaaagaga gtagtaaaat ctattaaagg ggacaaagac agcctatata 47580
ctacaagctt tctattttta tggcagagaa tgccattttc taagtaaaca gagaactgca 47640
tttgacctgc aatatcaaat gcatggattt gatgctttgg aaagcaactg ttttctgcgt 47700

-continued

```
taatctgggt gtcttccgtg aaatgtcctc ctgcctttgg cttaaacact agctttgtct  47760
acagccattc catcctgaac ctgcccaatc ttgtctgaat cctggtttca ccactgacaa  47820
gctgtgtgtc cttgggcaag ttacttcacc tgtctgtgct tcagagtcct catctgtgag  47880
ttggggaatc tggacagaat ctaccccata gggcgtagtg aggatgtgtt gaattatccc  47940
aagtggctac acagagtaag cactcaaatg atgtcatcgt tgtcatgatt gctgttacca  48000
gagcctagag ttcattctga tactcgagtc tgtggcccat ccagcccagg taaggaatag  48060
ttggaggagt tgggcatgtt cagcttgaag aggagacgac aggggatatg ggatagttga  48120
atctgtgaag ggcccccctgg gatgaagaac tggcatgttc tgtgtggctc cagggcactg  48180
agcaggaccc atttgccaaa gtctcaggga cacagtttct agctatagac agaaaaattt  48240
tctgtcactc agaggatgaa aatagaatga gccccccttaa gaggtaatga gctccctgtc  48300
attggaagga ttccagaaga gctaggtaac cactttaggt gctatcaagg ggcttttttc  48360
tttaaagtcc tttccaaaag cttctgagat tgcataaaca ataggaagcc atcttggtgc  48420
tttaacacaa actctcccca gtgatgaggg ttgagccaaa gccagattgg caagcagaga  48480
ggagacttgt gtacaaggag ttcctcgagt caattgcttt ttccttgttc tagccagcca  48540
gagggctcct gttggaaaac aggagaccgg agaggctgag gcctgaccaa accagcttct  48600
gcaggccagc tgggaggcca caactcctac ctacgggaaa actgaagggc atctctattt  48660
ttagattagc aaaagaaaat aaatttaagt ttgagtctcc tttgcaactt ttaaaagaca  48720
tctttattga gatgatcatt cacattctat aaaattcccc cactttgagt tacaattcag  48780
tggttttagt cttccttgat gattttgatg gtcttttctt aaggctcttg gaagacccag  48840
aagcctctca gacacaggtg ggtgtggagg gcgtagcaca gaggcagact tctcatttcc  48900
tgggtctccc ctttaatgac tctcagagac ccctccttcc ccctgcccct ggcttctacc  48960
ccaggggtgt agagttttgc cattttccaa gcagaacttc atttcctctt ctgtgtctac  49020
actctttgtg cttctttctt gccagctttt tctcctttgc ccgcccttcc ttccttcctt  49080
ccctccctcc ctccttccct ccttccctct ttccctcctt ccccccttcc acccttcccc  49140
ccttcccccc ttccctcctt ccttccttcc ctccttcctt ccttccttcc tgccttcctt  49200
ccttcctgcc ttccttcctt cctgccttcc ttccttcctt ccttccttcc ttccttcctt  49260
cctggtatgt gactaatttc tgtttcagga cataaatgtt gtccaggctg ttctttggtc  49320
tttctgttgg ataatggaca tttggcattg agagaggctg ctttttctga aatcatgttc  49380
ttggggccca gaacctaggt gtgtgcttct gactttgttt tcttcctgat ccaaattctg  49440
atatgtccat ttaaattgat ctagacccac agggcactgt gggacagatc ctcagtggaa  49500
catgactctg taacgagagc attttgtttt gtcaaaatga gaacatatta ttgcctttca  49560
tctgattgta aacataatac atgtttataa aacagtataa tgagacaaaa atgtagacac  49620
taataaggga aaatctccct aattgtattt ctcttcacag agaaagcccc tgttgggcat  49680
atatactcta gtttgtttat ttgtttgact acacatatat gtattctttt cttatgtata  49740
aaaattctga acatgcacat ttctgcaact actgttttca cttgatgatg catggacctc  49800
tctagagtgt acgtttcttc ttccttacaa agcagttggc ttcgcccagg gtacaccagg  49860
acacggtttt ggctctgtcc ccagggtgtc acgggaccag gggatgatct cacagggtct  49920
gccatctgcc ctgcctggcc ggaggctgca tcgagagggc caaggggcac cacgtgtcgt  49980
gggtactgtc aaacaagagc cttcagagcc ttccacagtc tttcttttgc ttcccagcat  50040
tgcttccccg ctggtggact ctgaatctag aactagctcc aggcgcctct ccaaattcag  50100
```

acgggagctg gggcactatt ataatgcaaa tctaggcaaa gccctcccaa taccaggatc 50160
cagaatgggg tggggccctt tgccctgaaa agctgtttag tttgaaaata caaacaggag 50220
acagaaaagt ttggctaaat taatggataa agttttaacg atggtaacca tagtagggtt 50280
catcgacagc cagcgatggt tctgaacact tgacatgtat taactcacct aatccccaca 50340
ttttacagac aatgcaaagg aggctctggg aggttgagtg acttgcccca aagtcgcaca 50400
gctcctaagt gaaggattcg gagtggactc caggcagcct ggtctgactc cctgcactgc 50460
gctgtgctta tctctggccc caatgccgcc atgcagaagt gtctgggggc actttgtctc 50520
tgtcagacag aattcggaga tgtgtatgct tgccctggta tggcacttct ctttttttga 50580
gacagaatct cactctgtca ccctggctgg agtgcagtgg catgatctca gctcactgca 50640
acctccgcct cccaggttca agcaattctt gtgcctcagc ctcccaagta gctgggatta 50700
tagatgtgca ccatcgtgcc tagctaaatt tttgtacttt tagtaaagat gttgttttgc 50760
tgtgttggcc aagctgatct cgaacttttg gcctcaagtg atctgcctac ctcagcctcc 50820
caaagtgctg ggattacagg catgagccac catgcctggc agtgtggcac ttcttacgtg 50880
tgttcagcgg acactgttta tcttctgtcc ctccaagacg gtgctgagct caggtcgttc 50940
attactggca gacaactgct gatttccaac agaattgcca tcctcttctc ccctgcgact 51000
ttcagagtgt gacctcagac tcaaaaatta gaagtgaaaa catcttaaaa actatcacct 51060
tttcttccta atcctcctct cccctccctg tcttccttgt tgtccccatc taatgaacta 51120
tcatggcaaa aagagcccat ttctggtcat tttctgtggc ctttcaaact cccacctacc 51180
ccactgctcc tgggtgcatt acccgaaagc tgagacttca gtgcagaaag tgccaggccc 51240
tctgtccccc cagatcgcct tccttgtctt ccctgtgctt gcctgtcaca ttgtgtgggt 51300
tccagcgctg gaaggaatga ggaacagatt ctctggttct ccttttgaag tttaccttcg 51360
ctccaccact tctgagacct tcccggaagt tgccccttgt ttctctcctc tccagggctg 51420
ccccagagct gcctctcacc tcttcctgct gtcaccccac caccatcagg gcagaagttg 51480
ggacaaagcc tctcctactg gctcctgctt ttctcccta ggtccagcct cctcttctcc 51540
atcttcagga gtctccttct ccactcacac gtcatgactt cagcacctcg catcagtcca 51600
gaatatgact gcttgttcaa gtgccacctt tctcatgcat ttttttctag tgacaatcac 51660
agccaccctg tggggcagga gtgtcatcat ccccatgttt caaatgaaga attgcagttc 51720
agagagggca agtgactggc ccagcctcaa cagctagcca gtggacccca ccagggcttc 51780
tgactccagt ccgggttccc tttccaccca aatccatgga gggagctgag ccgagaacag 51840
gtgtccttca ggaagacgtg aagccaaagc ctccacctcc aaactcaggg gcccagggag 51900
tccaggcacc catccactca caaggctgga tatggtgcat tccaggagag gggttggggg 51960
cgagtggcct ctctgtgtac ccgtggggat agatgcgcaa gtggcatcgc cacatcgtga 52020
gtcctggctt catgggtgag ctccaggtcc aacgagaagc caagcagggg gcccttcaag 52080
ctcagctttg ggcccgggtc ggggtacagg gtagagcggg cctccccagc ccctgccatg 52140
aggccaaggc agtgcatcgt tcgcagcgta cattcagaaa ccaaagccta ggagctggtt 52200
atcattccgg tttacagctg atggaagagc aggtgcttcc gagaacccac agtgctcttt 52260
ggccagtgac ccaagggtgc ctctgagagg cctcgcagca cccggaggtg ctgctgaggc 52320
aacgccctga ctgtaagaag gaccattcat cctcagagag tggccgtgat gctgctgcga 52380
cagtcccacc atccctcccg actctcactc ccaacagact tcccactgta aagctgaact 52440

-continued

```
ctccagcaaa tcacctctcg ccagactctc tcctcactct ctctgggtcc actagaggtt  52500
cctcagcctc tctttgcctt ggttttccca gctgtaaaat ggagcaaaga gggcctatgt  52560
acccacaaag gtgtggttgg agcgactcct cctacattag ggcctcgagt ggggcttcat  52620
gattggttgg tggaggtctc caaacccacc cagtgccacc gaaggctgag actgcagatg  52680
caatgccaca ggtgtccttc ctcagcctgg gcagctgaac atcatgtgta aaacggggat  52740
aataagataa taacagcccc ttgcacctat gtggctgtga ggattaaaca agataaatgt  52800
gtaacagtgc ctggctatag aaatatttac tcttgttatt aagggaagaa tatgtgtggc  52860
taaaaaggga tcgaagatgt aaaagccaat ccctccccct ctagcatatt taagggtaat  52920
gttgagttgg tttgtggacc atttgctgcc tgttagagct ggaaggtagg gaccccctct  52980
caacagcgat gctacaaatt atacccattg gaggtcaacc aaaagacaaa gcttattggc  53040
tggacatggt ggctcacacc tgtaatccta gcactttggg aggccaaggc aggcggatca  53100
cttgagatca ggagttcgag accagcctgg ccaacatggt gaaaccccat ccctactaaa  53160
aatacaaaaa ttagctgggc gtggtggtgc acacctgtaa tcccagctac tcaggaggct  53220
gaggcaggag aatcactaga acccaggagg tgaaggttgc agtgagccga gatcgcacca  53280
ctgtactcaa accgaggcaa cagagggaga cgcaatctca aaaaaaagaa aaaaagacaa  53340
agcttgttaa taccagcata ttgttaaggg aataaagtag gctgcagaac aactggtgta  53400
atatggtgcc atgtagggaa aattacatgt gtgcatagga gaggggtctg caaggttgtg  53460
ccctaagatg ttagagtggt tcctttgctt ttctctttta taattttgta tttgactttt  53520
aaataaggac cataaatcac ttttataaaa tacattctct ccagccccta ctactccttt  53580
aaagaataag agtggtttgc ccaagaaaga cagttttttt tgctctggtt ttcttgattc  53640
tgacatcaga ggaaactcct tctcatccac ttggggctct gggttcaggg gattcatttc  53700
aggcagatta aagtggtgac caggggcatt cgtggacaca gggagggaca ggagcaccat  53760
cagtttgtct cacacaacca ctgtcatcct cactgaaggc tgttgcctga tcaaaaacag  53820
tattgggcca ggcacggtgg ctcacacctg taataccacc actttgggag gctgaggtga  53880
gtggatcact tgaggtcagg agttcgagat caacctggcc aacatggtga aaccttgtct  53940
ctactaaaag ttcaaaaatt agccaggcgt ggtgggtgcc tgtagtccca gctacttggg  54000
aggctgaggc aggagaattg cttgaacccg agaggtagag gttgcagtga gccgagatgg  54060
caccaccaca ctccagcctg ggcgaccgag ggggactctg tcttaaaaaa aaaaaaaaaa  54120
aaaaaaaata tatatatata tatatgtcaa aaatggggta gtttttagat ctatagtagt  54180
tctaaaaaca aaggccatcc aagcatgaca gatttacaag cactattggc tattccagta  54240
gttacaatgg aggagagaag cttttagtta aaacaaacaa acaacacaac aaacccagaa  54300
accttaggtc aaaaccaaaa ttgtcctctc agacacaatc tgggaatttt ctcatgacag  54360
tgggcattag ccaactgaca tcagcagcaa ccatccgtgt gcacacagtg gcaccacctc  54420
ctcccaaaaa gcagccttca tctatgccct catacaatcg ttgattattc tctttggatt  54480
gaggcccgga attatttaag tttcttcttg ccagcatgag tctttccttt ctgtatgctc  54540
cttatcttct ctctttaatt tggcagttct gcttgaaatc tgggtctttc attagtagta  54600
gttcaatttg gttccagaac attctgtggt gtgatgcaat gtgaccagag ctcacacttc  54660
agagctcttc aagggccagt cttactgagc acctcccagt ggctgcctgt gtgctgggcg  54720
ccacttgtgg tgggcaggag agaggagggg acacaaaagg agacacagct ccttcttaga  54780
agctcaaagt tggggaccag ctgccacaga agagtatgtt tagcatctga gacaccaaga  54840
```

```
tccagcgtca caagggtgtt tattaagcct cctcatctct ttctttttct tttttttttt  54900
tttttttcctc aggcagtctt actctgtcac ccaggctgga gtgcagtggc atgatctcgg  54960
ctcactgcat gcaaccacca cctcccgggt ttaagcaatt ctcctgcctc agcctcccca  55020
gtagctggga ttacaggtgc ccaccaccac acccagctaa tttttgtgtt tttagtagag  55080
acagggtttc accatgttgg tcaggctggt ctcgaactcc tgacctcaga tgattcaccc  55140
acctcggcct cccagtgtgc tgggattaca ggtgtgagcc accgcgcctg gccttgctgt  55200
tgattcatct atagtatgtt tgacttgatg acctccagtt accttagaca gaggttctca  55260
tctaagctcc aactttccat ttcctttgtc ctcgtctttc cccttaaccc ctccacattt  55320
ctctcaaaat caccccactt ctaaaaaata ctgtttattt ttcttttaaa tttcaaatta  55380
tctatactca ttgaaataaa tcaaaatagc atggaataag cgaaaaaaat ggatcccacc  55440
cttccccact cccattccct agggctaacc atagttaacc atttaatgac taggtttttt  55500
tgttgttgtt atttttttatt tatttatttt gagacagagt cttactctgt cacccaggct  55560
ggagtgcagt ggtgtgatct cggctcactg caacctctgc ctcccaggtt caagcattct  55620
cctgcctctg cctcctgagt agctgggatt acaggtgcct gccaccacac ctggctaatt  55680
tttgtacttt tggtagagac agggtttctc aatgttagcc aggctggtct cgaactcctg  55740
gcctcaagtg atctgcccac cttggccttc caaaatactg ggattaaggt atgagccacc  55800
gcacccagcc ctcctgggct cttttccttt agttgcactc gctccccgct cctggagtag  55860
agggatttcc gagagactgt gggctccagc cttcacctag gcccaggact aggatgcctg  55920
ccctaacatt tatctttata ccttaaagca aaacagctgg accataagca ttcaagaaca  55980
aactgtgaat aaggagaaag ttctcccagg aaacaagagc tttagttatg ttgggccagc  56040
ccttatattc cttagctgtt accagtcact gcttgattta atctcggcta tcacttggcc  56100
tgacaggtct gctgctggtg ccaggatgtc tgggttttga agcctggctc cattacatac  56160
ttcctgtgtg accttgggca acttactcaa cctgtctgtt cctcagtttc cccagctgta  56220
ttatgtcagc ataatagttt gttgtgtgaa ttaaatgagg taataactgg aaatgcttca  56280
aacatggttc ctatcatgag aaatcctgct ttccgcctaa atgtgctgga aaattcctgg  56340
tggtgcagaa caggagacca gagcaaagga aagacagggt gcagaagcca aaaattacct  56400
tggagaacaa agcgcatgtt aaggttattt ttggattcta ggtttatctc tgcttggtct  56460
tcagttacct acaagagatc catttagggg atttttgttt gtttttaacg atagctttat  56520
tgagatataa ttcatatgcc ataaaagtca ctcttttaaa atgtttccgg tatattcaca  56580
aggctgtgca gccttccctg tccttgattc cagtctgagt ttttaactga agggataagg  56640
aggaccacgc tttccccaga ccagaaccgc gggccagggg gcgattccgc tgagtcaccg  56700
cgggcgcctg gtgcgcggcg gcggagcccg ggaccttcct tggctgcccc ctagcgaggg  56760
ccgcagcgca gcctgagaca cccgccgggg ccgctccacg gccgtcggat ttagactgga  56820
agctcggtcc aggtccccag cttgatgcgc ccgcggtgta ggagaccagc ccgactcgag  56880
cttcccctga gcccctggac tcttgactcc agcagggcct gggtaatgaa cgtcagctcc  56940
cctttcccaa aggggttgct ctgttgggaa ggcacccgtt tgatacagta gcatagagat  57000
gggttttagc atcaaaatat cagaattcaa gccttgctct ctgcttacta gctgtgtgac  57060
cctaaaaagg tttctgaacg tctctgagct tcagtttcct catcattcct tctcacgggg  57120
tggttgtgag cattacagag atcctctctg tgaagcccct gtgagtggct catcctgagg  57180
```

```
gctgaaataa acatgttatt aataatccaa aactggcaag ggatgttgac tggtccccct  57240
cccttgccca aggagctttc tagaacctga gttatcatta ccaaactgta ctgccttgag  57300
taagaaagtt agaaggaatg ggaaggatgg tggcaggtgg aggaaggcgg attggtcatc  57360
acctccttgc agcaagaaac agccccagat cgtgggaaac ctacagacct gctagacaga  57420
ctaggagcaa aagctggggc tttaagaatc cccagggagg ttctcctgag agagtagcca  57480
gttggatttt gtaagcagag atttgtttgg ggaggaggtg acaacgtagg gagcagaggg  57540
gcaaagctgt cgggaatcct gccttgaggg cagggatgtg tgttgggggg agttgggtca  57600
ctggggctcg gtggccttgg gcaagtttct acctctcagg tcctttaccc acctagggtc  57660
gccatcctgc ccacctcaca ggttacagtg agcctggatg cactgtcatg ggcaggtgcc  57720
caggaaaatg gcagacatgt tccaaacagc acgcagcatt ccccagtgat gcccagggtc  57780
accttggagg tgggcgagat gcctggggtt tctcgtccac cccacaacac ctcaggggac  57840
agccaaagct gtcccttcag gtaagctgca cagaagatgt gaactctgct gcaaagactc  57900
tattctttgg gagcaaaagg gacccagggt ctcacctgca catccctgtc cctgagggcc  57960
taggggttct tggaggcccc agccttggca aaatgaggaa gaaggtgaag gttgtctggg  58020
cccctgccag gctccttcct cggccacgca ctccccttcc tgcacacaca cccttctccc  58080
tccaccccat ctccattgtt gtcagaaaag tcacaataaa aaggtccata ttgtctagtt  58140
cccatacttt taatttttaa aattttattt atttatttat ttatgtattt tttgagacag  58200
agtcttaacc caggctggag ttcagtggca tgatctaggc tcactgcaac ctctccctcc  58260
tgggttcaag tgattctcat gcctcagcct cccgagtagc tgagattaca gatatgtgcc  58320
actatgccca gctaattttt gtatttttag tagagacggg gtttcaccat gttggccagg  58380
ctggtctcga actcctggcc tcaagtgatc tgcctgcctg agcctccgga agtgctggga  58440
tttcaggtgt gagccaccgc actcggctcc acactttca cttattaaaa gactgtggtg  58500
tccatcaatg gatgaatgaa taaaccaatg tggactatcc ctcccattac ccaaggaatg  58560
aagcacggag ccgtgccaag atctggattc acagtgaaag aagccagtca ccaaaagcca  58620
cgtgctgtgt gacttccctt atacgaaata tccagaagag atacatccat ggtgacagaa  58680
agtagatgag cagctgggga ctggcgaagg ggagaagggg gagcagctgt ctatgaggtc  58740
cagcctttct tctgggtttg gtgagaatgt tttggaacta gatagaggtg atagttgtac  58800
aacattgtga atgtactaaa tgccactgaa tcattcattt taaatcgttc tttacgttgc  58860
atgaatttta agtcaatcaa aaacagttgt ttgaaaagag aaaagcctat gggtagcggc  58920
agcagtgatt ggatttatga ttcgattcca tggctcatcc ctcccctgcc tcacccccctc  58980
gccctccgac gtcttcttct tttactctga actgttatct ttgttctcat ctctctctct  59040
ctctctcaac cctgcagaca cttttccctt tctttgtctg cccccaccct ccagatttcc  59100
gtgtctccag tgtctcccta cgaggcatga attgagactg ggagggtgtg attctgaaga  59160
aggcaccaac agtgactcag ctagcccctt cccccacccc gccccccggg cctcaattta  59220
gctaaaaaac cacagggacg gactcaggag gcaatacctt tccaagggtc cctaaaaaat  59280
gtcccatttt agtgtccagg tttcactcaa ctttagtgcc tcccctaaaa tgtgttcctt  59340
acctcccacc ccactgcatc taagtcactg cctgagaaaa caggattgag gaaaggagaa  59400
aggaagagag agagagagga ggagagagag agagagggag gaaggctgat ggatttagaa  59460
aagaagaaaa caagtggtct gaggaaaaca gccttggtgt gtttattttc ctgtctgtgt  59520
atcgcttctc ggccttttgg ctaagatcaa gtgtattttc ctgtctgtgt gtctcgctta  59580
```

-continued

```
gattacaggg atctgtgggt gatgacacgt ctggtccagg ctgcgtagtc acctcaaggg  59640
catgcttatt gatgtgtttt tcaattcact atctttgcat gggagtccca ggccaagagg  59700
cacagctgcg ccatttgtct gttggtttag atatccttta tccagttctt ccagagaaat  59760
catcctgccc ttctggagga ggtgggcagc aggggtcaga gatgggaggg aaaggaagga  59820
gccaggtcct tggctaggat gccagggtcc cctgcctctc acctggcctg ggctggaggc  59880
ctcctgctgt cctgtcactg atcactaccc cgccccagcc tcctgagtta gaagacacag  59940
gctaaagtag agtatttctt cattgaaaaa cccatacaaa ataaaggttc ataaaaaata  60000
aaaatttaga ctgggtgctg tggctcacac ctgtgatccc agcactttgg gaggccaagg  60060
caggtggatc gcttgagccc tggggttcat gaccagcctg ggcaacatag tgaaacccca  60120
tctctacaaa aaatacaaaa aattagccag gcatggtggt gcatacctgt ggtcccagct  60180
tctcagccta tggacccaca tagaatacaa tgtcagcata agaagggagc cctggggtca  60240
ccaaatggtt tgggcggcaa agaacctgaa ggttgagaga agtggcttgg ttacccagct  60300
gttggatgtg agacctggcc actgcttctt ccatacccta gacctgcacc ctgacatctc  60360
aagtaaaaag ttgggggatg ttttatggtc caggatgaag gaagggcagt gaggggcagc  60420
ggagcatcac tttgcatttc tgtctgcctc ttactggctg tgtgacctgg ggcaggtaac  60480
ttcccagact cctgggaatc ataacaccta tgatgatgat gatgatgatg atgatgatga  60540
tgatgacacc tacctcaagg attgccctga agggtcacag agatgcctgc aaggcacctg  60600
catggagcaa gcgccccttc tctggcaggt gctgggtgag cactacctgc tgccaggccc  60660
tggggctatg gcactgcgtg accctgcaag tcctacctgg cgaagctgtc gttcttgtgc  60720
tcagtcagtg ttggttgtaa gactgagaag agtcacttca ttttgctctc cagggacatc  60780
tttctgggtc ctattttctg cctatgtcaa gtagcgcctc aaggatgctc ctgaaaatgg  60840
gcttgtcttt cttaacatgg caggtaggtc ccaaagcatt agcatggggc agctgaccta  60900
gcccagccaa tgcagtgcag tgactcttgc aaccgagtct aatcagaagg tccatgaacc  60960
tacgagcatt tcctgtccca ggatcagggt ggaggctgag cctccctgct tagagattct  61020
tcccatgcat tccacttttt tccccaaaag aaaatattga cccttgagag gcacacagtt  61080
tatttatttt gcatagtaaa tagtagcctg tattttaagg atgagttgat ttctgcatca  61140
gcccctgtag gtcatcagcc ttctattggt gcatctgact ctctctagcc ctgcagggat  61200
ggtggagggg gaggggaagg agggatcttt attggaaacc aggacagtga gactcattgc  61260
cctgtcatct gctctgtggt gctgaatgag gcagcccaac agagaaatac cctgagcgag  61320
catccccagc ctccaaaaca gtggcgcatt gccctgagtc ctgggaatga cctttgattc  61380
tcctgctcct gacttggaac ccatggaaac ctctagaagc agctgaggaa aacccaacat  61440
gaaaagcaga actccacact gagaatatag gaggtgatcg gaacatacaa tgattcttgc  61500
taagaccgat tcacagtttt tcttttttttt cgatcgaaga aatactggag aagcctaaag  61560
aaggagtcta aaaactctgg cacgtgggcc aaaactgtcc ttgagctaag aatgattttc  61620
acatttttaa gtggttgaaa aatgaaataa aataagatga tgttttgtga cacatgaaag  61680
ctatgggaaa ttcaaattct aatatctata aatagtgttt tatcagaaca cagtcatgct  61740
catttattta tgctcgatgg ctgctttccc gctacaatta cgttgagcag ttacaacaga  61800
gaccacgtgg cccacaaagc cttacaatat ttactatctg gccctttcca gaaaaaaatg  61860
tgccgactct tgaccttaac ctcagcaatt tgggaggccg aggcaggcgg atcgcttgag  61920
```

```
ctctggagtt catgaccagc ctgggcaaca tagtaagact ccatctctac aaaaaataca  61980
aaacattagc caggcatggt ggtgcacacc tgtggtccta gccactcggg agactgaggt  62040
gggaggatcg cctgagccca ggaagtcgag gctgcagtga gctgtgatgg caccactgca  62100
cctcagcctg ggcgacagag caagaccttg tctccaaata aataaataat gcaaagtaaa  62160
ataaataaaa ccatataaaa aggaatcaat ttaaaattat aatgaaagct ggccgggcat  62220
ggtggctcac gcctgtaatc ccagcacttt gggaggctga ggtgggtgga tcacgaggcc  62280
aggagatcga gaccatcttg gctaacacgg tgaaaccccg tctctactaa aaatacaaaa  62340
aaaaaattag ccgggcacag tggcgggcgc ctgtagtccc agctactcgg gaggctgagg  62400
caggagaatg tcttgaaccc gggaggtgga gcttgcagtg agccgagatc gtgccacttg  62460
cagtccagcc tgggcgaaag agcgagactc cgtctcaaaa acaaaaacaa aaacaaaaac  62520
aaaaaaaaat tataatgaaa gccaaggggc atagtagaac aaattttcta gagctcatta  62580
agtcaaatga gtcaccagtt agtaaaacgc agtcacgggg aagagagggc aggattcttt  62640
gaagcagcgg ctctcctaaa aacaacccac ccttgtccag ctgccttccc tcctgagggt  62700
gttccctttg actgtgtgac ccccatcccc tatttcccaa ccgtccaagc ccacctctag  62760
cataatacga gcttttaatc cctctccctg accccaaccc gattttgaag cccagtctag  62820
tattttctca aatacacttc ttggctccat tccttccttt ccatcacctc tgccttttca  62880
ctgcatgctt ggaccactgc agtcagctcc ctatgaacag ttgctctcta cccatccaat  62940
cggccccgcc tgctgctgcc aaattcaccg agggcacctc tgtggtgctg cctgtggaca  63000
aagtccaagc cagccacctc acccacctac aggtgagtgg ggagcagcca gcgtgtccag  63060
tggtttaccc catcgccaca gacttggtga tgtgtcgatg tgcagagaag gggtgttggc  63120
agccacaaca caagcaaccc cgccccatgt gagatctaag atgggcgtgc tgggagccac  63180
ctctgagaat ccaacagaag gcagagggga gaacggctca cacggcacaa acactccttc  63240
cttttttttt tttctttttc ctttttgaaa ggagtctcac tctattgccc aggcaggagt  63300
gcagtggtgc aatctcagct cactgcaacc tccgcctcct aggttcaagc gattctccag  63360
cctcagcttc ccaagtagct gggattacag gtacactcca ccatgcccgg ctaatttttg  63420
tgtttttagt agagacgggg tttccctatg ttggccaggc tggtcttgag ctcctgacct  63480
caggtgatct gcctgccttg gcctcccaaa gtgctgggat tacaggtgtg agccatgggg  63540
cctagcctcc ttccatttaa atgtatgcct aatttgccca ttgagaacgg ctgagacgca  63600
ttttaagtgg ccagggtcta cttagagtta gtgctcatga ccaggcccag gtcaagcctg  63660
gctggccaga tggtgccttt gacctgctct gtctctgtgc aaaggaatga gctgaaggat  63720
gggggtgcag tgtgtgggca gtgggctggg gctggcagga ctcagtgact aagggaagag  63780
aactttcctc actaccagcc tgtcttttca gggcaccgcg gggggctttg ggacttggtg  63840
atgaacacag cacagagagc tgtccagcat gcgggtccct ggcttctcac acttcccagg  63900
ctccttcaga ggctctctcc aaagggagct gctctctcta gaacccatga atttggaata  63960
taggcaacca ctgcattggg gaccactgac ctcaaacata gagaccagag caaatggggc  64020
tcatcacgtg aaactcatct ggaactctag caggttcttt tatatatata tatatatata  64080
tatatttttt attattatac tttaagttct agggtacatg tgcacaacat gcaggtttgt  64140
tacatatgta tacatgtgcc atgttggtgt gctgcaccca ttaattcatc atttacatta  64200
ggtatatctc ctaatgctat ccctccccac tccccccacc ccacaacagg ccccagtgtg  64260
tgatgttccc cttcctgtgt ccaagtgttc tcattgttca attcccacct acgagtgaga  64320
```

-continued

```
acatgctgtg tttggttttt ttgtccttgc gatagtttgc tgagaatgat ggtttccagc  64380
ttcatccatg tccctacaaa ggacatgaac tcatcatttt ttatggctgc atagtattcc  64440
atggtgtata tgtgccacat tttcttaatc cagtctatca ttgttggaca tttgggttgg  64500
ttccaagtct ttgctattgt gaatagtgcc gcaataaaca tacgtgtgca tgtgtcttta  64560
taacagcatg atttatattc ctttggttat atacccagta atgagatggc tgggtcaaat  64620
ggtatttcta gttctagatc cctgaggaat cgccacactg tcttccacaa tggttgaact  64680
agtttacagt cctaccaaca gtgtaaaagt gttcctattt ctccacatcc tctccagcag  64740
ctgttgtttc ctgacttttt aatgatcgcc attctaactg gtgtgagatg ttatctcatg  64800
gtggttttga tttgcatttc tctgatggcc agtgatgatg agcatttttt cacatgtctg  64860
ttggcgaact ctagcagctt cttttcacaa gttcatggag agaggtttcc cactgaggga  64920
atcacatctg tctgatcaaa agaggcttgg gaaatggctc tcctgttcat tccctgaaaa  64980
cctctgatgg aaccactgcc actgtggcag ccccagcact ggcaccccag ccatgattgg  65040
tgccccagcc acatctctgc tgtgagcccc agagccctgg ttaattaatc atccacgtgt  65100
tgatggggag aggcccattc acaaaagcga cataaagccc agggagacgt ggccgtggca  65160
agaagggtgt gggactacat tccgccccca actgagagat tcagaaacca gaaaaaaatg  65220
gaaaaacata ctgtgctctt gggtgggaaa actaaatatc atgaagggag caatttttat  65280
agttttggcc tataatacaa ttccagccga aatcccagtg gaactttgag aatttgcagg  65340
aaaaaaaaaa atgtctaaag tacatctgga agacaaactt acaagaaggt caaataattt  65400
tgaaaaagaa aatgatatct aagcccacct agagaataag acttgagatc caaagctaaa  65460
tcaggaggct ctagcaaaat tgacagataa gcaggacaga gtgcatggtg cattcacctg  65520
gggaagaggg cagattggtc tacaaatagg cctgggtcca ctgactttag ctgttatatt  65580
tggggagaaa cttttcaacc tcactccatc ttaaacctaa aaatattcca gatgaattaa  65640
taaatataaa aaattagacc actaaaaatg tagaagaaaa tggatgatct ttctatacca  65700
tagagcaatg gaataaatca caaaggaaaa cagatttgac tatataaaac ttaaaccctg  65760
cccatcaaaa accatcagaa accaaaataa aaggcaacca actggagaag atagttgcca  65820
caaatatgat caagggttaa tgttattcat aaattaagag cccacacaag tcattagaat  65880
aagcactgag acctgaacag acaagcaaaa agaatgagag tgggtcggcg cggcggctca  65940
tgcctgtaat cccagcactt tggaaggctg aagcaggcgg atcacttgat cccaggagtt  66000
ccaacaccag cctgagcaac atggtgaaac cctgcctcta caaaagtcat aaatattagc  66060
cgggtgtgat ggcacacgcc tgtagtccca gctactcagg aggctgaggt gggtggatca  66120
cttgagcccg ggaggtagag tctgcagtga gccaagatca caccgctgca ctccagctgg  66180
agcaacagag tgagaccctg acttaaaaga aaaaaaaaaa aaaagaggag aaaaatgctg  66240
atctcactag taattaaaac atcaggccag gcgcagtggc tcacaccttt aatcccagca  66300
ctctgggagg ctgaggcagg cagatcactt gagatcagga gttctagacc agcttggcca  66360
acatggtgaa atcccgtctc tacaaaaaat acaaaaattc gccaagcgtg gtggcacatg  66420
cctgtgatcc cagctactcg ggaggctgag acaggagaat tgcttgaaca cgggaggcag  66480
aggttgcagt aagctgagat cgtaccattc cagtccagcc tgggctacag agcgagactc  66540
tgtcccagaa aaaattaaaa catcacatat ttaaacaact ctaggatatc atttaaaaaa  66600
acattaatag actgtttttt agagcacttt taggttcaca gtgaaactga gtggaaggta  66660
```

-continued

```
cagagacttc ccgtatgttc cctgccctcc acgtacagcc tcccccactg ccaacgtcct  66720
gcaccagagt ggtacacttg ttacaaccaa tgaatcctca ttaacatatc attatcaccc  66780
aagttcatag tttacattag taaaacatca tctttcatct ataagcacaa aaatttttg  66840
gcatttattt aggtgtatga ttaactcagt gttgacaaga ctcacacttc atacccactt  66900
gcactgcatc tgagaagcaa ttggtgtcta cagccgctac accctcaaca agcccgatct  66960
tgtttgaaaa gcaattggtg atgcttctca aaattctatg gacaaagtca gccgggcatg  67020
gtggctcatg cctgtaatcc ctaaactttg ggaggccgag gcaggcagat cacctgaggt  67080
ctggtgaaac cctgtctcta ctaaaaatgc aaaaattacc caggcatggt ggctggggcc  67140
tgtaatccca gctactcggg aggctgaggc aggagaatcg cttgaagcaa ggaggcggag  67200
gtttcagtga gccaagattg caccactgca ctccagcctg ggtgacaaga gtgaaactcc  67260
atctaaaaaa aaaaaattat ggacaaagtt tttcaaaaag atatttaatg caactttatt  67320
tgtaatattg gaacatctga ggccatttca gtgctaacta ttaggggatg gttaggaaaa  67380
tatggtacat atgtggaaag gaacatttgg tagttagtgc ccctgatgtt tacaaaggct  67440
tttagtgacc aacaaatgct catgctataa tcttatgtga aaaaagcaag tagcataatt  67500
gcaactatat ttttaatgca tagaataaaa ggctagaagg aaatatcaca gatccttgac  67560
atacattccc aaacctttgt aaatccgcgg attcatgaaa acagacacat ttgcacaagt  67620
gcctgatctt ttctgttata cattcattag aagtcaagcc ctggtgccac aaagtatctg  67680
ccttttcaaa tgtgatcaga atgttctctt ttgcttcaag gccatttttc acgaagcagt  67740
ggcatttttg cctcttcatc agagtcaccg tgtgccctgg aggactgaga acagcagagc  67800
cgttttagga tgggacaggg cagccaggag gattgggctc actccctact gagtgcctca  67860
ctcccgtaca gcccccatag aggaagaggg gttcaaattt attcctcagc cagatggcat  67920
gtgccgcctg tcctggaatt tcacatcact tatgatggac caaaattcca aaagctgaat  67980
ccatgattgt caaagtctgg tatggcagga tgtcaacagt aatcgtttct gggcagaggg  68040
atgattttct cttcccatct tgctttgtat aaatacattt tctataataa ggttgtatta  68100
cttttctcat caagaaatag caaagtactg ttttactcaa aatatgaata gagccaggca  68160
tggtggcagc ttatgcctgt aatcccaaca ctttgagagg cggatatggg aggatcactt  68220
tagcccagga gtttgagacc agcctgggca acatagtgag acccccgtcc ccactccccc  68280
aaagaaaacc cacaaagcat ttatcctgga ttattcacag gggccaaaaa aaaaaaaaaa  68340
ttcaggcctc ctatagccat gagctacgaa tatgaaaata tgcaaatgtg taagaaaagc  68400
cagcacatcc gatttttact tttactttca cacctctgtc caccatgttc caagagaaga  68460
aacttggtca ttgaaaggaa tagatcaaat ccaaagaaca aaaccactgt gctcattaaa  68520
cttcttagtg ttcacaaagc tttagctgca ggttgaatgg ggcaacccga attggctggc  68580
tcacctgggc tgcagggagc agagatcgcg acactgcact ccagcctggg caacaaagcg  68640
agactctatc tcaaaaaaaa aaaagttcat aaattcaaag ttatgaatta tttttaaaat  68700
aataataatt tacaataaag atgaggacaa agtgtgagta aatggtggtt tctatccagc  68760
tctgttgagc tgaagtggca tctccctgct ggggcttttg gggaagaagg gtgtgtgttg  68820
ctcttcagat cccaagcctc atgcccctac tgggccctgt ggggtgcttc tcagcccacc  68880
aggagagcca ccgttggaac acacacgtgg gggacctggt gggtgccggt gtggtgaatg  68940
ggggccacag cctgactcca ggaagccagc aaactcggag ctggaggagt caggacaccc  69000
ccgatgagtc aagagttggt tttgctgcca gttgacatct gattgaacca tctcttcact  69060
```

-continued

```
tctccgtgcc tcactttcct taccagacag gctctgctga tgctgtccct ctcctgttca  69120
gtcgtgccct caccgttaaa gagaaagagc aaactgctgg gcagcagcat tgattttttt  69180
aatgaagtgg aaagagagct gggaataaca agtcgggccc acctcacctg cctcacctgg  69240
tgggtttatt tgttttgttt tttttttttt gttttgagac agagtttcac cctgtcaccc  69300
aggctggagt gcagtggtgt aatctcagct cactgcaacc tccacctgcc aggttcaatt  69360
gattctcctg cctcagcctc cccagtagct gggattacag gcacctgcca catgcctggc  69420
taattattgt atttttagta gagatggggt tttaccatgt tggccaggct ggtctcgatc  69480
tcctgacctc aggtgatcca cccacctcgg cctcccaaag tgctgagatc acaggcgtga  69540
gccaccatgc ctggccgtca cctggtggtg ttgaatatga actgctgcgg tgttggtaaa  69600
ttaagcaagc agatagatgt aaataacgct tgggcaggaa tatggagcac gggatgagga  69660
tgggcggcca actgttagag agggtagcag ggaggctgag atctgcctgc catgaactgg  69720
gaggagaggc tcctctctct cttcaccccc actctgcccc ccaacactcc tcagaactta  69780
tcctctcctc ttctttcccc aggtgaactt tgaaccagga tggctgagcc ccgccaggag  69840
ttcgaagtga tggaagatca cgctgggacg tacgggttgg gggacaggaa agatcagggg  69900
ggctacacca tgcaccaaga ccaagagggt gacacggacg ctggcctgaa aggttagtgg  69960
acagccatgc acagcaggcc cagatcactg caagccaagg ggtggcggga acagtttgca  70020
tccagaattg caaagaaatt ttaaatacat tattgtctta gactgtcagt aaagtaaagc  70080
ctcattaatt tgagtgggcc aagataactc aagcagtgag ataatggcca gacacggtgg  70140
ctcacgcctg taatcccagc actttggaag gcccaggcag gaggatccct tgaggccagg  70200
aatttgagac cggcctgggc aacatagcaa gaccccgtct ctaaaataat ttaaaaatta  70260
gccaggtgtt gtggtgcatg tctatagtcc tagctactca ggatgctgag gcagaaggat  70320
cacttgagcc caggagttca aggttgcagt aagctgtgat tataaaactg cactccagcc  70380
tgagcaacag agcaagaccc tgtcaaaaaa aaaagaaaag aaaaaagaaa gaaagaaatt  70440
taccttgagt tacccacatg agtgaatgta gggacagaga ttttagggcc ttaacaatct  70500
ctcaaataca gggtactttt tgaggcatta gccacacctg ttagcttata aatcagtggt  70560
attgattagc atgtaaaata tgtgacttta aacattgctt tttatctctt acttagatca  70620
ggcctgagtg gcctctcttt agcaagagtt ggttagccct gggattctta ctgtagccac  70680
attaataaac aacatcgact tctaaacatt ctataatacc atcttttggc caaattgact  70740
tcgcctcttc ctctctcttt ccaaatgaaa tgtgtttcat ttcactgtca gaccacatgg  70800
ttggggaccc cacagagcac acagccctcc ctctgccttc ccatgctggc ccttcaccca  70860
ctgctggagt gccaggttgg tccaagggtt ggaccaagtt gtctgaggtt gtctcaaggt  70920
tggtcgaggc tgtctccgcg ctgggttgtg ctacaaggag cccttctttc catgggtgtg  70980
gctggcagtg agtgctcaca gcaacagccc acagtgcagc ccgagggcag gatggactca  71040
gtccctgcct ccatacccat ttctaaggag gcaaaatggc aaacactcta cttttctctt  71100
ttaatgctaa aaataagaaa acaccttgca gcccagggta tgggtagtgc atggaagccg  71160
tggagttgtg aggtgggaag tgacctctgc tggatatgtc tattcaggaa gattgctgga  71220
gtgggtgggg tctctgggag gtcccctgag tgtgggaagc tgggaccacc agctttctcg  71280
cacagggagt ggccatccca gcttggagag gttccaggac tggttgggag gcacgtttca  71340
gatttctatc tgttgaatca gcgaagatat tggattatga ggaatttggg aattaggaaa  71400
```

-continued

```
gtgggtgcag gtgggttggg ggtaggtgaa ggaagacatg ggcgtattgg gggagcaggg  71460
gctgctcaga ggtgttccag aagctctggg tgaggaggtg agagggaccg gggaatgcag  71520
ctcggcccag cctccctgcc tgaggtcagc catcacgtgg tgatggcaag atggaaatgt  71580
gctttctgac tgctccagcc agtgctgcca gattcagctc cccagggagg gcacctgaga  71640
ggctccaagc caggagatct gttttctcct ttgttttgtt tttttttgtt ttgttttgtt  71700
ttattatact ttaagttcta gggtacatgt gcacaacgtg caggtttgtt acatatgtat  71760
acatgtgcca tgttggtgtg ctgcacccat caacttgtca tttacattag gtatatctcc  71820
taatgctatc cctccccccct cccccccaccc cctgttttct cctttgaatc cttcttagag  71880
gccgggtgcg gtggctcacg cctgtaatcc cagcactttg ggaggctgcg gcaggaggat  71940
tgcttgagcc caggagttcc agaccagcct gggcaacata gtgagacctc gtctctacag  72000
ataataattt taaaaattat ccgggcatag tggcatgcac ctatagtccc agctactcaa  72060
gaggcagagg caggaggatc acttgagccc aggaggcgga ggttgccgtg agccaagatc  72120
ccaccactgc actccagcct gggcgacaga gacccccatg tcaaataata ataataataa  72180
ataaatcctt ctcagtccct tcctcactgt gtccccctcc actgaatttt tccacctcct  72240
ctcccacttc ccccactccc gctttccctc tccttctctc cccactccat ctttttcttt  72300
ctctgctgtt tctcgtccct ccctcctctc catcccacaa cactgcctac cctgtccctg  72360
ccccaccctg gtgctcagga tgtgtgaagt gaggggtggt agcccccaag acctcaaccc  72420
cgaaggttag cctgttgaaa ccactttctc ccagctgccc ccctggcagt tggtgctgct  72480
gggggaaact gggattgggg gccagatttt gcctcttttc ctgacaaaga gagatgaaga  72540
gttctctcac caggtgcctg ggactggggt gtgggtgtcc cagcctatcc cagcgcatct  72600
gttctgcatc atgattaata gtgctgcttt cagccgggcg cggtggctca cacctgtaat  72660
cccagcactt tgggaggcta aggtgggcag atcacaaggt caggagttcg agaccagcct  72720
ggccaacatg gtgaaacctc gtctctacta aaaatacaaa aattaaccag gtgtggtggt  72780
gggtgcctgt agtcccagct acttgggagg ctgaggcagg agaatcactt gaatctggga  72840
agcagaggtt gcagtgagcc aagatcgtgc cactgcactc cagcctgggt gacagagcga  72900
gactccgtcc taaaaaaaaa ggagttttgc tctgtcgccc aggctggagt gtagtggcgc  72960
catctcggct caccgcaacc tgcgcctccc gggtgcaagc gattctcctg cctcagcctc  73020
ccaagtagct aggattacag gcgcctacca ccacgcccgg ccagttcttg tatttttaga  73080
agagacgggg tttcaccctg ttggccaggc tcgtctggga ctcctgacct caggtaatcc  73140
gcccacctca gcctcccaaa gtgctgggat tgcaggcatg agccaccgtg cccagtcaac  73200
tccttctcaa aaaaaaaaaa atagtgctgc tttctctttc aagtgtcctg atttgggtga  73260
tagtaaatgc cactctactt ataagggatc tacctcagaa tgctaattgg gacatttttg  73320
tagcactcta ctgttggcag caggtgatgc tcacaacagc ccgtgagggt ggatgacgtc  73380
cgcttcacag atgacaaagg agcctcatgc tcagaccgtg ggctgccaga gcaggtccat  73440
ggctgcagcc ccacatggac catatttccc ccttgtcact ctttccacca agctcccttg  73500
gaacttcagt tattaagctc tcttgggtgg aatccaagtt agaatcacaa catgtgcctc  73560
atatggattg tgccagtgaa aaatgacatt ctatttagag gcagggcagc ctggcttaga  73620
gtcagtttaa aatatgtatt atgctgcaac aaatgtacca tgatcctgta agatgttcac  73680
aacaagggaa ctggatgtgg ggtatactgt ctgtactaac ttcacaagtt ttctgtaaat  73740
ctaaaactgt tccaaaataa caagttcgtt taaaattaac tccaggagac caggtacggt  73800
```

-continued

```
agctaatgcc tataatccca gcacttcgga aggctgaggc aggtggattg cttgagccca  73860
ggagtttgag acaagcctgg gcaacatggt gaaatcctgt ctctaaaaaa aatcacaaaa  73920
attagccagg tgtggtggcg cattcctgta gtcccagcta cttgcggggc tgaggtggga  73980
gaatcatctg agcccaggag tttgaggctg cagtgagctg tgattgtacc actgcactcc  74040
aacctgggca acagagcaag accctgtctc aaaaaacaaa aatgaaataa agtccaggaa  74100
agaagtaggt tttaccactc ttattttctg aagagaaaac taaatttaat gtgtaaagtg  74160
aggacaagtt caccaagtta gtgtttgagt tgcctaaaat atgtttgcta aaactattca  74220
aagctttcac ataaaacatg atcagaagtt ctatgccaaa acatatgtgt gtgtatatat  74280
atatgcacta tatatactgt atataaaaat gcaaaatcta aattgccaac cttttagaaa  74340
ttgctctgaa aggaaagcat ttcaagataa tttgcttacc caaagaatat actttccaag  74400
aaagcaagta atacttaagg tgttcataat cctcatcaaa ttaattcttg ctactgaaag  74460
cttacaagga gctgttttga tgtcgggtgt gacaggtttg acttggcaga aggtgtcact  74520
ttactaacaa cattttaaat aagtgacaga agacaagaaa ctacacgtta aatgccagaa  74580
caaagagtgt ctaagtggat gctaagagtt gaaatatggc tggatacctg cccaagagag  74640
ctgaaaagta gatgaaagtt ggttacctat aaactagtgc accctaatga attaaaaggt  74700
gttgatgagt taacttgtta tgccttccag ataagacatg caaatggggc ttcttcctcc  74760
ttcactactt ccaagggatt taacaaggag accaatgcaa atgataagga ctgtagggct  74820
caagctgggg acagattggg gaaaggggga ccatcatgcc catatagatg tccctgtgcc  74880
ctggcagtca aggctgctga aaaataacaa aacccagaag tctgcgtgat gctgcctctc  74940
catttgtcca aagccttctt gcggcagttt gcaggctttt gcaaaagctc caggaccaag  75000
gagctatgtt catgctggaa gcttgttcag gattagctgt tctttgtggg atgggtgcag  75060
ccagggccag gtgtccaggg acagtgtttt aacaaagggc atgaggtgtc tgatctcaca  75120
gtggaactcc acttgccttt ttttcatctt ctcattctgc ttcatgcaca gaaccagccc  75180
catcctgaaa ctgactctaa attactcccg ccccaggtgg agtgcctttc tcggagttca  75240
acagagcctt cctgtcgccc aagggacaac tccactgaat gcccaagcca cacccaaaac  75300
ctaacaagta aaaaccaaat tctgtgctcc cccatcctgg gccattcctg gtttctctac  75360
tgctgttggt gataccacca tcagcttgtc catcatgacc ctggccagtt cctcccacaa  75420
ccctccacag cacccaggga cctcacctcc attccatccg acacagatct cctcaccaca  75480
aaccttggtt ttgcaacagc agccatgaga cctttacacc ctccgccctt catcctgtcc  75540
cccactgagg ccccagagcc attccttaaa gcagcgcgcc acaaactata acccacaagc  75600
caattctggt acccagcctg ttttgcacag ccagtgaact gacaatgatc ttttcataca  75660
gccagaaaaa caaaacaaaa caaaaaacaa caaaaaaaaa ccccaccatt ctgagcatgt  75720
gacttccatg ttcaagatgt ctcatgttca gaaaggcccc tggaaaagga ggaaggggag  75780
ctgggcacaa agggagaccc tctcagctga gctcctccca tccagacatt ttcctggact  75840
tcctatccaa tgacttccct tagcttctta tcagccaccc ctgtctgccc aggaggctgg  75900
aagatgtggc cttttaactg ggcacagctc tgtcctctat catatcaggg ctctgttccc  75960
aaggagggta gagagaatgg acaccaggtg gaccctcagc agtctgtgcc acagagggag  76020
tgtttgcaat ttccagacta aaagtcccca tgtgcttgac ggggtatgtg actacaacgt  76080
gatgcttgac ttttcctcat atgaccagag ccactttgtc catctggtac aatgtcagct  76140
```

-continued atctgctagg ggccctccag gattcccagt caattccata tctgcatcac caccattggc 76200
actaaataaa ataaaatact caagttcctg ctggtgagca tgagcagtgc tacactgggc 76260
ccttcaacca aggtgacatg ataatgactg aaaataatca ctgccactta ttggggacgt 76320
ctcatctgcc aggcatggta caaagtgctt taaataagca ttcaacaatt tcatgctgac 76380
agaagccctg tgagccagtg gagctactac tatgcccatt atacagggga gaaaactgag 76440
gcagagagag gttaggtaat tcgctcagcc tcacacaacc aataggtggt ggagccagga 76500
tttgggcccc atctgcctga ctctctagag gctctatctt ccagtcttcc agagttgagt 76560
ctaagccatg aataggacaa ttagacagca gaggaaaccc attcagccac catgtgcatg 76620
aagagtaagg aatttctgtc atacagaggg gagtgaattc actgagctga gagctgagga 76680
accattgatc tgatggctga gacaccactg ggaagactgg agaggctttt ctgggcatgc 76740
agtgccaggc acaggaggag ctgagggaag atgactaaga ggtactggca aagaattcag 76800
aaattctgat ggaagcttta catgttacca tcacatccat ccatctatcc acccatccat 76860
ccacccatat cttcctccct ccacccaatc atgcatacat ccagtcatct atacaccacc 76920
cacccaccca tccatccatc catccatccc ttcatccatc ccatcatcca tccaattata 76980
catacatcca atcatatatc tgtacataat ccattcttcc ctcggttcat ccatccatcc 77040
attcatccat ccatccaccc atcccttcct tcatccttcc tatcatccat ccaatcatat 77100
atctgtacat aatccattct tccctcggtt catccatcca tccattcatc catccatcca 77160
cccatccctt ccttcatcct tcctatcatc catccaatca tacatatatc caatcataca 77220
tctgcacatc accagctcat ccatctatcc atttatccat ccatccttcc ttccatccat 77280
cattcatcca tcatacatac atctaaccat acatctctac atcattcatt cttccatcga 77340
ttcatccaat tatccatcat tccttcctcc atccatccca ttatccattt gatcatacat 77400
atatcatcta tacatcatcc attcatccat ccatccatcc atccacccat atcttcatcc 77460
aatcaatcat acatacatcg aatcatctac acatcaccca tccatccatc catccattca 77520
tctatccacc catccatcca tccatccatc cattcatcta tccacccatc catccatcca 77580
tccatccatc catccatgta accatccagt catatatcca attacacatc catccagtta 77640
tacattcata catgcatcta atcattcaat tatacataca cacatccata taattctaca 77700
tccaattata cctccatcca attacacatt catacaccca cctaataaat tattaattca 77760
tatatccatc catataatta tacatcaatt atacatccat ctaatcattc agtaattcac 77820
ccaccatcca gtcatctatc caataataca ttcatccaat catccatcca tccatccacc 77880
cattcatcca tccatccgtc cgtccaccca tcatggtatg agccatgatt taccacgatg 77940
gtcccctgtg gacagcccag gtggggcaga actgaaggga agcccagggc tgcccccata 78000
aacatttgcc tcctttacat ggatgagaac tagatccaca tgtataaatc ctcatgattt 78060
gaaggtgctt ttaccaacat tcactcatgg gattctccca ggagctctag gaggaggcag 78120
gtagagttga ggtcatctca cgcattttac agatgaggaa acggaggccc tgagaggcag 78180
gtccaaggcc acctgaccag aaagaagtgg aactgggact tgaacccagc catcttgccc 78240
cttggtccca tgctctctag cctgtaactc ctgcttcctg gtggggcatc tccaggagga 78300
ccctatcggc tggccatggg cctgccctgg agtcttttgc tctgtgtggc catccttcct 78360
ccctcaggag agtgtgtgct cccagagcac aggctgtatc ttctgagcat tttgtccctt 78420
cccagtacct agcactcagc tctgtataca ttgggctctc aagaattctc aaccttccag 78480
agtgtaaggc cttgacctgc tcagccctgg atactgcatg atgcattgat aagcccataa 78540

```
aataaccagg gcagattgac tcccagtggc caaagtgcca cagggaaggg acaattcagc  78600
ccttctagga ggaggaggag gtagttttct catttctatt aaggcaacaa aagctgcctt  78660
actaaggaca ttcttggtgg agggcgtgac tgtcaaccac tgtgatcatt tgggcctctc  78720
ttgcccaggc ttcccattct gaaaggacag ttttattgta ggtacacatg gctgccattt  78780
caaatgtaac tcacagcttg tccatcagtc cttggaggtc tttctatgaa aggagcttgg  78840
tggcgtccaa acaccaccca atgtccactt agaagtaagc accgtgtctg ccctgagctg  78900
actccttttc caaggaaggg gttggatcgc tgagtgtttt tccaggtgtc tacttgttgt  78960
taattaatag caatgacaaa gcagaaggtt catgcgtagc tcggctttct ggtatttgct  79020
gcccgttgac caatggaaga taaacctttg cctcaggtgg caccactagc tggttaagag  79080
gcactttgtc ctttcaccca ggagcaaacg cacatcacct gtgtcctcat ctgatggccc  79140
tggtgtgggg cacagtcgtg ttggcaggga gggaggtggg gttggtcccc tttgtgggtt  79200
tgttgcgagg ccgtgttcca gctgtttcca cagggagcga ttttcagctc cacaggacac  79260
tgctccccag ttcctcctga gaacaaaagg gggcgctggg gagaggccac cgttctgagg  79320
gctcactgta tgtgttccag aatctcccct gcagaccccc actgaggacg gatctgagga  79380
accgggctct gaaacctctg atgctaagag cactccaaca gcggaaggtg ggcccccctt  79440
cagacgcccc ctccatgcct ccagcctgtg cttagccgtg ctttgagcct ccctcctggc  79500
tgcatctgct gctccccctg gctgagagat gtgctcactc cttcggtgct ttgcaggaca  79560
gcgtggtggg agctgagcct tgcgtcgatg ccttgcttgc tggtgctgag tgtgggcacc  79620
ttcatcccgt gtgtgctctg gaggcagcca cccttggaca gtcccgcgca cagctccaca  79680
aagccccgct ccatacgatt gtcctcccac accccccttca aaagccccct cctctctctt  79740
tcttcagggg ccagtaggtc ccagagcagc catttggctg agggaagggg caggtcagtg  79800
gacatctgat cttggtttag tatccttcat tttgggggct ctgggtgtgg cctgggcctc  79860
tggactttgg ccacggtgtt tgttccagcc cttctcctaa cctgtccttt ccagacactc  79920
ggcatctagg ttattagcac ctcgcatact ttctgacatg ctcctcagtc ctgattttga  79980
ccatcttctc ttgcttccca tctgtgtcag tcaagactgc atttggctgt aagaaacaga  80040
aaccccaact aactgtggca tttacatgaa gaggtttact tttctcacat aatcagatgt  80100
ctagacttgg ccagcacctc aagggtcatt gatgctctcc tgtctttatt ttctgtcatc  80160
tttagtggtt ggattgttgc ctcatggtta caaagtggct gctgcacttc caggcatcac  80220
atctgccttt gaagcaggaa caagttgcaa agtaaagtgg ccaaaagggc cctgaaacta  80280
aatgtgtccc cttaggaaag caggagtttt cttgcaagtg gcaatcttct gcttatgtct  80340
cattggccag agctgggtct tacggccacc ccttgctgcg agcaaggctg ggacattgag  80400
cattttgccg tccaacctct ttagcagaat aaaccaaggg ggaagaacgt taatagtggc  80460
ttttgagtca ctagttggca gtatctgccc ctctatcttt ccatcctccc catggagttt  80520
caaggttcct ttctcagtac ttcttcaggc tctgcacgtt catttggatc ttgtgtcttg  80580
gggtgaaaaa ctggcccaag tgtctcccca agcatccacc tttggattaa tttggaaaat  80640
ggctgtcaag tgcccgcctc ttgcttggta taatgctaca gctttagagg acgcagcagg  80700
catgggcctt gccgctgagg ttcttagcct catgagaata tccagatcag attctcttgg  80760
ctccttctta gagccagtga tgcaagacac ttcctgctca tcttgtcggg acggttttac  80820
aagttgcctg ccatcctgag aaagtctaca aaacgatgcc agacctcatg ccagcttccc  80880
```

-continued

```
aagccttgac tctcagtgct ccctcaacag gattctggaa gaatctccca aacaagtcgc  80940
aatcccctct ggaccctgtg caggcatgag actcaagagc attggctccc accccctggtg  81000
gagggaacac tgctggggct gggatcttgc ctggttgctc cgcctgcacc caagacaacc  81060
ataattaaaa tgtccttcat tgaacttgga aagccttcaa agctgacaac tccttatgtg  81120
tacccggaaa ggcctgggag tgtgccaggg cattgctcgg gagggacgct gatttggaag  81180
catttacctg atgagagact gacagcagct cctggtagcc gagctttccc tcctgcctct  81240
gctgtgaagg tggacccatc caacagtcaa atgcctgact ctggacagga gcggacctat  81300
ttattgccat gcaagggact ctgcactttt gaattgtggg tcatgggctt ggatttaggg  81360
gttagagctg ggagaagtct tggaagtcac ctagagatga cactgccatt ttgcagatga  81420
ggaaaccgtc caatcaaaat ggaccaagga cttgcccaaa gcctcacagc aaaaccatag  81480
gcccccgcac taaccccaga gtccctgtgc tgtcttaaga atcaaatagt tgtaagcaat  81540
catctggttt tcagtatttc ttcttttaaa atgcctgggg ccatgcccag cagtctgttt  81600
cactgcagcg tttacacagg gctgccgggc tttcctggtg gatgagctgg gcggttcatg  81660
agccagaacc actcagcagc atgtcagtgt gcttcctggg gagctggtag caggggctcc  81720
gggccctact tcagggctgc tttctggcat atggctgatc cctcctcac tcctcctccc  81780
tgcattgctc ctgcgcaaga agcaaaggtg aggggctggg tatggctcgt cctggcccct  81840
ctaaggtgga tctcggtggt ttctagatgt gacagcaccc ttagtggatg agggagctcc  81900
cggcaagcag gctgccgcgc agccccacac ggagatccca gaaggaacca caggtgaggg  81960
taagccccag agacccccag gcagtcaagg ccctgctggg tgccccagct gacctgtgac  82020
agaagtgagg gagctttgcg tgtttatcct cctgtggggc aggaacatgg gtggattctg  82080
gctcctggga atcttgggtt gtgagtagct cgatgccttg gtgctcagtt acctccctgg  82140
ctgcctgcca gcctctcaga gcatttaggg ccttctggac ttctagatgc tcctcatctt  82200
gcctcagtca gcgcgtcagt tccagagact tctctgcagg gttttctggg gcaggtggtg  82260
gcagacccgt gccttcttga cacctgaggt cagtccaccc tcctgctcag actgcccagc  82320
acagggtcac ctcccaaggg gtggacccca agatcacctg agcgcacaga gggtgcagat  82380
gactggacca caccttttgg tgatcttaat gaggtggtcc cagaggagct cagacatgca  82440
atctagcatc cagttctggg actctgtctc cttttcaaac gtattcatgt agaacaggca  82500
tgacgagaat gccttgtcaa catgggtgat ggggaatcaa tcagacaggg cgccgggctc  82560
aaggctgcag tcacccaaga gtggctcagc ccaccaggcc ctaggaaacg cctgcacagc  82620
ctggagctcc tggagtcatt tccttcatgt cttcttcact gcacttacgt aaagatgcca  82680
gccattggtt tggtgatttg gagggtgccc agttgcccaa caagaaatgc agaagaggcc  82740
tagccaggat ttcaccagca gtggagagta gagaagatgt ggccagaaaa gagtttcctt  82800
tccctcctaa agatggtact ccctgcagct actggggaag cctgcagcat tctctagggc  82860
tctgtgtgtt gagagcagcc ccaccctggc cccttctgag tgcatttctg ctttgtgact  82920
tgatccgtga agtcccctga gatgggcaga ggggatgtcc tcgaagctgg ggcagagcct  82980
catccttgaa cgtgaaggac gtttgaagac tgtggcatga tcacaggatg agatcacagg  83040
gaacttgagt ttctctcctc ctctcccttc acagttattt cactgaggga aatccctccc  83100
ctgcccagaa tgaaaactct agccaactct tgacttttcc atcactccaa agtagttgaa  83160
agtacattag tctccacagt ggcaaaacag tgtgcaaaag ctaaataatt agaacagcca  83220
gtcccatgtg acagtcaaag cttctaactc cattcaaagt tgcagccatt cccctcgagg  83280
```

```
gctggcaggg aggggagggg taagagaaac aggaaggttc ttactgagtt ggtcctggtg  83340
tgagctgcgt cacactccct gcagaggttt caaggagact ctctctctct ctgtctccat  83400
ggggacctta tttgaattct tctactctta ccccagcctg ccatctccag ctatcctccc  83460
ctgaagagcc cttctgctgc gctggattct ggtggccatg tcatctcctc ggccccgtgg  83520
gagtctgaag atctggctgc agcctcacct ctgaggtcct gctagttgcc acctcttaaa  83580
catgatctga ggctcccatg cactctgacc tgtgcccaca tggggcccac gggaaacacg  83640
ctggcaagca aactgtgggt gtgcagacgg ttctcagggc tgcagcacct gtcctttgct  83700
ctgcccccaa agcaaggcca gcccatcttc catcctctag tgttccttgg tggggccctg  83760
accacagtcc accaggtccc taaccagagg ggacacacac caggtgtcct caatgtattg  83820
ccttgaaaca gttgtgctgg gactgtgatg gggggtggcc atgtagccac ccccaccacc  83880
cccaagccac tctctccaag gaaatcctcc taaagatccc tttacatcct ccatgtggtg  83940
gggaggttct agagttgggt gcatgtgtct tcagctactg acaatgcaga ccttagttgg  84000
cacctcgctc tggcctatcc tgtttgctgt tcttggcgct ccagtgaaac tccccatggg  84060
ccatccagtt ggggtgcagt gtggccaccc ccttgcaggt tcctgccttg ctggagagca  84120
cagggccctc ctggctcttg taaaacactc cccatggtac agagaggcca gcagtgatgt  84180
gaggcccaac ctccctccat ggtgttccca agcagctccc tttctggggt caaggggtgg  84240
caaagacagt gcagcgtcca atttctgact caagccgggc ctggctatcg cagctctgca  84300
ctgtgtgtga cagcaaggca actcacccag tgccgtggca gtgaccgtgt ccgaggaagc  84360
ctcctcacac cctctgtctc aaggactctg gcatttagct ggacttgctg tagctctgag  84420
cctttctgcc attgccatca ccttgtcaga aactcaggcc gaatctgcac tcagagttgt  84480
gcccaggcag ttgagccaac acttgctcag cgatattgtc acatgacaag gcactgtcac  84540
cactgggcgt cgtgggtagc gcagtgtcgg ctggatggac ccggagggtg tctgtgtcat  84600
gctagtgcta gtgatgggag ccccgtgagc ccattgcccg ccctcccatg ccctcagcag  84660
ctgcctgggg acagccaatg gcctgggtgt ttctgaggct accacatggc ttccaggaaa  84720
ctcgagaacc tttctctccc ttgcctacac tcttcacaca ggcctgtgct ggccagcggt  84780
ggggatccgg cattcctatc ttaggtgcag aaagtgactg actcattgca ggcctgggag  84840
ataagactga tggcccagcc agcaagatgt atggatttct cagaggcagt ggcctctgtc  84900
attgtcctca ggaaatgctg gtgattctgg tggcctgagg tcaatgcatg tcaacgtggc  84960
caacttgcct tataaacttt ttttctggac aattgcgtgc actgtcctgt aacagtgtcc  85020
tgttgtttat gatgcagaaa taggtgtttt taaagcctat tgattttggt actattaatg  85080
tggtcaggaa ctttctcagt ctttcttgtt tggggtgagc tgtggcttcc taaacaggaa  85140
cccaagacac ccccaaaagc tgctcaccag cactgccagc ctccctctta ccaagtagca  85200
cccgttcagg acattctgcg aaaggcattt gcccagaagt tgggaggaag gaaatgtaac  85260
attttggggc acctaccata tgccaggcac caggctaaac gtgttcacac aaattctctt  85320
actaaccctc accatccttc tacaagacaa actagtatct tcatcttggg gttcaagatg  85380
aggaaatgga ggctcagaga ggttgaatga atgccggtgc ctggatatga accccatctg  85440
cctgactccg caacccaggc aaagtctttc cttgaacttc ccagcagcca ctgcttagac  85500
acagcctcca caaccatggc tcagcagcaa attgcttctc tgacctcact cagcctgtgt  85560
gtccttgttg agtgaggcat tcaggaccct ggtcccaaag tggagaaagt ctttcctact  85620
```

```
aggtcatagc tacacctgca tgtgggtgct gtgccttttg tttagtgaac ttttatcacc  85680
agcatcctca gcaatgacat ttgcagagaa gccagagctg aggcaccttg gtattcttgg  85740
gatgtgactt tcctgaatgt ttaagggaaa atgcccgaag gtacagagag cttggtttct  85800
agtaaacaat aactgtcttg cttttacccc ccttcatttg ctgacacata caccagctga  85860
agaagcaggc attggagaca cccccagcct ggaagacgaa gctgctggtc acgtgaccca  85920
aggtcagtga actggaattg cctgccatga cttgggggtt ggggggaggg acatggggtg  85980
ggctctgccc tgaaaagatc atttggacct gagctctaat tcacaagtcc aggagatttt  86040
agggagttgg ttcttatcaa aggttggcta ctcagatata gaaagagccc tagtggtttt  86100
tttctaatac catttctggg taattcctaa ggcatttagt gttctgaaag atgctagcct  86160
tgtccagcct gggagttgag aatgaatgtc taacagaaac tctaggccgg gcgtggtggc  86220
tcacgcctct aatcccagca ctatgggaga cccaggtggg cagatcacct gaggtcagga  86280
gtttgagacc agcctggcca acatgtgaaa tcctgtctca ctacaaataa aaaaattagc  86340
cgggtgtggt ggtaggtgcc tataatccca gctactcagg aggctgaggc aggacaatcg  86400
ctcgaaccca ggaggtggac gttgcagtga gccgagatcg catcattgca ctccagcctg  86460
ggcaacaaaa gcaaaactcc gtctcaaaaa aaaaaaagaa actcaaatat gtgtgacagg  86520
cgattctcac tgcaggctgc cctgtggctg atccaggagc aaggccttaa ccatgtcatc  86580
cccaagcgat tgcttgtaaa ctttcttctg tgcagccttc aacccttatt atgattttct  86640
tctcaggaac caaactgctg tattcaagaa aggcagcttt gtgtaatcat ttatcataaa  86700
tatcttaaga aaaatcctag agattcctaa ttttaggaaa tgggagacct atggtactga  86760
tataatgtgg gctgggcttg ttttctgtca tttgctagat aaatgaactt gagagcctac  86820
tgtaaaatgt ggaagcttct agattgcaga agggctggaa agacactgtt cttttctccc  86880
gagtgatggg atctgtccag tatttagagc tgcctctgag gccatctgat tctaggagac  86940
tctgcctcgt tgaggatatt ttgaggccta actacacatt cctgccccca gagaggtcac  87000
agcctatagc aggctgatgt ttctcatgtc acatggcaca gaaaggcaca ttttcgttct  87060
caggctaaca aagagcttca aaaactatta gaagggacag tggctataag agaagaacct  87120
cagtcaatgt gtgaaattaa ctaggaacct ggctcctgtt tcttttaggt catgtttttc  87180
agcttaggta aaactagagg ctttgataaa gcatgacctc tagaaatcat tgcttttcat  87240
aaatggaagt gggtttgagt tttttctact gattgttagt gcaggtgatg tctacatgcc  87300
cccagaacat attccatgca acaaaaaaag cccaggtcac cgtctttgct gggaacttga  87360
cttttgtgct cactgaattt taagctttct gacagcagcc tggaatcatg gagggataaa  87420
gtacctatta gtaagatgga aaaaggtgtt tcaggttgga gctgcagtct gttgagagta  87480
agctatggga aggcctgtat acgaggggtg gacttttctt ctgtaagtgt ccagagacca  87540
ggcctcctga agagggcatg gggggcttaac ttacctggac tactgtgttt acaatactca  87600
tttatcttga actcctccta acccctgaga attgctacat ttagtatttg ctgagtactt  87660
cctagcatcc tagggaatca atagaacatt ctcccaacca ggctgggtgc ggtggctcat  87720
gtctgtaatc ccagcacttt gggaggccaa ggtaggcaga tcccttgagg ccaggagtgc  87780
aagactagcc tggctgacat ggtgaaaccc cgtctttact aaaaatacaa aagttagcca  87840
ggcatggtgg tacacacctg taatcccagc tacatgggag gagtaggagg caggagaatt  87900
gcttgaacct gggaggtgga ggttgctgtg agccgagatc atgccactgc actccagcct  87960
gggcgacaga gtgagtgaga ctctgtttaa aaaaaaaaaa aaaaaagaac attctcctaa  88020
```

```
cctggcttct tcctccaggg gtgtaattaa tcatgtcagt ttcctcattg atacacacac  88080
acacacacta caatcctgta tccattactt ttcaaggtac atttactatt tacgtttggg  88140
gtccttgtct ctttttaat agtgtttctt aaagtcttgt attatatcag agtacagtaa  88200
catcccagtc aagagcactc tagtaagctc taggaggaaa gcgacttccg gaaggcagtg  88260
gagacctgtc ctgttggggc agcatagggg cagcccctgc ctctggtcag ttctggcgct  88320
caggctcagg gttgcctctg ggctgttctt cccagagact gacaaagggc tcccataagg  88380
cacctgcaga gcctgtgaga agctgaagtc aatgttttcc tgacaccagt tgatctgtgc  88440
aggatccatt gatttaacca cctgctgtgt ggcatgcact gtggtcgatg ccaggaacag  88500
gaattggagg ggcccatgag catggccagt atcacaggct ggaggtgctg ctgcgctctg  88560
accgggcctc ttggggatga gcccatgtca accaccttgc ctccgatggg gtcgggccca  88620
caggttacct ttgtgtgtcc atgaccacac cttcctcccc gacctcatcc aaatctcttt  88680
cttttccaag cccctgaatc cttcagggct gcaggttttg tttaaagcag agctggtgag  88740
ttgcataggt tgttgcgttg ggactagatg gggtgttcaa agagttggga gttaaaaaac  88800
ataaagggta tttattagga gaaccaagga gtgtaattct cctgttctta atatgcggcc  88860
aggttaatga atgtcacgtg aatgaaccag aaaaaaatga agtgtgccct tgatcagctg  88920
ggttggtgtg cagcaagctg tgtgaccagg ggacagcagt ggtcctgagg gccgtcactg  88980
tctgccgtgc agagcccttc ctcccacggg ggcctacctc acctgtgcca agggcttgtc  89040
tgtggtcagt gacctggata gatctgaatg gggcttcttt ttcgaggagt cttatggcag  89100
gtctctcagt aaagactcca ttcttgatga tcacacattt tggattttcc aaatctgtca  89160
gagaatgggc ttgaggcggg gtttgtgggc actagtttca ctggtttcat ttaccaaaaa  89220
ggggagcaga agtcaagtat ggtggctcat ccctgtaatc ccagaggcaa gagaattgct  89280
tgagcccagg agttcgagac cagcctgagc aacataagga gaccccgtct ccacaaaaat  89340
gaaaaataac attttagtca gacgtggtgg catgcatctg tggtcccagc tgcttgggag  89400
ggtgagatgg gagggttgtt tgagccctgg agttaaagtt gcaatgagct gtgattgcac  89460
cactgcactc tagcctgggt gacagaacga gaccctgtct caaaaaaaaa aaaaaagaaa  89520
gaaaaaaagg aaaaaaaaaa ctcatgcctg taatcccagc actttgggga ccggggtggg  89580
cagatcacga ggtcaggaga tcaagactat cctagccaac atggtgaaac cccgtttcta  89640
ctaaaaatac aaaaattagc caggtgtggt ggcacgtgcc tgtaatccca gttactcggg  89700
aggctgaggc aggagaatcg cttgaaccag ggagtcagag gttgcagtga gctgagatcg  89760
tgccactgta ctccagcctg ggcgacagag tgagactctg tctcaaacca aaaaaaaggg  89820
gtggggggcg ggggcaggag aacagtgaga ggtagggaga ggaaagggga ttctcgctac  89880
acccaaacca gataccatct agaggctaga atctttggga ggctcaaatt ccctagaaag  89940
caggagaagc ttctgtagcc ctcccgcttt cccagtagat taagcccagg gcggctccag  90000
atgtgtgaca tgctctgtgc ccaaccagag cccatcatag gcagaggaat aacacccaca  90060
ccagaagggc cctcggaggt caccacgtcc aagaaccctc tttacagatg aggaaactga  90120
ggcccagaga ggggagagcc acctagcgag ctggtggcgg ctagaccagg agagctgtca  90180
ttccaagcaa gcaaaggcaa cgagacgagc ccagagctgt gctcccatct ctttgttagg  90240
gggcctggga tgccctctca gtgtcatttt gtccaggatg atgctccctc tcttaagcga  90300
ttaatgcgcc cttgctaacc ttttgctatc gctgcctctt caaaccagag gagttgagag  90360
```

```
ttccgggccg gcagaggaag gcgcctgaaa ggcccctggc caatgagatt agcgcccacg  90420
tccagcctgg accctgcgga gaggcctctg gggtctctgg gccgtgcctc ggggagaaag  90480
agccagaagc tcccgtcccg ctgaccgcga gccttcctca gcaccgtccc gtttgcccag  90540
cgcctcctcc aacaggaggc cctcaggagc cctccctgga gtggggacaa aaaggcgggg  90600
actgggccga gaagggtccg gcctttccga agcccgccac cactgcgtat ctccacacag  90660
agcctgaaag tggtaaggtg gtccaggaag gcttcctccg agagccaggc cccccaggtc  90720
tgagccacca gctcatgtcc ggcatgcctg gggctcccct cctgcctgag ggccccagag  90780
aggccacacg ccaaccttcg gggacaggac ctgaggacac agagggcggc cgccacgccc  90840
ctgagctgct caagcaccag cttctaggag acctgcacca ggaggggccg ccgctgaagg  90900
gggcaggggg caaagagagg ccggggagca aggaggaggt ggatgaagac cgcgacgtcg  90960
atgagtcctc cccccaagac tcccctccct ccaaggcctc cccagcccaa gatgggcggc  91020
ctccccagac agccgccaga gaagccacca gcatcccagg cttcccagcg gagggtgcca  91080
tccccctccc tgtggatttc ctctccaaag tttccacaga gatcccagcc tcagagcccg  91140
acgggcccag tgtagggcgg gccaaagggc aggatgcccc cctggagttc acgtttcacg  91200
tggaaatcac acccaacgtg cagaaggagc aggcgcactc ggaggagcat ttgggaaggg  91260
ctgcatttcc aggggcccct ggagaggggc cagaggcccg gggcccctct ttgggagagg  91320
acacaaaaga ggctgacctt ccagagccct ctgaaaagca gcctgctgct gctccgcggg  91380
ggaagcccgt cagccgggtc cctcaactca aaggtctgtg tcttgagctt cttcgctcct  91440
tccctgggga cctcccaggc ctcccaggct gcgggcactg ccactgagct tccaggcctc  91500
ccgactcctg ctgcttctga cgttcctagg acgccactaa atcgacacct gggtgcagct  91560
gctccactcc ctcggcctcc tcccgtgctc aggctgtggc cgcacgcgcc cctcacgctt  91620
gcccgccact ctgcatgtca ccagcacccc cgctccgtgc tccccacctt gtttgactct  91680
ctggccactt gatttgtcca caacggccca tcagcccaca ggaggtttgg tgggtgcctt  91740
ccaccgacag gatgacgggt gccctcatgg tgtctagaac tctccaaccc tcccatgtag  91800
gcataagcag ccccactttg cagatgagga aacggaggct cagagaagta cagtaacttg  91860
ccgaaggcca atgagtagta agtgacagag ccaggtttgg gatccaggta ggttgtctct  91920
gaaagacacg cctgtcctgc atcccacaac gcctcccagg aggtgctgga gtgtggacgc  91980
ctaacacaga gatgtgcagg gcacacacag caggtgacac acacagcatc cagaggtggc  92040
ccagagctca tgctgtgcct ttggcccagt gccctgcccc cacccactct gccttgtggc  92100
aggaagacaa ggagcagaca caagatctcc ctggtccaca tgccaccacc tccctctgca  92160
gaggacaagg ggatcctcat gctggcattg gagggggttg agcagggccc accttgagcc  92220
ctcaggagca cgaccacagc agccctgcag ggagggattg gtgggaggag agtcccaagt  92280
atcagggaga ggagagttgg tgtcccacag gagacctcag agccacaagg cgagcttgtt  92340
cataaatttg ggacccttag catttcacag ttatttgcag agcccagaaa tggatgttac  92400
tgaagctcac agttgcaagc atctgttaaa tttttattag attttacttt tagggaaaac  92460
tttgaaatgc tataaagaag cctgtgttta aaagttaaga cagaggctgg gggcgatggc  92520
tcacgcctgt aatctcagca ctttgggagg ccaaggcagg tggatcattt gaggttagga  92580
gttcgagacc agcctggcca acatggtgag accctgtctc tactaaaatt acaaaaaatt  92640
agctgggcgt ggtggcgggc acctgtagtc ccagctactg ggaggctgga agcaggataa  92700
gtgcttgaac ccaggaggcg gaggttacag tgagccaaga tcacaccact gtaccctaag  92760
```

cctgggcgac agagtgagac tctgtctcaa aaaataaaat aaaataaagt taagagagaa 92820
aaaaatatat cctatatcct ttgttaaatt ccaaaacagt aggggacaaa taactgactt 92880
gacaggttac tacaatattt cctgaaatga tgttttcttg aatactggcc tactagaggt 92940
tcataggtgt gtttggatta aaaaagagtt ccatggccca gtgactgggg gaaaaaaata 93000
aaagactaaa gtaagttaaa caggcttttc tgctgcagga cttgtcagag cctttaatgt 93060
actaatggcc attgtgaccc tctgagaagg tcacagagtg ggtttcccaa acttacttga 93120
ttctacctgc taacatttcc tggaggaagt ttgggaaatg ccgatttagc agattctttt 93180
gttgtgccgt ggatggtgct ggttgatgtg ggcaaaacaa agaacacgtg agtcagatcc 93240
gcctggggct cttactaaag tgcaggttcc caggtgccac tttaggctta cagacccagt 93300
tgtggggtaa gcctgggagt cttttagcag gtgattctgc cacatagtat agttggaaaa 93360
cctctgggca tactcattgc tggtccctct agaaatccag gtgacaatag ccaatgagaa 93420
gctccaagag acccagttgt ccatggggta gagggaatgt gatattgaaa ccaaagaaga 93480
aaatctatga tcagttttca gcagtgactg tcaagagaag gagaagggtg agttagcgct 93540
gatgctggct gacaggtcag cgggttggtt tcaccaagga gtgtgatgaa ggctgatgtt 93600
gtctgtggga atgtatgatg gtaactggtt tgtagctaat ttggggaagc agtgagaatt 93660
cgtgcccttt gaagaccagt aagtggcaag aaacccacca ggcctggctc agggctgggc 93720
tgggcttggc tcgtctcaga gcagctgggg ctggtggcca aagccaccat tagtgagggg 93780
caggccctgg gggtacaacc agcaactagg ggacaaagac aaccctgcca gcctctccta 93840
ttctggaggc gtgtgaccag aaatggagat gggttggtca gcataagatg gccaggaagg 93900
tggaaatcag gactgctggc aatctagcca catgggcagg ggagccgggt ggttccaggc 93960
agtttccaag gccaagaggg tgagcaggca cctcacaggg aatcagggcc aagcctggct 94020
gcagtgtgga gacaatgcac ccacccccat ccttggatct tgcaggaggc tgggtcctca 94080
ctgagctacc aacatccatg gccctgaggc ttttaaaaca cccatccatg gagtggggct 94140
ggtcccagtg gggtgaggct gaccctggca gaaacagggc aggagcctgt gggttaggga 94200
gactgcacct tccttagata gcctccatgc catcatgtcc ccgtgacagt ttctgctgcg 94260
tcccctctgc atggtcccac cctcggccag cctgctgccc cctcttgcca ggttgcgcta 94320
atcagtgacc ccagtgtgct gtgttgatac taacaatgcg aggcctagca gattcaaggg 94380
aaaagagaac caactgggtt tccaccagac ccaactaaac aaacatggac ctatcccaga 94440
gaaatccagc ttcaccacag ctggctttct gtgaacagtg aaaatggagt gtgacaagca 94500
ttcttatttt atattttatc agctcgcatg gtcagtaaaa gcaaagacgg gactggaagc 94560
gatgacaaaa aagccaaggt aagctgacga tgccacggag ctctgcagct ggtcaagttt 94620
acagagaagc tgtgctttat gtctgattca ttctcatata taatgtgggg agtatttgtc 94680
actaaagtac agctgtcatt taaagtgctt tgtattttgg ggcaggcttt taaaaagtcc 94740
agcatttatt agttttgata cttaccccag ggaagagcag ttggcaggtt catgaagtca 94800
tgctcctaat tccagctttc ttagtgtact ttcagtgaga ccctgacagt aaatgaaggt 94860
gtgtttgaaa accaaaccca ggacagtaaa tgaaggtgtg tttgaaaacc agccctagga 94920
cagtaaatga agccatcttc tcactgcata aactgcaccc agatctttgc ccatccttct 94980
cagtatttca cttcacccat tgtttactgt ctcaatgact ggggaaatgt ctggggaaat 95040
gctcccgtaa ttgcacagtg gcgtttttcc tggaaaatcc caccatggct ctagataaga 95100

```
cctatttttc ttaaaggtat ctaaaatttc cagcataaat tctgtctgaa acacctgaat  95160
tttaatcagt actggagccc ggagggcatc tccagttgcc acatagctct gagcattcag  95220
tggtgtgttg agggctgctc ccggaagtgc ctgcagagtc agggctcccc agcctcatct  95280
agtgaggcag tggaagggcc tgtggggatt tggagagctg gcctgggtct ctgaagtgat  95340
agtgacagct gcttgtcaat cacggtgcac atttagtgcc gggggcaggg ggcagggaat  95400
accagcctca tgcatgcatg cattcatttg ttccttcctt cattcattca ttcagtacac  95460
atgggtacaa catccctgcc ctggagttgc ccagagtcta gggaggggaa agatctatta  95520
ccctgggcct cggccagctg gggagtgctg ctggtggaga ggggccgtgt gcagcgaggg  95580
aaggaggagt cgtcaatacc cccaccccag ctttgctttc ttgtcatcag ccccagggcc  95640
ccagcctgtg tccctcctct cccattgcta cttcatctcc tgggtcctcc ttaccaagcc  95700
tgaccacaca gagggccttg gccgcttcca tggggaattg gaaagcaata agatagcatc  95760
ccctagaagc ccagtgaagt ctgggacagg acccttctct gagctctgac ttgctcttgg  95820
aaacacttcg aggcttagcc tccccacttt gtttcccaag agtgtgacct gttcccctcc  95880
aaacaccccc ttctcctcca gggccatgcc cacccgtcaa aatcccccac gggcaggacg  95940
aactgtgggt gtcagtcacc atctatcctg catcctggtt ccagggcccc ccccagcccc  96000
gcctccatag ggacaggcgt gcagacaccc gtccctggct gcttcctctt gtggaatggg  96060
ttcaaaagta agcagtgttg tttacactga caaactgaaa aaaaaagaaa aagagataac  96120
attggaggct tggcacagtg gctcatgcct gtaatcccag cactttggga ggctaaggtg  96180
ggaggatgtc cccagcccaa gagttctaga ccagcctggg caacatagca agaccccatc  96240
tcaaaaaaaa aatttaattg gccaggcaga ggtgggagga tcacttgaac ccaaagggtg  96300
gaggctgcag tgagccgtga tggcaccact gcactccagc cagggcaaca gagggagacc  96360
ctgtctctaa aacaaacaaa caaacaaaca aacaaaagag ttaacattgg ccagattagg  96420
attcaccaga tagtgttaat attagtttga tttgagactt taatcagaaa gcacatgtgt  96480
ggtgggggtg ggtgtaacct aagtcaggta gaatctttcc aacttggggg gggcacactc  96540
ctgattgtag ccatatgagt ctgtcagtgt ggtggaagag accatgggtt aatgggcagg  96600
taaaaaagca ccttgcctgg aattgagtag aaagtaaggc ccttcagacc ccgtgacaca  96660
cttggggaca ttttcttgag taacatccta agattcatgt accttgatga tctccatcaa  96720
cttactcatg tgaagcacct ttaaaccagt cgtctccaaa ttcaggggca cagtaacatc  96780
caacaggctg gagaaagaac gtactagaac ttccattcct ttttcatgtc ctcttctaaa  96840
agctttgtca gggccaggcg cggtggctca cgcctgtaat cccagcactt tgggaggccg  96900
agacgggtgg atcacgaggt caggagatcg agaccatcct ggctaacaca gtgaaacccc  96960
atctctacta aaaatacaaa aaaacgagcc gggcgtggtg gtgggcgcct gtagtcccag  97020
ctactcggga ggctgaggca ggagaatggc gtgaacccag gaggcagagc ttgcagtgag  97080
ccgagattgc accactgcag tccagcctgg gcgacagagc gagactccgt ctcaaaaaag  97140
aaaaagaaaa agaaaaagaa ctgtgattgg ggaggacggt cactttcctg ttcttactga  97200
tcagaaggga tattaagggt acctgattca aacagcctgg agatcactgc tttcaaccat  97260
tacctgcctt atttattttt agttactgtc ctttttttcag tttgtttccc tcctccatgt  97320
gctgactttt attttgattt tatttatgtt tatgtttaag acatccacac gttcctctgc  97380
taaaaccttg aaaaataggc cttgccttag ccccaaacac cccactcctg gtagctcaga  97440
ccctctgatc caaccctcca gccctgctgt gtgcccagag ccaccttcct ctcctaaaca  97500
```

cgtctcttct gtcacttccc gaactggcag ttctggagca aaggagatga aactcaaggt 97560
aaggaaacca cctttgaaaa gaaccaggct gctctgctgt ggtttgcaaa tgtggggttt 97620
gtttatttgt tttttagcct caaagacctt tcttcaaatg agttctggca tagaagcacc 97680
gtgtaaaata gttagaattc tgggcaaagg ggaaaagaga gctgggggcc atccctctca 97740
gcaccccaca ggctctcata gcagcagctc ctaagacacc tggtgggacc ttggtttcga 97800
aatcgctact ctaaggctgg gcacggtggc tcacacctgt aatcccagct ctttaggagg 97860
ccgaggaggg tggatcacct gagatcagga gttcgagacc agcctggcta acatggcaaa 97920
accctgtctc tactaaaaat acaaaaatta gccgggcgtg gtgttatgcg tggtggtaat 97980
cgcagctact cgggaggctg aggcacaagg attgcttgaa ccccagaggc agaggttgta 98040
gttagctcca gcttgggcga cagagcaaga ccctgtcgca aaaattgttt aaaaaacaaa 98100
cccaaaattg ctactctcat tgggttcctt tgcccattcc tgattttggc aagagaaatg 98160
cttccagatt gccctgatct gggtaggaca gcatcacgcc atagcaacac tgccccgtga 98220
gctcactgcc ccctcaacta gcttgtggtc cttggttaat gtcagtttct tttttgagtt 98280
tgtgttatgt ctaagggtca tctgctgggt aacggaaccc agggactgcc ctagtcccta 98340
gactgtgcca tgcccgactc tgccagcttt gtcagtgatg ctggtgctcg cctcctcggg 98400
tgctcgcctg gtctgagcac acccaaggag ttcttgaggc cttagggttg tttgcgagag 98460
aatgaaagaa cacgacctag ctctctttag catccttggt caggttcaac actgccccca 98520
ggggcctctg gtggagccaa ccaccatcag ccaaataaat ccataattag agtcagaaaa 98580
tggatgtctg catatgtgta gtgcactaat gtcctgccga tgattgacat ggagtggaga 98640
gtgacctgat cattgctgtg agctctgctg gccttggcac aactcatgct gataactaat 98700
gcacacagtt cctctgggag gaaatgtcct cagggaactt ggagtttggg tggggatgtg 98760
ggtttgtgtg cccagcaagc ccttgtggtt gtagcagaca ctagtggcat ctaggaggca 98820
aagggtcacc ccagtcttag ccacgttttg agtcaaggtg gcggagtggg gctggtgttg 98880
actcttggtg gcagtaactt ttcccaatgg tgaaaaaccc ctctatcatg tttcatttac 98940
agggggctga tggtaaaacg aagatcgcca caccgcgggg agcagcccct ccaggccaga 99000
agggccaggc caacgccacc aggattccag caaaaacccc gcccgctcca aagacaccac 99060
ccagctctgg taagaagaac gttctcttga atcttagagg aagctgaagc tctcagaggt 99120
acagccttca ttttaggagg ccttaggcca ctgagaatga ataacccctg gcagctggtc 99180
agcagcttgc agtttactaa gcactggagt cttcattgcc ttctcagtcc ttttgatttc 99240
tgaggcaaat gttgaatccc tacctttttt tttttttttc ttttgagaca gagtttcgct 99300
tttgttatcc aggccggagt gcagtggtgt gatctcagct cactgcatcc tccacctccc 99360
aggttcaagc gattctccta cctcagcctc cctagtagct gggattacag gcacctgcca 99420
ctatgcccgg ctaatttttt gtatttttag tagagacagg gtttcaccat gttggccagg 99480
ctggtctcga acgcctgacc tcaggtgatc cacctgcctc ggcctcccaa agtgctggga 99540
ttacaggcat gagccaccac tcccagcctg aatcctcact ttttatcaat gaagaaattg 99600
aggctgattc tgcagcatga taaaaaaaaa tacagaaaaa ggaaaaaaaa gaaagaaatc 99660
gagcctctga gagtttgctt gactgagtct aaccagctca ttttaaaccc gaggaaaatg 99720
cagtcacatg actactaagt ggcagctctc ggagcctctc tggccccaag tccagggttc 99780
catagaggca gccccagcat ggcatgtttt cagtccccaa atgagactct ggagacaaat 99840

```
gtctctggag acagagcagc agcctggata agtcacaatg ggtgacgtca ctcagggctc  99900
aacccctggg cagcttaact tgctagggac gttaggagtc tgctgcaaaa cctgagggtc  99960
ttagctgagc agtcacaggc tgggcccgtt gccctgggct cctgtgagta aaacccagtc 100020
aattttgagt acccagtaag gcatccattg agttattttg cagccaggag tgctattaag 100080
aacagtcgcg gctgggcgtg gtggctcatg cctgtaatcc cagcactttg ggaggccaag 100140
gtgggcggat cacctgaggt caggagttcg agaccagctt ggccaacatg gcaaaacccc 100200
gtctctaata aaaatacaaa ataattagct gggcgtggtg gcgggcgcct gtaatcccag 100260
cttctcagga gggtgaggaa ggagaatcac ttgaacccag gaggcagagg ttgcagtgag 100320
ctgagatcgc accattgcac tccagcctgg atgacaaaag tgagattcct tctcaaaaaa 100380
aaaaaaaaaa aaacagtcgt cctctttggg gattagggac agcctgcctg cctgcccgag 100440
cacttctctc ttccattgcc ccagtgaagt attccaggcc cctgggttta gactctgcac 100500
catgtagggg tgtctgacct gcacttgctc cttggtggca cgggcagcct atggcacttg 100560
ctgcgggctg tgaccaaagc ctggcctgga tcttggatct tggtgactct gcttctccct 100620
ggcctgaggg agctgcccag agcctgccca ccacctgctg cgtgtctttg cggtggcatt 100680
tctcgcacac atgccgtgcg gtggcacccc caaggatggc cattcactaa ggcccattgt 100740
ttttgtcttt tcgcttcgtg ttttctggcc tggtgttttt ctcatataca tgtgatccag 100800
ggataattcc cagaattttg acaggatttt aagtagcgtt tggatcctgc tgtttttttt 100860
tcacttaaca tcgggccagt tgactcacac tctgtttttt gttgttgttt ttttgagacg 100920
gagtctcact gtgtcaccca ggctgaagtg cagtggcaca atcttggcat actgcaacct 100980
ctgcttccca aattcaagca gtttcctgc ctcagcctcc tgagtagctg ggactacagg 101040
cacaggccac cacgccctgc taatttttgt atttttagta aagacagggt ttcaccattt 101100
tggccagcct agtctcgaac tcctgacctc aagtgatccg cccacctcgg cctcccaaag 101160
tgctgggatt acaggggact cacactttgt aacaacctga aacaacgtga tgcatttccc 101220
tttgggtctt acctgctctt cggtggctgc ctgcaggtgg agagaccctc ccccttgggc 101280
ccctcgacct tgtttcagaa tggggcccct gctgggccag ctgtgggtgc ctgccacgtg 101340
aaggactcat taaggccctg tttaagcctg atgataataa ggctttcgtg gatttttctc 101400
tttaagcgac taagcaagtc cagagaagac cacccccctgc agggcccaga tctgagagag 101460
gtactcggga gcctacttcg ctgggagcag cctccctttg cgtgtgtggc cattcactgg 101520
cttgtgtttc tagagccggg aggacccttt tctgcaatgc agggttcaca cagggttcgc 101580
agcctgaaga tggagcagtc cgaattctct tccctgtgca gtttgcgcag ctgtgtttgt 101640
ctgatgggct ttctaatcct gtgtgctctc cttgacttca gggacaatgg cattacaggc 101700
atgagccacc atgcctggct gtctccctat gtttcagatg aagacatagg cttaaggagg 101760
tcaggtgact tgcccacgac cactctgtaa ataagaggca tgaaaagtat ttggagccac 101820
caccaccaag cccactggtc accctgggtc tctgaagtca gggaggcagg aggatgggag 101880
gtctgaggag gcagagaggc tgagcctgga ggccctggag gccgaggccc catctgttgt 101940
ttccttatgt ggaaaataag aggcttcatt tgtcctattg ccacagagcg tactacttca 102000
ggaacatcca agacatggaa atccgcaggg cacggtggct cacgtctata atcccggcac 102060
tttgggaggt tgaggtggga gaatcgcttg aggccagaag ttcaagacca gcctgagcaa 102120
catagtcaga ccccgtctct ataaaaaaca ttatttttaa aaaagacatg gaagtcaaat 102180
tctaaaaact ggtgctggct gggtgcggtg gctcatgcct ataatcccag cactttggga 102240
```

ggccgaggcg ggtggatcac ctgaggtcag gagttcaaga ccagcctggc caacatggta 102300
aaacctctac taaagaaatc tttactgaaa atacaaaaat ccagtctcta ctaaaataag 102360
tctctactaa aaatacaaaa attagccagg cgtggtgctg cacacctgta atatcagcta 102420
ctcgggaggc tgaggcagga gactcgcttg atcccatgca gcggaggttg cagtgagccg 102480
agatcacgcc attgcactcc agcctgggca tcagaataag actccgtctc aaaaaaaaaa 102540
ccacaaaaaa acaaaacaac aacaaaagaa aactagtgct tattcgtcac tggccaagct 102600
gcccattggc tacatgggtg cttcaaagag ctgcccttct ccaggtctgg ccagcaggta 102660
tgtgttacag caaatgcctg gggcagcggc aggggcattg ctgcgggaag cttctggact 102720
tgcaggaaag ctaagttctc agactgcagg ggagctaagc acacctcggc acagggtgag 102780
gcctgcggtt ctcagacttc agtctttgtg gagcttgaga aaaatgaggc tttgcaggtc 102840
ccacccctag agattctgct ctatccactc ttgaagggga tcgagaaatt tgcattttgc 102900
aactcccact ttcctccttg aaagctccgg agattctgac gcagggttcc gtgggccaca 102960
ctttggaaaa tacagaccca tgagatagaa taccagactg ttgaagtgta acgggggcct 103020
gggaagtgca gtaacagaag caagtttgag ggtaaaggac acccagagga gggagggaca 103080
gcatctgcat ggagaggaga agagaccccc cagcagcttc cagggtgttg gaagggtgcg 103140
ctagtaactg ctatgcatgg caggtgggga actgtacgtc agggcacagc agcatgaagc 103200
ggtatggctc gtgtggacag ctagggacag gcaggcgtgg agcaggcatc ctgttctgaa 103260
ggccaaatcc cacagaggag ccagggtgct ggcaggagcc ctgaactagc cgaacagctg 103320
aacagctgaa cattcaccct gtggggaaag ggtcagaagc gtccaggctt gagggcacag 103380
ctgggtctcg tcactgcatc acccttattt aggataaagg ccctgaagaa ttgtattaga 103440
ggttggcaaa gcatatctac cacctcctgg agccacgctg gccgcaggga ttataattat 103500
ttccattttc aaattaaggc ctctgagctc agagagggga agttacttgt ctgaggccac 103560
acagcttgtt ggagcccatc tcttgaccca aagactgtgg agccgagttg gccacctctc 103620
tgggagcggg tattggatgg tggttgatgg ttttccattg ctttcctggg aaaggggtgt 103680
ctctgtccct aagcaaaaag gcagggagga agagatgctt ccccagggca gccgtctgct 103740
gtagctgcgc ttccaacctg gcttccacct gcctaaccca gtggtgagcc tgggaatgga 103800
cccacgggac aggcagcccc cagggccttt tctgacccca cccactcgag tcctggcttc 103860
actcccttcc ttccttccca ggtgaacctc caaaatcagg ggatcgcagc ggctacagca 103920
gccccggctc cccaggcact cccggcagcc gctcccgcac cccgtccctt ccaaccccac 103980
ccacccggga gcccaagaag gtggcagtgg tccgtactcc acccaagtcg ccgtcttccg 104040
ccaagagccg cctgcagaca gcccccgtgc ccatgccaga cctgaagaat gtcaagtcca 104100
agatcggctc cactgagaac ctgaagcacc agccgggagg cgggaaggtg agagtggctg 104160
gctgcgcgtg gaggtgtggg gggctgcgcc tggaggggta gggctgtgcc tggaagggta 104220
gggctgcgcc tggaggtgcg cggttgagcg tggagtcgtg ggactgtgca tggaggtgtg 104280
gggctccccg cacctgagca cccccgcata acaccccagt cccctctgga ccctcttcaa 104340
ggaagttcag ttctttattg ggctctccac tacactgtga gtgccctcct caggcgagag 104400
aacgttctgg ctcttctctt gccccttcag cccctgttaa tcggacagag atggcagggc 104460
tgtgtctcca cggccggagg ctctcatagt cagggcaccc acagcggttc cccacctgcc 104520
ttctgggcag aatacactgc cacccatagg tcagcatctc cactcgtggg ccatctgctt 104580
aggttgggtt cctctggatt ctggggagat tgggggttct gttttgatca gctgattctt 104640
ctgggagcaa gtgggtgctc gcgagctctc cagcttccta aaggtggaga agcacagact 104700
tcgggggcct ggcctggatc cctttcccca ttcctgtccc tgtgcccctc gtctgggtgc 104760
gttagggctg acatacaaag caccacagtg aaagaacagc agtatgcctc ctcactagcc 104820
aggtgtgggc gggtgggttt cttccaaggc ctctctgtgg ccgtgggtag ccacctctgt 104880
cctgcaccgc tgcagtcttc cctctgtgtg tgctcctggt agctctgcgc atgctcatct 104940
tcttataaga acaccatggc agctgggcgt agtggctcac gcctataatc ccagcacttt 105000
gggaggctga ggcaggcaga tcacgaggtc aggagttcga gaccaacctg accaacaggg 105060
tgaaacctcg tctctactaa aaatacaaaa atacctgggc gtggtggtgg tgcgcgccta 105120
taatcccagc tactcaggag gctgaggcag gagaatcgct tgaacccagg aggcagaggt 105180
tgcagtgagc cgagatagtg ccactgcact ccagtttgag caacagagcg agactctgtc 105240
tcaaaacaaa ataaaacaaa ccaaaaaaac ccaccatggc ttagggccca gcctgatgac 105300
ctcatttttc acttagtcac ctctctaaag gccctgtctc caaatagagt cacattctaa 105360
ggtacggggg tgttggggag gggggttagg gcttcaacat gtgaatttgc ggggaccaca 105420
attcagccca ggaccccgct cccgccaccc agcactgggg agctggggaa gggtgaagag 105480
gaggctgggg gtgagaagga ccacagctca ctctgaggct gcagatgtgc tgggccttct 105540
gggcactggg cctcggggag ctagggggct ttctggaacc ctgggcctgc gtgtcagctt 105600
gcctccccca cgcaggcgct ctccacacca ttgaagttct tatcacttgg gtctgagcct 105660
ggggcatttg gacggagggt ggccaccagt gcacatgggc accttgcctc aaaccctgcc 105720
acctcccccc acccaggatc ccccctgccc ccgaacaagc ttgtgagtgc agtgtcacat 105780
cccatcggga tggaaatgga cggtcgggtt aaaagggacg catgtgtaga ccctgcctct 105840
gtgcatcagg cctcttttga gagtccctgc gtgccaggcg gtgcacagag gtggagaaga 105900
ctcggctgtg ccccagagca cctcctctca tcgaggaaag gacagacagt ggctcccctg 105960
tggctgtggg gacaagggca gagctccctg gaacacagga gggagggaag gaagagaaca 106020
tctcagaatc tccctcctga tggcaaacga tccgggttaa attaaggtcc ggccttttcc 106080
tgctcaggca tgtggagctt gtagtggaag aggctctctg gaccctcatc caccacagtg 106140
gcctggttag agaccttggg gaaataactc acaggtgacc cagggcctct gtcctgtacc 106200
gcagctgagg gaaactgtcc tgcgcttcca ctggggacaa tgcgctccct cgtctccaga 106260
ctttccagtc ctcattcggt tctcgaaagt cgcctccaga agccccatct tgggaccacc 106320
gtgactttca ttctccaggg tgcctggcct tggtgctgcc caagacccca gaggggccct 106380
cactggcctt tcctgccttt tctcccattg cccacccatg cacccccatc ctgctccagc 106440
acccagactg ccatccagga tctcctcaag tcacataaca agcagcaccc acaaggtgct 106500
cccttccccc tagcctgaat ctgctgctcc ccgtctgggg ttccccgccc atgcacctct 106560
gggggcccct gggttctgcc ataccctgcc ctgtgtccca tggtggggaa tgtccttctc 106620
tccttatctc ttcccttccc ttaaatccaa gttcagttgc catctcctcc aggaagtctt 106680
cctggattcc cctctctctt cttaaagccc ctgtaaactc tgaccacact gagcatgtgt 106740
ctgctgctcc ctagtctggg ccatgagtga gggtggaggc caagtctcat gcatttttgc 106800
agcccccaca agactgtgca ggtggccggc cctcattgaa tgcggggtta atttaactca 106860
gcctctgtgt gagtggatga ttcaggttgc cagagacaga accctcagct tagcatggga 106920
agtagcttcc ctgttgaccc tgagttcatc tgaggttggc ttggaaggtg tgggcaccat 106980
ttggcccagt tcttacagct ctgaagagag cagcaggaat ggggctgagc agggaagaca 107040
actttccatt gaaggcccct ttcagggcca gaactgtccc tcccaccctg cagctgccct 107100
gcctctgccc atgaggggtg agagtcaggc gacctcatgc caagtgtaga aaggggcaga 107160
cgggagcccc aggttatgac gtcaccatgc tgggtggagg cagcacgtcc aaatctacta 107220
aagggttaaa ggagaaaggg tgacttgact tttcttgaga tattttgggg gacgaagtgt 107280
ggaaaagtgg cagaggacac agtcacagcc tcccttaaat gccaggaaag cctagaaaaa 107340
ttgtctgaaa ctaaacctca gccataacaa agaccaacac atgaatctcc aggaaaaaag 107400
aaaaagaaaa atgtcataca gggtccatgc acaagagcct ttaaaatgac ccgctgaagg 107460
gtgtcaggcc tcctcctcct ggactggcct gaaggctcca cgagcttttg ctgagacctt 107520
tgggtccctg tggcctcatg tagtacccag tatgcagtaa gtgctcaata aatgtttggc 107580
tacaaaagag gcaaagctgg cggagtctga agaatccctc aaccgtgccg gaacagatgc 107640
taacaccaaa gggaaaagag caggagccaa gtcacgtttg ggaacctgca gaggctgaaa 107700
actgccgcag attgctgcaa atcattgggg gaaaaacgga aaacgtctgt tttccccttt 107760
gtgcttttct ctgttttctt ctttgtgctt ttctctgttt tcaggatttg ctacagtgaa 107820
catagattgc tttggggccc caaatggaat tattttgaaa ggaaaatgca gataatcagg 107880
tggccgcact ggagcaccag ctgggtaggg gtagagattg caggcaagga ggaggagctg 107940
ggtggggtgc caggcaggaa gagcccgtag gccccgccga tcttgtggga gtcgtgggtg 108000
gcagtgttcc ctccagactg taaaagggag cacctggcgg gaagagggaa ttcttttaaa 108060
catcattcca gtgcccgagc ctcctggacc tgttgtcatc ttgaggtggg cctcccctgg 108120
gtgactctag tgtgcagcct ggctgagact cagtggccct gggttcttac tgctgacacc 108180
taccctcaac ctcaaccact gcggcctcct gtgcaccctg atccagtggc tcattttcca 108240
ctttcagtcc cagctctatc cctatttgca gtttccaagt gcctggtcct cagtcagctc 108300
agacccagcc aggccagccc ctggttccca catccccttt gccaagctca tccccgccct 108360
gtttggcctg cgggagtggg agtgtgtcca gacacagaga caaaggacca gcttttaaaa 108420
cattttgttg gggccaggtg tggtggctca cacctaatcc caacacctgg ggaggccaag 108480
gcagaaggat cacttgagtc caggagttca agaccagcct gggcaacata gggagaccct 108540
gtctctacaa ttttttttt aattagctgg gcctgttggc actctcctgt agttccagct 108600
actctagagg ctgaggtggg aggactgctt gagcctggga ggtcagggct gcaatgagcc 108660
atgttcacac cactgaacgc cagcctgggc gagaccctgt atcaaaaaag taaagtaaaa 108720
tgaatcctgt acgttatatt aaggtgcccc aaattgtact tagaaggatt tcatagtttt 108780
aaatactttt gttatttaaa aaattaaatg actgcagcat ataaattagg ttcttaatgg 108840
aggggaaaaa gagtacaaga aaagaaataa gaatctagaa acaaagataa gagcagaaat 108900
aaaccagaaa acacaacctt gcactcctaa cttaaaaaaa aaaatgaaga aaacacaacc 108960
agtaaaacaa catataacag cattaagagc tggctcctgg ctgggcgcgg tggcgcatgc 109020
ctgtaatccc aacactttgg gaggccgatg ctggaggatc acttgagacc aggagttcaa 109080
ggttgcagtg agctatgatc ataccactac accctagcct gggcaacaca gtgagactga 109140
gactctatta aaaaaaaaat gctggttcct tccttatttc attcctttat tcattcattc 109200
agacaacatt tatggggcac ttctgagcac caggctctgt gctaagagct tttgccccca 109260
gggtccaggc caggggacag gggcaggtga gcagagaaac agggccagtc acagcagcag 109320

-continued gaggaatgta ggatggagag cttggccagg caaggacatg cagggggagc agcctgcaca 109380
agtcagcaag ccagagaaga caggcagacc cttgtttggg acctgttcag tggcctttga 109440
aaggacagcc cccacccgga gtgctgggtg caggagctga aggaggatag tggaacactg 109500
caacgtggag ctcttcagag caaaagcaaa ataaacaact ggaggcagct ggggcagcag 109560
agggtgtgtg ttcagcacta aggggtgtga agcttgagcg ctaggagagt tcacactggc 109620
agaagagagg ttggggcagc tgcaagcctc tggacatcgc ccgacaggac agagggtggt 109680
ggacggtggc cctgaagaga ggctcagttc agctggcagt ggccgtggga gtgctgaagc 109740
aggcaggctg tcggcatctg ctggggacgg ttaagcaggg gtgagggccc agcctcagca 109800
gcccttcttg gggggtcgct gggaaacata gaggagaact gaagaagcag ggagtcccag 109860
ggtccatgca gggcgagaga gaagttgctc atgtggggcc caggctgcag gatcaggaga 109920
actggggacc ctgtgactgc cagcggggag aagggggtgt gcaggatcat gcccagggaa 109980
gggcccaggg gcccaagcat ggggggccct ggttggctct gagaagatgg agctaaagtc 110040
actttctcgg aggatgtcca ggccaatagt tgggatgtga agacgtgaag cagcacagag 110100
cctggaagcc caggatggac agaaacctac ctgagcagtg gggctttgaa agccttgggg 110160
cggggggtgc aatattcaag atggccacaa gatggcaata gaatgctgta actttcttgg 110220
ttctgggccg cagcctgggt ggctgcttcc ttccctgtgt gtattgattt gtttctcttt 110280
tttgagacag agtcttgctg ggttgcccag gctggagtgc agtggtgcga tcatagctca 110340
ctgcagcctt gaagtcctga gctcaagaga tccttccacc tcagcctcct gagtagttgg 110400
gaccacaggc ttgcaccaca gtgcccaact aatttcttat attttttgta gagatggggt 110460
ttcactgtgt cgcccaggat ggtcttgaac tcctgggctc aagtgatcct cctgcctcag 110520
cctcgcaaat tgctgggatt acaggtgtga gccaccatgc ccgaccttct ctttttaagg 110580
gcgtgtgtgt gtgtgtgtgt gtgtgggcgc actctcgtct tcaccttccc ccagccttgc 110640
tctgtctcta cccagtcacc tctgcccatc tctccgatct gtttctctct ccttttaccc 110700
ctctttcctc cctcctcata caccactgac cattatagag aactgagtat tctaaaaata 110760
cattttattt atttattttg agacagagtc tcactctgtc acccaggctg gagtgcagtg 110820
gtgcaatctc ggctcactgc aacctccgcc tcccaggttg aagcaactct cctgcctcag 110880
cctccctagt agctgggatt acaagcacac accaccatgc ctagcaaatt tttatatttt 110940
tagtagagga ggagtgtcac catgtttgcc aagctggtct caaactcctg gcctcaggtg 111000
atctgcctac cttggtctcc caaagtgctg ggattacagg tgtgagccac cacgcctgcc 111060
cttaaaaata cattatattt aatagcaaag ccccagttgt cactttaaaa agcatctatg 111120
tagaacattt atgtggaata aatacagtga atttgtacgt ggaatcgttt gcctctcctc 111180
aatcagggcc agggatgcag gtgagcttgg gctgagatgt cagaccccac agtaagtggg 111240
gggcagagcc aggctgggac cctcctctag gacagctctg taactctgag accctccagg 111300
catcttttcc tgtacctcag tgcttctgaa aaatctgtgt gaatcaaatc attttaaagg 111360
agcttgggtt catcactgtt taaaggacag tgtaaataat tctgaaggtg actctaccct 111420
gttatttgat ctcttctttg gccagctgac ttaacaggac atagacaggt tttcctgtgt 111480
cagttcctaa gctgatcacc ttggacttga agaggaggct tgtgtgggca tccagtgccc 111540
accccgggtt aaactcccag cagagtattg cactgggctt gctgagcctg gtgaggcaaa 111600
gcacagcaca gcgagcacca ggcagtgctg gagacaggcc aagtctgggc cagcctggga 111660
gccaactgtg aggcacggac ggggctgtgg ggctgtgggg ctgcaggctt ggggccaggg 111720
agggagggct gggctctttg gaacagcctt gagagaactg aacccaaaca aaaccagatc 111780
aaggtctagt gagagcttag ggctgctttg ggtgctccag gaaattgatt aaaccaagtg 111840
gacacacacc cccagcccca cctcaccaca gcctctcctt cagggtcaaa ctctgaccac 111900
agacatttct cccctgacta ggagttccct ggatcaaaat tgggagcttg caacacatcg 111960
ttctctccct tgatggtttt tgtcagtgtc tatccagagc tgaagtgtaa tatatatgtt 112020
actgtagctg agaaattaaa tttcaggatt ctgatttcat aatgacaacc attcctcttt 112080
tctctccctt ctgtaaatct aagattctat aaacggtgtt gacttaatgt gacaattggc 112140
agtagttcag gtctgctttg taaataccct tgtgtctatt gtaaaatctc acaaaggctt 112200
gttgcctttt ttgtggggtt agaacaagaa aaagccacat ggaaaaaaaa tttctttttt 112260 gttttttgt ttgcttgttt ttttgagaca gagtttcact ctgtcgccca ggctggagtg 112320
cagtggtgcg atctccgccc actgcaagct ccacctcccg ggttcatgct attctcctgt 112380
ctcagcctcc caagtagctg ggactgcagg tgcccgccac cacacctggc taattttttt 112440
gtatttttag tagagacggg gtttcaccgt gttagccagg atggtctcaa tctcctgacc 112500
tcgtcatctg cctgcctcgg cctcccaaag tgctgagatt acaggcgtga gccaccgtgc 112560
ccggccagaa aaaaacattt ctaagtatgt ggcagatact gaattattgc ttaatgtcct 112620
ttgattcatt tgtttaattt ctttaatgga ttagtacaga aaacaaagtt ctcttccttg 112680
aaaaactggt aagttttctt tgtcagataa ggagagttaa ataacccatg acatttccct 112740
ttttgcctcg gcttccagga agctcaaagt taaatgtaat gatcactctt gtaattatca 112800
gtgttgatgc ccttcccttc ttctaatgtt actctttaca ttttcctgct ttattattgt 112860
gtgtgttttc taattctaag ctgttcccac tcctttctga aagcaggcaa atcttctaag 112920
ccttatccac tgaaaagtta tgaataaaaa atgatcgtca agcctacagg tgctgaggct 112980
actccagagg ctgaggccag aggaccactt gagcccagga atttgagacc tgggctgggc 113040
agcatagcaa gactctatct ccattaaaac tatttttttt tatttaaaaa ataatccgca 113100
aagaaggagt ttatgtggga ttccttaaaa tcggagggtg gcatgaattg attcaaagac 113160
ttgtgcagag ggcgacagtg actccttgag aagcagtgtg agaaagcctg tcccacctcc 113220
ttccgcagct ccagcctggg ctgaggcact gtcacagtgt ctccttgctg gcaggagaga 113280
atttcaacat tcaccaaaaa gtagtattgt ttttattagg tttatgaggc tgtagccttg 113340
aggacagccc aggacaactt tgttgtcaca tagatagcct gtggctacaa actctgagat 113400
ctagattctt ctgcggctgc ttctgacctg agaaagttgc ggaacctcag cgagcctcac 113460
atggcctcct tgtccttaac gtggggacgg tgggcaagaa aggtgatgtg gcactagaga 113520
tttatccatc tctaaaggag gagtggattg tacattgaaa caccagagaa ggaattacaa 113580
aggaagaatt tgagtatcta aaaatgtagg tcaggcgctc ctgtgttgat tgcagggcta 113640
ttcacaatag ccaagatttg gaagcaaccc aagtgtccat caacagacaa atggataaag 113700
aaaatgtggt gcatatacac aatggaatac tattcagcca tgaaaaagaa tgagaatctg 113760
tcatttgaaa caacatggat ggaactggag gacattatgt taagtgaaat aagccagaca 113820
gaaggacaga cttcacatgt tctcacacat ttgtgggagc taaaaattaa actcatggag 113880
atagagagta gaaggatggt taccagaggc tgaggagggt ggaggggagc agggagaaag 113940
tagggatggt taatgggtac aaaaacgtag ttagcatgca tagatctagt attggatagc 114000
acagcagggt gacgacagcc aacagtaatt tatagtacat ttaaaaacaa ctaaaagagt 114060
gtaactggac tggctaacat ggtgaaaccc cgtctctact aaaaatacaa aaattagctg 114120
ggcacggtgg ctcacgcctg taatcccagc actttgggag gccgaggcgg gccgatcacg 114180
aggtcaggag atcgagacca tcctagctaa catggtgaaa ccccgtctct actacaaata 114240
caaaaaaaag aaaaaattag ccgggcatgg tggtgggcgc ctgtagtccc agctactcgg 114300
gaggctgagg caggagaatg gcgtgaaccc gggaggcgga gcttgcagtg agccgagatc 114360
gcgccactgc actccagcct gggcgacaag gcaagattct atctcaaaaa aataaaaata 114420
aaataaaata aaataataaa ataaaataaa ataaaataaa ataaaataaa taaaataaaa 114480
tgtataattg gaatgtttat aacacaagaa atgataaatg cttgaggtga tagataccccc 114540 attcaccgtg atgtgattat tgcacaatgt atgtctgtat ctaaatatct catgtacccc 114600
acaagtatat acacctacta tgtacccata taaatttaaa attaaaaaat tataaaacaa 114660
aaataaataa gtaaattaaa atgtaggctg gacaccgtgg ttcacgcctg taatcccagt 114720
gctttgtgag gctgaggtga gagaatcact tgagcccagg agtttgagac cggcctgggt 114780
gacatagcga gaccccatca tcacaaagaa tttttaaaaa ttagctgggc gtggtagcac 114840
ataccggtag ttccagctac ttgggagacc gaggcaggag gattgcttga gcccaggagt 114900
ttaaggctgc agtgagctac gatggcgcca ctgcattcca gcctgggtga cagagtgaga 114960
gcttgtctct attttaaaaa taataaaaag aataaataaa aataaattaa aatgtaaata 115020
tgtgcatgtt agaaaaaata cacccatcag caaaaagggg gtaaaggagc gatttcagtc 115080
ataattggag agatgcagaa taagccagca atgcagtttc ttttattttg gtcaaaaaaa 115140
ataagcaaaa caatgttgta aacacccagt gctggcagca atgtggtgag gctggctctc 115200
tcaccagggc tcacagggaa aactcatgca accctttttag aaagccatgt ggagagttgt 115260
accgagaggt tttagaatat ttataacttt gacccagaaa ttctattcta ggactctgtg 115320
ttatgaaaat aacccatcat atggaaaaag ctcctttcag aaagaggttc atgggaggct 115380
gtttgtattt tttttttcttt tgcatcaaat ccagctcctg caggactgtt tgtattattg 115440
aagtacaaag tggaatcaat acaaatgttg gatagcaggg gaacaatatt cacaaaatgg 115500
aatgggacat agtattaaac atagtgcttc tgatgaccgt agaccataga caatgcttag 115560
gatatgatat cacttctttt gttgtttttt gtattttgag acgaagtctc attctgtcac 115620
ccaggctgga gttcagtggc gccatctcag ctcactgcaa cctccatctc ccgggttcaa 115680
gctattctcc ttcctcaacc tcccgagtag ctgggttgcg caccaccatg cctggctaac 115740
ttttgtattt ttagtacaga cggggtttca ccacgttggc caggctgctc ttgaactcct 115800
gacgtcaggt gatccaccag ccttgacctc ccaaagtgct aggattacag gagccactgt 115860
acccagccta ggatatgata tcacttctta gagcaagata caaaattgca tgtgcacaat 115920
aattctacca agtataggta tacaggggta gttatatata aatgagactt caaggaaata 115980
caacaaaatg caatcgtgat tgtgttaggg tggtaagaaa acggtttttg ctttgatgag 116040
ctctgttttt taaaatcgtt atattttcta ataaaaatac atagtctttt gaaggaacat 116100
aaaagattat gaagaaatga gttagatatt gattcctatt gaagattcag acaagtaaaa 116160
ttaaggggaa aaaaaacggg atgaaccaga agtcaggctg gagttccaac cccagatccg 116220
acagcccagg ctgatggggc ctccagggca gtggtttcca cccagcattc tcaaaagagc 116280
cactgaggtc tcagtgccat tttcaagatt tcggaagcgg cctgggcacg gctggtcctt 116340
cactgggatc accacttggc aattatttac acctgagacg aatgaaaacc agagtgctga 116400
gattacaggc atggtggctt acgcttgtaa tcggctttgg gaagccgagg tgggctgatt 116460
gcttgagccc aggagtttca aactatcctg gacaacatag catgacctcg tctctacaaa 116520
aaatacaaaa aatttgccag gtgtggtggc atgtgcctgt ggtcccagct acttgggagg 116580
ctgaagtagg agaatcccct gagccctggg aagtcgaggc tgcactgagc cgtgatggtg 116640
tcactgcact ccagcctggg tgacaaagtg agaccctatc tcacaaagaa aaaaaacaaa 116700
acaaaaaacc caaagcacac tgtttccact gtttccagag ttcctgagag gaaaggtcac 116760
cgggtgagga agacgttctc actgatctgg cagagaaaat gtccagtttt tccaactccc 116820
taaaccatgg ttttctattt catagttctt aggcaaattg gtaaaaatca tttctcatca 116880
aaacgctgat attttcacac ctccctggtg tctgcagaaa gaaccttcca gaaatgcagt 116940
cgtgggagac ccatccaggc cacccctgct tatggaagag ctgagaaaaa gccccacggg 117000
agcatttgct cagcttccgt tacgcaccta gtggcattgt gggtgggaga gggctggtgg 117060
gtggatggaa ggagaaggca cagccccccc ttgcagggac agagccctcg tacagaaggg 117120
acaccccaca tttgtcttcc ccacaaagcg gcctgtgtcc tgcctacggg gtcagggctt 117180
ctcaaacctg gctgtgtgtc agaatcacca ggggaacttt tcaaaactag agagactgaa 117240
gccagactcc tagattctaa ttctaggtca gggctagggg ctgagattgt aaaaatccac 117300
aggtgattct gatgcccggc aggcttgaga acagccgcag ggagttctct gggaatgtgc 117360
cggtgggtct agccaggtgt gagtggagat gccggggaac ttcctattac tcactcgtca 117420
gtgtggccga acacattttt cacttgacct caggctggtg aacgctcccc tctggggttc 117480
aggcctcacg atgccatcct tttgtgaagt gaggacctgc aatcccagct tcgtaaagcc 117540
cgctggaaat cactcacact tctgggatgc cttcagagca gccctctatc ccttcagctc 117600
ccctgggatg tgactcgacc tcccgtcact ccccagactg cctctgccaa gtccgaaagt 117660
ggaggcatcc ttgcgagcaa gtaggcgggt ccagggtggc gcatgtcact catcgaaagt 117720
ggaggcgtcc ttgcgagcaa gcaggcgggt ccagggtggc gtgtcactca tcctttttttc 117780 tggctaccaa aggtgcagat aattaataag aagctggatc ttagcaacgt ccagtccaag 117840
tgtggctcaa aggataaatat caaacacgtc ccgggaggcg gcagtgtgag taccttcaca 117900
cgtcccatgc gccgtgctgt ggcttgaatt attaggaagt ggtgtgagtg cgtacacttg 117960
cgagacactg catagaataa atccttcttg ggctctcagg atctggctgc gacctctggg 118020
tgaatgtagc ccggctcccc acattccccc acacggtcca ctgttcccag aagcccccttc 118080 ctcatattct aggagggggt gtcccagcat ttctgggtcc cccagcctgc gcaggctgtg 118140
tggacagaat agggcagatg acggaccctc tctccggacc ctgcctggga agctgagaat 118200
acccatcaaa gtctccttcc actcatgccc agccctgtcc ccaggagccc catagcccat 118260
tggaagttgg gctgaaggtg gtggcacctg agactgggct gccgcctcct cccccgacac 118320
ctgggcaggt tgacgttgag tggctccact gtggacaggt gacccgtttg ttctgatgag 118380
cggacaccaa ggtcttactg tcctgctcag ctgctgctcc tacacgttca aggcaggagc 118440
cgattcctaa gcctccagct tatgcttagc ctgcgccacc ctctggcaga gactccagat 118500
gcaaagagcc aaaccaaagt gcgacaggtc cctctgccca gcgttgaggt gtggcagaga 118560
aatgctgctt ttggcccttt tagatttggc tgcctcttgc caggagtggt ggctcgtgcc 118620
tgtaattcca gcactttggg agactaaggc gggaggttcg cttgagccca ggagttcaag 118680
accagcctgg gcaacaatga gacccctgtg tctacaaaaa gaattaaaat tagccaggtg 118740
tggtggcacg cacctgtagt cccagctact tgggaggctg aggtgggagg attgcctgag 118800

-continued tccgggaggc ggaagttgca aggagccatg atcgcgccac tgcacttcaa cctaggcaac 118860
agagtgagac tttgtctcaa aaaacaatca tataataatt ttaaaataaa tagatttggc 118920
ttcctctaaa tgtccccggg gactccgtgc atcttctgtg gagtgtctcc gtgagattcg 118980
ggactcagat cctcaagtgc aactgaccca cccgataagc tgaggcttca tcatcccctg 119040
gccggtctat gtcgactggg cacccgaggc tcctctccca ccagctctct tggtcagctg 119100
aaagcaaact gttaacaccc tggggagctg gacgtatgag acccttgggg tgggaggcgt 119160
tgatttttga gagcaatcac ctggccctgg ctggcagtac cgggacactg ctgtggctcc 119220
ggggtgggct gtctccagaa aatgcctggc ctgaggcagc cacccgcatc cagcccagag 119280
ggtttattct tgcaatgtgc tgctgcttcc tgccctgagc acctggatcc cggcttctgc 119340
cctgaggccc cttgagtccc acaggtagca agcgcttgcc ctgcggctgc tgcatggggc 119400
taactaacgc ttcctcacca gtgtctgcta agtgtctcct ctgtctccca cgccctgctc 119460
tcctgtcccc ccagtttgtc tgctgtgagg ggacagaaga ggtgtgtgcc gcccccaccc 119520
ctgcccgggc ccttgttcct gggattgctg ttttcagctg tttgagcttt gatcctggtt 119580
ctctggcttc ctcaaagtga gctcggccag aggaggaagg ccatgtgctt tctggttgaa 119640
gtcaagtctg gtgccctggt ggaggctgtg ctgctgaggc ggagctgggg agagagtgca 119700
cacgggctgc gtggccaacc cctctgggta gctgatgccc aaagacgctg cagtgcccag 119760
gacatctggg acctccctgg ggcccgcccg tgtgtcccgc gctgtgttca tctgcgggct 119820
agcctgtgac ccgcgctgtg ctcgtctgcg ggctagcctg tgtcccgcgc tctgcttgtc 119880
tgcggtctag cctgtgacct ggcagagagc caccagatgt cccgggctga gcactgccct 119940
ctgagcacct tcacaggaag cccttctcct ggtgagaaga gatgccagcc cctggcatct 120000
gggggcactg gatccctggc ctgagcccta gcctctcccc agcctggggg cccccttccca 120060 gcaggctggc cctgctcctt ctctacctgg gacccttctg cctcctggct ggaccctgga 120120
agctctgcag ggcctgctgt ccccctccct gccctccagg tatcctgacc accggccctg 120180
gctcccactg ccatccactc ctctcctttc tggccgttcc ctggtccctg tcccagcccc 120240
cctccccctc tcacgagtta cctcacccag gccagaggga agagggaagg aggccctggt 120300
cataccagca cgtcctccca cctccctcgg ccctggtcca ccccctcagt gctggcctca 120360
gagcacagct ctctccaagc caggccgcgc gccatccatc ctccctgtcc cccaacgtcc 120420
ttgccacaga tcatgtccgc cctgacacac atgggtctca gccatctctg ccccagttaa 120480
ctccccatcc ataaagagca catgccagcc gacaccaaaa taattcggga tggttccagt 120540
ttagacctaa gtggaaggag aaaccaccac ctgccctgca ccttgttttt tggtgacctt 120600
gataaaccat cttcagccat gaagccagct gtctcccagg aagctccagg gcggtgcttc 120660
ctcgggagct gactgatagg tgggaggtgg ctgcccccctt gcaccctcag gtgaccccac 120720
acaaggccac tgctggaggc cctggggact ccaggaatgt caatcagtga cctgcccccc 120780
aggccccaca cagccatggc tgcatagagg cctgcctcca agggacctgt ctgtctgcca 120840
ctgtggagtc cctacagcgt gccccccaca ggggagctgg ttctttgact gagatcagct 120900
ggcagctcag ggtcatcatt cccagaggga gcggtgccct ggaggccaca ggcctcctca 120960
tgtgtgtctg cgtccgctcg agcttactga gacactaaat ctgttggttt ctgctgtgcc 121020
acctacccac cctgttggtg ttgctttgtt cctattgcta aagacaggaa tgtccaggac 121080
actgagtgtg caggtgcctg ctggttctca cgtccgagct gctgaactcc gctgggtcct 121140
gcttactgat ggtctttgct ctagtgcttt ccagggtccg tggaagcttt tcctggaata 121200
aagcccacgc atcgaccctc acagcgcctc ccctctttga ggcccagcag ataccccact 121260
cctgcctttc cagcaagatt tttcagatgc tgtgcatact catcatattg atcacttttt 121320
tcttcatgcc tgattgtgat ctgtcaattt catgtcagga aagggagtga catttttaca 121380
cttaagcgtt tgctgagcaa atgtctgggt cttgcacaat gacaatgggt ccctgttttt 121440
cccagaggct cttttgttct gcagggattg aagacactcc agtcccacag tccccagctc 121500
ccctggggca gggttggcag aatttcgaca acacattttt ccaccctgac taggatgtgc 121560
tcctcatggc agctgggaac cactgtccaa taagggcctg ggcttacaca gctgcttctc 121620
attgagttac acccttaata aaataatccc attttatcct ttttgtctct ctgtcttcct 121680
ctctctctgc ctttcctctt ctctctcctc ctctctcatc tccaggtgca aatagtctac 121740
aaaccagttg acctgagcaa ggtgacctcc aagtgtggct cattaggcaa catccatcat 121800
aaaccaggta gccctgtgga aggtgagggt tgggacggga gggtgcaggg ggtggaggag 121860
tcctggtgag gctggaactg ctccagactt cagaaggggc tggaaaggat attttaggta 121920
gacctacatc aaggaaagtg ttgagtgtga aacttgcggg agcccaggag gcgtggtggc 121980
tccagctcgc tcctgcccag gccatgctgc ccaagacaag gtgaggcggg agtgaagtga 122040
aataaggcag gcacagaaag aaagcacata ttctcggccg ggcgctgtgg ctcacgcctg 122100
taattccagc actttgggag gccaaggtgg gtggatcatg aggtcaggag attgagacca 122160
tcctggctaa cacagtgaaa ccccgtctct actaaaaata caaaaaatta gccgggcgtg 122220
gtggtgggcg cctgtagtcc cagctactcc ggaggctgag gcaggaaaat ggcgtgaacc 122280
cggaaggcgg agcttgcagt gagcggagtg agcagagatc gcgccactgc actccagcct 122340
gggcgacaga gcgagactcc gtctcaaaaa aaaaaagcac atgttctcgc ttctttgtgg 122400
gatccaggag atagagaata gaaggatggt taccagaggc tgggaagggt agtgagggga 122460
tggtgggggg atggtcaatg ggtacaaaaa aaatagaata agacctagta tttgatagtg 122520
caacagggtg actatagtca ataataattt aattgtacat ttaaaaataa ctaaaagata 122580
gccgggtgca gtggcttacg tctgtaatcc cagtactttg ggaggctgag gtgggcgttt 122640
gagaccagcc tggccaacat ggtgaaaccc catctctact aaaaatacaa aaattagcca 122700
ggcatggtgg cgggcgcctg taatcccagc tactcgggag gctgaggcag gagaatcact 122760
tgaacctggg aggcagaggt tgcagtgagc cgagatcttg ccactgcact ccagcctggg 122820
tgacagtgaa actccgtctc aaaaataaaa ataaaaatac agctgggcac ggtggctcac 122880
gcctgtaatc ccagcacttt gggaggccga ggcgagcgga tcacaaggtc aggagatata 122940
gaccatcctg gctaacacgg tgaaacccgg tctctactaa aaatacaaaa aattagccag 123000
gcgtggtggc aggtgcctat agtcccagct actcacaagg ctgaggcagg agaatggcat 123060
gaacctggga ggcggagctt gcagtgagcc gagattgtgc cactgcactc cagcctgggc 123120
gagagagtga gactccgtct caaaacaaaa acaaaaacaa aaacaaaaac aaacacacaa 123180
caaaaaccta aaagaatata aatggattgt ttgtaacaca aaggacaaat gtttgagggg 123240
atggataccc cattttccat gatgtgatta ttatacattg tgtgtctgta tcaaaacatc 123300
tcatgagccc cataaatata tacacctaac tatgtaccca caaaaattaa aaaaatatat 123360
tttttaaggt gaagagggag gcgagatgct ggccttaacc cctaacccgt tgttctccct 123420
gcaagctgtc cacagggcct ctcagactcg aggttcagct atatggatgc atgagcttgg 123480
tccccagcca acatgggaga cacttcacca tcggcagcag ctacagcaca ggaaccctgg 123540
gtcactgcca tgtcccctct gtgactttgt ttaaacagaa aatgatgctc tgggccggct 123600
gtggtggccc acacctataa tcccagcacc ttgggaggcg ggggtgggca gattgcctga 123660
ggtcaggagt tggagatcag cctggccgac atggcgaaac cccatgtcta ctaaaaatac 123720
aaaaactagc caggcatggt ggcacatgcc tgtaatccca gctacttggg aggctgaagc 123780
aggagaatca cttgaaccca ggaggcagag gctgagtgag ccaagatcgt gccaatgcac 123840
tccagcttgg gtgagggagt gagactccgt ctcaaaaaaa aaaaaaaaga aagaaaaaga 123900
aaagaaagtg atcctactgg aaccatgctt actcccctcc ccacctcaca ctgtgtagaa 123960
attagtgctg tcggccaggc gcggtggctc atgcctgtaa tcgcagcact ttgggaggcc 124020
aaggcaggcg gatcacgagg tcaggagatc aagaccatcc tggctaacac agtgaaaccc 124080
tgtctctact aaaaatacaa aaaattagcc gggcatggtg gcaggcacct gtagtcccaa 124140
ctacttggga ggctgaggca ggagaatggc atgaacctgg gaggcggagc ttgcagtgag 124200
ccaagatcgc gccactgcat accagcctag gtgacagagt gagactcagc aaaaaaagaa 124260
agaaagaaag aaagaaatca gtgctgtcta tacttctttc tgcagtgatg gaaatattct 124320
gtatctgtgc tgtccagtat agtagccact agctacatgt ggcacttgaa acatggctgg 124380
tacagttgag gaagagtggc tgccatatcg gacgacacag ctatagattc tgtcacccca 124440
ccccgagagt ccagagcggg gacttctgcc ttaggcccta ttcagggctg atttttactt 124500
gaacccttac tgtgggaaga gaaggccatg agaagttcag tctagaatgt gactccttat 124560
tttctggctc ccttggacac tttgtgggat ttagtctccc tgtggaaagt attccacaag 124620
tggtgccact accccagctg tgagagcagc tgggagctgc ttttgtcatc tttccctgga 124680
aagtcctgtg ggctgtctct tcctcatgcc ttgtcccatg cttgggcatg gtgtcaagcg 124740
tcaggaggga gaaagggtcc ttatttattt atttagagag ggacccttct tctgttccca 124800
ggctggagtg cagtggtgcg atctcggctc actgcaacct ccgcctcctg ggttcaagtg 124860
attctcctgc ctcagcctcc tgagtagctg agattacagg cacatgccaa catgcccggc 124920
taattttttt tttttttttt tttttttttt tttttttttt tttgagatgg agttgtactc 124980
tcattgccca ggctggaatg taatggcaca atctcggctc actgcaacct ccacctcctg 125040
gattcaagca attctcctgt ctcagcttcc caagtagctg ggattacagg tgcccgccac 125100
catgctcaac taatttttgt attttttttt tagtagagac gaggtttcac catgttggtc 125160
agactggtct caaactcctg acctcaggtg atccacctgc ctcggcctcc caaagtgcta 125220
ggattacagg catgagccac cacgcccggc ctgaaagggt tcttatttag tgtgcatttt 125280
gacattcaat ttaattccaa ggtcttgtgg ggtcatggtt tacaggatgt tgatatagaa 125340
aagacttcac ttaatgggcc gggcgcagtg gctcatgcct gtaatcccag cactttggga 125400
ggccgaggca ggcagatcag gaggtcagga gattgagacc atcctggcta acacagtgaa 125460
accccatctc tactgaaaat acaaaaaatt agctgggcgt ggtggcaggc acctgtagtc 125520
ccagccactc ggttggctga ggcaggagaa tggcatgaac ccgggaggcg gagcttgcag 125580
tgagcagaga ccatgccact gcactccagc ctgggcgaca gagcaagact ctgtctcaag 125640
aaaaaaaaaa aaaaacagac tttacttact ggaagccaac caatgtatat ttagagtaat 125700
ttttcctggg ctgagctgtc atttactttt gcagtatctc aagaagaaga gtttacagtg 125760
taaatatttg atgcacactt tgattatata gatgaagcaa actattttca agagctttgc 125820
aaggacttac ttgtatccaa acaccattct aaaaggagtc ttacctactt ctaaaggctg 125880
gtctctactt ggaaccactt gcttggccct ggttcaagtc ctgctgcaaa cctggaagtc 125940

-continued ctgtcattgt cttcttccct ccagagcagt ggcacccaat ctaattttg ctgtgcccca 126000 gcagcccctg gcactttgcc ctgtagactg cagacctcat gtaatgtatg ttaagtccac 126060
agaaccacag aagatgatgg caagatgctc ttgtgtgtgt tgtgttctag gaggtggcca 126120
ggtggaagta aaatctgaga agcttgactt caaggacaga gtccagtcga agattgggtc 126180
cctggacaat atcacccacg tccctggcgg aggaaataaa aaggtaaagg gggtagggtg 126240
ggttggatgc tgcccttggg tatatgggca ttaatcaagt tgagtggaca aaggctggtc 126300
cagttcccag aggaggaaaa cagaggcttc tgtgttgact ggctggatgt gggccctcag 126360
cagcatccag tgggtctcca ctgcctgtct caatcacctg gagctttagc acgtttcaca 126420
cctgggcccc aacctggaga ggctgaccaa tgggtctcag gggcagctcg gttgctggag 126480
tttttgtttt tatttatttt tatgtattta aggcagggtc tctgtattag tccattctca 126540
cactgctaat aaagacatac ccaagactgg gtaatttata aaggaaagag gtttaatgga 126600
ctcacagttc cacatggctg gggaggcctc aaaatcatgg cggaaggcaa aggagaagca 126660
aaggcatttc ttacatggcg acaggcaaga gagcgtgtgc aggggaactc ccatttataa 126720
aaccatcaga cctcatgaga tttattcact atcatgagaa cagcatggga aagacccgcc 126780
cccatgattc agttacctcc cactgggtcc ctcccatgac acatggaatt atgggagcta 126840
caattcaaga tgagatttgg gtggggacac agccaaacca tatcagtctc cctctgtcat 126900
ccaggctgga gtgcactggc atgatctcgg ctcactgcag cctctacctc cctgggtcag 126960
gtgatcttcc cacctcagcc tcccaggtag ctggaactac aggtacctgc cactatgcct 127020
ggctaaatat tttgtatttc ctgtggagac gaggttttgc cacgttgccc aggctggtct 127080
tgaactcctg aggtcaagca atatgcccac ctcggcctcc caaggtgctg ggattacagg 127140
tgtgagccac agtgctcggc ctaagtcact gcagttttta aagctcccag gtgattcttc 127200
agtgcagtca aaagtgagaa ctggctgggt gcggtggctc atgcctgtaa tcccagcacc 127260
ttgggaggcg aaggtgggca gatggcttga ggtcaggagt tcaagaccag cctggccaac 127320
atggtaaaac cccatctcta ctaaaaatac aaaagttagc tgggtgtggt ggtgcgtgcc 127380
tgtaatccca gctacttggg aggctgaggc atgagaattg cttgaaccca ggggacagag 127440
gttgtagtga gccgagatcg tgccactgca ctccagcctg ggcaacagag tgagattcca 127500
tctcacaaaa aaaaaaaaaa gcgagaacca ctgtcctagg ccctgatgtt tgcaggcaac 127560
taaaaaagga agtggacatc cccagtcagc tgtggcgcac caagaacaag tcatgggaac 127620
ataacctaat tttctaaatg ggttactagg cacttagagc aaaacaatga tgccgaaatc 127680
ctgatttcag caaagcctct gcctgcctgt cttggaagta tccacatgag gctgctgggg 127740
ccttggtgtc cccagcagtt tctagtctct aggtcttgct gtgggtgtct gtgcagtgag 127800
ggtgtgtgtg gcgctgggtg agctctgtct aggcctggca caggatgcgg tctggtagct 127860
gctgcttctc ttctgcagaa gcgcagccaa gcaccctctg ggtttcaggg cccacaccca 127920
gcctgaagtt ctgggagtgg ctcactttcc aaccttcagg gtctcccagc agctgactgg 127980
ggagtggtgg agggaaaagg gattgtatta gtccgttttc acgccgctga tgaagacata 128040
cccgatactg ggcagtctaa aagatagagg tctgatggac tcacagttcc acgtgactgg 128100
ggaggcctga caatcatggt ggaaggtgaa aggcttgtct cacacggtgg cagacaagag 128160
aaaagagctt gtgcagggga actccccttt ataaaaccat cagatctcgg gagacttatt 128220
cactatcatg agaacagcac gggaaagacc ctcctctatg attcaattac ctcccaccag 128280
gtccctccca caacatgtag gaattgtggg aactacaatt caagatgaca tttgggtggg 128340
gacacagcca aaccatatca gggcgtccca gaaagggtat agggtctgag acccaagtca 128400
gcatgagaaa gtatgcttct catggtggcc cagttgggtg gaagtggcag ccgggccgtc 128460
tttccaccag gccactcaag tagcagctga gagacccctg ccctggccag tccccgccct 128520
cccctcttgc cactgcctct ggttctgaac agatgggcac cctcatcttg tatttgtgat 128580
taatgtctaa caatgtagtt ttgtgagaag ggtttgctga tacagccttg ctgcagatgc 128640
tgcgaactgt ggcctggggc agaccttacc tccagacacg ccctgaggca ggggagggca 128700
ctggcccgta gctggccgag agctctcggg ttgcgcgaca gggatacttt tcagcggctg 128760
ggtcgctatc caaagtgaga aaacgaggag ggaccaggag gctgtccgcc tcaagagatg 128820
tgggggccag gtccagttat ctggggaagc agtaagcttc tctgctgttt ctaaccccag 128880
gcctcccctg gtctaaggca gggcctccca gcctcggggc actttaaaga tatctgggcc 128940
tggccccatc cccacagtct gactgagtgg gtctggatag ggcctgagca ttggtgattt 129000
cctgggtgaa aggaggcccc tcacagtctc tggaagcttc tctgtgttag gaaaagctct 129060
gggcttgact ctgctttgaa agtcaagatc cgcaaatcct ctcagcctca gtttctcctt 129120
cagcaagatg aaatggaaat gctgtaccta cgtcccgggg tggttgtgag acccaaaaaa 129180
gacaatgttc tggaaggttc ctggtgcgtt gcagtcctct aagaacctga gttagagcca 129240
cgctgagtct cagcttcttg gctccttctg tttcaaactc gtccatgtga tagctcagga 129300
agggtaggca gggccctgcc ccctactcag aaaacaccat cctggtcctg gggatccccg 129360
cagcattagt cccctgtttt cccagtgtat tgagaaaaat tgctaacaag cagtggggca 129420
caccaccagc ctcctgggtt cctttcagtt tggggatttt tggacattcc caggaatgtc 129480
ttaaaaaaca cttcaaaaaa cattaacata aatattttta tcaaagcctg tattaaatgg 129540
tctttcaaga aaatacagta acaggtcagg catggtggct catgcctgta accccagcac 129600
tttgggaggc caaggcaggc agatcacctg aaatcaggag ttcaagacca acctggccaa 129660
cacagccaaa tcccatctct acaaaaaata caaaaattag ctgggtgtgg tggcacacac 129720
ctgtagtccc agctacttgg gaggccgagg caggagaatt gcttgatccc ggaggcggag 129780
gttgcagtga gccgagatcg tgccactgca ctccagcgtg ggtgacaagg tgaatctttg 129840
tctcaaaaaa aaaaaaaaaa aaaagataaa atacagtata cagtaataga gaacaatcct 129900
tttttcaaag tagtgacccc aaatgaacaa aatatgcatc tagcttaaat gcgaacctgg 129960
ttttctctac gcccattcaa gcccctgcaa taggggccct tcaccccgca tccatggact 130020
cctaaaatta tatggaaaat ggctgtgtgt gagtgtggat ggacatgtgc acacatattt 130080
ttggctttac cagatgctca aagagcctag gacccaaaaa gggctgagaa tgaccgtgtc 130140
ggccacttca gggtcatcag gaattgctgt gcactgctca cttctccagt gaacactttc 130200
tgcttctgtg tttcctggta tcctttggga ctcctggcta ggtcatgtgt ttctctactt 130260
tcaaaagggc ttcagccagg cacgatggca tgagcctgta gtcccagttg ctctggaggt 130320
taaggtggga agattgcttg agcccaggaa tttgaggcca gcctgggcaa gtagataggt 130380
agatgattga tagatagata gatagataaa tagatggata gataagtcgc tagacagtca 130440
tccatccacc catccacaca taaaaaggcc tttgtcatgt catgttttgt ggcccacctg 130500
ccagtgttgc ccacagttgc tgcccctcca aactcatcag tcactggcaa acaggaggaa 130560
tgtgtggctc atgtctgggc atcagtggct gtgggagaca tccttgatct tctccagctt 130620
ctccttccac attttccttt gcaatctggc aatatctatt aaaataaaat gtgcatgcct 130680
tttgacctaa gagcttcact tctaggaccc acttacacgt gtgtgacatg atgttcatac 130740
gggtttattt atctgaggtt gttcatacac accattgcct gtaatcacta aaggcgggag 130800
cagcctacac atccatccac agaggagtag atgccttttg gtacatccgt ggcgacggaa 130860
tactaagcag cctgtgtatc tatacactca cacgtgtttg tttatgtgtg gaatatctct 130920
ggagggtaca caagaaactt aaaatgatca ctgtctctgg ggagggtacc tgggtgcctg 130980
ggaggcaggt cagggaagga gtgggcacag gtattaccaa ttggaagaca ataaaaacaa 131040
cagctcctgg ccaggcgcag tggctcacgc ctgtaatggc agcactctga gaggctgagg 131100
cgggcagatt gcttgcgtcc aggagttcaa gaccagcctg ggcaacatag caaaaccccg 131160
tttctattaa aaatacaaaa aattagccag gtgtggtggc atgcacctgt aatcccagct 131220
actcgggagg ctgaggtggg agaatcacct gagcctggga ggtcaaggct gcagtgaggt 131280
gagattgtgc caccgcactc tagcctgggc gatagagcaa gaccctgtct caaaaacaaa 131340
caaaaaacag tccctggcac tctgggccag gcctggcagg gcagttggca gggctggtct 131400
ttctctggca cttcatctca ccctccctcc cttcctcttc ttgcagattg aaacccacaa 131460
gctgaccttc cgcgagaacg ccaaagccaa gacagaccac ggggcggaga tcgtgtacaa 131520
gtcgccagtg gtgtctgggg acacgtctcc acggcatctc agcaatgtct cctccaccgg 131580
cagcatcgac atggtagact cgccccagct cgccacgcta gctgacgagg tgtctgcctc 131640
cctggccaag cagggtttgt gatcaggccc ctggggcggt caataattgt ggagaggaga 131700
gaatgagaga gtgtggaaaa aaaaagaata atgacccggc ccccgccctc tgcccccagc 131760
tgctcctcgc agttcggtta attggttaat cacttaacct gcttttgtca ctcggctttg 131820
gctcgggact tcaaaatcag tgatgggagt aagagcaaat ttcatctttc caaattgatg 131880
ggtgggctag taataaaata tttaaaaaaa aacattcaaa aacatggcca catccaacat 131940
ttcctcaggc aattcctttt gattcttttt tcttcccccct ccatgtagaa gagggagaag 132000
gagaggctct gaaagctgct tctgggggat ttcaagggac tgggggtgcc aaccacctct 132060
ggccctgttg tgggggtgtc acagaggcag tggcagcaac aaaggatttg aaacttggtg 132120
tgttcgtgga gccacaggca gacgatgtca accttgtgtg agtgtgacgg gggttggggt 132180
ggggcgggag gccacggggg aggccgaggc aggggctggg cagaggggag aggaagcaca 132240
agaagtggga gtgggagagg aagccacgtg ctggagagta gacatccccc tccttgccgc 132300
tgggagagcc aaggcctatg ccacctgcag cgtctgagcg gccgcctgtc cttggtggcc 132360
gggggtgggg gcctgctgtg ggtcagtgtg ccaccctctg cagggcagcc tgtgggagaa 132420
gggacagcgg gtaaaaagag aaggcaagct ggcaggaggg tggcacttcg tggatgacct 132480
ccttagaaaa gactgacctt gatgtcttga gagcgctggc ctcttcctcc ctccctgcag 132540
ggtagggggc ctgagttgag gggcttccct ctgctccaca gaaaccctgt tttattgagt 132600
tctgaaggtt ggaactgctg ccatgatttt ggccactttg cagacctggg actttagggc 132660
taaccagttc tctttgtaag gacttgtgcc tcttgggaga cgtccacccg tttccaagcc 132720
tgggccactg gcatctctgg agtgtgtggg ggtctgggag gcaggtcccg agccccctgt 132780
ccttcccacg gccactgcag tcacccctgt ctgcgccgct gtgctgttgt ctgccgtgag 132840
agcccaatca ctgcctatac ccctcatcac acgtcacaat gtcccgaatt cccagcctca 132900
ccacccccttc tcagtaatga ccctggttgg ttgcaggagg tacctactcc atactgaggg 132960
tgaaattaag ggaaggcaaa gtccaggcac aagagtggga ccccagcctc tcactctcag 133020
ttccactcat ccaactggga ccctcaccac gaatctcatg atctgattcg gttccctgtc 133080
tcctcctccc gtcacagatg tgagccaggg cactgctcag ctgtgaccct aggtgtttct 133140
gccttgttga catggagaga gccctttccc ctgagaaggc ctggcccctt cctgtgctga 133200
gcccacagca gcaggctggg tgtcttggtt gtcagtggtg gcaccaggat ggaagggcaa 133260
ggcacccagg gcaggcccac agtcccgctg tcccccactt gcaccctagc ttgtagctgc 133320
caacctccca gacagcccag cccgctgctc agctccacat gcatagtatc agccctccac 133380
acccgacaaa ggggaacaca ccccccttgga aatggttctt ttcccccagt cccagctgga 133440
agccatgctg tctgttctgc tggagcagct gaacatatac atagatgttg ccctgccctc 133500
cccatctgca ccctgttgag ttgtagttgg atttgtctgt ttatgcttgg attcaccaga 133560
gtgactatga tagtgaaaag aaaaaaaaaa aaaaaaaagg acgcatgtat cttgaaatgc 133620
ttgtaaagag gtttctaacc caccctcacg aggtgtctct cacccccaca ctgggactcg 133680
tgtggcctgt gtggtgccac cctgctgggg cctcccaagt tttgaaaggc tttcctcagc 133740
acctgggacc caacagagac cagcttctag cagctaagga ggccgttcag ctgtgacgaa 133800
ggcctgaagc acaggattag gactgaagcg atgatgtccc cttccctact tccccttggg 133860
gctccctgtg tcagggcaca gactaggtct tgtggctggt ctggcttgcg gcgcgaggat 133920
ggttctctct ggtcatagcc cgaagtctca tggcagtccc aaaggaggct tacaactcct 133980
gcatcacaag aaaaaggaag ccactgccag ctggggggat ctgcagctcc cagaagctcc 134040
gtgagcctca gccacccctc agactgggtt cctctccaag ctcgccctct ggaggggcag 134100
cgcagcctcc caccaagggc cctgcgacca cagcagggat tgggatgaat tgcctgtcct 134160
ggatctgctc tagaggccca agctgcctgc ctgaggaagg atgacttgac aagtcaggag 134220
acactgttcc caaagccttg accagagcac ctcagcccgc tgaccttgca caaactccat 134280
ctgctgccat gagaaaaggg aagccgcctt tgcaaaacat tgctgcctaa agaaactcag 134340
cagcctcagg cccaattctg ccacttctgg tttgggtaca gttaaaggca accctgaggg 134400
acttggcagt agaaatccag ggcctcccct ggggctggca gcttcgtgtg cagctagagc 134460
tttacctgaa aggaagtctc tgggcccaga actctccacc aagagcctcc ctgccgttcg 134520
ctgagtccca gcaattctcc taagttgaag ggatctgaga aggagaagga aatgtggggt 134580
agatttggtg gtggttagag atatgccccc ctcattactg ccaacagttt cggctgcatt 134640
tcttcacgca cctcggttcc tcttcctgaa gttcttgtgc cctgctcttc agcaccatgg 134700
gccttcttat acggaaggct ctgggatctc ccccttgtgg gggcaggctc ttggggccag 134760
cctaagatca tggtttaggg tgatcagtgc tggcagataa attgaaaagg cacgctggct 134820
tgtgatctta aatgaggaca atccccccag ggctgggcac tcctccccctc ccctcacttc 134880 tcccacctgc agagccagtg tccttgggtg ggctagatag gatatactgt atgccggctc 134940
cttcaagctg ctgactcact ttatcaatag ttccatttaa attgacttca gtggtgagac 135000
tgtatcctgt ttgctattgc ttgttgtgct atggggggag gggggaggaa tgtgtaagat 135060
agttaacatg ggcaaaggga gatcttgggg tgcagcactt aaactgcctc gtaacccttt 135120
tcatgatttc aaccacattt gctagaggga gggagcagcc acggagttag aggcccttgg 135180
ggtttctctt ttccactgac aggctttccc aggcagctgg ctagttcatt ccctccccag 135240
ccaggtgcag gcgtaggaat atggacatct ggttgctttg gcctgctgcc ctctttcagg 135300
ggtcctaagc ccacaatcat gcctccctaa gaccttggca tccttccctc taagccgttg 135360
gcacctctgt gccacctctc acactggctc cagacacaca gcctgtgctt ttggagctga 135420
gatcactcgc ttcaccctcc tcatctttgt tctccaagta aagccacgag gtcggggcga 135480
gggcagaggt gatcacctgc gtgtcccatc tacagacctg cggcttcata aaacttctga 135540
tttctcttca gctttgaaaa gggttaccct gggcactggc ctagagcctc acctcctaat 135600
agacttagcc ccatgagttt gccatgttga gcaggactat ttctggcact tgcaagtccc 135660
atgatttctt cggtaattct gagggtgggg ggagggacat gaaatcatct tagcttagct 135720
ttctgtctgt gaatgtctat atagtgtatt gtgtgtttta acaaatgatt tacactgact 135780
gttgctgtaa aagtgaattt ggaaataaag ttattactct gattaaataa ggtctccatt 135840
catggattcc aaggacaaga aagtcatata gaatgtctat tttttaagtt ctttcccacg 135900
cacccttaga taatttagct cagaacagga aatgatagta ttaataaaag ctggacatca 135960
ggattaacag ctctctctgg ggccctgaag gtgagagttc tcagacttgc tcatttgcag 136020
ttgcttcttt gtgatgctgg caaaccatcc tagtcccatt caaagggcaa tacaaagcct 136080
tgtggctgac ctcacgatgc agcactcagt ttgcaagacc ggcaccagtg tatgcaaacc 136140
tgagaaggtt ggggatgagg atatgggatc tttcatccct ggaaatttag tccagaggcc 136200
tggggctgga gcagaacacc aagccaatca gcttaatgaa tggcttagat tcctgctagg 136260
tttgcagagc tgccttcttt cctttggtac cttattatag attgaggagt atttctgcta 136320
aaccaagata gggataacca gatagcatct tcatagcaat gccacaaagg aaaacaaaaa 136380
caaaacagta atccatcata ttattcctta gtaactatgc caaggtcatg atactgaatc 136440
cttagattgt ttcaaaatac tacttttctt tgctcttcct gatgtgtttg ccaccgcagg 136500
cagatgttta agtaaaacag attttaactg cagctacaaa agcagcaaca ggccagcaaa 136560
agagaagtgc tatctcagag agcatggctt tcagagccac aagagacagc ctcactggct 136620
gtttcagctt gactgccatg caaagaagag agcagaggga gaaccagccc cacccactta 136680
ttcatcttgt acaaaaaaaa agcacctacc agcctaggct acatagtgag acactatctc 136740
cacaaaaaac ccacgaaaac tagctgggta tggtggcaca tgcctacagt cccagctact 136800
ggtaaggctg tggtgggagg atctcttgag gccaggaagg agatccaggc tgcagtgagc 136860
caagattgca ccactgcact ccagtctgga caatcgagca agatcccatc tcaaacaata 136920
aaaaaaaaaa gcgtgtaacc tcctcagaag aaagatgtta taatctcagg cagcaggcaa 136980
gaaccaatcc aggctctaag c 137001

<210> SEQ ID NO 2
<211> LENGTH: 6794
<212> TYPE: DNA
<213> ORGANISM: homo sapiens

<400> SEQUENCE: 2
aagggccctg aaactaaatg tgtcccctta ggaaagcagg agttttcttg caagtggcaa 60
tcttctgctt atgtctcatt ggccagagct gggtcttacg gccacccctt gctgcgagca 120
aggctgggac attgagcatt ttgccgtcca acctctttag cagaataaac caagggggaa 180
gaacgttaat agtggctttt gagtcactag ttggcagtat ctgcccctct atctttccat 240
cctccccatg gagtttcaag gttcctttct cagtacttct tcaggctctg cacgttcatt 300
tggatcttgt gtcttggggt gaaaaactgg cccaagtgtc tccccaagca tccacctttg 360
gattaatttg gaaaatggct gtcaagtgcc cgcctcttgc ttggtataat gctacagctt 420
tagaggacgc agcaggcatg ggccttgccg ctgaggttct tagcctcatg agaatatcca 480

-continued

```
gatcagattc tcttggctcc ttcttagagc cagtgatgca agacacttcc tgctcatctt    540
gtcgggacgg ttttacaagt tgcctgccat cctgagaaag tctacaaaac gatgccagac    600
ctcatgccag cttcccaagc cttgactctc agtgctccct caacaggatt ctggaagaat    660
ctcccaaaca agtcgcaatg ccctctggac cctgtgcagg catgagactc aagagcattg    720
gctcccaccc ctggtggagg gaacactgct ggggctggga tcttgcctgg ttgctccgcc    780
tgcacccaag acaaccataa ttaaaatgtc cttcattgaa cttggaaagc cttcaaagct    840
gacaactcct tatgtgtacc cggaaaggcc tgggagtgtg ccagggcatt gctcgggagg    900
gacgctgatt tggaagcatt tacctgatga gagactgaca gcagctcctg gtagccgagc    960
tttccctcct gcctctgctg tgaaggtgga cccatccaac agtcaaatgc ctgactctgg   1020
acaggagcgg acctatttat tgccatgcaa gggactctgc acttttgaat tgtgggtcat   1080
gggcttggat ttaggggtta gagctgggag aagtcttgga agtcacctag agatgacact   1140
gccattttgc agatgaggaa accgtccaat caaaatggac caaggacttg cccaaagcct   1200
cacagcaaaa ccataggccc ccgcactaac cccagagtcc ctgtgctgtc ttaaggatca   1260
aatagttgta agcaatcatc tggttttcag tatttcttct tttaaaatgc ctggggccat   1320
gcccagcagt ctgtttcact gcagcgttta cacagggctg ccgggctttc ctggtggatg   1380
agctgggcgg ttcatgagcc agaaccactc agcagcatgt cagtgtgctt cctggggagc   1440
tggtagcagg ggctccgggc cctacttcag ggctgctttc tggcatatgg ctgatcccct   1500
cctcactcct cctccctgca ttgctcctgc gcaagaagca aaggtgaggg gctgggtatg   1560
gctcgtcctg gcccctctaa ggtggatctc ggtggtttct agatgtgaca gcacccttag   1620
tggatgaggg agctcccggc aagcaggctg ccgcgcagcc ccacacggag atcccagaag   1680
gaaccacagg tgagggtaag ccccagagac ccccaggcag tcaaggccct gctgggtgcc   1740
ccagctgacc tgtgacagaa gtgagggagc tttgcgtgtt tatcctcctg tggggcagga   1800
acatgggtgg attctggctc ctgggaatct tgggttgtga gtagctcgat gccttggtgc   1860
tcagttacct ccctggctgc ctgccagcct ctcagagcat ttagggcctt ctggacttct   1920
agatgctcct catcttgcct cagtcagcgc gtcagttcca gagacttctc tgcagggttt   1980
tctggggcag gtggtggcag acccgtgcct tcttgacacc tgaggtcagt ccaccctcct   2040
gctcagactg cccagcacag ggtcacctcc caaggggtgg accccaagat cacctgagcg   2100
cacagagggt gcagatgact ggaccacacc ttttggtgat cttaatgagg tggtcccaga   2160
ggagctcaga catgcaatct agcatccagt tctgggactc tgtctccttt tcaaacgtat   2220
tcatgtagaa caggcatgac gagaatgcct tgtcaacatg ggtgatgggg aatcaatcag   2280
acagggcgcc gggctcaagg ctgcagtcac ccaagagtgg ctcagcccac caggccctag   2340
gaaacgcctg cacagcctgg agctcctgga gtcatttcct tcatgtcttc ttcactgcac   2400
ttacgtaaag atgccagcca ttggtttggt gatttggagg gtgcccagtt gcccaacaag   2460
aaatgcagaa gaggcctagc caggatttca ccagcagtgg agagtagaga agatgtggcc   2520
agaaaagagt ttcctttccc tcctaaagat ggtactccct gcagctactg gggaagcctg   2580
cagcattctc tagggctctg tgtgttgaga gcagccccac cctggcccct tctgagtgca   2640
tttctgcttt gtgacttgat ccgtgaagtc ccctgagatg ggcagagggg atgtcctcga   2700
agctggggca gagcctcatc cttgaacgtg aaggacgttt gaagactgtg gcatgatcac   2760
aggatgagat cacagggaac ttgagtttct ctcctcctct cccttcacag ttatttcact   2820
gagggaaatc cctcccctgc ccagaatgaa aactctagcc aactcttgac ttttccatca   2880
```

ctccaaagta gttgaaagta cattagtctc cacagtggca aaacagtgtg caaaagctaa 2940
ataattagaa cagccagtcc catgtgacag tcaaagcttc taactccatt caaagttgca 3000
gccattcccc tcgagggctg gcagggaggg gaggggtaag agaaacagga aggttcttac 3060
tgagttggtc ctggtgtgag ctgcgtcaca ctccctgcag aggtttcaag gagactctct 3120
ctctctctgt ctccatgggg accttatttg aattcttcta ctcttacccc agcctgccat 3180
ctccagctat cctcccctga agagcccttc tgctgcgctg gattctggtg gccatgtcat 3240
ctcctcggcc ccgtgggagt ctgaagatct ggctgcagcc tcacctctga ggtcctgcta 3300
gttgccacct cttaaacatg atctgaggct cccatgcact ctgacctgtg cccacatggg 3360
gcccacggga aacacgctgg caagcaaact gtgggtgtgc agacggttct cagggctgca 3420
gcacctgtcc tttgctctgc ccccaaagca aggccagccc atcttccatc ctctagtgtt 3480
ccttggtggg gccctgacca cagtccacca ggtccctaac cagaggggac acacaccagg 3540
tgtcctcaat gtattgcctt gaaacagttg tgctgggact gtgatggggg gtggccatgt 3600
agccaccccc accaccccca agccactctc tccaaggaaa tcctcctaaa gatcccttta 3660
catcctccat gtggtgggga ggttctagag ttgggtgcat gtgtcttcag ctactgacaa 3720
tgcagacctt agttggcacc tcgctctggc ctatcctgtt tgctgttctt ggcgctccag 3780
tgaaactccc catgggccat ccagttgggg tgcagtgtgg ccaccccctt gcaggttcct 3840
gccttgctgg agagcacagg gccctcctgg ctcttgtaaa acactcccca tggtacagag 3900
aggccagcag tgatgtgagg cccaacctcc ctccatggtg ttcccaagca gctccctttc 3960
tggggtcaag gggtggcaaa gacagtgcag cgtccaattt ctgactcaag ccgggcctgg 4020
ctatcgcagc tctgcactgt gtgtgacagc aaggcaactc acccagtgcc gtggcagtga 4080
ccgtgtccga ggaagcctcc tcacaccctc tgtctcaagg actctggcat ttagctggac 4140
ttgctgtagc tctgagcctt tctgccattg ccatcacctt gtcagaaact caggccgaat 4200
ctgcactcag agttgtgccc aggcagttga gccaacactt gctcagcgat attgtcacat 4260
gacaaggcac tgtcaccact gggcgtcgtg ggtagcgcag tgtcggctgg atggacccgg 4320
agggtgtctg tgtcatgcta gtgctagtga tgggagcccc gtgagcccat tgcccgccct 4380
cccatgccct cagcagctgc ctggggacag ccaatggcct gggtgtttct gaggctacca 4440
catggcttcc aggaaactcg agaacctttc tctcccttgc ctacactctt cacacaggcc 4500
tgtgctggcc agcggtgggg atccggcatt cctatcttag gtgcagaaag tgactgactc 4560
attgcaggcc tgggagataa gactgatggc ccagccagca agatgtatgg atttctcaga 4620
ggcagtggcc tctgtcattg tcctcaggaa atgctggtga ttctggtggc ctgaggtcaa 4680
tgcatgtcaa cgtggccaac ttgccttata aactttttttt ctggacaatt gcgtacactg 4740
tcctgtaaca gtgtcctgtt gtttatgatg cagaaatagg tgtttttaaa gcctattgat 4800
tttggtacta ttaatgtggt caggaacttt ctcagtcttt cttgtttggg gtgagctgtg 4860
gcttcctaaa caggaaccca agacaccccc aaaagctgct caccagcact gccagcctcc 4920
ctcttaccaa gtagcacccg ttcaggacat tctgcgaaag gcatttgccc agaagttggg 4980
aggaaggaaa tgtaacattt tggggcacct accatatgcc aggcaccagg ctaaacgtgt 5040
tcacacaaat tctcttacta accctcacca tccttctaca agacaaacta gtatcttcat 5100
cttggggttc aagatgagga aatggaggct cagagaggtt gaatgaatgc cggtgcctgg 5160
atatgaaccc catctgcctg actccgcaac ccaggcaaag tctttccttg aacttcccag 5220

```
cagccactgc ttagacacag cctccacaac catggctcag cagcaaattg cttctctgac   5280

ctcactcagc ctgtgtgtcc ttgttgagtg aggcattcag gaccctggtc ccaaagtgga   5340

gaaagtcttt cctactaggt catagctaca cctgcatgtg ggtgctgtgc cttttgttta   5400

gtgaactttt atcaccagca tcctcagcaa tgacatttgc agagaagcca gagctgaggc   5460

accttggtat tcttgggatg tgactttcct gaatgtttaa gggaaaatgc ccgaaggtac   5520

agagagcttg gtttctagta aacaataact gtcttgcttt taccccccttt catttgctga   5580

cacatacacc agctgaagaa gcaggcattg gagacacccc cagcctggaa gacgaagctg   5640

ctggtcacgt gacccaagct cgcatggtca gtaaaagcaa agacgggact ggaagcgatg   5700

acaaaaaagc caagggggct gatggtaaaa cgaagatcgc cacaccgcgg ggagcagccc   5760

ctccaggcca gaagggccag gccaacgcca ccaggattcc agcaaaaacc ccgcccgctc   5820

caaagacacc acccagctct ggtgaacctc caaaatcagg ggatcgcagc ggctacagca   5880

gccccggctc cccaggcact cccggcagcc gctcccgcac cccgtccctt ccaaccccac   5940

ccacccggga gcccaagaag gtggcagtgg tccgtactcc acccaagtcg ccgtcttccg   6000

ccaagagccg cctgcagaca gcccccgtgc ccatgccaga cctgaagaat gtcaagtcca   6060

agatcggctc cactgagaac ctgaagcacc agccgggagg cgggaaggtg caaatagtct   6120

acaaaccagt tgacctgagc aaggtgacct ccaagtgtgg ctcattaggc aacatccatc   6180

ataaaccagg aggtggccag gtggaagtaa aatctgagaa gcttgacttc aaggacagag   6240

tccagtcgaa gattgggtcc ctggacaata tcacccacgt ccctggcgga ggaaataaaa   6300

agattgaaac ccacaagctg accttccgcg agaacgccaa agccaagaca gaccacgggg   6360

cggagatcgt gtacaagtcg ccagtggtgt ctggggacac gtctccacgg catctcagca   6420

atgtctcctc caccggcagc atcgacatgg tagactcgcc ccagctcgcc acgctagctg   6480

acgaggtgtc tgcctccctg gccaagcagg gtttgtgatc aggcccctgg ggcggtcaat   6540

aattgtggag aggagagaat gagagagtgt ggaaaaaaaa agaataatga cccggccccc   6600

gccctctgcc cccagctgct cctcgcagtt cggttaattg gttaatcact taacctgctt   6660

ttgtcactcg gctttggctc gggacttcaa aatcagtgat gggagtaaga gcaaatttca   6720

tctttccaaa ttgatgggtg ggctagtaat aaaatattta aaaaaaaaca ttcaaaaaaa   6780

aaaaaaaaaa aagg                                                    6794

<210> SEQ ID NO 3
<211> LENGTH: 6816
<212> TYPE: DNA
<213> ORGANISM: homo sapiens
<220> FEATURE:
<221> NAME/KEY: CDS
<222> LOCATION: (323)...(2653)

<400> SEQUENCE: 3

ggacggccga gcggcagggc gctcgcgcgc gcccactagt ggccggagga gaaggctccc     60

gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca gg atg gct gag ccc cgc cag gag ttc gaa gtg     352
                         Met Ala Glu Pro Arg Gln Glu Phe Glu Val
                          1               5                  10
```

-continued

```
atg gaa gat cac gct ggg acg tac ggg ttg ggg gac agg aaa gat cag      400
Met Glu Asp His Ala Gly Thr Tyr Gly Leu Gly Asp Arg Lys Asp Gln
                15                  20                  25

ggg ggc tac acc atg cac caa gac caa gag ggt gac acg gac gct ggc      448
Gly Gly Tyr Thr Met His Gln Asp Gln Glu Gly Asp Thr Asp Ala Gly
            30                  35                  40

ctg aaa gaa tct ccc ctg cag acc ccc act gag gac gga tct gag gaa      496
Leu Lys Glu Ser Pro Leu Gln Thr Pro Thr Glu Asp Gly Ser Glu Glu
        45                  50                  55

ccg ggc tct gaa acc tct gat gct aag agc act cca aca gcg gaa gat      544
Pro Gly Ser Glu Thr Ser Asp Ala Lys Ser Thr Pro Thr Ala Glu Asp
    60                  65                  70

gtg aca gca ccc tta gtg gat gag gga gct ccc ggc aag cag gct gcc      592
Val Thr Ala Pro Leu Val Asp Glu Gly Ala Pro Gly Lys Gln Ala Ala
 75                  80                  85                  90

gcg cag ccc cac acg gag atc cca gaa gga acc aca gct gaa gaa gca      640
Ala Gln Pro His Thr Glu Ile Pro Glu Gly Thr Thr Ala Glu Glu Ala
                95                 100                 105

ggc att gga gac acc ccc agc ctg gaa gac gaa gct gct ggt cac gtg      688
Gly Ile Gly Asp Thr Pro Ser Leu Glu Asp Glu Ala Ala Gly His Val
            110                 115                 120

acc caa gag cct gaa agt ggt aag gtg gtc cag gaa ggc ttc ctc cga      736
Thr Gln Glu Pro Glu Ser Gly Lys Val Val Gln Glu Gly Phe Leu Arg
        125                 130                 135

gag cca ggc ccc cca ggt ctg agc cac cag ctc atg tcc ggc atg cct      784
Glu Pro Gly Pro Pro Gly Leu Ser His Gln Leu Met Ser Gly Met Pro
    140                 145                 150

ggg gct ccc ctc ctg cct gag ggc ccc aga gag gcc aca cgc caa cct      832
Gly Ala Pro Leu Leu Pro Glu Gly Pro Arg Glu Ala Thr Arg Gln Pro
155                 160                 165                 170

tcg ggg aca gga cct gag gac aca gag ggc ggc cgc cac gcc cct gag      880
Ser Gly Thr Gly Pro Glu Asp Thr Glu Gly Gly Arg His Ala Pro Glu
                175                 180                 185

ctg ctc aag cac cag ctt cta gga gac ctg cac cag gag ggg ccg ccg      928
Leu Leu Lys His Gln Leu Leu Gly Asp Leu His Gln Glu Gly Pro Pro
            190                 195                 200

ctg aag ggg gca ggg ggc aaa gag agg ccg ggg agc aag gag gag gtg      976
Leu Lys Gly Ala Gly Gly Lys Glu Arg Pro Gly Ser Lys Glu Glu Val
        205                 210                 215

gat gaa gac cgc gac gtc gat gag tcc tcc ccc caa gac tcc cct ccc     1024
Asp Glu Asp Arg Asp Val Asp Glu Ser Ser Pro Gln Asp Ser Pro Pro
    220                 225                 230

tcc aag gcc tcc cca gcc caa gat ggg cgg cct ccc cag aca gcc gcc     1072
Ser Lys Ala Ser Pro Ala Gln Asp Gly Arg Pro Pro Gln Thr Ala Ala
235                 240                 245                 250

aga gaa gcc acc agc atc cca ggc ttc cca gcg gag ggt gcc atc ccc     1120
Arg Glu Ala Thr Ser Ile Pro Gly Phe Pro Ala Glu Gly Ala Ile Pro
                255                 260                 265

ctc cct gtg gat ttc ctc tcc aaa gtt tcc aca gag atc cca gcc tca     1168
Leu Pro Val Asp Phe Leu Ser Lys Val Ser Thr Glu Ile Pro Ala Ser
            270                 275                 280

gag ccc gac ggg ccc agt gta ggg cgg gcc aaa ggg cag gat gcc ccc     1216
Glu Pro Asp Gly Pro Ser Val Gly Arg Ala Lys Gly Gln Asp Ala Pro
        285                 290                 295

ctg gag ttc acg ttt cac gtg gaa atc aca ccc aac gtg cag aag gag     1264
Leu Glu Phe Thr Phe His Val Glu Ile Thr Pro Asn Val Gln Lys Glu
    300                 305                 310

cag gcg cac tcg gag gag cat ttg gga agg gct gca ttt cca ggg gcc     1312
Gln Ala His Ser Glu Glu His Leu Gly Arg Ala Ala Phe Pro Gly Ala
315                 320                 325                 330
```

```
cct gga gag ggg cca gag gcc cgg ggc ccc tct ttg gga gag gac aca      1360
Pro Gly Glu Gly Pro Glu Ala Arg Gly Pro Ser Leu Gly Glu Asp Thr
                335                 340                 345

aaa gag gct gac ctt cca gag ccc tct gaa aag cag cct gct gct gct      1408
Lys Glu Ala Asp Leu Pro Glu Pro Ser Glu Lys Gln Pro Ala Ala Ala
            350                 355                 360

ccg cgg ggg aag ccc gtc agc cgg gtc cct caa ctc aaa gct cgc atg      1456
Pro Arg Gly Lys Pro Val Ser Arg Val Pro Gln Leu Lys Ala Arg Met
        365                 370                 375

gtc agt aaa agc aaa gac ggg act gga agc gat gac aaa aaa gcc aag      1504
Val Ser Lys Ser Lys Asp Gly Thr Gly Ser Asp Asp Lys Lys Ala Lys
    380                 385                 390

aca tcc aca cgt tcc tct gct aaa acc ttg aaa aat agg cct tgc ctt      1552
Thr Ser Thr Arg Ser Ser Ala Lys Thr Leu Lys Asn Arg Pro Cys Leu
395                 400                 405                 410

agc ccc aaa cac ccc act cct ggt agc tca gac cct ctg atc caa ccc      1600
Ser Pro Lys His Pro Thr Pro Gly Ser Ser Asp Pro Leu Ile Gln Pro
                415                 420                 425

tcc agc cct gct gtg tgc cca gag cca cct tcc tct cct aaa tac gtc      1648
Ser Ser Pro Ala Val Cys Pro Glu Pro Pro Ser Ser Pro Lys Tyr Val
            430                 435                 440

tct tct gtc act tcc cga act ggc agt tct gga gca aag gag atg aaa      1696
Ser Ser Val Thr Ser Arg Thr Gly Ser Ser Gly Ala Lys Glu Met Lys
        445                 450                 455

ctc aag ggg gct gat ggt aaa acg aag atc gcc aca ccg cgg gga gca      1744
Leu Lys Gly Ala Asp Gly Lys Thr Lys Ile Ala Thr Pro Arg Gly Ala
    460                 465                 470

gcc cct cca ggc cag aag ggc cag gcc aac gcc acc agg att cca gca      1792
Ala Pro Pro Gly Gln Lys Gly Gln Ala Asn Ala Thr Arg Ile Pro Ala
475                 480                 485                 490

aaa acc ccg ccc gct cca aag aca cca ccc agc tct gcg act aag caa      1840
Lys Thr Pro Pro Ala Pro Lys Thr Pro Pro Ser Ser Ala Thr Lys Gln
                495                 500                 505

gtc cag aga aga cca ccc cct gca ggg ccc aga tct gag aga ggt gaa      1888
Val Gln Arg Arg Pro Pro Pro Ala Gly Pro Arg Ser Glu Arg Gly Glu
            510                 515                 520

cct cca aaa tca ggg gat cgc agc ggc tac agc agc ccc ggc tcc cca      1936
Pro Pro Lys Ser Gly Asp Arg Ser Gly Tyr Ser Ser Pro Gly Ser Pro
        525                 530                 535

ggc act ccc ggc agc cgc tcc cgc acc ccg tcc ctt cca acc cca ccc      1984
Gly Thr Pro Gly Ser Arg Ser Arg Thr Pro Ser Leu Pro Thr Pro Pro
    540                 545                 550

acc cgg gag ccc aag aag gtg gca gtg gtc cgt act cca ccc aag tcg      2032
Thr Arg Glu Pro Lys Lys Val Ala Val Val Arg Thr Pro Pro Lys Ser
555                 560                 565                 570

ccg tct tcc gcc aag agc cgc ctg cag aca gcc ccc gtg ccc atg cca      2080
Pro Ser Ser Ala Lys Ser Arg Leu Gln Thr Ala Pro Val Pro Met Pro
                575                 580                 585

gac ctg aag aat gtc aag tcc aag atc ggc tcc act gag aac ctg aag      2128
Asp Leu Lys Asn Val Lys Ser Lys Ile Gly Ser Thr Glu Asn Leu Lys
            590                 595                 600

cac cag ccg gga ggc ggg aag gtg cag ata att aat aag aag ctg gat      2176
His Gln Pro Gly Gly Gly Lys Val Gln Ile Ile Asn Lys Lys Leu Asp
        605                 610                 615

ctt agc aac gtc cag tcc aag tgt ggc tca aag gat aat atc aaa cac      2224
Leu Ser Asn Val Gln Ser Lys Cys Gly Ser Lys Asp Asn Ile Lys His
    620                 625                 630

gtc ccg gga ggc ggc agt gtg caa ata gtc tac aaa cca gtt gac ctg      2272
Val Pro Gly Gly Gly Ser Val Gln Ile Val Tyr Lys Pro Val Asp Leu
```

```
635                 640                 645                 650

agc aag gtg acc tcc aag tgt ggc tca tta ggc aac atc cat cat aaa     2320
Ser Lys Val Thr Ser Lys Cys Gly Ser Leu Gly Asn Ile His His Lys
                655                 660                 665

cca gga ggt ggc cag gtg gaa gta aaa tct gag aag ctt gac ttc aag     2368
Pro Gly Gly Gly Gln Val Glu Val Lys Ser Glu Lys Leu Asp Phe Lys
            670                 675                 680

gac aga gtc cag tcg aag att ggg tcc ctg gac aat atc acc cac gtc     2416
Asp Arg Val Gln Ser Lys Ile Gly Ser Leu Asp Asn Ile Thr His Val
        685                 690                 695

cct ggc gga gga aat aaa aag att gaa acc cac aag ctg acc ttc cgc     2464
Pro Gly Gly Gly Asn Lys Lys Ile Glu Thr His Lys Leu Thr Phe Arg
    700                 705                 710

gag aac gcc aaa gcc aag aca gac cac ggg gcg gag atc gtg tac aag     2512
Glu Asn Ala Lys Ala Lys Thr Asp His Gly Ala Glu Ile Val Tyr Lys
715                 720                 725                 730

tcg cca gtg gtg tct ggg gac acg tct cca cgg cat ctc agc aat gtc     2560
Ser Pro Val Val Ser Gly Asp Thr Ser Pro Arg His Leu Ser Asn Val
                735                 740                 745

tcc tcc acc ggc agc atc gac atg gta gac tcg ccc cag ctc gcc acg     2608
Ser Ser Thr Gly Ser Ile Asp Met Val Asp Ser Pro Gln Leu Ala Thr
            750                 755                 760

cta gct gac gag gtg tct gcc tcc ctg gcc aag cag ggt ttg tga         2653
Leu Ala Asp Glu Val Ser Ala Ser Leu Ala Lys Gln Gly Leu
        765                 770                 775

tcaggcccct ggggcggtca ataattgtgg agaggagaga atgagagagt gtggaaaaaa   2713

aaagaataat gacccggccc ccgccctctg cccccagctg ctcctcgcag ttcggttaat   2773

tggttaatca cttaacctgc ttttgtcact cggctttggc tcgggacttc aaaatcagtg   2833

atgggagtaa gagcaaattt catctttcca aattgatggg tgggctagta ataaaatatt   2893

taaaaaaaaa cattcaaaaa catggccaca tccaacattt cctcaggcaa ttccttttga   2953

ttcttttttc ttccccctcc atgtagaaga gggagaagga gaggctctga aagctgcttc   3013

tgggggattt caagggactg gggtgccaa ccacctctgg ccctgttgtg gggtgtcac     3073

agaggcagtg gcagcaacaa aggatttgaa acttggtgtg ttcgtggagc cacaggcaga   3133

cgatgtcaac cttgtgtgag tgtgacgggg gttggggtgg ggcgggaggc cacgggggag   3193

gccgaggcag ggctgggca gaggggagag gaagcacaag aagtgggagt gggagaggaa    3253

gccacgtgct ggagagtaga catccccctc cttgccgctg ggagagccaa ggcctatgcc   3313

acctgcagcg tctgagcggc cgcctgtcct tggtggccgg gggtgggggc ctgctgtggg   3373

tcagtgtgcc accctctgca gggcagcctg tgggagaagg gacagcgggt aaaaagagaa   3433

ggcaagctgg caggagggtg gcacttcgtg gatgacctcc ttagaaaaga ctgaccttga   3493

tgtcttgaga gcgctggcct cttcctccct ccctgcaggg tagggggcct gagttgaggg   3553

gcttccctct gctccacaga aaccctgttt tattgagttc tgaaggttgg aactgctgcc   3613

atgattttgg ccactttgca gacctgggac tttagggcta accagttctc tttgtaagga   3673

cttgtgcctc ttgggagacg tccacccgtt tccaagcctg ggccactggc atctctggag   3733

tgtgtggggg tctgggaggc aggtcccgag ccccctgtcc ttcccacggc cactgcagtc   3793

accccgtctg cgccgctgtg ctgttgtctg ccgtgagagc ccaatcactg cctataccc    3853

tcatcacacg tcacaatgtc ccgaattccc agcctcacca ccccttctca gtaatgaccc   3913

tggttggttg caggaggtac ctactccata ctgagggtga aattaaggga aggcaaagtc   3973

caggcacaag agtgggaccc cagcctctca ctctcagttc cactcatcca actgggaccc   4033
```

tcaccacgaa tctcatgatc tgattcggtt ccctgtctcc tcctcccgtc acagatgtga 4093
gccagggcac tgctcagctg tgaccctagg tgtttctgcc ttgttgacat ggagagagcc 4153
ctttcccctg agaaggcctg gccccttcct gtgctgagcc cacagcagca ggctgggtgt 4213
cttggttgtc agtggtggca ccaggatgga agggcaaggc acccagggca ggcccacagt 4273
cccgctgtcc cccacttgca ccctagcttg tagctgccaa cctcccagac agcccagccc 4333
gctgctcagc tccacatgca tagtatcagc cctccacacc cgacaaaggg gaacacaccc 4393
ccttggaaat ggttcttttc ccccagtccc agctggaagc catgctgtct gttctgctgg 4453
agcagctgaa catatacata gatgttgccc tgccctcccc atctgcaccc tgttgagttg 4513
tagttggatt tgtctgttta tgcttggatt caccagagtg actatgatag tgaaaagaaa 4573
aaaaaaaaaa aaaaaggacg catgtatctt gaaatgcttg taaagaggtt tctaacccac 4633
cctcacgagg tgtctctcac ccccacactg ggactcgtgt ggcctgtgtg gtgccaccct 4693
gctggggcct cccaagtttt gaaaggcttt cctcagcacc tgggacccaa cagagaccag 4753
cttctagcag ctaaggaggc cgttcagctg tgacgaaggc ctgaagcaca ggattaggac 4813
tgaagcgatg atgtcccctt ccctacttcc ccttggggct ccctgtgtca gggcacagac 4873
taggtcttgt ggctggtctg gcttgcggcg cgaggatggt tctctctggt catagcccga 4933
agtctcatgg cagtcccaaa ggaggcttac aactcctgca tcacaagaaa aaggaagcca 4993
ctgccagctg gggggatctg cagctcccag aagctccgtg agcctcagcc acccctcaga 5053
ctgggttcct ctccaagctc gccctctgga ggggcagcgc agcctcccac caagggccct 5113
gcgaccacag cagggattgg gatgaattgc ctgtcctgga tctgctctag aggcccaagc 5173
tgcctgcctg aggaaggatg acttgacaag tcaggagaca ctgttcccaa agccttgacc 5233
agagcacctc agcccgctga ccttgcacaa actccatctg ctgccatgag aaaagggaag 5293
ccgcctttgc aaaacattgc tgcctaaaga aactcagcag cctcaggccc aattctgcca 5353
cttctggttt gggtacagtt aaaggcaacc ctgagggact tggcagtaga aatccagggc 5413
ctcccctggg gctggcagct tcgtgtgcag ctagagcttt acctgaaagg aagtctctgg 5473
gcccagaact ctccaccaag agcctccctg ccgttcgctg agtcccagca attctcctaa 5533
gttgaaggga tctgagaagg agaaggaaat gtggggtaga tttggtggtg gttagagata 5593
tgccccccctc attactgcca acagtttcgg ctgcatttct tcacgcacct cggttcctct 5653
tcctgaagtt cttgtgccct gctcttcagc accatgggcc ttcttatacg gaaggctctg 5713
ggatctcccc cttgtggggc aggctcttgg ggccagccta agatcatggt ttagggtgat 5773
cagtgctggc agataaattg aaaaggcacg ctggcttgtg atcttaaatg aggacaatcc 5833
ccccagggct gggcactcct cccctcccct cacttctccc acctgcagag ccagtgtcct 5893
tgggtgggct agataggata tactgtatgc cggctccttc aagctgctga ctcactttat 5953
caatagttcc atttaaattg acttcagtgg tgagactgta tcctgtttgc tattgcttgt 6013
tgtgctatgg ggggaggggg gaggaatgtg taagatagtt aacatgggca aagggagatc 6073
ttggggtgca gcacttaaac tgcctcgtaa cccttttcat gatttcaacc acatttgcta 6133
gagggaggga gcagccacgg agttagaggc ccttggggtt tctcttttcc actgacaggc 6193
tttcccaggc agctggctag ttcattccct ccccagccag gtgcaggcgt aggaatatgg 6253
acatctggtt gctttggcct gctgccctct ttcaggggtc ctaagcccac aatcatgcct 6313
ccctaagacc ttggcatcct tccctctaag ccgttggcac ctctgtgcca cctctcacac 6373

```
tggctccaga cacacagcct gtgcttttgg agctgagatc actcgcttca ccctcctcat   6433

ctttgttctc caagtaaagc cacgaggtcg gggcgagggc agaggtgatc acctgcgtgt   6493

cccatctaca gacctgcagc ttcataaaac ttctgatttc tcttcagctt tgaaaagggt   6553

taccctgggc actggcctag agcctcacct cctaatagac ttagccccat gagtttgcca   6613

tgttgagcag gactatttct ggcacttgca agtcccatga tttcttcggt aattctgagg   6673

gtggggggag ggacatgaaa tcatcttagc ttagctttct gtctgtgaat gtctatatag   6733

tgtattgtgt gttttaacaa atgatttaca ctgactgttg ctgtaaaagt gaatttggaa   6793

ataaagttat tactctgatt aaa                                           6816


<210> SEQ ID NO 4
<211> LENGTH: 5724
<212> TYPE: DNA
<213> ORGANISM: homo sapiens
<220> FEATURE:
<221> NAME/KEY: CDS
<222> LOCATION: (323)...(1561)

<400> SEQUENCE: 4

ggacggccga gcggcagggc gctcgcgcgc gcccactagt ggccggagga gaaggctccc     60

gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca gg atg gct gag ccc cgc cag gag ttc gaa gtg     352
                         Met Ala Glu Pro Arg Gln Glu Phe Glu Val
                          1               5                  10

atg gaa gat cac gct ggg acg tac ggg ttg ggg gac agg aaa gat cag      400
Met Glu Asp His Ala Gly Thr Tyr Gly Leu Gly Asp Arg Lys Asp Gln
                15                  20                  25

ggg ggc tac acc atg cac caa gac caa gag ggt gac acg gac gct ggc      448
Gly Gly Tyr Thr Met His Gln Asp Gln Glu Gly Asp Thr Asp Ala Gly
            30                  35                  40

ctg aaa gaa tct ccc ctg cag acc ccc act gag gac gga tct gag gaa      496
Leu Lys Glu Ser Pro Leu Gln Thr Pro Thr Glu Asp Gly Ser Glu Glu
        45                  50                  55

ccg ggc tct gaa acc tct gat gct aag agc act cca aca gcg gaa gct      544
Pro Gly Ser Glu Thr Ser Asp Ala Lys Ser Thr Pro Thr Ala Glu Ala
    60                  65                  70

gaa gaa gca ggc att gga gac acc ccc agc ctg gaa gac gaa gct gct      592
Glu Glu Ala Gly Ile Gly Asp Thr Pro Ser Leu Glu Asp Glu Ala Ala
 75                  80                  85                  90

ggt cac gtg acc caa gct cgc atg gtc agt aaa agc aaa gac ggg act      640
Gly His Val Thr Gln Ala Arg Met Val Ser Lys Ser Lys Asp Gly Thr
                95                 100                 105

gga agc gat gac aaa aaa gcc aag ggg gct gat ggt aaa acg aag atc      688
Gly Ser Asp Asp Lys Lys Ala Lys Gly Ala Asp Gly Lys Thr Lys Ile
            110                 115                 120

gcc aca ccg cgg gga gca gcc cct cca ggc cag aag ggc cag gcc aac      736
Ala Thr Pro Arg Gly Ala Ala Pro Pro Gly Gln Lys Gly Gln Ala Asn
        125                 130                 135

gcc acc agg att cca gca aaa acc ccg ccc gct cca aag aca cca ccc      784
Ala Thr Arg Ile Pro Ala Lys Thr Pro Pro Ala Pro Lys Thr Pro Pro
    140                 145                 150

agc tct ggt gaa cct cca aaa tca ggg gat cgc agc ggc tac agc agc      832
Ser Ser Gly Glu Pro Pro Lys Ser Gly Asp Arg Ser Gly Tyr Ser Ser
```

-continued

```
155                 160                 165                 170

ccc ggc tcc cca ggc act ccc ggc agc cgc tcc cgc acc ccg tcc ctt       880
Pro Gly Ser Pro Gly Thr Pro Gly Ser Arg Ser Arg Thr Pro Ser Leu
                175                 180                 185

cca acc cca ccc acc cgg gag ccc aag aag gtg gca gtg gtc cgt act       928
Pro Thr Pro Pro Thr Arg Glu Pro Lys Lys Val Ala Val Val Arg Thr
            190                 195                 200

cca ccc aag tcg ccg tct tcc gcc aag agc cgc ctg cag aca gcc ccc       976
Pro Pro Lys Ser Pro Ser Ser Ala Lys Ser Arg Leu Gln Thr Ala Pro
        205                 210                 215

gtg ccc atg cca gac ctg aag aat gtc aag tcc aag atc ggc tcc act      1024
Val Pro Met Pro Asp Leu Lys Asn Val Lys Ser Lys Ile Gly Ser Thr
    220                 225                 230

gag aac ctg aag cac cag ccg gga ggc ggg aag gtg cag ata att aat      1072
Glu Asn Leu Lys His Gln Pro Gly Gly Gly Lys Val Gln Ile Ile Asn
235                 240                 245                 250

aag aag ctg gat ctt agc aac gtc cag tcc aag tgt ggc tca aag gat      1120
Lys Lys Leu Asp Leu Ser Asn Val Gln Ser Lys Cys Gly Ser Lys Asp
                255                 260                 265

aat atc aaa cac gtc ccg gga ggc ggc agt gtg caa ata gtc tac aaa      1168
Asn Ile Lys His Val Pro Gly Gly Gly Ser Val Gln Ile Val Tyr Lys
            270                 275                 280

cca gtt gac ctg agc aag gtg acc tcc aag tgt ggc tca tta ggc aac      1216
Pro Val Asp Leu Ser Lys Val Thr Ser Lys Cys Gly Ser Leu Gly Asn
        285                 290                 295

atc cat cat aaa cca gga ggt ggc cag gtg gaa gta aaa tct gag aag      1264
Ile His His Lys Pro Gly Gly Gly Gln Val Glu Val Lys Ser Glu Lys
    300                 305                 310

ctt gac ttc aag gac aga gtc cag tcg aag att ggg tcc ctg gac aat      1312
Leu Asp Phe Lys Asp Arg Val Gln Ser Lys Ile Gly Ser Leu Asp Asn
315                 320                 325                 330

atc acc cac gtc cct ggc gga gga aat aaa aag att gaa acc cac aag      1360
Ile Thr His Val Pro Gly Gly Gly Asn Lys Lys Ile Glu Thr His Lys
                335                 340                 345

ctg acc ttc cgc gag aac gcc aaa gcc aag aca gac cac ggg gcg gag      1408
Leu Thr Phe Arg Glu Asn Ala Lys Ala Lys Thr Asp His Gly Ala Glu
            350                 355                 360

atc gtg tac aag tcg cca gtg gtg tct ggg gac acg tct cca cgg cat      1456
Ile Val Tyr Lys Ser Pro Val Val Ser Gly Asp Thr Ser Pro Arg His
        365                 370                 375

ctc agc aat gtc tcc tcc acc ggc agc atc gac atg gta gac tcg ccc      1504
Leu Ser Asn Val Ser Ser Thr Gly Ser Ile Asp Met Val Asp Ser Pro
    380                 385                 390

cag ctc gcc acg cta gct gac gag gtg tct gcc tcc ctg gcc aag cag      1552
Gln Leu Ala Thr Leu Ala Asp Glu Val Ser Ala Ser Leu Ala Lys Gln
395                 400                 405                 410

ggt ttg tga tcaggcccct ggggcggtca ataattgtgg agaggagaga              1601
Gly Leu

atgagagagt gtggaaaaaa aaagaataat gacccggccc ccgccctctg cccccagctg   1661

ctcctcgcag ttcggttaat tggttaatca cttaacctgc ttttgtcact cggctttggc   1721

tcgggacttc aaaatcagtg atgggagtaa gagcaaattt catctttcca aattgatggg   1781

tgggctagta ataaaatatt taaaaaaaaa cattcaaaaa catggccaca tccaacattt   1841

cctcaggcaa ttccttttga ttcttttttc ttccccctcc atgtagaaga gggagaagga   1901

gaggctctga aagctgcttc tgggggattt caagggactg ggggtgccaa ccacctctgg   1961

ccctgttgtg gggtgtcac agaggcagtg gcagcaacaa aggatttgaa acttggtgtg   2021
```

-continued

```
ttcgtggagc cacaggcaga cgatgtcaac cttgtgtgag tgtgacgggg gttggggtgg   2081
ggcgggaggc cacgggggag gccgaggcag gggctgggca gaggggagag gaagcacaag   2141
aagtgggagt gggagaggaa gccacgtgct ggagagtaga catccccctc cttgccgctg   2201
ggagagccaa ggcctatgcc acctgcagcg tctgagcggc cgcctgtcct tggtggccgg   2261
gggtgggggc ctgctgtggg tcagtgtgcc accctctgca gggcagcctg tgggagaagg   2321
gacagcgggt aaaaagagaa ggcaagctgg caggagggtg gcacttcgtg gatgacctcc   2381
ttagaaaaga ctgaccttga tgtcttgaga gcgctggcct cttcctccct ccctgcaggg   2441
tagggggcct gagttgaggg gcttccctct gctccacaga aaccctgttt tattgagttc   2501
tgaaggttgg aactgctgcc atgattttgg ccactttgca gacctgggac tttagggcta   2561
accagttctc tttgtaagga cttgtgcctc ttgggagacg tccacccgtt tccaagcctg   2621
ggccactggc atctctggag tgtgtggggg tctgggaggc aggtcccgag ccccctgtcc   2681
ttcccacggc cactgcagtc accccgtctg cgccgctgtg ctgttgtctg ccgtgagagc   2741
ccaatcactg cctataccc tcatcacacg tcacaatgtc ccgaattccc agcctcacca   2801
ccccttctca gtaatgaccc tggttggttg caggaggtac ctactccata ctgagggtga   2861
aattaaggga aggcaaagtc caggcacaag agtgggaccc cagcctctca ctctcagttc   2921
cactcatcca actgggaccc tcaccacgaa tctcatgatc tgattcggtt ccctgtctcc   2981
tcctcccgtc acagatgtga gccagggcac tgctcagctg tgaccctagg tgtttctgcc   3041
ttgttgacat ggagagagcc ctttcccctg agaaggcctg gccccttcct gtgctgagcc   3101
cacagcagca ggctgggtgt cttggttgtc agtggtggca ccaggatgga agggcaaggc   3161
acccagggca ggcccacagt cccgctgtcc cccacttgca ccctagcttg tagctgccaa   3221
cctcccagac agcccagccc gctgctcagc tccacatgca tagtatcagc cctccacacc   3281
cgacaaaggg gaacacaccc ccttggaaat ggttcttttc ccccagtccc agctggaagc   3341
catgctgtct gttctgctgg agcagctgaa catatacata gatgttgccc tgccctcccc   3401
atctgcaccc tgttgagttg tagttggatt tgtctgttta tgcttggatt caccagagtg   3461
actatgatag tgaaaagaaa aaaaaaaaaa aaaaaggacg catgtatctt gaaatgcttg   3521
taaagaggtt tctaacccac cctcacgagg tgtctctcac ccccacactg ggactcgtgt   3581
ggcctgtgtg gtgccaccct gctggggcct cccaagtttt gaaaggcttt cctcagcacc   3641
tgggacccaa cagagaccag cttctagcag ctaaggaggc cgttcagctg tgacgaaggc   3701
ctgaagcaca ggattaggac tgaagcgatg atgtcccctt ccctacttcc ccttggggct   3761
ccctgtgtca gggcacagac taggtcttgt ggctggtctg gcttgcggcg cgaggatggt   3821
tctctctggt catagcccga agtctcatgg cagtcccaaa ggaggcttac aactcctgca   3881
tcacaagaaa aaggaagcca ctgccagctg gggggatctg cagctcccag aagctccgtg   3941
agcctcagcc acccctcaga ctgggttcct ctccaagctc gccctctgga ggggcagcgc   4001
agcctcccac caagggccct gcgaccacag cagggattgg gatgaattgc ctgtcctgga   4061
tctgctctag aggcccaagc tgcctgcctg aggaaggatg acttgacaag tcaggagaca   4121
ctgttcccaa agccttgacc agagcacctc agcccgctga ccttgcacaa actccatctg   4181
ctgccatgag aaaagggaag ccgcctttgc aaaacattgc tgcctaaaga aactcagcag   4241
cctcaggccc aattctgcca cttctggttt gggtacagtt aaaggcaacc ctgagggact   4301
tggcagtaga aatccagggc ctcccctggg gctggcagct tcgtgtgcag ctagagcttt   4361
acctgaaagg aagtctctgg gcccagaact ctccaccaag agcctccctg ccgttcgctg   4421
```

```
agtcccagca attctcctaa gttgaaggga tctgagaagg agaaggaaat gtggggtaga   4481

tttggtggtg gttagagata tgcccccctc attactgcca acagtttcgg ctgcatttct   4541

tcacgcacct cggttcctct tcctgaagtt cttgtgccct gctcttcagc accatgggcc   4601

ttcttatacg gaaggctctg ggatctcccc cttgtggggc aggctcttgg ggccagccta   4661

agatcatggt ttagggtgat cagtgctggc agataaattg aaaaggcacg ctggcttgtg   4721

atcttaaatg aggacaatcc ccccagggct gggcactcct cccctcccct cacttctccc   4781

acctgcagag ccagtgtcct tgggtgggct agataggata tactgtatgc cggctccttc   4841

aagctgctga ctcactttat caatagttcc atttaaattg acttcagtgg tgagactgta   4901

tcctgtttgc tattgcttgt tgtgctatgg ggggaggggg gaggaatgtg taagatagtt   4961

aacatgggca aagggagatc ttggggtgca gcacttaaac tgcctcgtaa ccctttttcat  5021

gatttcaacc acatttgcta gagggaggga gcagccacgg agttagaggc ccttggggtt   5081

tctcttttcc actgacaggc tttcccaggc agctggctag ttcattccct ccccagccag   5141

gtgcaggcgt aggaatatgg acatctggtt gctttggcct gctgccctct ttcaggggtc   5201

ctaagcccac aatcatgcct ccctaagacc ttggcatcct tccctctaag ccgttggcac   5261

ctctgtgcca cctctcacac tggctccaga cacacagcct gtgcttttgg agctgagatc   5321

actcgcttca ccctcctcat ctttgttctc caagtaaagc cacgaggtcg gggcgagggc   5381

agaggtgatc acctgcgtgt cccatctaca gacctgcagc ttcataaaac ttctgatttc   5441

tcttcagctt tgaaaagggt taccctgggc actggcctag agcctcacct cctaatagac   5501

ttagccccat gagtttgcca tgttgagcag gactatttct ggcacttgca agtcccatga   5561

tttcttcggt aattctgagg gtggggggag ggacatgaaa tcatcttagc ttagctttct   5621

gtctgtgaat gtctatatag tgtattgtgt gttttaacaa atgatttaca ctgactgttg   5681

ctgtaaaagt gaatttggaa ataaagttat tactctgatt aaa                     5724
```

<210> SEQ ID NO 5
<211> LENGTH: 5631
<212> TYPE: DNA
<213> ORGANISM: homo sapiens
<220> FEATURE:
<221> NAME/KEY: CDS
<222> LOCATION: (323)...(1468)

<400> SEQUENCE: 5

```
ggacggccga gcggcagggc gctcgcgcgc gcccactagt ggccggagga gaaggctccc     60

gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca gg atg gct gag ccc cgc cag gag ttc gaa gtg     352
                         Met Ala Glu Pro Arg Gln Glu Phe Glu Val
                          1               5                  10

atg gaa gat cac gct ggg acg tac ggg ttg ggg gac agg aaa gat cag      400
Met Glu Asp His Ala Gly Thr Tyr Gly Leu Gly Asp Arg Lys Asp Gln
                 15                  20                  25

ggg ggc tac acc atg cac caa gac caa gag ggt gac acg gac gct ggc      448
Gly Gly Tyr Thr Met His Gln Asp Gln Glu Gly Asp Thr Asp Ala Gly
             30                  35                  40

ctg aaa gaa tct ccc ctg cag acc ccc act gag gac gga tct gag gaa      496
```

-continued

```
Leu Lys Glu Ser Pro Leu Gln Thr Pro Thr Glu Asp Gly Ser Glu Glu
        45                  50                  55

ccg ggc tct gaa acc tct gat gct aag agc act cca aca gcg gaa gct      544
Pro Gly Ser Glu Thr Ser Asp Ala Lys Ser Thr Pro Thr Ala Glu Ala
    60                  65                  70

gaa gaa gca ggc att gga gac acc ccc agc ctg gaa gac gaa gct gct      592
Glu Glu Ala Gly Ile Gly Asp Thr Pro Ser Leu Glu Asp Glu Ala Ala
75                  80                  85                  90

ggt cac gtg acc caa gct cgc atg gtc agt aaa agc aaa gac ggg act      640
Gly His Val Thr Gln Ala Arg Met Val Ser Lys Ser Lys Asp Gly Thr
                95                  100                 105

gga agc gat gac aaa aaa gcc aag ggg gct gat ggt aaa acg aag atc      688
Gly Ser Asp Asp Lys Lys Ala Lys Gly Ala Asp Gly Lys Thr Lys Ile
            110                 115                 120

gcc aca ccg cgg gga gca gcc cct cca ggc cag aag ggc cag gcc aac      736
Ala Thr Pro Arg Gly Ala Ala Pro Pro Gly Gln Lys Gly Gln Ala Asn
        125                 130                 135

gcc acc agg att cca gca aaa acc ccg ccc gct cca aag aca cca ccc      784
Ala Thr Arg Ile Pro Ala Lys Thr Pro Pro Ala Pro Lys Thr Pro Pro
    140                 145                 150

agc tct ggt gaa cct cca aaa tca ggg gat cgc agc ggc tac agc agc      832
Ser Ser Gly Glu Pro Pro Lys Ser Gly Asp Arg Ser Gly Tyr Ser Ser
155                 160                 165                 170

ccc ggc tcc cca ggc act ccc ggc agc cgc tcc cgc acc ccg tcc ctt      880
Pro Gly Ser Pro Gly Thr Pro Gly Ser Arg Ser Arg Thr Pro Ser Leu
                175                 180                 185

cca acc cca ccc acc cgg gag ccc aag aag gtg gca gtg gtc cgt act      928
Pro Thr Pro Pro Thr Arg Glu Pro Lys Lys Val Ala Val Val Arg Thr
            190                 195                 200

cca ccc aag tcg ccg tct tcc gcc aag agc cgc ctg cag aca gcc ccc      976
Pro Pro Lys Ser Pro Ser Ser Ala Lys Ser Arg Leu Gln Thr Ala Pro
        205                 210                 215

gtg ccc atg cca gac ctg aag aat gtc aag tcc aag atc ggc tcc act     1024
Val Pro Met Pro Asp Leu Lys Asn Val Lys Ser Lys Ile Gly Ser Thr
    220                 225                 230

gag aac ctg aag cac cag ccg gga ggc ggg aag gtg caa ata gtc tac     1072
Glu Asn Leu Lys His Gln Pro Gly Gly Gly Lys Val Gln Ile Val Tyr
235                 240                 245                 250

aaa cca gtt gac ctg agc aag gtg acc tcc aag tgt ggc tca tta ggc     1120
Lys Pro Val Asp Leu Ser Lys Val Thr Ser Lys Cys Gly Ser Leu Gly
                255                 260                 265

aac atc cat cat aaa cca gga ggt ggc cag gtg gaa gta aaa tct gag     1168
Asn Ile His His Lys Pro Gly Gly Gly Gln Val Glu Val Lys Ser Glu
            270                 275                 280

aag ctt gac ttc aag gac aga gtc cag tcg aag att ggg tcc ctg gac     1216
Lys Leu Asp Phe Lys Asp Arg Val Gln Ser Lys Ile Gly Ser Leu Asp
        285                 290                 295

aat atc acc cac gtc cct ggc gga gga aat aaa aag att gaa acc cac     1264
Asn Ile Thr His Val Pro Gly Gly Gly Asn Lys Lys Ile Glu Thr His
    300                 305                 310

aag ctg acc ttc cgc gag aac gcc aaa gcc aag aca gac cac ggg gcg     1312
Lys Leu Thr Phe Arg Glu Asn Ala Lys Ala Lys Thr Asp His Gly Ala
315                 320                 325                 330

gag atc gtg tac aag tcg cca gtg gtg tct ggg gac acg tct cca cgg     1360
Glu Ile Val Tyr Lys Ser Pro Val Val Ser Gly Asp Thr Ser Pro Arg
                335                 340                 345

cat ctc agc aat gtc tcc tcc acc ggc agc atc gac atg gta gac tcg     1408
His Leu Ser Asn Val Ser Ser Thr Gly Ser Ile Asp Met Val Asp Ser
            350                 355                 360
```

-continued

```
ccc cag ctc gcc acg cta gct gac gag gtg tct gcc tcc ctg gcc aag     1456
Pro Gln Leu Ala Thr Leu Ala Asp Glu Val Ser Ala Ser Leu Ala Lys
        365                 370                 375

cag ggt ttg tga tcaggcccct ggggcggtca ataattgtgg agaggagaga         1508
Gln Gly Leu
    380

atgagagagt gtggaaaaaa aaagaataat gacccggccc ccgccctctg cccccagctg   1568

ctcctcgcag ttcggttaat tggttaatca cttaacctgc ttttgtcact cggctttggc   1628

tcgggacttc aaaatcagtg atgggagtaa gagcaaattt catctttcca aattgatggg   1688

tgggctagta ataaaatatt taaaaaaaaa cattcaaaaa catggccaca tccaacattt   1748

cctcaggcaa ttccttttga ttcttttttc ttccccctcc atgtagaaga gggagaagga   1808

gaggctctga aagctgcttc tgggggattt caagggactg gggggtgccaa ccacctctgg  1868

ccctgttgtg gggtgtcac agaggcagtg gcagcaacaa aggatttgaa acttggtgtg    1928

ttcgtggagc cacaggcaga cgatgtcaac cttgtgtgag tgtgacgggg gttggggtgg   1988

ggcgggaggc cacgggggag gccgaggcag gggctgggca gaggggagag gaagcacaag   2048

aagtgggagt gggagaggaa gccacgtgct ggagagtaga catccccctc cttgccgctg   2108

ggagagccaa ggcctatgcc acctgcagcg tctgagcggc cgcctgtcct tggtggccgg   2168

gggtgggggc ctgctgtggg tcagtgtgcc accctctgca gggcagcctg tgggagaagg   2228

gacagcgggt aaaaagagaa ggcaagctgg caggagggtg gcacttcgtg gatgacctcc   2288

ttagaaaaga ctgaccttga tgtcttgaga gcgctggcct cttcctccct ccctgcaggg   2348

tagggggcct gagttgaggg gcttccctct gctccacaga aaccctgttt tattgagttc   2408

tgaaggttgg aactgctgcc atgattttgg ccactttgca gacctgggac tttagggcta   2468

accagttctc tttgtaagga cttgtgcctc ttgggagacg tccacccgtt tccaagcctg   2528

ggccactggc atctctggag tgtgtggggg tctgggaggc aggtcccgag ccccctgtcc   2588

ttcccacggc cactgcagtc accccgtctg cgccgctgtg ctgttgtctg ccgtgagagc   2648

ccaatcactg cctataccc tcatcacacg tcacaatgtc ccgaattccc agcctcacca    2708

ccccttctca gtaatgaccc tggttggttg caggaggtac ctactccata ctgagggtga   2768

aattaaggga aggcaaagtc caggcacaag agtgggaccc cagcctctca ctctcagttc   2828

cactcatcca actgggaccc tcaccacgaa tctcatgatc tgattcggtt ccctgtctcc   2888

tcctcccgtc acagatgtga gccagggcac tgctcagctg tgaccctagg tgtttctgcc   2948

ttgttgacat ggagagagcc ctttcccctg agaaggcctg gccccttcct gtgctgagcc   3008

cacagcagca ggctgggtgt cttggttgtc agtggtggca ccaggatgga agggcaaggc   3068

acccagggca ggcccacagt cccgctgtcc cccacttgca ccctagcttg tagctgccaa   3128

cctcccagac agcccagccc gctgctcagc tccacatgca tagtatcagc cctccacacc   3188

cgacaaaggg gaacacaccc ccttggaaat ggttcttttc ccccagtccc agctggaagc   3248

catgctgtct gttctgctgg agcagctgaa catatacata gatgttgccc tgccctcccc   3308

atctgcaccc tgttgagttg tagttggatt tgtctgttta tgcttggatt caccagagtg   3368

actatgatag tgaaaagaaa aaaaaaaaaa aaaaaggacg catgtatctt gaaatgcttg   3428

taaagaggtt tctaacccac cctcacgagg tgtctctcac ccccacactg ggactcgtgt   3488

ggcctgtgtg gtgccacccct gctggggcct cccaagtttt gaaaggcttt cctcagcacc  3548

tgggacccaa cagagaccag cttctagcag ctaaggaggc cgttcagctg tgacgaaggc   3608

ctgaagcaca ggattaggac tgaagcgatg atgtcccctt ccctacttcc ccttggggct   3668
```

```
ccctgtgtca gggcacagac taggtcttgt ggctggtctg gcttgcggcg cgaggatggt   3728
tctctctggt catagcccga agtctcatgg cagtcccaaa ggaggcttac aactcctgca   3788
tcacaagaaa aaggaagcca ctgccagctg gggggatctg cagctcccag aagctccgtg   3848
agcctcagcc acccctcaga ctgggttcct ctccaagctc gccctctgga ggggcagcgc   3908
agcctcccac caagggccct gcgaccacag cagggattgg gatgaattgc ctgtcctgga   3968
tctgctctag aggcccaagc tgcctgcctg aggaaggatg acttgacaag tcaggagaca   4028
ctgttcccaa agccttgacc agagcacctc agcccgctga ccttgcacaa actccatctg   4088
ctgccatgag aaaagggaag ccgcctttgc aaaacattgc tgcctaaaga aactcagcag   4148
cctcaggccc aattctgcca cttctggttt gggtacagtt aaaggcaacc ctgagggact   4208
tggcagtaga aatccagggc ctcccctggg gctggcagct tcgtgtgcag ctagagcttt   4268
acctgaaagg aagtctctgg gcccagaact ctccaccaag agcctccctg ccgttcgctg   4328
agtcccagca attctcctaa gttgaaggga tctgagaagg agaaggaaat gtggggtaga   4388
tttggtggtg gttagagata tgccccccctc attactgcca acagtttcgg ctgcatttct   4448
tcacgcacct cggttcctct tcctgaagtt cttgtgccct gctcttcagc accatgggcc   4508
ttcttatacg gaaggctctg ggatctcccc cttgtggggc aggctcttgg ggccagccta   4568
agatcatggt ttagggtgat cagtgctggc agataaattg aaaaggcacg ctggcttgtg   4628
atcttaaatg aggacaatcc ccccagggct gggcactcct cccctcccct cacttctccc   4688
acctgcagag ccagtgtcct tgggtgggct agataggata tactgtatgc cggctccttc   4748
aagctgctga ctcactttat caatagttcc atttaaattg acttcagtgg tgagactgta   4808
tcctgtttgc tattgcttgt tgtgctatgg ggggaggggg gaggaatgtg taagatagtt   4868
aacatgggca aagggagatc ttggggtgca gcacttaaac tgcctcgtaa ccctttttcat   4928
gatttcaacc acatttgcta gagggaggga gcagccacgg agttagaggc ccttggggtt   4988
tctcttttcc actgacaggc tttcccaggc agctggctag ttcattccct ccccagccag   5048
gtgcaggcgt aggaatatgg acatctggtt gctttggcct gctgccctct ttcaggggtc   5108
ctaagcccac aatcatgcct ccctaagacc ttggcatcct tccctctaag ccgttggcac   5168
ctctgtgcca cctctcacac tggctccaga cacacagcct gtgcttttgg agctgagatc   5228
actcgcttca ccctcctcat ctttgttctc caagtaaagc cacgaggtcg gggcgagggc   5288
agaggtgatc acctgcgtgt cccatctaca gacctgcagc ttcataaaac ttctgatttc   5348
tcttcagctt tgaaaagggt taccctgggc actggcctag agcctcacct cctaatagac   5408
ttagccccat gagtttgcca tgttgagcag gactatttct ggcacttgca agtcccatga   5468
tttcttcggt aattctgagg gtggggggag ggacatgaaa tcatcttagc ttagctttct   5528
gtctgtgaat gtctatatag tgtattgtgt gttttaacaa atgatttaca ctgactgttg   5588
ctgtaaaagt gaatttggaa ataaagttat tactctgatt aaa                     5631
```

<210> SEQ ID NO 6
<211> LENGTH: 5718
<212> TYPE: DNA
<213> ORGANISM: homo sapiens
<220> FEATURE:
<221> NAME/KEY: CDS
<222> LOCATION: (323)...(1555)

<400> SEQUENCE: 6

```
ggacggccga gcggcagggc gctcgcgcgc gcccactagt ggccggagga gaaggctccc     60
```

-continued

```
gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca gg atg gct gag ccc cgc cag gag ttc gaa gtg     352
                         Met Ala Glu Pro Arg Gln Glu Phe Glu Val
                         1               5                   10

atg gaa gat cac gct ggg acg tac ggg ttg ggg gac agg aaa gat cag      400
Met Glu Asp His Ala Gly Thr Tyr Gly Leu Gly Asp Arg Lys Asp Gln
                15                  20                  25

ggg ggc tac acc atg cac caa gac caa gag ggt gac acg gac gct ggc      448
Gly Gly Tyr Thr Met His Gln Asp Gln Glu Gly Asp Thr Asp Ala Gly
            30                  35                  40

ctg aaa gaa tct ccc ctg cag acc ccc act gag gac gga tct gag gaa      496
Leu Lys Glu Ser Pro Leu Gln Thr Pro Thr Glu Asp Gly Ser Glu Glu
        45                  50                  55

ccg ggc tct gaa acc tct gat gct aag agc act cca aca gcg gaa gat      544
Pro Gly Ser Glu Thr Ser Asp Ala Lys Ser Thr Pro Thr Ala Glu Asp
    60                  65                  70

gtg aca gca ccc tta gtg gat gag gga gct ccc ggc aag cag gct gcc      592
Val Thr Ala Pro Leu Val Asp Glu Gly Ala Pro Gly Lys Gln Ala Ala
75                  80                  85                  90

gcg cag ccc cac acg gag atc cca gaa gga acc aca gct gaa gaa gca      640
Ala Gln Pro His Thr Glu Ile Pro Glu Gly Thr Thr Ala Glu Glu Ala
                95                  100                 105

ggc att gga gac acc ccc agc ctg gaa gac gaa gct gct ggt cac gtg      688
Gly Ile Gly Asp Thr Pro Ser Leu Glu Asp Glu Ala Ala Gly His Val
            110                 115                 120

acc caa gct cgc atg gtc agt aaa agc aaa gac ggg act gga agc gat      736
Thr Gln Ala Arg Met Val Ser Lys Ser Lys Asp Gly Thr Gly Ser Asp
        125                 130                 135

gac aaa aaa gcc aag ggg gct gat ggt aaa acg aag atc gcc aca ccg      784
Asp Lys Lys Ala Lys Gly Ala Asp Gly Lys Thr Lys Ile Ala Thr Pro
    140                 145                 150

cgg gga gca gcc cct cca ggc cag aag ggc cag gcc aac gcc acc agg      832
Arg Gly Ala Ala Pro Pro Gly Gln Lys Gly Gln Ala Asn Ala Thr Arg
155                 160                 165                 170

att cca gca aaa acc ccg ccc gct cca aag aca cca ccc agc tct ggt      880
Ile Pro Ala Lys Thr Pro Pro Ala Pro Lys Thr Pro Pro Ser Ser Gly
                175                 180                 185

gaa cct cca aaa tca ggg gat cgc agc ggc tac agc agc ccc ggc tcc      928
Glu Pro Pro Lys Ser Gly Asp Arg Ser Gly Tyr Ser Ser Pro Gly Ser
            190                 195                 200

cca ggc act ccc ggc agc cgc tcc cgc acc ccg tcc ctt cca acc cca      976
Pro Gly Thr Pro Gly Ser Arg Ser Arg Thr Pro Ser Leu Pro Thr Pro
        205                 210                 215

ccc acc cgg gag ccc aag aag gtg gca gtg gtc cgt act cca ccc aag     1024
Pro Thr Arg Glu Pro Lys Lys Val Ala Val Val Arg Thr Pro Pro Lys
    220                 225                 230

tcg ccg tct tcc gcc aag agc cgc ctg cag aca gcc ccc gtg ccc atg     1072
Ser Pro Ser Ser Ala Lys Ser Arg Leu Gln Thr Ala Pro Val Pro Met
235                 240                 245                 250

cca gac ctg aag aat gtc aag tcc aag atc ggc tcc act gag aac ctg     1120
Pro Asp Leu Lys Asn Val Lys Ser Lys Ile Gly Ser Thr Glu Asn Leu
                255                 260                 265

aag cac cag ccg gga ggc ggg aag gtg caa ata gtc tac aaa cca gtt     1168
Lys His Gln Pro Gly Gly Gly Lys Val Gln Ile Val Tyr Lys Pro Val
```

```
            270                 275                 280

gac ctg agc aag gtg acc tcc aag tgt ggc tca tta ggc aac atc cat     1216
Asp Leu Ser Lys Val Thr Ser Lys Cys Gly Ser Leu Gly Asn Ile His
        285                 290                 295

cat aaa cca gga ggt ggc cag gtg gaa gta aaa tct gag aag ctt gac     1264
His Lys Pro Gly Gly Gly Gln Val Glu Val Lys Ser Glu Lys Leu Asp
    300                 305                 310

ttc aag gac aga gtc cag tcg aag att ggg tcc ctg gac aat atc acc     1312
Phe Lys Asp Arg Val Gln Ser Lys Ile Gly Ser Leu Asp Asn Ile Thr
315                 320                 325                 330

cac gtc cct ggc gga gga aat aaa aag att gaa acc cac aag ctg acc     1360
His Val Pro Gly Gly Gly Asn Lys Lys Ile Glu Thr His Lys Leu Thr
                335                 340                 345

ttc cgc gag aac gcc aaa gcc aag aca gac cac ggg gcg gag atc gtg     1408
Phe Arg Glu Asn Ala Lys Ala Lys Thr Asp His Gly Ala Glu Ile Val
            350                 355                 360

tac aag tcg cca gtg gtg tct ggg gac acg tct cca cgg cat ctc agc     1456
Tyr Lys Ser Pro Val Val Ser Gly Asp Thr Ser Pro Arg His Leu Ser
        365                 370                 375

aat gtc tcc tcc acc ggc agc atc gac atg gta gac tcg ccc cag ctc     1504
Asn Val Ser Ser Thr Gly Ser Ile Asp Met Val Asp Ser Pro Gln Leu
    380                 385                 390

gcc acg cta gct gac gag gtg tct gcc tcc ctg gcc aag cag ggt ttg     1552
Ala Thr Leu Ala Asp Glu Val Ser Ala Ser Leu Ala Lys Gln Gly Leu
395                 400                 405                 410

tga tcaggcccct ggggcggtca ataattgtgg agaggagaga atgagagagt         1605

gtggaaaaaa aaagaataat gacccggccc ccgccctctg cccccagctg ctcctcgcag   1665

ttcggttaat tggttaatca cttaacctgc ttttgtcact cggctttggc tcgggacttc   1725

aaaatcagtg atgggagtaa gagcaaattt catctttcca aattgatggg tgggctagta   1785

ataaaatatt taaaaaaaaa cattcaaaaa catggccaca tccaacattt cctcaggcaa   1845

ttccttttga ttcttttttc ttccccctcc atgtagaaga gggagaagga gaggctctga   1905

aagctgcttc tgggggattt caagggactg ggggtgccaa ccacctctgg ccctgttgtg   1965

ggggtgtcac agaggcagtg gcagcaacaa aggatttgaa acttggtgtg ttcgtggagc   2025

cacaggcaga cgatgtcaac cttgtgtgag tgtgacgggg gttggggtgg ggcgggaggc   2085

cacgggggag gccgaggcag gggctgggca gaggggagag gaagcacaag aagtgggagt   2145

gggagaggaa gccacgtgct ggagagtaga catccccctc cttgccgctg ggagagccaa   2205

ggcctatgcc acctgcagcg tctgagcggc cgcctgtcct tggtggccgg gggtgggggc   2265

ctgctgtggg tcagtgtgcc accctctgca gggcagcctg tgggagaagg gacagcgggt   2325

aaaaagagaa ggcaagctgg caggagggtg gcacttcgtg gatgacctcc ttagaaaaga   2385

ctgaccttga tgtcttgaga gcgctggcct cttcctccct ccctgcaggg tagggggcct   2445

gagttgaggg gcttccctct gctccacaga aaccctgttt tattgagttc tgaaggttgg   2505

aactgctgcc atgattttgg ccactttgca gacctgggac tttagggcta accagttctc   2565

tttgtaagga cttgtgcctc ttgggagacg tccacccgtt tccaagcctg ggccactggc   2625

atctctggag tgtgtggggg tctgggaggc aggtcccgag ccccctgtcc ttcccacggc   2685

cactgcagtc accccgtctg cgccgctgtg ctgttgtctg ccgtgagagc ccaatcactg   2745

cctatacccc tcatcacacg tcacaatgtc ccgaattccc agcctcacca ccccttctca   2805

gtaatgaccc tggttggttg caggaggtac ctactccata ctgagggtga aattaaggga   2865

aggcaaagtc caggcacaag agtgggaccc cagcctctca ctctcagttc cactcatcca   2925
```

```
actgggaccc tcaccacgaa tctcatgatc tgattcggtt ccctgtctcc tcctcccgtc   2985
acagatgtga gccagggcac tgctcagctg tgaccctagg tgtttctgcc ttgttgacat   3045
ggagagagcc ctttcccctg agaaggcctg gccccttcct gtgctgagcc cacagcagca   3105
ggctgggtgt cttggttgtc agtggtggca ccaggatgga agggcaaggc acccagggca   3165
ggcccacagt cccgctgtcc cccacttgca ccctagcttg tagctgccaa cctcccagac   3225
agcccagccc gctgctcagc tccacatgca tagtatcagc cctccacacc cgacaaaggg   3285
gaacacaccc ccttggaaat ggttcttttc ccccagtccc agctggaagc catgctgtct   3345
gttctgctgg agcagctgaa catatacata gatgttgccc tgccctcccc atctgcaccc   3405
tgttgagttg tagttggatt tgtctgttta tgcttggatt caccagagtg actatgatag   3465
tgaaaagaaa aaaaaaaaaa aaaaaggacg catgtatctt gaaatgcttg taaagaggtt   3525
tctaacccac cctcacgagg tgtctctcac ccccacactg ggactcgtgt ggcctgtgtg   3585
gtgccaccct gctggggcct cccaagtttt gaaaggcttt cctcagcacc tgggacccaa   3645
cagagaccag cttctagcag ctaaggaggc cgttcagctg tgacgaaggc ctgaagcaca   3705
ggattaggac tgaagcgatg atgtcccctt ccctacttcc ccttggggct ccctgtgtca   3765
gggcacagac taggtcttgt ggctggtctg gcttgcggcg cgaggatggt tctctctggt   3825
catagcccga agtctcatgg cagtcccaaa ggaggcttac aactcctgca tcacaagaaa   3885
aaggaagcca ctgccagctg gggggatctg cagctcccag aagctccgtg agcctcagcc   3945
acccctcaga ctgggttcct ctccaagctc gccctctgga ggggcagcgc agcctcccac   4005
caagggccct gcgaccacag cagggattgg gatgaattgc ctgtcctgga tctgctctag   4065
aggcccaagc tgcctgcctg aggaaggatg acttgacaag tcaggagaca ctgttcccaa   4125
agccttgacc agagcacctc agcccgctga ccttgcacaa actccatctg ctgccatgag   4185
aaaagggaag ccgcctttgc aaaacattgc tgcctaaaga aactcagcag cctcaggccc   4245
aattctgcca cttctggttt gggtacagtt aaaggcaacc ctgagggact tggcagtaga   4305
aatccagggc ctcccctggg gctggcagct tcgtgtgcag ctagagcttt acctgaaagg   4365
aagtctctgg gcccagaact ctccaccaag agcctccctg ccgttcgctg agtcccagca   4425
attctcctaa gttgaaggga tctgagaagg agaaggaaat gtggggtaga tttggtggtg   4485
gttagagata tgccccccctc attactgcca acagtttcgg ctgcatttct tcacgcacct   4545
cggttcctct tcctgaagtt cttgtgccct gctcttcagc accatgggcc ttcttatacg   4605
gaaggctctg ggatctcccc cttgtggggc aggctcttgg ggccagccta agatcatggt   4665
ttagggtgat cagtgctggc agataaattg aaaaggcacg ctggcttgtg atcttaaatg   4725
aggacaatcc ccccagggct gggcactcct cccctcccct cacttctccc acctgcagag   4785
ccagtgtcct tgggtgggct agataggata tactgtatgc cggctccttc aagctgctga   4845
ctcactttat caatagttcc atttaaattg acttcagtgg tgagactgta tcctgtttgc   4905
tattgcttgt tgtgctatgg ggggaggggg gaggaatgtg taagatagtt aacatgggca   4965
aagggagatc ttggggtgca gcacttaaac tgcctcgtaa cccttttcat gatttcaacc   5025
acatttgcta gagggaggga gcagccacgg agttagaggc ccttggggtt tctcttttcc   5085
actgacaggc tttcccaggc agctggctag ttcattccct ccccagccag gtgcaggcgt   5145
aggaatatgg acatctggtt gctttggcct gctgccctct ttcaggggtc ctaagcccac   5205
aatcatgcct ccctaagacc ttggcatcct tccctctaag ccgttggcac ctctgtgcca   5265
```

-continued

```
cctctcacac tggctccaga cacacagcct gtgcttttgg agctgagatc actcgcttca   5325

ccctcctcat ctttgttctc caagtaaagc cacgaggtcg gggcgagggc agaggtgatc   5385

acctgcgtgt cccatctaca gacctgcagc ttcataaaac ttctgatttc tcttcagctt   5445

tgaaaagggt taccctgggc actggcctag agcctcacct cctaatagac ttagccccat   5505

gagtttgcca tgttgagcag gactatttct ggcacttgca agtcccatga tttcttcggt   5565

aattctgagg gtggggggag ggacatgaaa tcatcttagc ttagctttct gtctgtgaat   5625

gtctatatag tgtattgtgt gttttaacaa atgatttaca ctgactgttg ctgtaaaagt   5685

gaatttggaa ataaagttat tactctgatt aaa                               5718


<210> SEQ ID NO 7
<211> LENGTH: 5811
<212> TYPE: DNA
<213> ORGANISM: homo sapiens
<220> FEATURE:
<221> NAME/KEY: CDS
<222> LOCATION: (323)...(1648)

<400> SEQUENCE: 7

ggacggccga gcggcagggc gctcgcgcgc gcccactagt ggccggagga gaaggctccc     60

gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca gg atg gct gag ccc cgc cag gag ttc gaa gtg     352
                         Met Ala Glu Pro Arg Gln Glu Phe Glu Val
                          1               5                  10

atg gaa gat cac gct ggg acg tac ggg ttg ggg gac agg aaa gat cag      400
Met Glu Asp His Ala Gly Thr Tyr Gly Leu Gly Asp Arg Lys Asp Gln
                15                  20                  25

ggg ggc tac acc atg cac caa gac caa gag ggt gac acg gac gct ggc      448
Gly Gly Tyr Thr Met His Gln Asp Gln Glu Gly Asp Thr Asp Ala Gly
            30                  35                  40

ctg aaa gaa tct ccc ctg cag acc ccc act gag gac gga tct gag gaa      496
Leu Lys Glu Ser Pro Leu Gln Thr Pro Thr Glu Asp Gly Ser Glu Glu
        45                  50                  55

ccg ggc tct gaa acc tct gat gct aag agc act cca aca gcg gaa gat      544
Pro Gly Ser Glu Thr Ser Asp Ala Lys Ser Thr Pro Thr Ala Glu Asp
    60                  65                  70

gtg aca gca ccc tta gtg gat gag gga gct ccc ggc aag cag gct gcc      592
Val Thr Ala Pro Leu Val Asp Glu Gly Ala Pro Gly Lys Gln Ala Ala
 75                  80                  85                  90

gcg cag ccc cac acg gag atc cca gaa gga acc aca gct gaa gaa gca      640
Ala Gln Pro His Thr Glu Ile Pro Glu Gly Thr Thr Ala Glu Glu Ala
                95                 100                 105

ggc att gga gac acc ccc agc ctg gaa gac gaa gct gct ggt cac gtg      688
Gly Ile Gly Asp Thr Pro Ser Leu Glu Asp Glu Ala Ala Gly His Val
            110                 115                 120

acc caa gct cgc atg gtc agt aaa agc aaa gac ggg act gga agc gat      736
Thr Gln Ala Arg Met Val Ser Lys Ser Lys Asp Gly Thr Gly Ser Asp
        125                 130                 135

gac aaa aaa gcc aag ggg gct gat ggt aaa acg aag atc gcc aca ccg      784
Asp Lys Lys Ala Lys Gly Ala Asp Gly Lys Thr Lys Ile Ala Thr Pro
    140                 145                 150

cgg gga gca gcc cct cca ggc cag aag ggc cag gcc aac gcc acc agg      832
Arg Gly Ala Ala Pro Pro Gly Gln Lys Gly Gln Ala Asn Ala Thr Arg
```

-continued

```
155                 160                 165                 170

att cca gca aaa acc ccg ccc gct cca aag aca cca ccc agc tct ggt      880
Ile Pro Ala Lys Thr Pro Pro Ala Pro Lys Thr Pro Pro Ser Ser Gly
                175                 180                 185

gaa cct cca aaa tca ggg gat cgc agc ggc tac agc agc ccc ggc tcc      928
Glu Pro Pro Lys Ser Gly Asp Arg Ser Gly Tyr Ser Ser Pro Gly Ser
            190                 195                 200

cca ggc act ccc ggc agc cgc tcc cgc acc ccg tcc ctt cca acc cca      976
Pro Gly Thr Pro Gly Ser Arg Ser Arg Thr Pro Ser Leu Pro Thr Pro
        205                 210                 215

ccc acc cgg gag ccc aag aag gtg gca gtg gtc cgt act cca ccc aag     1024
Pro Thr Arg Glu Pro Lys Lys Val Ala Val Val Arg Thr Pro Pro Lys
    220                 225                 230

tcg ccg tct tcc gcc aag agc cgc ctg cag aca gcc ccc gtg ccc atg     1072
Ser Pro Ser Ser Ala Lys Ser Arg Leu Gln Thr Ala Pro Val Pro Met
235                 240                 245                 250

cca gac ctg aag aat gtc aag tcc aag atc ggc tcc act gag aac ctg     1120
Pro Asp Leu Lys Asn Val Lys Ser Lys Ile Gly Ser Thr Glu Asn Leu
                255                 260                 265

aag cac cag ccg gga ggc ggg aag gtg cag ata att aat aag aag ctg     1168
Lys His Gln Pro Gly Gly Gly Lys Val Gln Ile Ile Asn Lys Lys Leu
            270                 275                 280

gat ctt agc aac gtc cag tcc aag tgt ggc tca aag gat aat atc aaa     1216
Asp Leu Ser Asn Val Gln Ser Lys Cys Gly Ser Lys Asp Asn Ile Lys
        285                 290                 295

cac gtc ccg gga ggc ggc agt gtg caa ata gtc tac aaa cca gtt gac     1264
His Val Pro Gly Gly Gly Ser Val Gln Ile Val Tyr Lys Pro Val Asp
    300                 305                 310

ctg agc aag gtg acc tcc aag tgt ggc tca tta ggc aac atc cat cat     1312
Leu Ser Lys Val Thr Ser Lys Cys Gly Ser Leu Gly Asn Ile His His
315                 320                 325                 330

aaa cca gga ggt ggc cag gtg gaa gta aaa tct gag aag ctt gac ttc     1360
Lys Pro Gly Gly Gly Gln Val Glu Val Lys Ser Glu Lys Leu Asp Phe
                335                 340                 345

aag gac aga gtc cag tcg aag att ggg tcc ctg gac aat atc acc cac     1408
Lys Asp Arg Val Gln Ser Lys Ile Gly Ser Leu Asp Asn Ile Thr His
            350                 355                 360

gtc cct ggc gga gga aat aaa aag att gaa acc cac aag ctg acc ttc     1456
Val Pro Gly Gly Gly Asn Lys Lys Ile Glu Thr His Lys Leu Thr Phe
        365                 370                 375

cgc gag aac gcc aaa gcc aag aca gac cac ggg gcg gag atc gtg tac     1504
Arg Glu Asn Ala Lys Ala Lys Thr Asp His Gly Ala Glu Ile Val Tyr
    380                 385                 390

aag tcg cca gtg gtg tct ggg gac acg tct cca cgg cat ctc agc aat     1552
Lys Ser Pro Val Val Ser Gly Asp Thr Ser Pro Arg His Leu Ser Asn
395                 400                 405                 410

gtc tcc tcc acc ggc agc atc gac atg gta gac tcg ccc cag ctc gcc     1600
Val Ser Ser Thr Gly Ser Ile Asp Met Val Asp Ser Pro Gln Leu Ala
                415                 420                 425

acg cta gct gac gag gtg tct gcc tcc ctg gcc aag cag ggt ttg tga     1648
Thr Leu Ala Asp Glu Val Ser Ala Ser Leu Ala Lys Gln Gly Leu
            430                 435                 440

tcaggcccct ggggcggtca ataattgtgg agaggagaga atgagagagt gtggaaaaaa   1708

aaagaataat gacccggccc ccgccctctg cccccagctg ctcctcgcag ttcggttaat   1768

tggttaatca cttaacctgc ttttgtcact cggctttggc tcgggacttc aaaatcagtg   1828

atgggagtaa gagcaaattt catctttcca aattgatggg tgggctagta ataaaatatt   1888

taaaaaaaaa cattcaaaaa catggccaca tccaacattt cctcaggcaa ttccttttga   1948
```

```
ttcttttttc ttccccctcc atgtagaaga gggagaagga gaggctctga aagctgcttc   2008
tgggggattt caagggactg gggtgccaa ccacctctgg ccctgttgtg ggggtgtcac   2068
agaggcagtg gcagcaacaa aggatttgaa acttggtgtg ttcgtggagc cacaggcaga   2128
cgatgtcaac cttgtgtgag tgtgacgggg gttggggtgg ggcgggaggc cacgggggag   2188
gccgaggcag gggctgggca gaggggagag gaagcacaag aagtgggagt gggagaggaa   2248
gccacgtgct ggagagtaga catccccctc cttgccgctg ggagagccaa ggcctatgcc   2308
acctgcagcg tctgagcggc cgcctgtcct tggtggccgg gggtgggggc ctgctgtggg   2368
tcagtgtgcc accctctgca gggcagcctg tgggagaagg gacagcgggt aaaaagagaa   2428
ggcaagctgg caggagggtg gcacttcgtg gatgacctcc ttagaaaaga ctgaccttga   2488
tgtcttgaga gcgctggcct cttcctccct ccctgcaggg tagggggcct gagttgaggg   2548
gcttccctct gctccacaga aaccctgttt tattgagttc tgaaggttgg aactgctgcc   2608
atgattttgg ccactttgca gacctgggac tttagggcta accagttctc tttgtaagga   2668
cttgtgcctc ttgggagacg tccacccgtt tccaagcctg ggccactggc atctctggag   2728
tgtgtggggg tctgggaggc aggtcccgag cccccctgtcc ttcccacggc cactgcagtc   2788
accccgtctg cgccgctgtg ctgttgtctg ccgtgagagc ccaatcactg cctataccc   2848
tcatcacacg tcacaatgtc ccgaattccc agcctcacca cccctctca gtaatgaccc   2908
tggttggttg caggaggtac ctactccata ctgagggtga aattaaggga aggcaaagtc   2968
caggcacaag agtgggaccc cagcctctca ctctcagttc cactcatcca actgggaccc   3028
tcaccacgaa tctcatgatc tgattcggtt ccctgtctcc tcctcccgtc acagatgtga   3088
gccagggcac tgctcagctg tgaccctagg tgtttctgcc ttgttgacat ggagagagcc   3148
ctttccccctg agaaggcctg gccccttcct gtgctgagcc cacagcagca ggctgggtgt   3208
cttggttgtc agtggtggca ccaggatgga agggcaaggc acccagggca ggcccacagt   3268
cccgctgtcc cccacttgca ccctagcttg tagctgccaa cctcccagac agcccagccc   3328
gctgctcagc tccacatgca tagtatcagc cctccacacc cgacaaaggg gaacacaccc   3388
ccttggaaat ggttcttttc ccccagtccc agctggaagc catgctgtct gttctgctgg   3448
agcagctgaa catatacata gatgttgccc tgccctcccc atctgcaccc tgttgagttg   3508
tagttggatt tgtctgttta tgcttggatt caccagagtg actatgatag tgaaaagaaa   3568
aaaaaaaaaa aaaaaggacg catgtatctt gaaatgcttg taaagaggtt tctaacccac   3628
cctcacgagg tgtctctcac ccccacactg ggactcgtgt ggcctgtgtg gtgccaccct   3688
gctggggcct cccaagtttt gaaaggcttt cctcagcacc tgggacccaa cagagaccag   3748
cttctagcag ctaaggaggc cgttcagctg tgacgaaggc ctgaagcaca ggattaggac   3808
tgaagcgatg atgtcccctt ccctacttcc ccttggggct ccctgtgtca gggcacagac   3868
taggtcttgt ggctggtctg gcttgcggcg cgaggatggt tctctctggt catagcccga   3928
agtctcatgg cagtcccaaa ggaggcttac aactcctgca tcacaagaaa aaggaagcca   3988
ctgccagctg gggggatctg cagctcccag aagctccgtg agcctcagcc accccctcaga   4048
ctgggttcct ctccaagctc gccctctgga ggggcagcgc agcctcccac caagggccct   4108
gcgaccacag cagggattgg gatgaattgc ctgtcctgga tctgctctag aggcccaagc   4168
tgcctgcctg aggaaggatg acttgacaag tcaggagaca ctgttcccaa agccttgacc   4228
agagcacctc agcccgctga ccttgcacaa actccatctg ctgccatgag aaaagggaag   4288
```

```
ccgcctttgc aaaacattgc tgcctaaaga aactcagcag cctcaggccc aattctgcca   4348

cttctggttt gggtacagtt aaaggcaacc ctgagggact tggcagtaga aatccagggc   4408

ctcccctggg gctggcagct tcgtgtgcag ctagagcttt acctgaaagg aagtctctgg   4468

gcccagaact ctccaccaag agcctccctg ccgttcgctg agtcccagca attctcctaa   4528

gttgaaggga tctgagaagg agaaggaaat gtggggtaga tttggtggtg gttagagata   4588

tgcccccctc attactgcca acagtttcgg ctgcatttct tcacgcacct cggttcctct   4648

tcctgaagtt cttgtgccct gctcttcagc accatgggcc ttcttatacg gaaggctctg   4708

ggatctcccc cttgtggggc aggctcttgg ggccagccta agatcatggt ttagggtgat   4768

cagtgctggc agataaattg aaaaggcacg ctggcttgtg atcttaaatg aggacaatcc   4828

ccccagggct gggcactcct cccctcccct cacttctccc acctgcagag ccagtgtcct   4888

tgggtgggct agataggata tactgtatgc cggctccttc aagctgctga ctcactttat   4948

caatagttcc atttaaattg acttcagtgg tgagactgta tcctgtttgc tattgcttgt   5008

tgtgctatgg ggggaggggg gaggaatgtg taagatagtt aacatgggca aagggagatc   5068

ttggggtgca gcacttaaac tgcctcgtaa cccttttcat gatttcaacc acatttgcta   5128

gagggaggga gcagccacgg agttagaggc ccttggggtt tctcttttcc actgacaggc   5188

tttcccaggc agctggctag ttcattccct ccccagccag gtgcaggcgt aggaatatgg   5248

acatctggtt gctttggcct gctgccctct ttcaggggtc ctaagcccac aatcatgcct   5308

ccctaagacc ttggcatcct tccctctaag ccgttggcac ctctgtgcca cctctcacac   5368

tggctccaga cacacagcct gtgcttttgg agctgagatc actcgcttca ccctcctcat   5428

ctttgttctc caagtaaagc cacgaggtcg gggcgagggc agaggtgatc acctgcgtgt   5488

cccatctaca gacctgcagc ttcataaaac ttctgatttc tcttcagctt tgaaaagggt   5548

taccctgggc actggcctag agcctcacct cctaatagac ttagccccat gagtttgcca   5608

tgttgagcag gactatttct ggcacttgca agtcccatga tttcttcggt aattctgagg   5668

gtggggggag ggacatgaaa tcatcttagc ttagctttct gtctgtgaat gtctatatag   5728

tgtattgtgt gttttaacaa atgatttaca ctgactgttg ctgtaaaagt gaatttggaa   5788

ataaagttat tactctgatt aaa                                           5811


<210> SEQ ID NO 8
<211> LENGTH: 5637
<212> TYPE: DNA
<213> ORGANISM: homo sapiens
<220> FEATURE:
<221> NAME/KEY: CDS
<222> LOCATION: (323)...(1474)

<400> SEQUENCE: 8

ggacggccga gcggcagggc gctcgcgcgc gcccactagt ggccggagga gaaggctccc     60

gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca gg atg gct gag ccc cgc cag gag ttc gaa gtg    352
                         Met Ala Glu Pro Arg Gln Glu Phe Glu Val
                          1               5                  10

atg gaa gat cac gct ggg acg tac ggg ttg ggg gac agg aaa gat cag      400
Met Glu Asp His Ala Gly Thr Tyr Gly Leu Gly Asp Arg Lys Asp Gln
```

-continued

```
                15                  20                  25

ggg ggc tac acc atg cac caa gac caa gag ggt gac acg gac gct ggc      448
Gly Gly Tyr Thr Met His Gln Asp Gln Glu Gly Asp Thr Asp Ala Gly
            30                  35                  40

ctg aaa gct gaa gaa gca ggc att gga gac acc ccc agc ctg gaa gac      496
Leu Lys Ala Glu Glu Ala Gly Ile Gly Asp Thr Pro Ser Leu Glu Asp
        45                  50                  55

gaa gct gct ggt cac gtg acc caa gct cgc atg gtc agt aaa agc aaa      544
Glu Ala Ala Gly His Val Thr Gln Ala Arg Met Val Ser Lys Ser Lys
    60                  65                  70

gac ggg act gga agc gat gac aaa aaa gcc aag ggg gct gat ggt aaa      592
Asp Gly Thr Gly Ser Asp Asp Lys Lys Ala Lys Gly Ala Asp Gly Lys
 75                  80                  85                  90

acg aag atc gcc aca ccg cgg gga gca gcc cct cca ggc cag aag ggc      640
Thr Lys Ile Ala Thr Pro Arg Gly Ala Ala Pro Pro Gly Gln Lys Gly
                95                 100                 105

cag gcc aac gcc acc agg att cca gca aaa acc ccg ccc gct cca aag      688
Gln Ala Asn Ala Thr Arg Ile Pro Ala Lys Thr Pro Pro Ala Pro Lys
            110                 115                 120

aca cca ccc agc tct ggt gaa cct cca aaa tca ggg gat cgc agc ggc      736
Thr Pro Pro Ser Ser Gly Glu Pro Pro Lys Ser Gly Asp Arg Ser Gly
        125                 130                 135

tac agc agc ccc ggc tcc cca ggc act ccc ggc agc cgc tcc cgc acc      784
Tyr Ser Ser Pro Gly Ser Pro Gly Thr Pro Gly Ser Arg Ser Arg Thr
    140                 145                 150

ccg tcc ctt cca acc cca ccc acc cgg gag ccc aag aag gtg gca gtg      832
Pro Ser Leu Pro Thr Pro Pro Thr Arg Glu Pro Lys Lys Val Ala Val
155                 160                 165                 170

gtc cgt act cca ccc aag tcg ccg tct tcc gcc aag agc cgc ctg cag      880
Val Arg Thr Pro Pro Lys Ser Pro Ser Ser Ala Lys Ser Arg Leu Gln
                175                 180                 185

aca gcc ccc gtg ccc atg cca gac ctg aag aat gtc aag tcc aag atc      928
Thr Ala Pro Val Pro Met Pro Asp Leu Lys Asn Val Lys Ser Lys Ile
            190                 195                 200

ggc tcc act gag aac ctg aag cac cag ccg gga ggc ggg aag gtg cag      976
Gly Ser Thr Glu Asn Leu Lys His Gln Pro Gly Gly Gly Lys Val Gln
        205                 210                 215

ata att aat aag aag ctg gat ctt agc aac gtc cag tcc aag tgt ggc     1024
Ile Ile Asn Lys Lys Leu Asp Leu Ser Asn Val Gln Ser Lys Cys Gly
    220                 225                 230

tca aag gat aat atc aaa cac gtc ccg gga ggc ggc agt gtg caa ata     1072
Ser Lys Asp Asn Ile Lys His Val Pro Gly Gly Gly Ser Val Gln Ile
235                 240                 245                 250

gtc tac aaa cca gtt gac ctg agc aag gtg acc tcc aag tgt ggc tca     1120
Val Tyr Lys Pro Val Asp Leu Ser Lys Val Thr Ser Lys Cys Gly Ser
                255                 260                 265

tta ggc aac atc cat cat aaa cca gga ggt ggc cag gtg gaa gta aaa     1168
Leu Gly Asn Ile His His Lys Pro Gly Gly Gly Gln Val Glu Val Lys
            270                 275                 280

tct gag aag ctt gac ttc aag gac aga gtc cag tcg aag att ggg tcc     1216
Ser Glu Lys Leu Asp Phe Lys Asp Arg Val Gln Ser Lys Ile Gly Ser
        285                 290                 295

ctg gac aat atc acc cac gtc cct ggc gga gga aat aaa aag att gaa     1264
Leu Asp Asn Ile Thr His Val Pro Gly Gly Gly Asn Lys Lys Ile Glu
    300                 305                 310

acc cac aag ctg acc ttc cgc gag aac gcc aaa gcc aag aca gac cac     1312
Thr His Lys Leu Thr Phe Arg Glu Asn Ala Lys Ala Lys Thr Asp His
315                 320                 325                 330

ggg gcg gag atc gtg tac aag tcg cca gtg gtg tct ggg gac acg tct     1360
```

-continued

```
Gly Ala Glu Ile Val Tyr Lys Ser Pro Val Val Ser Gly Asp Thr Ser
                335                 340                 345

cca cgg cat ctc agc aat gtc tcc tcc acc ggc agc atc gac atg gta     1408
Pro Arg His Leu Ser Asn Val Ser Ser Thr Gly Ser Ile Asp Met Val
            350                 355                 360

gac tcg ccc cag ctc gcc acg cta gct gac gag gtg tct gcc tcc ctg     1456
Asp Ser Pro Gln Leu Ala Thr Leu Ala Asp Glu Val Ser Ala Ser Leu
        365                 370                 375

gcc aag cag ggt ttg tga tcaggcccct ggggcggtca ataattgtgg            1504
Ala Lys Gln Gly Leu
    380

agaggagaga atgagagagt gtggaaaaaa aaagaataat gacccggccc ccgccctctg   1564

cccccagctg ctcctcgcag ttcggttaat tggttaatca cttaacctgc ttttgtcact   1624

cggctttggc tcgggacttc aaaatcagtg atgggagtaa gagcaaattt catctttcca   1684

aattgatggg tgggctagta ataaaatatt taaaaaaaaa cattcaaaaa catggccaca   1744

tccaacattt cctcaggcaa ttccttttga ttcttttttc ttccccctcc atgtagaaga   1804

gggagaagga gaggctctga aagctgcttc tgggggattt caagggactg ggggtgccaa   1864

ccacctctgg ccctgttgtg ggggtgtcac agaggcagtg gcagcaacaa aggatttgaa   1924

acttggtgtg ttcgtggagc cacaggcaga cgatgtcaac cttgtgtgag tgtgacgggg   1984

gttggggtgg ggcgggaggc cacgggggag gccgaggcag ggctgggca gaggggagag    2044

gaagcacaag aagtgggagt gggagaggaa gccacgtgct ggagagtaga catccccctc   2104

cttgccgctg ggagagccaa ggcctatgcc acctgcagcg tctgagcggc cgcctgtcct   2164

tggtggccgg gggtgggggc ctgctgtggg tcagtgtgcc accctctgca gggcagcctg   2224

tgggagaagg gacagcgggt aaaaagagaa ggcaagctgg caggagggtg gcacttcgtg   2284

gatgacctcc ttagaaaaga ctgaccttga tgtcttgaga gcgctggcct cttcctccct   2344

ccctgcaggg tagggggcct gagttgaggg gcttccctct gctccacaga aaccctgttt   2404

tattgagttc tgaaggttgg aactgctgcc atgattttgg ccactttgca gacctgggac   2464

tttagggcta accagttctc tttgtaagga cttgtgcctc ttgggagacg tccacccgtt   2524

tccaagcctg ggccactggc atctctggag tgtgtggggg tctgggaggc aggtcccgag   2584

ccccctgtcc ttcccacggc cactgcagtc accccgtctg cgccgctgtg ctgttgtctg   2644

ccgtgagagc ccaatcactg cctatacccc tcatcacacg tcacaatgtc ccgaattccc   2704

agcctcacca ccccttctca gtaatgaccc tggttggttg caggaggtac ctactccata   2764

ctgagggtga aattaaggga aggcaaagtc caggcacaag agtgggaccc cagcctctca   2824

ctctcagttc cactcatcca actgggaccc tcaccacgaa tctcatgatc tgattcggtt   2884

ccctgtctcc tcctcccgtc acagatgtga gccagggcac tgctcagctg tgaccctagg   2944

tgtttctgcc ttgttgacat ggagagagcc ctttcccctg agaaggcctg gccccttcct   3004

gtgctgagcc cacagcagca ggctgggtgt cttggttgtc agtggtggca ccaggatgga   3064

agggcaaggc acccagggca ggcccacagt cccgctgtcc cccacttgca ccctagcttg   3124

tagctgccaa cctcccagac agcccagccc gctgctcagc tccacatgca tagtatcagc   3184

cctccacacc cgacaaaggg gaacacaccc ccttggaaat ggttcttttc ccccagtccc   3244

agctggaagc catgctgtct gttctgctgg agcagctgaa catatacata gatgttgccc   3304

tgccctcccc atctgcaccc tgttgagttg tagttggatt tgtctgttta tgcttggatt   3364

caccagagtg actatgatag tgaaaagaaa aaaaaaaaaa aaaaaggacg catgtatctt   3424
```

-continued

```
gaaatgcttg taaagaggtt tctaacccac cctcacgagg tgtctctcac ccccacactg   3484
ggactcgtgt ggcctgtgtg gtgccaccct gctggggcct cccaagtttt gaaaggcttt   3544
cctcagcacc tgggacccaa cagagaccag cttctagcag ctaaggaggc cgttcagctg   3604
tgacgaaggc ctgaagcaca ggattaggac tgaagcgatg atgtcccctt ccctacttcc   3664
ccttggggct ccctgtgtca gggcacagac taggtcttgt ggctggtctg gcttgcggcg   3724
cgaggatggt tctctctggt catagcccga agtctcatgg cagtcccaaa ggaggcttac   3784
aactcctgca tcacaagaaa aaggaagcca ctgccagctg gggggatctg cagctcccag   3844
aagctccgtg agcctcagcc acccctcaga ctgggttcct ctccaagctc gccctctgga   3904
ggggcagcgc agcctcccac caagggccct gcgaccacag cagggattgg gatgaattgc   3964
ctgtcctgga tctgctctag aggcccaagc tgcctgcctg aggaaggatg acttgacaag   4024
tcaggagaca ctgttcccaa agccttgacc agagcacctc agcccgctga ccttgcacaa   4084
actccatctg ctgccatgag aaaagggaag ccgcctttgc aaaacattgc tgcctaaaga   4144
aactcagcag cctcaggccc aattctgcca cttctggttt gggtacagtt aaaggcaacc   4204
ctgagggact tggcagtaga aatccagggc ctcccctggg gctggcagct tcgtgtgcag   4264
ctagagcttt acctgaaagg aagtctctgg gcccagaact ctccaccaag agcctccctg   4324
ccgttcgctg agtcccagca attctcctaa gttgaaggga tctgagaagg agaaggaaat   4384
gtggggtaga tttggtggtg gttagagata tgccccccctc attactgcca acagtttcgg   4444
ctgcatttct tcacgcacct cggttcctct tcctgaagtt cttgtgccct gctcttcagc   4504
accatgggcc ttcttatacg gaaggctctg ggatctcccc cttgtggggc aggctcttgg   4564
ggccagccta agatcatggt ttagggtgat cagtgctggc agataaattg aaaaggcacg   4624
ctggcttgtg atcttaaatg aggacaatcc ccccagggct gggcactcct cccctcccct   4684
cacttctccc acctgcagag ccagtgtcct tgggtgggct agataggata tactgtatgc   4744
cggctccttc aagctgctga ctcactttat caatagttcc atttaaattg acttcagtgg   4804
tgagactgta tcctgtttgc tattgcttgt tgtgctatgg ggggaggggg gaggaatgtg   4864
taagatagtt aacatgggca aagggagatc ttggggtgca gcacttaaac tgcctcgtaa   4924
cccttttcat gatttcaacc acatttgcta gagggaggga gcagccacgg agttagaggc   4984
ccttggggtt tctcttttcc actgacaggc tttcccaggc agctggctag ttcattccct   5044
ccccagccag gtgcaggcgt aggaatatgg acatctggtt gctttggcct gctgccctct   5104
ttcaggggtc ctaagcccac aatcatgcct ccctaagacc ttggcatcct tccctctaag   5164
ccgttggcac ctctgtgcca cctctcacac tggctccaga cacacagcct gtgcttttgg   5224
agctgagatc actcgcttca ccctcctcat ctttgttctc caagtaaagc cacgaggtcg   5284
gggcgagggc agaggtgatc acctgcgtgt cccatctaca gacctgcagc ttcataaaac   5344
ttctgatttc tcttcagctt tgaaaagggt taccctgggc actggcctag agcctcacct   5404
cctaatagac ttagccccat gagtttgcca tgttgagcag gactatttct ggcacttgca   5464
agtcccatga tttcttcggt aattctgagg gtggggggag ggacatgaaa tcatcttagc   5524
ttagctttct gtctgtgaat gtctatatag tgtattgtgt gttttaacaa atgatttaca   5584
ctgactgttg ctgtaaaagt gaatttggaa ataaagttat tactctgatt aaa          5637
```

<210> SEQ ID NO 9
<211> LENGTH: 6762
<212> TYPE: DNA
<213> ORGANISM: homo sapiens

```
<220> FEATURE:
<221> NAME/KEY: CDS
<222> LOCATION: (323)...(2599)

<400> SEQUENCE: 9

ggacggccga gcggcagggc gctcgcgcgc gcccactagt ggccggagga gaaggctccc      60

gcggaggccg cgctgcccgc cccctcccct ggggaggctc gcgttcccgc tgctcgcgcc     120

tgcgccgccc gccggcctca ggaacgcgcc ctcttcgccg gcgcgcgccc tcgcagtcac     180

cgccacccac cagctccggc accaacagca gcgccgctgc caccgcccac cttctgccgc     240

cgccaccaca gccaccttct cctcctccgc tgtcctctcc cgtcctcgcc tctgtcgact     300

atcaggtgaa ctttgaacca gg atg gct gag ccc cgc cag gag ttc gaa gtg      352
                         Met Ala Glu Pro Arg Gln Glu Phe Glu Val
                          1               5                  10

atg gaa gat cac gct ggg acg tac ggg ttg ggg gac agg aaa gat cag      400
Met Glu Asp His Ala Gly Thr Tyr Gly Leu Gly Asp Arg Lys Asp Gln
                15                  20                  25

ggg ggc tac acc atg cac caa gac caa gag ggt gac acg gac gct ggc      448
Gly Gly Tyr Thr Met His Gln Asp Gln Glu Gly Asp Thr Asp Ala Gly
            30                  35                  40

ctg aaa gaa tct ccc ctg cag acc ccc act gag gac gga tct gag gaa      496
Leu Lys Glu Ser Pro Leu Gln Thr Pro Thr Glu Asp Gly Ser Glu Glu
        45                  50                  55

ccg ggc tct gaa acc tct gat gct aag agc act cca aca gcg gaa gat      544
Pro Gly Ser Glu Thr Ser Asp Ala Lys Ser Thr Pro Thr Ala Glu Asp
    60                  65                  70

gtg aca gca ccc tta gtg gat gag gga gct ccc ggc aag cag gct gcc      592
Val Thr Ala Pro Leu Val Asp Glu Gly Ala Pro Gly Lys Gln Ala Ala
 75                  80                  85                  90

gcg cag ccc cac acg gag atc cca gaa gga acc aca gct gaa gaa gca      640
Ala Gln Pro His Thr Glu Ile Pro Glu Gly Thr Thr Ala Glu Glu Ala
                95                 100                 105

ggc att gga gac acc ccc agc ctg gaa gac gaa gct gct ggt cac gtg      688
Gly Ile Gly Asp Thr Pro Ser Leu Glu Asp Glu Ala Ala Gly His Val
            110                 115                 120

acc caa gag cct gaa agt ggt aag gtg gtc cag gaa ggc ttc ctc cga      736
Thr Gln Glu Pro Glu Ser Gly Lys Val Val Gln Glu Gly Phe Leu Arg
        125                 130                 135

gag cca ggc ccc cca ggt ctg agc cac cag ctc atg tcc ggc atg cct      784
Glu Pro Gly Pro Pro Gly Leu Ser His Gln Leu Met Ser Gly Met Pro
    140                 145                 150

ggg gct ccc ctc ctg cct gag ggc ccc aga gag gcc aca cgc caa cct      832
Gly Ala Pro Leu Leu Pro Glu Gly Pro Arg Glu Ala Thr Arg Gln Pro
155                 160                 165                 170

tcg ggg aca gga cct gag gac aca gag ggc ggc cgc cac gcc cct gag      880
Ser Gly Thr Gly Pro Glu Asp Thr Glu Gly Gly Arg His Ala Pro Glu
                175                 180                 185

ctg ctc aag cac cag ctt cta gga gac ctg cac cag gag ggg ccg ccg      928
Leu Leu Lys His Gln Leu Leu Gly Asp Leu His Gln Glu Gly Pro Pro
            190                 195                 200

ctg aag ggg gca ggg ggc aaa gag agg ccg ggg agc aag gag gag gtg      976
Leu Lys Gly Ala Gly Gly Lys Glu Arg Pro Gly Ser Lys Glu Glu Val
        205                 210                 215

gat gaa gac cgc gac gtc gat gag tcc tcc ccc caa gac tcc cct ccc     1024
Asp Glu Asp Arg Asp Val Asp Glu Ser Ser Pro Gln Asp Ser Pro Pro
    220                 225                 230

tcc aag gcc tcc cca gcc caa gat ggg cgg cct ccc cag aca gcc gcc     1072
Ser Lys Ala Ser Pro Ala Gln Asp Gly Arg Pro Pro Gln Thr Ala Ala
235                 240                 245                 250
```

-continued

```
aga gaa gcc acc agc atc cca ggc ttc cca gcg gag ggt gcc atc ccc     1120
Arg Glu Ala Thr Ser Ile Pro Gly Phe Pro Ala Glu Gly Ala Ile Pro
                255                 260                 265

ctc cct gtg gat ttc ctc tcc aaa gtt tcc aca gag atc cca gcc tca     1168
Leu Pro Val Asp Phe Leu Ser Lys Val Ser Thr Glu Ile Pro Ala Ser
            270                 275                 280

gag ccc gac ggg ccc agt gta ggg cgg gcc aaa ggg cag gat gcc ccc     1216
Glu Pro Asp Gly Pro Ser Val Gly Arg Ala Lys Gly Gln Asp Ala Pro
        285                 290                 295

ctg gag ttc acg ttt cac gtg gaa atc aca ccc aac gtg cag aag gag     1264
Leu Glu Phe Thr Phe His Val Glu Ile Thr Pro Asn Val Gln Lys Glu
    300                 305                 310

cag gcg cac tcg gag gag cat ttg gga agg gct gca ttt cca ggg gcc     1312
Gln Ala His Ser Glu Glu His Leu Gly Arg Ala Ala Phe Pro Gly Ala
315                 320                 325                 330

cct gga gag ggg cca gag gcc cgg ggc ccc tct ttg gga gag gac aca     1360
Pro Gly Glu Gly Pro Glu Ala Arg Gly Pro Ser Leu Gly Glu Asp Thr
                335                 340                 345

aaa gag gct gac ctt cca gag ccc tct gaa aag cag cct gct gct gct     1408
Lys Glu Ala Asp Leu Pro Glu Pro Ser Glu Lys Gln Pro Ala Ala Ala
            350                 355                 360

ccg cgg ggg aag ccc gtc agc cgg gtc cct caa ctc aaa gct cgc atg     1456
Pro Arg Gly Lys Pro Val Ser Arg Val Pro Gln Leu Lys Ala Arg Met
        365                 370                 375

gtc agt aaa agc aaa gac ggg act gga agc gat gac aaa aaa gcc aag     1504
Val Ser Lys Ser Lys Asp Gly Thr Gly Ser Asp Asp Lys Lys Ala Lys
    380                 385                 390

aca tcc aca cgt tcc tct gct aaa acc ttg aaa aat agg cct tgc ctt     1552
Thr Ser Thr Arg Ser Ser Ala Lys Thr Leu Lys Asn Arg Pro Cys Leu
395                 400                 405                 410

agc ccc aaa cac ccc act cct ggt agc tca gac cct ctg atc caa ccc     1600
Ser Pro Lys His Pro Thr Pro Gly Ser Ser Asp Pro Leu Ile Gln Pro
                415                 420                 425

tcc agc cct gct gtg tgc cca gag cca cct tcc tct cct aaa tac gtc     1648
Ser Ser Pro Ala Val Cys Pro Glu Pro Pro Ser Ser Pro Lys Tyr Val
            430                 435                 440

tct tct gtc act tcc cga act ggc agt tct gga gca aag gag atg aaa     1696
Ser Ser Val Thr Ser Arg Thr Gly Ser Ser Gly Ala Lys Glu Met Lys
        445                 450                 455

ctc aag ggg gct gat ggt aaa acg aag atc gcc aca ccg cgg gga gca     1744
Leu Lys Gly Ala Asp Gly Lys Thr Lys Ile Ala Thr Pro Arg Gly Ala
    460                 465                 470

gcc cct cca ggc cag aag ggc cag gcc aac gcc acc agg att cca gca     1792
Ala Pro Pro Gly Gln Lys Gly Gln Ala Asn Ala Thr Arg Ile Pro Ala
475                 480                 485                 490

aaa acc ccg ccc gct cca aag aca cca ccc agc tct ggt gaa cct cca     1840
Lys Thr Pro Pro Ala Pro Lys Thr Pro Pro Ser Ser Gly Glu Pro Pro
                495                 500                 505

aaa tca ggg gat cgc agc ggc tac agc agc ccc ggc tcc cca ggc act     1888
Lys Ser Gly Asp Arg Ser Gly Tyr Ser Ser Pro Gly Ser Pro Gly Thr
            510                 515                 520

ccc ggc agc cgc tcc cgc acc ccg tcc ctt cca acc cca ccc acc cgg     1936
Pro Gly Ser Arg Ser Arg Thr Pro Ser Leu Pro Thr Pro Pro Thr Arg
        525                 530                 535

gag ccc aag aag gtg gca gtg gtc cgt act cca ccc aag tcg ccg tct     1984
Glu Pro Lys Lys Val Ala Val Val Arg Thr Pro Pro Lys Ser Pro Ser
    540                 545                 550

tcc gcc aag agc cgc ctg cag aca gcc ccc gtg ccc atg cca gac ctg     2032
Ser Ala Lys Ser Arg Leu Gln Thr Ala Pro Val Pro Met Pro Asp Leu
```

```
555                 560                 565                 570

aag aat gtc aag tcc aag atc ggc tcc act gag aac ctg aag cac cag     2080
Lys Asn Val Lys Ser Lys Ile Gly Ser Thr Glu Asn Leu Lys His Gln
                575                 580                 585

ccg gga ggc ggg aag gtg cag ata att aat aag aag ctg gat ctt agc     2128
Pro Gly Gly Gly Lys Val Gln Ile Ile Asn Lys Lys Leu Asp Leu Ser
            590                 595                 600

aac gtc cag tcc aag tgt ggc tca aag gat aat atc aaa cac gtc ccg     2176
Asn Val Gln Ser Lys Cys Gly Ser Lys Asp Asn Ile Lys His Val Pro
        605                 610                 615

gga ggc ggc agt gtg caa ata gtc tac aaa cca gtt gac ctg agc aag     2224
Gly Gly Gly Ser Val Gln Ile Val Tyr Lys Pro Val Asp Leu Ser Lys
    620                 625                 630

gtg acc tcc aag tgt ggc tca tta ggc aac atc cat cat aaa cca gga     2272
Val Thr Ser Lys Cys Gly Ser Leu Gly Asn Ile His His Lys Pro Gly
635                 640                 645                 650

ggt ggc cag gtg gaa gta aaa tct gag aag ctt gac ttc aag gac aga     2320
Gly Gly Gln Val Glu Val Lys Ser Glu Lys Leu Asp Phe Lys Asp Arg
                655                 660                 665

gtc cag tcg aag att ggg tcc ctg gac aat atc acc cac gtc cct ggc     2368
Val Gln Ser Lys Ile Gly Ser Leu Asp Asn Ile Thr His Val Pro Gly
            670                 675                 680

gga gga aat aaa aag att gaa acc cac aag ctg acc ttc cgc gag aac     2416
Gly Gly Asn Lys Lys Ile Glu Thr His Lys Leu Thr Phe Arg Glu Asn
        685                 690                 695

gcc aaa gcc aag aca gac cac ggg gcg gag atc gtg tac aag tcg cca     2464
Ala Lys Ala Lys Thr Asp His Gly Ala Glu Ile Val Tyr Lys Ser Pro
    700                 705                 710

gtg gtg tct ggg gac acg tct cca cgg cat ctc agc aat gtc tcc tcc     2512
Val Val Ser Gly Asp Thr Ser Pro Arg His Leu Ser Asn Val Ser Ser
715                 720                 725                 730

acc ggc agc atc gac atg gta gac tcg ccc cag ctc gcc acg cta gct     2560
Thr Gly Ser Ile Asp Met Val Asp Ser Pro Gln Leu Ala Thr Leu Ala
                735                 740                 745

gac gag gtg tct gcc tcc ctg gcc aag cag ggt ttg tga tcaggcccct      2609
Asp Glu Val Ser Ala Ser Leu Ala Lys Gln Gly Leu
            750                 755

ggggcggtca ataattgtgg agaggagaga atgagagagt gtggaaaaaa aaagaataat   2669

gacccggccc ccgccctctg cccccagctg ctcctcgcag ttcggttaat tggttaatca   2729

cttaacctgc ttttgtcact cggctttggc tcgggacttc aaaatcagtg atgggagtaa   2789

gagcaaattt catctttcca aattgatggg tgggctagta ataaaatatt taaaaaaaaa   2849

cattcaaaaa catggccaca tccaacattt cctcaggcaa ttccttttga ttcttttttc   2909

ttccccctcc atgtagaaga gggagaagga gaggctctga aagctgcttc tgggggattt   2969

caagggactg ggggtgccaa ccacctctgg ccctgttgtg ggggtgtcac agaggcagtg   3029

gcagcaacaa aggatttgaa acttggtgtg ttcgtggagc cacaggcaga cgatgtcaac   3089

cttgtgtgag tgtgacgggg gttggggtgg ggcgggaggc cacgggggag gccgaggcag   3149

gggctgggca gaggggagag gaagcacaag aagtgggagt gggagaggaa gccacgtgct   3209

ggagagtaga catccccctc cttgccgctg ggagagccaa ggcctatgcc acctgcagcg   3269

tctgagcggc cgcctgtcct tggtggccgg gggtgggggc ctgctgtggg tcagtgtgcc   3329

accctctgca gggcagcctg tgggagaagg gacagcgggt aaaaagagaa ggcaagctgg   3389

caggagggtg gcacttcgtg gatgacctcc ttagaaaaga ctgaccttga tgtcttgaga   3449

gcgctggcct cttcctccct ccctgcaggg taggggcct gagttgaggg gcttccctct    3509
```

```
gctccacaga aaccctgttt tattgagttc tgaaggttgg aactgctgcc atgattttgg   3569
ccactttgca gacctgggac tttagggcta accagttctc tttgtaagga cttgtgcctc   3629
ttgggagacg tccacccgtt tccaagcctg ggccactggc atctctggag tgtgtggggg   3689
tctgggaggc aggtcccgag ccccctgtcc ttcccacggc cactgcagtc accccgtctg   3749
cgccgctgtg ctgttgtctg ccgtgagagc ccaatcactg cctatacccc tcatcacacg   3809
tcacaatgtc ccgaattccc agcctcacca ccccttctca gtaatgaccc tggttggttg   3869
caggaggtac ctactccata ctgagggtga aattaaggga aggcaaagtc caggcacaag   3929
agtgggaccc cagcctctca ctctcagttc cactcatcca actgggaccc tcaccacgaa   3989
tctcatgatc tgattcggtt ccctgtctcc tcctcccgtc acagatgtga gccagggcac   4049
tgctcagctg tgaccctagg tgtttctgcc ttgttgacat ggagagagcc ctttcccctg   4109
agaaggcctg gccccttcct gtgctgagcc cacagcagca ggctgggtgt cttggttgtc   4169
agtggtggca ccaggatgga agggcaaggc acccagggca ggcccacagt cccgctgtcc   4229
cccacttgca ccctagcttg tagctgccaa cctcccagac agcccagccc gctgctcagc   4289
tccacatgca tagtatcagc cctccacacc cgacaaaggg gaacacaccc ccttggaaat   4349
ggttcttttc ccccagtccc agctggaagc catgctgtct gttctgctgg agcagctgaa   4409
catatacata gatgttgccc tgccctcccc atctgcaccc tgttgagttg tagttggatt   4469
tgtctgttta tgcttggatt caccagagtg actatgatag tgaaaagaaa aaaaaaaaaa   4529
aaaaaggacg catgtatctt gaaatgcttg taaagaggtt tctaacccac cctcacgagg   4589
tgtctctcac ccccacactg ggactcgtgt ggcctgtgtg gtgccaccct gctggggcct   4649
cccaagtttt gaaaggcttt cctcagcacc tgggacccaa cagagaccag cttctagcag   4709
ctaaggaggc cgttcagctg tgacgaaggc ctgaagcaca ggattaggac tgaagcgatg   4769
atgtcccctt ccctacttcc ccttggggct ccctgtgtca gggcacagac taggtcttgt   4829
ggctggtctg gcttgcggcg cgaggatggt tctctctggt catagcccga agtctcatgg   4889
cagtcccaaa ggaggcttac aactcctgca tcacaagaaa aaggaagcca ctgccagctg   4949
gggggatctg cagctcccag aagctccgtg agcctcagcc acccctcaga ctgggttcct   5009
ctccaagctc gccctctgga ggggcagcgc agcctcccac caagggccct gcgaccacag   5069
cagggattgg gatgaattgc ctgtcctgga tctgctctag aggcccaagc tgcctgcctg   5129
aggaaggatg acttgacaag tcaggagaca ctgttcccaa agccttgacc agagcacctc   5189
agcccgctga ccttgcacaa actccatctg ctgccatgag aaaagggaag ccgcctttgc   5249
aaaacattgc tgcctaaaga aactcagcag cctcaggccc aattctgcca cttctggttt   5309
gggtacagtt aaaggcaacc ctgagggact tggcagtaga aatccagggc ctcccctggg   5369
gctggcagct tcgtgtgcag ctagagcttt acctgaaagg aagtctctgg gcccagaact   5429
ctccaccaag agcctccctg ccgttcgctg agtcccagca attctcctaa gttgaaggga   5489
tctgagaagg agaaggaaat gtggggtaga tttggtggtg gttagagata tgccccccctc   5549
attactgcca acagtttcgg ctgcatttct tcacgcacct cggttcctct tcctgaagtt   5609
cttgtgccct gctcttcagc accatgggcc ttcttatacg gaaggctctg ggatctcccc   5669
cttgtggggc aggctcttgg ggccagccta agatcatggt ttagggtgat cagtgctggc   5729
agataaattg aaaaggcacg ctggcttgtg atcttaaatg aggacaatcc ccccagggct   5789
gggcactcct cccctcccct cacttctccc acctgcagag ccagtgtcct tgggtgggct   5849
```

```
agataggata tactgtatgc cggctccttc aagctgctga ctcactttat caatagttcc   5909

atttaaattg acttcagtgg tgagactgta tcctgtttgc tattgcttgt tgtgctatgg   5969

ggggaggggg gaggaatgtg taagatagtt aacatgggca aagggagatc ttggggtgca   6029

gcacttaaac tgcctcgtaa cccttttcat gatttcaacc acatttgcta gagggaggga   6089

gcagccacgg agttagaggc ccttggggtt tctcttttcc actgacaggc tttcccaggc   6149

agctggctag ttcattccct ccccagccag gtgcaggcgt aggaatatgg acatctggtt   6209

gctttggcct gctgccctct ttcaggggtc ctaagcccac aatcatgcct ccctaagacc   6269

ttggcatcct tccctctaag ccgttggcac ctctgtgcca cctctcacac tggctccaga   6329

cacacagcct gtgcttttgg agctgagatc actcgcttca ccctcctcat ctttgttctc   6389

caagtaaagc cacgaggtcg gggcgagggc agaggtgatc acctgcgtgt cccatctaca   6449

gacctgcagc ttcataaaac ttctgatttc tcttcagctt tgaaaagggt taccctgggc   6509

actggcctag agcctcacct cctaatagac ttagccccat gagtttgcca tgttgagcag   6569

gactatttct ggcacttgca agtcccatga tttcttcggt aattctgagg gtgggggag   6629

ggacatgaaa tcatcttagc ttagctttct gtctgtgaat gtctatatag tgtattgtgt   6689

gttttaacaa atgatttaca ctgactgttg ctgtaaaagt gaatttggaa ataaagttat   6749

tactctgatt aaa                                                      6762


<210> SEQ ID NO 10
<211> LENGTH: 5544
<212> TYPE: DNA
<213> ORGANISM: homo sapiens
<220> FEATURE:
<221> NAME/KEY: CDS
<222> LOCATION: (323)...(1381)

<400> SEQUENCE: 10

ggacggccga gcggcagggc gctcgcgcgc gcccactagt ggccggagga gaaggctccc     60

gcggaggccg cgctgcccgc cccctcccct ggggaggctc gcgttcccgc tgctcgcgcc    120

tgcgccgccc gccggcctca ggaacgcgcc ctcttcgccg gcgcgcgccc tcgcagtcac    180

cgccacccac cagctccggc accaacagca gcgccgctgc caccgcccac cttctgccgc    240

cgccaccaca gccaccttct cctcctccgc tgtcctctcc cgtcctcgcc tctgtcgact    300

atcaggtgaa ctttgaacca gg atg gct gag ccc cgc cag gag ttc gaa gtg     352
                         Met Ala Glu Pro Arg Gln Glu Phe Glu Val
                          1               5                  10

atg gaa gat cac gct ggg acg tac ggg ttg ggg gac agg aaa gat cag      400
Met Glu Asp His Ala Gly Thr Tyr Gly Leu Gly Asp Arg Lys Asp Gln
                15                  20                  25

ggg ggc tac acc atg cac caa gac caa gag ggt gac acg gac gct ggc      448
Gly Gly Tyr Thr Met His Gln Asp Gln Glu Gly Asp Thr Asp Ala Gly
            30                  35                  40

ctg aaa gct gaa gaa gca ggc att gga gac acc ccc agc ctg gaa gac      496
Leu Lys Ala Glu Glu Ala Gly Ile Gly Asp Thr Pro Ser Leu Glu Asp
        45                  50                  55

gaa gct gct ggt cac gtg acc caa gct cgc atg gtc agt aaa agc aaa      544
Glu Ala Ala Gly His Val Thr Gln Ala Arg Met Val Ser Lys Ser Lys
    60                  65                  70

gac ggg act gga agc gat gac aaa aaa gcc aag ggg gct gat ggt aaa      592
Asp Gly Thr Gly Ser Asp Asp Lys Lys Ala Lys Gly Ala Asp Gly Lys
 75                  80                  85                  90

acg aag atc gcc aca ccg cgg gga gca gcc cct cca ggc cag aag ggc      640
Thr Lys Ile Ala Thr Pro Arg Gly Ala Ala Pro Pro Gly Gln Lys Gly
```

-continued

```
                95                  100                 105

cag gcc aac gcc acc agg att cca gca aaa acc ccg ccc gct cca aag      688
Gln Ala Asn Ala Thr Arg Ile Pro Ala Lys Thr Pro Pro Ala Pro Lys
            110                 115                 120

aca cca ccc agc tct ggt gaa cct cca aaa tca ggg gat cgc agc ggc      736
Thr Pro Pro Ser Ser Gly Glu Pro Pro Lys Ser Gly Asp Arg Ser Gly
        125                 130                 135

tac agc agc ccc ggc tcc cca ggc act ccc ggc agc cgc tcc cgc acc      784
Tyr Ser Ser Pro Gly Ser Pro Gly Thr Pro Gly Ser Arg Ser Arg Thr
    140                 145                 150

ccg tcc ctt cca acc cca ccc acc cgg gag ccc aag aag gtg gca gtg      832
Pro Ser Leu Pro Thr Pro Pro Thr Arg Glu Pro Lys Lys Val Ala Val
155                 160                 165                 170

gtc cgt act cca ccc aag tcg ccg tct tcc gcc aag agc cgc ctg cag      880
Val Arg Thr Pro Pro Lys Ser Pro Ser Ser Ala Lys Ser Arg Leu Gln
                175                 180                 185

aca gcc ccc gtg ccc atg cca gac ctg aag aat gtc aag tcc aag atc      928
Thr Ala Pro Val Pro Met Pro Asp Leu Lys Asn Val Lys Ser Lys Ile
            190                 195                 200

ggc tcc act gag aac ctg aag cac cag ccg gga ggc ggg aag gtg caa      976
Gly Ser Thr Glu Asn Leu Lys His Gln Pro Gly Gly Gly Lys Val Gln
        205                 210                 215

ata gtc tac aaa cca gtt gac ctg agc aag gtg acc tcc aag tgt ggc     1024
Ile Val Tyr Lys Pro Val Asp Leu Ser Lys Val Thr Ser Lys Cys Gly
    220                 225                 230

tca tta ggc aac atc cat cat aaa cca gga ggt ggc cag gtg gaa gta     1072
Ser Leu Gly Asn Ile His His Lys Pro Gly Gly Gly Gln Val Glu Val
235                 240                 245                 250

aaa tct gag aag ctt gac ttc aag gac aga gtc cag tcg aag att ggg     1120
Lys Ser Glu Lys Leu Asp Phe Lys Asp Arg Val Gln Ser Lys Ile Gly
                255                 260                 265

tcc ctg gac aat atc acc cac gtc cct ggc gga gga aat aaa aag att     1168
Ser Leu Asp Asn Ile Thr His Val Pro Gly Gly Gly Asn Lys Lys Ile
            270                 275                 280

gaa acc cac aag ctg acc ttc cgc gag aac gcc aaa gcc aag aca gac     1216
Glu Thr His Lys Leu Thr Phe Arg Glu Asn Ala Lys Ala Lys Thr Asp
        285                 290                 295

cac ggg gcg gag atc gtg tac aag tcg cca gtg gtg tct ggg gac acg     1264
His Gly Ala Glu Ile Val Tyr Lys Ser Pro Val Val Ser Gly Asp Thr
    300                 305                 310

tct cca cgg cat ctc agc aat gtc tcc tcc acc ggc agc atc gac atg     1312
Ser Pro Arg His Leu Ser Asn Val Ser Ser Thr Gly Ser Ile Asp Met
315                 320                 325                 330

gta gac tcg ccc cag ctc gcc acg cta gct gac gag gtg tct gcc tcc     1360
Val Asp Ser Pro Gln Leu Ala Thr Leu Ala Asp Glu Val Ser Ala Ser
                335                 340                 345

ctg gcc aag cag ggt ttg tga tcaggcccct ggggcggtca ataattgtgg       1411
Leu Ala Lys Gln Gly Leu
            350

agaggagaga atgagagagt gtggaaaaaa aaagaataat gacccggccc ccgccctctg   1471

cccccagctg ctcctcgcag ttcggttaat tggttaatca cttaacctgc ttttgtcact   1531

cggctttggc tcgggacttc aaaatcagtg atgggagtaa gagcaaattt catctttcca   1591

aattgatggg tgggctagta ataaaatatt taaaaaaaaa cattcaaaaa catggccaca   1651

tccaacattt cctcaggcaa ttccttttga ttcttttttc ttccccctcc atgtagaaga   1711

gggagaagga gaggctctga aagctgcttc tgggggattt caagggactg ggggtgccaa   1771

ccacctctgg ccctgttgtg gggtgtcac agaggcagtg gcagcaacaa aggatttgaa    1831
```

```
acttggtgtg ttcgtggagc cacaggcaga cgatgtcaac cttgtgtgag tgtgacgggg   1891

gttggggtgg ggcgggaggc cacgggggag gccgaggcag gggctgggca gaggggagag   1951

gaagcacaag aagtgggagt gggagaggaa gccacgtgct ggagagtaga catccccctc   2011

cttgccgctg ggagagccaa ggcctatgcc acctgcagcg tctgagcggc cgcctgtcct   2071

tggtggccgg gggtgggggc ctgctgtggg tcagtgtgcc accctctgca gggcagcctg   2131

tgggagaagg gacagcgggt aaaaagagaa ggcaagctgg caggagggtg gcacttcgtg   2191

gatgacctcc ttagaaaaga ctgaccttga tgtcttgaga gcgctggcct cttcctccct   2251

ccctgcaggg tagggggcct gagttgaggg gcttccctct gctccacaga aaccctgttt   2311

tattgagttc tgaaggttgg aactgctgcc atgattttgg ccactttgca gacctgggac   2371

tttagggcta accagttctc tttgtaagga cttgtgcctc ttgggagacg tccacccgtt   2431

tccaagcctg ggccactggc atctctggag tgtgtggggg tctgggaggc aggtcccgag   2491

ccccctgtcc ttcccacggc cactgcagtc accccgtctg cgccgctgtg ctgttgtctg   2551

ccgtgagagc ccaatcactg cctatacccc tcatcacacg tcacaatgtc ccgaattccc   2611

agcctcacca ccccttctca gtaatgaccc tggttggttg caggaggtac ctactccata   2671

ctgagggtga aattaaggga aggcaaagtc caggcacaag agtgggaccc cagcctctca   2731

ctctcagttc cactcatcca actgggaccc tcaccacgaa tctcatgatc tgattcggtt   2791

ccctgtctcc tcctcccgtc acagatgtga gccagggcac tgctcagctg tgaccctagg   2851

tgtttctgcc ttgttgacat ggagagagcc ctttcccctg agaaggcctg gccccttcct   2911

gtgctgagcc cacagcagca ggctgggtgt cttggttgtc agtggtggca ccaggatgga   2971

agggcaaggc acccagggca ggcccacagt cccgctgtcc cccacttgca ccctagcttg   3031

tagctgccaa cctcccagac agcccagccc gctgctcagc tccacatgca tagtatcagc   3091

cctccacacc cgacaaaggg gaacacaccc ccttggaaat ggttcttttc ccccagtccc   3151

agctggaagc catgctgtct gttctgctgg agcagctgaa catatacata gatgttgccc   3211

tgccctcccc atctgcaccc tgttgagttg tagttggatt tgtctgttta tgcttggatt   3271

caccagagtg actatgatag tgaaaagaaa aaaaaaaaaa aaaaaggacg catgtatctt   3331

gaaatgcttg taaagaggtt tctaacccac cctcacgagg tgtctctcac ccccacactg   3391

ggactcgtgt ggcctgtgtg gtgccaccct gctggggcct cccaagtttt gaaaggcttt   3451

cctcagcacc tgggacccaa cagagaccag cttctagcag ctaaggaggc cgttcagctg   3511

tgacgaaggc ctgaagcaca ggattaggac tgaagcgatg atgtcccctt ccctacttcc   3571

ccttggggct ccctgtgtca gggcacagac taggtcttgt ggctggtctg gcttgcggcg   3631

cgaggatggt tctctctggt catagcccga agtctcatgg cagtcccaaa ggaggcttac   3691

aactcctgca tcacaagaaa aaggaagcca ctgccagctg gggggatctg cagctcccag   3751

aagctccgtg agcctcagcc acccctcaga ctgggttcct ctccaagctc gccctctgga   3811

ggggcagcgc agcctcccac caagggccct gcgaccacag cagggattgg gatgaattgc   3871

ctgtcctgga tctgctctag aggcccaagc tgcctgcctg aggaaggatg acttgacaag   3931

tcaggagaca ctgttcccaa agccttgacc agagcacctc agcccgctga ccttgcacaa   3991

actccatctg ctgccatgag aaaagggaag ccgcctttgc aaaacattgc tgcctaaaga   4051

aactcagcag cctcaggccc aattctgcca cttctggttt gggtacagtt aaaggcaacc   4111

ctgagggact tggcagtaga aatccagggc ctcccctggg gctggcagct tcgtgtgcag   4171
```

ctagagcttt acctgaaagg aagtctctgg gcccagaact ctccaccaag agcctccctg 4231 ccgttcgctg agtcccagca attctcctaa gttgaaggga tctgagaagg agaaggaaat 4291 gtggggtaga tttggtggtg gttagagata tgcccccctc attactgcca acagtttcgg 4351 ctgcatttct tcacgcacct cggttcctct tcctgaagtt cttgtgccct gctcttcagc 4411 accatgggcc ttcttatacg gaaggctctg ggatctcccc cttgtggggc aggctcttgg 4471 ggccagccta agatcatggt ttagggtgat cagtgctggc agataaattg aaaaggcacg 4531 ctggcttgtg atcttaaatg aggacaatcc ccccagggct gggcactcct cccctcccct 4591 cacttctccc acctgcagag ccagtgtcct tgggtgggct agataggata tactgtatgc 4651 cggctccttc aagctgctga ctcactttat caatagttcc atttaaattg acttcagtgg 4711 tgagactgta tcctgtttgc tattgcttgt tgtgctatgg ggggaggggg gaggaatgtg 4771 taagatagtt aacatgggca aagggagatc ttggggtgca gcacttaaac tgcctcgtaa 4831 cccttttcat gatttcaacc acatttgcta gagggaggga gcagccacgg agttagaggc 4891 ccttggggtt tctcttttcc actgacaggc tttcccaggc agctggctag ttcattccct 4951 ccccagccag gtgcaggcgt aggaatatgg acatctggtt gctttggcct gctgccctct 5011 ttcaggggtc ctaagcccac aatcatgcct ccctaagacc ttggcatcct tccctctaag 5071 ccgttggcac ctctgtgcca cctctcacac tggctccaga cacacagcct gtgcttttgg 5131 agctgagatc actcgcttca ccctcctcat ctttgttctc caagtaaagc cacgaggtcg 5191 gggcgagggc agaggtgatc acctgcgtgt cccatctaca gacctgcagc ttcataaaac 5251 ttctgatttc tcttcagctt tgaaaagggt taccctgggc actggcctag agcctcacct 5311 cctaatagac ttagccccat gagtttgcca tgttgagcag gactatttct ggcacttgca 5371 agtcccatga tttcttcggt aattctgagg gtggggggag ggacatgaaa tcatcttagc 5431 ttagctttct gtctgtgaat gtctatatag tgtattgtgt gttttaacaa atgatttaca 5491 ctgactgttg ctgtaaaagt gaatttggaa ataaagttat tactctgatt aaa 5544

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
ccttccctga aggttcctcc 20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
tcttattaat tatctgcacc 20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
ccagcttctt attaattatc 20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
taagatccag cttcttatta 20

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 15
ggacgtgtga aggtactc 18

<210> SEQ ID NO 16
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 16
gcccaagaag gatttatt 18

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
tcctgagagc ccaagaag 18

<210> SEQ ID NO 18
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 18
cagatcctga gagcccaa 18

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
tgaaggtact cacactgccg c 21

<210> SEQ ID NO 20
<211> LENGTH: 18
<212> TYPE: DNA

<213> ORGANISM: Artificial Sequence
<220> FEATURE:
<223> OTHER INFORMATION: Synthetic Oligonucleotide

<400> SEQUENCE: 20
tatctgcacc tttggtag 18

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
cgggaaggtg cagataatta ataag 25

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
ggacgtgttt gatattatcc tttgag 26

<210> SEQ ID NO 23
<211> LENGTH: 18
<212> TYPE: DNA
<213> ORGANISM: Artificial Sequence
<220> FEATURE:
<223> OTHER INFORMATION: Probe

<400> SEQUENCE: 23
agctggatct tagcaacg 18

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cactgagaac ctgaagcacc 20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
ggacgttgct aagatccagc t 21

<210> SEQ ID NO 26
<211> LENGTH: 26
<212> TYPE: DNA
<213> ORGANISM: Artificial Sequence
<220> FEATURE:
<223> OTHER INFORMATION: Probe

<400> SEQUENCE: 26
ttaattatct gcaccttccc gcctcc 26

-continued

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
ggataatatc aaacacgtcc cg 22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tgcctaatga gccacacttg 20

<210> SEQ ID NO 29
<211> LENGTH: 24
<212> TYPE: DNA
<213> ORGANISM: Artificial Sequence
<220> FEATURE:
<223> OTHER INFORMATION: Probe

<400> SEQUENCE: 29
gtctacaaac cagttgacct gagc 24

<210> SEQ ID NO 30
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 30
ugaagguacu cacacugccg c 21

<210> SEQ ID NO 31
<211> LENGTH: 18
<212> TYPE: RNA
<213> ORGANISM: Artificial Sequence
<220> FEATURE:
<223> OTHER INFORMATION: Synthetic Oligonucleotide

<400> SEQUENCE: 31
uaucugcacc uuugguag 18

<210> SEQ ID NO 32
<211> LENGTH: 141001
<212> TYPE: DNA
<213> ORGANISM: homo sapiens

<400> SEQUENCE: 32
aatttataaa ggaaaaaggt ttaattgact cacagttcag catgtctggg gaagtgttag 60
gaaacttaca atcatggcag aagagaaagc aaaccatcct ttctcacatg gtgacaggaa 120
gagcaaagcg gggtaagccc cttacaaaac caccagatct catgagaact cactatcacg 180
agaacaccat ggaggtaact gcccccatga ttcaattacc tcccaccagg tccctcccac 240
gacatgtggg gattatgcga actccaactc aagatgagat ttgggtgggg acacagccaa 300

-continued

```
accatatcag aagcttaacc ttctttggag catgattatt cagttgaacc taagttcagt    360
agtcacccag ttatgctgtc ttcagctact attttccata tgtttctcaa acatctgata    420
tatcacactg gctagtgcac tttcttccac cagcatacca tctcaattta ccactttaac    480
aattggactg ccactttgtg tcagggacta tctgtgctcc aactactaca agtgataagg    540
tcctcactga cagccaggga gcaagtgatc cagctctaaa actcacctta tcatctgctt    600
tcctagacca ctcctaacaa ccaactattc tgggttgagt tctccaagag gcagagagtt    660
caggatacag aatgttgttt tgtttttgtt gttgttgctg ttgttgtttg tgtgtgtgtt    720
tgggcttttt tgagacggag tctcactctg ttgcccaggt agaagtgcag tggcatgatc    780
tcagctccct gcaacctcca cctcctgggt ttaagtgatt cccctgcctc cacctcctga    840
gtagctggga ctacaagtgt gcgccaccac acccagctaa tttttgtgtt tttagtagaa    900
atggggtttt accatgttgg ctaggctgct cccaaactcc tgacctccag tgatccacct    960
acctctgcct cccaaagtgc tgggattaca ggcgtgagcc accacaccca gcccagaatg   1020
tttattagaa tgcacaatta ataccagagg cagtggggaa ggaaggactg agcagaggag   1080
gaagttgagt tgtgattcaa cccaacaact gcctggctgg catggggagc tctggagtta   1140
aatagggcca tcagactttc ccagtgtggg gccaacatga ctgggtcttt ataccccccac   1200
ctctgtcagt cactcaacgt ggtctccctg caacaaggtg actcttgcag ccgagacaat   1260
ccctgaaggg acagagggct gaagcctgtc tgccaacagc actcccagtg gctggaacaa   1320
gtccttccct ataggggaat ctgggcggca cacctccatc tccatgtcca tcacatacga   1380
tatcacagac atttaaatat tttgataact gtacataaga gtttccttta taatcttata   1440
gatcttattt tatgcatttg aaaatattct tctgagacag ggcttttatc atattgccat   1500
agggtgccac gatataaaaa aggttaaata ctctctgatt cagaagtatc caatgatgac   1560
ttctctctca tgcatttaat tgaaaatctg gtttttctcc ttctctgcta gttctctacc   1620
tctctcccca cctcccacat catagcctat tcacatatgt ctgaatctca tgatagacaa   1680
gttcaggttc ttttcccagg ttctttttac cacatccccc cacccccaca taaaaagtat   1740
atatggcaca gcctaggttc cacccaaatc ctttctcctc ttcttcctgg gcccacaact   1800
ctcctacata cattggtata ccttgcgctt agggatggcc atgtgactaa gttctaacag   1860
tggaacatga tcagatgcca cttccagcct ctaagacagc cagtgtgttt cctccataag   1920
ctccttctct tcctcccaac tggagactct aaatgatgac cctgcctcaa gcaagcaaac   1980
aacaagtccc tcaggggtgg tgtaggctgc aaatggaagg agcttgagtc ccaaaccttc   2040
cacggagaag gctggctacc aacctggatc actcacccaa gactgctcga agagttggtt   2100
tgaaccattg tgttttgggg tctatttatt acaacagttt agcttgcttt gtgaatagat   2160
ttagtggcag agcctccaaa ttctatagat acattgatct cagtcctaac cgcatctgga   2220
acaccattaa ataaaggaat tgcaaaccca gagaaggtaa tgaatttgtc taaggtcata   2280
caagatggct aggatcagga cccaactctc cagttttctt tcttctctgc tattctgcct   2340
tctgtgatcc tacataagtg ggcatgattg tataacatat gcggccatga gatttctctt   2400
tcagcaagag aaagggacag gaagaaagag agggaatgca ttttcttggc ctgaattagt   2460
gtgagccatt agttacctac attgactaaa ttatctggaa tgaacattca actctacatc   2520
acatatagtt aaaatgacag atctgcttaa gattgtttct agcatacgtt atttcaattt   2580
aggcaaatgt gaccattcag tgtgagggga ccatactgtc attaggtccc tgtcagttct   2640
caattatact gttatcttag agggggaaaa atgtgaaatt tgaatgtaga cgagtgttga   2700
```

-continued

```
tttgactgct acagtttatt ttacgtatag aaataaaata atgtgtagca aaagcattat   2760
tacaaagatg ataatgaaat aactagtatt tataatagta taatagtata gtatttataa   2820
tagtatgata gtttaatgac tatttgtcag atgttgtgta agaaacttta tacacacaca   2880
cacacacacc tcatttaatt cctgtatcaa tcaggataca ggacgctgtg gtaacaactc   2940
ctcaaatctc ggtggcttgc acaacaaatg cttatttctt tttttttttt gacaccaagt   3000
cttgctctgt aacaggctgg agtgcaatgg tgcaatctcg gctcactgca gcctctgcct   3060
cctgggttca agcgattctc ctgcctcagt ctctcgagta gctgggaaca caggcacgcg   3120
ccaccacatc tggctaattt ttgtgatttt agtagagatg ggatttcacc atgttgctca   3180
ggctggcctt gaactcctga cctcaagcga tccacccacc tcagcctccc aaagtgctgg   3240
gattacaggc atgagccact gcgcccagcc ccaaatgttt atttcttgct catgtgacat   3300
gtacttcctc gagtttttcc ttcctgagat ctaagctgaa ggaacagctc tctggagcca   3360
cgccattctg gtggcggaaa ggaagagtaa aagtggtaga accttgcaat gctcttgaag   3420
cgcctatttg gaatgtctac atcatgtaaa tggtaatgga caagtatgta taatccccac   3480
accaaaaaaa ggggacacta ttggggacaa taaccacatt tcaatgctgc aagacggata   3540
ttgactgcac ccccttccca ctttcagaaa gaagaagagt aattttgctg aactccttct   3600
agagactgga aatgtccctt ccagttgggg tgattaggga aggctttggt aaaatttgag   3660
ctagagtttg aaggttaggt agactactgg tgggtgaaga aagaacaagg acctttgtag   3720
gcaaaggaaa acctcagaat tacagaggtg gaaaaagagt tctagtcaag ccacttcagc   3780
tggctacaga gtaggtggga aagaaaatgg gaggacaagg gctcagatga tggggggttg   3840
gggcattggg gggacacttg aaagctaaac taaggggttg aacttaattt aggaggcagt   3900
tagaagcttt tacatatttt tgagcaagag agtgacataa ttaaaatgat ctgggccagg   3960
tgtggtggct cacacctgta atcccagcac tttgggaggc tgaggagctt gggtcacctg   4020
aggtcaggag atcgagacca gcctggccaa catggtgaaa tcccgtccta ctaaaaatac   4080
aaaaattagc cgggagtggt ggcatatgcc tgtaatccca gtagctggga ggctgagaca   4140
ggaaaatcgc ttgaacccgg gaaacaggtt gcagtgagcc gagatcgtgc cactgcactc   4200
cagcctgggc aacagagcga gactccatct caaaaaaaca aaacaaacac acacaaaaaa   4260
ccaaaaataa ataaataaaa tgatcacttc tgaatactga tctaactagg ggttgcaggg   4320
tgggctgata tagggagaaa ctggagagca aggagatcac taaggtccct acatgtccag   4380
aaccaagata gaggtcttga actaggatgg tggcagttag aacaacaaca acaaaaagtc   4440
aattccaggc tgagtgcagt ggctcatgcc tgtaatccca acgctttggg aggctgaggt   4500
gggagttaga aagcagcctg ggcaacactg caagacctcc tctctaaaaa aaaaaaaaaa   4560
aaaaagttag ccaggtgtgg tggtgcccac ctgtagtccc agcaactcag aaggctgagg   4620
tgggaagatt gcttgagccc caggagttca agcttgccgt gagctacgat tgtgccactg   4680
cactccagcc tgagcaagac cttgtctcca aaaaaaggtc aattccactg actttctaa   4740
ggtgtacacc atcaaggggc agctccatct ccaggccatt ggctcatgag acattctgta   4800
gtcagaaggc tagggcagat tgctttgagc aagcccccat ggtggttctc actcctactt   4860
ctttgggtat atgcccctct gtttaaaaat aaagttaata tgcatttaaa aaaaaaaagg   4920
agaaaaaggt cagttccaga aactgtgtga ataaagcatt ttacttgctt tttctattaa   4980
tctataacat atgttgattt tttaaaaaga atataagagc tatgcaaatt ggagcttcaa   5040
```

-continued

```
gacaacttcc catctcccta ggaggagatg gctgccctaa acccccctac atagaaatca   5100
tcccactgct tgggcttaaa cttgatgttg gggaaatgaa aaatccaagc taaggccgaa   5160
gcctggggcc tgggcgacca gcagaatgag gaccactggt cagtttcagg ctgaggtgcg   5220
tcttccaggg gacaatctct agctggccct taaacattca gacttcaagc tctatttaca   5280
gcataaaggt gtttcaaaag acgtgataca aataactgca aatgctctgc gatgtgttaa   5340
gcactgtttg aaattcgtct aatttaagat tttttttct gacgtaacgg ttagattcac   5400
gtttctttt ttttaagtac agttctactg tattgtaact gagttagctt gctttaagcc   5460
gatttgttaa ggaaaggatt caccttggtc agtaacaaaa aaggtgggaa aaaagcaagg   5520
agaaaggaag cagcctgggg gaaagagacc ttagccaggg gggcggtttc gggactacga   5580
agggtcgggg cggacggact cgagggccgg ccacgtggaa ggccgctcag gacttctgta   5640
ggagaggaca ccgccccagg ctgactgaaa gtaaagggca gcggacccag cggcggagcc   5700
actggccttg ccccgacccc gcatggcccg aaggaggaca cccacccccg caacgacaca   5760
aagactccaa ctacaggagg tggagaaagc gcgtgcgcca cggaacgcgc gtgcgcgctg   5820
cggtcagcgc cgcggcctga ggcgtagcgg gagggggacc gcgaaagggc agcgccgaga   5880
ggaacgagcc gggagacgcc ggacggccga gcggcagggc gctcgcgcgc gcccactagt   5940
ggccggagga gaaggctccc gcggaggccg cgctgcccgc cccctcccct ggggaggctc   6000
gcgttcccgc tgctcgcgcc tgcgccgccc gccggcctca ggaacgcgcc ctcttcgccg   6060
gcgcgcgccc tcgcagtcac cgccacccac cagctccggc accaacagca gcgccgctgc   6120
caccgcccac cttctgccgc cgccaccaca gccaccttct cctcctccgc tgtcctctcc   6180
cgtcctcgcc tctgtcgact atcaggtaag cgccgcggct ccgaaatctg cctcgccgtc   6240
cgcctctgtg caccctgcg ccgccgcccc tcgccctccc tctccgcaga ctggggcttc   6300
gtgcgccggg catcggtcgg ggccaccgca gggcccctcc ctgcctcccc tgctcggggg   6360
ctggggccag ggcggcctgg aaagggacct gagcaaggga tgcacgcacg cgtgagtgcg   6420
cgcgtgtgtg tgtgctggag ggtcttcacc accagattcg cgcagacccc aggtggaggc   6480
tgtgccggca gggtggggcg cggcggcggt gacttggggg agggggctgc ccttcactct   6540
cgactgcagc cttttgccgc aatgggcgtg tgtgtgtgtg tgtgtgtgtg tgtgtgtgtg   6600
tgtgtgtgtg gaggggtccg ataacgaccc ccgaaaccga atctgaaatc cgctgtccct   6660
gccgctgttc gccatcagct ctaagaaaga cgtggatcgg gttctagaaa agatgactcc   6720
ctgcacgccc ctccctgcac ctcccgagca gtgattccga cagggccttc actgcccctg   6780
attttaggcg ggggccggcc ccctcccctt ttcctccttc agaaacccgt aggggacatt   6840
tgggggctgg gagaaatcga ggagatgggg aggggtccac gcgctgtcac tttagttgcc   6900
cttccccctg cgcacgcctg gcacagagac gcgagcagcg ccgtgcctga gaacagtgcg   6960
cggatcccac tgtgcacgct cgcaaaggca gggttcacct ggcctggcga tgtggacgga   7020
ctcggcggcc gctggtcccc gttcgcgggc acgcacagcc gcagccacgc acggatgggc   7080
gcggggctgc aggtgcatct cggggcggat ttctttctca gcgctcggag cgcagggcgc   7140
ccggcgtgtg cgctccctgc cggaggcgcg gggctggcgc gcagggctcg cccctcactg   7200
cggcagtggg tgtggaccct ggtgggcgag gaagggggag gataggctgt gcctcctccc   7260
actcccgccc ccagcccccc tttttttccc cctcggaacg cgaggtgcca tctttttttcg   7320
gcgtgtcacg tctttacggt gccatgccaa accgggtggc cgggcttcat aggacagggc   7380
ggggcctggc attaaaggga gggggacaat cagcgctgaa atcttggcgt tttgctgctg   7440
```

```
cgggcgtgag cactgggggc gttcgcccag caccttcttc gggggctctt tgctttgtct   7500
gtagaggtta cgtgatctgc gctcccagcc ctggtttctg gcttttattc tgagggtgtt   7560
cagtcaacct ccccccctacg cccatgcgcc tctctttcct ttttcgctcc tcatttccga   7620
gcccattgtt ggatctcgag gcttgctggg ttcgatgaac tcgagtcaac cccccgaccc   7680
ccggcacgca tggaacgggc gtgaccgcgc gcagcctcgt ctcggagtct gccggcgccg   7740
ggaagcttct gaagggatgg gattcgagtc tccgtgcgcg ctgcgggcgg cggcagaggg   7800
atctcgcccc tccctacacc ccaagtgtcc tgagggccac gccacaccag gttgcccagc   7860
gagggacgct ggctacccat ccggggatgg gtggggagcc ctggcggggc ctctccggct   7920
ttacgccctg ttgcttcgcc tggccggaga atgtgaggaa ggggcataag gttactggtg   7980
cttcggccac acccatcttt ctgagcccac tggactgggc gcagaggggg gattgccatg   8040
gaaaccacag gtgtccggag aggggatctt ggggctggcc tcaccccttc cctgcggaga   8100
ttggggaccc tggggtaggg ggagccgcgc ccagtcggcc tcctggagga cacgggagga   8160
agccccgaac cccgcgcct gaggctgttt ctgattggcc cctggaggcc gcagacacgc   8220
agataggcgg ccctgggtgt atttttatta atattatgtc cgtactgatt aatattattt   8280
atcttaaata aatttcaccc gtgtccaagt tcaccgcgcc cccaaaaccg agtctggggc   8340
ggcaggggga actcctggcc aacgaatcca tgcctcgccc tcctgtgatg aacctggtac   8400
gcacggtttt ctggttaatt ctatcgctga aaactggtgc ggggggcgca cttctgagac   8460
ggaagagcat ctaggagctg aatcctccac gcgggtcgcc caggttgatc tgaatttctg   8520
gggaatggct tggctgcccg cccgggacca ggccgaccct ccttgacggt ggcgtagagg   8580
gctggagcct gggtactgcg aggctcctcg catggctggg cccgccgcga ggggttgcag   8640
agcggctcag ggatcgattc aagcatcgtc tctcctccct cgcccccaga cagagctggg   8700
cgcggggttc cccttccaga tggagcgagg gtctcggggt ggccccggaa aaggggagcc   8760
cgcggccacg gctacgtatt gccatctcgc gagcagagat gtcacctcct gcctttggag   8820
gaaagggagc ccggtgggga tgagcgcatt tagcccaatg ctgggaacaa agcgcactcc   8880
gcgcttctgc gatttcgctc cattttgaaa tgtgttggcg ctttggtggg gccgctgcgg   8940
tgggcaaggc cgggggcgct gttaatggag gaacctcagg gggacggtcc ttcgtaggaa   9000
actctatcct ggctctgcgc gcgctttaag gaaatggctt ccctccagga cctcgaggga   9060
tgcagctttt gcgcggatga cggtggggtg ctgaaccagc cggtgcgcct ctggaaatgt   9120
ctgggcacgg atcctggggc catcgacgac tcctccccat tcccagcagg cgggagctct   9180
tacattccga gcgagtgacc cctctcaccc tctggcgctc acacacctgt aactccaaac   9240
ctccgtctca gaatggtcca ggctggaagg gatgatgggg gctccgacag cgactgccta   9300
gctcacccct ctgcgtgctc aggctccagg ctcagcagga ccaatttgag ttctatctga   9360
tccccctcgg cccccttaact gacccatcct acaggagaca gggaaatgtc tttcctaccg   9420
cggttgattc tggggtgtca ttttgtgttt tgtgatggct gcttatattt actgtataag   9480
cattgtattt actgtataag cattgtatta taattactgt ataagctgct tatatttact   9540
gtataagcat ctccaaatcc tccctctacg taaacaaatt aatggataaa cagataagtg   9600
tatcccctgc ccccacccct gctacgcagg tccggagtga ctcttgaagc tcatacattc   9660
cttggccaag tttgcttctc taacagatgt ttatatagca ataacctggc ttggctcttg   9720
ggttcacctt tggacgattt ggggaagggg cttgttggct ttgctgggtt ttggatgagt   9780
```

-continued

```
gacagtccat gactgttcct gctggaaggg cgtgactttt aagtggtttc taatatcagg   9840
cattgctcct ccgacaggaa caaaagaaat ggatactgcc cataaattgt tagaaaactt   9900
agaatcgctt tgattgagga aaggttagat ttattccggt tggaaaaagt ggcctttcta   9960
ttaaacgtgc cctttgaccc tcatgccctt ggaggtcggt gccagcctgg agatgggata  10020
agattgtggt tttccttctg cctttttaac atctgttgtt acagtccatt tgttgaaaat  10080
ttaaagaaac tgttttattc cactttccct cagcatttat gtgtgtggtt tcagtagctc  10140
tgtggctata tgtacgaaca cgtgttattt ttccaattgg acatgtgata attttccaac  10200
tggaccttgc cttctattga tgtatttatt tagcatcttc cttactccct ccttgaaaaa  10260
gaatcactca aaaacaaata aaaacagccg taggggccta atacagtgct agacatacaa  10320
gaggtattcg gtccatacca aatggatttt atccatgaag gataaatggg gaaatacagt  10380
gggaagcagg tgggaaactg cgtttgactc tgctctttcc tccaccacca ctttcctcat  10440
caccgtgttc agagaccccc aaagccccct cacactccca gaaacacccc cctggccact  10500
cctaacttgc catgcccagg agttaggtgc ttccactagt gacatggagc tggcgtttgg  10560
ggggcacctc agcaggtgac gggaagagaa gaccccagcc tcaccagctg ggctgcagca  10620
gggagaggag tcctcatgtt ccagcaggga ctctcagctg ttttcctgta aaaccatggt  10680
tctcaactgg gggccactga gatgtctaga gagatgtttt tgttttcaca actcggggag  10740
ggtgctactg acatcttgtg ggtagaggcc aggaatgctg ttaaacatcc tacaaggaag  10800
gcacaggaca gtctcctaca tcaaaatatg acccagtccc aatgtcacca ctgctggggt  10860
tgacactggc actgctatct taattacatt cattgagtgt cttttaggag gccctattct  10920
aagtgcttgc taagattatc tcatttaatc ctcacaacac ttccgctatg tagcaggtgc  10980
tgttattatc tccgtgatgg ggaaactgaa gcacagagag ggttagtaac ttgctaaagg  11040
tcacagagcc agtgggtggt ggagctggtt gcctgacact agttccctcc cctctcagcc  11100
acatgtgggt ttacttggcc attgtggact agtctgggaa cccagatatg atctataaca  11160
ttgacccagt agaatattga ttccaaaacc actgtctcac aaatgaattt ttacaagagt  11220
ctgtaatcgg agcatgaccc agaataaggt tagggagatg tggagttaaa gctctcaatt  11280
tcttatctgg ccccgacaca gagagcaagg catttcactc tacattggtg ctctgtttat  11340
aaaacaaaga gcaaatatct cttcctaagg tccttaaacc tcttccccca atccagggtt  11400
tctggactgc tctgccatat gacggggcag ctggtttgat tgacccaggg aaggctggaa  11460
atcaagactg gggggatcaag acgtagattc agtgtggcca aggtcaagtc tctgaggttt  11520
agggacatca gatccccagc ttaggttctg tacctcggca aggtgaaagc gttggcgccc  11580
actgatgagg cctgctctga gattgtgggt gtgggttgag ttgggtgggc ataggcaagt  11640
cctcttgtaa gaatcttttg gcaaagatgg gcctgggagg cttttctcac ttcctggggc  11700
ccaggctttg caataagtat tccattatac tgtggtacct tggggctacc tgagaatcct  11760
ctgtctcgcc cctgttgcct tgccaaagag tttgctgtcc aagaattcct ttcctgtctc  11820
caggtgccat gctcctgcca cctctgccag gttccctgcc tgcccagatg gctcccaact  11880
gagtgtgagg aggaatttga gacaggtttt gagctttctg ggttctccag ttaggaaact  11940
ttctgtaagc atgcagatag aatgggcttc agcaaaatac aaactcgaac aacttccatg  12000
tatagtccct taattttctt tgcttttttc atatttcatc aggctccatg ctgagcccaa  12060
tcagggaccc gatagaaatc caaacaccat gtcagcgagt ccccaagaaa tgcattttgt  12120
gccaaggcta ttcaaggaag gtttgggagc agctcaaggg cagacactgt taccctcccc  12180
```

caggtcccca gtgcagggca gtgttctgca tgtggaggca gtttggccta atggttaagg 12240
aggtaggctc tgatcgggcc tcctgggcac aaatcccagc tccctgctca ctgtgagacc 12300
taagccatat tgtttagctg cttggagagt tttttgtcat ccacaacttg gagtatgatg 12360
gtacctgtct cacgggttgc catggggttc acacaagcta acccggtact cactagggcc 12420
aagcacatag taactgctca gtaaatggca tcatcggcgg tgtcctgtgg atgagtgctt 12480
gtgattggct gaatgaccag aggggtctaa agatcctggt gatggaatca gttgtacaga 12540
taaattgtta cactgagtag ggatcaagat aggaaaagtc ggcaactacc cagctcccct 12600
gcaccaaact gggcagaagt ggatcctctg aaaattgcac acacccatgt ttaaatgtac 12660
acacagaact cttgccacag gcaagcggag atttgtcatc tgctgtccct gcctcatctt 12720
cttcctgaaa tccactccat gccaggaata aactgcatgc tctccaccag cccaaactga 12780
cctgccttcc cgccagccat cccgggcagg gtgacctggc ttagtacatc gggttcagag 12840
atctttccag tttactcgtt gaataaaaag tgagggctga tcgagaaagt aatggcagtc 12900
agggaaggcg aaggaggtaa agaagagatt ttacaaatga agtaattcaa cagagtgctg 12960
acattggtaa actggcaaac agatttcagg gtggttggtt gagagtagag tagaaaagga 13020
ttaaataaag caaacttgtg gtgtactgaa tcttaggaat tccatgtatc caataagtat 13080
agtcatttat gaattaataa attcggccta agaagccttc ttatcgctta aatcaagact 13140
aagtaacaat atatcagttt taaaaagtca ttatatcaga aaatcattta aatgatacac 13200
atagatttcc aagattttac tttaaccgaa actatataaa tgtgaatttg ttcacccatc 13260
ttttgacaca gggctcaggt cttctcttgg tgtctggatc agccagttga aatttcttgt 13320
ctgttttgcc tatgccacat taataatgca ctgtctgggt cctccgattt cagtttggat 13380
tttgggttta cattgtggag tcatctgaat gcagaatcct tcagggattt tacttttttt 13440
tttttttttc atggtcttta ccatcccatt tgatagtaaa tattactcac ctttatgaag 13500
tctttccaaa acattcaact aaattttctt aaaatcattg aatgatttga agagcttatt 13560
cctcagcact tttactccat cagcttgcac cttatttttt aatctttttt tgagacggag 13620
tctcgctcta tcgcccaggc ttaagtgcaa tggcgcgatc ttggctcact gcgacctcca 13680
cctcctgggt tcaagcaatt ccgcctcagc ctccgccgta gccgggacta caggtacaca 13740
ccataatgct cggctgattt ttgtattttt gtagggatgg ggtatcgcca tgttggccag 13800
gctggtcccg aacttctgac ccaagtgatc cacccacctc ggcctcccaa agtgctggga 13860
ttacaggtgt gagccaccgc gcccggccag cttgcacctt atttaggata tgtgattatt 13920
atagcaagtc tggtgtacat acaagatttt gaatgggcac agatgacctt tagtaagtgc 13980
ttggctgtga taagaggcag tcctgactgc agatcaggct gtgtggaccc cagccttgca 14040
tgtttacaga ccttcatgtc ttattcttac agggtatcag aagaacacct actggggaaa 14100
cttataaatt agtaaaaggt gggcattctc cccgcccatc ttctgtctgt ctgccaggac 14160
tagcacagca ctttgaagtc attcacatag aatcccaact taagagggta aaatcctcct 14220
caacagactg aaaataagtt taaattccct ttgctatatt aactcccctg aggaaagagt 14280
cttagatcaa tgtccaacac taaaaacagt tttaaatcag caagtgagaa ttaaatctga 14340
agcaattgat aataatgttt cattcattcc tctcctttgg ccccgtccac cctactgcta 14400
aatccaggca tcaaagagaa gagggacata attatctcta gtcccagctg ctggttttcc 14460
ttccagccta tggcccagtt ttctgtttta ctgagaaggc tggtgatgtt atcttgggat 14520

-continued

```
ctaagtctgc agtttcacca caaaaagtcc agggatgcac tttcatgctt gtgtcctcct  14580
ccctgggata gcaaggatat tagaagaccc ctggctctgt aattgcttgt catgtgctct  14640
acagacgcca cagaatgcca agaacgaagt gctgggaagg acaaattcat ggaaccgtgg  14700
gacggtgctc ctcccccagc gtaaaggaca gctcctcctc ctgaattgga gccagcgttc  14760
taaatcatgt gtcaacagag ttgtcctgga tcggatccag ttctgccatt gatttgcagg  14820
tcatttcagt ggtacctgtt tccagttgtt cttaattgaa cagtggcacc aaactattgt  14880
cttgcctcat ccccctccca tggcctgtcc cccaaaaaga gacttcttgg gtaattaatc  14940
agggcaacat caggcagtct gggcgcggtg gctcacgcct gtaatcccag cactttggga  15000
ggccgaggcg ggcagatcat gaggttagga gattgagacc atcctggctt tgtgaaaccc  15060
cgtctctact aaaaatacaa aaaattagcc gggcgtggtg gcgggcgcct gtagtcccag  15120
ctactcgaga ggctgaggca ggggaatggc gtgaacccgg gaggtggagg ttgcagtgag  15180
ccgagatcgc accactgcac tctagcctgg gcgacagagc tagacttctt ctcaaaaaaa  15240
aaaaaaaaaa ggaatctctt tggttttata tatatttttt ttatatatat aatatatatt  15300
aaaatataat atatatattt atataatata atatataaat atattatata ttatatattt  15360
tatatattat atattatata tattatatat tatatattta tatatttata tattatatat  15420
atttatatat tatatattta tatatattat atatttatat ataatatata ttatatatta  15480
tatattatat attatatatt atatatttat atatattata tattatatat attatatatt  15540
atatatttat atattatata tttatatata ttatatatta tatattatat atttatatat  15600
tatatattta tatattatat atatttatat atattatata ttatatatta tatatgtata  15660
tattatatat gttatatatt atatatattt atatatataa tatattgtat atattatata  15720
tctaatatat tatatatatt atatatatta tatattataa tatatattat atattatata  15780
ttatatatat ttttatatat ataatatgta taatatataa tatatataaa aacatatata  15840
atatatatta tatattatat atatattata tatattatat atattaaata tattttatat  15900
atattatata tatatacaca tatatatata taaatgaggc caggctcggt ggctcacact  15960
tgtaatccca gcactgtggg aggatcactt gaagccagga gtctgagact agcctgggca  16020
acaaaacaag atcctgtctc tacaaaagga aactgtaaaa attagctggg catgatggca  16080
tgtgtctgta gccctagcta cttgggaggc cgaagcagga ggatcgcttg agcccaggag  16140
ttcaaggcta cagtgagcta tgattgtccc atagcactcc agcctgggta acacagcaag  16200
gccctgtctc taaacttttt ttttttaatt ctatttatat ttacatgtat ttaaatgtga  16260
atattcacta cctatttgtt gcatgcctgc atttttttata ctgggcttgc caaaaacccg  16320
aacagctttc tactttgaca atgtatcaga atttaaatca gcaatatgtt aataagccaa  16380
gcaaaggtta tatatgcaaa taaaactgtt gtctataacc tcctgttaca ctggggcaca  16440
gcaaaagtca tggtgtagtc gcatgtgaac ctgtcccttt catagctgct cattgccagg  16500
aaacatcagg aatagccatt tggaagagtc atcagccctc ccaccatccg ttttctgtct  16560
tgtcttttcc ctatgagcag gggaaattcc acgctggccc caatccccag tgcagcggct  16620
cagcctctgc ctctgctgct ggtccccatg aggccagctt agaaacggag gattttgcag  16680
aacatcccta aatccgcttg aataatgaag tgatcattca taaactcacc tgaaccttat  16740
taaaacctat ttaatatttt tcctggataa tcctataggg ataacttgcc tcctgggctt  16800
ctctccaccg ggttcagttc ttcctttagt ggtgaagttc ctcccttctt agcatctcaa  16860
ctgtgcctga gaaaaggcca gtggcggctg cactctgttc cctgtggagt gttaataaag  16920
```

actgaataaa ttgaaataaa tccctttcaa tgtcattaag tgctataaat aatcatgaac 16980
caatgttcga tggctgatga gaaatgcaag aaaaaatttt taatcagtag gattcataag 17040
ttgacaatct gggccaagtt aaaaaaaata aaaataaaaa gacttttaaa aagatcttat 17100
cgtttgttac cagtaagact gaattccaga agcaagctac tccctcattt gtgggcccct 17160
gttatcactg gctgcttagg gttgccaagc cctgaattca tttgtcaact aagagatttt 17220
tggccaagat taagatttcc catgcctcca tatttccatc tgagaaatgg agattatact 17280
gtcttccccc tcagaatgga tgataatgtg gtctctcttc tgttcgcata gtcatagaac 17340
tgaaataaaa caacttaaga gaattccttt gagcttctca gaagtgctgc agggctgggg 17400
gatgcctccc aggagccgca gtcaggtgct gatctgaagt ctttggtggg ctgactttag 17460
cctgacctga aatagtatag ctgctgccac ctggctccct tagcgtcagt cagacggtgc 17520
agctggttcc taggggtgag ggctgagcca gcagggtccg tgcccaggag ggatgcatgg 17580
gtggccacag cccagcctgc actgatcttg tctgtcccct tctttggaag gaaggagccc 17640
caaaccaggg tgcaagacag tgggtggggg tgccttgagc atgacctcaa gtgatttcca 17700
gcccctgcca gtgctgactt ctctggggaa gggctgggac ttccttctgg gctcaagtca 17760
cgacccttgg atggaatttc ctgggagctt ttctgttttt tctggagttt tcagtttttt 17820
cctaaccaga cagggacttg gtacagaatc tcatattcta attatgccta ggagcagcct 17880
ctccccacca ctcacagtgt ttagcatgtg acaggaatcg attaaggcat gagtgattaa 17940
attaaagcca ggcattgact tggatggtgt aatattctga catctgtttg gtgtcaaagg 18000
cacggggcag gcgcgttaat tgaactgctt gcacctggca tttgaattga gccagagcgg 18060
ggctaaagtc agtttgcctt caccctgtaa atggagggtt tctccggagc gtggatggtg 18120
ggaggtattt cagggtgtat gcataacccc caccctgaca atggcccatc tcttctccag 18180
cgtggccagg tttgagtgcc agtcctgggt gtccagtggc cccatagcct tgcgttttag 18240
taaaatgctg cccccattac cacctggtct gtgcacttcg gtcactggaa tttgccatct 18300
tccagtcccg aatgtggcaa gccatggagc cttaagctct tctccctcca catcctggaa 18360
cagacccgcc agtttcttcc aggcattgcc tcagtttgcc cctctgtttc cagtcacact 18420
ctcaccagcg ataaaatgat tttagacctt atcatctcac cctcggatcc ttatggaaac 18480
aataatgagt tgttccctgt ttcaattcca aaattcatat ccaatccgtt ttgcatgcca 18540
ttgccaaatt cctcccagag caaccccgtc acctgccctg gccctctcca agtgtggtcc 18600
tgccatgggc atcgcctgct aagccaagct ggcctcgagc tgcctgcccg ggtccccaca 18660
ccttggctca cctccctgcc cagtcccgcc tcctgccagc ctgccctgtg gctccttcat 18720
agatgccgtg ctctttctgc cccttgctca cccatggcag ccttgcccct ctctccctgc 18780
cccacccccct atttaaattg acctgacctt cctcagtgtc catcttcccc gaagctttcc 18840
ccagccttgg cactcaaggt ccagaggcta cgcgtttcct ctcacctgtg gcagcgccgt 18900
gctccccagt gcctcacagt ttccttcttg cccccgcttc ctgtgtagga ctcatctgcc 18960
cacaggttgc acgtcctgtg agggcaagga ctgtgtctta tgtgactttc cttctccagt 19020
cacagagctg ggcacataga tagctcaaaa ccctctttat taacacagtt ggatgttgag 19080
aaatcaaaca ggccaatgtc aaatgagctc tccttattta aatcaagtca gttctccacc 19140
tcctagcact cagttccagt actctatata catggaaata ataaaaaaca catttccttt 19200
gaaacattct ataatcgttc ctttgcccta cttcagacca acttaacgca ctccccattg 19260
gtccaaatga gttttgctat acgaagatgc tgataataat agcagcagtg gattattctg 19320
ctaaaaccat tgcctcgtta atcctcagtc ccgaggtggg gattattatc ctcattttgc 19380
agagaagcaa actgagactc agagatttca cagctgggga gggagccagc tcatccctct 19440
gtccaggccc aagctctctc ccgcttgcct tcctgcctct gcaacctcag agcatccccc 19500
atctggttct actgcctgtg ctagtcgtgc aggagccaaa agacacgtct ttagtgctaa 19560
ggactggaga agccatgccc tccagcctct gtgaatgggt catatgtaac atgagcctgg 19620
agaaattatt tgaaaccaaa ggcaagcctc taaaccaggc tgctgcttca tggcgccggt 19680
gacggcagaa ccaaatttag tgctgtgggc aggtccacac ttatcaaata gagaagctca 19740
tttttcttcc ggctcacatc aagcatgaaa aatgttcaca catacccccc acacacacat 19800
gctttccgga ggggtccatg tggctagagg ctggaagatg tggatgagag gagcctggca 19860
ggtaagccca gggaagatga cattcagctt cccagacagc atctacaggg agaaatttaa 19920
ttaaaagtgg ggcggtttcc ctgagcaagg cagacaaagt cagccctcta ctgttaagaa 19980
aaagggtcac agtgagaggg gaggtgagga gactgagtct gtattttcta gtctgttggg 20040
ctacactacc tgatccccct tcctcaaaaa tccactttac tttccccatg tctacaccaa 20100
tgtggttcac actctgggac caggaaaagg gggagtgatg gggaacagag aagggaggag 20160
ctcacacagc tgaggctggg gttatgcata tcgaattact tagaatttgc aacctcacag 20220
ggtactttca tggcgttgaa atacacttcc cacagccacc ctccctctaa ctaaaagcaa 20280
gagtcatttc tcagttctgg tcttgcctcc cacgttctcc tccacattta agaaaatcca 20340
ccagctacaa agtgaagata ccatatgtga tatcccaccc tagtttctgt tttatcaggg 20400
tttggagcag gtggagcagg cagagggatc atttcagcct ataaattgta ttaagggtga 20460
gtactgagtc attcttcaag aaaagtttta gaagcatcca aaactgaagg gtggagccac 20520
ctggagacag tatcatcagt cctggccccg agcatggcct gcataggccc ccatggatcc 20580
cagcgggagc tgcagagtgc gggcaccttg gcacacagcc ctgagtgcaa aattaggagc 20640
tgggcagagg gcatctctct gtcgccattg ggcagcccag ggcacactgg tcatagcctt 20700
agaccacgaa caccctgtgc ccgggggaca gatgcaacca gtgtgccctg ggctgcccaa 20760
tggcaacaga gagatcgaca cctggacccc atgtcacggg gactccacta ctaaggctcc 20820
taagactgcc accttccagt gggataagcc ctgcctccta ctgggcccac aatgtgcaga 20880
gaacacttgg gactacctgg ctttctggat acacaaatat tgatccaatc tggactaatt 20940
agaaggtcag tcccaataac aaatcgaagt cagctgggcg tgatggctca ctcctataat 21000
cccagcactt tgggaggctg aggtgggcag atcatttgaa gccagaagtt caagaccagc 21060
ctgggcaaca tagcaaaacc ctgtctctac taaaaataca aataattagg ctgggtgtgg 21120
tggctcatgc ctgtaatccc aacagtttgg gaggctgagg caggtggtca cctgaggtca 21180
ggagtttgag accagcctgg ccaacagggt gaaaccccgt gtctactaaa aacataaaaa 21240
ttagccaagc atgatggcat gtgcctataa tcctggctac tagggaggct gagacaggag 21300
agaatcgctt gaatccagga ggtggttgca gtgagctgag atggtgccac tgcactccag 21360
cctggttgac agagcaagac tctgtctcaa aaaaaaaaaa aaaaaaaaaa aagccatgcc 21420
tggtggagca ctacgtgtaa tctcagctat ttgggaggct gaggcacgag aatcacttga 21480
acctgggagg cagtggttgc agtgagctga gatcgcgcca ctgcactcca gcctgggcga 21540
cagagtgagt gagactccat ttcaaaaaaa taataaatct gagtcacttt aatattgtta 21600
tttggatgtc aacctctagg tgtttgagac aggagagtga tatgggggca ctggaaacac 21660

-continued

```
acaggcacgg ggtgtcctca cacttgggta gcccacacga tgtgatttca gggtgctggg  21720
aggtcccccc actccccaaa ttactaacaa gtggatagta ctttacagtt tatatgatct  21780
catttgattc ttaacatgag cctgtgagtg aaaaattcct tcccctcttc tacagattag  21840
gacgttgaga ttcagggagg ttcagaggga ttcagggaag tcaagtggca cctggagtcc  21900
cgtggctaat ttgaggccgg taggggattc gaacccagga tttgtgcttc ttatgcctgg  21960
gcttctgctc cctggggcat ggtcttcccc ctagctttcc cattcactgc tttagcctag  22020
gggtcctacc ctttattaaa ctgccagtgc ctcactgctt ttctccccca aagacaaaaa  22080
aaaagtgttt ttgcttttgt tttgtttttc atgggcagag acctggaatt tcagcttgag  22140
aatttgtgcc atatgataaa taaatcaaca gatggctttt tccttaaaaa aaaaaaaaaa  22200
aaaaactaag atgtatttgc agtgaggcat aatttgtacc aaaaagtgct caccacactg  22260
tagtcatggg ggcaggaggc agccgcgggt gaagggagaa atcttggagt ccaggcagcc  22320
cccttctggg ctgaactggg gagctggggg tgctgccagc cctgccaggt tctcctagga  22380
ggcggcagct catatggctg tgggaggagg cagagggagc ctcatatgca cccacatttc  22440
cagggatcta gaagacagaa ggaggaaaac caccatcatg ttaaagcaga cagttaggta  22500
acacatcctg taatacaagt tattttttcc acatctaaag gctaaaaata gttgttagaa  22560
tttaaagata attggtaaat gagtttctat ccttctagtt tcacatcaaa tggaatcatg  22620
ctgccttcac atcactagtg cccgttattt gtgtttaatt tccacaatgt tgtctaattc  22680
cactctttgg gcttccccag ggatccagcc tccctcactc gcccatcgca gggagatgct  22740
ttattcatct ttgtgtcttc tgtgccgggc atagcgcatg gcacagaata agcactcagt  22800
aattgattca cgagtgaata aatggatgag tgggtgagtt caatattgac tacaaaaacc  22860
ctaaggccac actggtgagt ggctgcgcct gtagtcccag ctgctgggga atctgaggca  22920
ggaggatctc ttgagcccag gagtttgaaa ctagcctggg cgatatagcg agaacctgtc  22980
tcaaatgaca aaaacagggc caggtgcagt ggctcacgcc tggaatccca gcactttagg  23040
aggccaagat gggaggatca cttgaggcca ggagtccgag accagcctgg gcaacatagg  23100
gagaccctgt ctctacaaaa aattttttaa aaattagctg ggcatggcgg tgtgcgcttg  23160
tagtcccagc tactcaggag gctgaggcag gaggatcact tgagcccagg aaattgaggc  23220
tgcagcgagc catgatggca ccactgcact gcagcctggg cgtcagaacg agacctgctc  23280
tcaaaaaaac aaacaaacaa caaaaaaaaa ggctttctta aagagacttg agaacagaaa  23340
ggggaacaga tacataactt atatatttat ttgttcatct ttccaccttc ctggagggtg  23400
gaggggaaca ggtctgtatt tggagttttg aatgctaaaa gtgggaatac atgtactgtt  23460
tgccatgatc tgttcaaaag ttaagccaaa tgccttagat tctcctgaaa actggaatgc  23520
cactgtaaac tataagcccc acttcaaaga taaaagatct tgatgaacag ggctgggtct  23580
gtggactggg cctctcccca ccacacaagg aagggtggtg ccagttgaag gaaaatcact  23640
taaatccttg ctgtctccta ataaggtgtg gtcccaggta gggctgtcag aattagcaaa  23700
ttaaaacaca gggcatctgt gaaaattaga atttcagata acaacaaata attggcatag  23760
gctgcataat gtccctcaaa gatatcaggt cctaatctcc agaacctgta aatgtgatct  23820
tatttggaaa aggggtcttt gtagatgtgg ttaaattaag gattttgaga tggggggatt  23880
atcctgtatt atctaggtag gtcctaaatg cagtcacact catccttgta agaggaagga  23940
agagagagat ggaaaacaca gaagagaaga caatgtggtg atggaggcag agattggagt  24000
```

gaggtggcca caagccaagg actgctggca gctaccagca gccagaaaag tccaggaacc 24060
aattctctct tggagctcca gagggagtgt ggccctgctg acaccttagc ttcaacctag 24120
tgatcctgat tttggacttt ggccttcaga agtgtgaggg aatgaatatc tgttgtttta 24180
agccaccaag tttatggtca tttcctacag cagccacagg aatcaaaaac agtaagtatg 24240
tcccatgcaa tgtttgtgac acacaccaaa aatattactt gttgttcacc tgaaattcaa 24300
atttaactgg gtctcctgta ttttatttgg ccaacctagt tcccaggccc aaagaaagag 24360
gcttttgaaa tttgcaagaa agctggttgg agctgtcaga aagtggactt tgtaaacaca 24420
gtaccaccga accaatttga actgtactac ctctagacaa aagagagggc agtcagacag 24480
ttgttcgtga tttcttcttt caacagtcat ttgagcactt actacaaaac agaagctatg 24540
tgtaagggtg gaggcgttag ctgttaatca ggacctccag gctaagtttc tgtattagtc 24600
cgttttcacg ctgctgataa agacataccc gagactgggg aatttacaaa agaaagaggt 24660
ttaattggac ttacagttcc aagtggctgg ggaagcctca caatcatggc agaaggcaag 24720
gaggagcaag ccacatctta catggatggc agcagacaga cagggagaga gagcttgtgc 24780
aggggaactc ctctttttaa aaccatcaga tctcgttaga cttattcact atcaagagaa 24840
cagcacagaa aagacctgcc cccatgattc agttacttcc caccagatcc ctcccacaac 24900
atgtgggaat tcaagatgag atttgttacc atatcagtta ccaacccttc cagataaatc 24960
acgtgaaata tcgccattaa cagagtgagc tcaggtggtt cttcagtgca tttctgatac 25020
ctgaaccttc cctgggaatt tcacagacca tcaggctctc caccctttga tagcaggata 25080
gcagggccca ggttctgcag gaggagatgt taccacaggc ctgaaaggga gggaggggca 25140
gatgctacag gaagatgctg gctctggatt cgctggagga gctttcaagg gaagtagata 25200
cacactgtct ccatcatttc atgtccatca cactctaaaa tgctttggac aagaagcaaa 25260
tgttaaagac aaatgtggcc cattttcctg tacaaagagg gctgctccca tgccaggcta 25320
ttggcactgg tgggcatgag gcttctctgc tgccctggcc ggggggttct ctcactcacc 25380
attggctctc tgacacctgg agagaccacc acccttgggc tttcatgatg ctcacagaat 25440
ccacactgtt ggagctttaa ggagcctgga tcaactggaa caggcaggga gtactaggac 25500
agcccagcat tgccccaaaa tatccaggcc tgataaaaga gaaaaacagg tagctcacag 25560
gaaaaggata aaaaaaggag gagggattta acatgaaaag gtgcttgatc tccctcataa 25620
taaaaagact gctgattcca tccaggcaag tgacagaaaa aaaaaaatta atttaaaaag 25680
actgctgata aaaccacagc gagacactgc tgctcaggga tctgagggtg tgggcagcca 25740
ggctgccacg catcatgggt cggagaggaa gaccacaccc ctggagcaga gggcggctga 25800
tctgtcagat gccctttgac agcacctcag cttccaagaa ttaacccttt ctatgtgagc 25860
agaggcatcc atggggggac acactggtga atcatctgtt atgtagaagt ctggaaaaca 25920
tcaggatgga actggtgaaa taagtgtggc ctctgacgga atggagcggt ccgtctgcac 25980
tgctgcgggt gcccctcaga tcctgtgggt cagtgagaaa agcagtgagg aacaaggcag 26040
gtactgtgta ctgtcctctg cgtgcaagga aggccagcgc atgcaacaga gtccacacag 26100
acatagccta actctggaag gaagaatgag aatgcagttt cagtggtggc ctctggtggg 26160
gagaaactgg gtgaagggag atgtcatttc catttctcta ctattaattt tgtattacca 26220
tgcttaaatg ttacttttta cctttttttt tttttttgag acagggtctc tctctgttgc 26280
ccaggcagga gtgcagtggt acaatcatgg ttcactgcag cctgaacctc ccaggctcaa 26340
gcaatcctcc cacctcagcc tcctgagtag ctgggactat aggcacgcat accaccgtgc 26400

```
ccagctattt tttttaatca agatggagtt tttctatgtt gcccaggctg gtctcaagct  26460
cctggactca agcaatcctc ctgcctcagc ctcccaaagg gctgagatta aaacgtgagt  26520
caccctgccc agccaattgc tttttaaaaa agattaaatg catgtatacg ctcaggcatc  26580
agcacacttg gaaaggatga aaatatccgg aagaagggtt cttttaaaag gctcctcaag  26640
tgatgctggc aggcatgacg aatgtccctg gtcacaaaag ctctgatctg gcctaaccct  26700
gtcatgttag agactggagt gcgtgtgtgt gcgcgcaaag tgtgggggga tgggggtgag  26760
tgtgtgtggt gtgtaagcat gagtgtgtat gtgtgtggtg tgggggtgtg tgctgtgtga  26820
gcgtgtgtga gtctgtgtgt gtagtgtgtg tgtgaagtat gtggtgtgta tgtgtgacgt  26880
gaggtgtgtg tggtgtgtga gttgtgtatg gtgtgtgcat gagcatgtgt gtgggcatgt  26940
gatgtgtgtg tggtgtgtaa gcatgtgtga gtgtgtatgt ttgagcatgt gtggtgtgtt  27000
gtgatatgtg tgtggtgtgt gagcatgtgt gtgtgatgtg tctgtgtgtg gtgtgtgtga  27060
gcatgtgtgt tgtgtgtgtg gtgcatgtgt gtggcgtgtg agcgtgtgtg tgcattgtgt  27120
ctgtgagcat gtgtgagtgt gtgtgtgttc agcatatata aggcatgtaa ctgaacacag  27180
cactttagag ggctctcctg gagtcagagg gggtgggtag gaggagaagg gaggtgggct  27240
agtgtgctga agtatctact ccttgtcata gtctgtgaca acccagacta gcccatgagc  27300
caccctgttc cctgcatttc caatgagacc tcggtggaca tgttccctga ggtgaggctg  27360
actgatgtca tttgacgatc ttgatgccaa atccttttat atcaaaaaca accagaacac  27420
tctcttttct cttagtgctt tcacccagat gaccacattt catcctccca gccactctgg  27480
gccaggtggc actgctggtt tgaaagggag gtctcccctg gagtaacttc cgtgggcgga  27540
ttcacaccct gcccacagtc ctgtcccagt cagcccacca tggtggtctc cggttcctcc  27600
agaattcccg cttttcagct catccccaca ttcccggagg gactgagagc gcagccccag  27660
ggccctgctc tttgggggcc gtctctacac ccagagaagc agcaaggcat tcctaggttt  27720
ctctttcaga tgcagaactt cagtgttcag agatgttccc actggtcctg agagggctca  27780
gttcagcttt aatgactgcg ctgttgcgtg tgctctgcag agggcgggtg gcccagcgtg  27840
gctgactgca gttttcctga cgtggagccc gagcctgccc cgctgtttat taattaagga  27900
tcactctgct tgcagaaccc tgaactcccc agaactgtga ggtgggagaa ccccgagagg  27960
ccacctggcc ccacttccca cctgctgccc aaaccccctc tctgccttcc tgacagtcac  28020
cccaactccc agtgatcccc atcaaccatc tgacaagggg actgagaggg aagagaaagg  28080
aggggcccaa agaggaaggt aaaactgtcg ggaacagccc ccaaatgtgt gacagccttc  28140
agtggagttg cccactttcc cttttctcct ccctgcagga cctcccttct ccccagtcct  28200
ccccaacttc tgaggttaca ttgagaaaag tctgcagaga ggtgccagca tcacaaggtg  28260
ttaaggacca cgagtttggc attttaacag atgccagagc cacttgagaa atgtggtaac  28320
taagcccaga gaggtacagt taacctcccc agagtcacac agcaggttca tggcaaagct  28380
ggactagcac aggtgtcctt cccctgcaga tccccttctg tgccccacat cacctccctc  28440
cagtgtctgg gccacctgga gatgggccct cagactcacc cggccagagg tgccatctca  28500
tgggagaggt ctggccagga agcatcgata tttgagatcc caagaaatga agacttggcc  28560
tgtcagatga cagacttcgg tcatgggaac acgtgatctg ttttacacat gcgtcccctc  28620
agcagcagct ttccagaaca ttcccacttt cttctgtagt gagaagaact ctttccctgc  28680
agcctcctgc ccaactcctc cttcagtgtc tttgcttcag tgtctttgat aaaccattct  28740
```

gctttgcaga gtgcgagctc tgccttgcag ggttcgcatc tgcctgtgct gagtaaccaa 28800
cgctaaggtc gagtggtcgg tcacctctca taagagctag ggttgtctca tgctgatgac 28860
taggacttgc cctcaaggag aaaaataaat caaaacaaaa gcaaaaacag caaacatgca 28920
tctcttaaag aaggctctga gtccaggtaa atttccttcc actgaagcag ccaggctgaa 28980
ttcgaattat ctttgcccct gcttaaaaac taatgcaaat tttcctagag aatatccact 29040
aattcctgga gggggcatgg gcattcctga tgcccatgag aggaccattt gctcttccct 29100
cagtatgcta aataacagaa gcgacatttg ttgctggaaa gtatcagtga agttaataag 29160
gtttttcttg cccagggtga gggaacagtt cccaatgaca aatgctgtat gggaaggggc 29220
tgtagaactg ccagcccctt tggtccatcc gtaaagtgaa ctctgtggat cctggaggat 29280
tccagcgtct tttttttttt ttcttttttt ttaagacaga gccttgctgt cacccaggct 29340
ggagtgcagt ggcacgatct cagttcactg caacctccgc ctcccgggtt caagcgattc 29400
tcatgtctcg gcctcccgag cagcaagact acaggtgcgc accaccatgc ccgactaatt 29460
tttgtattat tagtagagac gggggtttca ctctgttggc caggctggtc tcaaactcct 29520
gacctcaggt gatccacccg cctcagcctc ccaaagtgct gggattacag gcatgagcca 29580
ccatgcccag ccagcatctt tcatttttct gtctgctttg gccctttcct ctctcactgt 29640
cttccttttc catttccaaa gtcagtccat ctcactatta gcacaaaaac tgctagagcg 29700
cttgtcattg gtcatctctc cctgcacctg gctggtctgt tcttggccac tgaagcgttt 29760
cccccagctg ttgctttaat cattttattg ttattatgcc ttacttaaga aatggatatg 29820
agatgcattt acctgtctct tcctgccact ctgcagagcc agtaagatgt ggtggaaagg 29880
gcccaggctt tggaggaggg ctggctgggg ttggatcttg gctgcccccct actagctgtg 29940
tgaccttggg taagtagctg gacctctctg agcctggttc ggaatcatag cacctctctt 30000
tcagggctgc tgtaaggaat agcagtggtg tgtataaagc agagcgcaca gccagcaact 30060
ggcccctagc cacactgctg agcacctact gtgataagct gccattgtgg tgtgtgaagc 30120
aaaggggaaa catgcctgct gtagtgagct tcctgtaggg caggttgtag aaccagaggt 30180
gggttccaag gttacaaagg gactcttagt gtattagtct gttctcacat tactataaag 30240
acctacctga gactggatca tttataaaga aaagaggttt aattggctca cattggctgg 30300
gtgcggtggc tcacgcctgt aatcccagca ttttgggagg ccaaggccgg cggatcactt 30360
gaggtcagga atttgagacc agcctggcca acatggtgaa accctgtctc ttctaaaata 30420
aaatacaaaa attagctggc catggtggtg tgcgcctgga atcccagcta ctcaggaggc 30480
tgaggtggaa gaattgcttg agcccgggag gtggaggttg cagtgagcca agatcgcccc 30540
actgcactct agcctgggca gcagactgag actctgtctc aataaaaaaa aaaaaaaaga 30600
aaagaaaaag aattgcaaga aataaattat tgtttatgag ctatatggtc tgtggtacct 30660
tgttgtggga ctgggagtct tggcgtctcc ctgaccctgc ctgttgctgc agcaccgctc 30720
agccctgcct gctccctacc tgcctcccct cggcctctcc tgcctccacc gggcccctgg 30780
tgcctcctct agagacagtc ctcctgggac cgattgtgtt ctcacttaca cgaggcatcc 30840
aggactacag ataaccagag gaaggggcgc ccccccgcc tgccctcctc cctggcatcc 30900
tcacgctgca gaggtcagag cctcatccca gccccttacc tgcccctact ctgtggagaa 30960
ccgtggtcag ttcgccaggc cggatccacg aacggccttg tggaagatgg tgagctcaca 31020
cccagagctg gctccgatga ccctgtctcc tttacatgtt tctaccttcc cctccctacc 31080
ttcccccact gctgggcgca gagtggaggc agatgaggtt taaagctcag aagggcttaa 31140

```
acgggttggg gcgcagtggc tcatgcctgt aatcccggca ctttgggagg ccaaggcaga  31200
ggatcacttg agcccaggag ttcgagacca acctgagcaa catagtgaga ccgcgtctct  31260
acaaaaaata aaataaataa aattagcttt gcagggtggc atgcacctgc agtccctgct  31320
actcagaagg ctgaggtggg aggatcgctt gtgcccagga gtttgaggct gcagtgagct  31380
atgctggcac cacagcactc cagcctgagt aacagaatga gatcctgtct caaaacaaac  31440
aaacaaacaa acaaaagaag gcttaaaggg ggctccaggt gggcttggca gcacaaagct  31500
atgaagttct atcttagaca caagttctgt tactgggcct ttgcaggctg gcctgggtac  31560
ctggctgcca tagacaggga accttccaga tgagctgcag gcgtggagca caggagccag  31620
ggtgctcttc ctgggctctg tccacaggca gaacgtacac agtctttgta cacgtccggc  31680
ggctctggtg cctatttttg tttgtgtttt tcttttgttt ggggggatgg atttggtttc  31740
ccccgagccc tctgtcctcc tgtcacctgg ctggtgctcg gcaatgttga ccagctgcct  31800
ggctggagtt ggcagtggct aaggctgtga cagctaacat gttcctgagt cctctcattt  31860
cttcaccata atgccctgtt gagtttgcag atactgtctc tgtttttatc tcccggggaa  31920
actgaggctc agagtggcta ggccaccttc ccatggtccc tcagctcatg agggccacac  31980
agggcattgc ggtggccttc tcctcagcct tgaccctccg gccccagcat tgctgcctca  32040
aggggtctcc tctgctgagc cgtgcacctt ctgcctggca gctccaactc tgtggctgtg  32100
ttcagtggct cagcactgcc ccttgaccct ccctggcctt ctgcggatgc cagactggag  32160
cactctgaca aggtctgggg tggttgtatg ggtcctgtga cctctataca cctcccagtg  32220
cctgggaatc ctgcagatac accctcctta gccgtcccta accatagagg acatttctga  32280
ggtccccgag agagtggggc acccctgcag gatccaactg ctgggcccag gaaggatagc  32340
agcagcatga ggggttccat tagccacaaa ctcacggcat ggaaccttca cccacctcgc  32400
ccctcatctg ctgtttagca cctggcacgc cgtgtatact tactgattat tacattttaa  32460
tggcaaatta tagtggcaaa cgtatgcatc tttgcacaat tgttgtacag catgatgaac  32520
aagtcattaa tagtaaagaa taaatgtgaa agtgagaaaa atctgactgc caaagttttt  32580
actccttcct tccctcccca gacttttaaa tgaaagttta gggataatcc cttagttgtc  32640
ctgctagtag gacttgcaat taaaagaatt gggccaagaa cacttctacg cttctccttt  32700
taggtttggg tgtaaattcg gggtatttct cactgatgaa agcctggtgc agggcagacc  32760
gtgggaagct ttcatttccg gaatggacca tcaacatccc ttggagaaga attctcttct  32820
ccagacccag acctggtgtc ctggcaccca ttgggcaagt gggtcctaga agacaaacct  32880
ggtcagagcc tggaggctgc ttagcattcc ccacgcacat tagcagctcg gagagctcag  32940
gaagccgcag cccctccttg cctcaccagc ctggatcagg acagcatccc ctggaagaca  33000
cacagggcct ggcctctgat tacccagcct ggagggaaag ctcaatcgag catcatgtca  33060
cccggtgccc ccatgcaggg tggcactggt gagaccccca agccaatgat accacctcac  33120
aggagtgcag gcccattgtg gccagatcat cttgactttt caagataaat cagaaatcgt  33180
atttccatga gatatcccta tttgcaagtg atggtgacta aattagaagt ttttgaatat  33240
tgtaacatgt tcgtaggctg tttgtctggt ttaaactcta tctggaggaa ttcaagctag  33300
acttcaggaa taacttcttg aggcaaggat tttgagacct tagggaaaga aggacgtctt  33360
gggggtattc tgactgttgt cctcctggaa gggaagaaca gagaactaga agactgccct  33420
tagcgaagtt caaagcacct aagcccggga ccctcagcaa gtgttcttga gtcacagatt  33480
```

```
ctccctgagg cgcctctttc tggctccata gaatggctga ttctgtaact cggtgagttt  33540
gcttttttttt tttcctccat cacccaggct ggagtgcagt gaagctggag tgccgtggag  33600
cgatcactgc aacctctgtc tcccaggttc aagcaattct ccttcctcag cctcccaagt  33660
agctgggatt acaagcatgc agcaccacac ctggctaatt tttgtgtttt taatagagac  33720
ggcccgaagt gctaggatta caggcatgag ccaccgcggc cagccataac tctgtgactc  33780
ttgttacaaa ggccttatat tttgctcttt gagggtggtt ttggtttgat gcctgttggt  33840
tgccatcttt taactaggga tgttttatca aaatgcccag ccaaagtgtc caaacaaatt  33900
ataccttaaa gtttgaaaat gtctggcact tctaattcaa tgcctgttgt gccaggcact  33960
gggctgctga ggaactgagt cccgtccctg caggctagct agagaacaca cacacacaca  34020
cacacacaca cacacacaga gtggtcttac aagtcagttt tatattctac ctatatgcaa  34080
taaaggtatt attatgttga ggtgccttga tataaaaatt tttcttaaag gagaggatgc  34140
ctaaaacagg cattacctga aacctcctct ctccagcatt ggttgtcttc tgtcatgact  34200
cagggttttc actgagaatg ggatggaaat gtggtctaaa gatagggcca atgttgggac  34260
tggatcccct ctgggaagtc agaccaggct agggcaggtc cttgaagcca tcaggaaaag  34320
cctctggagc cagaaacaaa acaaaaaaaa aatggtgtta actaaactca gtctcaaatc  34380
ctgaatagga ctcaagtcaa gcaaaataat taaaggagtt agcaaagggc aagtcagaga  34440
gaccgagcaa caccaatgtc ttccgggagc cctgtggcga gtgacagagc ctggactctg  34500
gagtagaact catcttgtgt cttcttctgc cactcgttag ctgggtgacc ttgagccaag  34560
ccccttaacc tcttggaccc tatgttctta tctctaagta ggggctggta atatcttccc  34620
ctttgaggaa tgccctctaa ggggtgttgt gaagattcgg taaggtggca ggggtaggac  34680
tcctggccag aaacaggcac ataataaatg ctaagtctct ccttctctcc acctgctgga  34740
tgctgtagat actaaggatt tcgatgtgaa tgagacaaaa cccctgcctt ccaggagcct  34800
ttgagaatca gagaactaga cccatttcca gaacaagggg atgcagggtc tggataaagt  34860
tttggggatc aatagagcag agggctccca gaggatccca tagggttgac tcctaactca  34920
agggcatgag acaaccccca ggaagggcac cctggaaggg gtccggctgt ccctgattta  34980
cttgtgggca ctgggggaat gcccggagcc atccagccct cagggctctg tgtgattctg  35040
ggttcctccc ataaaagata atcagattct ttcacgttaa tgtctttctc cacctcattg  35100
cacatcatgc agctattcat tgactcagca agtatcagct ttgcatgcga ccttggccta  35160
cccactttag cttttagtaa tagctccctt cttgaataat acaaccagtg gggaaacaga  35220
acctaactct tacctctggg aggcttattt gctttgagaa catatgtcct gcagttttgt  35280
tcatatggca gtgaagtttc gtgcacacac tctagagcca ggcagcctgg gttcaaagcg  35340
cagctctgcc aggtcctaac tgcatgaatt tgggcaagtc gctcaacctc tccatgcctg  35400
agtttcctca tctgtaagat tggagcaatg gtaatacctg ctttttaggg ttgagaagag  35460
aattaaatga attaagatgg gtaaagtgct tagagtggag ctttgcaagt agtaagtgct  35520
atgtaagtgt tcgatttaaa atgaaagacc cttaaataca ttctttgttc atttcacaag  35580
cccttcattt cacaacctta catttcacaa ccaagctctg tctcccctgg aatccagcca  35640
taactctgct cacaagtgtg agacaggccc cagcagagct gcacgaagag gagagaaggc  35700
agccccccag actcccaacc ccctgtccaa gatggcaaaa ccagaacaca gcctctgtac  35760
caccccagca ggtattcaga atctgcaatc tccaaagccc acttcaattg taaatgtaga  35820
gccacgtgcg ctttaagtca cctgtcactc tggaggctct tttgctcagt tcctcaccat  35880
```

tagcagggat gacagggagt gcaggagtgc ggtcgactcc cagatattgg agagcgctgg 35940
gctagctgcc cattctcccg gcctccactc ctctttgctg tccagccatc acttgctctt 36000
tgaaggcaaa caaaacagaa aacagtgcca aaagtatggg aagaaagcca gcttctcccc 36060
tggggtgcct gtgatgccat gcccaccctc cctgaccacg cagcccctgt ggaccctcag 36120
ggccccaagc ccccatttcc atcacatgcg tacacccatg tgtgtccata gccgcccatc 36180
tcagtcaata aggctgctcc tgcccacttg gaatagtggt gacaaccagg agtggcttat 36240
gggaactatc ccaatggcct gacagcatgt ccgctgcaaa ccgctgaggt aggacactgc 36300
cctcatgtct agctgatcag caagaggcgc agttgctttc ttaggtaaca ttgctgctgt 36360
gtcctggcca ttgctggggg gtggcactta atctacacca gaattttccc tcctgtatct 36420
tccaagctgc ttggatcttg gtgctgaatt aggttggact ttgtcttgtg gggaagggag 36480
gactatagac cctcaacgta agcaatggtc agactattct aagaaaactc gccgaattaa 36540
agcatgaggt aaatttagtt ctgacttctg tccaccccac tgccactgtc cccttttatc 36600
ccatgatccc ttgcttttct tttcctcctc tctccctatc tcttgtgttt gacgcatgat 36660
aggaattcag aaatatatgt ttgtggattt gtttattcac gtagcaaacc atttcttgag 36720
tgcctaccat gggccaggta gaatgggcgg ccccgggctg cagtggtttc ttcagcccct 36780
ctccagggtt tacactgtgc aagacggttt gtgatgggtc ctcccatcga ggaccacact 36840
cttctttctc tgtgcccctt ggtcctcagt ctctgacccc acttcaaagg cagcattcac 36900
tcagggaagc tcccatacaa tgctagtcag agtaaaagtt tggacaaatt gccaggaagc 36960
agcttgtcag tatgcataaa cagcctttaa aatattacta ctctttgacc cagaatttca 37020
cttctaggaa tctgtcctaa ggaagtagtc acatgcaaaa gatttatgta ccaagatgtt 37080
catcaaagtg ttgttttata acaggaagtc tcagaagctg gataaatatc caacctctgg 37140
aaatggttag atagaatagt atgtagccat tagaaaatta tgtctatggg gtttaaaatg 37200
tcatgggaaa acacttctga cataaaagag catgagaact gtatatttag cataatctta 37260
actatgtttt agaatgcaca ggaaaaaaat gtacaaacat attcatagtg atgtctctgg 37320
tggtaggatt atgatcagta agtacttctg tctcttcata ttttcctgta tttgataata 37380
catgcatatg ttgtttttaa aataagaaaa attttaagtt taaaattgga gctgaaaagt 37440
gtttttaggt caggcgaggt ggctcacacc tgtaatagca ccactttggg aggctgaggc 37500
agtcagatca cttgagccca ggagttcgag accagcctgg ccaacatggt gaaaccccat 37560
ctctactaaa aataaaaaaa ttagccatgt gtggtggcac acatctgtaa tcccagctac 37620
ttgggaggct gaggcatgag aattgcttga acccaggagg tggaggttgc agtgagccaa 37680
gatcgtgcca ctgcactcta gtctgggcaa cagagtaaga ctctatgtca aagaaaaaaa 37740
aaaaagaaaa gccttttttaa acagtagcag acataactat ataatcctta ctaagctgtc 37800
ggtcaaattt ttatttatat atttatttta ttcatttatt atttttagac agggtctcac 37860
tctgttgccc aggctggagt acagtggcgt gatcatggct ctcttcaaac ttgacctccc 37920
gggctcaagt gatcctccca tcttagcctc ccaagtagat gggaccacag gtgcatacca 37980
ccacacctgg ctaatttttt ttattttttta tttttagaga tggtgtttac tatgttgccc 38040
aggctagtct caaactcctg ggctcaagct atcctcccac ctcggcctcc cgaagtgctg 38100
gggttaccag catgagccac tgtacccagc cctcaaattt ttaaaaatct ataagagaca 38160
ttattggaca attagagaaa ttcacatatg gacttataat agtatcagag tgtgtggtgt 38220
gatggttctg gagggaatgg actttttctt tggagacagg cttttctatg cccacccttt 38280
tatcttgcta acttatcatc atccaggttc cagcagaaac attacttccc ccaggaaatt 38340
tcttaagggt gcagtatcat gatgtctgca gcaaattctc aaatagctca ggaaaaaagt 38400
acgtgtgtgg tatgagtgtg tgtatgtatg tgtgtatata tatacacata tatacacata 38460
tatatacata tatgtgtata tatatacata tatgtgtata tatatacaca cacatacaca 38520
tatatataca cacacacata catacatgta tttttatata attatatatg cagagagtgc 38580
aaatgttgcc aagttaaaga ttggtgagtc taggtgaagg gaatatggta tttattgtat 38640
tatttgtgca actttttctta agtttgaaaa ttttcaaaac aaaaaattgg aggaagaagg 38700
catgccagtc taccccaagc cctccattgg aatgctgaaa atctaaacaa tgtgatttgg 38760
caatttcatt tcttttctgt tgtgggccag tagtccttag atgttgggga agggggtagt 38820
cgctgaggtg tggttgactt aggatggaag aagcagaagt caagactccc agggtcaaag 38880
tggtttgctc tgctgaccca agtgtgggag gcccagagtc agcgtttcag gtgtgctaat 38940
tcagcatggt tctattcacg gccaaagtcc accctgggca cctctctggc agcaatcttg 39000
ggtgactcta ctaaggccag gcctccatga ccctatgtct ggatcccata tctccacctc 39060
tcccactgtc tcaggaacgg tgcttagctt tttcttttcc ctctcctgtc ttctttgcca 39120
gcatgtagaa agtttaaata attcccctct ttacaacaaa acaaaacata ccccccttcag 39180
tcaaccaccc tagctctctt ctccttttcc cagccagatt tttttaaaag catcctaggc 39240
caggcgcggt gactcacgcc tgtaattcca gcactttggg aggccaaggt gggtggatca 39300
caaggtcagg agatcgagac catcctggct aacatggtga aaccccatct ctactaaaaa 39360
tacaaaaaag tagccgggag tggtggcagg tgcctgtagt cccagctact cgggaggctg 39420
aggcaggaga atggcgtgaa cctggtaggc ggaggttgca gtgagccgag atggcgccac 39480
tgcactccag cctgggtgac agagtgagac tccgtctcag gaaaaaaaaa aaaaaaaaaa 39540
aaaaaagcat cctcagcact ttggcaactc catctcctcc caacatgtcc ctgttactgg 39600
aatccagcca ggactcagcc ccgatctttc tactctaacc agttgtctca gttaacaagg 39660
acaggtttat gctgcagtga caaacaagat cccaaattct tgtggcttca cacatctggc 39720
accacctcat cttccagcct taggagtcat cttttagttc cttgaaaact ctttacagtt 39780
ttctgttggg gccttgtcat atactattcc cctggaatgt tctttcctat cccctccctt 39840
tcaccttgct aacttgtgcc catccttcag gtctcagcag aaacatcact tccttgggga 39900
agttttctcc aacacccaca ctacacaggt gtcccatcta cactcctatg actttgtggt 39960
acttgtctca cttcattttc cactgccttc cccacaaggc acctgcacaa gggcaaggac 40020
cgtaccactg tacctatgtc actcattgct gtggtcacct gcactctggc tgcctacctt 40080
aactacacat tagaatcacc tgaggagctt ttaaagccac aatgcaagac tccaccctag 40140
gccaattgga tccaaatccc tggggtaggg ccagacatca gtggagttat atatacatat 40200
atatattttg tttgtttgtt tgtttgtttt ttgagacaga gttttgctct gtcacccagg 40260
ctggagtgca gtggcgcgat cttggctcac tgcaagctcc gcctctcggg ttcacaccat 40320
tctcctgcct cagcctcctg agtggctgga actacaagtg ctcgccacca cgcccagcta 40380
attttttttgt gtttttagta gagatggggt ttcaccgtgt tagccaggat ggtctcgatc 40440
tcctgacctc atgatctgcc tgcctcatca gcctcccaga gtgctgggat tacaggcatg 40500
agccactgca cccggccatc agtggatata tttttaaagc actgcagaga attctgttgc 40560
atcagcttga gaaccactga tctgccttgt gcttcacatt taaaactttt ttttaatgaa 40620
taaataaacc ccaaaaaatt aatctcccta agcctcccta gaagatagga tggtaaggat 40680
attttcctag gtaaaaatat gttaatttca tatttcatga aatttcatgt ttcatttcaa 40740
tcaagctctg tcatacacct tacatggggc aagcccagtg cctgggcagg gtgtaattat 40800
actcattaca caggcaagga aaagtcacat taggtgatgg agcacaaata ggcagttaat 40860
ggtttcaggg ctagttagga tatgtttgtc tttcaattgc aagtaataga agcccaaaga 40920
aattggttat ttatataata taattgattg gttcccaaat ttgaaaaatt caggaataga 40980
cccagcttag gtacagctgg atccagtcac tcaaacaatg tcacaaagaa ccctttgaca 41040
ggaatgtatc ctgtgttgac tctactttgc tctgagtagt ctttccccag gtgatgataa 41100
aaatggtcat catcgccagg cttgtgtcct gtttagtagg aatatacaag aagagctcag 41160
taaatgctgg ccccaccact aagcaaaaac aaaacttttg ttgttgttat tgttgtttta 41220
aataacagct tagacctttc ttctttcctt gttattctct ttcatctgta atccagtttt 41280
ctacttctga agtatagaat gttctgatga tttattcttc attacccaca acttgcacat 41340
gtttatttaa aaatgccagg attgcctggc cgttgtgtgc tgttaacctt tgtttgctgt 41400
tagtggatcc ctgaagttca ggctcccagg ggagcagata atgggtatcc agttcctgca 41460
atatccaccc tctggcaagc caagttcctt cctgggtaag gttttgccta cctgcattcc 41520
tagggaagtt tctgggcctg accaccaagc cagctctgag aaggggtgca taagccccac 41580
catgctttgg ctctgtccct atagaatatt ttatgttgtt actgaaaact aaaggaagat 41640
gggtgcggtg gctcatgcct gtaatcccag cactttggga ggccaagaca gattgatcac 41700
tcgatgccag gagttcaaga ccagcctggc caacatggtg aaaccttgtc tctacaaaaa 41760
caaaacaaaa caaaaattag ccgggtatgg tggcatgcac ctgtggtacc agctactcaa 41820
gaggctgagg cacaagaatc tcttgaacct gggaggtaga ggttgcagtg agccgagatc 41880
gcactactgc attccagcct gggtgacaga gcaagattct gtctccaaaa aaaaaaaaaa 41940
aaagaaaagg aaagctaaag gagagagact aaaatgatat caggttcctg gagaacaaac 42000
agacatgatt ttgcttcatg gcaggacagc cggaagaagt gggattatat cctcacatta 42060
caaataagaa aactgagact cagaatggtt aagtcacttg tcccaggcca cacagccagt 42120
aaattacaga aacagaattt gaacccaaat cttccagctc caaagcttgt gttcttttca 42180
ctacctcctg cttaattttt taatttctaa gattagaccc ttcatctatc catgacacct 42240
gcctgtcatc ccctgaaaaa aggtgaacgc cgttcagaaa tttttctagc ctgagctcac 42300
tcccagttca cttattttg ctttgtcatg gctgcccagt ccccacttgt agaccaggaa 42360
taggtcatgg ctgcggggac tacacgctgt cgctgctgca agggccggcc tctgtttccg 42420
gggctgagtg ggggccagac ctgccaggag caccatcttc tgtgggtcct gcctggatgt 42480
cacatcccgg ccccaagaag tcactgcaaa ccttcgtatt attgagcttc acatcctaga 42540
atttgctgtc actgtggctg ctgcatgaag ttgtcctgag agaaacgggc attgtcatta 42600
acagggaaat tgatggtctg ggggaaaagt catcctcatt ctcttgcaga tctatgggtg 42660
attgagactg gctgatgttg aaggggtttc tcagccatcg tgtgccatgt tatggaacag 42720
tggtgtagcc agccatttga cacccagcgc tgacctttgt ttaacaacct cacctatata 42780
tgacaaaatg attgtcagaa ataatcgtgt aatgaaatga ctgtaataat ggccagaaaa 42840
gaaacgcaga tagtaaaatg tttctcttgt tgaactctgt acatataatt gcaccaggat 42900
ttttttcaaa taaaaagtaa atattatact acaaaaaagg gaaaaagcac aagcatttat 42960

-continued taaatagctt tctatatctt tctgagtttt gatcctttga ttgcagactg atgtaatatt 43020
ttatgtaaat cattgcttgg ttactaagtg aactttaaga aaagtgagac gtctgcagaa 43080
gttgcccata atttagcagc tactgtattg taccattgat gtacggcttt attttcttga 43140
ttaattattt aaacaatata attcacaatt ttaaaataat aaatttccac ttaaaatggt 43200
atttaaactc agcaaaatat atcatctatg agtaaaattt gtatttacca agcaaaaata 43260
ttacagtttg tggttcacat gctgtctcac tgttttaaat tttaaataca aaaactccaa 43320
gtaggctggg tgtggtggct cacacctgta atcccagtac tttgggaggc tgaggcaggc 43380
atatcgcttg agttcaggag ttcaagattt gcctgggcaa catagtgaga tcctgtctct 43440
actgaaaaca attagctggg tgtggtggca catgcctgcg gtcccagcta ctcaggaggc 43500
tgagatagga ggatcacttg aaccctgggg gacagaggtt gcagtgaggc aagattgcac 43560
cactgcactc cagcctgggt gacagattga gaccctgtct caaaaaaaga aaaaaaaaaa 43620
agaaacacaa aaactccagg tggtcgcaca gaatgacagg actgaagtaa cttagctcca 43680
atttctgtct tcataatcac tgtcctacca ttgtctgtgc ttagaatcta cttgcttaat 43740
gcaggaacat gtgttctcac agagatggaa aatgcaaatg gcgccagaag caagctggaa 43800
attctgaacc attaagaatt tactctctgc caggcacggt ggctcacgcc tgtaatccca 43860
ggactttggg aggctgaggc aggcagatca tctgaggtca ggagttcaag accagcctgg 43920
ccaacatggt gaaacttcat ctctacaaaa atacaaaaat tagccaggca tgatggtggg 43980
tgcctgtaat cccagctact cgggaggctg aggcaggaga atcgcttgca cctgagaggt 44040
ggaggttgca gtgagccgag atctatctgc accattgcac ttcagcctgg gagacagagt 44100
aagactccat ctcaaaaaaa aaaaaaaaaa aaaagaactt actctcaaaa taaatacgtg 44160
tggctgactc cacatatggt agggccaact gtataactag aagttctcca aataacttct 44220
gtggagaaaa aaaagtttat taaaggttaa ctttttaaa gtgctaacta gaaccttact 44280
aacactgaga tcgcaccaat tgtttataac ttagacaggg ccgggtgcag tggctcatgc 44340
ctataatccc aacactttgg gaggccgagg caggtggatc acttgatgtc aggagttcga 44400
gaccagccta accaacatga tgaaacccca tctctactaa aaatacaaaa attagccagg 44460
cacggtggta cacgcctgta atcccagcta ctggggaggg tgaggcagga gaatctcttg 44520
aacccaggag gcggagattg cagtgggcca agatcgcacc attgcactct agccccagca 44580
acaagagtga aactctgttt caaacaaaca aacaaaaaaa aaaacctctt ggaccaggaa 44640
aatatttttt aagggaggag tattttatca ctggcattgt ttaggattgc aggcacatga 44700
tgctaatgaa aagcagacta actattagtt ggttttatta ctgtttttga actctctctc 44760
tcccttttt ttttttttga gacagagtct ctctctctgt cacccaggct ggaatgcagt 44820
gactgcagtc tcagctcact acatcctctg cctcctcagt tcaagtgatt ctcgtgcctc 44880
agcctcccga gtagctggga ttacagggca ccacaccagg ctaagttttt gtatttttag 44940
tagaggcagg gtttcaccat gttgcccagg ctggtctcaa actcctggcc tcaagcgatc 45000
tgcccatctt gacctcccaa agtgttggga ttacaggcgt gagccaccgt gcctagccct 45060
gtttttgaac tctctagaga cagtccagcc ccttattact tgtcctgagg cagctgctcc 45120
cttcacctgg cccccgcat tgtgttccgg acccttgtcc tggtggtgct aaagaatatc 45180
tctgtcgatc ctttggggac tggggaaact gaggcccagt gccacgcgat gccatttgtt 45240
cagggaagat taggtcatct gctaggtccc cagtcacttg accttcttcc cagacaggaa 45300
gaagctgctc tgggtctctc agtgctccac gtgtctttgc acattgaaat gttttctgat 45360

```
ttttttttt ttttttgct gttacattta cttttaaaaa ataacaagca ataaaatgtt  45420
acatttgaga aggttgaaat gagaattgat ttgagttaaa ttctagcaga tttttcttag  45480
aagaatgata tcatcatctc cagctacctg caattgatct actctgaatt aagaaagaga  45540
cttccatttg ttgtttatat tttgcactct tgatgtgttt ctttaaatta tggtcatggg  45600
ccaggtgtag gagctcacac ctgtaatccc agcaccttgg gactctgagg agggaggatc  45660
actggaggcc aggagttcaa gacctcgtct gtacagtaaa ttttaaaaat tagccaggca  45720
tggtagcatt cacctgtagt cttagctact tgggaggctg agatgggagg attgcttgag  45780
ccagaacttt gaggctacag tgagttattt tcacgccact gccctctagc ctggctgaca  45840
gagcaagacc tgcctcaaaa aaataagtaa aaaataaatt aaatttcaat cattagcagt  45900
cattaggata tttaaataca gtatgttgaa tcaaagttac gcatgtgtgt attttttttt  45960
ccagagagtt gtttatcatg tgggttttaa tttaacttta aaaaaatgtt ggctggacag  46020
ttgcccaaat ggtatcatca gccatttggt tgagaacgta tgtcctgcgg gctcctctgt  46080
cactggagtt ttgctagctg acagccactg gctagttaga gactgcagtc agcacagatg  46140
caggcgtgga cttgcgcacg taaccatgtc aatgcaaagc catcacttct taaaaattct  46200
gaaccctgct gtctgagatg gtggtgcagc ggatagaact ctgctctaag aggcagtagc  46260
taattccatg tcttctttgc ccttgactag ctgagtgact ttgcacatgg ggcttgcctc  46320
tctgttgcct tgtctgcaaa gtggaatcat cttttccttg ctagacagaa ggtggaccct  46380
ggacctatgg ccttttttgag tttccccccc gcttcttaga aggacctctg atcctactga  46440
gtttaatacc cacgggttaa taattgggaa aagcaaagga agcgcttctg tttaggtaat  46500
tatatgcatg tttttgtctt tttctggctg gaaagatatc caagccactg ggaaggtccg  46560
tggctaccca gggtagccct ctctggggag ggctgctata tccaagagcc cctcatgaga  46620
atttgaaaat cgaccatggt agggcctgct gacttttgac agctaatggt gtgctgagaa  46680
ttgtccctcc aaagatgcct ttccattccc tcgggagagt ctgggcagcc cctactgggg  46740
gctgggatgc tggctcttcc ctcagcctcc accccaactg ctctcttccc tcctcccctc  46800
cccagccccc taatttctct cacaaggctt tgttctgcag caacctttcc taatgcagtc  46860
ctggcctctt cgcagcttca ttacataacc ttccgtggac tcctggtcca aggatcaccc  46920
cagaaagcca gtcagaggta ggcacgcagc tggggtccat ttacttacct tccccacccc  46980
ctcggaactc agaggtggtg caggaatttg gactccaaga attaacagct ccaccaccat  47040
caccagagcc aaaactcagg atgcatgtgc ttcatctgct gcttatttcc agctgagagc  47100
cagtggtgcc atggttcctt agggagccgg tcccctgatg ccggctcctg gccccaaatc  47160
tctctgatcc gggctcttcc agaatgtctt gtctccacca tcgcctttga ccaatggtgt  47220
ccctttgcct ggtaatgtcc cctttgcctg atgatggccc tgtcactcct ctctttagca  47280
cagaggaggc tgtttcatcc cttcaagcct gccctccctt caagtcttag ctcaagttca  47340
ccttctccgc agagccttct ccaatcttct tgactacgtc tcctctcagc tccagcaacc  47400
tctgtctctg gcactgattc cttacttagc taagagaatc acagacactt ggggctcagg  47460
acaatctgct ttctctcttc ttacccatgg ccttggactg tgtgtacctc tttgtctcca  47520
ctcccaaacc caacccccag agggcagaga gcatgttgtc tgtccctttg ctcagcatga  47580
agccatgcgt gtggtagatc ggcagagttc cataacttgt gttgaccgag gggtcacttt  47640
gctctgaaat taccccctgtg tccttcagta tttgcacaga tagcttcctg gccagaccga  47700
```

atatatccaa gggcatggcc cacctctgct cctgtttcca ggtccctggt gggggttagt 47760
tcatgccttc ctcataatct gcccactggc ctggtcctca aggtcttccc aactgctcag 47820
ccagagttga gaaaatgggt cgctccatcc tgtttgtgtc gttctctcct tcctggccca 47880
ctctcctgcc cacaggtatc caggggctgc ctgtagcatt agaggacata catgcacatg 47940
cgtgggcatg ggacactcac gtagcctcca agcacagcat caataatgca ttctgtgctt 48000
tatagcatgg aaagctgctc taaactttat tacacagtgg acatgtctga agcagctccc 48060
aaatccaccc ctgagtgtgt tggaattggc aagcctatca cttgggagtc tagttttttt 48120
gttcgttaat aatagatgct tcctgtggcc ccagcttggc aattttgatt taaagtgatc 48180
ttaactgaag agactaatgg acgggtctga atttgtgcct tttaagcaca aagtattgct 48240
cttaattaac tggattctat cctttgagca ggcagaggcc ttcccccaag ggcgtcatta 48300
acgatccaca tctggacatc ttccaaagcc ttcttctgtt tcaggccaac cgcaggtgtg 48360
ttcctgaaca cccaggaggc tatgagagcc acatatgcct cccaaataca cacagtgtgc 48420
atgcccaggg acatagagca gtgtgcaaag tcccattcca tctctctcca cctgggagag 48480
gatggctctt ctgtctgatt catggctcaa agtggtaaag gagctcccca ctccccgtcc 48540
cacgcctact cagagtctgc aaatatgtat gcgatatgag agctcgtcag ttagctgtct 48600
tcagtgtggc gcacatttga ggagtctgac tcccctccag cacaggccaa tgtgcactgc 48660
tctcctatct ttgtaccccc actgttgcac tgtgcagagg ttggagccat agaagtacca 48720
gagctgtgaa aggagaggcc ccctctcacc tctgccctgg tctccatccc cactttctct 48780
aggaagctag taggtgctga caggggagag aagggagggg aggggtccag aaacagtggc 48840
tcatgcctgc aatcctagca ctttgggagg ctgaggcagg aggatcattt gaggtcagga 48900
gtttgagacc agcctgggca atgtagcaag accctatctc tacaaaaaga aaaaatgtaa 48960
ttagctgggt gtggtggtgg gcacctgtag tcctagctac ttgggaggat gaggtgggag 49020
gattgcttga gcccaagagt ttgaggttac agtaagctgt gattgcacca ctgcactcca 49080
gcctgggcaa cagagctgag accctatctc aaaaaaagaa aaaaaaaaag aaaggagaga 49140
gagagaaaga aaagaaaaga aaaaaaaaaa agaagggaag ggaaagccca gaagagtgtg 49200
gggagaggag gcggccgtca ttctggggcc ctcagtgtgc acaaccagat aacacatgct 49260
ctgtgggctt ttgtaccatt ttgcttgagc ataaagaaag gaaggctgcc cctaaataga 49320
aagcactctg gaggcaaaca aatctgactc caatcctggc cctgccactt tcccagctga 49380
ggacttagac aagcacccta gcctcttgga cattctcaga gccatctgct gcaagtgggt 49440
gctgccatac ccaccttact gggcaggctt gggggaccaa gggtggtaaa tggctcagtc 49500
tttcatgatg cggccacaca gcaggtgcgc catccaggtc catttctttc cttcctttcc 49560
cccaaatcaa gttgtcatta aagtactagt ccacattaat gaaatcaact gtattaattt 49620
tctatttgct gctataataa atcatcagaa atttagtggc ttaaaccaac acaaatgtat 49680
taccttacag ttctggaggc cagaagccct ccataggtgt cactgggctg aaatcaaggt 49740
tttggcaagg ttgcggtcct ttctggaggg tccaggggag aatccatttt cttccttttt 49800
ccagcttcta aaggtttcat gcattccttg gctcatgatc ttctatagct atagtcagaa 49860
aaattttcca tcaatcatct tcaaagccag caatggcagg atgagtcctc acatcacctt 49920
gctctgacac cagttctctg cctccctctt ccacatgtca ggaccctcat gattactttg 49980
ggctcactct gataatctgg gatgatctct ctattttaga gtcagctgac tgggaacctt 50040
aattccatct acaaccccaa ttcctctttg ccatgtacag tgacatattc acaggttctg 50100
gggattagga cgagcctgtc tctgaaaggc tactttacat gaaaattcat ttttttaatt 50160
aagatttttt tttcctcttg agacaaggtc tcactctatg gttcaggctg gagtgcagtg 50220
gtatgatcac agctcactgc agcctcgacg tctctgggct caggtgatcc tcccacctca 50280
gcttccctag tagctggaac tacaggggtg agcccccatg cccagctaat tttttttttt 50340
tttttttttt gagacagagt ctcactcagt cacccaggct ggtgtgcagt ggtgcaatct 50400
cagctcacag caacctccgc ctcctgggtt caagtgattc ttgtgcctca gcctcccaag 50460
gagctgggac tacaggtgtg caccaccacg cccgactaat ttttgtattt ttagtaaaga 50520
tggggtttca ccatgttggc caggctggtc tcaaactcct gatctcaagt gatccaccaa 50580
cctcagcctc tcaaagtgct gggattacag gtgtaagcca acatgcccgg ccccagctaa 50640
tttttaaata ttttttttgt agagatgggg ttttaccatt ttgtctaggc tggtcttgaa 50700
ctcctgggct caagcaaacc tcccaccttg gtctcccaaa gtgctgggat tacagcatga 50760
gccactgcac tcggccttaa gagaagattt aataattaat actttacaac aagatctgga 50820
agaggtggga tgagtaacta aatgaggata caagtaaccc gggtcatatt tgctaatacc 50880
cttggtcaca ttgaacttga tatcttatca gattttccta atcagctcct ttagcagcag 50940
tgttgcagca tcttatctca ttttgttttt tgtttttttg cctagcacat gcctgtaaat 51000
cactggattg aggtgtttag atgtttgttg tcctttggat gcttcttata aatccatatt 51060
tcatggctcc ctggaaagtg ctatgcaaat gataagctgc aaggatggaa aggaaattgc 51120
agtgctcctg aattgtaaat gggcttttac gaggaggttt ctaattactc gctctttctc 51180
ttgaactgag gagttgaagt gtaggtggca gatccataac agataatcat gtgtgtgatg 51240
tgacttcagc ctgagcgtcg aggaccaagt cacagagcag gaacagccac tctccagtgt 51300
ccttggggct acgtctgagg agaacctggg atttcatata tgacctgcac tggctggggg 51360
gctctcttga cgtaacgtgt tccctctgag catgttacag attctgacat tcttatgttc 51420
cttctgtgga gagacatgta cttagtgacc taactcactt tagcatattt ttgctcatcg 51480
tttgtgtagc ttaaaggaat cagataatta ccccctcccc actactttcg gaagcacaaa 51540
tgcaatgccc tagaattgta ctggggactc aaaaagaaaa gagagtagta aaatctatta 51600
aaggggacaa agacagccta tatactacaa gctttctatt tttatggcag agaatgccat 51660
tttctaagta aacagagaac tgcatttgac ctgcaatatc aaatgcatgg atttgatgct 51720
ttggaaagca actgttttct gcgttaatct gggtgtcttc cgtgaaatgt cctcctgcct 51780
ttggcttaaa cactagcttt gtctacagcc attccatcct gaacctgccc aatcttgtct 51840
gaatcctggt ttcaccactg acaagctgtg tgtccttggg caagttactt cacctgtctg 51900
tgcttcagag tcctcatctg tgagttgggg aatctggaca gaatctaccc catagggcgt 51960
agtgaggatg tgttgaatta tcccaagtgg ctacacagag taagcactca aatgatgtca 52020
tcgttgtcat gattgctgtt accagagcct agagttcatt ctgatactcg agtctgtggc 52080
ccatccagcc caggtaagga atagttggag gagttgggca tgttcagctt gaagaggaga 52140
cgacagggga tatgggatag ttgaatctgt gaagggcccc ctgggatgaa gaactggcat 52200
gttctgtgtg gctccagggc actgagcagg acccatttgc caaagtctca gggacacagt 52260
ttctagctat agacagaaaa attttctgtc actcagagga tgaaaataga atgagccccc 52320
ttaagaggta atgagctccc tgtcattgga aggattccag aagagctagg taaccacttt 52380
aggtgctatc aaggggcttt tttctttaaa gtcctttcca aaagcttctg agattgcata 52440
aacaatagga agccatcttg gtgctttaac acaaactctc cccagtgatg agggttgagc 52500
caaagccaga ttggcaagca gagaggagac ttgtgtacaa ggagttcctc gagtcaattg 52560
ctttttcctt gttctagcca gccagagggc tcctgttgga aaacaggaga ccggagaggc 52620
tgaggcctga ccaaaccagc ttctgcaggc cagctgggag gccacaactc ctacctacgg 52680
gaaaactgaa gggcatctct atttttagat tagcaaaaga aaataaattt aagtttgagt 52740
ctcctttgca acttttaaaa gacatcttta ttgagatgat cattcacatt ctataaaatt 52800
cccccacttt gagttacaat tcagtggttt tagtcttcct tgatgatttt gatggtcttt 52860
tcttaaggct cttggaagac ccagaagcct ctcagacaca ggtgggtgtg gagggcgtag 52920
cacagaggca gacttctcat ttcctgggtc tcccctttaa tgactctcag agacccctcc 52980
ttccccctgc ccctggcttc taccccaggg gtgtagagtt ttgccatttt ccaagcagaa 53040
cttcatttcc tcttctgtgt ctacactctt tgtgcttctt tcttgccagc tttttctcct 53100
ttgcccgccc ttccttcctt ccttccctcc ctcccccctt ccctccttcc ctctttccct 53160
ccttcccccc ttccaccctt ccccccttcc ccccttccct ccttccttcc ttccttcctg 53220
cctgccttcc ttccttcctt ccttccttcc ttccttcctt ccttccttcc ttcctggtat 53280
gtgactaatt tctgtttcag gacataaatg ttgtccaggc tgttctttgg tctttctgtt 53340
ggataatgga catttggcat tgagagaggc tgctttttct gaaatcatgt tcttggggcc 53400
cagaacctag gtgtgtgctt ctgactttgt tttcttcctg atccaaattc tgatatgtcc 53460
atttaaattg atctagaccc acagggcact gtgggacaga tcctcagtgg aacatgactc 53520
tgtaacgaga gcattttgtt ttgtcaaaat gagaacatat tattgccttt catctgattg 53580
taaacataat acatgtttat aaaacagtat aatgagacaa aaatgtagac actaataagg 53640
gaaaatctcc ctaattgtat ttctcttcac agagaaagcc cctgttgggc atatatactc 53700
tagtttgttt atttgtttga ctacacatat atgtattctt ttcttatgta taaaaattct 53760
gaacatgcac atttctgcaa ctactgtttt cacttgatga tgcatggacc tctctagagt 53820
gtacgtttct tcttccttac aaagcagttg gcttcgccca gggtgcacca ggacacggtt 53880
ttggctctgt ccccagggtg tcacgggacc aggggatgat ctcacagggt ctgccatctg 53940
ccctgcctgg ccggaggctg catcgagagg gccaaggggc accacgtgtc gtgggtactg 54000
tcaaacaaga gccttcagag ccttccacag tctttctttt gcttcccagc attgcttccc 54060
cgctggtgga ctctgaatct agaactagct ccaggcgcct ctccaaattc agacgggagc 54120
tggggcacta ttataatgca aatctaggca aagccctccc aataccagga tccagaatgg 54180
ggtggggccc tttgccctga aaagctgttt agtttgaaaa tacaaacagg agacagaaaa 54240
gtttggctaa attaatggat aaagttttaa cgatggtaac catagtaggg ttcatcgaca 54300
gccagcgatg gttctgaaca cttgacatgt attaactcac ctaatcccca cattttacag 54360
acaatgcaaa ggaggctctg ggaggttgag tgacttgccc caaagtcgca cagctcctaa 54420
gtgaaggatt cggagtggac tccaggcagc ctggtctgac tccctgcact gcgctgtgct 54480
tatctctggc cccaatgccg ccatgcagaa gtgtctgggg gcactttgtc tctgtcagac 54540
agaattcgga gatgtgtatg cttgccctgg tatggcactt ctcttttttt gagacagaat 54600
ctcactctgt caccctggct ggagtgcagt ggcatgatct cagctcactg caacctccgc 54660
ctcccaggtt caagcaattc ttgtgcctca gcctcccaag tagctgggat tatagatgtg 54720
caccatcgtg cctagctaaa tttttgtact tttagtaaag atgttgtttt gctgtgttgg 54780
ccaagctgat ctcgaacttt tggcctcaag tgatctgcct acctcagcct cccaaagtgc 54840
tgggattaca ggcatgagcc accatgcctg gcagtgtggc acttcttacg tgtgttcagc 54900
ggacactgtt tatcttctgt ccctccaaga cggtgctgag ctcaggtcgt tcattactgg 54960
cagacaactg ctgatttcca acagaattgc catcctcttc tcccctgcga ctttcagagt 55020
gtgacctcag actcaaaaat tagaagtgaa aacatcttaa aaactatcac cttttcttcc 55080
taatcctcct ctcccctccc tgtcttcctt gttgtcccca tctaatgaac tatcatggca 55140
aaaagagccc atttctggtc attttctgtg gcctttcaaa ctcccaccta ccccactgct 55200
cctgggtgca ttacccgaaa gctgagactt cagtgcagaa agtgccaggc cctctgtccc 55260
cccagatcgc cttccttgtc ttccctgtgc ttgcctgtca cattgtgtgg gttccagcgc 55320
tggaaggaat gaggaacaga ttctctggtt ctccttttga agtttacctt cgctccacca 55380
cttctgagac cttcccggaa gttgcccctt gtttctctcc tctccagggc tgccccagag 55440
ctgcctctca cctcttcctg ctgtcacccc accaccatca gggcagaagt tgggacaaag 55500
cctctcctac tggctcctgc ttttctccct taggtccagc ctcctcttct ccatcttcag 55560
gagtctcctt ctccactcac acgtcatgac ttcagcacct cgcatcagtc cagaatatga 55620
ctgcttgttc aagtgccacc tttctcatgc attttttttct agtgacaatc acagccaccc 55680
tgtggggcag gagtgtcatc atccccatgt ttcaaatgaa gaattgcagt tcagagaggg 55740
caagtgactg gcccagcctc aacagctagc cagtggaccc caccagggct tctgactcca 55800
gtccgggttc cctttccacc caaatccatg gagggagctg agccgagaac aggtgtcctt 55860
caggaagacg tgaagccaaa gcctccacct ccaaactcag gggcccaggg agtccaggca 55920
cccatccact cacaaggctg gatatggtgc attccaggag aggggttggg ggcgagtggc 55980
ctctctgtgt acccgtgggg atagatgcgc aagtggcatc gccacatcgt gagtcctggc 56040
ttcatgggtg agctccaggt ccaacgagaa gccaagcagg gggcccttca agctcagctt 56100
tgggcccggg tcggggtaca gggtagagcg ggcctcccca gcccctgcca tgaggccaag 56160
gcagtgcatc gttcgcagcg tacattcaga aaccaaagcc taggagctgg ttatcattcc 56220
ggtttacagc tgatggaaga gcaggtgctt ccgagaaccc acagtgctct ttggccagtg 56280
acccaagggt gcctctgaga ggcctcgcag cacccggagg tgctgctgag gcaacgccct 56340
gactgtaaga aggaccattc atcctcagag agtggccgtg atgctgctgc gacagtccca 56400
ccatccctcc cgactctcac tcccaacaga cttcccactg taaagctgaa ctctccagca 56460
aatcacctct cgccagactc tctcctcact ctctctgggt ccactagagg ttcctcagcc 56520
tctctttgcc ttggttttcc cagctgtaaa atggagcaaa gagggcctat gtacccacaa 56580
aggtgtggtt ggagcgactc ctcctacatt agggcctcga gtggggcttc atgattggtt 56640
ggtggaggtc tccaaaccca cccagtgcca ccgaaggctg agactgcaga tgcaatgcca 56700
caggtgtcct tcctcagcct gggcagctga acatcatgtg taaaacgggg ataataagat 56760
aataacagcc ccttgcacct atgtggctgt gaggattaaa caagataaat gtgtaacagt 56820
gcctggctat agaaatattt actcttgtta ttaagggaag aatatgtgtg gctaaaaagg 56880
gatcgaagat gtaaaagcca atccctcccc ctctagcata tttaagggta atgttgagtt 56940
ggtttgtgga ccatttgctg cctgttagag ctggaaggta gggacccccct ctcaacagcg 57000
atgctacaaa ttatacccat tggaggtcaa ccaaaagaca aagcttattg gctggacatg 57060
gtggctcaca cctgtaatcc tagcactttg ggaggccaag gcaggcggat cacttgagat 57120
caggagttcg agaccagcct ggccaacatg gtgaaacccc atccctacta aaaatacaaa 57180

```
aattagctgg gcgtggtggt gcacacctgt aatcccagct actcaggagg ctgaggcagg  57240
agaatcacta gaacccagga ggtgaaggtt gcagtgagcc gagatcgcac cactgtactc  57300
aaaccgaggc aacagaggga gacgcaatct caaaaaaaaa gaaaaaaaga caaagcttgt  57360
taataccagc atattgttaa gggaataaag taggctgcag aacaactggt gtaatatggt  57420
gccatgtagg gaaaattaca tgtgtgcata ggagaggggt ctgcaaggtt gtgccctaag  57480
atgttagagt ggttcctttg cttttctctt ttataatttt gtatttgact tttaaataag  57540
gaccataaat cacttttata aaatacattc tctccagccc ctactactcc tttaaagaat  57600
aagagtggtt tgcccaagaa agacagtttt ttttgctctg gttttcttga ttctgacatc  57660
agaggaaact gcttctcatc cacttggggc tctgggttca ggggattcat ttcaggcaga  57720
ttaaagtggt gaccaggggc attcgtggac acagggaggg acaggagcac catcagtttg  57780
tctcacacaa ccactgtcat cctcactgaa ggctgttgcc tgatcaaaaa cagtattggg  57840
ccaggcacgg tggctcacac ctgtaatacc accactttgg gaggctgagg tgagtggatc  57900
acttgaggtc aggagttcga gatcaacctg gccaacatgg tgaaaccttg tctctactaa  57960
aagttcaaaa attagccagg cgtggtgggt gcctgtagtc ccagctactt gggaggctga  58020
ggcaggagaa ttgcttgaac ccgagaggta gaggttgcag tgagccgaga tggcaccacc  58080
acactccagc ctgggcgacc gagggggact ctgtcttaaa aaaaaaaaaa aaaaatatat  58140
atatatatat atatatatgt caaaaatggg gtagttttta gatctatagt agttctaaaa  58200
acaaaggcca tccaagcatg acagatttac aagcactatt ggctattcca gtagttacaa  58260
tggaggagag aagcttttag ttaaaacaaa caaacaacac aacaaaccca gaaaccttag  58320
gtcaaaacca aaattgtcct ctcagacaca atctgggaat tttctcatga cagtgggcat  58380
tagccaactg acatcagcag caaccatccg tgtgcacaca gtggcaccac ctcctcccaa  58440
aaagcagcct tcatctatgc cctcatacaa tcgttgatta ttctctttgg attgaggccc  58500
ggaattattt aagtttcttc ttgccagcat gagtctttcc tttctgtatg ctccttatct  58560
tctctcttta atttggcagt tctgcttgaa atctgggtct ttcattagta gtagttcaat  58620
ttggttccag aacattctgt ggtgtgatgc aatgtgacca gagctcacac ttcagagctc  58680
ttcaagggcc agtcttactg agcacctccc agtggctgcc tgtgtgctgg gcgccacttg  58740
tggtgggcag gagagaggag gggacacaaa aggagacaca gctccttctt agaagctcaa  58800
agttggggac cagctgccac agaagagtat gtttagcatc tgagacacca agatccagcg  58860
tcacaagggt gtttattaag cctcctcatc tctttctttt tcttttttttt tttttttttc  58920
ctcaggcagt cttactctgt cacccaggct ggagtgcagt ggcatgatct cggctcactg  58980
catgcaacca ccacctcccg ggtttaagca attctcctgc ctcagcctcc ccagtagctg  59040
ggattacagg tgcccaccac cacacccagc taatttttgt gtttttagta gagacagggt  59100
ttcaccatgt tggtcaggct ggtctcgaac tcctgacctc agatgattca cccacctcgg  59160
cctcccagtg tgctgggatt acaggtgtga gccaccgcgc ctggccttgc tgttgattca  59220
tctatagtat gtttgacttg atgacctcca gttaccttag acagaggttc tcatctaagc  59280
tccaactttc catttccttt gtcctcgtct ttccccttaa cccctccaca tttctctcaa  59340
aatcacccca cttctaaaaa atactgttta tttttctttt aaatttcaaa ttatctatac  59400
tcattgaaat aaatcaaaat agcatggaat aagcgaaaaa aatggatccc acccttcccc  59460
actcccattc cctagggcta accatagtta accatttaat gactaggttt ttttgttgtt  59520
gttatttttt atttatttat tttgagacag agtcttactc tgtcacccag gctggagtgc  59580
```

agtggtgtga tctcggctca ctgcaacctc tgcctcccag gttcaagcat tctcctgcct 59640
ctgcctcctg agtagctggg attacaggtg cctgccacca cacctggcta atttttgtac 59700
ttttggtaga gacagggttt ctcaatgtta gccaggctgg tctcgaactc ctggcctcaa 59760
gtgatctgcc caccttggcc ttccaaaata ctgggattaa ggtatgagcc accgcaccca 59820
gccctcctgg gctcttttcc tttagttgca ctcgctcccc gctcctggag tagagggatt 59880
tccgagagac tgtgggctcc agccttcacc taggcccagg actaggatgc ctgccctaac 59940
atttatcttt ataccttaaa gcaaaacagc tggaccataa gcattcaaga acaaactgtg 60000
aataaggaga aagttctccc aggaaacaag agctttagtt ctgttgggcc agcccttata 60060
ttccttagct gttaccagtc actgcttgat ttaatctcgg ctatcacttg gcctgacagg 60120
tctgctgctg gtgccaggat gtctgggttt tgaagcctgg ctccattaca tacttcctgt 60180
gtgaccttgg gcaacttact caacctgtct gttcctcagt ttccccagct gtattatgtc 60240
agcataatag tttgttgtgt gaattaaatg aggtaataac tggaaatgct tcaaacatgg 60300
ttcctatcat gagaaatcct gctttccgcc taaatgtgct ggaaaattcc tggtggtgca 60360
gaacaggaga ccagagcaaa ggaaagacag ggtgcagaag ccaaaaatta ccttggagaa 60420
caaagcgcat gttaaggtta tttttggatt ctaggtttat ctctgcttgg tcttcagtta 60480
cctgcaagag atccatttag gggatttttg tttgttttta acgatagctt tattgagata 60540
taattcatat gccataaaag tcactctttt aaaatgtttc cggtatattc acaaggctgt 60600
gcagccttcc ctgtccttga ttccagtctg agtttttaac tgaagggata aggaggacca 60660
cgctttcccc agaccagaac cgcgggccag ggggcgattc tgctgagtca ccgcgggcgc 60720
ctggtgcgcg gcggcggagc ccgggacctt ccttggctgc cccctagcga gggccgcagc 60780
gcagcctgag acacccgccg gggccgctcc acggccgtcg gatttagact ggaagctcgg 60840
tccaggtccc cagcttgatg cgcccgcggt gtaggagacc agcccgactc gggcttcccc 60900
tgagcccctg gactcttgac tccagcaggg cctgggtaat gaacgtcagc tccccttccc 60960
caaaggggtt gctctgttgg gaaggcaccc gtttgataca gtagcataga gatgggtttt 61020
agcatcaaaa tatcagaatt caagccttgc tctctgctta ctagctgtgt gaccctaaaa 61080
aggtttctga acgtctctga gcttcagttt cctcatcatt ccttctcacg gggtggttgt 61140
gagcattaca gagatcctct ctgtgaagcc cctgtgagtg gctcatcctg agggctgaaa 61200
taaacatgtt attaataatc caaaactggc aagggatgtt gactggtccc cctcccttgc 61260
ccaaggagct ttctagaacc tgagttatca ttaccaaact gtactgcctt gagtaagaaa 61320
gttagaagga atgggaagga tggtggcagg tggaggaagg cggattggtc atcacctcct 61380
tgcagcaaga aacagcccca gatcgtggga aacctacaga cctgctagac agactaggag 61440
caaaagctgg ggctttaaga atccccaggg aggttctcct gagagagtag ccagttggat 61500
tttgtaagca gagatttgtt tggggaggag gtgacaacgt agggagcaga ggggcaaagc 61560
tgtcgggaat cctgccttga gggcagggat gtgtgttggg gggagttggg tcactggggc 61620
tcggtggcct tgggcaagtt tctacctctc aggtccttta cccacctagg gtcgccatcc 61680
tgcccacctc acaggttaca gtgagcctgg atgcactgtc atgggcaggt gcccaggaaa 61740
atggcagaca tgttccaaac agcacgcagc attccccagt gatgcccagg gtcaccttgg 61800
aggtgggcga gatgcctggg gtttctcgtc caccccacaa cacctcaggg gacagccaaa 61860
gctgtccctt caggtaagct gcacagaaga tgtgaactct gctgcaaaga ctctattctt 61920

```
tgggagcaaa agggacccag ggtctcacct gcacatccct gtccctgagg gcctaggggt  61980
tcttggaggc cccagccttg gcaaaatgag gaagaaggtg aaggttgtct gggcccctgc  62040
caggctcctt cctcggccac gcactcccct tcctgcacac acacccttct ccctccaccc  62100
catctccatt gttgtcagaa aagtcacaat aaaaaggtcc atattgtcta gttcccatac  62160
ttttaatttt taaaatttta tttatttatt tatttatgta ttttttgaga cagagtctta  62220
acccaggctg gagttcagtg gcatgatcta ggctcactgc aacctctccc tcctgggttc  62280
aagtgattct catgcctcag cctcccgagt agctgagatt acagatatgt gccactatgc  62340
ccagctaatt tttgtatttt tagtagagac ggggtttcac catgttggcc aggctggtct  62400
cgaactcctg gcctcaagtg atctgcctgc ctgagcctcc ggaagtgctg ggatttcagg  62460
tgtgagccac cgcactcggc tccacacttt tcacttatta aaagactgtg gtgtccatca  62520
atggatgaat gaataaacca atgtggacta tccctcccat tacccaagga atgaagcacg  62580
gagccgtgcc aagatctgga ttcacagtga aagaagccag tcaccaaaag ccacgtgctg  62640
tgtgacttcc cttatacgaa atatccagaa gagatacatc catggtgaca gaaagtagat  62700
gagcagctgg ggactggcga aggggagaag ggggagcagc tgtctatgag gtccagcctt  62760
tcttctgggt ttggtgagaa tgttttggaa ctagatagag gtgatagttg tacaacattg  62820
tgaatgtact aaatgccact gaatcattca ttttaaatcg ttctttacgt tgcatgaatt  62880
ttaagtcaat caaaaacagt tgtttgaaaa gagaaaagcc tatgggtagc ggcagcagtg  62940
attggattta tgattcgatt ccatggctca tccctcccct gcctcacccc ctcgccctcc  63000
gacgtcttct tcttttactc tgaactgtta tctttgttct catctctctc tctctctctc  63060
aaccctgcag acacttttcc ctttctttgt ctgcccccac cctccagatt tccgtgtctc  63120
cagtgtctcc ctacgaggca tgaattgaga ctgggagggt gtgattctga agaaggcacc  63180
aacagtgact cagctagccc cttcccccac cccgcccccc gggcctcaat ttagctaaaa  63240
aaccacaggg acggactcag gaggcaatac ctttccaagg gtccctaaaa aatgtcccat  63300
tttagtgtcc aggtttcact caactttagt gcctccccta aaatgtgttc cttacctccc  63360
accccactgc atctaagtca ctgcctgaga aaacaggatt gaggaaagga gaaaggaaga  63420
gagagagaga ggaggagaga gagagagagg gaggaaggct gatggattta gaaaagaaga  63480
aaacaagtgg tctgaggaaa acagccttgg tgtgtttatt ttcctgtctg tgtatcgctt  63540
ctcggccttt tggctaagat caagtgtatt ttcctgtctg tgtgtctcgc ttagattaca  63600
gggatctgtg ggtgatgaca cgtctggtcc aggctgcgta gtcacctcaa gggcatgctt  63660
attgatgtgt ttttcaattc actatctttg catgggagtc ccaggccaag aggcacagct  63720
gcgccatttg tctgttggtt tagatatcct ttatccagtt cttccagaga aatcatcctg  63780
cccttctgga ggaggtgggc agcaggggtc agagatggga gggaaaggaa ggagccaggt  63840
ccttggctag gatgccaggg tcccctgcct ctcacctggc ctgggctgga ggcctcctgc  63900
tgtcctgtca ctgatcacta ccccgcccca gcctcctgag ttagaagaca caggctaaag  63960
tagagtattt cttcattgaa aaacccatac aaaataaagg ttcataaaaa ataaaaattt  64020
agactgggtg ctgtggctca cacctgtgat cccagcactt tgggaggcca aggcaggtgg  64080
atcgcttgag ccctggggtt catgaccagc ctgggcaaca tagtgaaacc ccatctctac  64140
aaaaaataca aaaaattagc caggcatggt ggtgcatacc tgtggtccca gcttctcagc  64200
ctatggaccc acatagaata caatgtcagc ataagaaggg agccctgggg tcaccaaatg  64260
gtttgggcgg caaagaacct gaaggttgag agaagtggct tggttaccca gctgttggat  64320
```

gtgagacctg gccactgctt cttccatacc ctagacctgc accctgacat ctcaagtaaa 64380
aagttggggg atgttttatg gtccaggatg aaggaagggc agtgaggggc agcggagcat 64440
cactttgcat ttctgtctgc ctcttactgg ctgtgtgacc tggggcaggt aacttcccag 64500
actcctggga atcataacac ctatgatgat gatgatgatg atgatgatga tgacacctac 64560
ctcaaggatt gccctgaagg gtcacagaga tgcctgcaag gcacctgcat ggagcaagcg 64620
ccccttctct ggcaggtgct gggtgagcac tacctgctgc caggccctgg ggctatggca 64680
ctgcgtgacc ctgcaagtcc tacctggcga agctgtcgtt cttgtgctca gtcagtgttg 64740
gttgtaagac tgagaagagt cacttcattt tgctctccag ggacatcttt ctgggtccta 64800
ttttctgcct atgtcaagta gcgcctcaag gatgctcctg aaaatgggct tgtctttctt 64860
aacatggcag gtaggtccca aagcattagc atggggcagc tgacctagcc cagccaatgc 64920
agtgcagtga ctcttgcaac cgagtctaat cagaaggtcc atgaacctac gagcatttcc 64980
tgtcccagga tcagggtgga ggctgagcct ccctgcttag agattcttcc catgcattcc 65040 actttttcc ccaaaagaaa atattgaccc ttgagaggca cacagtttat ttattttgca 65100
tagtaaatag tagcctgtat tttaaggatg agttgatttc tgcatcagcc cctgtaggtc 65160
atcagccttc tattggtgca tctgactctc tctagccctg cagggatggt ggagggggag 65220
gggaaggagg gatctttatt ggaaaccagg acagtgagac tcattgccct gtcatctgct 65280
ctgtggtgct gaatgaggca gcccaacaga gaaataccct gagcgagcat ccccagcctc 65340
caaaacagtg gcgcattgcc ctgagtcctg ggaatgacct ttgattctcc tgctcctgac 65400
ttggaaccca tggaaacctc tagaagcagc tgaggaaaac ccaacatgaa aagcagaact 65460
ccacactgag aatataggag gtgatcggaa catacaatga ttcttgctaa gaccgattca 65520
cagtttttct ttttttcga tcgaagaaat actggagaag cctaaagaag gagtctaaaa 65580
actctggcac gtgggccaaa actgtccttg agctaagaat gattttcaca tttttaagtg 65640
gttgaaaaat gaaataaaat aagatgatgt tttgtgacac atgaaagcta tgggaaattc 65700
aaattctaat atctataaat agtgttttat cagaacacag tcatgctcat ttatttatgc 65760
tcgatggctg ctttcccgct acaattacgt tgagcagtta caacagagac cacgtggccc 65820
acaaagcctt acaatattta ctatctggcc ctttccagaa aaaaatgtgc cgactcttga 65880
ccttaacctc agcaatttgg gaggccgagg caggcggatc gcttgagctc tggagttcat 65940
gaccagcctg ggcaacatag taagactcca tctctacaaa aaatacaaaa cattagccag 66000
gcatggtggt gcacacctgt ggtcctagcc actcgggaga ctgaggtggg aggatcgcct 66060
gagcccagga agtcgaggct gcagtgagct gtgatggcac cactgcacct cagcctgggc 66120
gacagagcaa gaccttgtct ccaaataaat aaataatgca aagtaaaata aataaaacca 66180
tataaaaagg aatcaattta aaattataat gaaagctggc cgggcatggt ggctcacgcc 66240
tgtaatccca gcactttggg aggctgaggt gggtggatca cgaggccagg agatcgagac 66300
catcttggct aacacggtga aaccccgtct ctactaaaaa tacaaaaaaa aaattagccg 66360
ggcacagtgg cgggcgcctg tagtcccagc tactcgggag gctgaggcag gagaatgtct 66420
tgaacccggg aggtggagct tgcagtgagc cgagatcgtg ccacttgcag tccagcctgg 66480
gcgaaagagc gagactccgt ctcaaaaaca aaaacaaaaa caaaaacaaa aaaaaattat 66540
aatgaaagcc aaggggcata gtagaacaaa ttttctagag ctcattaagt caaatgagtc 66600
accagttagt aaaacgcagt cacggggaag agagggcagg attctttgaa gcagcggctc 66660
tcctaaaaac aacccaccct tgtccagctg ccttccctcc tgagggtgtt ccctttgact 66720
gtgtgacccc catcccctat ttcccaaccg tccaagccca cctctagcat aatacgagct 66780
tttaatccct ctccctgacc ccaacccgat tttgaagccc agtctagtat tttctcaaat 66840
acacttcttg gctccattcc ttcctttcca tcacctctgc cttttcactg catgcttgga 66900
ccactgcagt cagctcccta tgaacagttg ctctctaccc atccaatcgg ccccgcctgc 66960
tgctgccaaa ttcaccgagg gcacctctgt ggtgctgcct gtggacaaag tccaagccag 67020
ccacctcacc cacctacagg tgagtgggga gcagccagcg tgtccagtgg tttaccccat 67080
cgccacagac ttggtgatgt gtcgatgtgc agagaagggg tgttggcagc cacaacacaa 67140
gcaaccccgc cccatgtgag atctaagatg ggcgtgctgg gagccacctc tgagaatcca 67200
acagaaggca gaggggagaa cggctcacac ggcacaaaca ctccttcctt tttttttttt 67260
ctttttcctt tttgaaagga gtctcactct attgcccagg caggagtgca gtggtgcaat 67320
ctcagctcac tgcaacctcc gcctcctagg ttcaagcgat tctccagcct cagcttccca 67380
agtagctggg attacaggta cactccacca tgcccggcta atttttgtgt ttttagtaga 67440
gacggggttt ccctatgttg gccaggctgg tcttgagctc ctgacctcag gtgatctgcc 67500
tgccttggcc tcccaaagtg ctgggattac aggtgtgagc catggggcct agcctccttc 67560
catttaaatg tatgcctaat ttgcccattg agaacggctg agacgcattt taagtggcca 67620
gggtctactt agagttagtg ctcatgacca ggcccaggtc aagcctggct ggccagatgg 67680
tgcctttgac ctgctctgtc tctgtgcaaa ggaatgagct gaaggatggg ggtgcagtgt 67740
gtgggcagtg ggctggggct ggcaggactc agtgactaag ggaagagaac tttcctcact 67800
accagcctgt cttttcaggg caccgcgggg ggctttggga cttggtgatg aacacagcac 67860
agagagctgt ccagcatgcg ggtccctggc ttctcacact tcccaggctc cttcagaggc 67920
tctctccaaa gggagctgct ctctctagaa cccatgaatt tggaatatag gcaaccactg 67980
cattggggac cactgacctc aaacatagag accagagcaa atggggctca tcacgtgaaa 68040
ctcatctgga actctagcag gttcttttat atatatatat atatatatat atatatatat 68100
atatatatat atatatatat tttttattat tatactttaa gttctagggt acatgtgcac 68160
aacatgcagg tttgttacat atgtatacat gtgccatgtt ggtgtgctgc acccattaat 68220
tcatcattta cattaggtat atctcctaat gctatccctc cccactcccc ccaccccaca 68280
acaggcccca gtgtgtgatg ttccccttcc tgtgtccaag tgttctcatt gttcaattcc 68340
cacctacgag tgagaacatg ctgtgtttgg ttttttgtc cttgcgatag tttgctgaga 68400
atgatggttt ccagcttcat ccatgtccct acaaaggaca tgaactcatc attttttatg 68460
gctgcatagt attccatggt gtatatgtgc cacattttct taatccagtc tatcattgtt 68520
ggacatttgg gttggttcca agtctttgct attgtgaata gtgccgcaat aaacatacgt 68580
gtgcatgtgt ctttataaca gcatgattta tattcctttg gttatatacc cagtaatgag 68640
atggctgggt caaatggtat ttctagttct agatccctga ggaatcgcca cactgtcttc 68700
cacaatggtt gaactagttt acagtcctac caacagtgta aaagtgttcc tatttctcca 68760
catcctctcc agcagctgtt gtttcctgac tttttaatga tcgccattct aactggtgtg 68820
agatgttatc tcatggtggt tttgatttgc atttctctga tggccagtga tgatgagcat 68880
tttttcacgt gtctgttggc gaactctagc agcttctttt cacaagttca tggagagagg 68940
tttcccactg agggaatcac atctgtctga tcaaaagagg cttgggaaat ggctctcctg 69000
ttcattccct gaaaacctct gatggaacca ctgccactgt ggcagcccca gcactggcac 69060
cccagccatg attggtgccc cagccacatc tctgctgtga gccccagagc cctggttaat 69120
taatcatcca cgtgttgatg gggagaggcc cattcacaaa agcgacataa agcccaggga 69180
gacgtggccg tggcaagaag ggtgtgggac tacattccgc ccccaactga gagattcaga 69240
aaccagaaaa aaatggaaaa acatactgtg ctcttgggtg ggaaaactaa atatcatgaa 69300
gggagcaatt tttatagttt tggcctataa tacaattcca gccgaaatcc cagtggaact 69360
ttgagaattt gcaggaaaaa aaaaaatgtc taaagtacat ctggaagaca aacttacaag 69420
aaggtcaaat aattttgaaa aagaaaatga tatctaagcc cacctagaga ataagacttg 69480
agatccaaag ctaaatcagg aggctctagc aaaattgaca gataagcagg acagagtgca 69540
tggtgcattc acctggggaa gagggcagat tggtctacaa ataggcctgg gtccactgac 69600
tttagctgtt atatttgggg agaaactttt caacctcact ccatcttaaa cctaaaaata 69660
ttccagatga attaataaat ataaaaaatt agaccactaa aaatgtagaa gaaaatggat 69720
gatctttcta taccatagag caatggaata aatcacaaag gaaaacagat ttgactatat 69780
aaaacttaaa ccctgcccat caaaaaccat cagaaaccaa aataaaaggc aaccaactgg 69840
agaagatagt tgccacaaat atgatcaagg gttaatgtta ttcataaatt aagagcccac 69900
acaagtcatt agaataagca ctgagacctg aacagacaag caaaaagaat gagagtgggt 69960
cggcgcggcg gctcatgcct gtaatcccag cactttggaa ggctgaagca ggcggatcac 70020
ttgatcccag gagttccaac accagcctga gcaacatggt gaaaccctgc ctctacaaaa 70080
gtcataaata ttagccgggt gtgatggcac acgcctgtag tcccagctac tcaggaggct 70140
gaggtgggtg gatcacttga gcccgggagg tagagtctgc agtgagccaa gatcacaccg 70200
ctgcactcca gctggagcaa cagagtgaga ccctgactta aaagaaaaaa aaaaaaaaag 70260
aggagaaaaa tgctgatctc actagtaatt aaaacatcag gccaggcgca gtggctcaca 70320
cctttaatcc cagcactctg ggaggctgag gcaggcagat cacttgagat caggagttct 70380
agaccagctt ggccaacatg gtgaaatccc gtctctacaa aaaatacaaa aattcgccaa 70440
gcgtggtggc acatgcctgt gatcccagct actcgggagg ctgagacagg agaattgctt 70500
gaacacggga ggcagaggtt gcagtaagct gagatcgtac cattccagtc cagcctgggc 70560
tacagagcga gactctgtcc cagaaaaaat taaaacatca catatttaaa caactctagg 70620
atatcattta aaaaaacatt aatagactgt tttttagagc acttttaggt tcacagtgaa 70680
actgagtgga aggtacagag acttcccgta tgttccctgc cctccacgta cagcctcccc 70740
cactgccaac gtcctgcacc agagtggtac acttgttaca accaatgaat cctcattaac 70800
atatcattat cacccaagtt catagtttac attagtaaaa catcatcttt catctataag 70860
cacaaaaatt ttttggcatt tatttaggtg tatgattaac tcagtgttga caagactcac 70920
acttcatacc cacttgcact gcatctgaga agcaattggt gtctacagcc gctacaccct 70980
caacaagccc gatcttgttt gaaaagcaat tggtgatgct tctcaaaatt ctatggacaa 71040
agtcagccgg gcatggtggc tcatgcctgt aatccctaaa ctttgggagg ccgaggcagg 71100
cagatcacct gaggtctggt gaaaccctgt ctctactaaa aatgcaaaaa ttacccaggc 71160
atggtggctg gggcctgtaa tcccagctac tcgggaggct gaggcaggag aatcgcttga 71220
agcaaggagg cggaggtttc agtgagccaa gattgcacca ctgcactcca gcctgggtga 71280
caagagtgaa actccatcta aaaaaaaaaa attatggaca aagtttttca aaaagatatt 71340
taatgcaact ttatttgtaa tattggaaca tctgaggcca tttcagtgct aactattagg 71400
ggatggttag gaaaatatgg tacatatgtg gaaaggaaca tttggtagtt agtgcccctg 71460
atgtttacaa aggcttttag tgaccaacaa atgctcatgc tataatctta tgtgaaaaaa 71520
gcaagtagca taattgcaac tatattttta atgcatagaa taaaaggcta gaaggaaata 71580
tcacagatcc ttgacataca ttcccaaacc tttgtaaatc cgcggattca tgaaaacaga 71640
cacatttgca caagtgcctg atcttttctg ttatacattc attagaagtc aagccctggt 71700
gccacaaagt atctgccttt tcaaatgtga tcagaatgtt ctcttttgct tcaaggccat 71760
ttttcacgaa gcagtggcat ttttgcctct tcatcagagt caccgtgtgc cctggaggac 71820
tgagaacagc agagccgttt taggatggga cagggcagcc aggaggattg ggctcactcc 71880
ctactgagtg cctcactccc gtacagcccc catagaggaa gaggggttca aatttattcc 71940
tcagccagat ggcatgtgcc gcctgtcctg gaatttcaca tcacttatga tggaccaaaa 72000
ttccaaaagc tgaatccatg attgtcaaag tctggtatgg caggatgtca acagtaatcg 72060
tttctgggca gagggatgat ttctcttcc catcttgctt tgtataaata cattttctat 72120
aataaggttg tattactttt ctcatcaaga aatagcaaag tactgtttta ctcaaaatat 72180
gaatagagcc aggcatggtg gcagcttatg cctgtaatcc caacactttg agaggcggat 72240
atgggaggat cactttagcc caggagtttg agaccagcct gggcaacata gtgagacccc 72300
cgtccccact cccccaaaga aaacccacaa agcatttatc ctggattatt cacaggggcc 72360
aaaaaaaaaa aaaaaaattc aggcctccta tagccatgag ctacgaatat gaaaatatgc 72420
aaatgtgtaa gaaaagccag cacatccgat ttttactttt actttcacac ctctgtccac 72480
catgttccaa gagaagaaac ttggtcattg aaaggaatag atcaaatcca aagaacaaaa 72540
ccactgtgct cattaaactt cttagtgttc acaaagcttt agctgcaggt tgaatggggc 72600
aacccgaatt ggctggctca cctgggctgc agggagcaga gatcgcgaca ctgcactcca 72660
gcctgggcaa caaagcgaga ctctatctca aaaaaaaaaa agttcataaa ttcaaagtta 72720
tgaattattt ttaaaataat aataatttac aataaagatg aggacaaagt gtgagtaaat 72780
ggtggtttct atccagctct gttgagctga agtggcatct ccctgctggg gcttttgggg 72840
aagaagggtg tgtgttgctc ttcagatccc aagcctcatg cccctactgg gccctgtggg 72900
gtgcttctca gcccaccagg agagccaccg ttggaacaca cacgtggggg acctggtggg 72960
tgccggtgtg gtgaatgggg gccacagcct gactccagga agccagcaaa ctcggagctg 73020
gaggagtcag gacacccccg atgagtcaag agttggtttt gctgccagtt gacatctgat 73080
tgaaccatct cttcacttct ccgtgcctca ctttccttac cagacaggct ctgctgatgc 73140
tgtccctctc ctgttcagtc gtgccctcac cgttaaagag aaagagcaaa ctgctgggca 73200
gcagcattga ttttttaat gaagtggaaa gagagctggg aataacaagt cgggcccacc 73260
tcacctgcct cacctggtgg gtttatttgt tttgtttttt ttttttgtt ttgagacaga 73320
gtttcaccct gtcacccagg ctggagtgca gtggtgtaat ctcagctcac tgcaacctcc 73380
acctgccagg ttcaattgat tctcctgcct cagcctcccc agtagctggg attacaggca 73440
cctgccacat gcctggctaa ttattgtatt tttagtagag atggggtttt accatgttgg 73500
ccaggctggt ctcgatcccc tgacctcagg tgatccaccc acctcggcct cccaaagtgc 73560
tgagatcaca ggcgtgagcc accatgcctg gccgtcacct ggtggtgttg aatatgaact 73620
gctgcggtgt tggtaaatta agcaagcaga tagatgtaaa taacgcttgg gcaggaatat 73680
ggagcacggg atgaggatgg gcggccaact gttagagagg gtagcaggga ggctgagatc 73740
tgcctgccat gaactgggag gagaggctcc tctctctctt cacccccact ctgcccccca 73800
acactcctca gaacttatcc tctcctcttc tttccccagg tgaactttga accaggatgg 73860
ctgagccccg ccaggagttc gaagtgatgg aagatcacgc tgggacgtac gggttggggg 73920
acaggaaaga tcaggggggc tacaccatgc accaagacca agagggtgac acggacgctg 73980
gcctgaaagg ttagtggaca gccatgcaca gcaggcccag atcactgcaa gccaaggggt 74040
ggcgggaaca gtttgcatcc agaattgcaa agaaatttta aatacattat tgtcttagac 74100
tgtcagtaaa gtaaagcctc attaatttga gtgggccaag ataactcaag cagtgagata 74160
atggccagac acggtggctc acgcctgtaa tcccagcact ttggaaggcc caggcaggag 74220
gatcccttga ggccaggaat ttgagaccgg cctgggcaac atagcaagac cccgtctcta 74280
aaataattta aaaattagcc aggtgttgtg gtgcatgtct atagtcctag ctactcagga 74340
tgctgaggca gaaggatcac ttgagcccag gagttcaagg ttgcagtaag ctgtgattat 74400
aaaactgcac tccagcctga gcaacagagc aagaccctgt caaaaaaaaa agaaaagaaa 74460
aaagaaagaa agaaatttac cttgagttac ccacatgagt gaatgtaggg acagagattt 74520
tagggcctta acaatctctc aaatacaggg tactttttga ggcattagcc acacctgtta 74580
gcttataaat cagtggtatt gattagcatg taaaatatgt gactttaaac attgcttttt 74640
atctcttact tagatcaggc ctgagtggcc tctctttagc aagagttggt tagccctggg 74700
attcttactg tagccacatt aataaacaac atcgacttct aaacattcta taataccatc 74760
ttttggccaa attgacttcg cctcttcctc tctctttcca aatgaaatgt gtttcatttc 74820
actgtcagac cacatggttg gggaccccac agagcacaca gccctccctc tgccttccca 74880
tgctggccct tcacccactg ctggagtgcc aggttggtcc aagggttgga ccaagttgtc 74940
tgaggttgtc tcaaggttgg tcgaggctgt ctccgcgctg ggttgtgcta caaggagccc 75000
ttctttccat gggtgtggct ggcagtgagt gctcacagca acagcccaca gtgcagcccg 75060
agggcaggat ggactcagtc cctgcctcca tacccatttc taaggaggca aaatggcaaa 75120
cactctactt ttctctttta atgctaaaaa taagaaaaca ccttgcagcc cagggtatgg 75180
gtagtgcatg gaagccgtgg agttgtgagg tgggaagtga cctctgctgg atatgtctat 75240
tcaggaagat tgctggagtg ggtggggtct ctgggaggtc ccctgagtgt gggaagctgg 75300
gaccaccagc tttctcgcac agggagtggc catcccagct tggagaggtt ccaggactgg 75360
ttgggaggca cgtttcagat ttctatctgt tgaatcagcg aagatattgg attatgagga 75420
atttgggaat taggaaagtg ggtgcaggtg ggttgggggt aggtgaagga agacatgggc 75480
gtattggggg agcaggggct gctcagaggt gttccagaag ctctgggtga ggaggtgaga 75540
gggaccgggg aatgcagctc ggcccagcct ccctgcctga ggtcagccat cacgtggtga 75600
tggcaagatg gaaatgtgct ttctgactgc tccagccagt gctgccagat tcagctcccc 75660
agggagggca cctgagaggc tccaagccag gagatctgtt ttctcctttg ttttgttttt 75720
ttttgttttg ttttgtttta ttatacttta agttctaggg tacatgtgca caacgtgcag 75780
gtttgttaca tatgtataca tgtgccatgt tggtgtgctg cacccatcaa cttgtcattt 75840
acattaggta tatctcctaa tgctatccct ccccccctccc cccacccccct gttttctcct 75900
ttgaatcctt cttagaggcc gggcgcggtg gctcacgcct gtaatcccag cactttggga 75960
ggctgcggca ggaggattgc ttgagcccag gagttccaga ccagcctggg caacatagtg 76020
agacctcgtc tctacagata ataattttaa aaattatccg ggcatagtgg catgcaccta 76080
tagtcccagc tactcaagag gcagaggcag gaggatcact tgagcccagg aggcggaggt 76140
tgccgtgagc caagatccca ccactgcact ccagcctggg cgacagagac ccccatgtca 76200
aataataata ataataaata aatccttctc agtcccttcc tcactgtgtc cccctccact 76260
gaatttttcc acctcctctc ccacttcccc cactcccgct ttccctctcc ttctctcccc 76320
actccatctt tttctttctc tgctgtttct cgtccctccc tcctctccat cccacaacac 76380
tgcctaccct gtccctgccc caccctggtg ctcaggatgt gtgaagtgag gggtggtagc 76440
ccccaagacc tcaaccccga aggttagcct gttgaaacca ctttctccca gctgcccccc 76500
tggcagttgg tgctgctggg ggaaactggg attgggggcc agattttgcc tcttttcctg 76560
acaaagagag atgaagagtt ctctcaccag gtgcctggga ctggggtgtg ggtgtcccag 76620
cctatcccag cgcatctgtt ctgcatcatg attaatagtg ctgctttcag ccgggcgcgg 76680
tggctcacac ctgtaatccc agcactttgg gaggctaagg tgggcagatc acaaggtcag 76740
gagttcgaga ccagcctggc caacatggtg aaacctcgtc tctactaaaa atacaaaaat 76800
taaccaggtg tggtggtggg tgcctgtagt cccagctact tgggaggctg aggcaggaga 76860
atcacttgaa tctgggaagc agaggttgca gtgagccaag atcgtgccac tgcactccag 76920
cctgggtgac agagtgagac tccgtcctaa aaaaaaagga gttttgctct gtcgcccagg 76980
ctggagtgta gtggcgccat ctcggctcac cgcaacctgc gcctcccggg tgcaagcgat 77040
tctcctgcct cagcctccca agtagctagg attacaggcg cctaccacca cgcctggcca 77100
gttcttgtat ttttagaaga gacggggttt caccctgttg gccaggctcg tctgggactc 77160
ctgacctcag gtaatccgcc cacctcagcc tcccaaagtg ctgggattgc aggcatgagc 77220
caccgtgccc agtcaactcc ttctcaaaaa aaaaaaaata gtgctgcttt ctctttcaag 77280
tgtcctgatt tgggtgatag taaatgccac tctacttata agggatctac ctcagaatgc 77340
taattgggac atttttgtag cactctactg ttggcagcag gtgatgctca caacagcccg 77400
tgagggtgga tgacgtccgc ttcacagatg acaaaggagc ctcatgctca gaccgtgggc 77460
tgccagagca ggtccatggc tgcagcccca catggaccat atttcccccct tgtcactctt 77520
tccaccaagc tcccttggaa cttcagttat taagctctct tgggtggaat ccaagttaga 77580
atcacaacat gtgcctcata tggattgtgc cagtgaaaaa tgacattcta tttagaggca 77640
gggcagcctg gcttagagtc agtttaaaat atgtattatg ctgcaacaaa tgtaccatga 77700
tcctgtaaga tgttcacaac aagggaactg gatgtggggt atactgtctg tactaacttc 77760
acaagttttc tgtaaatcta aaactgttcc aaaataacaa gttcgtttaa aattaactcc 77820
aggagaccag gtacggtagc taatgcctat aatcccagca cttcggaagg ctgaggcagg 77880
tggattgctt gagcccagga gtttgagaca agcctgggca acatggtgaa atcctgtctc 77940
taaaaaaaat cacaaaaatt agccaggtgt ggtggcgcat tcctgtagtc ccagctactt 78000
gcggggctga ggtgggagaa tcatctgagc ccaggagttt gaggctgcag tgagctgtga 78060
ttgtaccact gcactccaac ctgggcaaca gagcaagacc ctgtctcaaa aaacaaaaat 78120
gaaataaagt ccaggaaaga agtaggtttt accactctta ttttctgaag agaaaactaa 78180
atttaatgtg taaagtgagg acaagttcac caagttagtg tttgagttgc ctaaaatatg 78240
tttgctaaaa ctattcaaag ctttcacata aaacatgatc agaagttcta tgccaaaaca 78300
tatgtgtgtg tatatatata tgcactatat atactgtata taaaaatgca aaatctaaat 78360
tgccaacctt ttagaaattg ctctgaaagg aaagcatttc aagataattt gcttacccaa 78420
agaatatact ttccaagaaa gcaagtaata cttaaggtgt tcataatcct catcaaatta 78480
attcttgcta ctgaaagctt acaaggagct gttttgatgt cgggtgtgac aggtttgact 78540
tggcagaagg tgtcacttta ctaacaacat tttaaataag tgacagaaga caagaaacta 78600
cacgttaaat gccagaacaa agagtgtcta agtggatgct aagagttgaa atatggctgg 78660
atacctgccc aagagagctg aaaagtagat gaaagttggt tacctataaa ctagtgcacc 78720
ctaatgaatt aaaaggtgtt gatgagttaa cttgttatgc cttccagata agacatgcaa 78780
atggggcttc ttcctccttc actacttcca agggatttaa caaggagacc aatgcaaatg 78840
ataaggactg tagggctcaa gctggggaca gattggggaa agggggacca tcatgcccat 78900
atagatgtcc ctgtgccctg gcagtcaagg ctgctgaaaa ataacaaaac ccagaagtct 78960
gcgtgatgct gcctctccat ttgtccaaag ccttcttgcg gcagtttgca ggcttttgca 79020
aaagctccag gaccaaggag ctatgttcat gctggaagct tgttcaggat tagctgttct 79080
ttgtgggatg ggtgcagcca gggccaggtg tccagggaca gtgttttaac aaagggcatg 79140
aggtgtctga tctcacagtg gaactccact tgcctttttt tcatcttctc attctgcttc 79200
atgcacagaa ccagccccat cctgaaactg actctaaatt actcccgccc caggtggagt 79260
gcctttctcg gagttcaaca gagccttcct gtcgcccaag ggacaactcc actgaatgcc 79320
caagccacac ccaaaaccta acaagtaaaa accaaattct gtgctccccc atcctgggcc 79380
attcctggtt tctctactgc tgttggtgat accaccatca gcttgtccat catgaccctg 79440
gccagttcct cccacaaccc tccacagcac ccagggacct cacctccatt ccatccgaca 79500
cagatctcct caccacaaac cttggttttg caacagcagc catgagacct ttacaccctc 79560
cgcccttcat cctgtccccc actgaggccc cagagccatt ccttaaagca gcgcgccaca 79620
aactataacc cacaagccaa ttctggtacc cagcctgttt tgcacagcca gtgaactgac 79680
aatgatcttt tcatacagcc agaaaaacaa aacaaaacaa aaaacaacaa aaaaaaaccc 79740
caccattctg agcatgtgac ttccatgttc aagatgtctc atgttcagaa aggcccctgg 79800
aaaaggagga aggggagctg ggcacaaagg gagaccctct cagctgagct cctcccatcc 79860
agacattttc ctggacttcc tatccaatga cttcccttag cttcttatca gccacccctg 79920
tctgcccagg aggctggaag atgtggcctt ttaactgggc acagctctgt cctctatcat 79980
atcagggctc tgttcccaag gagggtagag agaatggaca ccaggtggac cctcagcagt 80040
ctgtgccaca gagggagtgt ttgcaatttc cagactaaaa gtccccatgt gcttgacggg 80100
gtatgtgact acaacgtgat gcttgacttt tcctcatatg accagagcca ctttgtccat 80160
ctggtacaat gtcagctatc tgctaggggc cctccaggat tcccagtcaa ttccatatct 80220
gcatcaccac cattggcact aaataaaata aaatactcaa gttcctgctg gtgagcatga 80280
gcagtgctac actgggccct tcaaccaagg tgacatgata atgactgaaa ataatcactg 80340
ccacttattg ggacgtctc atctgccagg catggtacaa agtgctttaa ataagcattc 80400
aacaatttca tgctgacaga agccctgtga gccagtggag ctactactat gcccattata 80460
caggggagaa aactgaggca gagagaggtt aggtaattcg ctcagcctca cacaaccaat 80520
aggtggtgga gccaggattt gggccccatc tgcctgactc tctagaggct ctatcttcca 80580
gtcttccaga gttgagtcta agccatgaat aggacaatta gacagcagag gaaacccatt 80640
cagccaccat gtgcatgaag agtaaggaat ttctgtcata cagaggggag tgaattcact 80700
gagctgagag ctgaggaacc attgatctga tggctgagac accactggga agactggaga 80760
ggcttttctg ggcatgcagt gccaggcaca ggaggagctg agggaagatg actaagaggt 80820
actggcaaag aattcagaaa ttctgatgga agctttacat gttaccatca catccatcca 80880
tctatccacc catccatcca cccatatctt cctccctcca cccaatcatg catacatcca 80940
gtcatctata caccacccac ccacccatcc atccatccat ccatcccttc atccatccca 81000
tcatccatcc aattatacat acatccaatc atatatctgt acataatcca ttcttccctc 81060
ggttcatcca tccatccatt catccatcca tccacccatc ccttccttca tccttcctat 81120
catccatcca atcatatatc tgtacataat ccattcttcc ctcggttcat ccatccatcc 81180
attcatccat ccatccaccc atcccttcct tcatccttcc tatcatccat ccaatcatac 81240
atatatccaa tcatacatct gcacatcacc agctcatcca tctatccatt tatccatcca 81300
tccttccttc catccatcat tcatccatca tacatacatc taaccataca tctctacatc 81360
attcattctt ccatcgattc atccaattat ccatcattcc ttcctccatc catcccatta 81420
tccatttgat catacatata tcatctatac atcatccatt catccatcca tccatccatc 81480
cacccatatc ttcatccaat caatcataca tacatcgaat catctacaca tcacccatcc 81540
atccatccat ccattcatct atccacccat ccatccatcc atccatccat tcatctatcc 81600
acccatccat ccatccatcc atccatccat ccatgtaacc atccagtcat atatccaatt 81660
acacatccat ccagttatac attcatacat gcatctaatc attcaattat acatacacac 81720
atccatataa ttctacatcc aattatacct ccatccaatt acacattcat acacccacct 81780
aataaattat taattcatat atccatccat ataattatac atcaattata catccatcta 81840
atcattcagt aattcaccca ccatccagtc atctatccaa taatacattc atccaatcat 81900
ccatccatcc atccacccat tcatccatcc atccgtccgt ccacccatca tggtatgagc 81960
catgatttac cacgatggtc ccctgtggac agcccaggtg gggcagaact gaagggaagc 82020
ccagggctgc ccccataaac atttgcctcc tttacatgga tgagaactag atccacatgt 82080
ataaatcctc atgatttgaa ggtgctttta ccaacattca ctcatgggat tctcccagga 82140
gctctaggag gaggcaggta gagttgaggt catctcacgc attttacaga tgaggaaacg 82200
gaggccctga gaggcaggtc caaggccacc tgaccagaaa gaagtggaac tgggacttga 82260
acccagccat cttgcccctt ggtcccatgc tctctagcct gtaactcctg cttcctggtg 82320
gggcatctcc aggaggaccc tatcggctgg ccatgggcct gccctggagt cttttgctct 82380
gtgtggccat ccttcctccc tcaggagagt gtgtgctccc agagcacagg ctgtatcttc 82440
tgagcatttt gtcccttccc agtacctagc actcagctct gtatacattg ggctctcaag 82500
aattctcaac cttccagagt gtaaggcctt gacctgctca gccctggata ctgcatgatg 82560
cattgataag cccataaaat aaccagggca gattgactcc cagtggccaa agtgccacag 82620
ggaagggaca attcagccct tctaggagga ggaggaggta gttttctcat ttctattaag 82680
gcaacaaaag ctgccttact aaggacattc ttggtggagg gcgtgactgt caaccactgt 82740
gatcatttgg gcctctcttg cccaggcttc ccattctgaa aggacagttt tattgtaggt 82800
acacatggct gccatttcaa atgtaactca cagcttgtcc atcagtcctt ggaggtcttt 82860
ctatgaaagg agcttggtgg cgtccaaaca ccacccaatg tccacttaga agtaagcacc 82920
gtgtctgccc tgagctgact ccttttccaa ggaaggggtt ggatcgctga gtgtttttcc 82980
aggtgtctac ttgttgttaa ttaatagcaa tgacaaagca gaaggttcat gcgtagctcg 83040
gctttctggt atttgctgcc cgttgaccaa tggaagataa acctttgcct caggtggcac 83100
cactagctgg ttaagaggca ctttgtcctt tcacccagga gcaaacgcac atcacctgtg 83160
tcctcatctg atggccctgg tgtggggcac agtcgtgttg gcagggaggg aggtggggtt 83220
ggtccccttt gtgggtttgt tgcgaggccg tgttccagct gtttccacag ggagcgattt 83280

```
tcagctccac aggacactgc tccccagttc ctcctgagaa caaaaggggg cgctggggag  83340
aggccaccgt tctgagggct cactgtatgt gttccagaat ctcccctgca gacccccact  83400
gaggacggat ctgaggaacc gggctctgaa acctctgatg ctaagagcac tccaacagcg  83460
gaaggtgggc cccccttcag acgccccctc catgcctcca gcctgtgctt agccgtgctt  83520
tgagcctccc tcctggctgc atctgctgct cccccctggct gagagatgtg ctcactcctt  83580
cggtgctttg caggacagcg tggtgggagc tgagccttgc gtcgatgcct tgcttgctgg  83640
tgctgagtgt gggcaccttc atcccgtgtg tgctctggag gcagccaccc ttggacagtc  83700
ccgcgcacag ctccacaaag ccccgctcca tacgattgtc ctcccacacc cccttcaaaa  83760
gccccctcct ctctctttct tcaggggcca gtaggtccca gagcagccat ttggctgagg  83820
gaaggggcag gtcagtggac atctgatctt ggtttagtat ccttcatttt gggggctctg  83880
ggtgtggcct gggcctctgg actttggcca cggtgtttgt tccagccctt ctcctaacct  83940
gtcctttcca gacactcggc atctaggtta ttagcacctc gcatactttc tgacatgctc  84000
ctcagtcctg attttgacca tcttctcttg cttcccatct gtgtcagtca agactgcatt  84060
tggctgtaag aaacagaaac cccaactaac tgtggcattt acatgaagag gtttactttt  84120
ctcacataat cagatgtcta gacttggcca gcacctcaag ggtcattgat gctctcctgt  84180
ctttattttc tgtcatcttt agtggttgga ttgttgcctc atggttacaa agtggctgct  84240
gcacttccag gcatcacatc tgcctttgaa gcaggaacaa gttgcaaagt aaagtggcca  84300
aaagggccct gaaactaaat gtgtcccctt aggaaagcag gagttttctt gcaagtggca  84360
atcttctgct tatgtctcat tggccagagc tgggtcttac ggccacccct tgctgcgagc  84420
aaggctggga cattgagcat tttgccgtcc aacctcttta gcagaataaa ccaaggggga  84480
agaacgttaa tagtggcttt tgagtcacta gttggcagta tctgcccctc tatctttcca  84540
tcctccccat ggagtttcaa ggttcctttc tcagtacttc ttcaggctct gcacgttcat  84600
ttggatcttg tgtcttgggg tgaaaaactg gcccaagtgt ctccccaagc atccaccttt  84660
ggattaattt ggaaaatggc tgtcaagtgc ccgcctcttg cttggtataa tgctacagct  84720
ttagaggacg cagcaggcat gggccttgcc gctgaggttc ttagcctcat gagaatatcc  84780
agatcagatt ctcttggctc cttcttagag ccagtgatgc aagacacttc ctgctcatct  84840
tgtcgggacg gttttacaag ttgcctgcca tcctgagaaa gtctacaaaa cgatgccaga  84900
cctcatgcca gcttcccaag ccttgactct cagtgctccc tcaacaggat tctggaagaa  84960
tctcccaaac aagtcgcaat gccctctgga ccctgtgcag gcatgagact caagagcatt  85020
ggctcccacc cctggtggag ggaacactgc tggggctggg atcttgcctg gttgctccgc  85080
ctgcacccaa gacaaccata attaaaatgt ccttcattga acttggaaag ccttcaaagc  85140
tgacaactcc ttatgtgtac ccggaaaggc ctgggagtgt gccagggcat tgctcgggag  85200
ggacgctgat ttggaagcat ttacctgatg agagactgac agcagctcct ggtagccgag  85260
ctttccctcc tgcctctgct gtgaaggtgg acccatccaa cagtcaaatg cctgactctg  85320
gacaggagcg gacctattta ttgccatgca agggactctg cacttttgaa ttgtgggtca  85380
tgggcttgga tttaggggtt agagctggga gaagtcttgg aagtcaccta gagatgacac  85440
tgccattttg cagatgagga aaccgtccaa tcaaaatgga ccaaggactt gcccaaagcc  85500
tcacagcaaa accataggcc cccgcactaa ccccagagtc cctgtgctgt cttaaggatc  85560
atatagttgt aagcaatcat ctggttttca gtatttcttc ttttaaaatg cctggggcca  85620
```

-continued tgcccagcag tctgtttcac tgcagcgttt acacagggct gccgggcttt cctggtggat 85680
gagctgggcg gttcatgagc cagaaccact cagcagcatg tcagtgtgct tcctggggag 85740
ctggtagcag gggctccggg ccctacttca gggctgcttt ctggcatatg gctgatcccc 85800
tcctcactcc tcctccctgc attgctcctg cgcaagaagc aaaggtgagg ggctgggtat 85860
ggctcgtcct ggcccctcta aggtggatct cggtggtttc tagatgtgac agcaccctta 85920
gtggatgagg gagctcccgg caagcaggct gccgcgcagc cccacacgga gatcccagaa 85980
ggaaccacag gtgagggtaa gccccagaga cccccaggca gtcaaggccc tgctgggtgc 86040
cccagctgac ctgtgacaga agtgagggag ctttgcgtgt ttatcctcct gtggggcagg 86100
aacatgggtg gattctggct cctgggaatc ttgggttgtg agtagctcga tgccttggtg 86160
ctcagttacc tccctggctg cctgccagcc tctcagagca tttagggcct tctggacttc 86220
tagatgctcc tcatcttgcc tcagtcagcg cgtcagttcc agagacttct ctgcagggtt 86280
ttctggggca ggtggtggca gacccgtgcc ttcttgacac ctgaggtcag tccaccctcc 86340
tgctcagact gcccagcaca gggtcacctc ccaaggggtg gaccccaaga tcacctgagc 86400
gcacagaggg tgcagatgac tggaccacac cttttggtga tcttaatgag gtggtcccag 86460
aggagctcag acatgcaatc tagcatccag ttctgggact ctgtctcctt ttcaaacgta 86520
ttcatgtaga acaggcatga cgagaatgcc ttgtcaacat gggtgatggg gaatcaatca 86580
gacagggcgc cgggctcaag gctgcagtca cccaagagtg gctcagccca ccaggcccta 86640
ggaaacgcct gcacagcctg gagctcctgg agtcatttcc ttcatgtctt cttcactgca 86700
cttacgtaaa gatgccagcc attggtttgg tgatttggag ggtgcccagt tgcccaacaa 86760
gaaatgcaga agaggcctag ccaggatttc accagcagtg gagagtagag aagatgtggc 86820
cagaaaagag tttcctttcc ctcctaaaga tggtactccc tgcagctact ggggaagcct 86880
gcagcattct ctagggctct gtgtgttgag agcagcccca ccctggcccc ttctgagtgc 86940
atttctgctt tgtgacttga tccgtgaagt cccctgagat gggcagaggg gatgtcctcg 87000
aagctggggc agagcctcat ccttgaacgt gaaggacgtt tgaagactgt ggcatgatca 87060
caggatgaga tcacagggaa cttgagtttc tctcctcctc tcccttcaca gttatttcac 87120
tgagggaaat ccctcccctg cccagaatga aaactctagc caactcttga cttttccatc 87180
actccaaagt agttgaaagt acattagtct ccacagtggc aaaacagtgt gcaaaagcta 87240
aataattaga acagccagtc ccatgtgaca gtcaaagctt ctaactccat tcaaagttgc 87300
agccattccc ctcgagggct ggcagggagg ggaggggtaa gagaaacagg aaggttctta 87360
ctgagttggt cctggtgtga gctgcgtcac actccctgca gaggtttcaa ggagactctc 87420
tctctctctg tctccatggg gaccttattt gaattcttct actcttaccc cagcctgcca 87480
tctccagcta tcctcccctg aagagccctt ctgctgcgct ggattctggt ggccatgtca 87540
tctcctcggc cccgtgggag tctgaagatc tggctgcagc ctcacctctg aggtcctgct 87600
agttgccacc tcttaaacat gatctgaggc tcccatgcac tctgacctgt gcccacatgg 87660
ggcccacggg aaacacgctg gcaagcaaac tgtgggtgtg cagacggttc tcagggctgc 87720
agcacctgtc ctttgctctg cccccaaagc aaggccagcc catcttccat cctctagtgt 87780
tccttggtgg ggccctgacc acagtccacc aggtccctaa ccagagggga cacacaccag 87840
gtgtcctcaa tgtattgcct tgaaacagtt gtgctgggac tgtgatgggg ggtggccatg 87900
tagccacccc caccaccccc aagccactct ctccaaggaa atcctcctaa agatcccttt 87960
acatcctcca tgtggtgggg aggttctaga gttgggtgca tgtgtcttca gctactgaca 88020

```
atgcagacct tagttggcac ctcgctctgg cctatcctgt ttgctgttct tggcgctcca  88080
gtgaaactcc ccatgggcca tccagttggg gtgcagtgtg gccacccccct tgcaggttcc  88140
tgccttgctg gagagcacag ggccctcctg gctcttgtaa aacactcccc atggtacaga  88200
gaggccagca gtgatgtgag gcccaacctc cctccatggt gttcccaagc agctcccttt  88260
ctggggtcaa ggggtggcaa agacagtgca gcgtccaatt tctgactcaa gccgggcctg  88320
gctatcgcag ctctgcactg tgtgtgacag caaggcaact cacccagtgc cgtggcagtg  88380
accgtgtccg aggaagcctc ctcacaccct ctgtctcaag gactctggca tttagctgga  88440
cttgctgtag ctctgagcct ttctgccatt gccatcacct tgtcagaaac tcaggccgaa  88500
tctgcactca gagttgtgcc caggcagttg agccaacact tgctcagcga tattgtcaca  88560
tgacaaggca ctgtcaccac tgggcatcgt gggtagcgca gtgtcggctg gatggacccg  88620
gagggtgtct gtgtcatgct agtgctagtg atgggagccc cgtgagccca ttgcccgccc  88680
tcccatgccc tcagcagctg cctggggaca gccaatggcc tgggtgtttc tgaggctacc  88740
acatggcttc caggaaactc gagaaccttt ctctcccttg cctacactct tcacacaggc  88800
ctgtgctggc cagcggtggg gatccggcat tcctatctta ggtgcagaga gtgactgact  88860
cattgcaggc ctgggagata agactgatgg cccagccagc aagatgtatg gatttctcag  88920
aggcagtggc ctctgtcatt gtcctcagga aatgctggtg attctggtgg cctgaggtca  88980
atgcatgtca acgtggccaa cttgccttat aaactttttt tctggacaat tgcgtgcact  89040
gtcctgtaac agtgtcctgt tgtttatgat gcagaaatag gtgtttttaa agcctattga  89100
ttttggtact attaatgtgg tcaggaactt tctcagtctt tcttgtttgg ggtgagctgt  89160
ggcttcctaa acaggaaccc aagacacccc caaaagctgc tcaccagcac tgccagcctc  89220
cctcttacca agtagcaccc gttcaggaca ttctgcgaaa ggcatttgcc cagaagttgg  89280
gaggaaggaa atgtaacatt ttggggcacc taccatatgc caggcaccag gctaaacgtg  89340
ttcacacaaa ttctcttact aaccctcacc atccttctac aagacaaact agtatcttca  89400
tcttggggtt caagatgagg aaatggaggc tcagagaggt tgaatgaatg ccggtgcctg  89460
gatatgaacc ccatctgcct gactccgcaa cccaggcaaa gtctttcctt gaacttccca  89520
gcagccactg cttagacaca gcctccacaa ccatggctca gcagcaaatt gcttctctga  89580
cctcactcag cctgtgtgtc cttgttgagt gaggcattca ggaccctggt cccaaagtgg  89640
agaaagtctt tcctactagg tcatagctac acctgcatgt gggtgctgtg ccttttgttt  89700
agtgaacttt tatcaccagc atcctcagca atgacatttg cagagaagcc agagctgagg  89760
caccttggta ttcttgggat gtgactttcc tgaatgttta agggaaaatg cccgaaggta  89820
cagagagctt ggtttctagt aaacaataac tgtcttgctt ttacccccct tcatttgctg  89880
acacatacac cagctgaaga agcaggcatt ggagacaccc ccagcctgga agacgaagct  89940
gctggtcacg tgacccaagg tcagtgaact ggaattgcct gccatgactt gggggttggg  90000
gggagggaca tggggtgggc tctgccctga aaagatcatt tggacctgag ctctaattca  90060
caagtccagg agattttagg gagttggttc ttatcaaagg ttggctactc agatatagaa  90120
agagccctag tggttttttt ctaataccat ttctgggtaa ttcctaaggc atttagtgtt  90180
ctgaaagatg ctagccttgt ccagcctggg agttgagaat gaatgtctaa cagaaactct  90240
aggccgggcc tggtggctca cgcctctaat cccagcacta tgggagaccc aggtgggcag  90300
atcacctgag gtcaggagtt tgagaccagc ctggccaaca tgtgaaatcc tgtctcacta  90360
```

-continued

```
caaataaaaa aattagccgg gtgtggtggt aggtgcctat aatcccagct actcaggagg  90420
ctgaggcagg acaatcgctc gaacccagga ggtggacgtt gcagtgagcc gagatcgcat  90480
cattgcactc cagcctgggc aacaaaagca aaactccgtc tcaaaaaaaa aaaagaaact  90540
caaatatgtg tgacaggcga ttctcactgc aggctgccct gtggctgatc caggagcaag  90600
gccttaacca tgtcatcccc aagcgattgc ttgtaaactt tcttctgtgc agccttcaac  90660
ccttattatg attttcttct caggaaccaa actgctgtat tcaagaaagg cagctttgtg  90720
taatcattta tcataaatat cttaagaaaa atcctagaga ttcctaattt taggaaatgg  90780
gagacctatg gtactgatat aatgtgggct gggcttgttt tctgtcattt gctagataaa  90840
tgaacttgag agcctactgt aaaatgtgga agcttctaga ttgcagaagg gctggaaaga  90900
cactgttctt ttctcccgag tgatgggatc tgtccagtat ttagagctgc ctctgaggcc  90960
atctgattct aggagactct gcctcgttga ggatattttg aggcctaact acacattcct  91020
gcccccagag aggtcacagc ctatagcagg ctgatgtttc tcatgtcaca tggcacagaa  91080
aggcacattt tcgttctcag gctaacaaag agcttcaaaa actattagaa gggacagtgg  91140
ctataagaga agaacctcag tcaatgtgtg aaattaacta ggaacctggc tcctgtttct  91200
tttaggtcat gtttttcagc ttaggtaaaa ctagaggctt tgataaagca tgacctctag  91260
aaatcattgc ttttcataaa tggaagtggg tttgagtttt ttctactgat tgttagtgca  91320
ggtgatgtct acatgccccc agaacatatt ccatgcaaca aaaaaagccc aggtcaccgt  91380
ctttgctggg aacttgactt ttgtgctcac tgaattttaa gctttctgac agcagcctgg  91440
aatcatggag ggataaagta cctattagta agatggaaaa aggtgtttca ggttggagct  91500
gcagtctgtt gagagtaagc tatgggaagg cctgtatacg aggggtggac ttttcttctg  91560
taagtgtcca gagaccaggc ctcctgaaga gggcatgggg gcttaactta cctggactac  91620
tgtgtttaca atactcattt atcttgaact cctcctaacc cctgagaatt gctacattta  91680
gtatttgctg agtacttcct agcatcctag ggaatcaata gaacattctc ccaaccaggc  91740
tgggtgcggt ggctcatgtc tgtaatccca gcactttggg aggccaaggt aggcagatcc  91800
cttgaggcca ggagtgcaag actagcctgg ctgacatggt gaaaccccgt ctttactaaa  91860
aatacaaaag ttagccaggc atggtggtac acacctgtaa tcccagctac atgggaggag  91920
taggaggcag gagaattgct tgaacctggg aggtggaggt tgctgtgagc cgagatcatg  91980
ccactgcact ccagcctggg cgacagagtg agtgagactc tgtttaaaaa aaaaaaaaaa  92040
aagaacattc tcctaacctg gcttcttcct ccaggggtgt aattaatcat gtcagtttcc  92100
tcattgatac acacacacac acactacaat cctgtatcca ttacttttca aggtacattt  92160
actatttacg tttggggtcc ttgtctcttt tttaatagtg tttcttaaag tcttgtatta  92220
tatcagagta cagtaacatc ccagtcaaga gcactctagt aagctctagg aggaaagcga  92280
cttccggaag gcagtggaga cctgtcctgt tggggcagca taggggcagc ccctgcctct  92340
ggtcagttct ggcgctcagg ctcagggttg cctctgggct gttcttccca gagactgaca  92400
aagggctccc ataaggcacc tgcagagcct gtgagaagct gaagtcaatg ttttcctgac  92460
accagttgat ctgtgcagga tccattgatt taaccacctg ctgtgtggca tgcactgtgg  92520
tcgatgccag gaacaggaat tggaggggcc catgagcatg gccagtatca caggctggag  92580
gtgctgctgc gctctgaccg ggcctcttgg ggatgagccc atgtcaacca ccttgcctcc  92640
gatggggtcg ggcccacagg ttacctttgt gtgtccatga ccacaccttc ctccccgacc  92700
tcatccaaat ctctttcttt tccaagcccc tgaatccttc agggctgcag gttttgttta  92760
```

aagcagagct ggtgagttgc ataggttgtt gcattgggac tagatggggt gttcaaagag 92820
ttgggagtta aaaaacataa agggtattta ttaggagaac caaggagtgt aattctcctg 92880
ttcttaatat gcggccaggt taatgaatgt cacgtgaatg aaccagaaaa aaatgaagtg 92940
tgcccttgat cagctgggtt ggtgtgcagc aagctgtgtg accaggggac agcagtggtc 93000
ctgagggccg tcactgtctg ccgtgcagag cccttcctcc cacgggggcc tacctcacct 93060
gtgccaaggg cttgtctgtg gtcagtgacc tggatagatc tgaatggggc ttctttttcg 93120
aggagtctta tggcaggtct ctcagtaaag actccattct tgatgatcac acattttgga 93180
ttttccaaat ctgtcagaga atgggcttga ggcggggttt gtgggcacta gtttcactgg 93240
tttcatttac caaaaagggg agcagaagtc aagtatggtg gctcatccct gtaatcccag 93300
aggcaagaga attgcttgag cccaggagtt cgagaccagc ctgagcaaca taaggagacc 93360
ccgtctccac aaaaatgaaa aataacattt tagtcagacg tggtggcatg catctgtggt 93420
cccagctgct tgggagggtg agatgggagg gttgtttgag ccctggagtt aaagttgcaa 93480
tgagctgtga ttgcaccact gcactctagc ctgggtgaca gaacgagacc ctgtctcaaa 93540
aaaaaaaaaa aagaaagaaa gaaaggaaaa aaaaaactca tgcctgtaat cccagcactt 93600
tggggaccgg ggtgggcaga tcacgaggtc aggagatcaa gactatcctg gccaacatgg 93660
tgaaaccccg tttctactaa aaatacaaaa attagccagg tgtggtggca cgtgcctgta 93720
atcccagtta ctcgggaggc tgaggcagga gaatcgcttg aaccagggag tcagaggttg 93780
cagtgagctg agatcgtgcc actgtactcc agcctgggcg acagagtgag actctgtctc 93840
aaaccaaaaa aaaggggtgg ggggcggggg caggagaaca gtgagaggta gggagaggaa 93900
aggggattct cgctacaccc aaaccagata ccatctagag gctagaatct ttgggaggct 93960
caaattccct agaaagcagg agaagcttct gtagccctcc cgctttccca gtagattaag 94020
cccagggcgg ctccagatgt gtgacatgct ctgtgcccaa ccagagccca tcataggcag 94080
aggaataaca cccacaccag aagggccctc ggaggtcacc acgtccaaga accctcttta 94140
cagatgagga aactgaggcc cagagagggg agagccacct agcgagctgg tggcggctag 94200
accaggagag ctgtcattcc aagcaagcaa aggcaacgag acgagcccag agctgtgctc 94260
ccatctcttt gttagggggc ctgggatgcc ctctcagtgt cattttgtcc aggatgatgc 94320
tccctctctt aagcgattaa tgcgcccttg ctaacctttt gctatcgctg cctcttcaaa 94380
ccagaggagt tgagagttcc gggccggcag aggaaggcgc ctgaaaggcc cctggccaat 94440
gagattagcg cccacgtcca gcctggaccc tgcggagagg cctctggggt ctctgggccg 94500
tgcctcgggg agaaagagcc agaagctccc gtcccgctga ccgcgagcct tcctcagcac 94560
cgtcccgttt gcccagcgcc tcctccaaca ggaggccctc aggagccctc cctggagtgg 94620
ggacaaaaag gcggggactg ggccgagaag ggtccggcct ttccgaagcc cgccaccact 94680
gcgtatctcc acacagagcc tgaaagtggt aaggtggtcc aggaaggctt cctccgagag 94740
ccaggccccc caggtctgag ccaccagctc atgtccggca tgcctggggc tcccctcctg 94800
cctgagggcc ccagagaggc cacacgccaa ccttcgggga caggacctga ggacacagag 94860
ggcggccgcc acgcccctga gctgctcaag caccagcttc taggagacct gcaccaggag 94920
gggccgccgc tgaagggggc agggggcaaa gagaggccgg ggagcaagga ggaggtggat 94980
gaagaccgcg acgtcgatga gtcctccccc caagactccc ctccctccaa ggcctcccca 95040
gcccaagatg ggcggcctcc ccagacagcc gccagagaag ccaccagcat cccaggcttc 95100
ccagcggagg gtgccatccc cctccctgtg gatttcctct ccaaagtttc cacagagatc 95160
ccagcctcag agcccgacgg gcccagtgta gggcgggcca aagggcagga tgccccccctg 95220
gagttcacgt ttcacgtgga aatcacaccc aacgtgcaga aggagcaggc gcactcggag 95280
gagcatttgg gaagggctgc atttccaggg gcccctggag aggggccaga ggcccggggc 95340
ccctctttgg gagaggacac aaaagaggct gaccttccag agccctctga aaagcagcct 95400
gctgctgctc cgcgggggaa gcccgtcagc cgggtccctc aactcaaagg tctgtgtctt 95460
gagcttcttc gctccttccc tggggacctc ccaggcctcc caggctgcgg gcactgccac 95520
tgagcttcca ggcctcccga ctcctgctgc ttctgacgtt cctaggacgc cactaaatcg 95580
acacctgggt gcagctgctc cactccctcg gcctcctccc gtgctcaggc tgtggccgca 95640
cgcgcccctc acgcttgccc gccactctgc atgtcaccag cacccccgct ccgtgctacc 95700
caccttgttt gactctctgg ccacttgatt tgtccacaac ggcccatcag cccacaggag 95760
gtttggtggg tgccttccac cgacaggatg acgggtgccc tcatggtgtc tagaactctc 95820
caaccctccc atgtaggcat aagcagcccc actttgcaga tgaggaaacg gaggctcaga 95880
gaagtacagt aacttgccga aggccaatga gtagtaagtg acagagccag gtttgggatc 95940
caggtaggtt gtctctgaaa gacacgcctg tcctgcatcc cacaacgcct cccaggaggt 96000
gctggagtgt ggacgcctaa cacagagatg tgcagggcac acacagcagg tgacacacac 96060
agcatccaga ggtggcccag agctcatgct gtgcctttgg cccagtgccc tgcccccacc 96120
cactctgcct tgtggcagga agacaaggag cagacacaag atctccctgg tccacatgcc 96180
accacctccc tctgcagagg acaaggggat cctcatgctg gcattggagg gggttgagca 96240
gggcccacct tgagccctca ggagcacgac cacagcagcc ctgcagggag ggattggtgg 96300
gaggagagtc ccaagtatca gggagaggag agttggtgtc ccacaggaga cctcagagcc 96360
acaaggcgag cttgttcata aatttgggac ccttagcatt tcacagttat ttgcagagcc 96420
cagaaatgga tgttactgaa gctcacagtt gcaagcatct gttaaatttt tattagattt 96480
tacttttagg gaaaactttg aaatgctata aagaagcctg tgtttaaaag ttaagacaga 96540
ggctgggggc gatggctcac gcctgtaatc tcagcacttt gggaggccaa ggcaggtgga 96600
tcatttgagg ttaggagttc gagaccagcc tggccaacat ggtgagaccc tgtctctact 96660
aaaattacaa aaaattagct gggcgtggtg gcgggcacct gtagtcccag ctactgggga 96720
ggctgaagca ggataagtgc ttgaacccag gaggcagagg ttacagtgag ccaagatcac 96780
accactgtac cctaagcctg ggcgacagag tgagactctg tctcaaaaaa taaaataaaa 96840
taaagttaag agagaaaaaa atatatccta tatcctttgt taaattccaa aacagtaggg 96900
gacaaataac tgacttgaca ggttactaca atatttcctg aaatgatgtt ttcttgaata 96960
ctggcctact agaggttcat aggtgtgttt ggattaaaaa agagttccat ggcccagtga 97020
ctgggggaaa aaaataaaag actaaagtaa gttaaacagg cttttctgct gcaggacttg 97080
tcagagcctt taatgtacta atggccattg tgaccctctg agaaggtcac agagtgggtt 97140
tcccaaactt acttgattct acctgctaac atttcctgga ggaagtttgg gaaatgccga 97200
tttagcagat tcttttgttg tgccgtggat ggtgctggtt gatgtgggca aaacaaagaa 97260
cacgtgagtc agatccgcct ggggctctta ctaaagtgca ggttcccagg tgccacttta 97320
ggcttacaga cccagttgtg gggtaagcct gggagtcttt tagcaggtga ttctgccaca 97380
tagtatagtt ggaaaacctc tgggcatact cattgctggt ccctctagaa atccaggtga 97440
caatagccaa tgagaagctc caagagaccc agttgtccat ggggtagagg gaatgtgata 97500
ttgaaaccaa agaagaaaat ctatgatcag ttttcagcag tgactgtcaa gagaaggaga 97560
agggtgagtt agcgctgatg ctggctgaca ggtcagcggg ttggtttcac caaggagtgt 97620
gatgaaggct gatgttgtct gtgggaatgt atgatggtaa ctggtttgta gctaatttgg 97680
ggaagcagtg agaattcgtg ccctttgaag accagtaagt ggcaagaaac ccaccaggcc 97740
tggctcaggg ctgggctggg cttggctcgt ctcagagcag ctggggctgg tggccaaagc 97800
caccattagt gaggggcagg ccctgggggt acaaccagca actaggggac aaagacaacc 97860
ctgccagcct ctcctattct ggaggcgtgt gaccagaaat ggagatgggt tggtcagcat 97920
aagatggcca ggaaggtgga aatcaggact gctggcaatc tagccacatg ggcaggggag 97980
ccgggtggtt ccaggcagtt tccaaggcca agagggtgag caggcacctc acagggaatc 98040
agggccaagc ctggctgcag tgtggagaca atgcacccac ccccatcctt ggatcttgca 98100
ggaggctggg tcctcactga gctaccaaca tccatggccc tgaggctttt aaaacaccca 98160
tccatggagt ggggctggtc ccagtggggt gaggctgacc ctggcagaaa cagggcagga 98220
gcctgtgggt tagggagact gcaccttcct tagatagcct ccatgccatc atgtccccgt 98280
gacagtttct gctgcgtccc ctctgcatgg tcccaccctc ggccagcctg ctgccccctc 98340
ttgccaggtt gcgctaatca gtgaccccag tgtgctgtgt tgatactaac aatgcgaggc 98400
ctagcagatt caagggaaaa gagaaccaac tgggtttcca ccagacccaa ctaaacaaac 98460
atggacctat cccagagaaa tccagcttca ccacagctgg ctttctgtga acagtgaaaa 98520
tggagtgtga caagcattct tattttatat tttatcagct cgcatggtca gtaaaagcaa 98580
agacgggact ggaagcgatg acaaaaaagc caaggtaagc tgacgatgcc acggagctct 98640
gcagctggtc aagtttacag agaagctgtg ctttatgtct gattcattct catatataat 98700
gtggggagta tttgtcacta aagtacagct gtcatttaaa gtgctttgta ttttggggca 98760
ggcttttaaa aagtccagca tttattagtt ttgatactta ccccagggaa gagcagttgg 98820
caggttcatg aagtcatgct cctaattcca gctttcttag tgtactttca gtgagaccct 98880
gacagtaaat gaaggtgtgt ttgaaaacca aacccaggac agtaaatgaa ggtgtgtttg 98940
aaaaccagcc ctaggacagt aaatgaagcc atcttctcac tgcataaact gcacccagat 99000
cttcgcccat ccttctcagt atttcacttc acccattgtt tactgtctca atgactgggg 99060
aaatgtctgg ggaaatgctc ccgtaattgc acagtggcgt tttcctggga aaatcccacc 99120
atggctctag ataagaccta tttttcttaa aggtatctaa aatttccagc ataaattctg 99180
tctgaaacac ctgaatttta atcagtactg gagcccggag ggcatctcca gttgccacat 99240
agctctgagc attcagtggt gtgttgaggg ctgctcccgg aagtgcctgc agagtcaggg 99300
ctccccagcc tcatctagtg aggcagtgga agggcctgtg gggatttgga gagctggcct 99360
gggtctctga agtgatagtg acagctgctt gtcaatcacg gtgcacattt agtgctgggg 99420
gcagggggca gggaatacca gcctcatgca tgcatgcatt catttgttcc ttccttcatt 99480
cattcattca gtacacatgg gtacaacatc cctgccctgg agttgcccag agtctaggga 99540
ggggaaagat ctattaccct gggcctcggc cagctgggga gtgctgctgg tggagagggg 99600
ccgtgtgcag cgagggaagg aggagtcgtc aataccccca ccccagcttt gctttcttgt 99660
catcagcccc agggccccag cctgtgtccc tcctctccca ttgctacttc atctcctggg 99720
tcctccttac caagcctgac cacacagagg gccttggccg cttccatggg gaattggaaa 99780
gcaataagat agcatcccct agaagcccag tgaagtctgg gacaggaccc ttctctgagc 99840

-continued

```
tctgacttgc tcttggaaac acttcgaggc ttagcctccc cactttgttt cccgagagtg  99900
tgacctgttc ccctccaaac accccccttct cctccagggc catgcccacc cgtcaaaatc  99960
ccccacgggc aggacgaact gtgggtgtca gtcaccatct atcctgcatc ctggttccag 100020
ggcccccccc agccccgcct ccatagggac aggcgtgcag acacccgtcc ctggctgctt 100080
cctcttgtgg aatgggttca aaagtaagca gtgttgttta cactgacaaa ctgaaaaaaa 100140
aagaaaaaga gataacattg gaggcttggc acagtggctc atgcctgtaa tcccagcact 100200
ttgggaggct aaggtgggag gatgtcccca gcccaagagt tctagaccag cctgggcaac 100260
atagcaagac cccatctcaa aaaaaaaatt taattggcca ggcagaggtg ggaggatcac 100320
ttgaacccaa agggtggagg ctgcagtgag ccgtgatggc accactgcac tccagccagg 100380
gcaacagagg gagaccctgt ctctaaaaca aacaaacaaa caaacaaaca aaagagttaa 100440
cattggccag attaggattc accagatagt gttaatatta gtttgatttg agactttaat 100500
cagaaagcac atgtgtggtg ggggtgggtg taacctaagt caggtagaat ctttccaact 100560
tggggggggc acactcctga ttgtagccat atgagtctgt cagtgtggtg gaagaggcca 100620
tgggttaatg ggcaggtaaa aaagcacctt gcctggaatt gagtagaaag taaggccctt 100680
cagaccccgt gacacacttg ggacattttt cttgagtaac atcctaagat tcatgtacct 100740
tgatgatctc catcaactta ctcatgtgaa gcacctttaa accagtcgtc tccaaattca 100800
ggggcacagt aacatccaac aggctggaga aagaacgtac tagaacttcc attccttttt 100860
catgtcctct tctaaaagct ttgtcagggc caggcgcggt ggctcacgcc tgtaatccca 100920
gcactttggg aggccgagac gggtggatca cgaggtcagg agatcgagac catcctggct 100980
aacacagtga aaccccatct ctactaaaaa tacaaaaaaa cgagccgggc gtggtggtgg 101040
gcgcctgtag tcccagctac tcgggaggct gaggcaggag aatggcgtga acccaggagg 101100
cagagcttgc agtgagccga gattgcacca ctgcagtcca gcctgggcga cagagcgaga 101160
ctccgtctca aaaaagaaaa agaaaaagaa aaagaactgt gattggggag gacggtcact 101220
ttcctgttct tactgatcag aagggatatt aagggtacct gattcaaaca gcctggagat 101280
cactgctttc aaccattacc tgccttattt atttttagtt actgtccttt tttcagtttg 101340
tttccctcct ccatgtgctg acttttattt tgattttatt tatgtttatg tttaagacat 101400
ccacacgttc ctctgctaaa accttgaaaa ataggccttg ccttagcccc aaacacccca 101460
ctcctggtag ctcagaccct ctgatccaac cctccagccc tgctgtgtgc ccagagccac 101520
cttcctctcc taaatacgtc tcttctgtca cttcccgaac tggcagttct ggagcaaagg 101580
agatgaaact caaggtaagg aaaccacctt tgaaaagaac caggctgctc tgctgtggtt 101640
tgcaaatgtg gggtttgttt atttgttttt tagcctcaaa gacctttctt caaatgagtt 101700
ctggcataga agcaccgtgt aaaatagtta gaattctggg caaaggggaa aagagagctg 101760
ggggccatcc ctctcagcac cccacaggct ctcatagcag cagctcctaa gacacctggt 101820
gggaccttgg tttcgaaatc gctactctaa ggctgggcac ggtggctcac acctgtaatc 101880
ccagctcttt aggaggccga ggagggtgga tcacctgaga tcaggagttc gagaccagcc 101940
tggctaacat ggcaaaaccc tgtctctact aaaaatacaa aaattagccg ggcgtggtgg 102000
tatgcgtggt ggtaatcgca gctactcggg aggctgaggc acaaggattg cttgaacccc 102060
agaggcagag gttgtagtta gctccagctt gggcgacaga gcaagaccct gtcgcaaaaa 102120
ttgtttaaaa aacaaaccca aaattgctac tctcattggg ttcctttgcc cattcctgat 102180
tttggcaaga gaaatgcttc cagattgccc tgatctgggt aggacagcat cacgccatag 102240
```

caacactgcc ccgtgagctc actgccccct caactagctt gtggtccttg gttaatgtca 102300
gtttcttttt tgagtttgtg ttatgtctaa gggtcatctg ctgggtaacg gaacccaggg 102360
actgccctag tccctagact gtgccatgcc cgactctgcc agctttgtca gtgatgctgg 102420
tgctcgcctc ctcgggtgct cgcctggtct gagcacaccc aaggagttct tgaggcctta 102480
gggttgtttg cgagagaatg aaagaacacg acctagctct ctttagcatc cttggtcagg 102540
ttcaacactg cccccagggg cctctggtgg agccaaccac catcagccaa ataaatccat 102600
aattagagtc agaaaatgga tgtctgcata tgtgtagtgc actaatgtcc tgccgatgat 102660
tgacatggag tggagagtga cctgatcatt gctgtgagct ctgctggcct tggcacaact 102720
catgctgata actaatgcac acagttcctc tgggaggaaa tgtcctcagg gaacttggag 102780
tttgggtggg gatgtgggtt tgtgtgccca gcaagccctt gtggttgtag cagacactag 102840
tggcatctag gaggcaaagg gtcaccccag tcttagccac gttttgagtc aaggtggcgg 102900
agtggggctg gtgttgactc ttggtggcag taacttttcc caatggtgaa aaacccctct 102960
atcatgtttc atttacaggg ggctgatggt aaaacgaaga tcgccacacc gcggggagca 103020
gcccctccag gccagaaggg ccaggccaac gccaccagga ttccagcaaa aaccccgccc 103080
gctccaaaga caccacccag ctctggtaag aagaacgttc tcttgaatct tagaggaagc 103140
tgaagctctc agaggtacag ccttcatttt aggaggcctt aggccactga gaatgaataa 103200
cccctggcag ctggtcagca gcttgcagtt tactaagcac tggagtcttc attgccttct 103260
cagtcctttt gatttctgag gcaaatgttg aatccctacc tttttttttt tttttctttt 103320
gagacagagt ttcgcttttg ttatccaggc cggagtgcag tggtgtgatc tcagctcact 103380
gcatcctcca cctcccaggt tcaagcgatt ctcctacctc agcctcccta gtagctggga 103440
ttacaggcac ctgccactat gcccggctaa ttttttgtat ttttagtaga gacagggttt 103500
caccatgttg gccaggctgg tctcgaacgc ctgacctcag gtgatccacc tgcctcggcc 103560
tcccaaagtg ctgggattac aggcatgagc caccactccc agcctgaatc ctcacttttt 103620
atcaatgaag aaattgaggc tgattctgca gcatgataaa aaaaaataca gaaaaaggaa 103680
aaaaaagaaa gaaatcgagc ctctgagagt ttgcttgact gagtctaacc agctcatttt 103740
aaacccgagg aaaatgcagt cacatgacta ctaagtggca gctctcggag cctctctggc 103800
cccaagtcca gggttccata gaggcagccc cagcatggca tgttttcagt ccccaaatga 103860
gactctggag acaaatgtct ctggagacag agcagcagcc tggataagtc acaatgggtg 103920
acgtcactca gggctcaacc cctgggcagc ttaacttgct agggacgtta ggagtctgct 103980
gcaaaacctg agggtcttag ctgagcagtc acaggctggg cccgttgccc tgggctcctg 104040
tgagtaaaac ccagtcaatt ttgagtaccc agtaaggcat ccattgagtt attttgcagc 104100
caggagtgct attaagaaca gtcgcggctg ggcgtggtgg ctcatgcctg taatcccagc 104160
actttgggag gccaaggtgg gcggatcacc tgaggtcagg agttcgagac cagcttggcc 104220
aacatggcaa aaccccgtct ctaataaaaa tacaaaataa ttagctgggc gtggtggcgg 104280
gcgcctgtaa tcccagcttc tcaggagggt gaggaaggag aatcacttga acccaggagg 104340
cagaggttgc agtgagctga gatcgcacca ttgcactcca gcctggatga caaaagtgag 104400
attccttctc aaaaaaaaaa aaaaaaaaac agtcgtcctc tttggggatt agggacagcc 104460
tgcctgcctg cccgagcact tctctcttcc attgccccag tgaagtattc caggcccctg 104520
ggtttagact ctgcaccatg taggggtgtc tgacctgcac ttgctccttg gtggcacggg 104580
cagcctatgg cacttgctgc gggctgtgac caaagcctgg cctggatctt ggatcttggt 104640
gactctgctt ctccctggcc tgagggagct gcccagagcc tgcccaccac ctgctgcgtg 104700
tctttgcggt ggcatttctc gcacacatgc cgtgcagtgg cacccccaag gatggccatt 104760
cactaaggcc cattgttttt gtcttttcgc ttcgtgtttt ctggcctggt gtttttctca 104820
tatacatgtg atccagggat aattcccaga attttgacag gattttaagt agcgtttgga 104880
tcctgctgtt ttttttcac ttaacatcgg gccagttgac tcacactctg tttttgttg 104940
ttgttttttt gagacggagt ctcactgtgt cacccaggct gaagtgcagt ggcacaatct 105000
tggcatactg caacctctgc ttcccaaatt caagcagttt tcctgcctca gcctcctgag 105060
tagctgggac tacaggcaca ggccaccacg ccctgctaat tttgtattt ttagtaaaga 105120
cagggtttca ccattttggc cagcctagtc tcgaactcct gacctcaagt gatccgccca 105180
cctcggcctc ccaaagtgct gggattacag gggactcaca ctttgtaaca acctgaaaca 105240
acgtgatgca tttccctttg ggtcttacct gctcttcggt ggctgcctgc aggtggagag 105300
accctccccc ttgggcccct cgaccttgtt tcagaatggg gcccctgctg ggccagctgt 105360
gggtgcctgc cacgtgaagg actcattaag gccctgttta agcctgatga taataaggct 105420
ttcgtggatt tttctcttta agcgactaag caagtccaga gaagaccacc ccctgcaggg 105480
cccagatctg agagaggtac tcgggagcct acttcgctgg gagcagcctc cctttgcgtg 105540
tgtggccatt cactggcttg tgtttctaga gccgggagga cccttttctg caatgcaggg 105600
ttcacacagg gttcgcagcc tgaagatgga gcagtccgaa ttctcttccc tgtgcagttt 105660
gcgcagctgt gtttgtctga tgggctttct aatcctgtgt gctctccttg acttcaggga 105720
caatggcatt acaggcatga gccaccatgc ctggctgtct ccctatgttt cagatgaaga 105780
cataggctta aggaggtcag gtgacttgcc cacgaccact ctgtaaataa gaggcatgaa 105840
aagtatttgg agccaccacc accaagccca ctggtcaccc tgggtctctg aagtcaggga 105900
ggcaggagga tgggaggtct gaggaggcag agaggctgag cctggaggcc ctggaggccg 105960
aggccccatc tgttgtttcc ttatgtggaa aataagaggc ttcgtttgtc ctattgccac 106020
agagcgtact acttcaggaa catccaagac atggaaatcc gcagggcacg gtggctcacg 106080
tctataatcc cggcactttg ggaggttgag gtgggagaat cgcttgaggc cagaagttca 106140
agaccagcct gagcaacata gtcagacccc gtctctataa aaaacattat ttttaaaaaa 106200
gacatggaag tcaaattcta aaaactggtg ctggctgggt gcggtggctc atgcctataa 106260
tcccagcact ttgggaggcc gaggcgggtg gatcacctga ggtcaggagt tcaagaccag 106320
cctggccaac atggtaaaac ctctactaaa gaaatcttta ctgaaaatac aaaaatccag 106380
tctctactaa aataagtctc tactaaaaat acaaaaatta gccaggcgtg gtgctgcaca 106440
cctgtaatat cagctactcg ggaggctgag gcaggagact cgcttgatcc catgcagcgg 106500
aggttgcagt gagccgagat cacgccattg cactccagcc tgggcatcag aataagactc 106560
cgtctcaaaa aaaaaaccac aaaaaaaacaa aacaacaaca aaagaaaact agtgcttatt 106620
cgtcactggc caagctgccc attggctaca tgggtgcttc aaagagctgc ccttctccag 106680
gtctggccag caggtatgtg ttacagcaaa tgcctggggc agcggcaggg gcattgctgc 106740
gggaagcttc tggacttgca ggaaagctaa gttctcagac tgcaggggag ctaagcacac 106800
ctcggcacag ggtgaggcct gcggttctca gacttcagtc tttgtggagc ttgagaaaaa 106860
tgaggctttg caggtcccac ccctagagat tctgctctat ccactcttga aggggatcga 106920
gaaatttgca ttttgcaact cccactttcc tccttgaaag ctccggagat tctgacgcag 106980
ggttccgtgg gccacacttt ggaaaataca gacccatgag atagaatacc agactgttga 107040
agtgtaacgg gggcctggga agtgcagtaa cagaagcaag tttgagggta aaggacaccc 107100
agaggaggga gggacagcat ctgcatggag aggagaagag accccccagc agcttccagg 107160
gtgttggaag ggtgcgctag taactgctat gcatggcagg tggggaactg tacgtcaggg 107220
cacagcagca tgaagcggta tggctcgtgt ggacagctag ggacaggcag gcgtggagca 107280
ggcatcctgt tctgaaggcc aaatcccaca gaggagccag ggtgctggca ggagccctga 107340
actagccgaa cagctgaaca gctgaacatt caccctgtgg ggaaagggtc agaagcgtcc 107400
aggcttgagg gcacagctgg gtctcgtcac tgcatcaccc ttatttagga taaaggccct 107460
gaagaattgt attagaggtt ggcaaagcat atctaccacc tcctggagcc acgctggccg 107520
cagggattat aattatttcc attttcaaat taaggcctct gagctcagag aggggaagtt 107580
acttgtctga ggccacacag cttgttggag cccatctctt gacccaaaga ctgtggagcc 107640
gagttggcca cctctctggg agcgggtatt ggatggtggt tgatggtttt ccattgcttt 107700
cctgggaaag gggtgtctct gtccctaagc aaaaaggcag ggaggaagag atgcttcccc 107760
agggcagccg tctgctgtag ctgcgcttcc aacctggctt ccacctgcct aacccagtgg 107820
tgagcctggg aatggaccca cgggacaggc agcccccagg gccttttctg accccaccca 107880
ctcgagtcct ggcttcactc ccttccttcc ttcccaggtg aacctccaaa atcaggggat 107940
cgcagcggct acagcagccc cggctcccca ggcactcccg gcagccgctc ccgcaccccg 108000
tcccttccaa ccccacccac ccgggagccc aagaaggtgg cagtggtccg tactccaccc 108060
aagtcgccgt cttccgccaa gagccgcctg cagacagccc ccgtgcccat gccagacctg 108120
aagaatgtca agtccaagat cggctccact gagaacctga agcaccagcc gggaggcggg 108180
aaggtgagag tggctggctg cgcgtggagg tgtggggggc tgcgcctgga ggggtagggc 108240
tgtgcctgga agggtagggc tgcgcctgga ggtgcgcggt tgagcgtgga gtcgtgggac 108300
tgtgcatgga ggtgtggggc tccccgcacc tgagcacccc cgcataacac cccagtcccc 108360
tctggaccct cttcaaggaa gttcagttct ttattgggct ctccactaca ctgtgagtgc 108420
cctcctcagg cgagagaacg ttctggctct tctcttgccc cttcagcccc tgttaatcgg 108480
acagagatgg cagggctgtg tctccacggc cggaggctct catagtcagg gcacccacag 108540
cggttcccca cctgccttct gggcagaata cactgccacc cataggtcag catctccact 108600
cgtgggccat ctgcttaggt tgggttcctc tggattctgg ggagattggg ggttctgttt 108660
tgatcagctg attcttctgg gagcaagtgg gtgctcgcga gctctccagc ttcctaaagg 108720
tggagaagca cagacttcgg gggcctggcc tggatccctt tccccattcc tgtccctgtg 108780
cccctcgtct gggtgcgtta gggctgacat acaaagcacc acagtgaaag aacagcagta 108840
tgcctcctca ctagccaggt gtgggcgggt gggtttcttc caaggcctct ctgtggccgt 108900
gggtagccac ctctgtcctg caccgctgca gtcttccctc tgtgtgtgct cctggtagct 108960
ctgcgcatgc tcatcttctt ataagaacac catggcagct gggcgtagtg gctcacgcct 109020
ataatcccag cactttggga ggctgaggca ggcagatcac gaggtcagga gttcgagacc 109080
aacctgacca acagggtgaa acctcgtctc tactaaaaat acaaaaatac ctgggcgtgg 109140
tggtggtgcg cgcctataat cccagctact caggaggctg aggcaggaga atcgcttgaa 109200
cccaggaggc agaggttgca gtgagccgag atagtgccac tgcactccag tttgagcaac 109260
agagcgagac tctgtctcaa aacaaaataa aacaaaccaa aaaaacccac catggcttag 109320

-continued ggcccagcct gatgacctca tttttcactt agtcacctct ctaaaggccc tgtctccaaa 109380
tagagtcaca ttctaaggta cgggggtgtt ggggaggggg gttagggctt caacatgtga 109440
atttgcgggg accacaattc agcccaggac cccgctcccg ccacccagca ctggggagct 109500
ggggaagggt gaagaggagg ctgggggtga gaaggaccac agctcactct gaggctgcag 109560
atgtgctggg ccttctgggc actgggcctc ggggagctag gggctttct ggaaccctgg 109620 gcctgcgtgt cagcttgcct cccccacgca ggcgctctcc acaccattga agttcttatc 109680
acttgggtct gagcctgggg catttggacg gagggtggcc accagtgcac atgggcacct 109740
tgcctcaaac cctgccacct ccccccaccc aggatccccc ctgcccccga acaagcttgt 109800
gagtgcagtg tcacatccca tcgggatgga aatggacggt cgggttaaaa gggacgcatg 109860
tgtagaccct gcctctgtgc atcaggcctc ttttgagagt ccctgcgtgc caggcggtgc 109920
acagaggtgg agaagactcg gctgtgcccc agagcacctc ctctcatcga ggaaaggaca 109980
gacagtggct cccctgtggc tgtggggaca agggcagagc tccctggaac acaggaggga 110040
gggaaggaag agaacatctc agaatctccc tcctgatggc aaacgatccg ggttaaatta 110100
aggtccggcc ttttcctgct caggcatgtg gagcttgtag tggaagaggc tctctggacc 110160
ctcatccacc acagtggcct ggttagagac cttggggaaa taactcacag gtgacccagg 110220
gcctctgtcc tgtaccgcag ctgagggaaa ctgtcctgcg cttccactgg ggacaatgcg 110280
ctccctcgtc tccagacttt ccagtcctca ttcggttctc gaaagtcgcc tccagaagcc 110340
ccatcttggg accaccgtga ctttcattct ccagggtgcc tggccttggt gctgcccaag 110400
accccagagg ggccctcact ggcctttcct gccttttctc ccattgccca cccatgcacc 110460
cccatcctgc tccagcaccc agactgccat ccaggatctc ctcaagtcac ataacaagca 110520
gcacccacaa ggtgctccct tccccctagc ctgaatctgc tgctccccgt ctggggttcc 110580
ccgcccatgc acctctgggg gcccctgggt tctgccatac cctgccctgt gtcccatggt 110640
ggggaatgtc cttctctcct tatctcttcc cttcccttaa atccaagttc agttgccatc 110700
tcctccagga agtcttcctg gattcccctc tctcttctta aagcccctgt aaactctgac 110760
cacactgagc atgtgtctgc tgctccctag tctgggccat gagtgagggt ggaggccaag 110820
tctcatgcat ttttgcagcc cccacaagac tgtgcaggtg gccggccctc attgaatgcg 110880
gggttaattt aactcagcct ctgtgtgagt ggatgattca ggttgccaga gacagaaccc 110940
tcagcttagc atgggaagta gcttccctgt tgaccctgag ttcatctgag gttggcttgg 111000
aaggtgtggg caccatttgg cccagttctt acagctctga agagagcagc aggaatgggg 111060
ctgagcaggg aagacaactt tccattgaag gcccctttca gggccagaac tgtccctccc 111120
accctgcagc tgccctgcct ctgcccatga ggggtgagag tcaggcgacc tcatgccaag 111180
tgtagaaagg ggcagatggg agccccaggt tatgacgtca ccatgctggg tggaggcagc 111240
acgtccaaat ctactaaagg gttaaaggag aaagggtgac ttgacttttc ttgagatatt 111300
ttgggggacg aagtgtggaa aagtggcaga ggacacagtc acagcctccc ttaaatgcca 111360
ggaaagccta gaaaaattgt ctgaaactaa acctcagcca taacaaagac caacacatga 111420
atctccagga aaaaagaaaa agaaaaatgt catacagggt ccatgcacaa gagcctttaa 111480
aatgacccgc tgaagggtgt caggcctcct cctcctggac tggcctgaag gctccacgag 111540
cttttgctga gacctttggg tccctgtggc ctcatgtagt acccagtatg cagtaagtgc 111600
tcaataaatg tttggctaca aaagaggcaa agctggcgga gtctgaagaa tccctcaacc 111660
gtgccggaac agatgctaac accaaaggga aaagagcagg agccaagtca cgtttgggaa 111720
cctgcagagg ctgaaaactg ccgcagattg ctgcaaatca ttgggggaaa aacggaaaac 111780
gtctgttttc ccctttgtgc ttttctctgt tttcttcttt gtgcttttct ctgttttcag 111840
gatttgctac agtgaacata gattgctttg gggccccaaa tggaattatt ttgaaaggaa 111900
aatgcagata atcaggtggc cgcactggag caccagctgg gtaggggtag agattgcagg 111960
caaggaggag gagctgggtg gggtgccagg caggaagagc ccgtaggccc cgccgatctt 112020
gtgggagtcg tgggtggcag tgttccctcc agactgtaaa agggagcacc tggcgggaag 112080
agggaattct tttaaacatc attccagtgc ccgagcctcc tggacctgtt gtcatcttga 112140
ggtgggcctc ccctgggtga ctctagtgtg cagcctggct gagactcagt ggccctgggt 112200
tcttactgct gacacctacc ctcaacctca accactgcgg cctcctgtgc accctgatcc 112260
agtggctcat tttccacttt cagtcccagc tctatcccta tttgcagttt ccaagtgcct 112320
ggtcctcagt cagctcagac ccagccaggc cagcccctgg ttcccacatc ccctttgcca 112380
agctcatccc cgccctgttt ggcctgcggg agtgggagtg tgtccagaca cagagacaaa 112440
ggaccagctt ttaaaacatt ttgttggggc caggtgtggt ggctcacacc taatcccaac 112500
acctggggag gccaaggcag aaggatcact tgagtccagg agttcaagac cagcctgggc 112560
aacataggga gaccctgtct ctacaatttt tttttaatt agctgggcct gttggcactc 112620
tcctgtagtt ccagctactc tagaggctga ggtgggagga ctgcttgagc ctgggaggtc 112680
agggctgcaa tgagccatgt tcacaccact gaacgccagc ctgggcgaga ccctgtatca 112740
aaaaagtaaa gtaaaatgaa tcctgtacgt tatattaagg tgccccaaat tgtacttaga 112800
aggatttcat agttttaaat acttttgtta tttaaaaaat taaatgactg cagcatataa 112860
attaggttct taatggaggg gaaaaagagt acaagaaaag aaataagaat ctagaaacaa 112920
agataagagc agaaataaac cagaaaacac aaccttgcac tcctaactta aaaaaaaaaa 112980
tgaagaaaac acaaccagta aaacaacata taacagcatt aagagctggc tcctggctgg 113040
gcgcggtggc gcatgcctgt aatcccaaca ctttgggagg ccgatgctgg aggatcactt 113100
gagaccagga gttcaaggtt gcagtgagct atgatcatac cactacaccc tagcctgggc 113160
aacacagtga gactgagact ctattaaaaa aaaaatgctg gttccttcct tatttcattc 113220
ctttattcat tcattcagac aacatttatg gggcacttct gagcaccagg ctctgtgcta 113280
agagcttttg cccccagggt ccaggccagg ggacaggggc aggtgagcag agaaacaggg 113340
ccagtcacag cagcaggagg aatgtaggat ggagagcttg gccaggcaag gacatgcagg 113400
gggagcagcc tgcacaagtc agcaagccag agaagacagg cagaccccttg tttgggacct 113460 gttcagtggc ctttgaaagg acagcccccca cccggagtgc tgggtgcagg agctgaagga 113520
ggatagtgga acactgcaac gtggagctct tcagagcaaa agcaaaataa acaactggag 113580
gcagctgggg cagcagaggg tgtgtgttca gcactaaggg gtgtgaagct tgagcgctag 113640
gagagttcac actggcagaa gagaggttgg ggcagctgca agcctctgga catcgcccga 113700
caggacagag ggtggtggac ggtggccctg aagagaggct cagttcagct ggcagtggcc 113760
gtgggagtgc tgaagcaggc aggctgtcgg catctgctgg ggacggttaa gcaggggtga 113820
gggcccagcc tcagcagccc ttcttggggg gtcgctggga aacatagagg agaactgaag 113880
aagcagggag tcccagggtc catgcagggc gagagagaag ttgctcatgt ggggcccagg 113940
ctgcaggatc aggagaactg gggaccctgt gactgccagc ggggagaagg gggtgtgcag 114000
gatcatgccc agggaagggc ccaggggccc aagcatgggg gggcctggtt ggctctgaga 114060
agatggagct aaagtcactt tctcggagga tgtccaggcc aatagttggg atgtgaagac 114120
gtgaagcagc acagagcctg gaagcccagg atggacagaa acctacctga gcagtggggc 114180
tttgaaagcc ttggggcggg gggtgcaata ttcaagatgg ccacaagatg gcaatagaat 114240
gctgtaactt tcttggttct gggccgcagc ctgggtggct gcttccttcc ctgtgtgtat 114300
tgatttgttt ctcttttttg agacagagtc ttgctgggtt gcccaggctg gagtgcagtg 114360
gtgcgatcat agctcactgc agccttgaag tcctgagctc aagagatcct tccacctcag 114420
cctcctgagt agttgggacc acaggcttgc accacagtgc ccaactaatt tcttatattt 114480
tttgtagaga tggggtttca ctgtgtcgcc caggatggtc ttgaactcct gggctcaagt 114540
gatcctcctg cctcagcctc gcaaattgct gggattacag gtgtgagcca ccatgcccga 114600
ccttctcttt ttaagggcgt gtgtgtgtgt gtgtgtgtgt gggcgcactc tcgtcttcac 114660
cttcccccag ccttgctctg tctctaccca gtcacctctg cccatctctc cgatctgttt 114720
ctctctcctt ttacccctct ttcctccctc ctcatacacc actgaccatt atagagaact 114780
gagtattcta aaaatacatt ttatttattt attttgagac agagtctcac tctgtcaccc 114840
aggctggagt gcagtggtgc aatctcggct cactgcaacc tccgcctccc aggttgaagc 114900
aactctcctg cctcagcctc cctagtagct gggattacaa gcacacacca ccatgcctag 114960
caaattttta tatttttagt agaggagggg tgtcaccatg tttgccaagc tggtctcaaa 115020
ctcctggcct caggtgatct gcctaccttg gtctcccaaa gtgctgggat tacaggtgtg 115080
agccaccacg cctgccctta aaaatacatt atatttaata gcaaagcccc agttgtcact 115140
ttaaaaagca tctatgtaga acatttatgt ggaataaata cagtgaattt gtacgtggaa 115200
tcgtttgcct ctcctcaatc agggccaggg atgcaggtga gcttgggctg agatgtcaga 115260
ccccacagta agtggggggc agagccaggc tgggaccctc ctctaggaca gctctgtaac 115320
tctgagaccc tccaggcatc ttttcctgta cctcagtgct tctgaaaaat ctgtgtgaat 115380
caaatcattt taaaggagct tgggttcatc actgtttaaa ggacagtgta aataattctg 115440
aaggtgactc taccctgtta tttgatctct tctttggcca gctgacttaa caggacatag 115500
acaggttttc ctgtgtcagt tcctaagctg atcaccttgg acttgaagag gaggcttgtg 115560
tgggcatcca gtgcccaccc cgggttaaac tcccagcaga gtattgcact gggcttgctg 115620
agcctggtga ggcaaagcac agcacagcga gcaccaggca gtgctggaga caggccaagt 115680
ctgggccagc ctgggagcca actgtgaggc acggacgggg ctgtggggct gtggggctgc 115740
aggcttgggg ccagggaggg agggctgggc tctttggaac agccttgaga gaactgaacc 115800
caaacaaaac cagatcaagg tctagtgaga gcttagggct gctttgggtg ctccaggaaa 115860
ttgattaaac caagtggaca cacaccccca gccccacctc accacagcct ctccttcagg 115920
gtcaaactct gaccacagac atttctcccc tgactaggag ttccctggat caaaattggg 115980
agcttgcaac acatcgttct ctcccttgat ggtttttgtc agtgtctatc cagagctgaa 116040
gtgtaatata tatgttactg tagctgagaa attaaatttc aggattctga tttcataatg 116100
acaaccattc ctcttttctc tcccttctgt aaatctaaga ttctataaac ggtgttgact 116160
taatgtgaca attggcagta gttcaggtct gctttgtaaa taccccttgtg tctattgtaa 116220 aatctcacaa aggcttgttg cctttttttgt ggggttagaa caagaaaaag ccacatggaa 116280
aaaaaatttc tttttgtttt ttttgtttgc ttgttttttt gagacagagt ttcactctgt 116340
cgcccaggct ggagtgcagt ggtgcgatct ccgcccactg caagctccac ctcccgggtt 116400
catgctattc tcctgtctca gcctcccaag tagctgggac tgcaggtgcc cgccaccaca 116460
cctggctaat ttttttgtat ttttagtaga gacggggttt caccgtgtta gccaggatgg 116520
tctcaatctc ctgacctcgt catctgcctg cctcggcctc ccaaagtgct gagattacag 116580
gcgtgagcca ccgtgcccgg ccagaaaaaa acatttctaa gtatgtggca gatactgaat 116640
tattgcttaa tgtcctttga ttcatttgtt taatttcttt aatggattag tacagaaaac 116700
aaagttctct tccttgaaaa actggtaagt tttctttgtc agataaggag agttaaataa 116760
cccatgacat ttcccttttt gcctcggctt ccaggaagct caaagttaaa tgtaatgatc 116820
actcttgtaa ttatcagtgt tgatgccctt cccttcttct aatgttactc tttacatttt 116880
cctgctttat tattgtgtgt gttttctaat tctaagctgt tcccactcct ttctgaaagc 116940
aggcaaatct tctaagcctt atccactgaa aagttatgaa taaaaaatga tcgtcaagcc 117000
tacaggtgct gaggctactc cagaggctga ggccagagga ccacttgagc ccaggaattt 117060
gagacctggg ctgggcagca tagcaagact ctatctccat taaaactatt ttttttattt 117120
taaaaaataa tccgcaaaga aggagtttat gtgggattcc ttaaaatcgg agggtggcat 117180
gaattgattc aaagacttgt gcagagggcg acagtgactc cttgagaagc agtgtgagaa 117240
agcctgtccc acctccttcc gcagctccag cctgggctga ggcactgtca cagtgtctcc 117300
ttgctggcag gagagaattt caacattcac caaaaagtag tattgttttt attaggttta 117360
tgaggctgta gccttgagga cagcccagga caactttgtt gtcacataga tagcctgtgg 117420
ctacaaactc tgagatctag attcttctgt ggctgcttct gacctgagaa agttgcggaa 117480
cctcagcgag cctcacatgg cctccttgtc cttaacgtgg ggacggtggg caagaaaggt 117540
gatgtggcac tagagattta tccatctcta aaggaggagt ggattgtaca ttgaaacacc 117600
agagaaggaa ttacaaagga agaatttgag tatctaaaaa tgtaggtcag gcgctcctgt 117660
gttgattgca gggctattca caatagccaa gatttggaag caacccaagt gtccatcaac 117720
agacaaatgg ataaagaaaa tgtggtgcat atacacaatg gaatactatt cagccatgaa 117780
aaagaatgag aatctgtcat ttgaaacaac atggatggaa ctggaggaca ttatgttaag 117840
tgaaataagc cagacagaag gacagacttc acatgttctc acacatttgt gggagctaaa 117900
aattaaactc atggagatag agagtagaag gatggttacc agaggctgag gagggtggag 117960
gggagcaggg agaaagtagg gatggttaat gggtacaaaa acgtagttag catgcataga 118020
tctagtattg gatagcacag cagggtgacg acagccaaca gtaatttata gtacatttaa 118080
aaacaactaa aagagtgtaa ttggactggc taacatggtg aaaccccgtc tctactaaaa 118140
atacaaaaat tagctgggca tggtggctca cgcctgtaat cccagcactt tgggaggccg 118200
aggcgggccg atcacgaggt caggagatcg agaccatcct agctaacatg gtgaaacccc 118260
gtctctacta caaatacaaa aaaaagaaaa aattagccgg gcatggtggt gggcgcctgt 118320
agtcccagct actcgggagg ctgaggcagg agaatggcgt gaacccggga ggcggagctt 118380
gcagtgagcc gagatcgcgc cactgcactc cagcctgggc gacaaggcaa gattctatct 118440
caaaaaaata aaaataaaat aaaataaaat aataaaataa aataaaataa aataaaataa 118500
ataaaataaa ataaaatgta taattggaat gtttataaca caagaaatga taaatgcttg 118560
aggtgataga taccccattc accgtgatgt gattattgca caatgtatgt ctgtatctaa 118620
atatctcatg taccccacaa gtatatacac ctactatgta cccatataaa tttaaaatta 118680
aaaaattata aaacaaaaat aaataagtaa attaaaatgt aggctggaca ccgtggttca 118740
cgcctgtaat cccagtgctt tgtgaggctg aggtgagaga atcacttgag cccaggagtt 118800

-continued tgagaccggc ctgggtgaca tagcgagacc ccatcatcac aaagaatttt taaaaattag 118860
ctgggcgtgg tagcacatac cggtagttcc agctacttgg gagaccgagg caggaggatt 118920
gcttgagccc aggagtttaa ggctgcagtg agctacgatg gcgccactgc attccagcct 118980
gggtgacaga gtgagagctt gtctctattt taaaaataat aaaaagaata aataaaaata 119040
aattaaaatg taaatatgtg catgttagaa aaaatacacc catcagcaaa aagggggtaa 119100
aggagcgatt tcagtcataa ttggagagat gcagaataag ccagcaatgc agtttctttt 119160
attttggtca aaaaaaataa gcaaaacaat gttgtaaaca cccagtgctg gcagcaatgt 119220
ggtgaggctg gctctctcac cagggctcac agggaaaact catgcaaccc ttttagaaag 119280
ccatgtggag agttgtaccg agaggtttta gaatatttat aactttgacc cagaaattct 119340
attctaggac tctgtgttat gaaaataacc catcatatgg aaaaagctcc tttcagaaag 119400
aggttcatgg gaggctgttt gtattttttt tttctttgca tcaaatccag ctcctgcagg 119460
actgtttgta ttattgaagt acaaagtgga atcaatacaa atgttggata gcaggggaac 119520
aatattcaca aaatggaatg ggacatagta ttaaacatag tgcttctgat gaccgtagac 119580
catagacaat gcttaggata tgatatcact tcttttgttg ttttttgtat tttgagacga 119640
agtctcattc tgtcacccag gctggagttc agtggcgcca tctcagctca ctgcaacctc 119700
catctcccgg gttcaagcta ttctccttcc tcaacctccc gagtagctgg gttgcgcacc 119760
accatgcctg gctaactttt gtatttttag tacagacggg gtttcaccac gttggccagg 119820
ctgctcttga actcctgacg tcaggtgatc caccagcctt gacctcccaa agtgctagga 119880
ttacaggagc cactgtaccc agcctaggat atgatatcac ttcttagagc aagatacaaa 119940
attgcatgtg cacaataatt ctaccaagta taggtataca ggggtagtta tatataaatg 120000
agacttcaag gaaatacaac aaaatgcaat cgtgattgtg ttagggtggt aagaaaacgg 120060
tttttgcttt gatgagctct gtttttttaaa atcgttatat tttctaataa aaatacatag 120120
tcttttgaag gaacataaaa gattatgaag aaatgagtta gatattgatt cctattgaag 120180
attcagacaa gtaaaattaa ggggaaaaaa aacgggatga accagaagtc aggctggagt 120240
tccaacccca gatccgacag cccaggctga tggggcctcc agggcagtgg tttccaccca 120300
gcattctcaa aagagccact gaggtctcag tgccattttc aagatttcgg aagcggcctg 120360
ggcacggctg gtccttcact gggatcacca cttggcaatt atttacacct gagacgaata 120420
aaaaccagag tgctgagatt acaggcatgg tggcttacgc ttgtaatcgg ctttgggaag 120480
ccgaggtggg ctgattgctt gagcccagga gtttcaaact atcctggaca acatagcatg 120540
acctcgtctc tacaaaaaat acaaaaaatt tgccaggtgt ggtggcatgt gcctgtggtc 120600
ccagctactt gggaggctga agtaggagaa tcccctgagc cctgggaagt cgaggctgca 120660
ctgagccgtg atggtgtcac tgcactccag cctgggtgac aaagtgagac cctatctcac 120720
aaagaaaaaa aacaaaacaa aaaacccaaa gcacactgtt tccactgttt ccagagttcc 120780
tgagaggaaa ggtcaccggg tgaggaagac gttctcactg atctggcaga gaaaatgtcc 120840
agtttttcca actccctaaa ccatggtttt ctatttcata gttcttaggc aaattggtaa 120900
aaatcatttc tcatcaaaac gctgatattt tcacacctcc ctggtgtctg cagaaagaac 120960
cttccagaaa tgcagtcgtg ggagacccat ccaggccacc cctgcttatg gaagagctga 121020
gaaaaagccc cacgggagca tttgctcagc ttccgttacg cacctagtgg cattgtgggt 121080
gggagagggc tggtgggtgg atggaaggag aaggcacagc ccccccttgc agggacagag 121140
ccctcgtaca gaagggacac cccacatttg tcttccccac aaagcggcct gtgtcctgcc 121200
tacggggtca gggcttctca aacctggctg tgtgtcagaa tcaccagggg aacttttcaa 121260
aactagagag actgaagcca gactcctaga ttctaattct aggtcagggc taggggctga 121320
gattgtaaaa atccacaggt gattctgatg cccggcaggc ttgagaacag ccgcagggag 121380
ttctctggga atgtgccggt gggtctagcc aggtgtgagt ggagatgccg gggaacttcc 121440
tattactcac tcgtcagtgt ggccgaacac atttttcact tgacctcagg ctggtgaacg 121500
ctcccctctg gggttcaggc ctcacgatgc catccttttg tgaagtgagg acctgcaatc 121560
ccagcttcgt aaagcccgct ggaaatcact cacacttctg ggatgccttc agagcagccc 121620
tctatccctt cagctcccct gggatgtgac tcaacctccc gtcactcccc agactgcctc 121680
tgccaagtcc gaaagtggag gcatccttgc gagcaagtag gcgggtccag ggtggcgcat 121740
gtcactcatc gaaagtggag gcgtccttgc gagcaagcag gcgggtccag ggtggcgtgt 121800
cactcatcct tttttctggc taccaaaggt gcagataatt aataagaagc tggatcttag 121860
caacgtccag tccaagtgtg gctcaaagga taatatcaaa cacgtcccgg gaggcggcag 121920
tgtgagtacc ttcacacgtc ccatgcgccg tgctgtggct tgaattatta ggaagtggtg 121980
tgagtgcgta cacttgcgag acactgcata gaataaatcc ttcttgggct ctcaggatct 122040
ggctgcgacc tctgggtgaa tgtagcccgg ctccccacat tcccccacac ggtccactgt 122100
tcccagaagc cccttcctca tattctagga gggggtgtcc cagcatttct gggtccccca 122160
gcctgcgcag gctgtgtgga cagaataggg cagatgacgg accctctctc cggaccctgc 122220
ctgggaagct gagaataccc atcaaagtct ccttccactc atgcccagcc ctgtccccag 122280
gagccccata gcccattgga agttgggctg aaggtggtgg cacctgagac tgggctgccg 122340
cctcctcccc cgacacctgg gcaggttgac gttgagtggc tccactgtgg acaggtgacc 122400
cgtttgttct gatgagcgga caccaaggtc ttactgtcct gctcagctgc tgctcctaca 122460
cgttcaaggc aggagccgat tcctaagcct ccagcttatg cttagcctgc gccaccctct 122520
ggcagagact ccagatgcaa agagccaaac caaagtgcga caggtccctc tgcccagcgt 122580
tgaggtgtgg cagagaaatg ctgcttttgg cccttttaga tttggctgcc tcttgccagg 122640
agtggtggct cgtgcctgta attccagcac tttgggagac taaggcggga ggttcgcttg 122700
agcccaggag ttcaagacca gcctgggcaa caatgagacc cctgtgtcta caaaaagaat 122760
taaaattagc caggtgtggt ggcacgcacc tgtagtccca gctacttggg aggctgaggt 122820
gggaggattg cctgagtccg ggaggcggaa gttgcaagga gccatgatcg cgccactgca 122880
cttcaaccta ggcaacagag tgagactttg tctcaaaaaa caatcatata ataattttaa 122940
aataaataga tttggcttcc tctaaatgtc cccggggact ccgtgcatct tctgtggagt 123000
gtctccgtga gattcgggac tcagatcctc aagtgcaact gacccacccg ataagctgag 123060
gcttcatcat cccctggccg gtctatgtcg actgggcacc cgaggctcct ctcccaccag 123120
ctctcttggt cagctgaaag caaactgtta acaccctggg gagctggacg tatgagaccc 123180
ttggggtggg aggcgttgat ttttgagagc aatcacctgg ccctggctgg cagtaccggg 123240
acactgctgt ggctccgggg tgggctgtct ccagaaaatg cctggcctga ggcagccacc 123300
cgcatccagc ccagagggtt tattcttgca atgtgctgct gcttcctgcc ctgagcacct 123360
ggatcccggc ttctgccctg aggccccttg agtcccacag gtagcaagcg cttgccctgc 123420
ggctgctgca tggggctaac taacgcttcc tcaccagtgt ctgctaagtg tctcctctgt 123480
ctcccacgcc ctgctctcct gtccccccag tttgtctgct gtgaggggac agaagaggtg 123540
tgtgccgccc ccacccctgc ccgggccctt gttcctggga ttgctgtttt cagctgtttg 123600
agctttgatc ctggttctct ggcttcctca aagtgagctc ggccagagga ggaaggccat 123660
gtgctttctg gttgaagtca agtctggtgc cctggtggag gctgtgctgc tgaggcggag 123720
ctggggagag agtgcacacg ggctgcgtgg ccaacccctc tgggtagctg atgcccaaag 123780
acgctgcagt gcccaggaca tctgggacct ccctggggcc cgcccgtgtg tcccgcgctg 123840
tgttcatctg cgggctagcc tgtgacccgc gctgtgctcg tctgcgggct agcctgtgtc 123900
ccgcgctctg cttgtctgcg gtctagcctg tgacctggca gagagccacc agatgtcccg 123960
ggctgagcac tgccctctga gcaccttcac aggaagccct tctcctggtg agaagagatg 124020
ccagcccctg gcatctgggg gcactggatc cctggcctga gccctagcct ctccccagcc 124080
tgggggcccc ttcccagcag gctggccctg ctccttctct acctgggacc cttctgcctc 124140
ctggctggac cctggaagct ctgcagggcc tgctgtcccc ctccctgccc tccaggtatc 124200
ctgaccaccg gccctggctc ccactgccat ccactcctct cctttctggc cgttccctgg 124260
tccctgtccc agccccccctc cccctctcac gagttacctc acccaggcca gagggaagag 124320
ggaaggaggc cctggtcata ccagcacgtc ctcccacctc cctcggccct ggtccacccc 124380
ctcagtgctg gcctcagagc acagctctct ccaagccagg ccgcgcgcca tccatcctcc 124440
ctgtccccca acgtccttgc cacagatcat gtccgccctg acacacatgg gtctcagcca 124500
tctctgcccc agttaactcc ccatccataa agagcacatg ccagctgaca ccaaaataat 124560
tcgggatggt tccagtttag acctaagtgg aaggagaaac caccacctgc cctgcacctt 124620 gtttttttggt gaccttgata aaccatcttc agccatgaag ccagctgtct cccaggaagc 124680
tccagggcgg tgcttcctcg ggagctgact gataggtggg aggtggctgc cccccttgcac 124740 cctcaggtga ccccacacaa ggccactgct ggaggccctg gggactccag gaatgtcaat 124800
cagtgacctg ccccccaggc cccacacagc catggctgca tagaggcctg cctccaaggg 124860
acctgtctgt ctgccactgt ggagtcccta cagcgtgccc cccacagggg agctggttct 124920
ttgactgaga tcagctggca gctcagggtc atcattccca gagggagcgg tgccctggag 124980
gccacaggcc tcctcatgtg tgtctgcgtc cgctcgagct tactgagaca ctaaatctgt 125040
tggtttctgc tgtgccacct acccaccctg ttggtgttgc tttgttccta ttgctaaaga 125100
caggaatgtc caggacactg agtgtgcagg tgcctgctgg ttctcacgtc cgagctgctg 125160
aactccgctg ggtcctgctt actgatggtc tttgctctag tgctttccag ggtccgtgga 125220
agcttttcct ggaataaagc ccacgcatcg accctcacag cgcctcccct ctttgaggcc 125280
cagcagatac cccactcctg cctttccagc aagatttttc agatgctgtg catactcatc 125340
atattgatca ctttttttctt catgcctgat tgtgatctgt caatttcatg tcaggaaagg 125400
gagtgacatt tttacactta agcgtttgct gagcaaatgt ctgggtcttg cacaatgaca 125460
atgggtccct gtttttccca gaggctcttt tgttctgcag ggattgaaga cactccagtc 125520
ccacagtccc cagctcccct ggggcagggt tggcagaatt tcgacaacac atttttccac 125580
cctgactagg atgtgctcct catggcagct gggaaccact gtccaataag ggcctgggct 125640
tacacagctg cttctcattg agttacaccc ttaataaaat aatcccattt tatccttttt 125700
gtctctctgt cttcctctct ctctgccttt cctcttctct ctcctcctct ctcatctcca 125760
ggtgcaaata gtctacaaac cagttgacct gagcaaggtg acctccaagt gtggctcatt 125820
aggcaacatc catcataaac caggtagccc tgtggaaggt gagggttggg acgggagggt 125880
gcagggggtg gaggagtcct ggtgaggctg gaactgctcc agacttcaga aggggctgga 125940
aaggatattt taggtagacc tacatcaagg aaagtgttga gtgtgaaact tgcgggagcc 126000
caggaggcgt ggtggctcca gctcgctcct gcccaggcca tgctgcccaa gacaaggtga 126060
ggcgggagtg aagtgaaata aggcaggcac agaaagaaag cacatattct cggccgggcg 126120
ctgtggctca cgcctgtaat tccagcactt tgggaggcca aggtgggtgg atcatgaggt 126180
caggagattg agaccatcct ggctaacaca gtgaaacccc gtctctacta aaaatacaaa 126240
aaattagccg ggcgtggtgg tgggcgcctg tagtcccagc tactccggag gctgaggcag 126300
gaaaatggcg tgaacccgga aggcggagct tgcagtgagc ggagtgagca gagatcgcgc 126360
cactgcactc cagcctgggc gacagagcga gactccgtct caaaaaaaaa aagcacatgt 126420
tctcgcttct ttgtgggatc caggagatag agaatagaag gatggttacc agaggctggg 126480
aagggtagtg aggggatggt ggggggatgg tcaatgggta caaaaaaaat agaataagac 126540
ctagtatttg atagtgcaac agggtgacta tagtcaataa taatttaatt gtacatttaa 126600
aaataactaa aagatagccg ggtgcagtgg cttacgtctg taatcccagt actttgggag 126660
gctgaggtgg gcgtttgaga ccagcctggc caacatggtg aaaccccatc tctactaaaa 126720
atacaaaaat tagccaggca tggtggcggg cgcctgtaat cccagctact cgggaggctg 126780
aggcaggaga atcacttgaa cctgggaggc agaggttgca gtgagccgag atcttgccac 126840
tgcactccag cctgggtgac agtgaaactc cgtctcaaaa ataaaaataa aaatacagct 126900
gggcacggtg gctcacgcct gtaatcccag cactttggga ggccgaggcg agcggatcac 126960
aaggtcagga gatatagacc atcctggcta acacggtgaa acccggtctc tactaaaaat 127020
acaaaaaatt agccaggcgt ggtggcaggt gcctatagtc ccagctactc acaaggctga 127080
ggcaggagaa tggcatgaac ctgggaggcg gagcttgcag tgagccgaga ttgtgccact 127140
gcactccagc ctgggcgaga gagtgagact ccgtctcaaa acaaaaacaa aaacaaaaac 127200
aaaaacaaac acacaacaaa aacctaaaag aatataaatg gattgtttgt aacacaaagg 127260
acaaatgttt gaggggatgg ataccccatt ttccatgatg tgattattat acattgtgtg 127320
tctgtatcaa aacatctcat gagccccata aatatataca cctaactatg tacccacaaa 127380
aattaaaaaa atatattttt taaggtgaag agggaggcga gatgctggcc ttaaccccta 127440
acccgttgtt ctccctgcaa gctgtccaca gggcctctca gactcgaggt tcagctatat 127500
ggatgcatga gcttggtccc cagccaacat gggagacact tcaccatcgg cagcagctac 127560
agcacaggaa ccctgggtca ctgccatgtc ccctctgtga ctttgtttaa acagaaaatg 127620
atgctctggg ccggctgtgg tggcccacac ctataatccc agcaccttgg gaggcggggg 127680
tgggcagatt gcctgaggtc aggagttgga gatcagcctg gccgacatgg cgaaacccca 127740
tgtctactaa aaatacaaaa actagccagg catggtggca catgcctgta atcccagcta 127800
cttgggaggc tgaagcagga gaatcacttg aacccaggag gcagaggctg agtgagccaa 127860
gatcgtgcca atgcactcca gcttgggtga gggagtgaga ctccgtctca aaaaaaaaaa 127920
aaaagaaaga aaaagaaaag aaagtgatcc tactggaacc atgcttactc ccctccccac 127980
ctcacactgt gtagaaatta gtgctgtcgg ccaggcgcgg tggctcatgc ctgtaatcgc 128040
agcactttgg gaggccaagg caggcggatc acgaggtcag gagatcaaga ccatcctggc 128100
taacacagtg aaaccctgtc tctactaaaa atacaaaaaa ttagccgggc atggtggcag 128160
gcacctgtag tcccaactac ttgggaggct gaggcaggag aatggcatga acctgggagg 128220
cggagcttgc agtgagccaa gatcgcgcca ctgcatacca gcctaggtga cagagtgaga 128280

```
ctcagcaaaa aaagaaagaa agaaagaaag aaatcagtgc tgtctatact tctttctgca 128340
gtgatggaaa tattctgtat ctgtgctgtc cagtatagta gccactagct acatgtggca 128400
cttgaaacat ggctggtaca gttgaggaag agtggctgcc atatcggacg acacagctat 128460
agattctgtc accccacccc gagagtccag agcggggact tctgccttag gccctattca 128520
gggctgattt ttacttgaac ccttactgtg ggaagagaag gccatgagaa gttcagtcta 128580
gaatgtgact ccttattttc tggctccctt ggacactttg tgggatttag tctccctgtg 128640
gaaagtattc cacaagtggt gccaccaccc cagctgtgag agcagctggg agctgctttt 128700
gtcatctttc cctggaaagt cctgtgggct gtctcttcct catgccttgt cccatgcttg 128760
ggcatggtgt caagcgtcag gagggagaaa gggtccttat ttatttattt agagagggac 128820
ccttcttctg ttcccaggct ggagtgcagt ggtgcgatct cggctcactg caacctccgc 128880
ctcctgggtt caagtgattc tcctgcctca gcctcctgag tagctgagat tacaggcaca 128940
tgccaacatg cctggctaat tttttttttt tttttttttt tttttttttg agatggagtt 129000
gtactctcat tgcccaggct ggaatgtaat ggcacaatct cggctcactg caacctccac 129060
ctcctggatt caagcaattc tcctgtctca gcttcccaag tagctgggat tacaggtgcc 129120
cgccaccatg ctcaactaat ttttgtattt tttttttagt agagacgagg tttcaccatg 129180
ttggtcagac tggtctcaaa ctcctgacct caggtgatcc acctgcctcg gcctcccaaa 129240
gtgctaggat tacaggcatg agccaccacg cccggcctga aagggttctt atttagtgtg 129300
cattttgaca ttcaatttaa ttccaaggtc ttgtggggtc atggtttaca ggatgttgat 129360
atagaaaaga cttcacttaa tgggccgggc gcagtggctc atgcctgtaa tcccagcact 129420
ttgggaggcc gaggcaggca gatcaggagg tcaggagatt gagaccatcc tggctaacac 129480
agtgaaaccc catctctact gaaaatacaa aaaattagct gggcgtggtg gcaggcacct 129540
gtagtcccag ccactcggtt ggctgaggca ggagaatggc atgaacccgg gaggcggagc 129600
ttgcagtgag cagagaccat gccactgcac tccagcctgg gcgacagagc aagactctgt 129660
ctcaagaaaa aaaaaaaaaa aacagacttt acttactgga agccaaccaa tgtatattta 129720
gagtaatttt tcctgggctg agctgtcatt tacttttgca gtatctcaag aagaagagtt 129780
tacagtgtaa atatttgatg cacactttga ttatatagat gaagcaaact attttcaaga 129840
gctttgcaag gacttacttg tatccaaaca ccattctaaa ggagtcttac ctacttctaa 129900
aggctggtct ctacttggaa ccacttgctt ggccctggtt caagtcctgc tgcaaacctg 129960
gaagtcctgt cattgtcttc ttccctccag agcagtggca cccaatctaa tttttgctgt 130020
gccccagcag cccctggcac tttgccctgt agactgcaga cctcatgtaa tgtatgttaa 130080
gtccacagaa ccacagaaga tgatggcaag atgctcttgt gtgtgttgtg ttctaggagg 130140
tggccaggtg gaagtaaaat ctgagaagct tgacttcaag gacagagtcc agtcgaagat 130200
tgggtccctg gacaatatca cccacgtccc tggcggagga aataaaaagg taaaggggggt 130260
agggtgggtt ggatgctgcc cttgggtata tgggcattaa tcaagttgag tggacaaagg 130320
ctggtccagt tcccagagga ggaaaacaga ggcttctgtg ttgactggct ggatgtgggc 130380
cctcagcagc atccagtggg tctccactgc ctgtctcaat cacctggagc tttagcacgt 130440
ttcacacctg ggccccaacc tggagaggct gaccaatggg tctcaggggc agctcggttg 130500
ctggagtttt tgtttttatt tatttttatg tatttaaggc agggtctctg tattagtcca 130560
ttctcacact gctaataaag acatacccaa gactgggtaa tttataaagg aaagaggttt 130620
aatggactca cagttccaca tggctgggga ggcctcaaaa tcatggcgga aggcaaagga 130680
```

gaagcaaagg catttcttac atggcgacag gcaagagagc gtgtgcaggg gaactcccat 130740
ttataaaacc atcagacctc atgagattta ttcactatca tgagaacagc atgggaaaga 130800
cccgccccca tgattcagtt acctcccact gggtccctcc catgacacat ggaattatgg 130860
gagctacaat tcaagatgag atttgggtgg ggacacagcc aaaccatatc agtctccctc 130920
tgtcatccag gctggagtgc actggcatga tctcggctca ctgcagcctc tacctccctg 130980
ggtcaggtga tcttcccacc tcagcctccc aggtagctgg aactacaggt acctgccact 131040
atgcctggct aaatattttg tatttcctgt ggagacgagg ttttgccacg ttgcccaggc 131100
tggtcttgaa ctcctgaggt caagcaatat gcccacctcg gcctcccaag gtgctgggat 131160
tacaggtgtg agccacagtg ctcggcctaa gtcactgcag tttttaaagc tcccaggtga 131220
ttcttcagtg cagtcaaaag tgagaactgg ctgggtgcgg tggctcatgc ctgtaatccc 131280
agcaccttgg gaggcgaagg tgggcagatg gcttgaggtc aggagttcaa gaccagcctg 131340
gccaacatgg taaaacccca tctctactaa aaatacaaaa gttagctggg tgtggtggtg 131400
cgtgcctgta atcccagcta cttgggaggc tgaggcatga gaattgcttg aacccagggg 131460
acagaggttg tagtgagccg agatcgtgcc actgcactcc agcctgggca acagagtgag 131520
attccatctc acaaaaaaaa aaaaaaaagc gagaaccact gtcctaggcc ctgatgtttg 131580
caggcaacta aaaaaggaag tggacatccc cagtcagctg tggcgcacca agaacaagtc 131640
atgggaacat aacctaattt tctaaatggg ttactaggca cttagagcaa aacaatgatg 131700
ccgaaatcct gatttcagca aagcctctgc ctgcctgtct tggaagtatc cacatgaggc 131760
tgctggggcc ttggtgtccc cagcagtttc tagtctctag gtcttgctgt gggtgtctgt 131820
gcagtgaggg tgtgtgtggc gctgggtgag ctctgtctag gcctggcaca ggatgcggtc 131880
tggtagctgc tgcttctctt ctgcagaagc gcagccaagc accctctggg gtttcaggcc 131940
cacacccagc ctgaagttct gggagtggct cactttccaa ccttcagggt ctcccagcag 132000
ctgactgggg agtggtggag ggaaaaggga ttgtattagt ccgttttcac gccgctgatg 132060
aagacatacc cgatactggg cagtctaaaa gatagaggtc tgatggactc acagttccac 132120
gtgactgggg aggcctgaca atcatggtgg aaggtgaaag gcttgtctca cacggtggca 132180
gacaagagaa aagagcttgt gcaggggaac tcccctttat aaaaccatca gatctcggga 132240
gacttattca ctatcatgag aacagcacgg gaaagaccct cctctatgat tcaattacct 132300
cccaccaggt ccctcccaca acatgtagga attgtgggaa ctacaattca agatgacatt 132360
tgggtgggga cacagccaaa ccatatcagg gcgtcccaga aagggtatag ggtctgagac 132420
ccaagtcagc atgagaaagt atgcttctca tggtggccca gttgggtgga agtggcagcc 132480
gggccgtctt tccaccaggc cactcaagta gcagctgaga gacccctgcc ctggccagtc 132540
cccgccctcc cctcttgcca ctgcctctgg ttctgaacag atgggcaccc tcatcttgta 132600
tttgtgatta atgtctaaca atgtagtttt gtgagaaggg tttgctgata cagccttgct 132660
gcagatgctg cgaactgtgg cctggggcag accttacctc cagacacgcc ctgaggcagg 132720
ggagggcact ggcccgtagc tggccgagag ctctcgggtt gcgcgacagg gatacttttc 132780
agcggctggg tcgctatcca aagtgagaaa acgaggaggg accaggaggc tgtccgcctc 132840
aagagatgtg ggggccaggt ccagttatct ggggaagcag taagcttctc tgctgtttct 132900
aaccccaggc ctcccctggt ctaaggcagg gcctcccagc ctcggggcac tttaaagata 132960
tctgggcctg gccccatccc cacagtctga ctgagtgggt ctggataggg cctgagcatt 133020

-continued ggtgatttcc tgggtgaaag gaggcccctc acagtctctg gaagcttctc tgtgttagga 133080
aaagctctgg gcttgactct gctttgaaag tcaagatccg caaatcctct cagcctcagt 133140
ttctccttca gcaagatgaa atggaaatgc tgtacctacg tcccggggtg gttgtgagac 133200
ccaaaaaaga caatgttctg gaaggttcct ggtgcgttgc agtcctctaa gaacctgagt 133260
tagagccacg ctgagtctca gcttcttggc tccttctgtt tcaaactcgt ccatgtgata 133320
gctcaggaag ggtaggcagg gccctgcccc ctactcagaa aacaccatcc tggtcctggg 133380
gatccccgca gcattagtcc cctgttttcc cagtgtattg agaaaaattg ctaacaagca 133440
gtggggcaca ccaccagcct cctgggttcc tttcagtttg gggatttttg gacattccca 133500
ggaatgtctt aaaaaacact tcaaaaaaca ttaacataaa tatttttatc aaagcctgta 133560
ttaaatggtc tttcaagaaa atacagtaac aggtcaggca tggtggctca tgcctgtaac 133620
cccagcactt tgggaggcca aggcaggcag atcacctgaa atcaggagtt caagaccaac 133680
ctggccaaca cagccaaatc ccatctctac aaaaaataca aaaattagct gggtgtggtg 133740
gcacacacct gtagtcccag ctacttggga ggccgaggca ggagaattgc ttgatcccgg 133800
aggcggaggt tgcagtgagc tgagatcgtg ccactgcact ccagcgtggg tgacaaggtg 133860
aatctttgtc tcaaaaaaaa aaaaaaaaaa aagataaaat acagtataca gtaatagaga 133920
acaatccttt tttcaaagta gtgaccccaa atgaacaaaa tatgcatcta gcttaaatgc 133980
gaacctggtt ttctctacgc ccattcaagc ccctgcaata ggggcccttc accccgcatc 134040
catggactcc taaaattata tggaaaatgg ctgtgtgtga gtgtggatgg acatgtgcac 134100
acatattttt ggctttacca gatgctcaaa gagcctagga cccaaaaagg gctgagaatg 134160
accgtgtcgg ccacttcagg gtcatcagga attgctgtgc actgctcact tctccagtga 134220
acactttctg cttctgtgtt tcctggtatc ctttgggact cctggctagg tcatgtgttt 134280
ctctactttc aaaagggctt cagccaggca cgatggcatg agcctgtagt cccagttgct 134340
ctggaggtta aggtgggaag attgcttgag cccaggaatt tgaggccagc ctgggcaagt 134400
agataggtag atgattgata gatagataga tagataaata gatggataga taagtcgcta 134460
gacagtcatc catccaccca tccacacata aaaaggcctt tgtcatgtca tgttttgtgg 134520
cccacctgcc agtgttgccc acagttgctg cccctccaaa ctcatcagtc actggcaaac 134580
aggaggaatg tgtggctcat gtctgggcat cagtggctgt gggagacatc cttgatcttc 134640
tccagcttct ccttccacat tttcctttgc aatctggcaa tatctattaa aataaaatgt 134700
gcatgccttt tgacctaaga gcttcacttc taggacccac ttacacgtgt gtgacatgat 134760
gttcatacgg gtttatttat ctgaggttgt tcatacacac cattgcctgt aatcactaaa 134820
ggcgggagca gcctacacat ccatccacag aggagtagat gccttttggt acatccgtgg 134880
cgacggaata ctaagcagcc tgtgtatcta tacactcaca cgtgtttgtt tatgtgtgga 134940
atatctctgg agggtacaca agaaacttaa aatgatcact gtctctgggg agggtacctg 135000
ggtgcctggg aggcaggtca gggaaggagt gggcacaggt attaccaatt ggaagacaat 135060
aaaaacaaca gctcctggcc aggcgcagtg gctcacgcct gtaatggcag cactctgaga 135120
ggctgaggcg ggcagattgc ttgcgtccag gagttcaaga ccagcctggg caacatagca 135180
aaaccccgtt tctattaaaa atacaaaaaa ttagccaggt gtggtggcat gcacctgtaa 135240
tcccagctac tcgggaggct gaggtgggag aatcacctga gcctgggagg tcaaggctgc 135300
agtgaggtga gattgtgcca ccgcactcta gcctgggcga tagagcaaga ccctgtctca 135360
aaaacaaaca aaaaacagtc cctggcactc tgggccaggc ctggcagggc agttggcagg 135420
gctggtcttt ctctggcact tcatctcacc ctccctccct tcctcttctt gcagattgaa 135480
acccacaagc tgaccttccg cgagaacgcc aaagccaaga cagaccacgg ggcggagatc 135540
gtgtacaagt cgccagtggt gtctggggac acgtctccac ggcatctcag caatgtctcc 135600
tccaccggca gcatcgacat ggtagactcg ccccagctcg ccacgctagc tgacgaggtg 135660
tctgcctccc tggccaagca gggtttgtga tcaggcccct ggggcggtca ataattgtgg 135720
agaggagaga atgagagagt gtggaaaaaa aaagaataat gacccggccc ccgccctctg 135780
cccccagctg ctcctcgcag ttcggttaat tggttaatca cttaacctgc ttttgtcact 135840
cggctttggc tcgggacttc aaaatcagtg atgggagtaa gagcaaattt catctttcca 135900
aattgatggg tgggctagta ataaaatatt taaaaaaaaa cattcaaaaa catggccaca 135960
tccaacattt cctcaggcaa ttccttttga ttcttttttc ttccccctcc atgtagaaga 136020
gggagaagga gaggctctga aagctgcttc tgggggattt caagggactg ggggtgccaa 136080
ccacctctgg ccctgttgtg gggtgtcac agaggcagtg gcagcaacaa aggatttgaa 136140
acttggtgtg ttcgtggagc cacaggcaga cgatgtcaac cttgtgtgag tgtgacgggg 136200
gttggggtgg ggcgggaggc cacgggggag gccgaggcag gggctgggca gaggggagag 136260
gaagcacaag aagtgggagt gggagaggaa gccacgtgct ggagagtaga catccccctc 136320
cttgccgctg ggagagccaa ggcctatgcc acctgcagcg tctgagcggc cgcctgtcct 136380
tggtggccgg gggtgggggc ctgctgtggg tcagtgtgcc accctctgca gggcagcctg 136440
tgggagaagg gacagcgggt aaaaagagaa ggcaagctgg caggagggtg gcacttcgtg 136500
gatgacctcc ttagaaaaga ctgaccttga tgtcttgaga gcgctggcct cttcctccct 136560
ccctgcaggg tagggggcct gagttgaggg gcttccctct gctccacaga aaccctgttt 136620
tattgagttc tgaaggttgg aactgctgcc atgattttgg ccactttgca gacctgggac 136680
tttagggcta accagttctc tttgtaagga cttgtgcctc ttgggagacg tccacccgtt 136740
tccaagcctg ggccactggc atctctggag tgtgtggggg tctgggaggc aggtcccgag 136800
ccccctgtcc ttcccacggc cactgcagtc accccgtctg cgccgctgtg ctgttgtctg 136860
ccgtgagagc ccaatcactg cctatacccc tcatcacacg tcacaatgtc ccgaattccc 136920
agcctcacca ccccttctca gtaatgaccc tggttggttg caggaggtac ctactccata 136980
ctgagggtga aattaaggga aggcaaagtc caggcacaag agtgggaccc cagcctctca 137040
ctctcagttc cactcatcca actgggaccc tcaccacgaa tctcatgatc tgattcggtt 137100
ccctgtctcc tcctcccgtc acagatgtga gccagggcac tgctcagctg tgaccctagg 137160
tgtttctgcc ttgttgacat ggagagagcc ctttcccctg agaaggcctg gccccttcct 137220
gtgctgagcc cacagcagca ggctgggtgt cttggttgtc agtggtggca ccaggatgga 137280
agggcaaggc acccagggca ggcccacagt cccgctgtcc cccacttgca ccctagcttg 137340
tagctgccaa cctcccagac agcccagccc gctgctcagc tccacatgca tagtatcagc 137400
cctccacacc cgacaaaggg gaacacaccc ccttggaaat ggttcttttc ccccagtccc 137460
agctggaagc catgctgtct gttctgctgg agcagctgaa catatacata gatgttgccc 137520
tgccctcccc atctgcaccc tgttgagttg tagttggatt tgtctgttta tgcttggatt 137580
caccagagtg actatgatag tgaaaagaaa aaaaaaaaaa aaaaaggacg catgtatctt 137640
gaaatgcttg taaagaggtt tctaacccac cctcacgagg tgtctctcac ccccacactg 137700
ggactcgtgt ggcctgtgtg gtgccaccct gctggggcct cccaagtttt gaaaggcttt 137760

-continued cctcagcacc tgggacccaa cagagaccag cttctagcag ctaaggaggc cgttcagctg 137820
tgacgaaggc ctgaagcaca ggattaggac tgaagcgatg atgtcccctt ccctacttcc 137880
ccttggggct ccctgtgtca gggcacagac taggtcttgt ggctggtctg gcttgcggcg 137940
cgaggatggt tctctctggt catagcccga agtctcatgg cagtcccaaa ggaggcttac 138000
aactcctgca tcacaagaaa aaggaagcca ctgccagctg gggggatctg cagctcccag 138060
aagctccgtg agcctcagcc acccctcaga ctgggttcct ctccaagctc gccctctgga 138120
ggggcagcgc agcctcccac caagggccct gcgaccacag cagggattgg gatgaattgc 138180
ctgtcctgga tctgctctag aggcccaagc tgcctgcctg aggaaggatg acttgacaag 138240
tcaggagaca ctgttcccaa agccttgacc agagcacctc agcccgctga ccttgcacaa 138300
actccatctg ctgccatgag aaaagggaag ccgcctttgc aaaacattgc tgcctaaaga 138360
aactcagcag cctcaggccc aattctgcca cttctggttt gggtacagtt aaaggcaacc 138420
ctgagggact tggcagtaga aatccagggc ctcccctggg gctggcagct tcgtgtgcag 138480
ctagagcttt acctgaaagg aagtctctgg gcccagaact ctccaccaag agcctccctg 138540
ccgttcgctg agtcccagca attctcctaa gttgaaggga tctgagaagg agaaggaaat 138600
gtggggtaga tttggtggtg gttagagata tgccccccctc attactgcca acagtttcgg 138660
ctgcatttct tcacgcacct cggttcctct tcctgaagtt cttgtgccct gctcttcagc 138720
accatgggcc ttcttatacg gaaggctctg ggatctcccc cttgtggggc aggctcttgg 138780
ggccagccta agatcatggt ttagggtgat cagtgctggc agataaattg aaaaggcacg 138840
ctggcttgtg atcttaaatg aggacaatcc ccccagggct gggcactcct cccctcccct 138900
cacttctccc acctgcagag ccagtgtcct tgggtgggct agataggata tactgtatgc 138960
cggctccttc aagctgctga ctcactttat caatagttcc atttaaattg acttcagtgg 139020
tgagactgta tcctgtttgc tattgcttgt tgtgctatgg ggggaggggg gaggaatgtg 139080
taagatagtt aacatgggca aagggagatc ttggggtgca gcacttaaac tgcctcgtaa 139140 ccctttttcat gatttcaacc acatttgcta gagggaggga gcagccacgg agttagaggc 139200
ccttggggtt tctcttttcc actgacaggc tttcccaggc agctggctag ttcattccct 139260
ccccagccag gtgcaggcgt aggaatatgg acatctggtt gctttggcct gctgccctct 139320
ttcaggggtc ctaagcccac aatcatgcct ccctaagacc ttggcatcct tccctctaag 139380
ccgttggcac ctctgtgcca cctctcacac tggctccaga cacacagcct gtgcttttgg 139440
agctgagatc actcgcttca ccctcctcat ctttgttctc caagtaaagc cacgaggtcg 139500
gggcgagggc agaggtgatc acctgcgtgt cccatctaca gacctgcagc ttcataaaac 139560
ttctgatttc tcttcagctt tgaaaagggt taccctgggc actggcctag agcctcacct 139620
cctaatagac ttagccccat gagtttgcca tgttgagcag gactatttct ggcacttgca 139680
agtcccatga tttcttcggt aattctgagg gtggggggag ggacatgaaa tcatcttagc 139740
ttagctttct gtctgtgaat gtctatatag tgtattgtgt gttttaacaa atgatttaca 139800
ctgactgttg ctgtaaaagt gaatttggaa ataaagttat tactctgatt aaataaggtc 139860
tccattcatg gattccaagg acaagaaagt catatagaat gtctattttt taagttcttt 139920
cccacgcacc cttagataat ttagctcaga acaggaaatg atagtattaa taaaagctgg 139980
acatcaggat taacagctct ctctggggcc ctgaaggtga gagttctcag acttgctcat 140040
ttgcagttgc ttctttgtga tgctggcaaa ccatcctagt cccattcaaa gggcaataca 140100
aagccttgtg gctgacctca cgatgcagca ctcagtttgc aagaccggca ccagtgtatg 140160

-continued

```
caaacctgag aaggttgggg atgaggatat gggatctttc atccctggaa atttagtcca 140220

gaggcctggg gctggagcag aacaccaagc caatcagctt aatgaatggc ttagattcct 140280

gctaggtttg cagagctgcc ttctttcctt tggtacctta ttatagattg aggagtattt 140340

ctgctaaacc aagataggga taaccagata gcatcttcat agcaatgcca caaaggaaaa 140400

caaaaacaaa acagtaatcc atcatattat tccttagtaa ctatgccaag gtcatgatac 140460

tgaatcctta gattgtttca aaatactact tttctttgct cttcctgatg tgtttgccac 140520

cgcaggcaga tgtttaagta aaacagattt taactgcagc tacaaaagca gcaacaggcc 140580

agcaaaagag aagtgctatc tcagagagca tggctttcag agccacaaga gacagcctca 140640

ctggctgttt cagcttgact gccatgcaaa gaagagagca gagggagaac cagcccccacc 140700

cacttattca tcttgtacaa aaaaaaagca cctaccagcc taggctacat agtgagacac 140760

tatctccaca aaaaacccac gaaaactagc tgggtatggt ggcacatgcc tacagtccca 140820

gctactggta aggctgtggt gggaggatct cttgaggcca ggaaggagat ccaggctgca 140880

gtgagccaag attgcaccac tgcactccag tctggacaat cgagcaagat cccatctcaa 140940

acaataaaaa aaaaaagcgt gtaacctcct cagaagaaag atgttataat ctcaggcagc 141000

a                                                                 141001
```

METHODS FOR MODULATING TAU EXPRESSION FOR REDUCING SEIZURE AND MODIFYING A NEURODEGENERATIVE SYNDROME

GOVERNMENTAL RIGHTS

This invention was made with government support under P50AG005681 awarded by the National Institute on Aging and K08NS074194 awarded by the National Institute of Neurological Disorders and Stroke/American Federation for Aging Research. The government has certain rights in the invention.

SEQUENCE LISTING

The present application is being filed along with a Sequence Listing in electronic format. The Sequence Listing is provided as a file entitled BIOL0210WOSEQ.txt created Mar. 14, 2013, which is approximately 436 KB in size. The information in the electronic format of the sequence listing is incorporated herein by reference in its entirety.

FIELD

Provided are methods for treating, preventing, or ameliorating neurodegenerative diseases, including tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome by inhibiting expression of Tau or modulating the splicing of Tau in an animal. Certain embodiments are directed to methods, compounds and compositions for treating, preventing or ameliorating a seizure disorder by inhibiting expression of Tau or modulating the splicing of Tau in an animal.

BACKGROUND

The primary function of Tau is to bind to and stabilize microtubules, which are important structural components of the cytoskeleton involved in mitosis, cytokinesis, and vesicular transport. Tau is found in multiple tissues, but is particularly abundant in axons of neurons. In humans, there are six isoforms of Tau that are generated by alternative splicing of exons 2, 3, and 10. Splicing of exons 2 and 3 at the N-terminus of the protein leads to inclusion of zero, one, or two 29 amino acid acidic domains and is termed 0N, 1N, or 2N Tau respectively. The influence of these domains on Tau function is not fully clear, though may play a role in interactions with the plasma membrane. Inclusion of exon 10 at the C-terminus leads to inclusion of the microtubule binding domain encoded by exon 10. Since there are 3 microtubule binding domains elsewhere in Tau, this Tau isoform (with exon 10 included) is termed 4R Tau, where 'R' refers to the number of repeats of microtubule binding domains. Tau without exon 10 is termed 3R Tau. Since more microtubule binding domains (4R compared with 3R) increases the binding to microtubules, 4R Tau presumably significantly increases microtubule binding and assembly. The ratio of 3R/4R Tau is developmentally regulated, with fetal tissues expressing exclusively 3R Tau and adult human tissues expressing approximately equal levels of 3R/4R Tau. Deviations from the normal ratio of 3R/4R Tau are characteristic of neurodegenerative FTD Tauopathies. It is not known how changing the 3R/4R Tau ratio at a later stage in the adult animal will affect Tau pathogenesis.

Serine-threonine directed phosphorylation regulates the microtubule binding ability of Tau. Hyperphosphorylation promotes detachment of Tau from microtubules. Other post translational modifications of Tau have been described; however the significance of these is unclear. Phosphorylation of Tau is also developmentally regulated with higher phosphorylation in fetal tissues and much lower phosphorylation in the adult. One characteristic of neurodegenerative disorders is aberrantly increased Tau phosphorylation.

The microtubule network is involved in many important processes within the cell including structural integrity needed for maintaining morphology of cells and operating transport machinery. Since binding of Tau to microtubules stabilizes microtubules, Tau is likely to be a key mediator of some of these processes and disruption of normal Tau in neurodegenerative diseases may disrupt some of these key cellular processes.

One of the early indicators that Tau may be important in neurodegenerative syndromes was the recognition that Tau is a key component of neurofibrillary inclusions in Alzheimer's disease. In fact, neurofibrillary inclusions are aggregates of hyperphosphorylated Tau protein. Along with amyloid beta containing plaques, neurofibrillary inclusions are a hallmark of Alzheimer's disease and correlate significantly with cognitive impairment. 95% of Tau accumulations in AD are found in neuronal processes and is termed neuritic dystrophy. The process(es) whereby this microtubule associated protein becomes disengaged from microtubules and forms accumulations of proteins and how this relates to neuronal toxicity is not well understood.

Neuronal Tau inclusions are a pathological characteristic of not only Alzheimer's disease, but also a subset of Frontotemporal dementia (FTD), PSP, and CBD. The link between Tau and neurodegeneration was solidified by the discovery that mutations in the Tau gene cause a subset of FTD. These genetic data have also highlighted the importance of the 3R:4R ratio of Tau. Many of the Tau mutations that cause FTD lead to a change in Tau splicing which leads to preferential inclusion of exon 10, and thus to increased 4R Tau. The overall Tau levels are normal. Whether the Tau isoform change or the amino acid change or both cause neurodegeneration remains unknown. Recent data suggest that PSP may also be associated with an increased 4R:3R Tau ratio and thus may be amenable to a similar splicing strategy.

To help understand the influence of Tau ratios on neurodegeneration, a mouse model based on one of the splicing Tau mutations (N279K) has been generated using a minigene that includes the Tau promoter and the flanking intronic sequences of exon 10. As in humans, these mice demonstrate increased levels of 4R Tau compared with transgenics expressing WT Tau and develop behavioral and motor abnormalities as well as accumulations of aggregated Tau in the brain and spinal cord.

The protein "Tau" has been associated with multiple diseases of the brain including Alzheimer's disease, frontotemporal dementia, progressive supranuclear palsy, corticobasal ganglionic degeneration, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration and others. Tau-associated disorders such as AD are the most common cause of dementia in the elderly. AD affects an estimated 15 million people worldwide and 40% of the population above 85 years of age. AD is characterized by two pathological hallmarks: Tau neurofibrillary inclusions (NFT) and amyloid-β (Aβ) plaques.

In seizure disorders, the brain's electrical activity is periodically disturbed, resulting in some degree of temporary brain dysfunction. Normal brain function requires an orderly, organized, coordinated discharge of electrical impulses. Electrical impulses enable the brain to communicate with the spinal cord, nerves, and muscles as well as within itself. Seizures may result when the brain's electrical activity is disrupted. There are two basic types of seizures; epileptic and nonepileptic. Epileptic seizures have no apparent cause or trigger and occur repeatedly. Nonepileptic seizures are triggered or provoked by a disorder or another condition that irritates the brain. Certain mental disorders can cause seizure symptoms referred to as psychogenic nonepileptic seizures.

Alzheimer's Disease (AD) is known to be a clinical risk factor for late onset seizures. Multiple AD mouse models recapitulate this increased seizure susceptibility. Within the last 5 years, many of these AD models have been studied in the setting of mouse tau knockout (tau−/−). Increased seizure susceptibility was ameliorated in these amyloid-depositing tau knockout lines. Further, tau−/− alone interestingly appeared to be protective against chemically induced seizures.

Anticonvulsants represent the common treatment regime for seizures. However, anticonvulsants are ineffective in a significant percent of people with a seizure disorder and for these individuals, surgery is the only option. Amidst the lack of available treatments for seizure disorders and neurodegenerative diseases, certain methods of the present embodiments provide methods for treating, preventing or ameliorating a seizure disorder and neurodegenerative diseases by inhibiting expression of Tau or modulating the splicing of Tau in an animal.

SUMMARY

Provided herein are methods for modulating levels of Tau mRNA and protein in cells, tissues, and animals. Also provided herein are methods for modulating splicing of Tau mRNA in cells, tissues, and animals. Also provided herein are methods for modulating the expression product of a Tau mRNA in cells, tissues, and animals.

In certain embodiments, modulation can occur in a cell or tissue. In certain embodiments, the cell or tissue is in an animal. In certain embodiments, the animal is human. In certain embodiments, Tau mRNA levels are reduced. In certain embodiments, Tau protein levels are reduced. In certain embodiments, splicing of Tau mRNA is modulated. In certain embodiments, the expression product of a Tau mRNA is modulated. In certain embodiments, exclusion of Tau exon 10 is promoted. In certain embodiments, expression of the 4R isoform of Tau RNA or protein is reduced. In certain embodiments, expression of the 3R isoform of Tau RNA or protein is increased. In certain embodiments, expression of the 4R isoform of Tau RNA or protein is reduced and expression of the 3R isoform of Tau RNA or protein is increased. In certain embodiments, hyperphosphorylated Tau is reduced. Such reduction and modulation can occur in a time-dependent manner or in a dose-dependent manner.

Several embodiments are drawn to methods of reducing or decreasing seizures in a subject. In certain embodiments, methods are provided for reducing the risk for seizure in a subject. In certain embodiments, the seizures are related to neurodegenerative disorders. In certain embodiments, the neurodegenerative disorder is a tau-associated disorder. In certain embodiments, the tau-associated disorder or neurodegenerative disorder is Alzheimer's disease, frontotemporal dementia, progressive supranuclear palsy, corticobasal ganglionic degeneration, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration. Certain embodiments are drawn to a method of decreasing seizures in a subject with a high 4R:3R tau isoform ratio. In certain embodiments, the methods comprise administering an antisense agent to the subject, wherein the agent decreases expression of tau or decreases the 4R:3R tau ratio in the central nervous system of the subject.

Also provided are methods useful for preventing, treating, and ameliorating diseases, disorders, and conditions associated with Tau. In certain embodiments, such diseases, disorders, and conditions associated with Tau are neurodegenerative diseases. In certain embodiments, the neurodegenerative disease is any of Alzheimer's Disease, Fronto-temporal Dementia (FTD), FTDP-17, Progressive Supranuclear Palsy, Chronic Traumatic Encephalopathy, Epilepsy, or Dravet's Syndrome. In certain embodiments, one or more symptoms of a neurodegenerative disease is ameliorated, prevented, or delayed (progression slowed). In certain embodiments, the symptom is memory loss, anxiety, or loss of motor function. In certain embodiments, neurodegenerative function is improved. In certain embodiments, neurofibrillary inclusions are reduced.

Such diseases, disorders, and conditions can have one or more risk factors, causes, or outcomes in common. Certain risk factors and causes for development of a neurodegenerative disease include genetic predisposition and older age.

In certain embodiments, methods of treatment include administering a Tau antisense compound to an individual in need thereof. The antisense compound may inhibit expression of Tau or modulate splicing of Tau. In certain embodiments, the antisense compound is a single-stranded antisense oligonucleotide. In certain embodiments, the single-stranded antisense oligonucleotide is complementary to a Tau nucleic acid.

The present disclosure provides the following non-limiting numbered embodiments:

Embodiment 1

A method of reducing seizures or risk of seizures in an animal comprising administering a Tau-specific inhibitor to the subject, wherein incidence of seizures or severity of seizures is reduced.

Embodiment 2

The method of embodiment 1, wherein the animal is a human.

Embodiment 3

The method of embodiments 1-2, wherein the Tau-specific inhibitor is an antisense compound.

Embodiment 4

A method comprising administering a Tau antisense compound to an animal for treating a Tau associated disease and thereby ameliorating at least one symptom of the Tau associated disease.

Embodiment 5

A method comprising:
(a) identifying an animal having a Tau associated disease; and
(b) administering a Tau antisense compound and thereby ameliorating at least one symptom of the Tau associated disease.

Embodiment 6

The method of embodiments 4-5, wherein the animal is a human.

Embodiment 7

The method of embodiments 4-6, wherein the symptom is any one of incidence of seizures, seizure severity, presence of neurofibrillary inclusions, loss of memory, loss of cognition, decreased motor function, or bradykinesia.

Embodiment 8

The method of embodiments 4-8, wherein the Tau associated disease is a neurodegenerative disease.

Embodiment 9

The method of embodiment 8, wherein the neurodegenerative disease is selected from among Alzheimer's Disease, Fronto-temporal Dementia (FTD), FTDP-17, Progressive Supranuclear Palsy, Chronic Traumatic Encephalopathy, Epilepsy, and Dravet's Syndrome.

Embodiment 10

The method of embodiments 3-9, wherein the antisense compound comprises a single-stranded antisense oligonucleotide complementary to a Tau nucleic acid.

Embodiment 11

The method of embodiments 1-10, wherein expression of Tau RNA or expression of Tau protein is reduced.

Embodiment 12

The method of embodiments 1-10, wherein expression of the 4R isoform of Tau RNA or expression of the 4R isoform of Tau protein is reduced.

Embodiment 13

The method of embodiments 1-10, wherein expression of the 3R isoform of Tau RNA or expression of the 3R isoform of Tau protein is increased.

Embodiment 14

The method of embodiments 1-10, wherein expression of the 4R isoform of Tau RNA is reduced and expression of the 3R isoform of Tau RNA is increased.

Embodiment 15

The method of embodiments 1-10, wherein expression of the 4R isoform of Tau protein is reduced and expression of the 3R isoform of Tau protein is increased.

Embodiment 16

The method of embodiments 10-15, wherein the single-stranded antisense oligonucleotide comprises at least one modification.

Embodiment 17

The method of embodiment 10-16, wherein the single-stranded antisense oligonucleotide is specifically hybridizable to a human Tau nucleic acid.

Embodiment 18

The method of embodiments 10-17, wherein the single-stranded antisense oligonucleotide is at least 75%, at least 80%, at least 85%, at least 90%, or at least 95% complementary to an equal length portion of a human Tau nucleic acid.

Embodiment 19

The method of embodiments 10-18, wherein the single-stranded antisense oligonucleotide is 100% complementary to a human Tau nucleic acid.

Embodiment 20

The method of embodiments 16-19, wherein the single-stranded antisense oligonucleotide comprises at least one modified internucleoside linkage.

Embodiment 21

The method of embodiment 20, wherein each internucleoside linkage of the single-stranded antisense oligonucleotide is a modified internucleoside linkage.

Embodiment 22

The method of embodiments 20-21, wherein the modified internucleoside linkage is a phosphorothioate internucleoside linkage.

Embodiment 23

The method of embodiments 16-22, comprising at least one modified nucleoside.

Embodiment 24

The method of embodiments 16-23, wherein the single-stranded antisense oligonucleotide comprises at least one modified nucleoside having a modified sugar.

Embodiment 25

The method of embodiment 24, wherein the single-stranded antisense oligonucleotide comprises at least one modified nucleoside comprising a bicyclic sugar.

Embodiment 26

The method of embodiment 25, wherein the bicyclic sugar comprises a 4' to 2' bridge selected from among: 4'-(CH2)n-O-2', wherein n is 1 or 2; and 4'-CH2-O—CH2-2'.

Embodiment 27

The method of embodiment 25, wherein the bicyclic sugar comprises a 4'-CH(CH3)-O-2' bridge.

Embodiment 28

The method of embodiment 24, wherein the at least one modified nucleoside having a modified sugar comprises a non-bicyclic 2'-modified sugar moiety.

Embodiment 29

The method of embodiment 28, wherein the 2'-modified sugar moiety comprises a 2'-O-methoxyethyl group.

Embodiment 30

The method of embodiment 28, wherein the 2'-modified sugar moiety comprises a 2'-O-methyl group.

Embodiment 31

The method of embodiment 24, wherein the at least one modified nucleoside having a modified sugar comprises a sugar surrogate.

Embodiment 32

The method of embodiment 31, wherein the sugar surrogate is a morpholino.

Embodiment 33

The method of embodiment 31, wherein the sugar surrogate is a peptide nucleic acid.

Embodiment 34

The method of embodiments 23-33, wherein each nucleoside is modified.

Embodiment 35

The method of embodiments 10-34, wherein the single-stranded antisense oligonucleotide comprises at least one modified nucleobase.

Embodiment 36

The method of embodiment 35, wherein the modified nucleobase is a 5'-methylcytosine.

Embodiment 37

The method of embodiment 16-35, wherein the single-stranded antisense oligonucleotide comprises:

(a) a gap segment consisting of linked deoxynucleosides;

(b) a 5' wing segment consisting of linked nucleosides;

(c) a 3' wing segment consisting of linked nucleosides;

wherein the gap segment is positioned immediately adjacent to and between the 5' wing segment and the 3' wing segment and wherein each nucleoside of each wing segment comprises a modified sugar.

Embodiment 38

The method of embodiment 37, wherein the single-stranded antisense oligonucleotide comprises:

(a) a gap segment consisting of ten linked deoxynucleosides;

(b) a 5' wing segment consisting of five linked nucleosides;

(c) a 3' wing segment consisting of five linked nucleosides;

wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

Embodiment 39

The method of embodiments 10-37, wherein the single-stranded antisense oligonucleotide consists of 15, 16, 17, 18, 19, 20, 21, 22, 23, 24, or 25 linked nucleosides.

Embodiment 40

The method of any preceding embodiment, wherein the administering is parenteral administration.

Embodiment 41

The method of embodiment 40, wherein the parenteral administration is any of injection or infusion.

Embodiment 42

The method of embodiments 40-41, wherein the parenteral administration is any of intrathecal administration or intracerebroventricular administration.

Embodiment 43

A method comprising administering a Tau antisense compound to an animal for treating a Tau associated disease and thereby reducing neurofibrillary inclusions.

Embodiment 44

A method comprising administering a Tau antisense compound to an animal for treating a Tau associated disease and thereby improving neurological function.

Embodiment 45

A method comprising:

(a) identifying an animal having a Tau associated disease; and (b) administering a Tau antisense compound and thereby reducing neurofibrillary inclusions.

Embodiment 46

A method comprising:

(a) identifying an animal having a Tau associated disease; and (b) administering a Tau antisense compound and thereby improving neurological function.

Embodiment 47

The method of embodiments 43-46, wherein the animal is a human.

Embodiment 48

The method of embodiments 43-47, wherein the antisense compound comprises a single-stranded antisense oligonucleotide complementary to a Tau nucleic acid.

Embodiment 49

The method of embodiments 43-48, wherein the Tau associated disease is a neurodegenerative disease.

Embodiment 50

The method of embodiment 49, wherein the neurodegenerative disease is selected from among Alzheimer's Disease, Fronto-temporal Dementia (FTD), FTDP-17, Progressive Supranuclear Palsy, Chronic Traumatic Encephalopathy, Epilepsy, and Dravet's Syndrome.

Embodiment 51

The method of embodiments 43-50, wherein the expression of Tau RNA or expression of Tau protein is reduced.

Embodiment 52

The method of embodiments 43-50, wherein expression of the 4R isoform of Tau RNA or expression of the 4R isoform of Tau protein is reduced.

Embodiment 53

The method of embodiments 43-50, wherein expression of the 3R isoform of Tau RNA or expression of the 3R isoform of Tau protein is increased.

Embodiment 54

The method of embodiments 43-50, wherein expression of the 4R isoform of Tau RNA is reduced and expression of the 3R isoform of Tau RNA is increased.

Embodiment 55

The method of embodiments 43-50, wherein expression of the 4R isoform of Tau protein is reduced and expression of the 3R isoform of Tau protein is increased.

Embodiment 56

The method of embodiments 48-55, wherein the single-stranded antisense oligonucleotide comprises at least one modification.

Embodiment 57

The method of embodiment 48-56, wherein the single-stranded antisense oligonucleotide is specifically hybridizable to a human Tau nucleic acid.

Embodiment 58

The method of embodiments 48-57, wherein the single-stranded antisense oligonucleotide is at least 75%, at least 80%, at least 85%, at least 90%, or at least 95% complementary to an equal length portion of a human Tau nucleic acid.

Embodiment 59

The method of embodiments 48-58, wherein the single-stranded antisense oligonucleotide is 100% complementary to a human Tau nucleic acid.

Embodiment 60

The method of embodiments 56-59, wherein the single-stranded antisense oligonucleotide comprises at least one modified internucleoside linkage.

Embodiment 61

The method of embodiment 60, wherein each internucleoside linkage of the single-stranded antisense oligonucleotide is a modified internucleoside linkage.

Embodiment 62

The method of embodiments 60-61, wherein the modified internucleoside linkage is a phosphorothioate internucleoside linkage.

Embodiment 63

The method of embodiments 56-62, comprising at least one modified nucleoside.

Embodiment 64

The method of embodiments 56-63, wherein the single-stranded antisense oligonucleotide comprises at least one modified nucleoside having a modified sugar.

Embodiment 65

The method of embodiment 64, wherein the single-stranded antisense oligonucleotide comprises at least one modified nucleoside comprising a bicyclic sugar.

Embodiment 66

The method of embodiment 65, wherein the bicyclic sugar comprises a 4' to 2' bridge selected from among: 4'-(CH2)n-O-2', wherein n is 1 or 2; and 4'-CH2-O—CH2-2'.

Embodiment 67

The method of embodiment 65, wherein the bicyclic sugar comprises a 4'-CH(CH3)-O-2' bridge.

Embodiment 68

The method of embodiment 64, wherein the at least one modified nucleoside having a modified sugar comprises a non-bicyclic 2'-modified sugar moiety.

Embodiment 69

The method of embodiment 68, wherein the 2'-modified sugar moiety comprises a 2'-O-methoxyethyl group.

Embodiment 70

The method of embodiment 68, wherein the 2'-modified sugar moiety comprises a 2'-O-methyl group.

Embodiment 71

The method of embodiment 64, wherein the at least one modified nucleoside having a modified sugar comprises a sugar surrogate.

Embodiment 72

The method of embodiment 71, wherein the sugar surrogate is a morpholino.

Embodiment 73

The method of embodiment 71, wherein the sugar surrogate is a peptide nucleic acid.

Embodiment 74

The method of embodiments 63-73, wherein each nucleoside is modified.

Embodiment 75

The method of embodiments 48-74, wherein the single-stranded antisense oligonucleotide comprises at least one modified nucleobase.

Embodiment 76

The method of embodiment 75, wherein the modified nucleobase is a 5'-methylcytosine.

Embodiment 77

The method of embodiment 56-75, wherein the single-stranded antisense oligonucleotide comprises:

(a) a gap segment consisting of linked deoxynucleosides;

(b) a 5' wing segment consisting of linked nucleosides;

(c) a 3' wing segment consisting of linked nucleosides;

wherein the gap segment is positioned immediately adjacent to and between the 5' wing segment and the 3' wing segment and wherein each nucleoside of each wing segment comprises a modified sugar.

Embodiment 78

The method of embodiment 77, wherein the single-stranded antisense oligonucleotide comprises:

(d) a gap segment consisting of ten linked deoxynucleosides;

(e) a 5' wing segment consisting of five linked nucleosides;

(f) a 3' wing segment consisting of five linked nucleosides;

wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

Embodiment 79

The method of embodiments 48-77, wherein the single-stranded antisense oligonucleotide consists of 15, 16, 17, 18, or 19 linked nucleosides.

Embodiment 80

The method of embodiments 48-78, wherein the single-stranded antisense oligonucleotide consists of 20 linked nucleosides.

Embodiment 81

The method of embodiments 48-77, wherein the single-stranded antisense oligonucleotide consists of 21, 22, 23, 24, or 25 linked nucleosides.

Embodiment 82

The method of embodiments 43-82 preceding embodiment, wherein the administering is parenteral administration.

Embodiment 83

The method of embodiment 82, wherein the parenteral administration is any of injection or infusion.

Embodiment 84

The method of embodiments 82-83, wherein the parenteral administration is any of intrathecal administration or intracerebroventricular administration.

Embodiment 85

The method of embodiments 43-84, wherein at least one symptom of a Tau associated disease is ameliorated.

Embodiment 86

The method of embodiments 43-85, wherein at least one symptom of a Tau associated disease is prevented.

Embodiment 87

The method of embodiments 43-86, wherein progression of at least one symptom of a Tau associated disease is slowed.

Embodiment 88

The method of embodiments 85-87, wherein the at least one symptom is any of memory loss, anxiety, loss of motor function, incidence of seizures, severity of seizures, and excitotoxicity.

Embodiment 89

A method of decreasing seizures in a subject with a high 4R:3R tau isoform ratio, the method comprising administering an antisense oligonucleotide to the subject, wherein the method decreases the 4R:3R tau ratio in the central nervous system of the subject.

Embodiment 90

The method of embodiment 89, wherein the high 4R:3R tau isoform ratio in the subject is caused by a splicing defect.

Embodiment 91

The method of embodiment 89, further comprising decreasing the accumulation of aggregated tau in the brain and spinal cord of the subject.

Embodiment 92

The method of embodiment 89, wherein the antisense oligonucleotide is an o methyl oligonucleotide.

Embodiment 93

The method of embodiment 89, wherein the oligonucleotide is administered using a single bolus administration.

Embodiment 94

The method of embodiment 89, wherein the oligonucleotide is administered using a pump.

Embodiment 95

The method of embodiment 89, wherein the total amount of tau in the central nervous system is not changed.

Embodiment 96

A method of modifying a neurodegenerative syndrome in a subject with a high 4R:3R tau isoform ratio, the method comprising administering an antisense oligonucleotide to the central nervous system of the subject, wherein the antisense oligonucleotide decreases the high 4R:3R tau ratio in the central nervous system of the subject.

Embodiment 97

The method of embodiment 89, wherein the high 4R:3R tau isoform ratio in the subject is caused by a splicing defect.

Embodiment 98

The method of embodiment 89, wherein the neurodegenerative syndrome is a neurodegenerative syndrome associated with tau.

Embodiment 99

The method of embodiment 91, wherein the neurodegenerative syndrome neurodegenerative syndrome associated with tau is associated with tau multimerization.

Embodiment 100

The method of embodiment 89, wherein the neurodegenerative syndrome is Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal degeneration, argyrophilic grain disease, supranuclear palsy, corticobasal degeneration, frontotemporal dementia, or frontotemporal lobar degeneration.

Embodiment 101

The method of embodiment 89, wherein the neurodegenerative syndrome is Alzheimer's disease, progressive supranuclear palsy, corticobasal degeneration, or frontotemporal dementia.

Embodiment 102

The method of embodiment 89, wherein modifying a neurodegenerative disease improves the behavioral phenotype of the subject.

Embodiment 103

The method of embodiment 95, wherein the behavioral phenotype of the subject is seizures.

Embodiment 104

The method of embodiment 89, wherein modifying a neurodegenerative disease slows the progression of neurodegenerative disease development in the subject.

Embodiment 105

The method of embodiment 89, wherein modifying a neurodegenerative disease decreases the accumulation of aggregated tau in the brain and spinal cord of the subject.

Embodiment 106

The method of embodiment 89, wherein the antisense oligonucleotide is an o methyl oligonucleotide.

Embodiment 107

The method of embodiment 89, wherein the oligonucleotide is administered using a single bolus administration.

Embodiment 108

The method of embodiment 89, wherein the oligonucleotide is administered using a pump.

Embodiment 109

The method of embodiment 89, wherein the abnormal 4R:3R tau ratio in the central nervous system is decreased without decreasing the total amount of tau in the central nervous system.

Embodiment 110

The method of embodiment 89, wherein the antisense oligo alters the splicing of a nucleic acid encoding tau.

Embodiment 111

A method of reducing seizures or risk of seizures in a subject comprising administering tau-specific inhibitor to the subject, wherein seizures or risk of seizures in the subject is reduced.

Embodiment 112

The method of embodiment 111, wherein the tau-specific inhibitor is a transcriptional inhibitor.

Embodiment 113

The method of embodiment 112, wherein the transcriptional inhibitor is an oligonucleotide.

Embodiment 114

The method of embodiment 113, wherein the oligonucleotide comprises a nucleobase sequence at least 80%, at least 85%, at least 90%, at least 95%, at least 96%, at least 97%, at least 98%, 99% or at least 100% complementary to an equal length portion of a nucleic acid encoding Tau such as any one of SEQ ID NOs: 1-10.

Embodiment 115

The method of embodiment 113 or 114, wherein the oligonucleotide is a modified oligonucleotide.

Embodiment 116

The method of embodiment 113 or 114, wherein the oligonucleotide is an antisense oligonucleotide.

Embodiment 117

The method of any of embodiment 113-115, wherein the oligonucleotide is a single-stranded oligonucleotide.

Embodiment 118

The method of any of embodiments 113-116, wherein the oligonucleotide consists of 12 to 30 linked nucleosides.

Embodiment 119

The method of any of embodiments 113-118, wherein oligonucleotide comprises at least one modified internucleoside linkage.

Embodiment 120

The method of any of embodiments 119, wherein the modified internucleoside linkage is a phosphorothioate internucleoside linkage.

Embodiment 121

The method of any of embodiments 119, wherein each modified internucleoside linkage is a phosphorothioate internucleoside linkage.

Embodiment 122

The method of any of embodiments 113-121, wherein the oligonucleotide comprises at least one modified sugar moiety.

Embodiment 123

The method of embodiment 122, wherein the modified sugar moiety is a bicyclic sugar moiety.

Embodiment 124

The method of embodiment 122, wherein the modified sugar moiety is a 2' substituted sugar moiety.

Embodiment 125

The method of embodiment 124, wherein the 2' substituted sugar moiety is selected from among: 2'-O-methoxyethyl (2'-MOE), 2'-OMe, or 2'-Fl.

Embodiment 126

The method of any of embodiments 113-124, wherein the oligonucleotide comprises at least one modified nucleobase.

Embodiment 127

The method of embodiment 126, wherein the modified nucleobase is a 5-methylcytosine.

Embodiment 128

The method of any of embodiment 113-126, wherein the oligonucleotide is a chimeric oligonucleotide.

Embodiment 129

The method of any of embodiments 113-127, wherein the oligonucleotide comprises: (i) a gap segment consisting of linked deoxynucleosides; (ii) a 5' wing segment consisting of linked nucleosides; (iii) a 3' wing segment consisting of linked nucleosides, wherein the gap segment is positioned immediately adjacent to and between the 5' wing segment and the 3' wing segment and wherein each nucleoside of each wing segment comprises a modified sugar.

Embodiment 130

The method of embodiment 128, wherein the oligonucleotide comprises: (i) a gap segment consisting of ten linked deoxynucleosides; (ii) a 5' wing segment consisting of five linked nucleosides; (iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

Embodiment 131

The method of embodiment 111-130, wherein the inhibitor is administered to the CNS of the subject.

Embodiment 132

The method of embodiment 131, wherein the inhibitor is administered by intrathecal or intracerebral vascular administration.

Embodiment 133

The method of embodiment 131 or 132, wherein the administration is by bolus or infusion.

Embodiment 134

The method of any of embodiments 131-133, wherein the administration is by a pump.

Embodiment 135

A method of reducing seizures or the risk of seizures in a subject comprising administering a tau splice modulating agent to the subject, wherein the seizures or risk of seizures in the subject is reduced.

Embodiment 136

A method of reducing seizures or the risk of seizures in a subject comprising administering an oligonucleotide consists of 12 to 30 linked nucleosides, wherein the oligonucleotide comprises a nucleobase sequence at least 80%, at least 85%, at least 90%, at least 95%, at least 96%, at least 97%, at least 98%, 99% or at least 100% complementary to an equal length portion of a nucleic acid encoding Tau such as any one of SEQ ID NOs:1-10 and, wherein the seizures or risk of seizures in the subject is reduced.

Embodiment 137

The method of embodiment 135, wherein the tau splice modulating agent is an oligonucleotide.

Embodiment 138

The method of embodiment 136-137, wherein the oligonucleotide comprises at least one modified nucleoside.

Embodiment 139

The method of embodiment 138, wherein at least one modified nucleoside comprises a modified sugar moiety.

Embodiment 140

The method of embodiment 139, wherein at least one modified sugar moiety is a 2'-substituted sugar moiety.

Embodiment 141

The method of embodiment 140, wherein the 2'-substitutent of at least one 2'-substituted sugar moiety is selected from among: 2'-OMe, 2'-F, and 2'-MOE.

Embodiment 142

The method of embodiment 140, wherein the 2'-substituent of at least one 2'-substituted sugar moiety is a 2'-MOE.

Embodiment 143

The method of embodiments 139, wherein at least one modified sugar moiety is a bicyclic sugar moiety.

Embodiment 144

The method of embodiment 143, wherein at least one bicyclic sugar moiety is LNA or cEt.

Embodiment 145

The method of embodiment 139, wherein at least one modified sugar moiety is a sugar surrogate.

Embodiment 146

The method of embodiment 145, wherein at least one sugar surrogate is a morpholino.

Embodiment 147

The method of embodiment 145, wherein at least one sugar surrogate is a modified morpholino.

Embodiment 148

The method of embodiments 136-147, wherein the oligonucleotide comprises at least 5 modified nucleosides, each independently comprising a modified sugar moiety.

Embodiment 149

The method of embodiments 136-148, wherein the oligonucleotide comprises at least 10 modified nucleosides, each independently comprising a modified sugar moiety.

Embodiment 150

The method of embodiments 136-499, wherein the oligonucleotide comprises at least 15 modified nucleosides, each independently comprising a modified sugar moiety.

Embodiment 151

The method of embodiments 136-150, wherein each nucleoside of the oligonucleotide is a modified nucleoside, each independently comprising a modified sugar moiety Embodiment 152

The method of embodiments 136-141, wherein the oligonucleotide comprises at least two modified nucleosides comprising modified sugar moieties that are the same as one another.

Embodiment 153

The method of embodiments 136-147, wherein the oligonucleotide comprises at least two modified nucleosides comprising modified sugar moieties that are different from one another.

Embodiment 154

The method of embodiments 136-147, wherein the oligonucleotide comprises a modified region of at least 5 contiguous modified nucleosides.

Embodiment 155

The method of embodiments 136-147, wherein the oligonucleotide comprises a modified region of at least 10 contiguous modified nucleosides.

Embodiment 156

The method of embodiments 136-147, wherein the oligonucleotide comprises a modified region of at least 15 contiguous modified nucleosides.

Embodiment 157

The method of embodiments 136-147, wherein the oligonucleotide comprises a modified region of at least 20 contiguous modified nucleosides.

Embodiment 158

The method of embodiments 154-157, wherein each modified nucleoside of the modified region has a modified sugar moiety independently selected from among: 2'-F, 2'-OMe, 2'-MOE, cEt, LNA, morpholino, and modified morpholino.

Embodiment 159

The method of embodiments 154-158, wherein the modified nucleosides of the modified region each comprise the same modification as one another.

Embodiment 160

The method of embodiment 159, wherein the modified nucleosides of the modified region each comprise the same 2'-substituted sugar moiety.

Embodiment 161

The method of embodiment 160, wherein the 2'-substituted sugar moiety of the modified nucleosides of the region of modified nucleosides is selected from 2'-F, 2'-OMe, and 2'-MOE.

Embodiment 162

The method of embodiment 160, wherein the 2'-substituted sugar moiety of the modified nucleosides of the region of modified nucleosides is 2'-MOE.

Embodiment 163

The method of embodiment 159, wherein the modified nucleosides of the region of modified nucleosides each comprise the same bicyclic sugar moiety.

Embodiment 164

The method of embodiment 163, wherein the bicyclic sugar moiety of the modified nucleosides of the region of modified nucleosides is selected from LNA and cEt.

Embodiment 165

The method of embodiment 159, wherein the modified nucleosides of the region of modified nucleosides each comprises a sugar surrogate.

Embodiment 166

The method of embodiment 165, wherein the sugar surrogate of the modified nucleosides of the region of modified nucleosides is a morpholino.

Embodiment 167

The method of embodiment 165, wherein the sugar surrogate of the modified nucleosides of the region of modified nucleosides is a modified morpholino.

Embodiment 168

The method of embodiments 136-167, wherein the oligonucleotide comprises no more than 4 contiguous naturally occurring nucleosides.

Embodiment 169

The method of embodiments 136-167, wherein each nucleoside of the oligonucleotide is a modified nucleoside.

Embodiment 170

The method of embodiment 169, wherein each modified nucleoside comprises a modified sugar moiety.

Embodiment 171

The method of embodiment 170, wherein the modified nucleosides of the modified oligonucleotide comprise the same modification as one another.

Embodiment 172

The method of embodiment 171, wherein the modified nucleosides of the modified oligonucleotide each comprise the same 2'-substituted sugar moiety.

Embodiment 173

The method of embodiment 172, wherein the 2'-substituted sugar moiety of the modified oligonucleotide is selected from 2'-F, 2'-OMe, and 2'-MOE.

Embodiment 174

The method of embodiment 172, wherein the 2'-substituted sugar moiety of the modified oligonucleotide is 2'-MOE.

Embodiment 175

The method of embodiment 171, wherein the modified nucleosides of the oligonucleotide each comprise the same bicyclic sugar moiety.

Embodiment 176

The method of embodiment 175, wherein the bicyclic sugar moiety is selected from LNA and cEt.

Embodiment 177

The method of embodiment 169, wherein the modified nucleosides of the oligonucleotide each comprises a sugar surrogate.

Embodiment 178

The method of embodiment 177, wherein the sugar surrogate is a morpholino.

Embodiment 179

The method of embodiment 178, wherein the sugar surrogate is a modified morpholino.

Embodiment 180

The method of embodiments 136-179, wherein the oligonucleotide comprises at least one modified internucleoside linkage.

Embodiment 181

The method of embodiments 136-180, wherein each internucleoside linkage is a modified internucleoside linkage.

Embodiment 182

The method of embodiments 178-181, the modified internucleoside linkage is a phosphorothioate internucleoside linkage.

Embodiment 183

The method of embodiments 136-149, wherein each internucleoside linkage is a modified internucleoside linkage and wherein each internucleoside linkage comprises the same modification.

Embodiment 184

The method of embodiment 183, wherein each internucleoside linkage is a phosphorothioate internucleoside linkage.

Embodiment 185

The method of embodiment 135-184, wherein the subject has a high 4R-3R tau isoform ratio.

Embodiment 186

The method of embodiments 135-185, wherein 4R:3R tau ratio is reduced in the central nervous system of the subject.

Embodiment 187

The method of embodiments 185, wherein the high 4R:3R tau isoform ratio in the subject is caused by a splicing defect.

Embodiment 188

The method of embodiments 135-187, wherein the total amount of tau in the central nervous system is not changed.

Embodiment 189

The method of embodiments 111-188, wherein the agent, inhibitor or oligonucleotide is administered to the CNS of the subject.

Embodiment 190

The method of embodiment 189, wherein the inhibitor is administered by intrathecal or intracerebral vascular administration.

Embodiment 191

The method of embodiments 189-190, wherein the administration is by bolus or infusion.

Embodiment 192

The method of embodiments 189-191, wherein the oligonucleotide is administered using a pump.

Embodiment 193

The method of embodiments 111-192, wherein the subject has a tau-associated disease.

Embodiment 194

The method of embodiment 193, wherein the tau-associated disease is selected from among: Alzheimer's disease, progressive supranuclear palsy, dementia pugilistica, frontotemporal dementia, parkinsonism linked to chromosome, LyticoBodig disease, tangle-predominant dementia, ganglioglioma, gangliocytoma, meningioangiomatosis, subacute sclerosing panencephalitis, lead encephalopathy, tuberous sclerosis, HalіervordenSpatz disease, Pick's disease, corticobasal degeneration, argyrophilic grain disease, supranuclear palsy, corticobasal degeneration, frontotemporal dementia, or frontotemporal lobar degeneration.

Embodiment 195

The method of embodiments 111-194 wherein the subject has a seizure disorder.

Embodiment 196

The method of embodiment 195, wherein the seizure disorder is selected from among:epilepsy, meningitis, brain strokes, injury-associated seizures, brain injury, juvenile myoclonic epilepsy, infantile spasms, reflex epilepsy, and febrile seizures.

Embodiment 197

The method of embodiments 111-196 wherein the subject has a neurological disorder.

Embodiment 198

The method of any of the preceding embodiments, wherein the antisense oligonucleotide has the nucleobase sequence of SEQ ID NO: 12.

Embodiment 199

The method of any of the preceding embodiments, wherein the antisense oligonucleotide has the nucleobase sequence of SEQ ID NO: 13.

Embodiment 200

The method of any of the preceding embodiments, wherein the antisense oligonucleotide has the nucleobase sequence of SEQ ID NO: 14.

Embodiment 201

The method of any of the preceding embodiments, wherein the antisense oligonucleotide has the nucleobase sequence of SEQ ID NO: 15.

Embodiment 202

The method of any of the preceding embodiments, wherein the antisense oligonucleotide has the nucleobase sequence of SEQ ID NO: 16.

Embodiment 203

The method of any of the preceding embodiments, wherein the antisense oligonucleotide has the nucleobase sequence of SEQ ID NO: 17.

Embodiment 204

The method of any of the preceding embodiments, wherein the antisense oligonucleotide has the nucleobase sequence of SEQ ID NO: 18.

Embodiment 205

An antisense oligonucleotide comprising 20 linked modified nucleosides and having the sequence of SEQ ID NO: 12, wherein each internucleoside linkage is a phosphorothioate linkage and each modified nucleoside comprises a 2'-O-methoxyethyl group.

Embodiment 206

An antisense oligonucleotide comprising 20 linked modified nucleosides and having the sequence of SEQ ID NO: 13, wherein each internucleoside linkage is a phosphorothioate linkage and each modified nucleoside comprises a 2'-O-methoxyethyl group.

Embodiment 207

An antisense oligonucleotide comprising 20 linked modified nucleosides and having the sequence of SEQ ID NO: 14, wherein each internucleoside linkage is a phosphorothioate linkage and each modified nucleoside comprises a 2'-O-methoxyethyl group.

Embodiment 208

An antisense oligonucleotide comprising 18 linked modified nucleosides and having the sequence of SEQ ID NO: 15, wherein each internucleoside linkage is a phosphorothioate linkage and each modified nucleoside comprises a 2'-O-methoxyethyl group.

Embodiment 209

An antisense oligonucleotide comprising 18 linked modified nucleosides and having the sequence of SEQ ID NO: 16, wherein each internucleoside linkage is a phosphorothioate linkage and each modified nucleoside comprises a 2'-O-methoxyethyl group.

Embodiment 210

An antisense oligonucleotide comprising 18 linked modified nucleosides and having the sequence of SEQ ID NO: 17, wherein each internucleoside linkage is a phosphorothioate linkage and each modified nucleoside comprises a 2'-O-methoxyethyl group.

Embodiment 211

An antisense oligonucleotide comprising 18 linked modified nucleosides and having the sequence of SEQ ID NO: 18, wherein each internucleoside linkage is a phosphorothioate linkage and each modified nucleoside comprises a 2'-O-methoxyethyl group.

DETAILED DESCRIPTION

Figure 1:
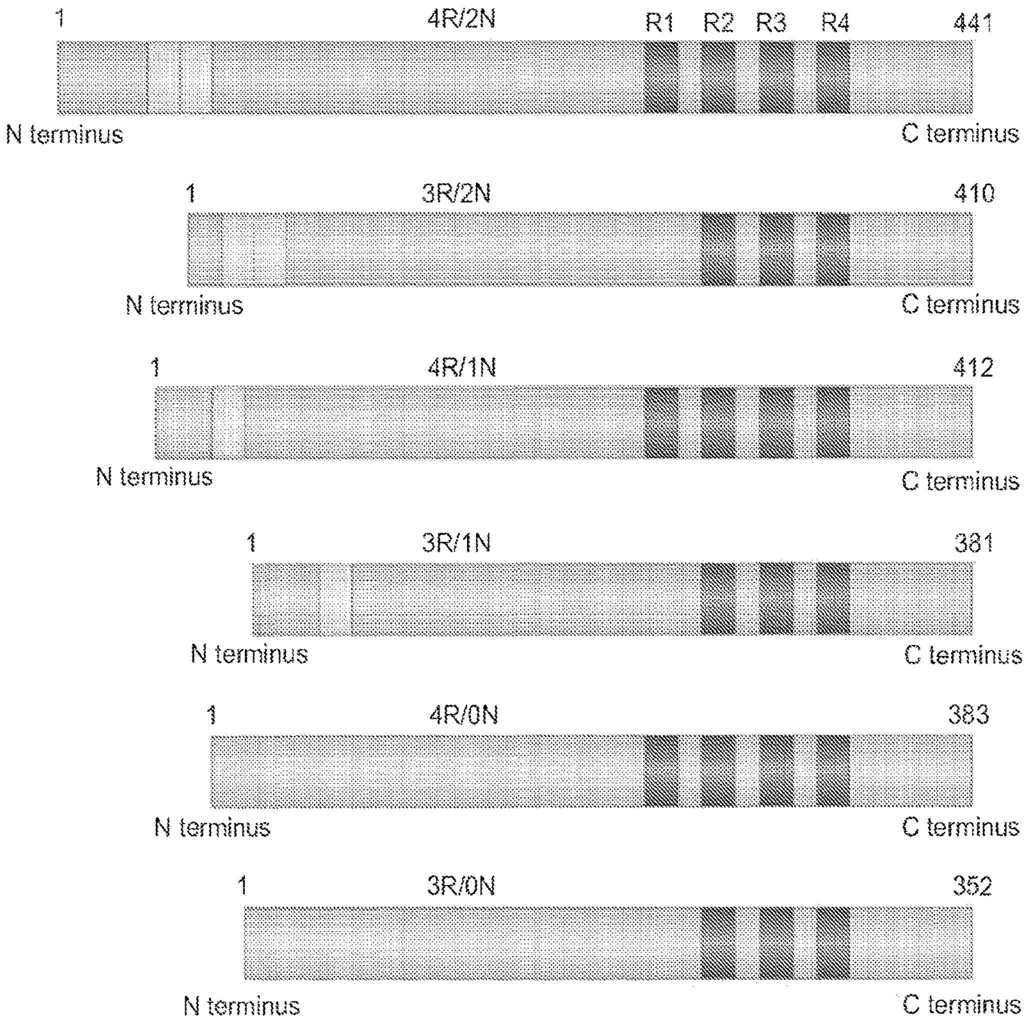
FIG. 1 depicts a graphical representation of Tau isoforms. The isoforms can differ from each other in the number of tubulin-binding domains (three or four repeats located in the C-terminal half of the protein) and are referred to as 3R or 4R Tau isoforms, respectively. They can also differ in the presence or absence of either one or two 29-amino-acid-long, highly acidic inserts at the N-terminal portion of the protein (the projection domain). Between the projection domain and the microtubule-binding domain lies a basic proline-rich region.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. Where permitted, all documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Treatment of Neurodegenerative Syndrome and Seizures

A method of modifying neurodegenerative disease has been developed. Using the methods of the invention, it is now possible to alter the ratio of tau isoforms associated with multiple diseases of the brain. Advantageously, the invention provides a method of bypassing the blood brain barrier to specifically target the generation of certain tau isoforms in the central nervous system, may be administered for an extended period of time using proven technology, and has been demonstrated to provide widespread distribution of therapy throughout the brain and spinal cord where it is most efficient.

I. Method

The present invention provides a method of modifying a neurodegenerative syndrome in a subject by administering an antisense oligonucleotide to the central nervous system. Generally speaking, the antisense oligonucleotide alters splicing of the nucleic acid encoding tau and decreases the abnormal 4R:3R tau ratio in the central nervous system of the subject.

(a) subject

According to the invention, the subject may be any subject that expresses 3R and 4R isoforms of tau. In some embodiments, a subject is a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In an exemplary embodiment, the subject may be a human.

The subject may be suffering from a neurodegenerative syndrome or may be at risk of developing a neurodegenerative syndrome. In some embodiments, the subject may be suffering from a neurodegenerative syndrome. In other embodiments, the subject may be at risk of developing a neurodegenerative syndrome. Neurodegenerative syndromes are as described further below.

(b) Neurodegenerative Syndrome

The method of the invention comprises modifying a neurodegenerative syndrome. In some embodiments, a neurodegenerative syndrome may be any neurodegenerative syndrome associated with tau. Non limiting examples of a neurodegenerative disorder associated with tau may include Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, supranuclear palsy, corticobasal degeneration, frontotemporal dementia, or frontotemporal lobar degeneration. In some embodiments, the method of the invention comprises modifying frontotemporal dementia (FTD). In other embodiments, the method of the invention comprises modifying Alzheimer's disease (AD). In yet other embodiments, the method of the invention comprises modifying progressive supranuclear palsy. In other embodiments, the method of the invention comprises modifying corticobasalganglionic degeneration.

As used herein, the term "modifying a neurodegenerative syndrome" may refer to curing the neurodegenerative syndrome, slowing the course of development of the syndrome, reversing the course of the syndrome, or improving the behavioral phenotype of a subject having a neurodegenerative syndrome. In some embodiments, the method of the invention modifies a neurodegenerative syndrome by curing the neurodegenerative syndrome. In other embodiments, the method of the invention modifies a neurodegenerative syndrome by slowing the progression of the syndrome.

In yet other embodiments, the method of the invention modifies a neurodegenerative syndrome by improving the behavioral phenotype of a subject having a neurodegenerative syndrome. For instance, the symptoms for subjects suffering from Alzheimer's disease may be the mild early symptoms associated with the neurodegenerative syndrome such as mild forgetfulness of recent events, activities, the names of familiar people or things, and the inability to solve simple math problems. The symptoms may also be the moderate symptoms associated with the neurodegenerative syndrome such as forgetting how to do simple tasks such as grooming, speaking, understanding, reading, or writing. Alternatively, the symptoms may be the severe symptoms associated with the neurodegenerative syndrome such as becoming anxious or aggressive, and wandering away from home. Subjects with AD may also have an increased risk of seizures. The symptoms for subjects suffering from progressive supranuclear palsy may include loss of balance, lunging forward when mobilizing, fast walking, bumping into objects or people, falls, changes in personality, general slowing of movement, visual symptoms, dementia (typically including loss of inhibition and ability to organize information), slurring of speech, difficulty swallowing, and difficulty moving the eyes, particularly in the vertical direction, poor eyelid function, contracture of the facial muscles, a backward tilt of the head with stiffening of the neck muscles, sleep disruption, urinary incontinence and constipation. The symptoms for subjects suffering from FTD may include personality changes, cognitive impairment, and motor symptoms. The symptoms for subjects suffering from corticobasalganglionic degeneration are similar to symptoms in patients suffering from FTD and Parkinson's disease and may include shaking, rigidity, slowness of movement and difficulty with walking and gait, cognitive and behavioural problems, dementia, sensory, sleep and emotional problems. In preferred embodiments, the method of the invention modifies a neurodegenerative syndrome by decreasing the risk of seizures.

(c) Differential Splicing in Tau

The invention describes a method of modifying a neurodegenerative syndrome by altering the splicing of a nucleic acid encoding tau. Tau is a protein found in multiple tissues, but is particularly abundant in axons of neurons. The primary function of tau is to bind to and stabilize microtubules, which are important structural components of the cytoskeleton involved in mitosis, cytokinesis and vesicular transport. In humans, there are six isoforms of tau that are generated by alternative splicing of exons 2, 3, and 10. Splicing of exons 2 and 3 at the N-terminus of the protein leads to inclusion of zero, one or two 29 amino acid, acidic domains and is termed 0N, 1N, or 2N tau respectively. Inclusion of exon 10 at the C-terminus leads to inclusion of the microtubule binding domain encoded by exon 10. Since there are 3 mictrotubule binding domains elsewhere in tau, this tau isoform (with exon 10 included) is termed 4R tau, where R refers to the number of repeats of microtubule binding domains. (FIG. 1). Tau without exon 10 is termed 3R tau. In healthy subjects, the ratio of 3R:4R tau is developmentally regulated, with fetal tissues expressing almost exclusively 3R tau and adult human tissues expressing approximately equal levels of 3R/4R tau. Deviations from the normal ratio of 3R/4R tau are characteristic of neurodegenerative syndromes such as FTD tauopathies. In essence, the method decreases the 4R:3R tau ratio in the central nervous system of the subject.

The 4R:3R tau ratio in the central nervous system of the subject may be normal, low or high. As used herein, a "normal 4R:3R tau ratio" in the central nervous system signifies a 4R:3R tau ratio in the central nervous system that is substantially the same as the 4R:3R tau ratio in the central nervous system of a subject from the same species and of approximately the same age not suffering from a neurodegenerative disease. In some embodiments, the method decreases the normal 4R:3R tau ratio in the central nervous system of a subject. In other embodiments, the method decreases an low 4R:3R tau ratio in the central nervous system of a subject.

In preferred embodiments, the method decreases a high 4R:3R tau ratio in the central nervous system of a subject. In exemplary embodiments, the method decreases a high 4R:3R tau ratio caused by a defect in splicing of the nucleic acid encoding tau in the subject. Defects in splicing of the nucleic acid encoding tau in the subject may be caused, for instance, by genetic mutations altering the splicing of the nucleic acid encoding tau and leading to a high 4R:3R tau ratio. A mutation may be either a substitution mutation or a deletion mutation which creates a new, aberrant, splice element. Non-limiting examples of genetic mutations that may alter the splicing of the nucleic acid encoding tau and lead to a high 4R:3R tau ratio may include N279K, P301S, 280, L284L, N296H, N296N, 296N, P301S, G303V, E10+11, E10+12, E10+13, E+10+14 and E10+16, and E10+19.

(d) Antisense Oligonucleotide

A method of the invention decreases the 4R:3R tau ratio in the central nervous system of a subject by altering the splicing of a nucleic acid encoding tau using an antisense oligonucleotide. An antisense oligonucleotide is a single stranded ribonucleic acid or deoxyribonucleic acid complementary to a chosen sequence. Antisense oligonucleotides may target a specific, complementary, coding or non-coding, nucleic acid. Depending on the antisense oligonucleotide used, the binding of the oligonucleotide to its target nucleic acid sequence may or may not activate RNAse H. In some embodiments, the antisense oligonucleotide activates RNAse H, which degrades the target nucleic acid. In preferred embodiments, the antisense oligonucleotide does not activate RNAse H. In an exemplary embodiment, the antisense oligonucleotide of the invention is complementary to the nucleic acid sequence encoding tau, does not activate RNAse H, and disrupts the splicing of the nucleic acid encoding tau to reduce the 4R:3R tau ratio.

Methods of making antisense oligonucleotides which do not activate RNase H are known in the art. See, e.g., U.S. Pat. No. 5,149,797 incorporated herein by reference. Such antisense oligonucleotides may contain one or more structural modification which sterically hinders or prevents binding of RNase H to a duplex molecule comprising the oligonucleotide, but does not substantially hinder or disrupt duplex formation. Antisense oligonucleotides that do not activate RNAse H may include oligonucleotides wherein at least one, two or more of the internucleotide bridging phosphate residues are modified phosphates, such as methyl phosphonates, methyl phosphonothioates, phosphoromorpholidates, phosphoropiperazidates and phosphoramidates. For instance, every other one of the internucleotide bridging phosphate residues may be a modified phosphate, contain a 2' loweralkyl moiety (e.g., C1-C4, linear or branched, saturated or unsaturated alkyl, such as methyl, ethyl, ethenyl, propyl, 1-propenyl, 2-propenyl, and isopropyl) or a combination thereof. In preferred embodiments, the antisense oligonucleotide of the invention that does not activate RNAse H, and disrupts the splicing of the nucleic acid encoding tau to reduce the 4R:3R tau ratio is a 2'-O-(2-methoxyethyl) (MOE)-modified antisense oligonucleotide.

Other methods of modifying an oligonucleotide to hinder binding of RNAse H may be found in P. Furdon et al., Nucleic Acids Res. 17, 9193-9204 (1989); S. Agrawal et al., Proc. Natl. Acad. Sci. USA 87, 1401-1405 (1990); C. Baker et al., Nucleic Acids Res. 18, 3537-3543 (1990); B. Sproat et al., Nucleic Acids Res. 17, 3373-3386 (1989); R. Walder and J. Walder, Proc. Natl. Acad. Sci. USA 85, 5011-5015 (1988) the disclosures of all of which are incorporated herein, in their entirety, by reference.

The antisense oligonucleotide of the invention may be a deoxyribonucleotide oligonucleotide or a ribonucleotide oligonucleotide. The antisense oligonucleotide may be any length provided it binds selectively to the intended location. In general, the antisense oligonucleotide may be from 8, 10 or 12 nucleotides in length up to 20, 30, or 50 nucleotides in length.

The antisense oligonucleotide of the invention may disrupt the splicing of the nucleic acid encoding tau to reduce the 4R:3R tau ratio. The splicing process is a series of reactions, mediated by splicing factors, which is carried out on RNA after transcription but before translation, in which the intron(s) are removed, and the exons joined together sequentially so that the protein may be translated. Each intron is defined by a 5' splice site, a 3' splice site, and a branch point situated there between. An antisense oligonucleotide may block these splice elements when the oligonucleotide either fully or partially overlaps the element, or binds to the pre-mRNA at a position sufficiently close to the element to disrupt the binding and function of the splicing factors which would ordinarily mediate the particular splicing reaction which occurs at that element. The antisense oligonucleotide may block a variety of different splice elements to carry out the instant invention. For instance, the antisense oligonucleotide may block a mutated element, a cryptic element, or a native element; it may block a 5' splice site, a 3' splice site, or a branch point.

The term "antisense oligonucleotide" includes the physiologically and pharmaceutically acceptable salts thereof:

i.e., salts that retain the desired biological activity of the parent compound and do not impart undesired toxicological effects thereto. Examples of such salts are (a) salts formed with cations such as sodium, potassium, NH4+, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

(e) Administration

Antisense oligonucleotides of the invention may be administered to a subject by several different means. For instance, oligonucleotides may generally be administered parenteraly, intraperitoneally, intravascularly, or intrapulmonarily in dosage unit formulations containing conventional nontoxic pharmaceutically acceptable carriers, adjuvants, and vehicles as desired. In a preferred embodiment, the oligonucleotide may be administered parenterally. The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Delivery methods are preferably those that are effective to circumvent the blood-brain barrier and are effective to deliver agents to the central nervous system. For example, delivery methods may include the use of nanoparticles. The particles may be of any suitable structure, such as unilamellar or plurilamellar, so long as the antisense oligonucleotide is contained therein. Positively charged lipids such as N-[1-(2,3-dioleoyloxi)propyl]-N, N,N-trimethyl-amoniummethylsulfate, or "DOTAP," are particularly preferred for such particles and vesicles. The preparation of such lipid particles is well known in the art. See, e.g., U.S. Pat. No. 4,880,635 to Janoff et al.; U.S. Pat. No. 4,906,477 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

In one preferred embodiment, the oligonucleotide may be administered in a bolus directly into the central nervous system. The oligonucleotides may be administered to the subject in a bolus once, or multiple times. In some preferred embodiments, the oligonucleotides may be administered once. In other preferred embodiments, the oligonucleotides may be administered multiple times. When administered multiple times, the oligonucleotides may be administered at regular intervals or at intervals that may vary during the treatment of a subject. In some embodiments, the oligonucleotides may be administered multiple times at intervals that may vary during the treatment of a subject. In some embodiments, the oligonucleotides may be administered multiple times at regular intervals.

In another preferred embodiment, the oligonucleotide may be administered by continuous infusion into the central nervous system. Non-limiting examples of methods that may be used to deliver the oligonucleotide into the central nervous system by continuous infusion may include pumps, wafers, gels, foams and fibrin clots. In a preferred embodiment, the oligonucleotide may be delivered into the central nervous system by continuous infusion using an osmotic pump. An osmotic minipump contains a high-osmolality chamber that surrounds a flexible, yet impermeable, reservoir filled with the targeted delivery composition-containing vehicle. Subsequent to the subcutaneous implantation of this minipump, extracellular fluid enters through an outer semi-permeable membrane into the high-osmolality chamber, thereby compressing the reservoir to release the targeted delivery composition at a controlled, pre-determined rate. The targeted delivery composition, released from the pump, may be directed via a catheter to a stereotaxically placed cannula for infusion into the cerebroventricular space. In an exemplary embodiment, the oligonucleotide may be delivered into the central nervous system by continuous infusion using a pump as described in the Examples.

One of skill in the art will recognize that the amount and concentration of the composition administered to a subject will depend in part on the subject, the reason for the administration, and the method of administration. In some embodiments, when the oligonucleotide is administered in a bolus into the central nervous system, the oligonucleotide may be administered to the subject in an amount of about 0.1, 0.2, 0.3, 0.4, 0.5, 1, 1.5, 2, 2.5, 3, 3.5, 4, 4.5, 5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/kg or more.

In other embodiments, when the oligonucleotide is administered by continuous infusion using a pump into the central nervous system, the oligonucleotide may be administered to the subject in an amount of about 0.1, 0.2, 0.3, 0.4, 0.5, 1, 1.5, 2, 2.5, 3, 3.5, 4, 4.5, 5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/kg or more. In some embodiments, the oligonucleotide may be administered by continuous infusion for 1, 2, 3, 4, 5, 6, 7, 8, 9, 10, 11, 12, 13, 14, 15, 16, 178, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 days or longer. In one embodiment, the oligonucleotide may be administered by continuous infusion for 20, 21, 22, 23, 24, 25, 26, 27, 28, 29, 30, 31, 32, 33, 34, 35 days or longer. In another embodiment, the oligonucleotide may be administered by continuous infusion for 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 days or longer. In yet another embodiment, the oligonucleotide may be administered by continuous infusion for 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 days or longer. Longer continuous infusions of the antisense oligonucleotide may also be envisioned using existing pump technology as is known in the art.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-O$(CH_2)_2$—$OCH_3$ and MOE) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Tau", it is implied that the Tau levels are inhibited within a range of 63% and 77%.

"Acceptable safety profile" means a pattern of side effects that is within clinically acceptable limits.

"Active pharmaceutical agent" means the substance or substances in a pharmaceutical composition that provide a therapeutic benefit when administered to an individual. For example, in certain embodiments an antisense oligonucleotide targeted to Tau is an active pharmaceutical agent.

"Active target region" means a target region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Agent" means an active substance that can provide a therapeutic benefit when administered to an animal. "First Agent" means a therapeutic compound described herein. For example, a first agent can be an antisense oligonucleotide targeting Tau. "Second agent" means a second therapeutic compound described herein (e.g. a second antisense oligonucleotide targeting Tau) and/or a non-Tau therapeutic compound.

"Amelioration" or "ameliorate" or "ameliorating" refers to a lessening of at least one indicator, sign, or symptom of a disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, $F_{ab}$ region, and $F_c$ region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing. Antisense mechanisms include, without limitation, RNase H mediated antisense; RNAi mechanisms, which utilize the RISC pathway and include, without limitation, siRNA, ssRNA, and microRNA mechanisms; and occupancy based mechanisms, including, without limitation uniform modified olionucleotides. Certain antisense compounds may act through more than one such mechanism and/or through additional mechanisms.

"Antisense oligonucleotide" (also "oligo") means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon on the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Constrained ethyl nucleoside" (also cEt nucleoside) means a nucleoside comprising a bicyclic sugar moiety comprising a 4'-$CH(CH_3)$—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Complementarity" means the capacity for pairing between nucleobases of a first nucleic acid and a second nucleic acid.

"Comply" means the adherence with a recommended therapy by an individual.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Cure" means a method or course that restores health or a prescribed treatment for an illness.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dosage unit" means a form in which a pharmaceutical agent is provided, e.g. pill, tablet, or other dosage unit known in the art.

"Dose" means a specified quantity of a pharmaceutical agent provided in a single administration, or in a specified time period. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In other embodiments, the pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Duration" means the period of time during which an activity or event continues. In certain embodiments, the duration of treatment is the period of time during which doses of a pharmaceutical agent are administered.

"Effective amount" in the context of modulating an activity or of treating or preventing a condition means the administration of that amount of active ingredient to a subject in need of such modulation, treatment or prophylaxis, either in a single dose or as part of a series, that is effective for modulation of that effect, or for treatment or prophylaxis or improvement of that condition. The effective amount will vary depending upon the health and physical condition of the subject to be treated, the taxonomic group of subjects to be treated, the formulation of the composition, the assessment of the medical situation, and other relevant factors.

"Efficacy" means the ability to produce a desired effect.

"Excitotoxicity" the pathological process by which nerve cells are damaged and killed by excessive stimulation by neurotransmitters.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Fully modified motif" refers to an antisense compound comprising a contiguous sequence of nucleosides wherein essentially each nucleoside is a sugar modified nucleoside having uniform modification.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Tau nucleic acid" or Tau DNA" means any nucleic acid encoding Tau. For example, in certain embodiments, a Tau nucleic acid includes, without limitation, any viral DNA sequence encoding a Tau genome or portion thereof, any RNA sequence transcribed from a DNA sequence including any mRNA sequence encoding a Tau protein.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Identifying an animal having a Tau-related disease or disorder" means identifying an animal having been diagnosed with a Tau-related disease or disorder; or, identifying an animal having any symptom of Tau-related disease or disorder including, but not limited to a neurodegenerative disorder associated with Tau.

"Immediately adjacent" means there are no intervening elements between the immediately adjacent elements.

"Individual" means a human or non-human animal selected for treatment or therapy.

"Individual compliance" means adherence to a recommended or prescribed therapy by an individual.

"Induce", "inhibit", "potentiate", "elevate", "increase", "decrease" or the like, e.g., which denote quantitative differences between two states, refer to at least statistically significant differences between the two states. For example, "an amount effective to inhibit the activity or expression of Tau" means that the level of activity or expression of Tau in a treated sample will differ statistically significantly from the level of Tau activity or expression in untreated cells. Such terms are applied to, for example, levels of expression, and levels of activity.

"Inhibiting Tau" means reducing the level or expression of a Tau mRNA, DNA and/or protein. In certain embodiments, Tau is inhibited in the presence of an antisense compound targeting Tau, including an antisense oligonucleotide targeting Tau, as compared to expression of Tau mRNA, DNA and/or protein levels in the absence of a Tau antisense compound, such as an antisense oligonucleotide.

"Inhibiting the expression or activity" refers to a reduction, blockade of the expression or activity and does not necessarily indicate a total elimination of expression or activity.

"Internucleoside linkage" refers to the chemical bond between nucleosides.

"Intraperitoneal administration" means administration through infusion or injection into the peritoneum.

"Intravenous administration" means administration into a vein.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-$CH_2$—O-2') LNA, (B) β-D-Methyleneoxy (4'-$CH_2$—O-2') LNA, (C) Ethyleneoxy (4'-$(CH_2)_2$—O-2') LNA, (D) Aminooxy (4'-$CH_2$—O—N(R)-2') LNA and (E) Oxyamino (4'-$CH_2$—N(R)—O-2') LNA, as depicted below.

(A)

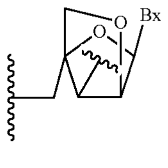

-continued (B)

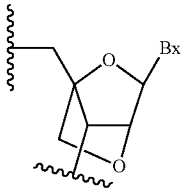

(C)

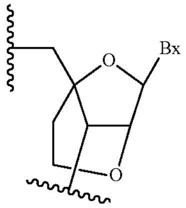

(D)

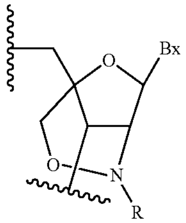

(E)

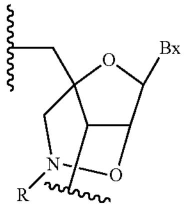

As used herein, LNA compounds include, but are not limited to, compounds having at least one bridge between the 4' and the 2' position of the sugar wherein each of the bridges independently comprises 1 or from 2 to 4 linked groups independently selected from —$[C(R_1)(R_2)]_n$—, —$C(R_1)$=$C(R_2)$—, —$C(R_1)$=N—, —C(=$NR_1$)—, —C(=O)—, —C(=S)—, —O—, —$Si(R_1)_2$—, —$S(=O)_x$— and —$N(R_1)$—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: —$[C(R_1)(R_2)]_n$—, —$[C(R_1)(R_2)]_n$—O—, —$C(R_1R_2)$—$N(R_1)$—O— or —$C(R_1R_2)$—O—$N(R_1)$—. Furthermore, other bridging groups encompassed with the definition of LNA are 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—$N(R_1)$-2' and 4'-$CH_2$—N($R_1$)—O-2'-bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-$CH_2$—O-2') bridge to form the bicyclic sugar moiety. The bridge can also be a methylene (—$CH_2$—) group connecting the 2' oxygen atom and the 4' carbon atom, for which the term methyleneoxy (4'-$CH_2$—O-2') LNA is used. Furthermore; in the case of the bicylic sugar moiety having an ethylene bridging group in this position, the term ethyleneoxy (4'-$CH_2CH_2$—O-2') LNA is used. α-L-methyleneoxy (4'-$CH_2$—O-2'), an isomer of methyleneoxy (4'-$CH_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Neurodegenerative disorder" means a chronic progressive neuropathy characterized by selective loss of neurons in motor, sensory, or cognitive systems. Neurodegenerative disorders include, but are not limited to, Tau-associated disorders.

"Neurofibrillary inclusion" means intraneuronal aggregates largely composed of insoluble hyperphosphorylated tau protein. In certain embodiments, neurofibrillary inclusions may be measured through various means including SPECT perfusion imaging, functional MRI, and PET scans. In certain embodiments, reduction of neurofibrillary inclusions may be inferred by improved scores on cognitive exams such as the Mini-Mental State Exam (MMSE) and the Alzheimer's Disease Assessment Scale Cognitive Behavior Section (ADAS-cog).

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (sRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" (also "oligo") means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, "peptide" refers to polypeptides and proteins.

"Pharmaceutically acceptable carrier" means a medium or diluent that does not interfere with the structure of the oligonucleotide. Certain such carriers enable pharmaceutical compositions to be formulated as, for example, tablets, pills, dragees, capsules, liquids, gels, syrups, slurries, suspension and lozenges for the oral ingestion by a subject.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Pharmaceutical agent" means a substance that provides a therapeutic benefit when administered to an individual. For example, in certain embodiments, an antisense oligonucleotide targeted to Tau is a pharmaceutical agent.

"Pharmaceutical composition" means a mixture of substances suitable for administering to a subject. For example, a pharmaceutical composition may comprise an antisense oligonucleotide and a sterile aqueous solution. In certain embodiments, a pharmaceutical composition shows activity in free uptake assay in certain cell lines.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevention" or "preventing" refers to delaying or forestalling the onset or development of a condition or disease for a period of time from hours to days, preferably weeks to months.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Recommended therapy" means a therapeutic regimen recommended by a medical professional for the treatment, amelioration, or prevention of a disease.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Scrambled oligo" or "scrambled" or "ISIS 141923" is a 5-10-5 MOE gapmer with no known target having the sequence of SEQ ID NO: 11.

"Segments" are defined as smaller or sub-portions of regions within a target nucleic acid.

"Shortened" or "truncated" versions of antisense oligonucleotides Taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

"Sites," as used herein, are defined as unique nucleobase positions within a target nucleic acid.

"Slows progression" means decrease in the development of the said disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subcutaneous administration" means administration just below the skin.

"Subject" means a human or non-human animal selected for treatment or therapy.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Tau-associated disease" means any neurological or neurodegenerative disease associated with Tau. Non-limiting examples of Tau-associated disorders include Alzheimer's disease, progressive supranuclear palsy, dementia pugilistica, frontotemporal dementia, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, corticobasal ganglionic degeneration, argyrophilic grain disease, supranuclear palsy, corticobasal degeneration, frontotemporal dementia, or frontotemporal lobar degeneration.

"Tauopathy" means disorders characterized by a build-up of Tau protein in the brain.

"Tau-specific inhibitor" includes but is not limited to a "antisense compound" targeted to Tau.

"Therapeutically effective amount" means an amount of a pharmaceutical agent that provides a therapeutic benefit to an individual.

"Treatment" refers to administering a composition to effect an alteration or improvement of the disease or condition.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Validated target segment" is defined as at least an 8-nucleobase portion (i.e. 8 consecutive nucleobases) of a target region to which an active oligomeric compound is targeted.

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide for methods of administering a Tau antisense compound targeting a Tau nucleic acid for the treatment of a Tau associated disease. In certain embodiments, the Tau nucleic acid is any of the sequences set forth in GENBANK Accession NT_010783.14 truncated from nucleotides 2624000 to U.S. Pat. No. 2,761,000 (incorporated herein as SEQ ID NO: 1); GENBANK Accession No. AK226139.1 (incorporated herein as SEQ ID NO: 2); GENBANK Accession No. NM_001123066.3 (incorporated herein as SEQ ID NO: 3); GENBANK Accession No. NM_001123067.3 (incorporated herein as SEQ ID NO: 4); GENBANK Accession No. NM_001203251.1 (incorporated herein as SEQ ID NO: 5); GENBANK Accession No. NM_001203252.1 (incorporated herein as SEQ ID NO: 6); GENBANK Accession No. NM_005910.5 (incorporated herein as SEQ ID NO: 7); GENBANK Accession No. NM_016834.4 (incorporated herein as SEQ ID NO: 8); GENBANK Accession No. NM_016835.4 (incorporated herein as SEQ ID NO: 9); or GENBANK Accession No. NM_016841.4 (incorporated herein as SEQ ID NO: 10).

A method of treating a Tau associated disease with antiense compounds has been developed. In certain embodiments, neurofibrillary inclusions are reduced. In certain embodiments, neurological function is improved. In certain embodiments, the antisense compounds reduce expression of Tau mRNA and protein. In certain embodiments, the antisense compounds alter the ratio of Tau isoforms. In certain embodiments, the splicing alteration is a decrease in 4R:3R Tau ratio in the central nervous system of the subject. In certain embodiments, the splicing alteration results in a normal 4R:3R Tau ratio. Advantageously, several embodiments provide methods of bypassing the blood brain barrier to specifically target Tau in the central nervous system, administer for an extended period of time, and achieve widespread distribution of therapy throughout the brain and spinal cord where it is most effective.

Certain embodiments provide methods for the treatment, prevention, or amelioration of diseases, disorders, and conditions associated with Tau in an individual in need thereof. Also contemplated are methods for the preparation of a medicament for the treatment, prevention, or amelioration of a disease, disorder, or condition associated with Tau. Tau associated diseases, disorders, and conditions include neurodegenerative diseases. In certain embodiments, the neurodegenerative disease may be any of Alzheimer's Disease, frontotemporal Dementia (FTD), FTDP-17, Progressive Supranuclear Palsy (PSP), Chronic Traumatic Encephalopathy (CTE), Corticobasal Ganglionic Degeneration (CBD), epilepsy, Dravet's Syndrome, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, supranuclear palsy, corticobasal degeneration, or frontotemporal lobar degeneration.

Described herein are methods comprising administering a Tau antisense compound to an animal for treating a Tau associated disease and thereby reducing neurofibrillary inclusions.

Described herein are methods comprising administering a Tau antisense compound to an animal for treating a Tau associated disease and thereby improving neurological function.

Described herein are methods comprising: (i) identifying an animal having a Tau associated disease; and (ii) administering a Tau antisense compound and thereby reducing neurofibrillary inclusions.

Described herein are methods comprising: (i) identifying an animal having a Tau associated disease; and (ii) administering a Tau antisense compound and thereby improving neurological function.

In certain embodiments, the animal is a human.

In certain embodiments, the antisense compound comprises a single-stranded antisense oligonucleotide complementary to a Tau nucleic acid.

In certain embodiments, the Tau nucleic acid is any of SEQ ID NO: 1-10.

In certain embodiments, the antisense compounds for use in the methods may comprise a single-stranded antisense oligonucleotide comprising a nucleobase sequence at least 80%, at least 85%, at least 90%, at least 95%, at least 96%, at least 97%, at least 98%, or at least 99% complementary to an equal length portion of SEQ ID NOs:1-10. In certain embodiments, the compound may comprise a single-stranded antisense oligonucleotide comprising a nucleobase sequence 100% complementary to an equal length portion of SEQ ID NOs: 1-10.

In certain embodiments, the Tau associated disease is a neurodegenerative disease.

In certain embodiments, the neurodegenerative disease is selected from among Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

In certain embodiments, expression of Tau RNA or expression of Tau protein is reduced.

In certain embodiments, expression of the 4R isoform of Tau RNA or expression of the 4R isoform of Tau protein is reduced.

In certain embodiments, expression of the 3R isoform of Tau RNA or expression of the 3R isoform of Tau protein is increased.

In certain embodiments, expression of the 4R isoform of Tau RNA is reduced and expression of the 3R isoform of Tau RNA is increased.

In certain embodiments, expression of the 4R isoform of Tau protein is reduced and expression of the 3R isoform of Tau protein is increased.

In certain embodiments, the single-stranded antisense oligonucleotide comprises at least one modification.

In certain embodiments, the single-stranded antisense oligonucleotide is specifically hybridizable to a human Tau nucleic acid.

In certain embodiments, the single-stranded antisense oligonucleotide is at least 75%, at least 80%, at least 85%, at least 90%, or at least 95% complementary to an equal length portion of a human Tau nucleic acid.

In certain embodiments, the single-stranded antisense oligonucleotide is 100% complementary to a human Tau nucleic acid.

In certain embodiments, the single-stranded antisense oligonucleotide comprises at least one modified internucleoside linkage.

In certain embodiments, each internucleoside linkage of the single-stranded antisense oligonucleotide is a modified internucleoside linkage.

In certain embodiments, the modified internucleoside linkage is a phosphorothioate internucleoside linkage.

In certain embodiments, the antisense oligonucleotide comprises at least one modified nucleoside.

In certain embodiments, the single-stranded antisense oligonucleotide comprises at least one modified nucleoside having a modified sugar.

In certain embodiments, the single-stranded antisense oligonucleotide comprises at least one modified nucleoside comprising a bicyclic sugar.

In certain embodiments, the bicyclic sugar comprises a 4' to 2' bridge selected from among: 4'-(CH2)n-O-2', wherein n is 1 or 2; and 4'-CH2-O—CH2-2'.

In certain embodiments, the bicyclic sugar comprises a 4'-CH(CH3)-O-2' bridge.

In certain embodiments, the at least one modified nucleoside having a modified sugar comprises a non-bicyclic 2'-modified sugar moiety.

In certain embodiments, the 2'-modified sugar moiety comprises a 2'-O-methoxyethyl group.

In certain embodiments, the 2'-modified sugar moiety comprises a 2'-O-methyl group.

In certain embodiments, the at least one modified nucleoside having a modified sugar comprises a sugar surrogate.

In certain embodiments, the sugar surrogate is a morpholino.

In certain embodiments, the sugar surrogate is a peptide nucleic acid.

In certain embodiments, each nucleoside is modified.

In certain embodiments, the single-stranded antisense oligonucleotide comprises at least one modified nucleobase.

In certain embodiments, the modified nucleobase is a 5'-methylcytosine.

In certain embodiments, the single-stranded antisense oligonucleotide comprises:

a gap segment consisting of linked deoxynucleosides;

a 5' wing segment consisting of linked nucleosides;

a 3' wing segment consisting of linked nucleosides;

wherein the gap segment is positioned immediately adjacent to and between the 5' wing segment and the 3' wing segment and wherein each nucleoside of each wing segment comprises a modified sugar.

In certain embodiments, the single-stranded antisense oligonucleotide comprises:

a gap segment consisting of ten linked deoxynucleosides;

a 5' wing segment consisting of five linked nucleosides;

a 3' wing segment consisting of five linked nucleosides;

wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the single-stranded antisense oligonucleotide consists of 15, 16, 17, 18, or 19 linked nucleosides.

In certain embodiments, the single-stranded antisense oligonucleotide consists of 20 linked nucleosides.

In certain embodiments, the single-stranded antisense oligonucleotide consists of 21, 22, 23, 24, or 25 linked nucleosides.

In certain embodiments, the administering is parenteral administration.

In certain embodiments, the parenteral administration is any of injection or infusion.

In certain embodiments, the parenteral administration is any of intrathecal administration or intracerebroventricular administration.

In certain embodiments, at least one symptom of a Tau associated disease is ameliorated.

In certain embodiments, at least one symptom of a Tau associated disease is prevented.

In certain embodiments, progression of at least one symptom of a Tau associated disease is slowed.

In certain embodiments, at least one symptom is any of memory loss, anxiety, loss of motor function, incidence of seizures, severity of seizures, and excitotoxicity.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a Tau nucleic acid is 10 to 30 subunits in length. In certain embodiments, an antisense compound targeted to a Tau nucleic acid is 12 to 30 subunits in length. In certain embodiments, an antisense compound targeted to a Tau nucleic acid is 12 to 22 subunits in length. In certain embodiments, an antisense compound targeted to a Tau nucleic acid is 14 to 30 subunits in length. In certain embodiments, an antisense compound targeted to a Tau nucleic acid is 14 to 20 subunits in length. In certain embodiments, an antisense compound targeted to a Tau nucleic acid is 15 to 30 subunits in length. In certain embodiments, an antisense compound targeted to a Tau nucleic acid is 15 to 20 subunits in length. In certain embodiments, an antisense compound targeted to a Tau nucleic acid is 16 to 30 subunits in length. In certain embodiments, an antisense compound targeted to a Tau nucleic acid is 16 to 20 subunits in length. In certain embodiments, an antisense compound targeted to a Tau nucleic acid is 17 to 30 subunits in length. In certain embodiments, an antisense compound targeted to a Tau nucleic acid is 17 to 20 subunits in length. In certain embodiments, an antisense compound targeted to a Tau nucleic acid is 18 to 30 subunits in length. In certain embodiments, an antisense compound targeted to a Tau nucleic acid is 18 to 21 subunits in length. In certain embodiments, an antisense compound targeted to a Tau nucleic acid is 18 to 20 subunits in length. In certain embodiments, an antisense compound targeted to a Tau nucleic acid is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound targeted to a Tau nucleic acid is 14 subunits in length. In certain embodiments, an antisense compound targeted to a Tau nucleic acid is 16 subunits in length. In certain embodiments, an antisense compound targeted to a Tau nucleic acid is 17 subunits in length. In certain embodiments, an antisense compound targeted to a Tau nucleic acid is 18 subunits in length. In certain embodiments, an antisense compound targeted to a Tau nucleic acid is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments, an antisense compound targeted to a Tau nucleic acid is a single stranded ribonucleic acid or deoxyribonucleic acid antisense oligonucleotide. Antisense oligonucleotides may target a specific, complementary, coding or non-coding, nucleic acid. Depending on the antisense oligonucleotide used, the binding of the oligonucleotide to its target nucleic acid sequence may or may not activate RNAse H. In some embodiments, the antisense oligonucleotide activates RNAse H, which degrades the target nucleic acid. The antisense oligonucleotides of several embodiments may be any length provided it binds selectively to the intended location. In general, the antisense oligonucleotide may be from 8, 10 or 12 nucleotides in length up to 20, 30, or 50 nucleotides in length.

In certain embodiments antisense oligonucleotides targeted to a Tau nucleic acid may be shortened or truncated. For example, a single subunit may be deleted from the 5' end (5' truncation), or alternatively from the 3' end (3' truncation). A shortened or truncated antisense compound targeted to a Tau nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (*Proc. Natl Acad. Sci. USA* 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J. Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a Tau nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

In certain embodiments, the antisense compounds are uniform sugar-modified oligonucleotides. Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—$CH_3$, among others), and bicyclic sugar modified nucleosides. In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides."Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, Y is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30, or more nucleosides. Thus, gapmers described herein include, but are not limited to, for example, 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, antisense compounds targeted to a Tau nucleic acid possess a 5-8-5 gapmer motif.

In certain embodiments, an antisense compound targeted to a Tau nucleic acid has a gap-narrowed motif. In certain embodiments, a gap-narrowed antisense oligonucleotide targeted to a Tau nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-(CH2)n-O-2' bridge, wherein n is 1 or 2; and 4'-CH2-O—CH2-2'. In certain embodiments, the bicyclic sugar is comprises a 4'-CH(CH3)-O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

In certain embodiments, an antisense compound targeted to a Tau nucleic acid is uniformly modified. In certain embodiments, the antisense compound comprises 12, 13, 14, 15, 16, 17, 18, 19, 20, 21, 22, 23, 24, or 25 nucleosides. In certain embodiments, each nucleoside is chemically modified. In certain embodiments, the chemical modification comprises a non-bicyclic 2'-modified sugar moiety. In certain embodiments, the 2'-modified sugar moiety comprises a 2'-O-methoxyethyl group. In certain embodiments, the 2'-modified sugar moiety comprises a 2'-O-methyl group.

Target Nucleic Acids, Target Regions and Nucleotide Sequences

Nucleotide sequences that encode Tau include, without limitation, the following: GENBANK Accession NT_010783.14 truncated from nucleotides 2624000 to U.S. Pat. No. 2,761,000 (incorporated herein as SEQ ID NO: 1); GENBANK Accession No. AK226139.1 (incorporated herein as SEQ ID NO: 2); GENBANK Accession No. NM_001123066.3 (incorporated herein as SEQ ID NO: 3); GENBANK Accession No. NM_001123067.3 (incorporated herein as SEQ ID NO: 4); GENBANK Accession No. NM_001203251.1 (incorporated herein as SEQ ID NO: 5); GENBANK Accession No. NM_001203252.1 (incorporated herein as SEQ ID NO: 6); GENBANK Accession No. NM_005910.5 (incorporated herein as SEQ ID NO: 7); GENBANK Accession No. NM_016834.4 (incorporated herein as SEQ ID NO: 8); GENBANK Accession No. NM_016835.4 (incorporated herein as SEQ ID NO: 9); or GENBANK Accession No. NM_016841.4 (incorporated herein as SEQ ID NO: 10).

It is understood that the sequence set forth in each SEQ ID NO contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Tau can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specfcally exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Tau mRNA levels are indicative of inhibition of Tau expression. Reductions in levels of a Tau protein are also indicative of inhibition of target mRNA expression. In certain embodiments, reductions in the 4R isoform of Tau mRNA levels are indicative of modulation of Tau splicing. Reductions in levels of the 4R isoform of Tau protein are also indicative of modulation of Tau splicing. In certain embodiments, increases in the 3R isoform of Tau mRNA levels are indicative of modulation of Tau splicing. Increases in levels of the 3R isoform of Tau protein are also indicative of modulation of Tau splicing. Reduction in percent of cells staining positive for hyperphosphorylated Tau are indicative of inhibition of Tau expression or modulation of Tau splicing. Improvement in neurological function is indicative of inhibition of Tau expression or modulation of Tau splicing. Improved memory and motor function are indicative of inhibition of Tau expression or modulation of Tau splicing. Reduction of neurofibrillary inclusions is indicative of inhibition of Tau expression or modulation of Tau splicing.

Hybridization

In some embodiments, hybridization occurs between an antisense compound disclosed herein and a Tau nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a Tau nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a Tau nucleic acid).

Non-complementary nucleobases between an antisense compound and a Tau nucleic acid may be tolerated provided that the antisense compound remains able to specifically hybridize to a target nucleic acid. Moreover, an antisense compound may hybridize over one or more segments of a Tau nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a Tau nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a Tau nucleic acid, or a target region, or a target segment or target sequence thereof. As used herein, “fully complementary” means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and for the second nucleic acid. For example, a 20 nucleobase portion of a 30 nucleobase antisense compound can be “fully complementary” to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a Tau nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a Tau nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a Tau nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Oligomeric compounds provided herein may comprise one or more monomers, including a nucleoside or nucleotide, having a modified sugar moiety. For example, the furanosyl sugar ring of a nucleoside or nucleotide can be modified in a number of ways including, but not limited to, addition of a substituent group and bridging of two non-geminal ring atoms to form a Locked Nucleic Acid (LNA).

In certain embodiments, oligomeric compounds comprise one or more monomers having a bicyclic sugar. In certain embodiments, the monomer is an LNA. In certain such embodiments, LNAs include, but are not limited to, (A) α-L-Methyleneoxy (4'-$CH_2$—O-2') LNA, (B) β-D-Methyleneoxy (4'-$CH_2$—O-2') LNA, (C) Ethyleneoxy (4'-$(CH_2)_2$—O-2') LNA, (D) Aminooxy (4'-$CH_2$—O—N(R)-2') LNA and (E) Oxyamino (4'-$CH_2$—N(R)—O-2') LNA, as depicted below.

(A)

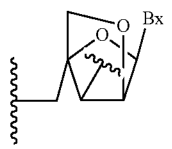

(B)

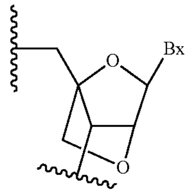

(C)

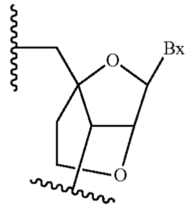

(D)

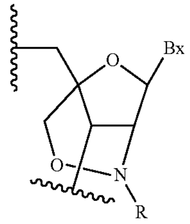

(E)

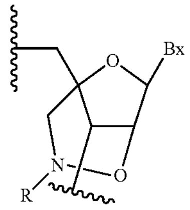

In certain embodiments, LNA compounds include, but are not limited to, compounds having at least one bridge between the 4' and the 2' position of the sugar wherein each of the bridges independently comprises 1 or from 2 to 4 linked groups independently selected from —$[C(R_1)(R_2)]_n$—, —$C(R_1)$=$C(R_2)$—, —$C(R_1)$=N—, —C(=$NR_1$)—, —C(=O)—, —C(=S)—, —O—, —$Si(R_1)_2$—, —$S(=O)_x$— and —$N(R_1)$—;

wherein:

x is 0, 1, or 2;

n is 1, 2, 3, or 4;

each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In one embodiment, each of the bridges of the LNA compounds is, independently, —$[C(R_1)(R_2)]_n$—, —$[C(R_1)(R_2)]_n$—O—, —$C(R_1R_2)$—$N(R_1)$—O— or —$C(R_1R_2)$—O—$N(R_1)$—. In another embodiment, each of said bridges is, independently, 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—$N(R_1)$-2' and 4'-$CH_2$—$N(R_1)$—O-2'- wherein each $R_1$ is, independently, H, a protecting group or $C_1$-$C_{12}$ alkyl.

Certain LNA's have been prepared and disclosed in the patent literature as well as in scientific literature (see for example: issued U.S. Pat. Nos. 7,053,207; 6,268,490; 6,770,748; 6,794,499; 7,034,133; 6,525,191; 7,696,345; 7,569,575; 7,314,923; 7,217,805; and 7,084,125, hereby incorporated by reference herein in their entirety.

Also provided herein are LNAs in which the 2'-hydroxyl group is connected, to the 4' carbon atom of the ribosyl sugar ring, thereby forming a methyleneoxy (4'-$CH_2$—O-2') bridge to form the bicyclic sugar moiety (reviewed in Elayadi et al., *Curr. Opinion Invens. Drugs,* 2001, 2, 558-561; Braasch et al., Chem. Biol., 2001, 8 1-7; and Orum et al., *Curr. Opinion Mol. Ther.,* 2001, 3, 239-243; see also U.S. Pat. No. 6,670,461). Furthermore, the bridge can also be a methylene (—$CH_2$—) group connecting the 2' oxygen atom to the 4' carbon atom of the sugar ring, for which the term methyleneoxy (4'-$CH_2$—O-2') LNA is used. In the case of the bicylic sugar moiety having an ethylene bridging group in this position, the term ethyleneoxy (4'-$CH_2CH_2$—O-2') LNA is used (Singh et al., Chem. Commun., 1998, 4, 455-456: Morita et al., *Bioorganic Medicinal Chemistry,* 2003, 11, 2211-2226). Methyleneoxy (4'-$CH_2$—O-2') LNA and other bicyclic sugar analogs display very high duplex thermal stabilities with complementary DNA and RNA (Tm=+3 to +10° C.), stability towards 3'-exonucleolytic degradation and good solubility properties. Potent and nontoxic antisense oligonucleotides comprising LNAs have been described (Wahlestedt et al., *Proc. Natl. Acad. Sci. U.S.A.,* 2000, 97, 5633-5638).

An isomer of methyleneoxy (4'-$CH_2$—O-2') LNA that has also been discussed is α-L-methyleneoxy (4'-$CH_2$—O-2') LNA which has been shown to have superior stability against a 3'-exonuclease. The α-L-methyleneoxy (4'-$CH_2$—O-2') LNA's were incorporated into antisense gapmers and chimeras that showed potent antisense activity (Frieden et al., *Nucleic Acids Research,* 2003, 21, 6365-6372).

The synthesis and preparation of adenine, cytosine, guanine, 5-methylcytosine, thymine and uracil LNAs having a methyleneoxy (4'-$CH_2$—O-2') bridge, along with their oligomerization, and nucleic acid recognition properties have been described (Koshkin et al., *Tetrahedron,* 1998, 54, 3607-3630). LNAs and preparation thereof are also described in WO 98/39352 and WO 99/14226, incorporated by reference herein.

Analogs of various LNA nucleosides that have 4' to 2' bridging groups such as 4'-$CH_2$—O-2' (methyleneoxy) and 4'-$CH_2$—S-2' (methylene-thio), have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-LNA, a novel comformationally restricted high-affinity oligonucleotide analog has been described in the art (Singh et al., J. Org. Chem., 1998, 63, 10035-10039). In addition, 2'-amino- and 2'-methylamino-LNA's have been prepared and the thermal stability of their duplexes with complementary RNA and DNA strands has been previously reported.

As used herein, "bicyclic nucleoside" refers to a nucleoside comprising a bridge connecting two carbon atoms of the sugar ring, thereby forming a bicyclic sugar moiety. In certain embodiments, the bridge connects the 2' carbon and another carbon of the sugar ring.

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom of the sugar ring.

One carbocyclic bicyclic nucleoside having a 4'-$(CH_2)_3$-2' bridge and the alkenyl analog, bridge 4'-CH═CH—$CH_2$-2', have been described (see, e.g., Freier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

Many other bicyclic and tricyclic sugar surrogate ring systems are also known in the art that can be used to modify nucleosides for incorporation into antisense compounds as provided herein (see, e.g., review article: Leumann, J. C, *Bioorganic & Medicinal Chemistry,* 2002, 10, 841-854). Such ring systems can undergo various additional substitutions to further enhance their activity. Such ring systems can undergo various additional substitutions to enhance activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_n$—$CH_3$, $O(CH_2)_nONH_2$, $OCH_2C(=O)N(H)CH_3$, and $O(CH_2)_nON[(CH_2)_n$—$CH_3]_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$, $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, "2'-modified nucleoside" or "2'-substituted nucleoside" refers to a nucleoside comprising a sugar comprising a substituent at the 2' position of a furanose ring other than H or OH. 2' modified nucleosides include, but are not limited to, nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—$CH_2$—C(═O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to modification of the 2' position of the furanosyl sugar ring to comprise a fluoro group.

As used herein, "2'-OMe" or "2'-$OCH_3$" or "2'-O-methyl" each refers to modification at the 2' position of the furanosyl sugar ring to comprise a —$OCH_3$ group.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA). Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

(i) ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

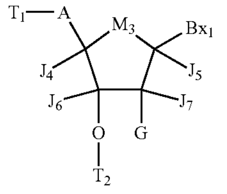

IIc wherein:

$T_1$ is an optionally protected phosphorus moiety;

$T_2$ is an internucleoside linking group linking the compound of Formula IIc to the oligomeric compound;

A has one of the formulas:

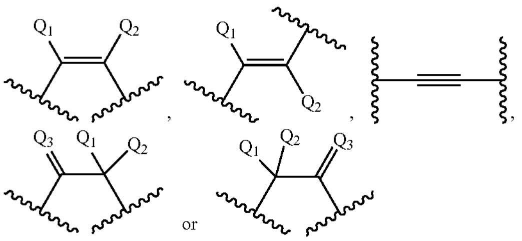

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15}){=}C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20}){=}C(R_{21})$, $C[{=}C(R_{20})(R_{21})]$ and $C({=}O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or $O—[C(R_8)(R_9)]_n—[(C{=}O)_m—X_1]_j—Z$;

each $R_8$ and $R_9$ is, independently, H, halogen, $C_1$-$C_6$ alkyl or substituted $C_1$-$C_6$ alkyl; $X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC({=}X_2)J_1$, $OC({=}X_2)—N(J_1)(J_2)$ and $C({=}X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH═CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

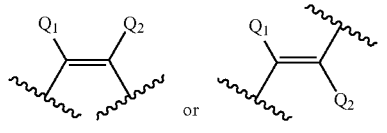

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

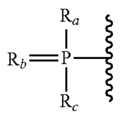

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2—CH{=}CH_2$, $O(CH_2)_2—OCH_3$, $O(CH_2)_2—SCH_3$, $O(CH_2)_2—OCF_3$, $O(CH_2)_3—N(R_{10})(R_{11})$, $O(CH_2)_2—ON(R_{10})(R_{11})$, $O(CH_2)_2—O(CH_2)_2—N(R_{10})(R_{11})$, $OCH_2C({=}O)—N(R_{10})(R_{11})$, $OCH_2C({=}O)—N(R_{12})—(CH_2)_2—N(R_{10})(R_{11})$ or $O(CH_2)_2—N(R_{12})—C({=}NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2—CH{=}CH_2$, $O(CH_2)_2—OCH_3$, $O(CH_2)_2—O(CH_2)_2—N(CH_3)_2$, $OCH_2C({=}O)—N(H)CH_3$, $OCH_2C({=}O)—N(H)—(CH_2)_2—N(CH_3)_2$ or $OCH_2—N(H)—C({=}NH)NH_2$. In certain embodiments, G is F, $OCH_3$ or $O(CH_2)_2—OCH_3$. In certain embodiments, G is $O(CH_2)_2—OCH_3$.

In certain embodiments, the 5'-terminal nucleoside has Formula IIe:

a.

IIe

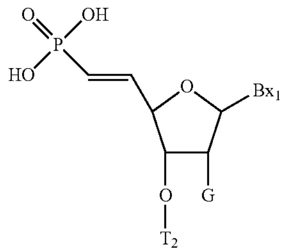

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

$$-(A)_2-(B)_x-(A)_2-(C)_y-(A)_3-$$

wherein: A is a first type of modified nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

$$5'-(Q)-(AB)_xA_y-(D)_z$$

wherein:

Q is a nucleoside comprising a stabilized phosphate moiety. In certain embodiments, Q is a nucleoside having Formula IIc or IIe;

A is a first type of modified nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

$5'-(Q)-(A)_x-(D)_z$ wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS |

(ii) siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is an eRNA. In certain embodiment, the degradation of the targeted eRNA is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfill a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der weals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), microRNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target eRNAs by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as Taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

In certain embodiments, antisense oligonucleotides do not activate RNAse H. In several aspects, antisense oligonucleotides that do not activate RNAse H are complementary to a nucleic acid sequence encoding Tau and disrupts the splicing of the nucleic acid encoding Tau to reduce the 4R:3R Tau ratio.

The antisense oligonucleotide of several embodiments may disrupt the splicing of the nucleic acid encoding Tau to reduce the 4R:3R Tau ratio. The splicing process is a series of reactions, mediated by splicing factors, which is carried out on RNA after transcription but before translation, in which the intron(s) are removed, and the exons joined together sequentially so that the protein may be translated. Each intron is defined by a 5' splice site, a 3' splice site, and a branch point situated there between. An antisense oligonucleotide may block these splice elements when the oligonucleotide either fully or partially overlaps the element, or binds to the pre-mRNA at a position sufficiently close to the element to disrupt the binding and function of the splicing factors which would ordinarily mediate the particular splicing reaction which occurs at that element. The antisense oligonucleotide may block a variety of different splice elements to carry out certain embodiments. For instance, the antisense oligonucleotide may block a mutated element, a cryptic element, or a native element; it may block a 5' splice site, a 3' splice site, or a branch point.

Methods of making antisense oligonucleotides which do not activate RNase H are known in the art. See, e.g., U.S. Pat. No. 5,149,797 incorporated herein by reference. Such antisense oligonucleotides may contain one or more structural modification which sterically hinders or prevents binding of RNase H to a duplex molecule comprising the oligonucleotide, but does not substantially hinder or disrupt duplex formation. Antisense oligonucleotides that do not activate RNAse H may include oligonucleotides wherein at least one, two or more of the internucleotide bridging phosphate residues are modified phosphates, such as methyl phosphonates, methyl phosphonothioates, phosphoromorpholidates, phosphoropiperazidates and phosphoramidates. For instance, every other one of the internucleotide bridging phosphate residues may be a modified phosphate, contain a 2' loweralkyl moiety (e.g., C1-C4, linear or branched, saturated or unsaturated alkyl, such as methyl, ethyl, ethenyl, propyl, 1-propenyl, 2-propenyl, and isopropyl) or a combination thereof. In preferred embodiments, the antisense oligonucleotide of the invention that does not activate RNAse H, and disrupts the splicing of the nucleic acid encoding Tau to reduce the 4R:3R Tau ratio is a 2'-O-(2-methoxyethyl) (MOE)-modified antisense oligonucleotide.

Other methods of modifying an oligonucleotide to hinder binding of RNAse H may be found in P. Furdon et al., Nucleic Acids Res. 17, 9193-9204 (1989); S. Agrawal et al., Proc. Natl. Acad. Sci. USA 87, 1401-1405 (1990); C. Baker et al., Nucleic Acids Res. 18, 3537-3543 (1990); B. Sproat et al., Nucleic Acids Res. 17, 3373-3386 (1989); R. Walder and J. Walder, Proc. Natl. Acad. Sci. USA 85, 5011-5015 (1988) the disclosures of all of which are incorporated herein, in their entirety, by reference.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a Tau nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a Tau nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of an antisense compound which are cleaved by endogenous nucleases within the body, to form the active antisense compound.

In certain embodiments, an antisense oligonucleotide can include a physiologically and pharmaceutically acceptable salts thereof: i.e., salts that retain the desired biological activity of the parent compound and do not impart undesired toxicological effects thereto. Examples of such salts are (a) salts formed with cations such as sodium, potassium, NH4+, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Administration

Antisense oligonucleotides of certain embodiments may be administered to a subject by several different means. For instance, oligonucleotides may generally be administered parenterally, intraperitoneally, intravascularly, or intrapulmonarily in dosage unit formulations containing conventional nontoxic pharmaceutically acceptable carriers, adjuvants, and vehicles as desired. In a preferred embodiment, the oligonucleotide may be administered parenterally.

The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Delivery methods are preferably those that are effective to circumvent the blood-brain barrier and are effective to deliver agents to the central nervous system. For example, delivery methods may include the use of nanoparticles. The particles may be of any suitable structure, such as unilamellar or plurilamellar, so long as the antisense oligonucleotide is contained therein.

Positively charged lipids such as N-[1-(2,3-dioleoyloxi)propyl)-N, N,N-trimethylamoniummethylsulfate, or "DOTAP," are particularly preferred for such particles and vesicles. The preparation of such lipid particles is well known in the art. See, e.g., U.S. Pat. No. 4,880,635 to Janoff et al.; U.S. Pat. No. 4,906,477 to Kurono et al.: U.S. Pat. No. 4,911,928 to Wallach; U.S. Pat. No. 4,917,951 to Wallach; U.S. Pat. No. 4,920,016 to Allen et al.: U.S. Pat. No. 4,921,757 to Wheatley et al.; etc.

In one embodiment, the compounds provided herein may be administered in a bolus directly into the central nervous system. The compounds provided herein may be administered to the subject in a bolus once, or multiple times. In some preferred embodiments, the compounds provided herein may be administered once. In other preferred embodiments, the compounds provided herein may be administered multiple times. When administered multiple times, the compounds provided herein may be administered at regular intervals or at intervals that may vary during the treatment of a subject. In some embodiments, the compounds provided herein may be administered multiple times at intervals that may vary during the treatment of a subject. In some embodiments, the compounds provided herein may be administered multiple times at regular intervals.

In another preferred embodiment, the compounds provided herein may be administered by continuous infusion into the central nervous system. Non-limiting examples of methods that may be used to deliver the compounds provided herein into the central nervous system by continuous infusion may include pumps, wafers, gels, foams and fibrin clots. In a preferred embodiment, the compounds provided herein may be delivered into the central nervous system by continuous infusion using an osmotic pump. An osmotic mini pump contains a high-osmolality chamber that surrounds a flexible, yet impermeable, reservoir filled with the targeted delivery composition-containing vehicle. Subsequent to the subcutaneous implantation of this minipump, extracellular fluid enters through an outer semi-permeable membrane into the high-osmolality chamber, thereby compressing the reservoir to release the targeted delivery composition at a controlled, pre-determined rate. The targeted delivery composition, released from the pump, may be directed via a catheter to a stereotaxically placed cannula for infusion into the cerebroventricular space. In certain embodiments, the compounds provided herein may be delivered into the central nervous system by continuous infusion using a pump as described in the Examples.

In another preferred embodiment, the compounds provided herein may be delivered into the central nervous system by intrathecal administration. A catheter may be placed in the intrathecal lumbar space of the animal. The proximal end of the catheter may be attached to a dosing pedestal that may extend through the skin. In further embodiments, the compounds provided herein may be administered as a bolus injection. In other embodiments, the compounds provided herein may be administered as a continuous infusion.

Conjugated Antisense compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Tau nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, SH-SY5Y and A172.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a Tau nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invitrogen, Inc. Eugene, Oreg.). Methods of RNA quantification by RIBOGREEN are Taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Tau nucleic acid. Methods for designing real-time PCR probes and primers are well known in the art, and may include the use of software such as PRIMER EXPRESS Software (Applied Biosystems, Foster City, Calif.).

Quantitative Real-Time PCR Analysis of Target DNA Levels

Quantitation of target DNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Gene (or DNA) target quantities obtained by real time PCR are normalized using either the expression level of a gene whose expression is constant, such as cyclophilin A, or by quantifying total DNA using RIBOGREEN (Invitrogen, Inc. Carlsbad, Calif.). Cyclophilin A expression is quantified by real time PCR, by being run simultaneously with the target, multiplexing, or separately. Total DNA is quantified using RIBOGREEN RNA quantification reagent (Invitrogen, Inc. Eugene, Oreg.). Methods of DNA quantification by RIBOGREEN are Taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Tau nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of Tau nucleic acids can be assessed by measuring Tau protein levels. Protein levels of Tau can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of Tau and produce phenotypic changes. Testing may be performed in non-transgenic animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, subcutaneous, intrathecal, and intracerebroventricular. Calculation of antisense oligonucleotide dosage and dosing frequency is within the abilities of those skilled in the art, and depends upon factors such as route of administration and animal body weight. Following a period of treatment with antisense oligonucleotides, RNA is isolated from brain tissue and changes in Tau nucleic acid expression are measured. Changes in Tau DNA levels are also measured. Changes in Tau protein levels are also measured. Changes in Tau splicing are also measured.

Tau Splicing

Certain embodiments provided herein relate to differential splicing in tau. Accordingly, several embodiments provide methods of treating a tau associated disease by lowering tau or altering the splicing of a nucleic acid encoding tau. Tau is a protein found in multiple tissues, but is particularly abundant in axons of neurons. The primary function of tau is to bind to and stabilize microtubules, which are important structural components of the cytoskeleton involved in mitosis, cytokinesis and vesicular transport. In humans, there are six isoforms of tau that are generated by alternative splicing of exons 2, 3, and 10. Splicing of exons 2 and 3 at the N-terminus of the protein leads to inclusion of zero, one or two 29 amino acid, acidic domains and is termed ON, 1N, or 2N tau respectively. Inclusion of exon 10 at the C-terminus leads to inclusion of the microtubule binding domain encoded by exon 10. Since there are 3 mictrotubule binding domains elsewhere in tau, this tau isoform (with exon 10 included) is termed 4R tau, where R refers to the number of repeats of microtubule binding domains. Tau without exon 10 is termed 3R tau. In healthy subjects, the ratio of 3R:4R tau is developmentally regulated, with fetal tissues expressing exclusively 3R tau and adult human tissues expressing approximately equal levels of 3R/4R tau. Deviations from the normal ratio of 3R:4R tau are characteristic of neurodegenerative syndromes such as FTD tauopathies. In essence, the method decreases the 4R:3R tau ratio in the central nervous system of the subject.

The 4R:3R tau ratio in the central nervous system of the subject may be normal, low or high. As used herein, a "normal 4R:3R tau ratio" in the central nervous system signifies a 4R:3R tau ratio in the central nervous system that is substantially the same as the 4R:3R tau ratio in the central nervous system of a subject from the same species and of approximately the same age not suffering from a neurodegenerative disease. In some embodiments, the method decreases the normal 4R:3R tau ratio in the central nervous system of a subject. In other embodiments, the method decreases a low 4R:3R tau ratio in the central nervous system of a subject.

In certain embodiments, the method decreases a high 4R:3R tau ratio in the central nervous system of a subject. In certain embodiments, the method decreases a high 4R:3R tau ratio caused by a defect in splicing of the nucleic acid encoding tau in the subject. Defects in splicing of the nucleic acid encoding tau in the subject may be caused, for instance, by genetic mutations altering the splicing of the nucleic acid encoding tau and leading to a high 4R:3R tau ratio. A mutation may be either a substitution mutation or a deletion mutation which creates a new, aberrant, splice element. Non-limiting examples of genetic mutations that may alter the splicing of the nucleic acid encoding tau and lead to a high 4R:3R tau ratio may include N279K, P301S, L1280, L284L, N296H, N296N, L1296N, P301 S, G303V, E10+11, E10+12, E10+13, E+10+14 and E10+16, and E10+19. Certain embodiments relate to a method of decreasing the 4R:3R tau ratio in the central nervous system of a subject by lowering expression of tau or altering the splicing of a nucleic acid encoding tau administering an antisense compound to the subject.

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome. In certain embodiments, the individual has been identified as having a Tau associated disease. In certain embodiments, provided herein are methods for prophylactically reducing Tau expression in an individual. In certain embodiments, provided herein are methods for prophylactically modulating Tau splicing in an individual. Certain embodiments include treating an individual in need thereof by administering to an individual a therapeutically effective amount of an antisense compound targeted to a Tau nucleic acid.

In certain embodiments, administration of a therapeutically effective amount of an antisense compound targeted to a Tau nucleic acid is accompanied by monitoring of Tau levels and Tau isoform in an individual, to determine an individual's response to administration of the antisense compound. An individual's response to administration of the antisense compound may be used by a physician to determine the amount and duration of therapeutic intervention.

In certain embodiments, administration of an antisense compound targeted to a Tau nucleic acid results in reduction of Tau expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a Tau nucleic acid results in reduction of the 4R isoform of Tau expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a Tau nucleic acid results in reduced memory loss, reduced anxiety, improved motor function in an animal, and/or reduced incidence or severity of seizures. In certain embodiments, administration of a Tau antisense results in reduced memory loss, reduced anxiety, improved motor function; and/or reduced incidence or severity of seizures by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to Tau are used for the preparation of a medicament for treating a patient suffering or susceptible to a neurodegenerative disease including Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome.

Certain Splicing Compounds

In certain embodiments, splicing compounds are useful for treating neurodegenerative syndromes. In certain embodiments, such splicing compounds promote the exclusion of exon 10, resulting in shifting tau isoform from 4R Tau (which is associated with neurodegenerative syndrome) to 3R Tau. In certain embodiments, such splicing compounds are antisense oligonucleotides wherein each nucleoside comprises a high affinity modification. In certain embodiments, the splicing compound is complementary to a human Tau genetic sequence. In certain embodiments, the splicing compound is complementary to SEQ ID NO: 1 (GENBANK Accession No. NT_010783.14 truncated from nucleotides 2624000 to 2761000).

Certain splicing compounds for use in the claimed methods are described hereinbelow in the examples and include ISIS 415883, ISIS 415885, ISIS 415887, ISIS 549595, ISIS 549617, ISIS 549619, and ISIS 549620.

ISIS 415883 is 20 nucleobases in length having the sequence (5' to 3') TCTTATTAATTATCTGCACC (SEQ ID NO: 12) and each nucleoside comprises a 2'-MOE modification. Each internucleoside linkage is a phosphorothioate linkage and all cytosine residues are 5-methylcytosines.

ISIS 415885 is 20 nucleobases in length having the sequence (5' to 3') CCAGCTTCTTATTAATTATC (SEQ ID NO: 13) and each nucleoside comprises a 2'-MOE modification. Each internucleoside linkage is a phosphorothioate linkage and all cytosine residues are 5-methylcytosines.

ISIS 415887 is 20 nucleobases in length having the sequence (5' to 3') TAAGATCCAGCTTCTTATTA (SEQ ID NO: 14) and each nucleoside comprises a 2'-MOE modification. Each internucleoside linkage is a phosphorothioate linkage and all cytosine residues are 5-methylcytosines.

ISIS 549595 is 18 nucleobases in length having the sequence (5' to 3') GGACGTGTGAAGGTACTC (SEQ ID NO: 15) and each nucleoside comprises a 2'-MOE modification. Each internucleoside linkage is a phosphorothioate linkage and all cytosine residues are 5-methylcytosines.

ISIS 549617 is 18 nucleobases in length having the sequence (5' to 3') GCCCAAGAAGGATTTATT (SEQ ID NO: 16) and each nucleoside comprises a 2'-MOE modification. Each internucleoside linkage is a phosphorothioate linkage and all cytosine residues are 5-methylcytosines.

ISIS 549619 is 18 nucleobases in length having the sequence (5' to 3') TCCTGAGAGCCCAAGAAG (SEQ ID NO: 17) and each nucleoside comprises a 2'-MOE modification. Each internucleoside linkage is a phosphorothioate linkage and all cytosine residues are 5-methylcytosines.

ISIS 549620 is 18 nucleobases in length having the sequence (5' to 3') CAGATCCTGAGAGCCCAA (SEQ ID NO: 18) and each nucleoside comprises a 2'-MOE modification. Each internucleoside linkage is a phosphorothioate linkage and all cytosine residues are 5-methylcytosines.

Certain Comparator Compounds

In certain embodiments, splicing compounds described herein are compared to certain comparator compounds. In certain embodiments, the splicing compounds described herein perform better than comparator compounds in terms of in vitro or in vivo efficacy, potency, or tolerability. In certain embodiments, the comparator compound is complementary to a human Tau genetic sequence. In certain embodiments, the splicing compound is complementary to SEQ ID NO: 1 (GENBANK Accession No. NT_010783.14 truncated from nucleotides 2624000 to 2761000).

Certain comparator compounds are described hereinbelow in the examples and include ISIS 617782 and ISIS 617781.

ISIS 617782 is 21 nucleosides in length having the sequence (5' to 3') TGAAGGTACTCACACTGCCGC (SEQ ID NO: 19) and each nucleoside comprises a 2'-$OCH_3$ modification. Each internucleoside linkage is a phosphorothioate linkage and all cytosine residues are 5-methylcytosines.

ISIS 617781 is 18 nucleosides in length having the sequence (5' to 3') TATCTGCACCTTTGGTAG (SEQ ID NO: 20) and each nucleoside comprises a 2'-$OCH_3$ modification. Each internucleoside linkage is a phosphorothioate linkage and all cytosine residues are 5-methylcytosines.

As described hereinbelow, ISIS 415883 achieved an IC50 of 0.65 nM in a 6 point dose response curve (0, 0.1, 0.3, 1, 3, 10, or 30 nM) in cultured A172 cells transfected using Lipofectamine2000®, whereas ISIS 617781 achieved an IC50 of 20.25 nM. Human Tau primer probe set 10_11 was used. Thus, ISIS 415883 is more potent than the comparator compound ISIS 617781. See Example 8 hereinbelow.

As described hereinbelow, ISIS 549595, ISIS 549617, ISIS 549619, and ISIS 549620 achieved 20%, 31.8%, 41.7%, and 35.6% (respectively) Tau exon 10 mRNA expression relative to untreated control levels in cultured A172 cells transfected using Lipofectamine2000® with 5 nM oligonucleotide using human Tau primer probe set 10_11. ISIS 617781 achieved 65% Tau exon 10 mRNA expression relative to untreated control levels in cultured A172 cells transfected using Lipofectamine2000® with 10 nM oligonucleotide using human Tau primer probe set 10_11. Therefore, ISIS 549595, ISIS 549617, ISIS 549619, and ISIS 549620 are more efficacious than comparator compound ISIS 617781 even when ISIS 617781 is administered at 2x the dose of ISIS 549595, ISIS 549617, ISIS 549619, and ISIS 549620. See Examples 8 and 9 hereinbelow.

As described hereinbelow, ISIS 549595, ISIS 549619, ISIS 549620 achieved 26%, 42%, and 35% (respectively) Tau exon 10 mRNA expression relative to untreated control levels in cultured A172 cells transfected using Lipofectamine2000® with 5 nM oligonucleotide using human Tau primer probe set 9_10 R5. ISIS 617782 achieved 55% Tau exon 10 mRNA expression relative to untreated control levels in cultured A172 cells transfected using Lipofectamine2000® with 3 nM and 34% Tau exon 10 mRNA expression relative to untreated control levels in cultured A172 cells transfected using Lipofectamine2000® with 10 nM oligonucleotide using human Tau primer probe set 9_10 R5. See Examples 8 and 10 hereinbelow.

EXAMPLE

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example Set 1

The following examples illustrate various iterations of the invention.

Introduction to Examples 1-7

Accumulation of proteinaceous aggregates is one of the defining hallmarks of neurodegenerative diseases. How these proteins cause disease and how they are subsequently cleared has remained an enigma. Tau, a microtubule binding protein, is one such aggregated protein found in multiple neurodegenerative syndromes including Frontotemporal dementia (FTD), Alzheimer's disease (AD), Progressive Supranuclear Palsy, and Corticobasalganglionic Degeneration. Understanding tau mediated neurodegeneration may lead to important therapeutic strategies for these disorders. Studies in the examples below focus on how to prevent the behavioral effects and pathological abnormalities in mouse models of dementia by decreasing tau levels and by changing the ratio of two different tau isoforms, 3R and 4R tau.

The primary function of tau is to bind to and stabilize microtubules, which are important structural components of the cytoskeleton involved in mitosis, cytokinesis and vesicular transport. Tau is found in multiple tissues, but is particularly abundant in axons of neurons. In humans, there are six isoforms of tau that are generated by alternative splicing of exons 2, 3, and 10. Splicing of exons 2 and 3 at the N-terminus of the protein leads to inclusion of zero, one or two 29 amino acid, acidic domains and is termed 0N, 1N, or 2N tau respectively. The influence of these domains on tau function is not clear. Inclusion of exon 10 at the C-terminus leads to inclusion of the microtubule binding domain encoded by exon 10. Since there are 3 mictrotubule binding domains elsewhere in tau, this tau isoform (with exon 10 included) is termed 4R tau, where R refers to the number of repeats of microtubule binding domains. (FIG. 1). Tau without exon 10 is termed 3R tau. Since more microtubule binding domains (4R compared with 3R) probably increases the binding to microtubules, 4R tau presumably changes the microtubule binding characteristics. The ratio of 3R/4R tau is developmentally regulated, with fetal tissues expressing almost exclusively 3R tau and adult human tissues expressing approximately equal levels of 3R/4R tau. Deviations from the normal ratio of 3R/4R tau are characteristic of neurodegenerative FTD tauopathies. It is not known how changing the 3R/4R tau ratio at a later stage in the adult animal will affect tau pathogenesis.

Serine-threonine directed phosphorylation regulates the microtubule binding ability of tau. Phosphorylation promotes detachment of tau from microtubules. Other post translational modifications of tau have been described; however the significance of these is unclear. Phosphorylation of tau is also developmentally regulated with higher phosphorylation in fetal tissues and much lower phosphorylation in the adult. One characteristic of neurodegenerative disorders is aberrantly increased tau phosphorylation.

The microtubule network is involved in many important processes within the cell including structural integrity needed for maintaining morphology of cells and operating transport machinery. Since binding of tau to microtubules stabilizes microtubules, tau is likely to be a key mediator of some of these processes and disruption of normal tau in neurodegenerative diseases may disrupt some of these key cellular processes. Given the data suggesting an important role for tau in normal cellular processes, it is surprising that the tau knockout animals do not have an obvious phenotype.

One of the early indicators that tau may be important in neurodegenerative syndromes was the recognition that tau is a key component of neurofibrillary tangles in Alzheimer's disease. Along with amyloid beta containing plaques, neurofibrillary tangles are a hallmark of Alzheimer's disease and correlate significantly with cognitive impairment. 95% of tau accumulations in AD are found in neuronal processes and is termed neuritic dystrophy. The process(es) whereby this microtubule associated protein becomes disengaged from microtubules and forms accumulations of proteins and how this relates to neuronal toxicity is not well understood. Recent experiments suggest that tau may be a key mediator of amyloid beta induced toxicity. Tau knockout animals are protected from amyloid beta induced toxicity. The animals do develop amyloid beta plaques, but do not develop the behavioral phenotype typical of transgenic amyloid-3 depositing mice. Given the developmental regulation of tau isoforms and the adult onset of AD, it is important to understand whether decreasing levels of tau in the adult animal will provide neuroprotection as suggested by this experiment where tau is deleted developmentally as well as in the adult. Measuring the effect of decreasing levels of tau on neurodegeneration in Alzheimer's mice and FTD model mice is another central question of the examples below. Data from late onset Alzheimer's disease patients suggest that among patients with Alzheimer's disease increased CSF tau may lead to earlier age of onset, implying that tau is not only a component of the pathology of Alzheimer's disease, but may directly influence the course of disease. This reinforces the possibility that decreasing tau levels in patients may slow the course of Alzheimer's disease patients.

Neuronal tau inclusions are a pathological characteristic of not only Alzheimer's disease, but also a subset of Frontotemporal dementia (FTD), PSP, and CBD. The link between tau and neurodegeneration was solidified by the discovery that mutations in the tau gene cause a subset of FTD. These genetic data have also highlighted the importance of the 3R:4R ratio of tau. Many of the tau mutations that cause FTD lead to a change in tau splicing which leads to preferential inclusion of exon 10, and thus to increased 4R tau. The overall tau levels are normal. Whether the tau isoform change or the amino acid change or both cause neurodegeneration remains unknown. Recent data suggest that PSP may also be associated with an increased 4R:3R tau ratio and thus may be amenable to a similar splicing strategy.

To help understand the influence of tau ratios on neurodegeneration, a mouse model based on one of the splicing tau mutations (N279K) has been generated using a minigene that includes the tau promoter and the flanking intronic sequences of exon 10. As in humans, these mice demonstrate increased levels of 4R tau compared with transgenics expressing WT tau and develop behavioral and motor abnormalities as well as accumulations of aggregated tau in the brain and spinal cord. Very interestingly, additional transgenic lines in which N279K mutation was driven by a CMV promoter were also generated. These CMV-N279K animals have exclusively 4R tau at both fetal and adult stages and do not develop any disease. Therefore it is unlikely that N279K toxicity arises from the N279K amino acid change since CMV-N279K mice have the same mutation. Similarly, expression of increased 4R alone presumably does not cause disease since the CMV-N279K mice express equal levels of 4R tau, but do not develop disease. Rather, these data suggest that tau pathogenesis depends on the shift away from the normal 4R:3R ratio and/or the tau promoter itself. A critical unaddressed question is whether decreasing the 4R:3R ratios in the adult animals will prevent neurodegeneration.

Figure 2:
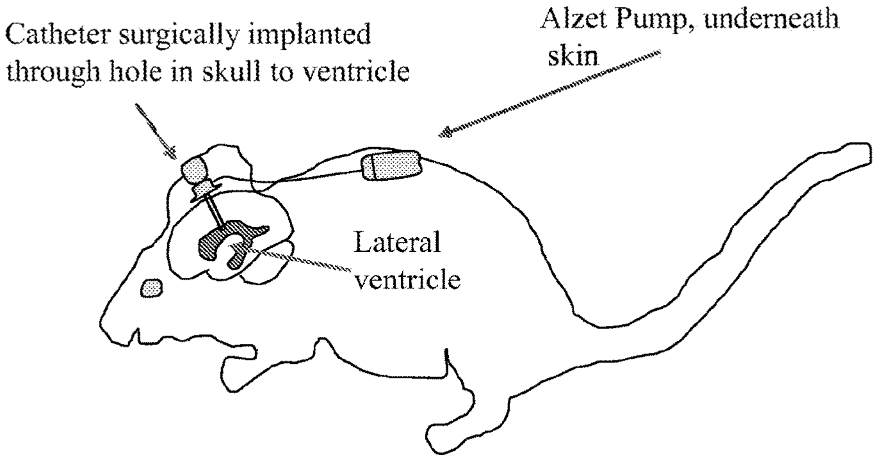
FIG. 2 depicts a diagram describing delivery of antisense oligonucleotides. Under anesthesia (inhaled isoflourane/oxygen mixture), a small hole is drilled in skull through which a catheter is placed in the lateral ventricle. The catheter is connected via plastic tubing to an osmotic pump (Alzet pump) which is embedded in a subcutaneous pocket on the back of the animal. Oligos are delivered continuously via this method. Changing the pump can be done easily by removing the osmotic pump without disturbing the indwelling catheter.

Antisense oligonucleotides are used to achieve tau knockdown and to modulate tau splicing. The inventors have pioneered the use of antisense oligonucleotides in the central nervous system. Although the oligos do not cross the blood brain barrier, this issue is solved by infusing the oligos directly into the cerebral spinal fluid (CSF) that circulates throughout the brain and the spinal cord. Direct CSF infusion of oligos is done using an osmotic pump (Alzet pump) connected via plastic tubing to a catheter implanted in the right lateral ventricle, the space within the brain filled with cerebral spinal fluid (FIG. 2). The pump delivers drug at a constant rate into the ventricle. Previous data from the inventors demonstrate a widespread distribution of oligos throughout the brain and spinal cord of both rat and Rhesus monkey, target specificity, and neuroprotection in an animal model of ALS based on expression of mutant SOD1G93A. Surprisingly, the antisense oligos penetrate deeply and evenly into the brain parenchyma targeting all regions of the brain.

Typical antisense oligos are designed to decrease gene expression by activating RNAse H, thus cleaving the target mRNA to which the oligo binds. Oligos may also be designed not to activate RNAse H, but to bind to introns or exon/intron boundaries and promote inclusion or exclusion of a particular exon. This strategy has been successful in mice for SMN, the gene whose absence causes spinal muscular atrophy. A similar strategy to promote exclusion of exon 10 and thus decrease the 4R to 3R tau ratio is described below. Decreasing the abnormal 4R:3R tau ratio may be sufficient to decrease the behavioral deficits and the pathological changes in the tau N279K mice, even though the tau protein sequence remains abnormal.

Example 1. Mouse Tau Knockdown In Vitro

Figure 3:
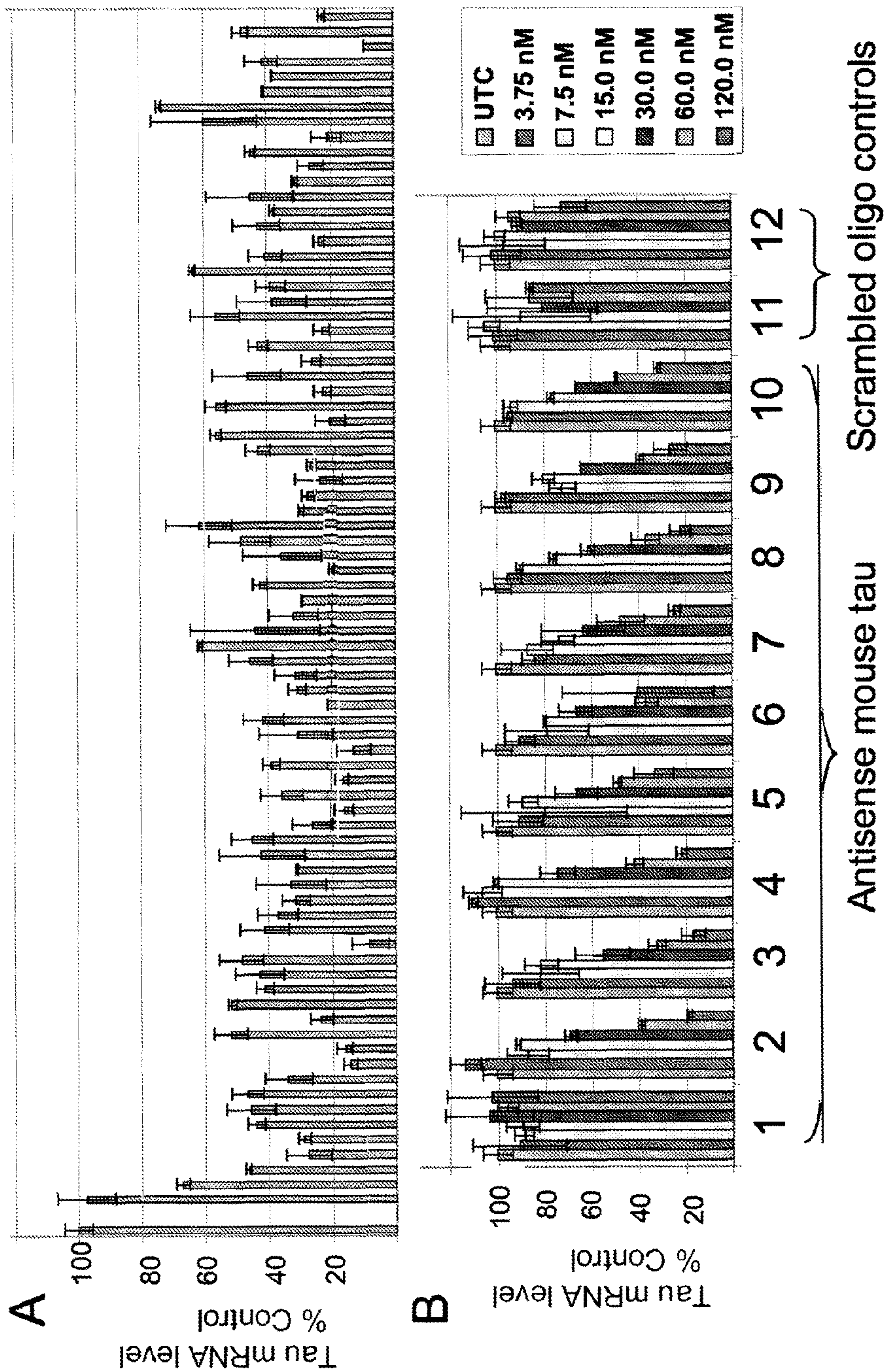
FIG. 3 depicts two plots showing mouse tau mRNA levels are decreased by mouse tau antisense oligos in vitro. (A) 80 antisense oligonucleotides, 120 nM, against mouse tau were transfected by cytofectin into cultured B16-F10 (murine melanoma cells). Each bar represents tau mRNA levels 48 hours after transfection with a different antisense oligonucleotide measured in triplicate cultures compared with untransfected cells (UTC, 100%). (B) Mouse tau mRNA 48 hours after transfection. Antisense oligos against mouse tau that demonstrated decreased levels of mouse tau in the initial screen (part A) were tested in cultured B16-F10 (murine melanoma cells line) cells transfected by cytofectin with increasing antisense oligos to mouse tau (1-10) or two scrambled oligonucleotide controls, (11, 12). Nine of 10 oligos showed an appropriate dose response in this subsequent screen. Untransfected cells=100%. These oligos are excellent candidates for in vivo testing of mouse tau knockdown.

Antisense oligonucleotides that decrease levels of tau mRNA in tissue culture have been identified. 80 antisense oligos designed to decrease mouse tau levels were screened by transfection into a murine cell line (FIG. 3A). From these results, 10 antisense oligos were judged to have relative good activity in this assay. These 10 oligos were tested in a dose response curve in a murine cell line (FIG. 3B). Nine of 10 oligos were active in this assay, demonstrating >80% decrease in tau mRNA compared with non-transfected controls. Two different scrambled oligos caused 15% knockdown at the highest dose and no effect on tau mRNA levels at lower doses.

Certain active oligos (i.e., oligonucleotides) in this assay, demonstrating >80% decrease in tau mRNA compared with non-transfected controls were taken forward in additional studies.

Example 2. Mouse Tau Knockdown In Vivo. (Effect of Antisense Inhibition of Murine Tau by Systemic Administration in a Murine Model)

Antisense oligonucleotides from the study described above were selected for testing in vivo. The antisense oligonucleotides were designed as 5-10-5 MOE gapmers, and are 20 nucleosides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment as a 2'-MOE modification. The internucleoside linkages throughout the gapmer are phosphorothioate (P═S) linkages. All cytosine residues throughout the gapmer are 5-methylcytosines.

From the above in vitro study (FIG. 3), 5 oligos were selected to test in vivo. First, the oligos were tested by intraperitoneal delivery of 37.5 mg/kg three times per week x 3 weeks. After 3 weeks, a piece of liver and a sample of blood were collected. The blood was used to test for generic toxicity by measuring "liver enzymes", which are proteins found in the liver that are detectable in serum. In the setting of liver toxicity, these enzymes (ALT and AST) are increased. Liver enzymes were changed less than 2 fold indicating that these oligos are not likely to be toxic.

mRNA was isolated from liver and mouse Tau mRNA levels were measured by QPCR using GAPDH as a control. Three of the oligos (#2, 4, 5) decreased tau mRNA levels by about 50%, but there was substantial variability in the results, which is partly attributed to low abundance of tau mRNA in the liver samples (data not shown).

Example: Effect of Antisense Inhibition of Tau by Direct Hippocampal Administration As a further test of the oligos, oligos 2, 4, 5 were screened by direct hippocampal injection. Saline, or a scrambled oligo, or 50 μg of antisense oligonucleotide was infused by stereotactic injection into the right hippocampus of a 60 day old non-transgenic mouse. After one week, mice were euthanized and the area surrounding the injection was isolated and used to prepare mRNA. Mouse tau mRNA levels were decreased >75% in all tau antisense oligo injected hippocampi (FIG. 4A).

Example: Effect of Antisense Inhibition of Tau by Intraventricular Administration Since the treatment paradigm for modulating behavior in the transgenic amyloid-3 depositing mice will involve treatment of the entire brain using intraventricular injection of antisense oligonucleotides, the most active antisense oligo (Tau 5, FIG. 4A) was next tested by intraventricular injection.

Study 1

Saline or tau #5 was infused into the right lateral ventricle (of 8 week old C57BL6 mice) at 100 μg/day using an indwelling catheter connected to an Alzet osmotic pump buried in a subcutaneous pocket on the back of the animal (as described in FIG. 2). After 30 days, animals were euthanized and mRNA was prepared from a section of right frontal cortex. Tau mRNA levels were analyzed by QPCR. Using GAPDH as a normalizer, the knockdown of tau mRNA was about 95% in the animals treated with antisense oligonucleotide (FIG. 4B). Tau protein was also clearly decreased by Tau5 antisense oligonucleotide (FIG. 4C).

Study 2

Efficacy of lower doses of the Tau5 oligo (i.e., oligonucleotide) was also tested.

The current dose of 100 μg/day was tolerated well without any evidence of toxicity. Efficacy of lower doses of the tau5 oligo (i.e., oligonucleotide) were also tested using 25, 50 and 100 μg/day with the Alzet pump system. Four to five 8 week old non-transgenic BL6 mice per group were used. The lowest dose tested (25 μg/day) was still effective at knocking down relative brain tau levels (Figures).

Study 3

Figure 6:
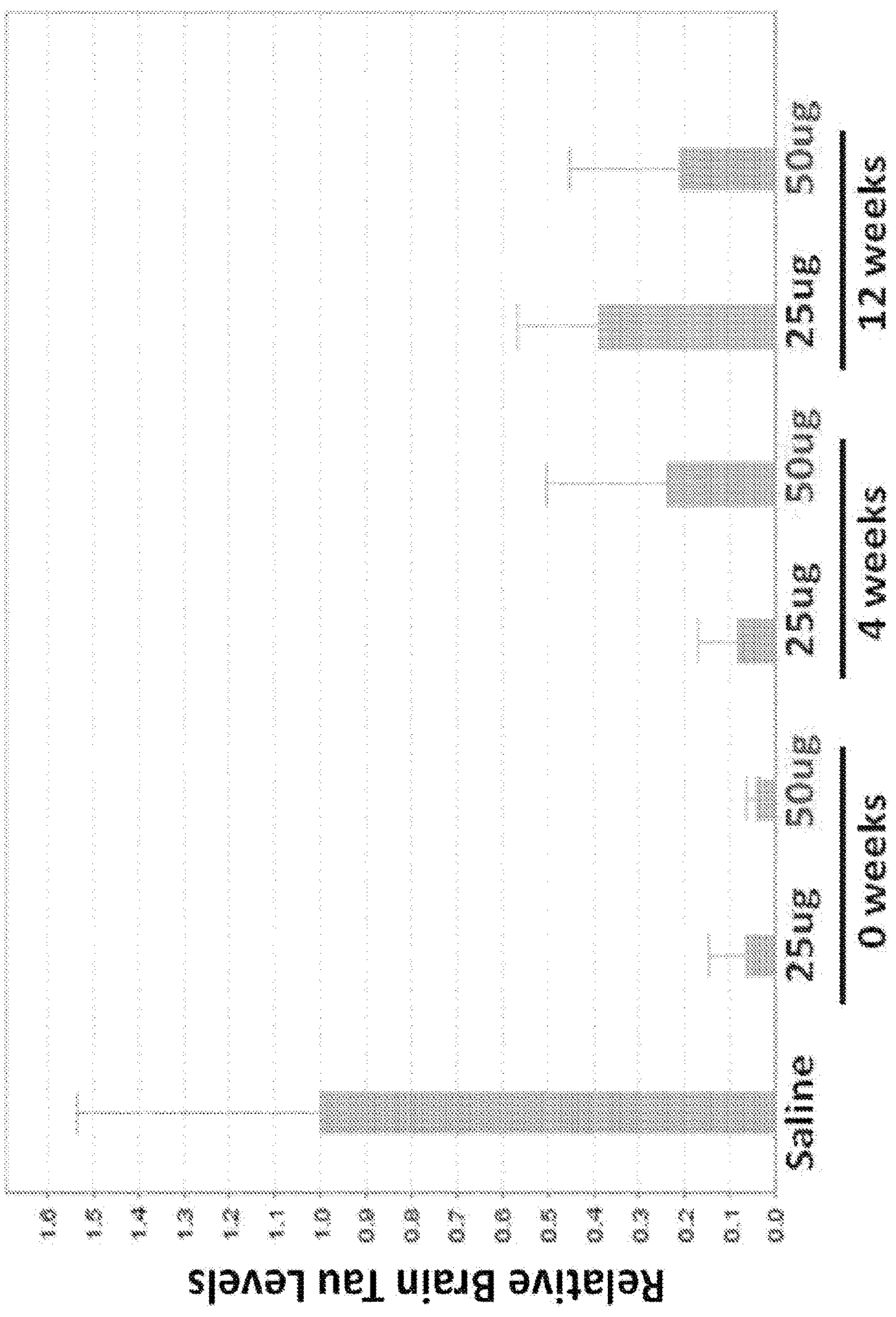
FIG. 6 depicts a plot representing the relative brain tau levels 0, 4 and 12 weeks after infusion of the knockdown oligo.

In addition, the half life of tau5 oligo after intraventricular infusion with the Alzet pump was also tested. Intraventricular infusions using 8 weeks old non-transgenic BL6 mice were as described above, using 3-6 mice per group. Tau5 oligo was infused at 25 and 50 μg/day for 1 month. Brains were then collected immediately after infusion, or 1 month, and 3 months after infusion. Brain tau levels were still significantly lower 12 weeks after infusion (FIG. 6).

Example: Duration of Action of Tau#5 ASO by Intraventricular Administration

Figure 7A:
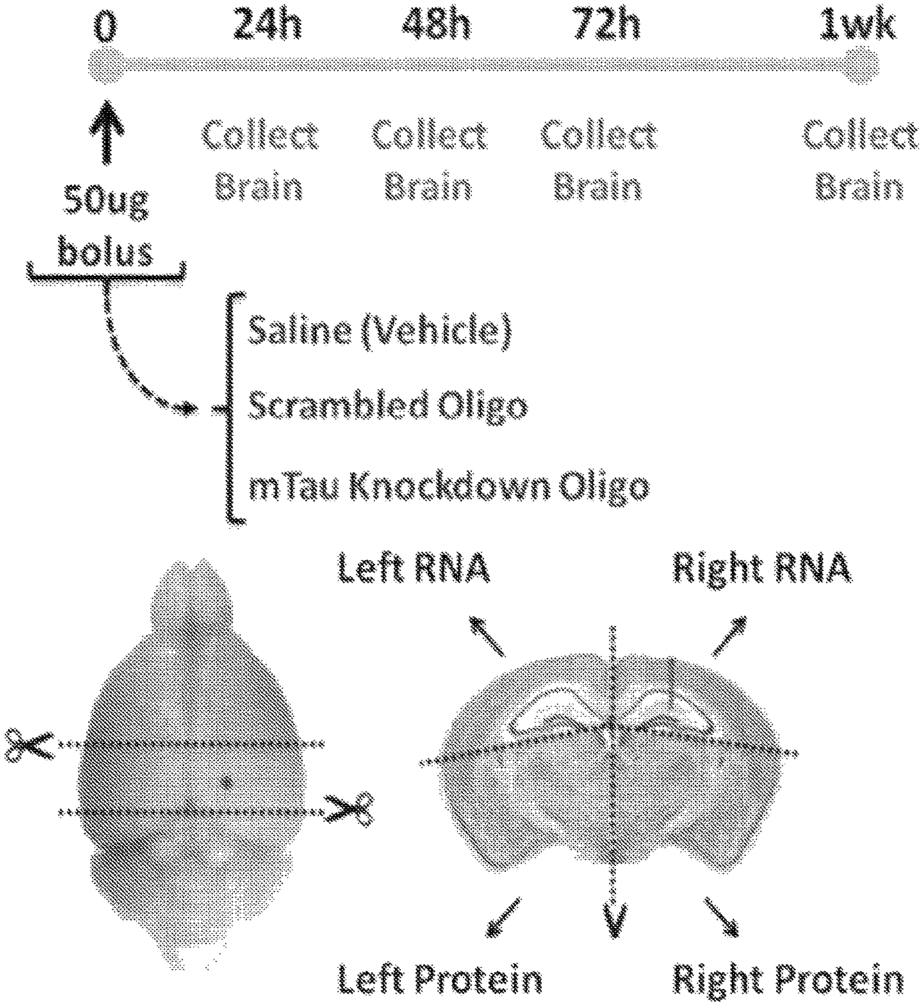
FIG. 7 depicts (A) the experimental setup and tissue collection, (B) a plot representing the total endogenous mouse tau mRNA levels 24, 48 and 72 hours after administration of the oligo, and (C) a Western blot of total endogenous mouse tau protein levels and GAPDH levels up to one month after administration of the oligo.
Figure 7B:
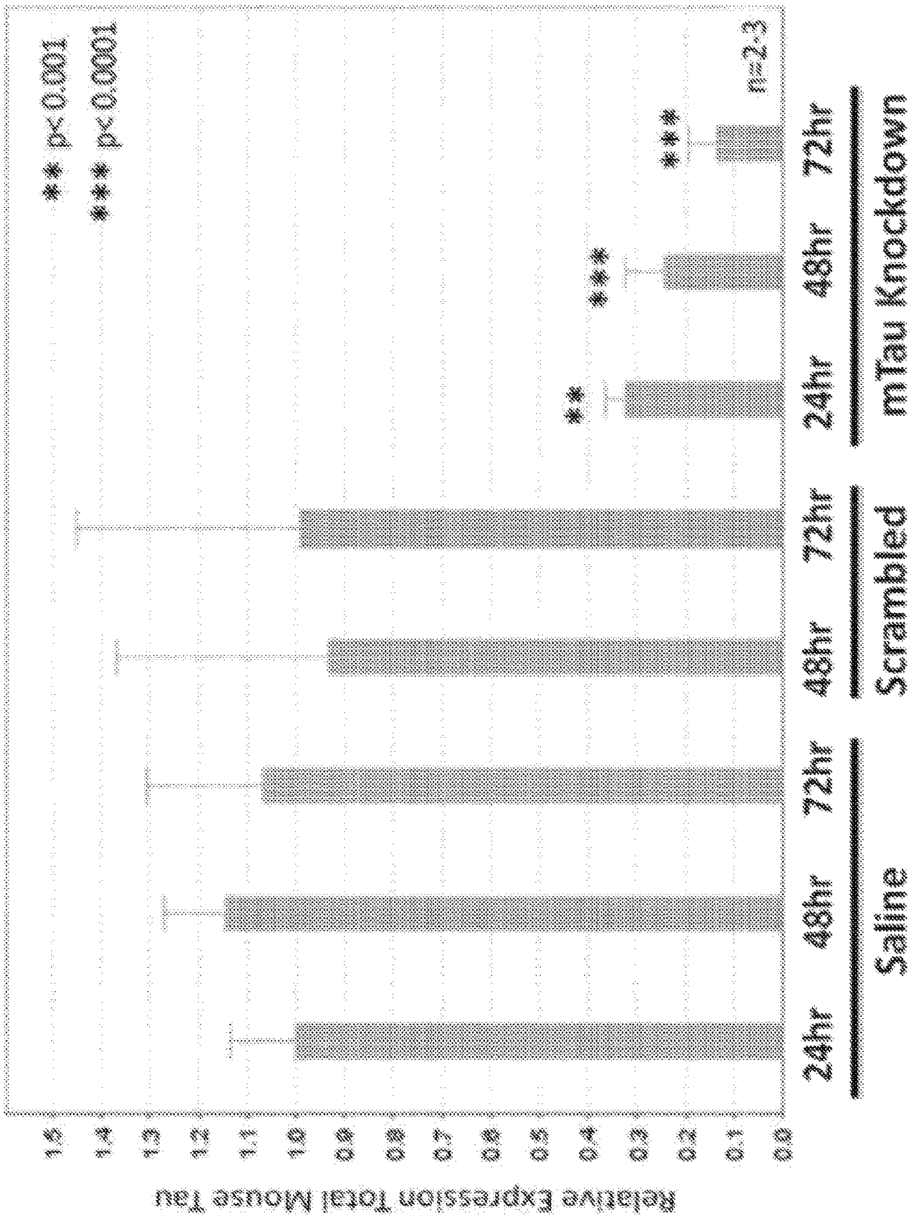
Figure 7C:
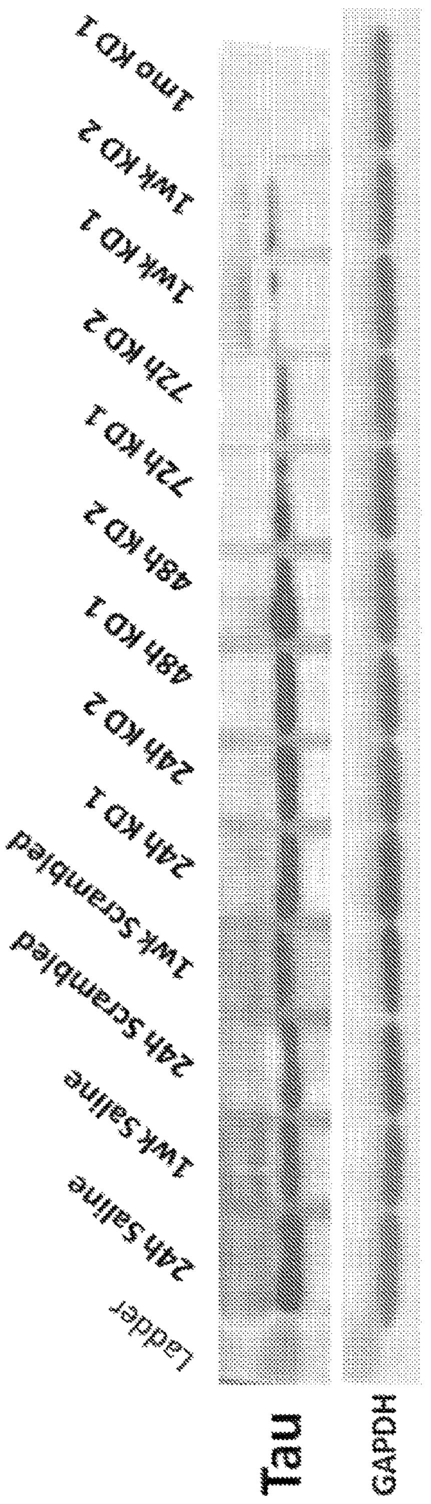

To further characterize tau knockdown using antisense oligos, tau5 oligo was used to test duration of onset after injection of the oligo into mice (FIG. 7). In short, a 50 μg hippocampal bolus was injected (1 μl of 50 μg/μl solution was infused at 0.2 μl/min for 5 minutes) into 12 week old C57BL6 mice, brains were collected at 25 hours, 48 hours, and 72 hours post-injection (+/−2 hours). Four pieces of brain were collected—Right RNA, Right protein, Left RNA, Left protein (FIG. 7A). The right RNA and Right Protein pieces were used for qRT-PCR (FIG. 7B) and Western blot analysis (FIG. 7C), respectively. Tau mRNA levels significantly drop even after only 24 hours post bolus and continue to drop at 48 and 72 hours (FIG. 7B). Tau protein levels do not appear to decrease by the 24 and 48 hour time points by Western blot (FIG. 7C), suggesting that there is a lag between the mRNA knockdown and protein knockdown of tau. However, by 72 hours the protein levels begin to decrease such that by 1 week there is a significant decrease in tau protein levels (FIG. 7C).

Example 3. Changing Human Tau Splicing

Figure 9:
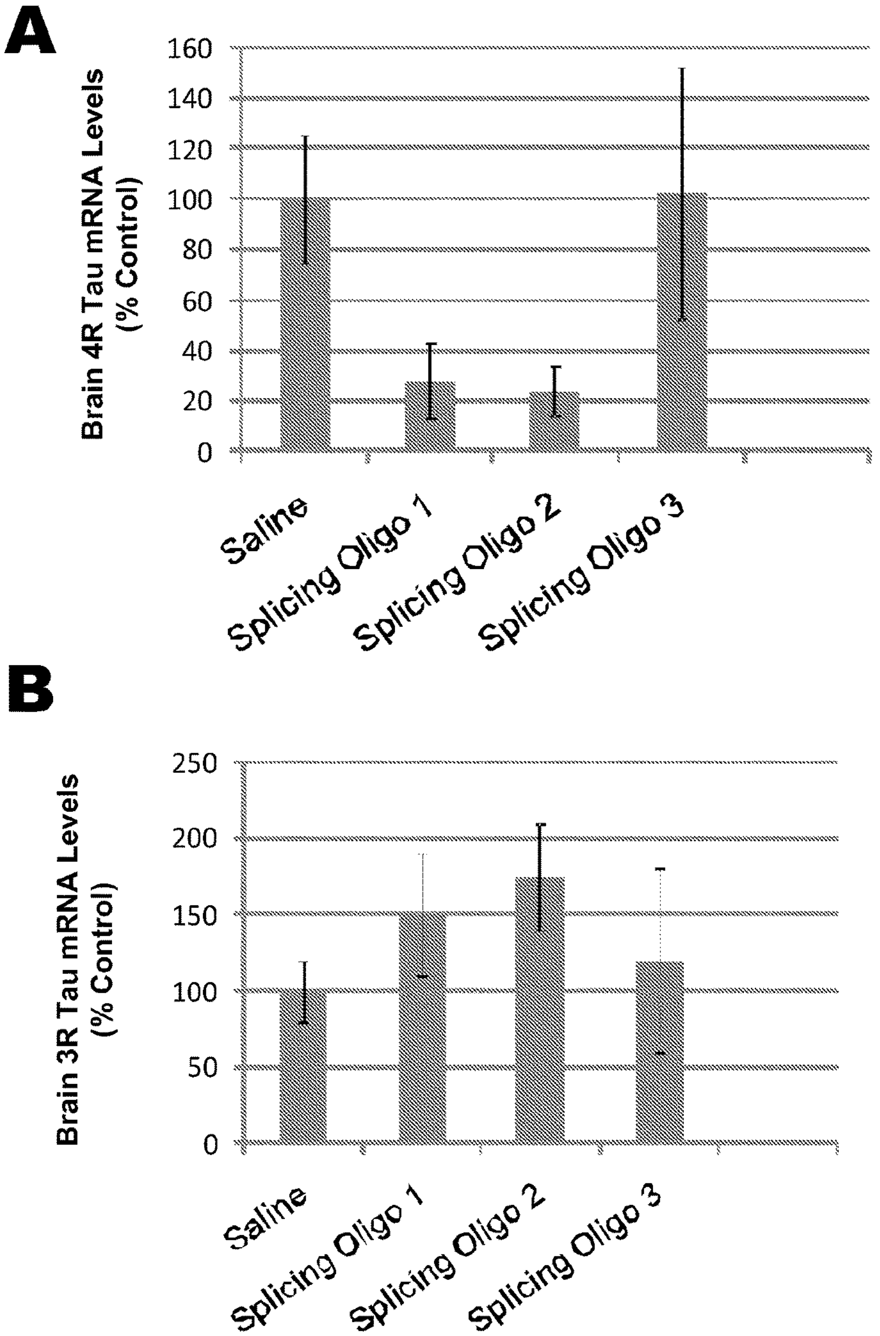
FIG. 9 depicts two plots showing tau splicing oligos decrease 4R tau. Oligos designed to specifically decrease 4R tau levels (50 μg) or saline were injected into the hippocampus by stereotactic injection into htau mice that express full length human tau. Mice were euthanized after one week and brain parenchyma was examined for human 4R tau mRNA (A) and for human tau 3R tau mRNA (B) by QPCR. GAPDH mRNA was used to normalize samples. (N=4 for saline, and 2 for each oligo, Avg+/−range).

Saline or splicing oligos (i.e., "splicing oligo 1" also ISIS 415883, "splicing oligo 2" also ISIS 415885, and "splicing oligo 3" also ISIS 415887) which dramatically shifted the tau isoforms from mainly 4R with some 3R tau to mostly 3R tau with some 4R tau in an in vitro study, and designed to specifically decrease 4R tau levels, were infused into the hippocampus by stereotactic injection into htau mice that express full length human tau. Mice were euthanized after one week and brain parenchyma was examined for human 4R tau mRNA and for human 3R tau mRNA by QPCR (FIG. 9). The oligos clearly decrease 4R tau levels. They also appear to increase 3R levels. These data demonstrate the oligos are active in vivo.

Figure 8:
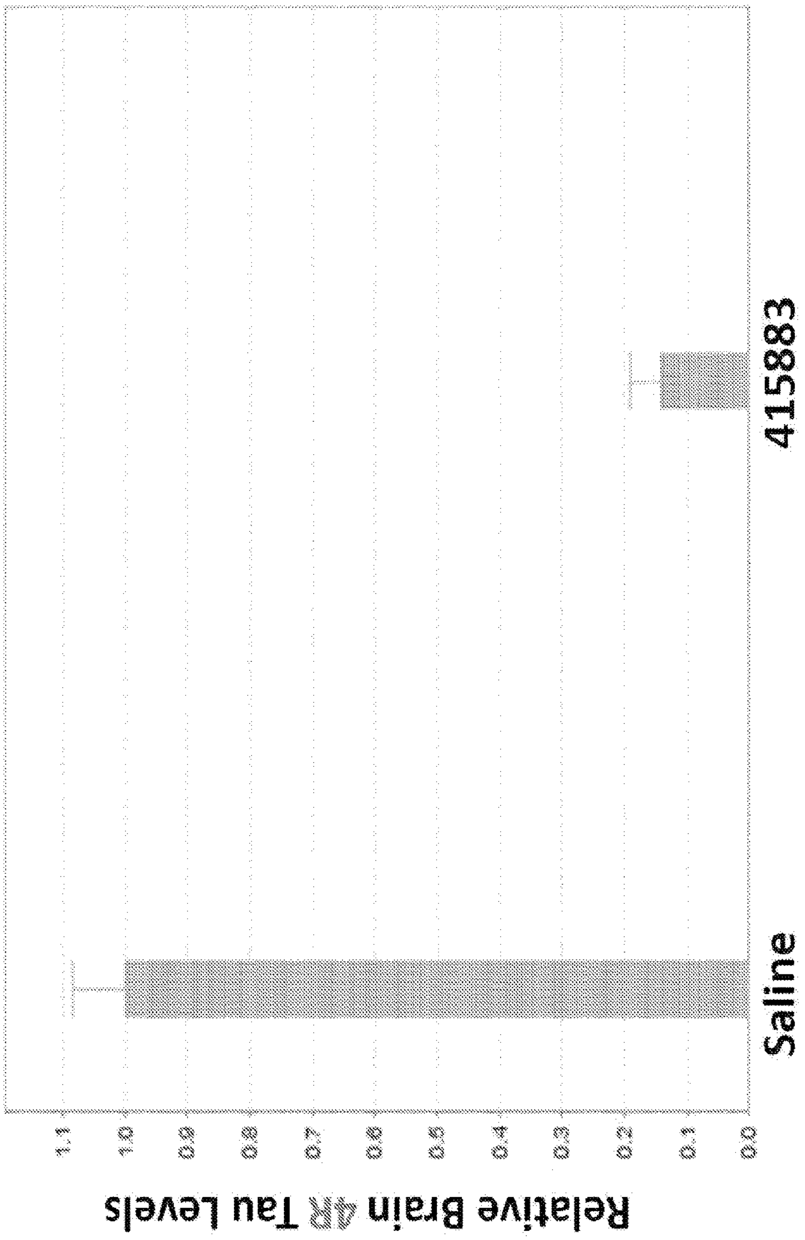
FIG. 8 depicts a plot representing the relative brain 4R tau levels after a one month intraventricular infusion of the splicing oligo.

The effect of tau415883 on 4R tau was also tested after intraventricular infusion with the Alzet pump was also tested. Intraventricular infusions using 14 week old non-transgenic BL6 mice were as described above, using 11-12 mice per group. Tau415883 oligo was infused at 50 μg/day for 28 days. Relative brain 4R tau levels were significantly lower (FIG. 8).

Figure 10:
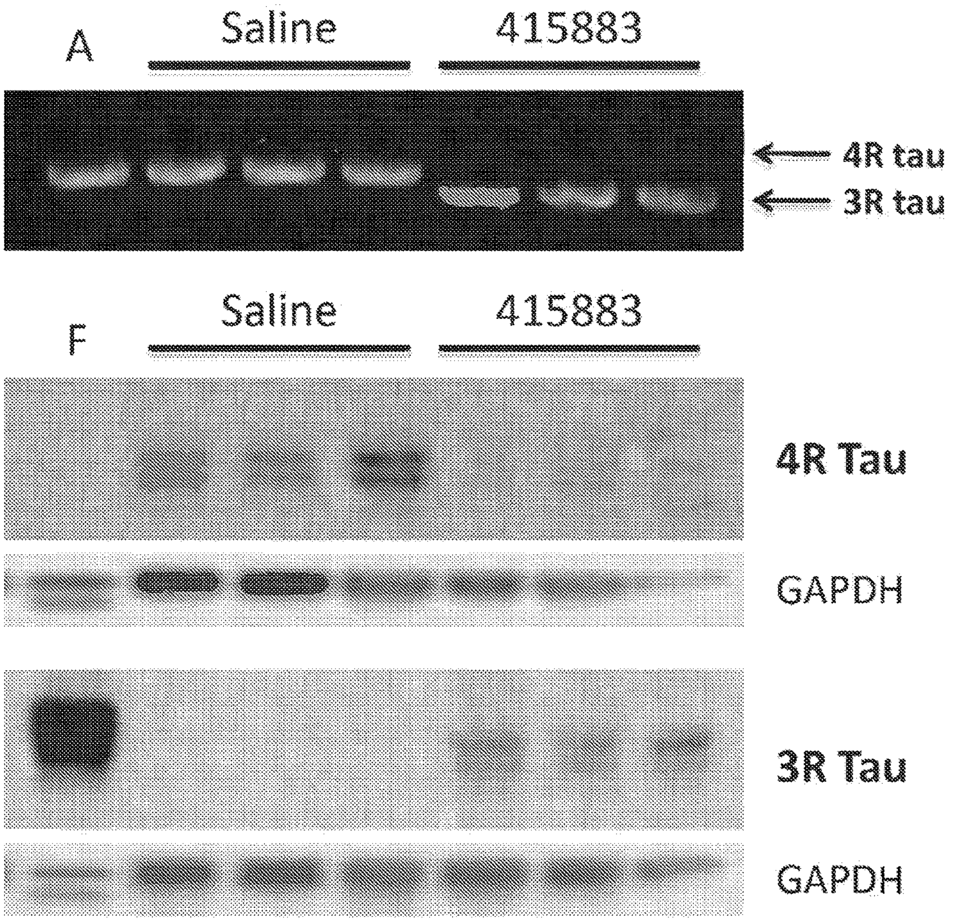
FIG. 10 depicts RT-PCR and Western blot results of a one month intraventricular infusion with a splicing oligo. 100 ng of starting RNA was used for the RT-PCR. A=Adult mouse with no pump. 20 μg protein was loaded for the Western blots. F=E18 fetal rat whole brain homogenate. 4R Tau antibody (RD4) was used at a 1:500 dilution. 3R Tau antibody (RD3) was used at a 1:500 dilution. GAPDH antibody was used at a 1:10,000 dilution.

A similar experiment was performed using a month intraventricular infusion (FIG. 10).

Example 4. PTZ Induced Seizures

Example: Effect Antisense Inhibition of Tau on PTZ Induced Seizures

Figure 11A:
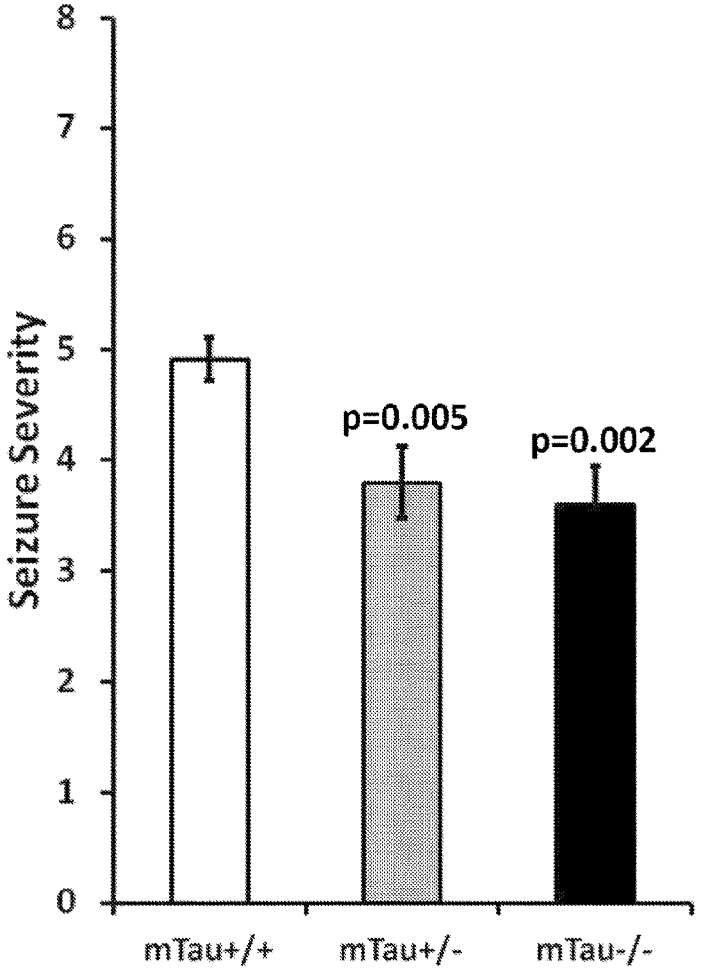
FIG. 11 depicts two plots of (A) seizure severity in mTau+/+, mTau+/−, and mTau−/− mice, and (B) percentage of mice with various stages of seizures in mTau+/+, mTau+/−, and mTau−/− mice.
Figure 11B:
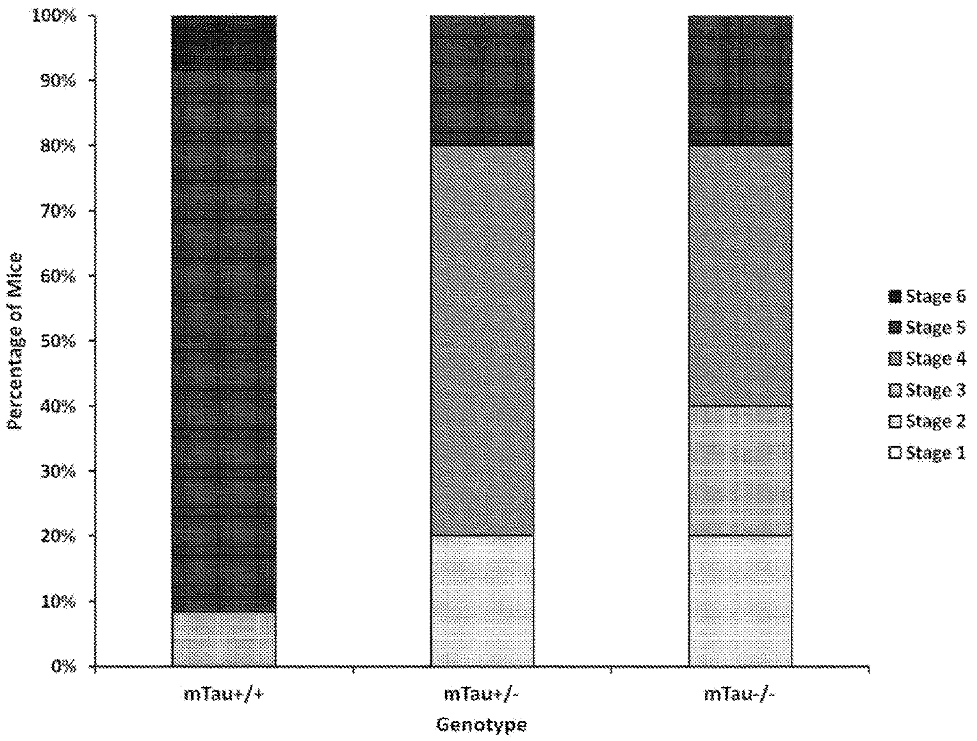

Seizures were induced and quantified in various mice using pentelenetetrazoll (PTZ). The mice are videotaped for 15 minutes and scored later in a blinded fashion. The final stage reached is recorded. In short, 50 mg/kg PTZ was injected ip into mTau−/−, and mTau+/− mice. mTau+/+ mice were used as control. Mice deficient for mTau were more resistant to PTZ induced seizures (FIGS. 11A and 11B).

Figure 12A:
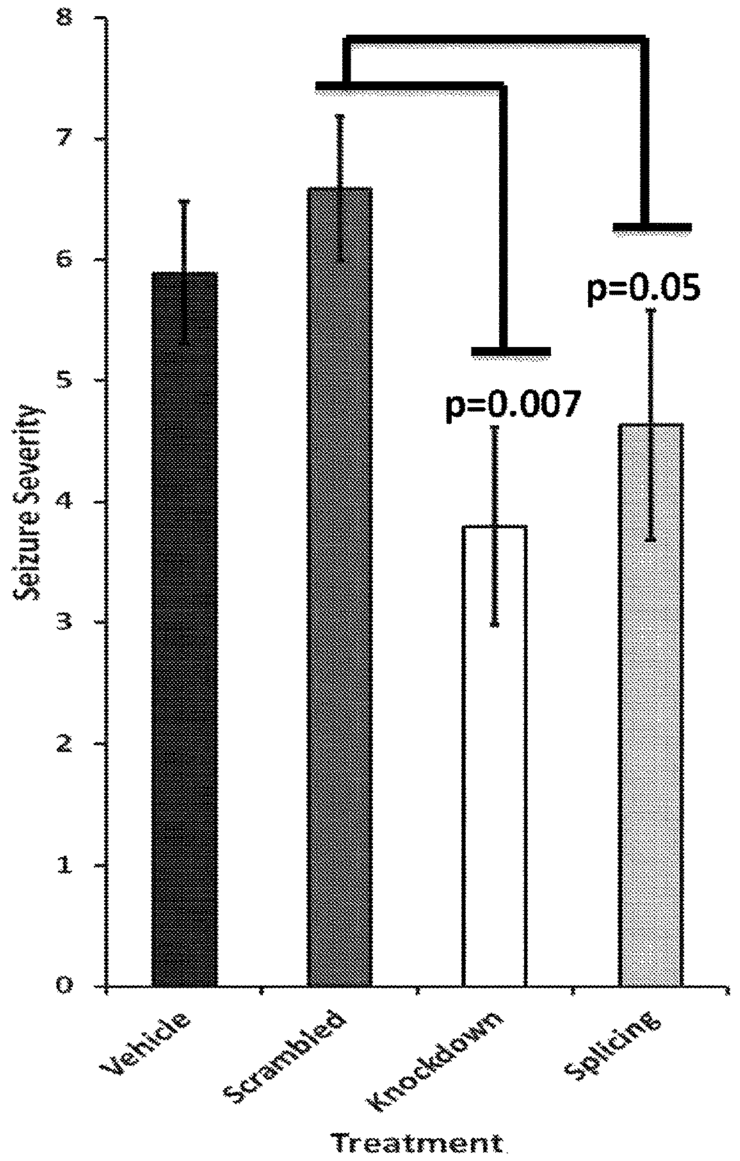
FIG. 12 depicts two plots of (A) seizure severity in mice treated with a knockdown oligo or a splicing oligo, and (B) percentage of mice treated with a knockdown oligo or a splicing oligo with various stages of seizures.
Figure 12B:
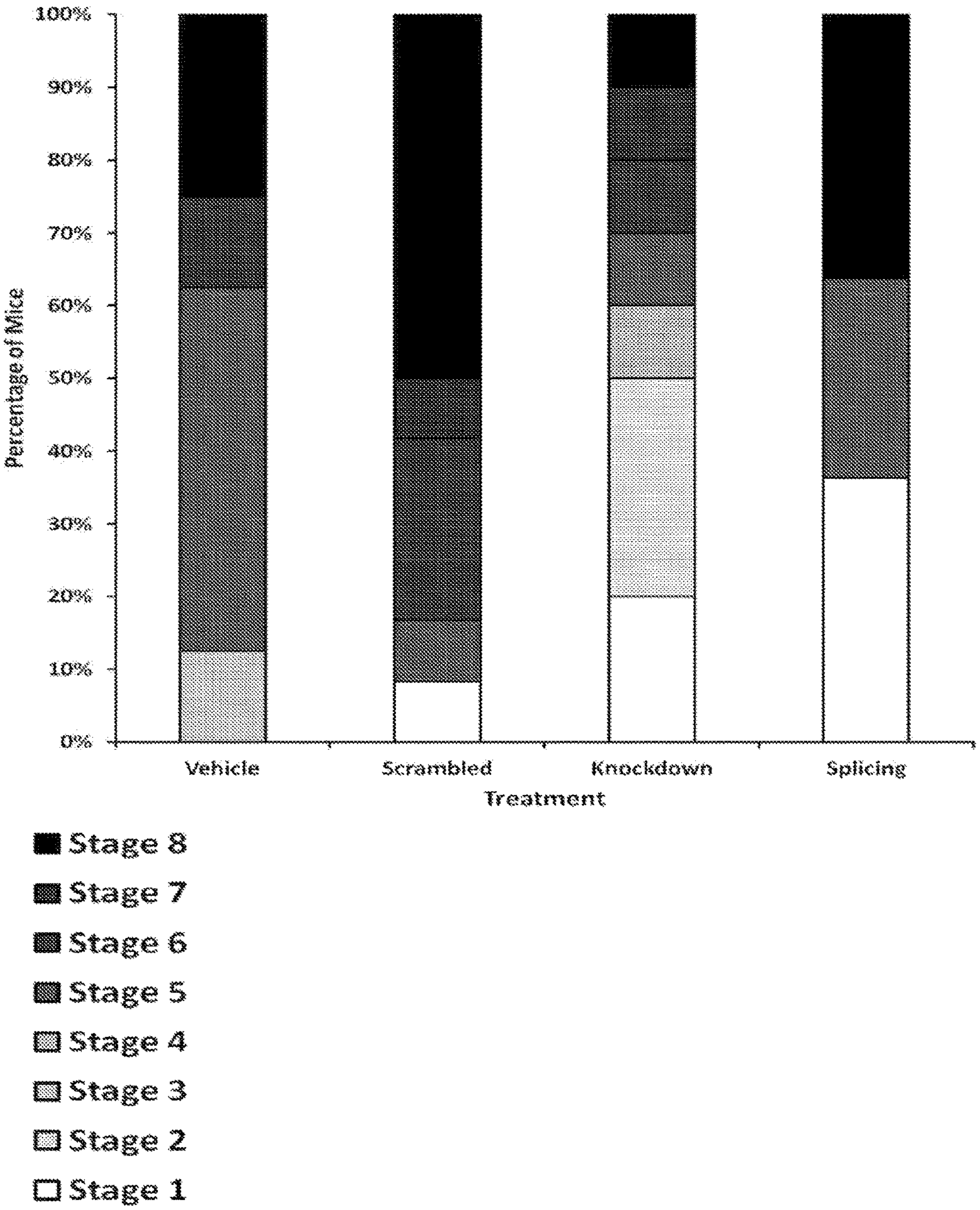

Seizures were also induced and measured in mice treated with a tau knockdown oligo or a tau splicing oligos (also ISIS 415883). In short 3 month old C57/BL6 males were dosed for 28 days with 25 μg/day of oligo. The pumps were removed, and the animals were allowed to sit for 3 weeks post-pump removal before seizure induction. Seizures were induced using 55 mg/kg of PTZ using ip injection. The mice are videotaped for 15 minutes and scored later in a blinded fashion. The results show that the knockdown and the splicing oligos were capable of protecting mice against PTZ induced seizures (FIGS. 12A and 12B).

Figure 13:
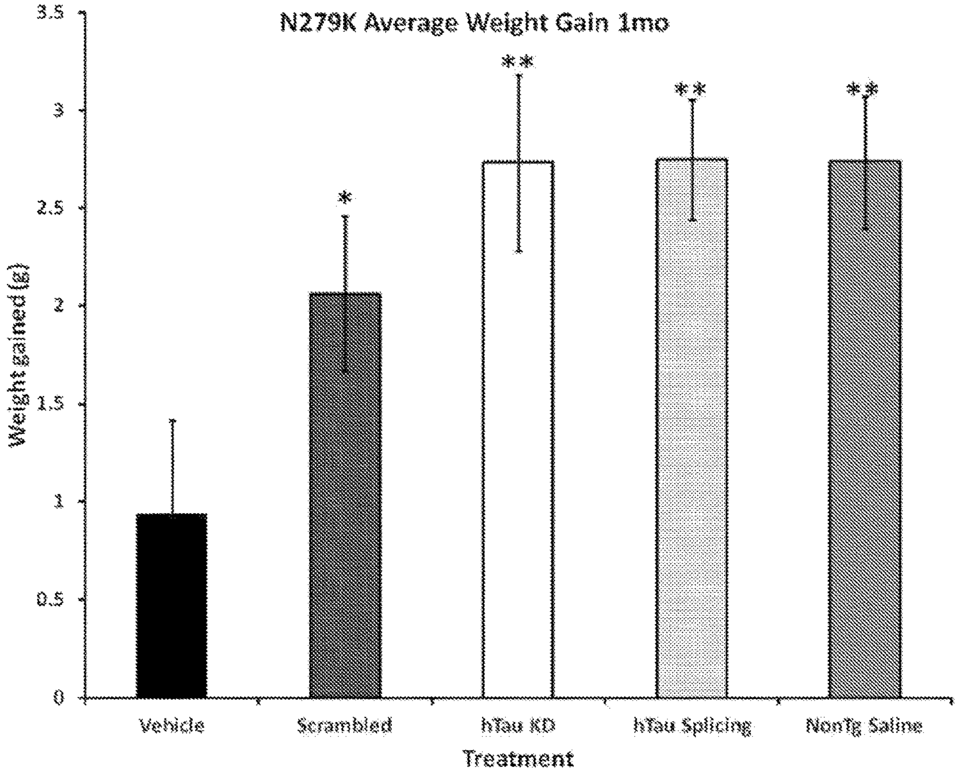
FIG. 13 depicts a plot showing the average weight gain by a N279K mouse treated with vehicle, a scrambled oligonucleotide, a human tau knockdown oligonucleotide, a human tau splicing oligonucleotide and nonTg saline.

Example 5. Effect of Knockdown and Splicing Oligonucleotides on Weight Gain in N297K Mice N279K mice treated with vehicle, a scrambled oligonucleotide, a human tau knockdown oligonucleotide, a human tau splicing oligonucleotide (i.e., ISIS 415883) and nonTg saline. The results show that mice treated with the human tau knockdown oligonucleotide, the human tau splicing oligonucleotide and nonTg saline gained significantly more weight than mice treated with vehicle alone (FIG. 13).

Example 6. Reversing Splicing Deficit in N279K Tauopathy Mice by Decreasing 4R Tau Levels Decreasing 4R tau levels in adult N279K exon 10 mutation mice may improve behavioral and pathological phenotype in these mice. Tau N279K mice are based on one of the tau mutations which causes aberrant splicing of tau, by promoting inclusion of exon 10. Inclusion of exon 10 leads to increased 4R compared with 3R tau, without affecting overall levels of tau. The mice typically develop motor and cognitive behavioral abnormalities at 6 months including deficits on rotarod and on water maze. These deficits are worse at 12 months. As is typical of a variety of tau models, approximately 25% of these animals develop severe motor weakness and die before the rest of the cohort (on average at 45 weeks old). The percentage of animals with this profound motor deficit may be measured in each group and these animals may not be included in other behavioral tests. Brain pathological changes are mild at 6 months and prominent at 1 year. The changes include increased tau and phosphotau staining in neurons and astrocytes, and increased caspase 3 activation. Pathology also included positive Gallyas silver staining in neurons, a stain that detects abnormal filaments such as those composed of aggregated tau as well as Fluorojade B positive staining, indicative of degenerating neuronal cells.

The goal of the treatment is to decrease the 4R:3R ratio in the N279K mice, which is increased by the N279K mutation and which causes preferential inclusion of exon 10. As has been demonstrated in vivo (FIG. 9), Tau splicing oligos that decrease the inclusion of Exon 10 and thus decrease the 4R:3R tau ratio may be used. Antisense oligos that alter splicing, a control oligo, or saline may be infused into the right lateral ventricle of N279K mice, at 3 months of age. Since pathology starts at 6 months of age, 3 months was chosen to be presymptomatic. The control groups are animals treated with saline alone or a control oligo. Both may be compared to animals treated with an oligo that decreases 4R:3R ratios. Each of the groups may be compared with non-transgenic, untreated mice.

The three groups of N279K mice (saline, oligo control, 4R:3R tau splicing oligo) and a group of non-transgenic mice without pumps may be examined at ages 6 months and 12 months for behavioral analysis. Including the non-transgenic mice in the behavioral studies may document that the N279K mice animals do indeed develop behavioral deficits and help understand to what degree treatment is able to prevent behavioral abnormalities. In terms of the statistical comparisons and treatment effect in the N279K mice, the important comparison may be the saline and oligo control compared to the 4R:3R tau splicing oligo. Mice that develop acute motor weakness (25% expected) may be determined to be dead when they are no longer able to right themselves after being placed on their backs for 30 seconds. There is no primary analysis planned for these animals, though tissues may be retained for any possible future analyses and the number of animals with this phenotype in each group may be scored. In conjunction with the Washington University Behavioral Core, for animals that do not develop overt weakness, radial arm Morris water maze may be analyzed at 6 months and 12 months. Rotarod performance may also be analyzed. At 1 year of age, mice may be euthanized. Just prior to euthanasia, CSF may be collected. Brains may then be collected. The left half of the brain may be fixed with 10% formalin, cyroprotected with sucrose and sectioned for immunocytochemistry of tau, phosphotau, and activated Caspase 3. Gallyas staining and fluorojade staining may also be performed. The right half of the brain may be used for biochemical analyses. Total tau mRNA and protein levels, and 4R:3R ratios may be analyzed.

Given the preliminary data described in the examples above, reversing the splicing deficit in the N279K mice with antisense oligos is likely. Previous data suggest that pathogenesis arises from the change in the ratio of 3R to 4R tau rather than the absolute levels or the missense variant in the 4R containing protein. This is evidenced by tau mice with the N279K minigene construct driven by the CMV promoter. These animals have increased levels of 4R tau both fetally and in the adult animal. However, they do not develop any tau pathology or behavioral abnormalities. Thus it is the tau promoter itself and/or the switch to increased 4R:3R that appears to be important for disease. These experiments may address an important question regarding whether changing tau ratios in the adult animal may be beneficial.

Example: Effect of Antisense Oligonucleotide Treatment on Human Tau Splicing in N279K Tauopathy Mice The effect of ASOs (i.e., antisense oligonucleotides) on tau splicing was tested in vivo. N279K tauopathy mice (Dawson, H. N. et al., Neurosci. 27:9155-9168, 2007) were used in this assay. Tau N279K mice are based on one of the tau mutations which causes aberrant splicing of tau by promoting inclusion of exon 10. Inclusion of exon 10 leads to increased 4R compared to 3R, without affecting overall levels of tau. The effect of ASOs in the splicing of exon 10 and the resulting 4R:3R ratio in these mice was evaluated.

Study 1

Figure 20A:
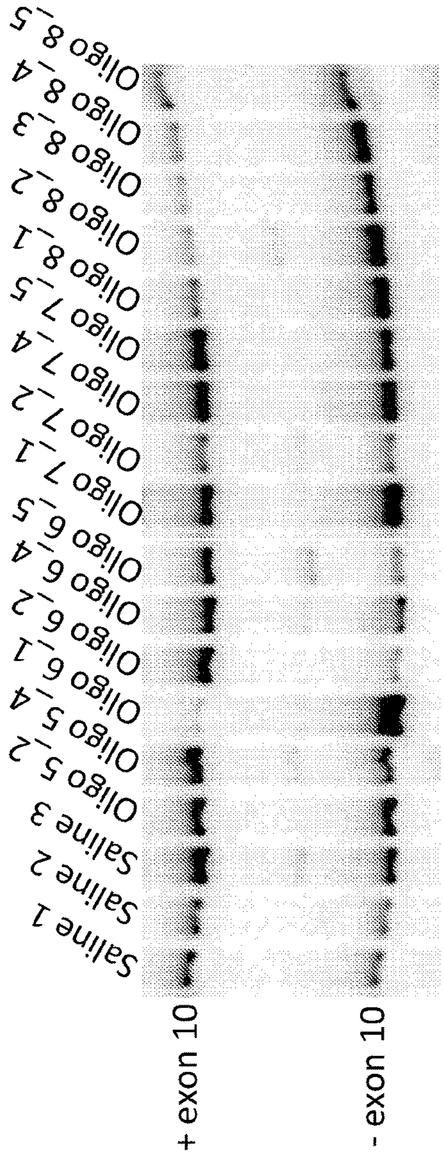
FIG. 20 depicts a picture (A) and a graph (B) showing ASO screen for Tau splicing in N279K mice. ICV infusion 60 micrograms/day for 28 days. Mice were sacrificed on the 29th day, and the cortex tissue around the cannula was collected.
Figure 20B:
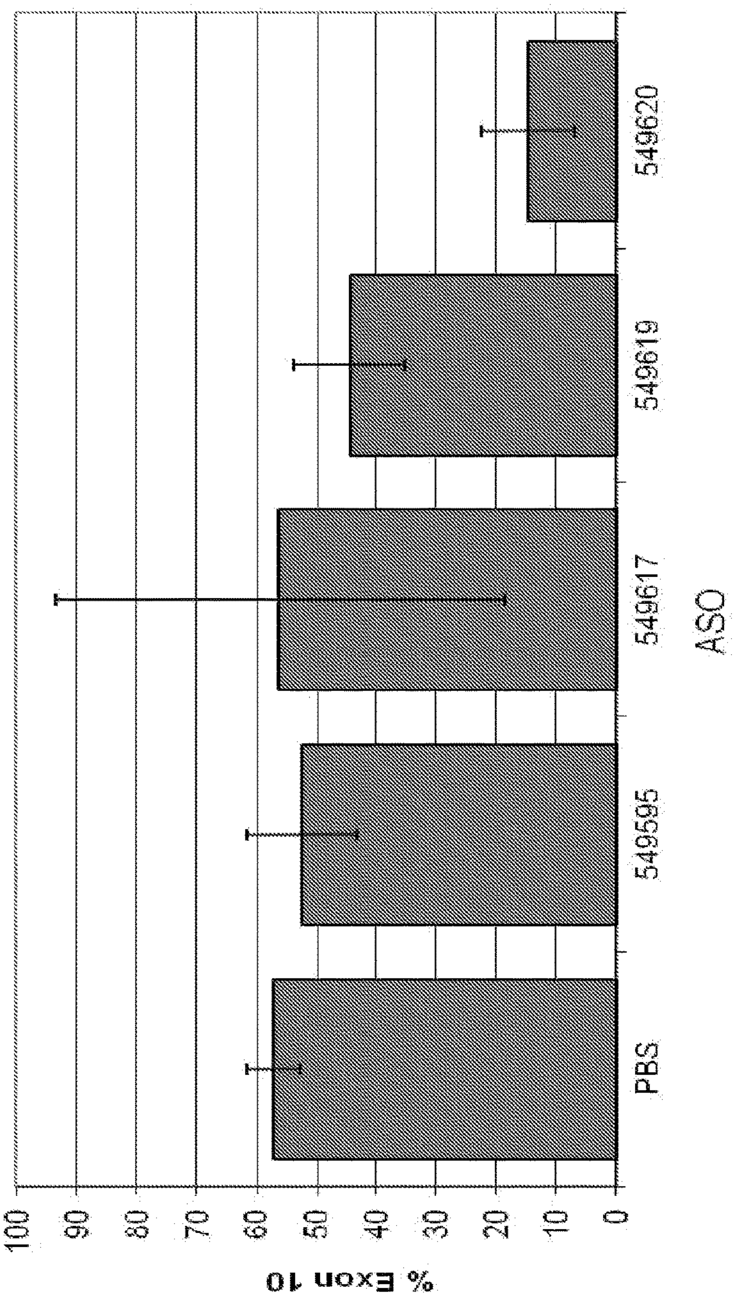
Figure 21A:
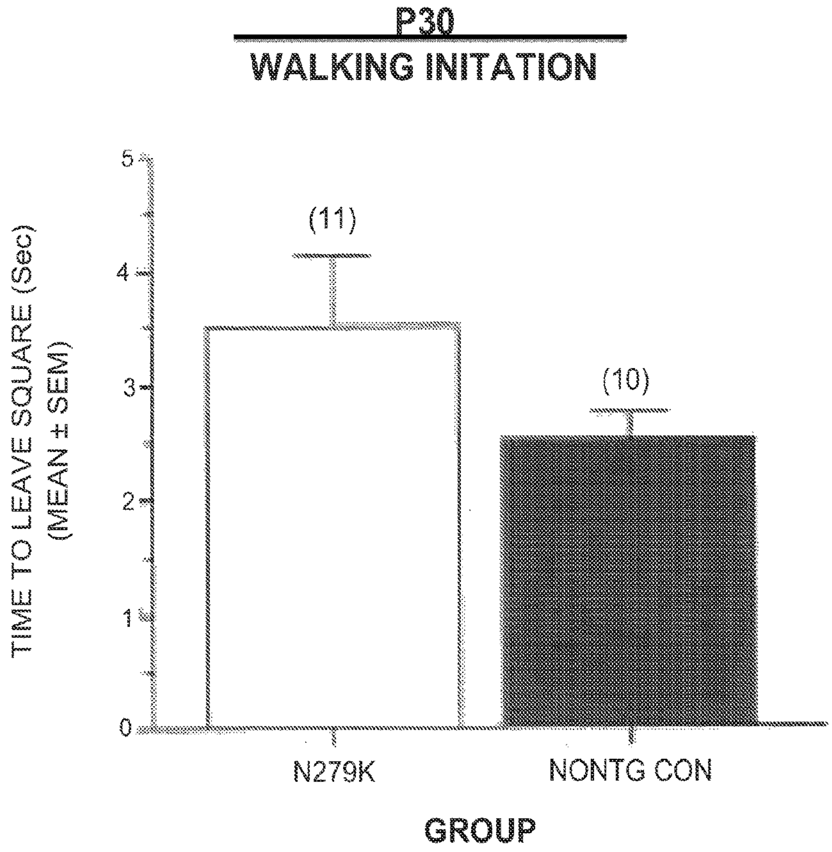
FIG. 21 depicts graphs showing N279K baseline behavioral deficits.
Figure 21B:
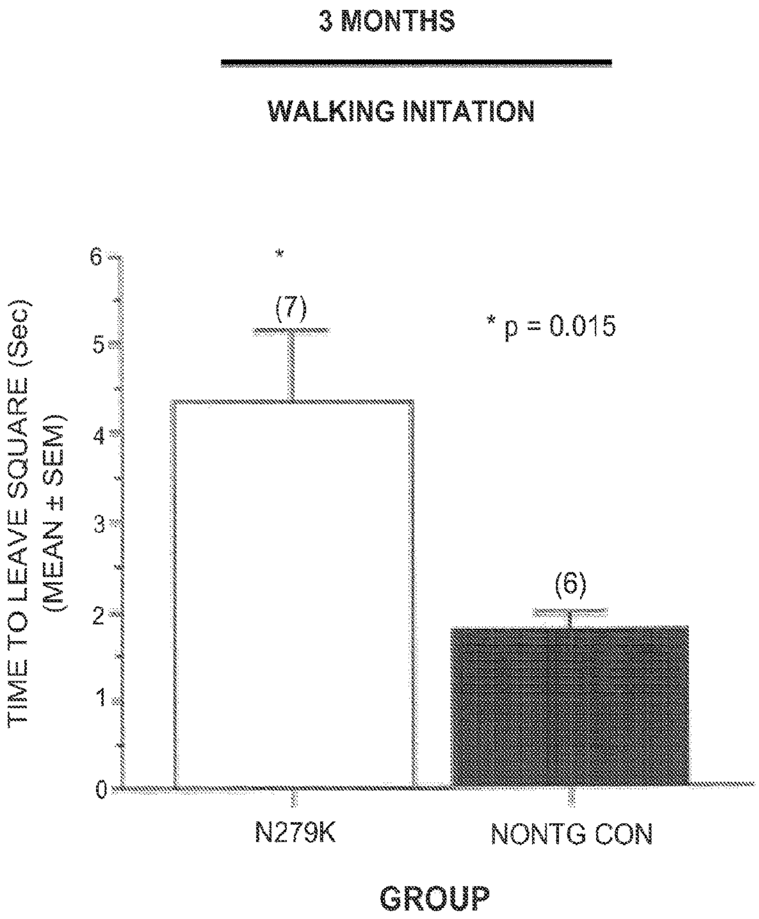
Figure 21C:
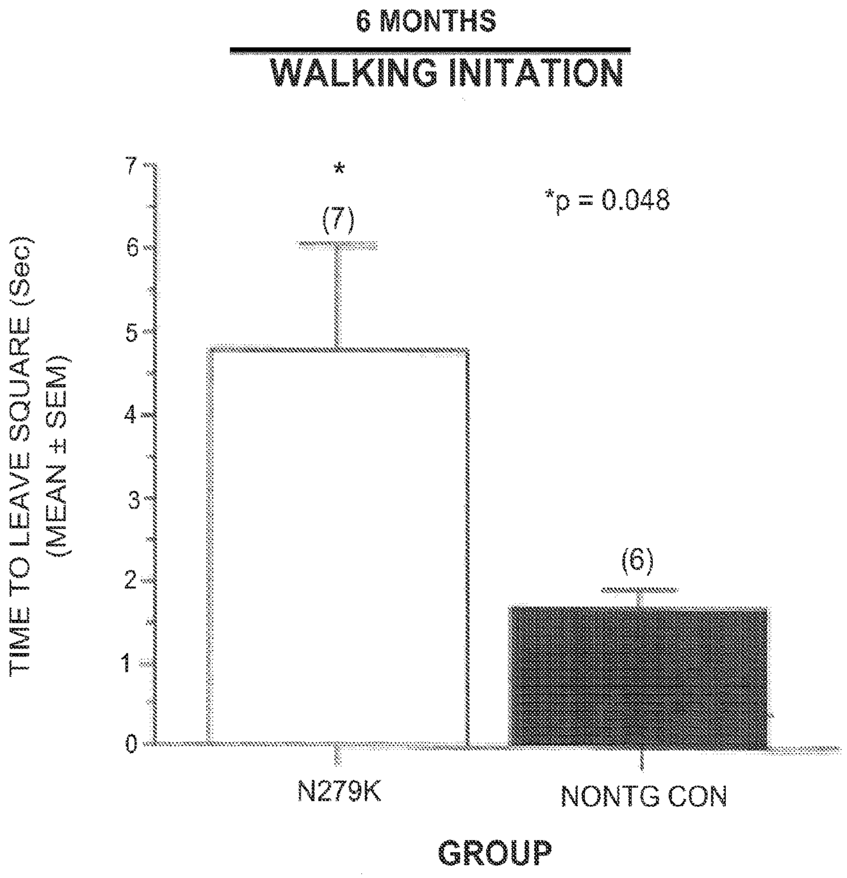
Figure 21D:
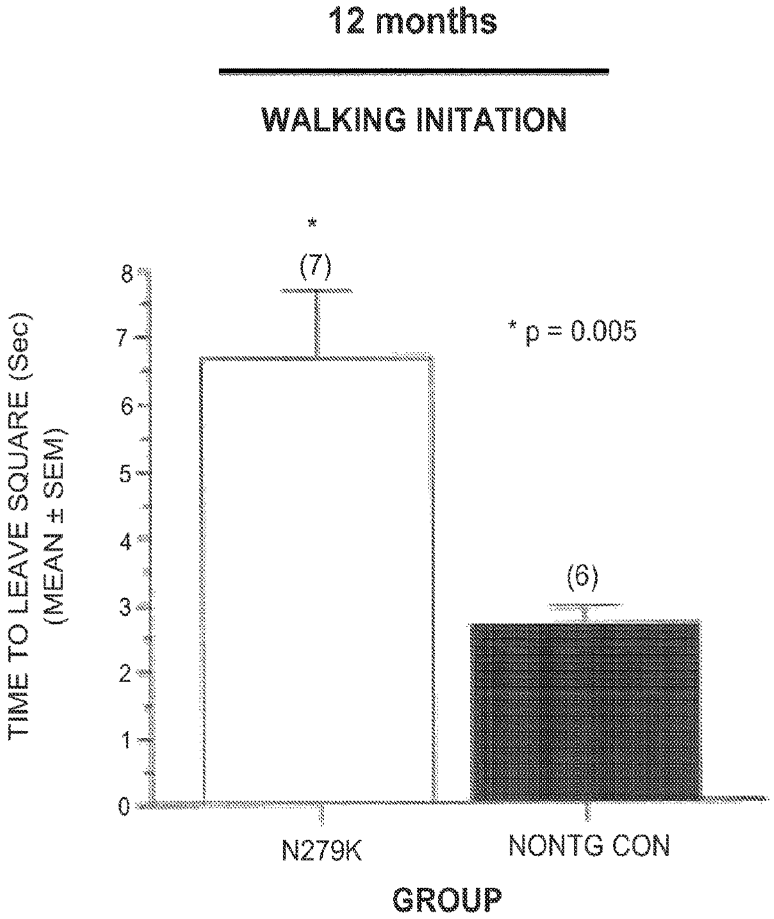
Figure 22:
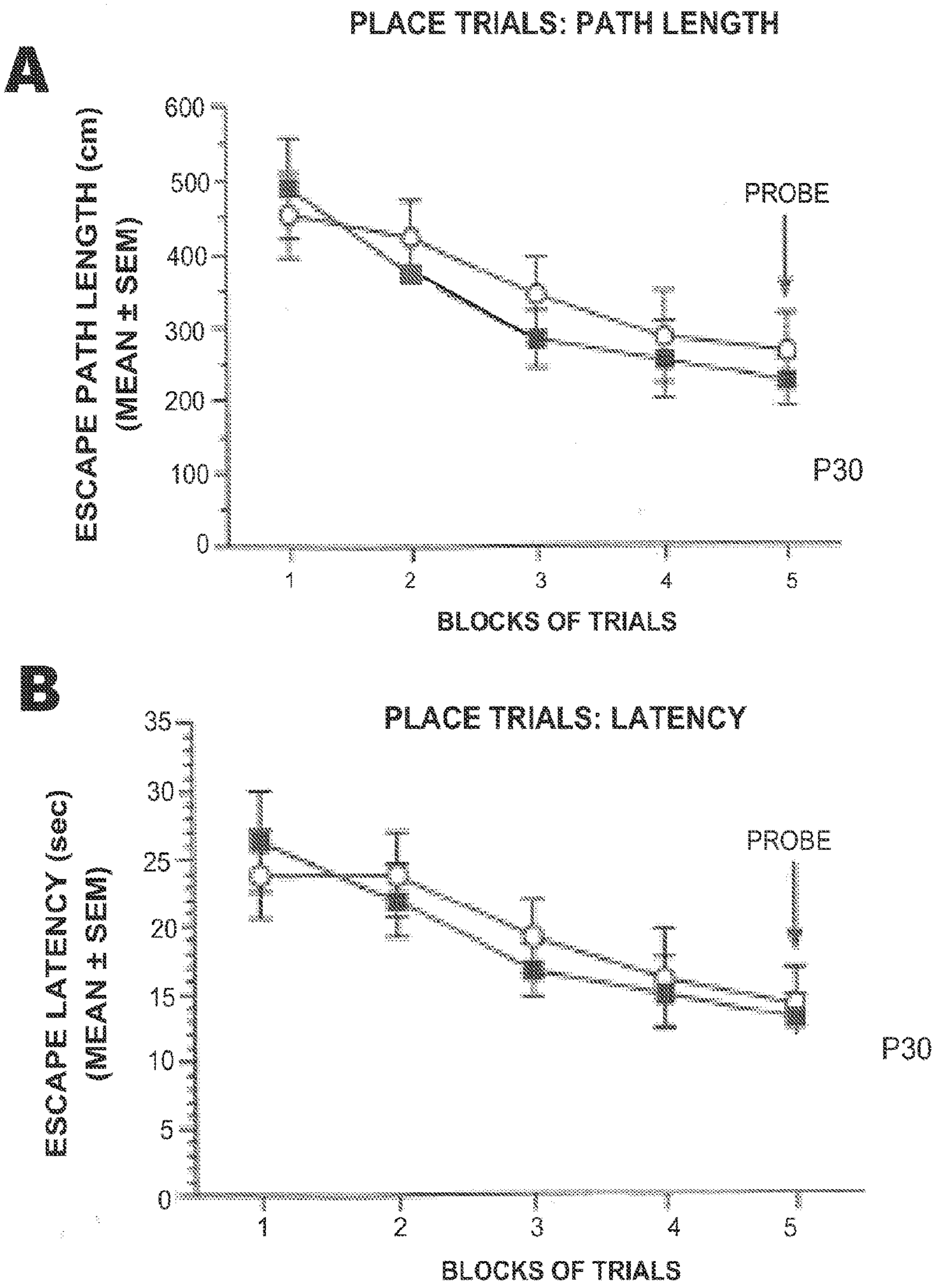
FIG. 22 depicts graphs showing Morris water navigation at different timepoints.
Figure 22C:
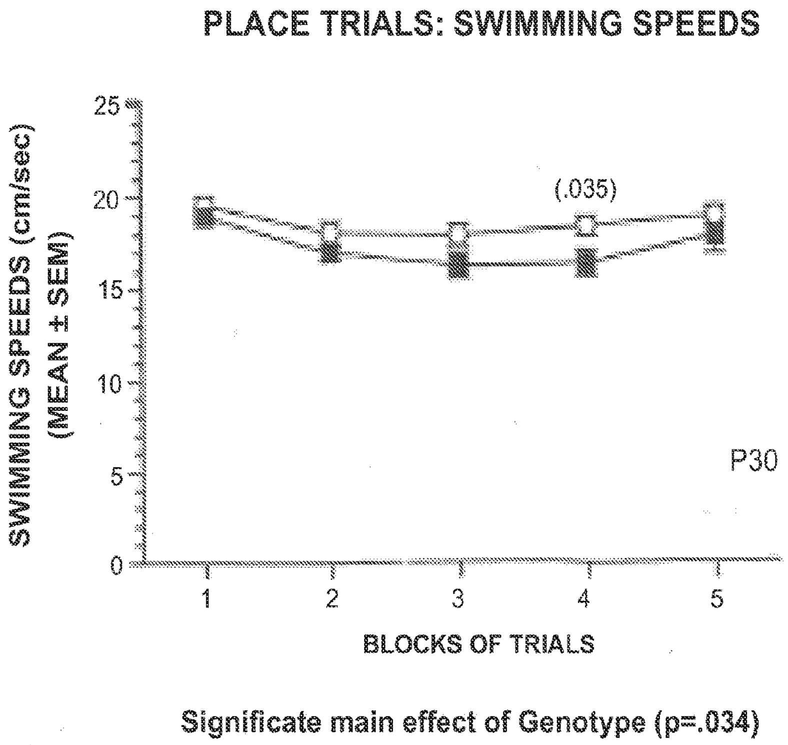
Figure 22D:
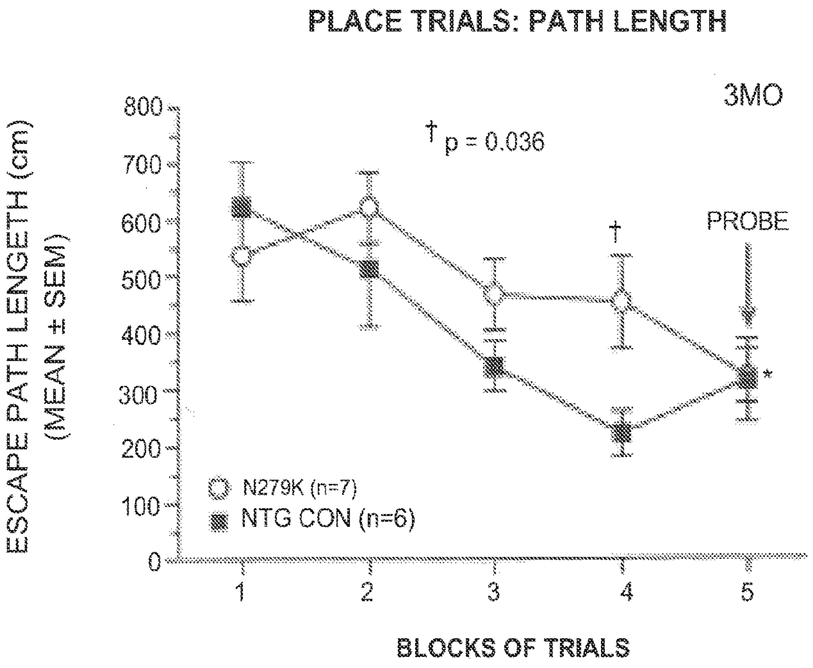
Figure 22E:
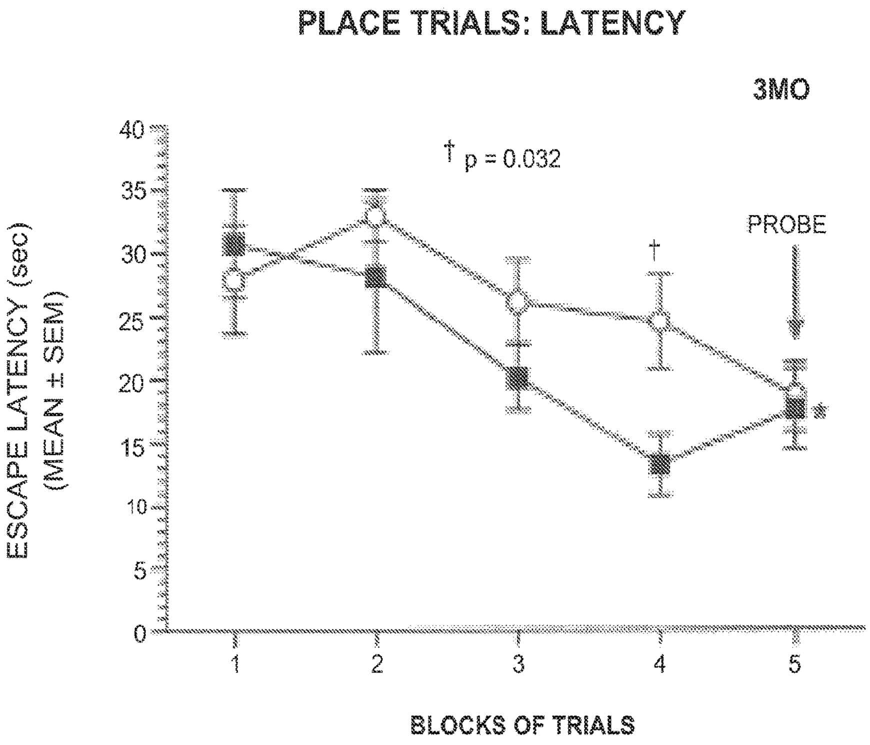
Figure 22F:
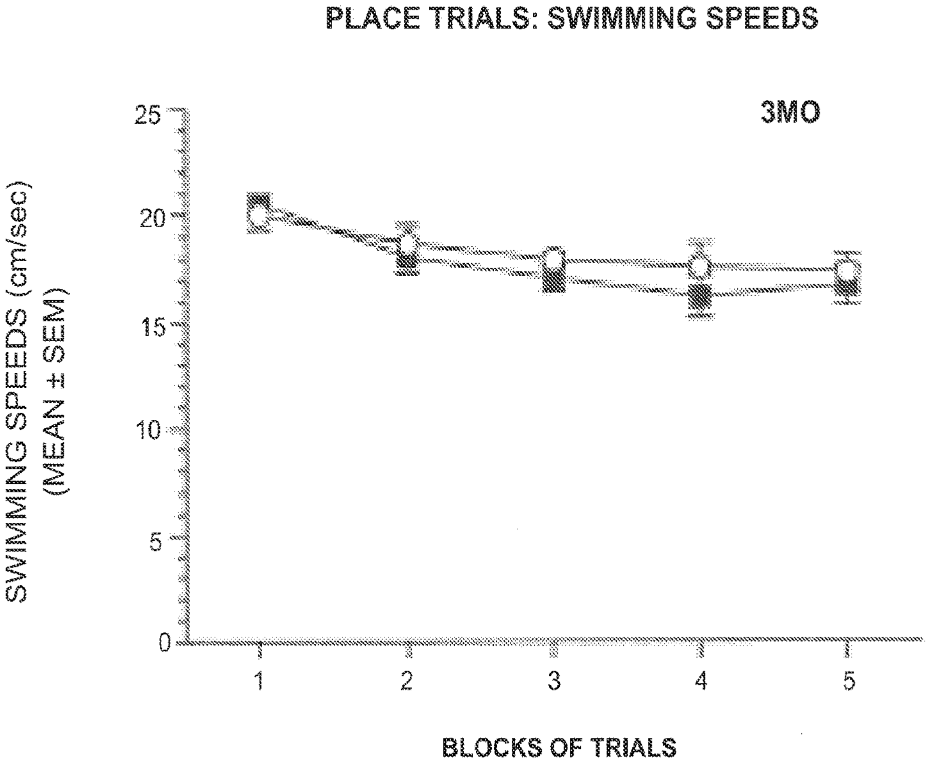
Figure 22G:
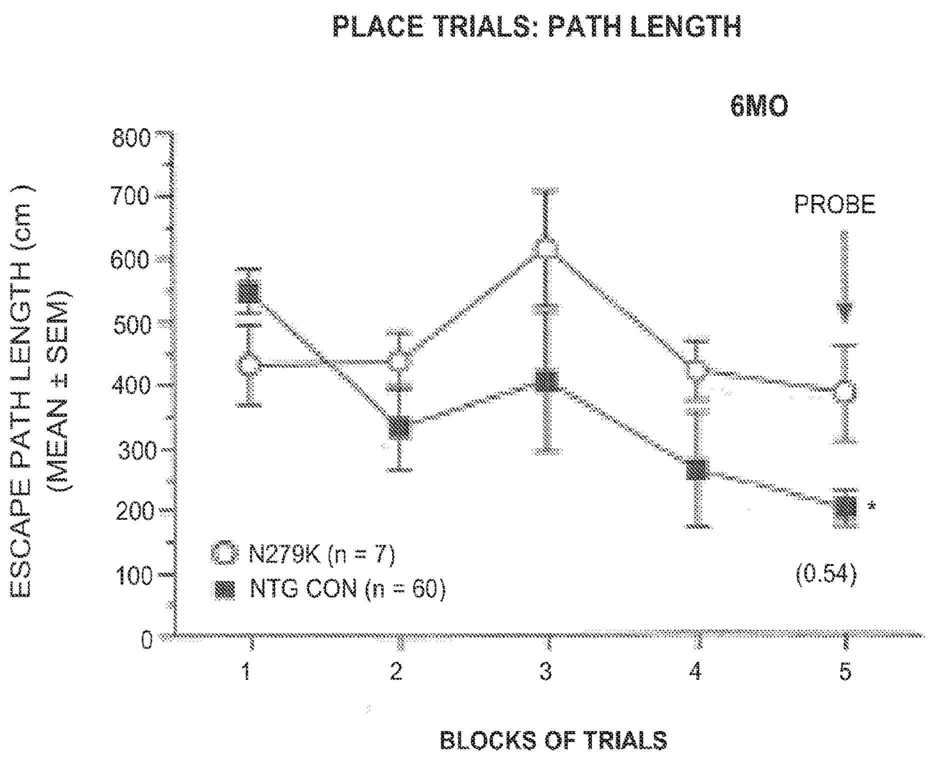
Figure 22H:
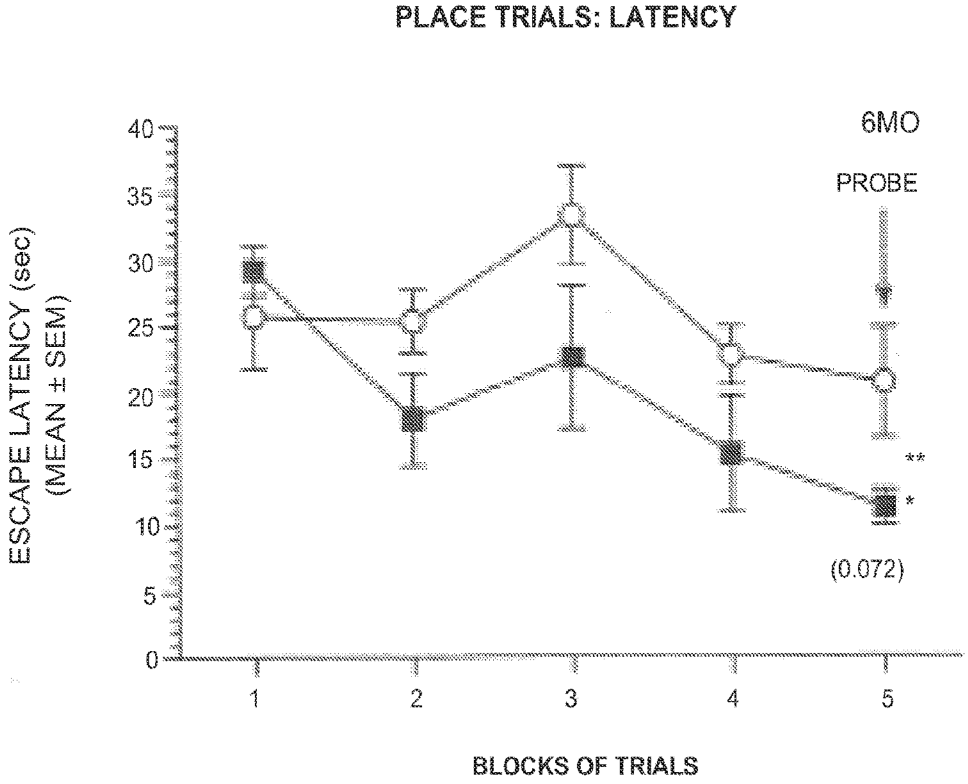
Figure 22I:
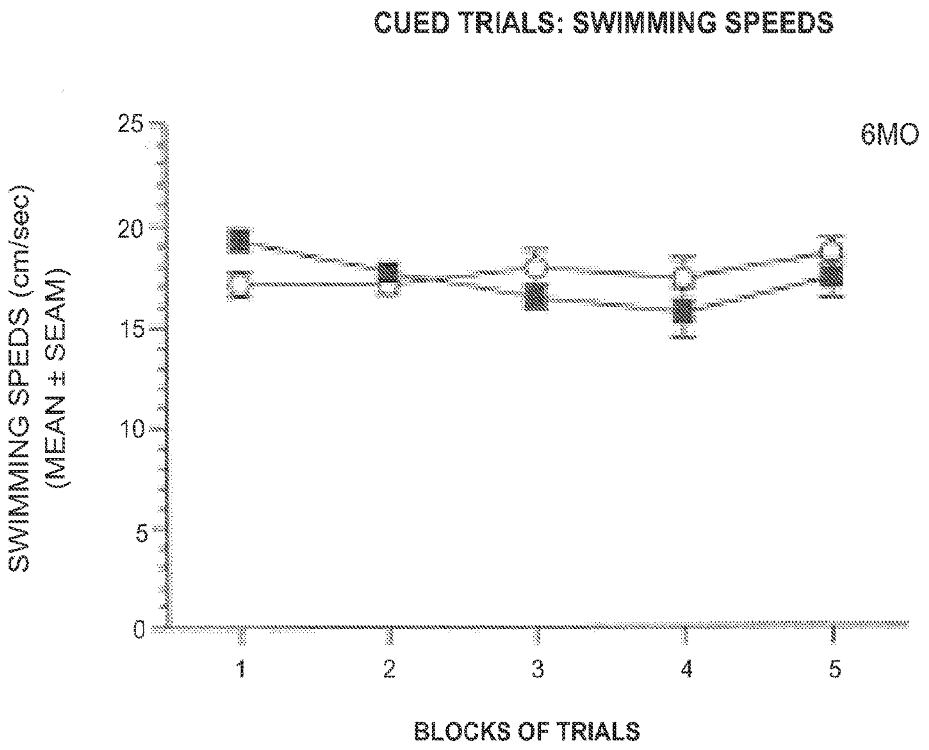
Figure 23:
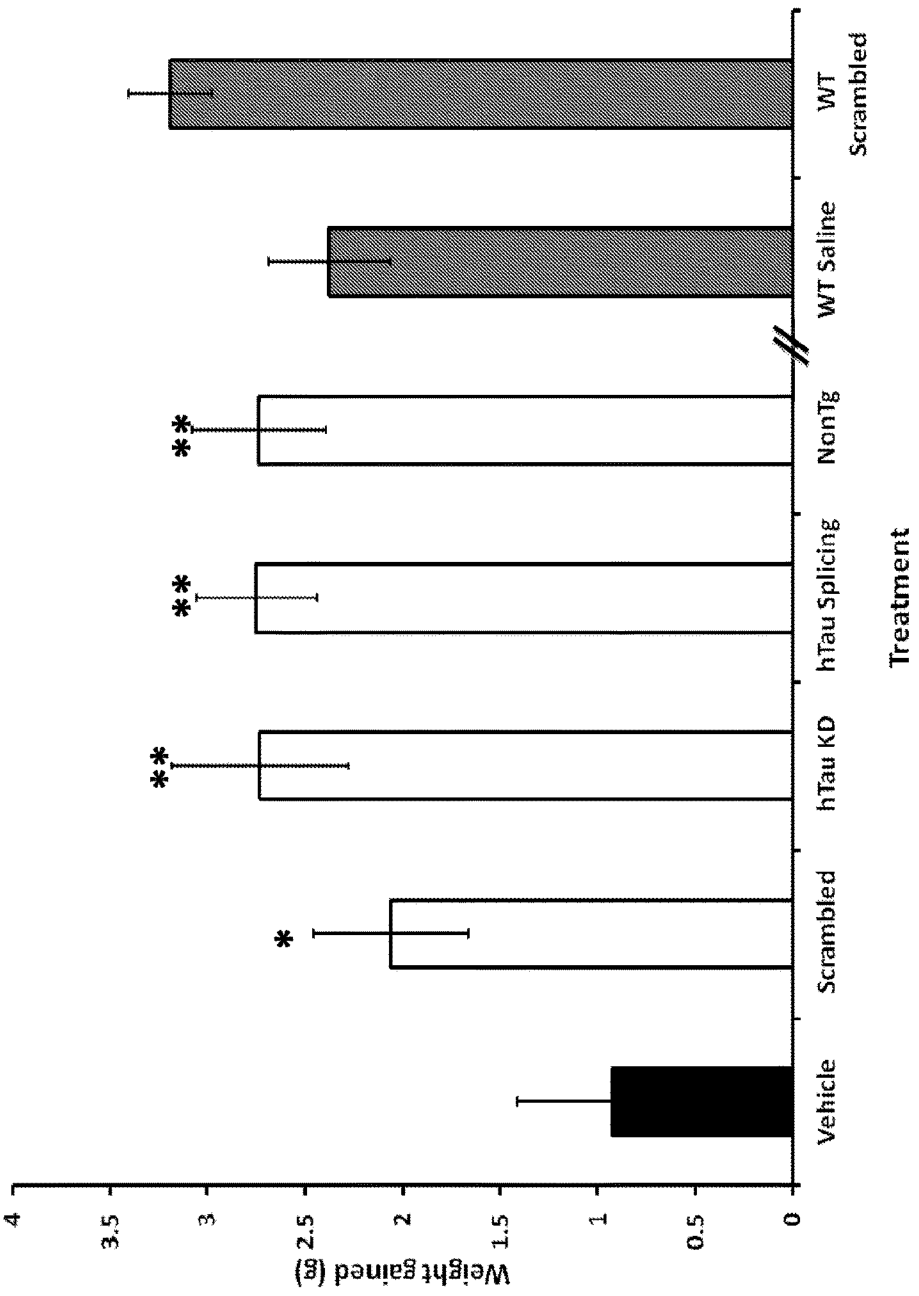
FIG. 23 depicts a graph showing N279K average weight gain after 1 month with various antisense treatments.
Figure 24:
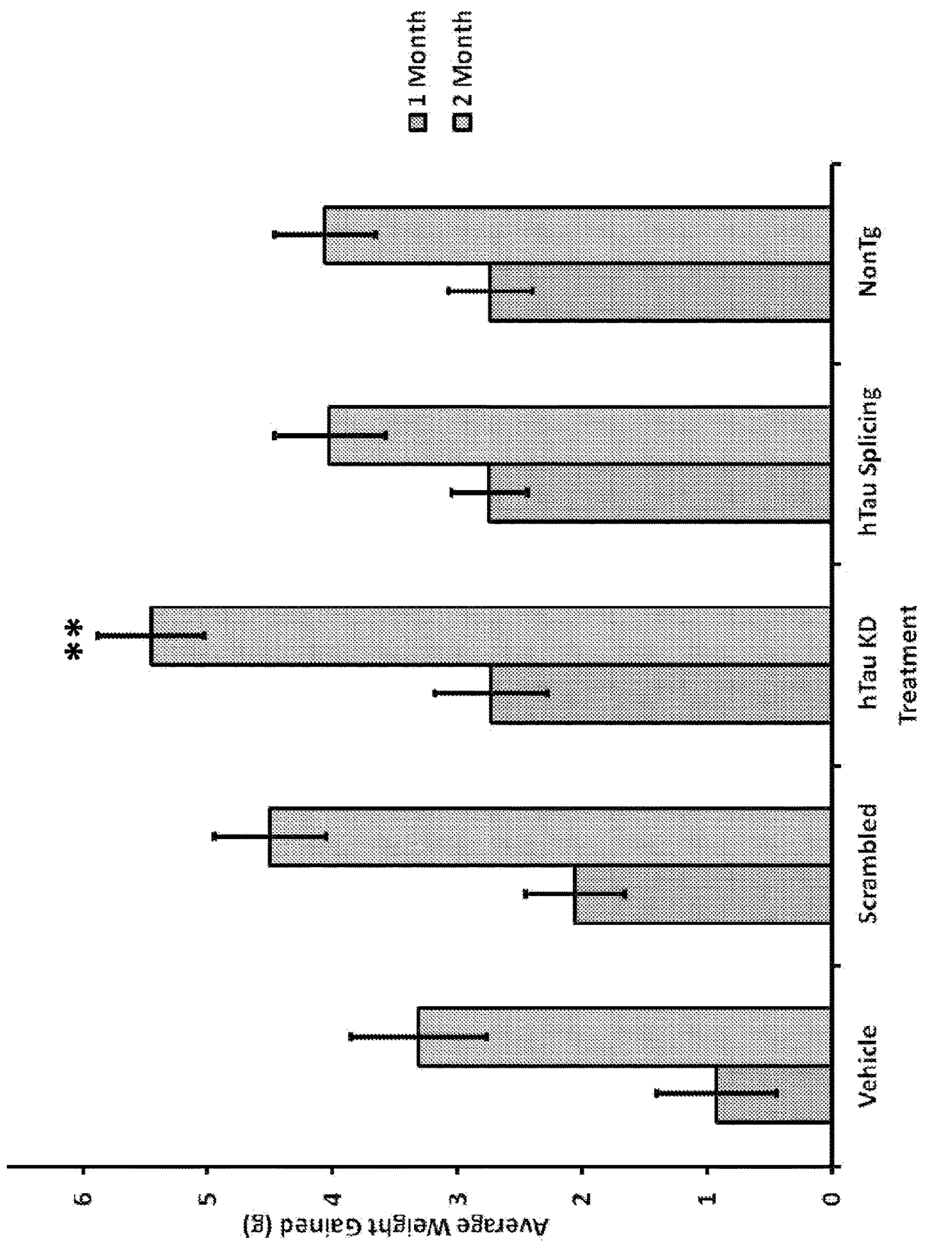
FIG. 24 depicts a graph showing N279K average weight gain after 1 and 2 months with various antisense treatments.

Transgenic mice were infused with PBS or 60 μg/day ASO (i.e., ISIS 549595, ISIS 549617, ISIS 549619, and ISIS 549620) for 28 days. Mice were sacrificed on the $29^{th}$ day, and cortical tissue around the cannula was collected and examined for human 4R tau mRNA and for human 3R tau mRNA by QPCR (FIG. 20). Treatment with ASO decreased 4R tau levels and increased 3R levels.

Example 7. Modulating Tau Levels in Mice with Alzheimer's Disease-Like Pathology For an amyloid precursor protein (APP) transgenic model the J20 line (Table 1) may be used, which expresses an hAPP minigene with the Swedish (K670M/N671L) and Indiana (V717F) familial Alzheimer's disease (AD) mutations under control of the PDGF promoter. Behavioral deficits in the J20 line Alzheimer's mice typically occur at 4-7 months and include deficits in the Morris water and exploration of a new environment. In addition, about 15% of the animals die early (by 6-8 months) for unclear reasons, but perhaps related to seizures. The death typically occurs in an animal that otherwise appeared well the previous day and is presumably secondary to an acute event. J20 line APP mice with one or both copies of mouse tau deleted are protected from amyloid beta induced toxicity as evidenced by better performance on the Morris water maze, open field exploration, and a normal lifespan in all the animals. Amyloid plaque deposition occurs in only a few J20 animals at 2-4 months, 50% at 6 months, and nearly 100% by 8-10 months. Tau deletion does not affect amyloid plaque levels in the J20 line.

Figure 4:
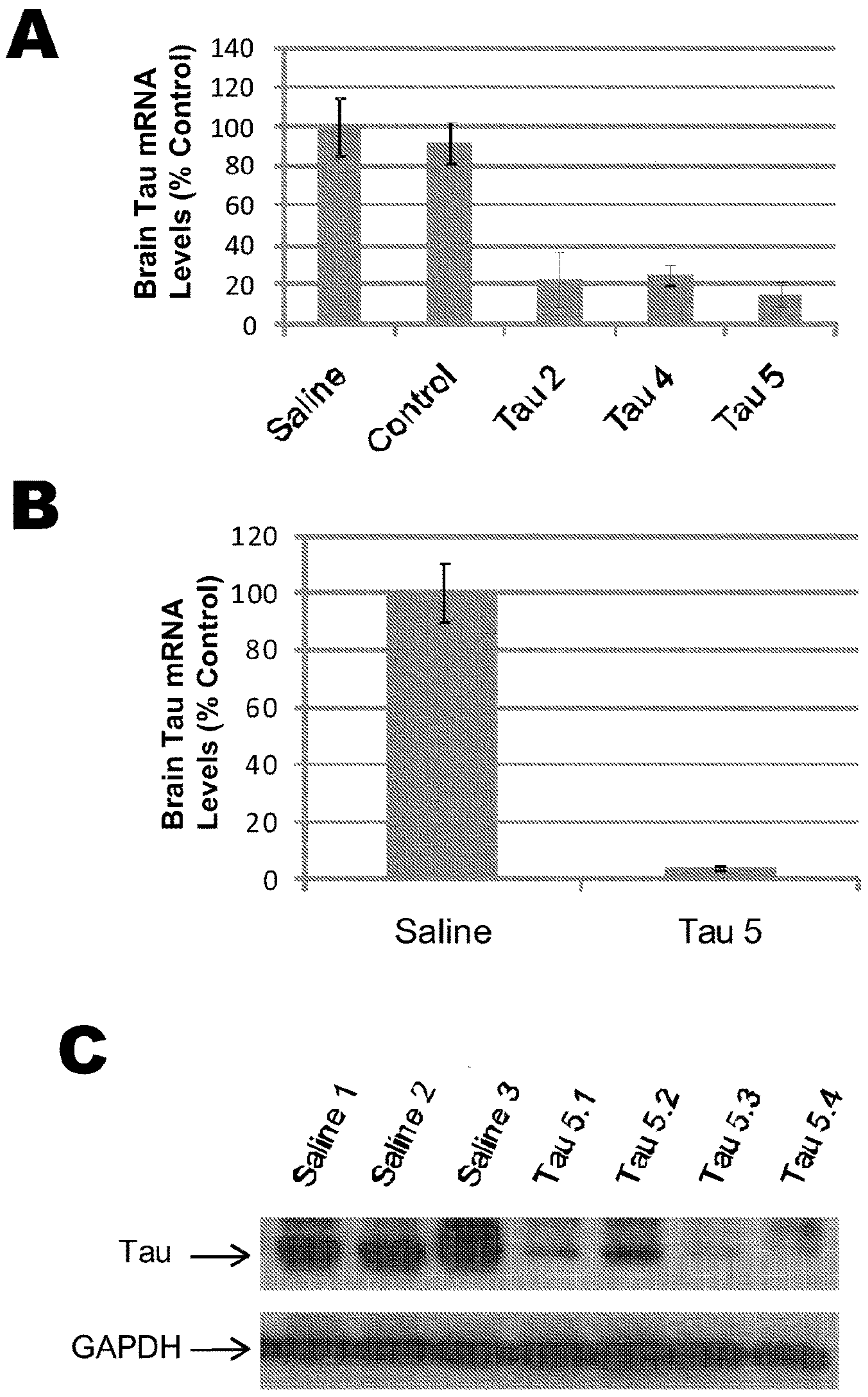
FIG. 4 depicts two plots and a Western blot showing antisense oligos decrease mouse tau levels in the brain. (A) Saline, control scrambled oligo, or 50 μg of antisense oligos directed against mouse tau were injected into the hippocampus by stereotactic injection. Mice were euthanized after one week and brain parenchyma was examined for mouse tau mRNA levels by QPCR. GAPDH mRNA was used to normalize samples. All three oligos used in this paradigm decreased mouse tau by >75%. Individual antisense oligos were labeled 1-5. Oligos 1 and 3 were not tested in this paradigm. (N=5 Avg+/−SD). (B, C) Since oligo Tau5 worked well in the intraparenchymal (hippocampal) injection in (A), Tau5 was further tested by infusing this oligo into the right lateral ventricle for 1 month, at 100 μg/day via an osmotic pump connected to a catheter in the right lateral ventricle. Mice were euthanized after 1 month and right temporal parietal cortex was examined for mouse tau mRNA levels (N=4, Avg+/−SD), (B) and mouse tau protein levels (C). Protein data from three saline animals and 4 Tau5 treated animals are shown. Tau protein levels are clearly reduced. GAPDH was used a loading control and shows no change.
Figure 5:
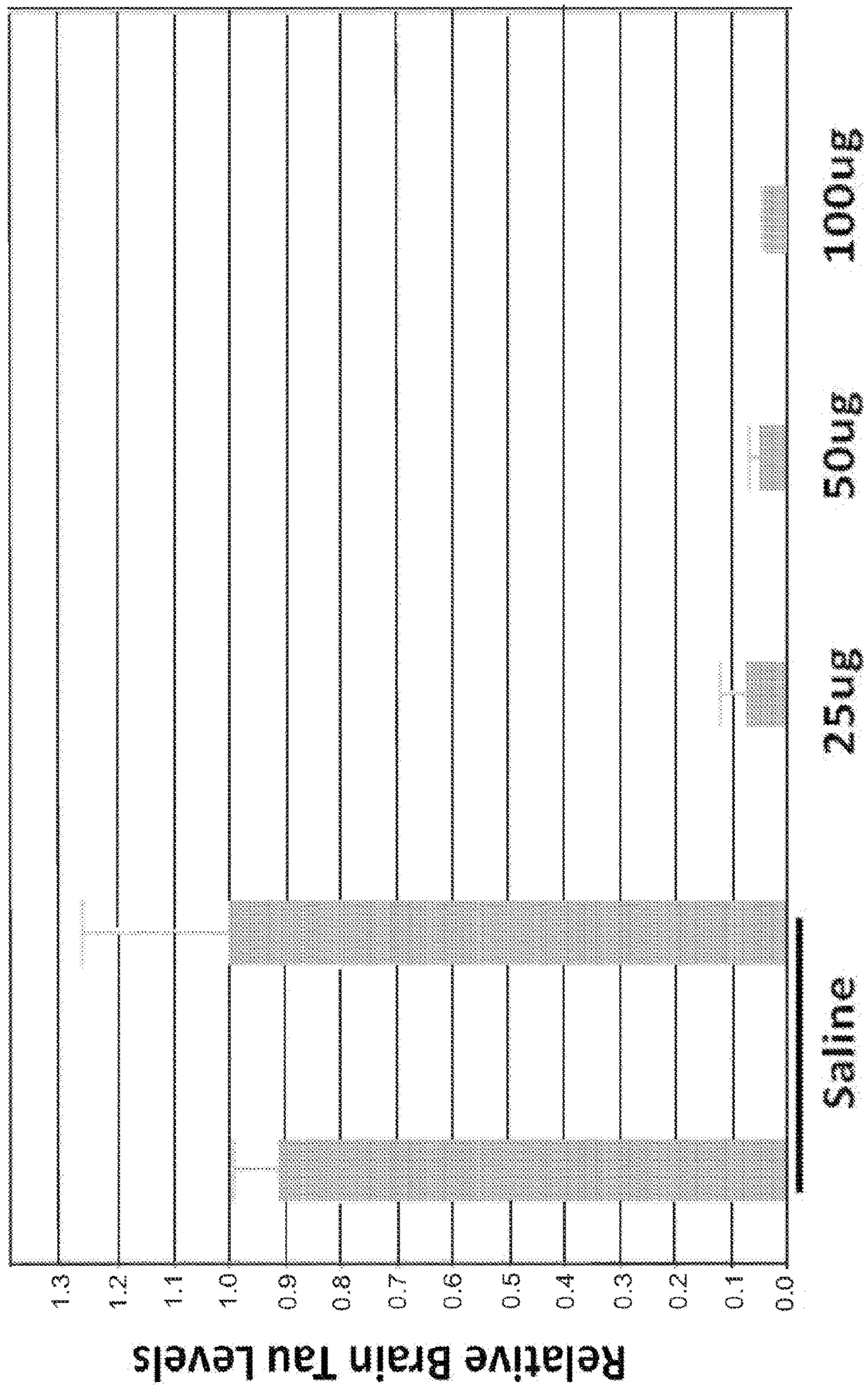
FIG. 5 depicts a plot representing the relative brain tau levels after infusion of 25, 50 and 100 μg of the knockdown oligo.

J20 line Alzheimer's mice at age 3 months old may be treated with Tau 5 oligo, an antisense oligonucleotide that clearly decreases mouse tau mRNA and protein (FIG. 4). There may be two control groups, one may be treated with saline and another with a scrambled antisense oligonucleotide control. Since behavioral deficits become apparent between 4 and 7 months of age, and since the J20 line does not have amyloid beta accumulation at 2-4 months, 3 months was chosen as presymptomatic. Treatment may consist of placement of an intraventricular catheter connected to an osmotic pump filled with oligo or saline.

Each litter of animals may be divided into male and female groups. Males and females may then be equally and randomly assigned to a treatment paradigm. Following surgeries, cage cards indicating treatment group may be replaced with animal number assignments such that the technician following the mice may be blinded to the treatment strategy.

The three groups of J20 APP mice (saline, oligo control, antisense oligo against tau) and a group of non-transgenic mice may be examined at ages 6 months and 12 months for cognitive function on water maze, y maze, and the exploration of new environment. Including the non-transgenic mice in the behavioral studies may document that the J20 APP animals do indeed develop behavioral deficits and help understand to what degree treatment is able to prevent behavioral abnormalities. In terms of the statistical comparisons and treatment effect in the J20 APP mice, the important comparison may be the saline and oligo control compared to the antisense oligo against tau. These behavioral studies may be performed in conjunction with the Animal Behavioral Core at Washington University run by Dr. David Wozniak. This core is open to all Washington University investigators, is located within an animal facility, and has a wide array of experience with behavioral measures (hopecenter.wustl.edu/cores/animalBehavior). At one year of age animals may be euthanized. Immediately before euthanasia, cerebral spinal fluid may be drawn. Brains may then be collected. The left half of the brain may be fixed with 10% formalin, cyroprotected with sucrose and sectioned for immunocytochemistry of amyloid beta from the genu of the corpus callosum through the caudal extent of the hippocampus. The percent surface area covered by immunoreactive amyloid beta deposits (percent A13 load) as identified with a rabbit pan A13 antibody may be quantified following stereological principles as described. The right half of the brain may be used for biochemical analyses. It may be confirmed that Amyloid beta levels are not changed, including CSF amyloid beta, and that tau mRNA and protein levels are indeed decreased in the treated animals using tissue homogenate. The J20 APP do recapitulate some aspects of Alzheimer's disease, including amyloid beta deposition and cognitive changes. However, they do not develop tau pathology. Thus tau pathological examinations may not be performed for this set of experiments although tissue may be retained for potential analysis of this or any other measures suggested by future work in the field.

It is expected that decreasing overall tau levels in adult APP transgenic mice may protect the mice from amyloid 13 induced toxicity.

Methods for Examples 1-7

Screening and Identifying Effective Antisense Oligonucleotides

The overall goal is to identify one or two antisense oligos with potent efficacy and no toxicity that may be used in the subsequent studies. Though this initial work is labor intensive and time consuming, identifying the best oligo in these initial studies will be essential for successfully completing the interesting treatment part of this project using transgenic mice. The antisense oligonucleotides are produced by Isis Pharmaceuticals, Inc. The oligonucleotides used are 20-mer phosphorothioate, 2'-O-(2-methoxyethyl) (MOE)-modified antisense oligonucleotides.

Step 1.) In vitro screen: Approximately 80 oligonucleotides are typically screened in vitro in cultured cells. This process typically identifies 8-10 oligos that show good efficacy and could be used for in vivo knockdown.

Step 2.) Brain and spinal cord screen: Prior experience has demonstrated that these antisense oligos will not reach the brain and the spinal cord following delivery in the periphery (intraperitoneal, subcutaneous, or venous), presumably because the oligos do not cross the blood brain barrier. Because the oligos do not cross the blood brain barrier, the antisense oligos need to be delivered directly to the brain. Two methods are used to screen oligos in the brain. The first is a direct brain parenchymal injection. This is an excellent method for screening oligos because the technique is straightforward, does not require insertion of a pump, and leads to reproducible oligo effects after 1 week. This technique addresses the question of whether the oligo is active in the brain.

The second method for screening is intraventricular delivery through an osmotic pump for 1 month. This leads to more widespread delivery as would be required for treatment of an animal model. Cerebral spinal fluid bathes the brain and spinal cord and thus serves as a drug delivery system to the entire brain and spinal cord. To deliver drugs to the cerebral spinal fluid, a catheter is placed in the lateral ventricle. To access the lateral ventricle, a small hole is drilled in the skull (using a stereotaxic apparatus) and a catheter which is connected to an osmotic pump (Alzet) is inserted. The continuous infusion into the right lateral ventricle delivers drug to the cerebral spinal fluid, which is then widely distributed throughout the brain and spinal cord. The typical dose is 100 μg/day for 28 days, and may be optimized for individual oligos. The osmotic pump lasts for 30 days, but can be replaced with a new pump by making a small incision in the skin, disconnecting the plastic tubing, reconnecting to a new pump and then resuturing the skin. These catheters have been maintained for more than 9 months. Mice tolerate this procedure well.

Tolerability of Antisense Oligonucleotides:

Part of the screen in brain involves an assessment of the tolerability of the oligo. One concern with this technology that is often raised is the toxicity associated with many first generation antisense oligonucleotides. Use of the new "second generation" oligos has demonstrated decreased toxicities for the following reasons. First, oligo chemistry has greatly improved over the past decade. The current "second generation" oligos include modifications to increase potency and decrease immune stimulation. Second, there is now better understanding of the biology causing some immune reactions to oligos. Phosphorothioate oligodeoxynucleotides, such as those used here are well recognized to activate cells of the immune system predominantly through interaction with Toll-like receptor 9 (TLR-9), although there are TLR-9 independent pathways as well. Avoiding certain particularly immunogenic sequence motifs and the current chemistries helps to minimize this immune stimulation. Third, careful attention paid to choosing the most potent oligos, minimizes toxicity by using smaller doses. 25-50 fold less oligo is now used to produce the same effects achieved with earlier chemistries. Fourth, the current set of oligos is produced with minimal impurities and no measurable endotoxin, which were a likely source of earlier oligo related toxicities.

Despite these reassurances, the best measure of toxicity of a particular oligo for these animal studies is observation of the animal. Animals are observed behaviorally for any signs of abnormalities and weighed weekly. Loss of weight would be considered a sign of toxicity. Signs of weakness, decreased mobility, infection, and ruffed coat are monitored. This toxicity screen also involves a brain survey for inflammation including H&E, and astroglial/microglial stains. Thus far both the tau knockdown and tau splicing oligos used in these studies have been well tolerated. In addition, the exact same oligo chemistry has been well tolerated in the periphery (subcutaneous injection) by greater than 500 patients in clinical trials.

Mice

Mice used in these studies and planned studies are detailed in Table 1.

TABLE 1

| Mouse Line | Transgene | Promoter | Behavorial Changes | Pathology | Experimental |
|---|---|---|---|---|---|
| N279K | Human tau minigene containing Exon 10 and flanking intronic sequence | Human Tau | Deficits in radial arm water maze and rotarod at 6 months. 25% develops ever motor weakness by 6 months. | Accumulation of tau, phosphotau in neurons, astrocytes. Present at 6 months, worse at 12 months. | N279K mutation leads to increased 4R compared to 3R tau. Does decreasing 4R:3R tau ratio in adult mice improve behavior/pathology? |
| J20 APP | hAPP minigene with Swedish (K670M/N671L) and Indiana (V717F) familial AD mutations | PDGF | Deficits on Morris water maze, y maze, exploration of new environment at 4-7 months. 15% premature death for unclear reasons by 6-8 months. | Amyloid beta deposition. No obvious tau pathology | Does decreasing mouse tau in adult mice improve behavior/pathology? |

Example Set 2

Figure 14:
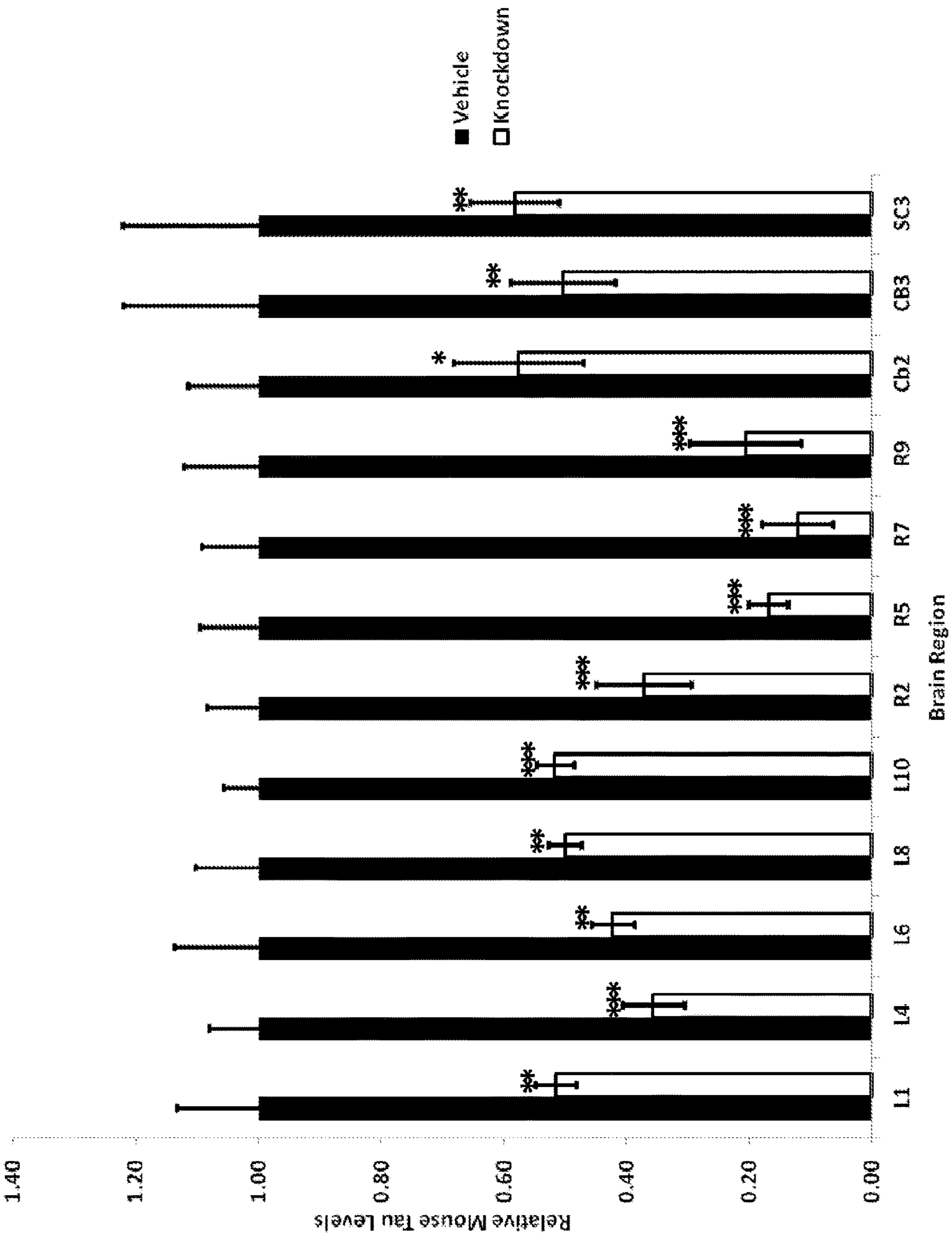
FIG. 14 depicts a graph showing the relative mouse tau levels in different brain regions with vehicle or a knockdown oligo.
Figure 27:
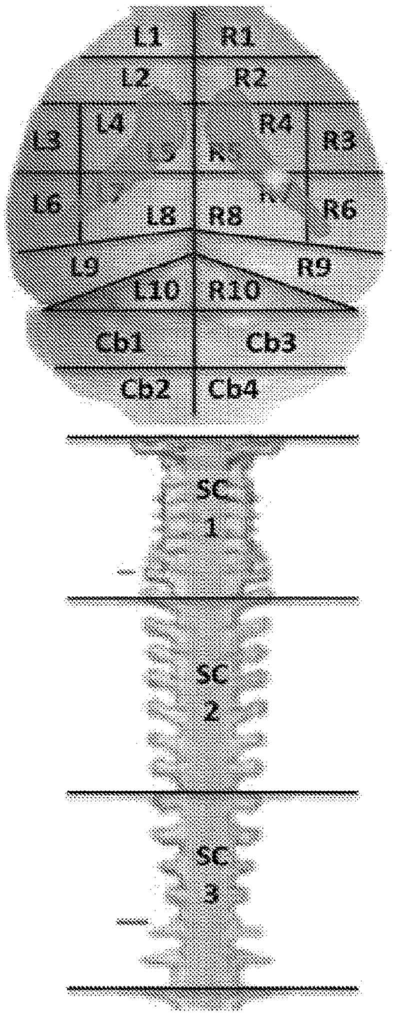
FIG. 27 provides a diagram of each CNS section used for mRNA and protein analysis in Example 6 (Example set 3).

Example 6: Evaluation of Wide-Spread Tau Knockdown In Vivo with Antisense Oligonucleotides To evaluate tau knockdown in different brain regions using antisense oligos, tau#5 oligo was used in C57/Bl6 mice (FIG. 14). A map of the brain regions is provided in FIG. 27.

C57/Bl6 mice were administered 25 µg/day tau#5 or PBS by intraventricular infusion with the Alzet pump for 28 days. Pumps were then removed and the mice were allowed to rest for an additional 14 days. Brains were then collected. Sections of brain were collected for RNA analysis using qRT-PCR.

Tau mRNA levels significantly decreased in all sections of the brain examined (FIG. 14).

Example 7: Effect of Antisense Inhibition of Tau in P301S Mice

The effect of treatment with ASOs#6, 9, 12, and 13 was evaluated in P301S mice. P301S mice develop filamentous tau lesions at 6 months of age that progressively result in hippocampal and entorhinal cortical atrophy by 9-12 months of age (Yoshiyama, Y. et al., Neuron 53: 337-351, 2007).

Groups of P301 S mice were infused with PBS or 100 µg of antisense oligonucleotide into the right lateral ventricle by the Alzet pump for 14 days. The pumps were then removed and mice were allowed to rest for 14 days. The mice were euthanized and tissues were collected and used to prepare mRNA.

Figure 15:
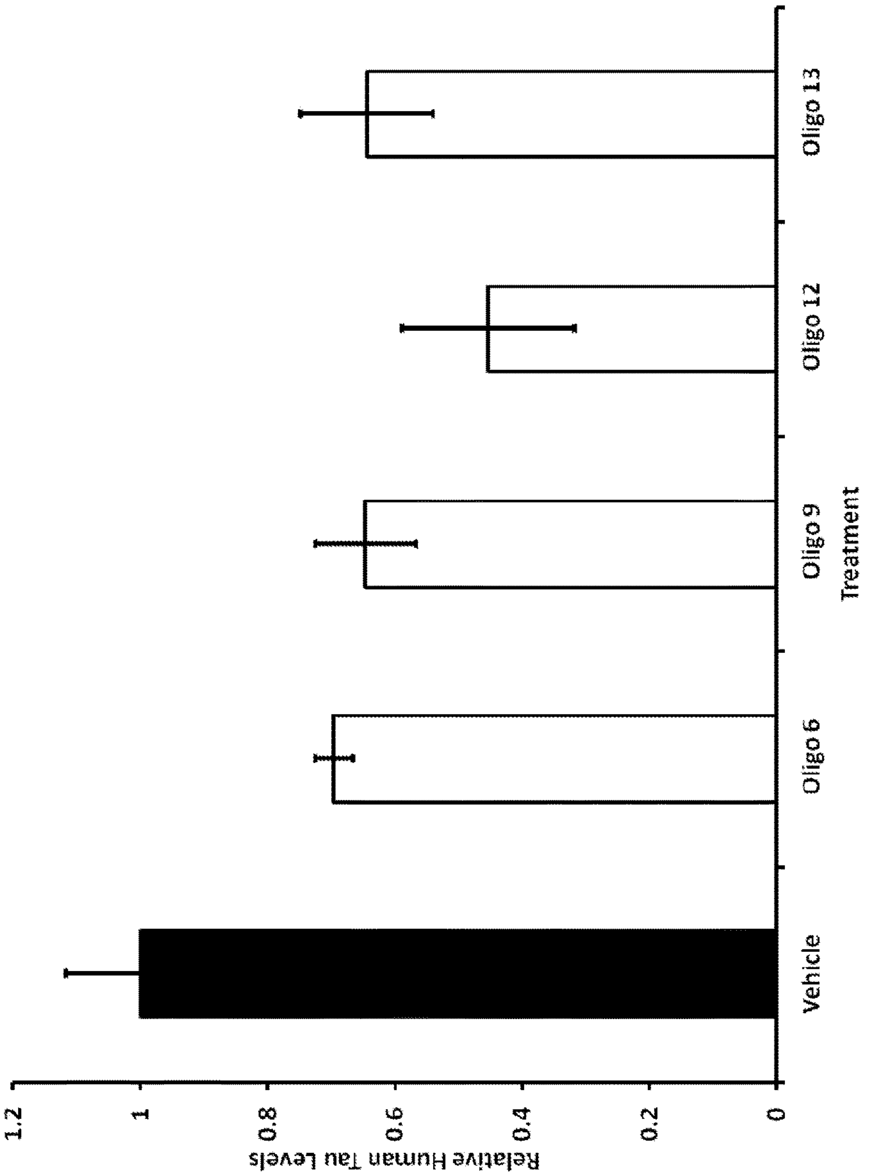
FIG. 15 depicts a graph showing the relative human tau levels in P301S mice treated with four different antisense oligos.
Figure 16:
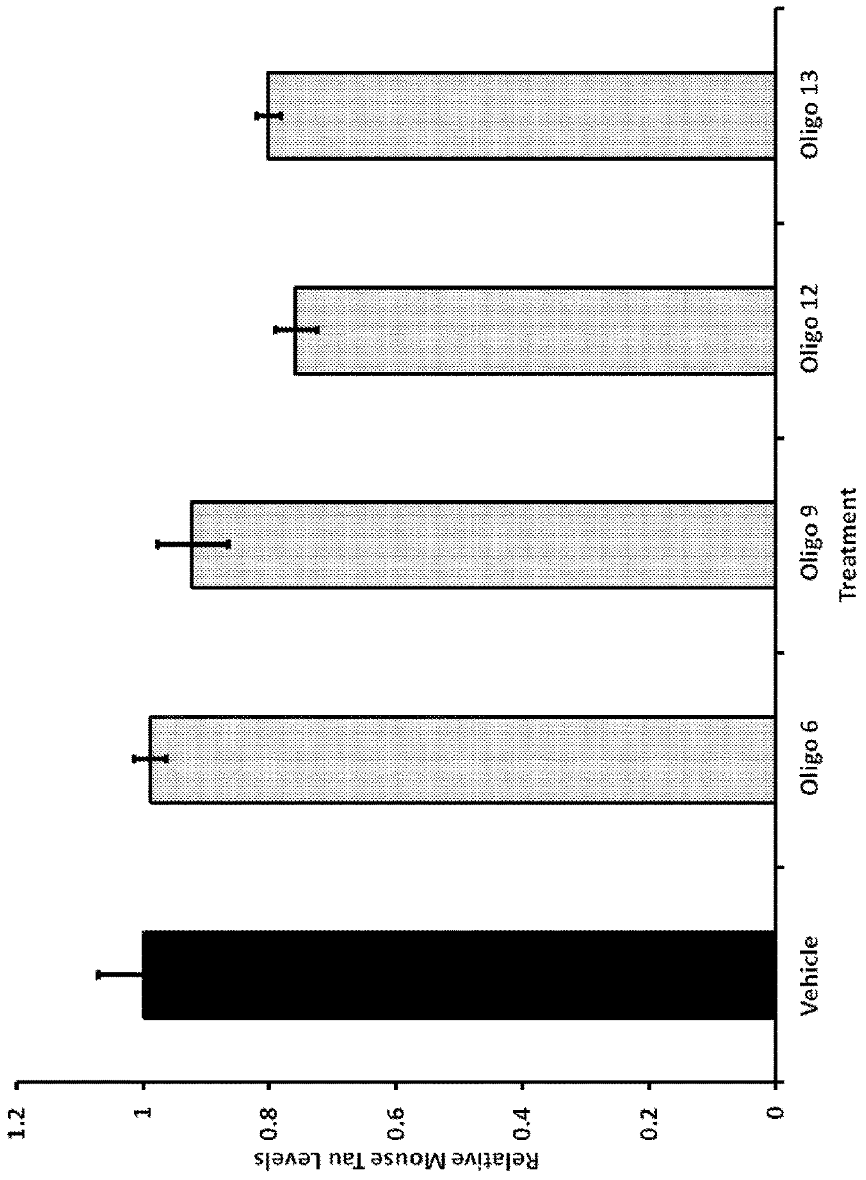
FIG. 16 depicts a graph showing the relative mouse tau levels in P301S mice treated with four different antisense oligos.
Figure 17:
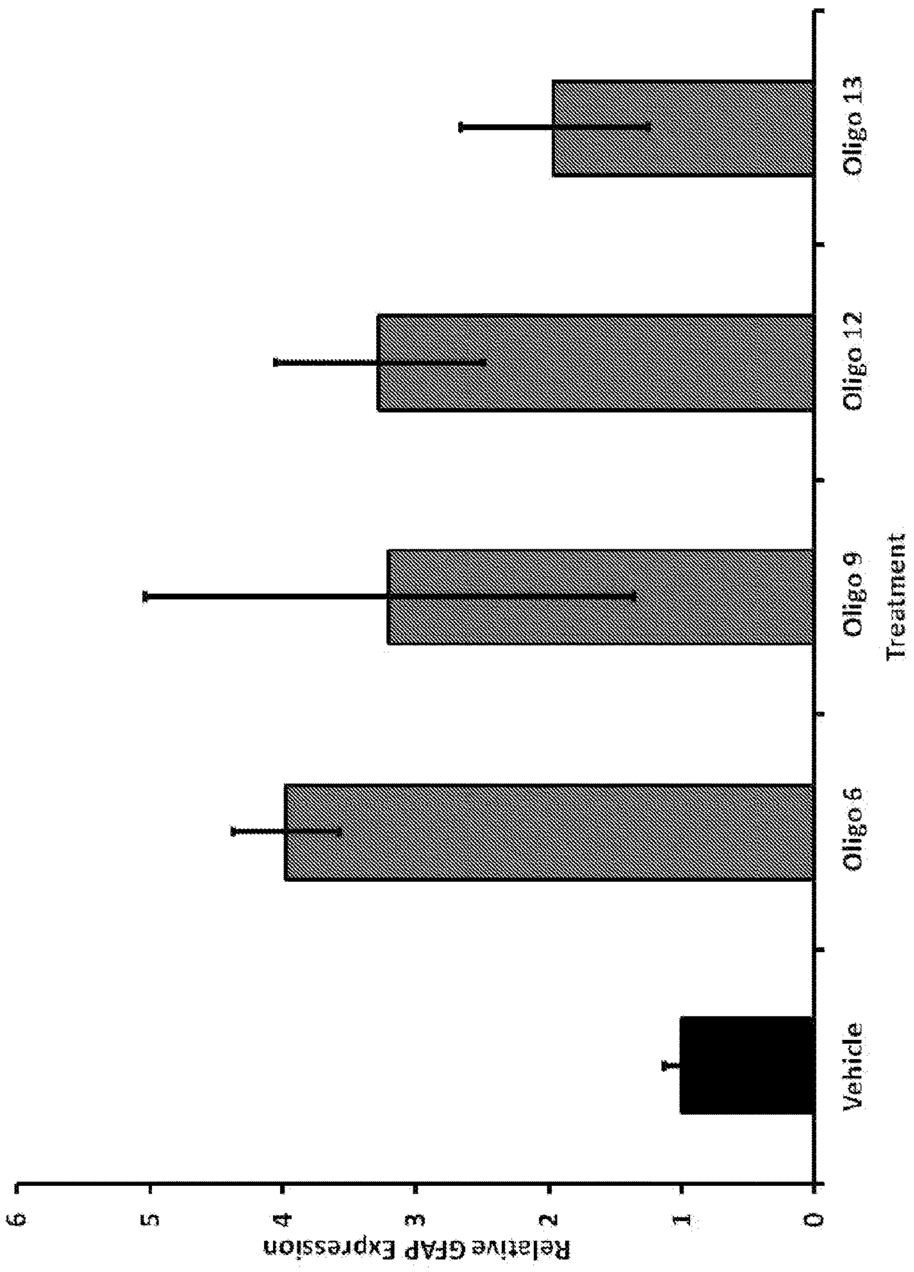
FIG. 17 depicts a graph showing the relative GFAP expression in P301S mice treated with four different antisense oligos.
Figure 18A:
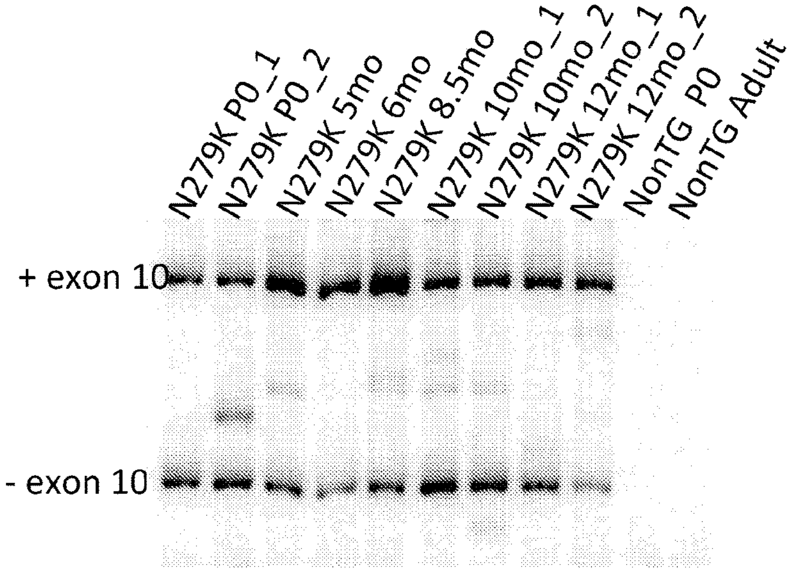
FIG. 18 depicts a picture (A) and a graph (B) showing tau splicing in N279K mice over time.
Figure 18B:
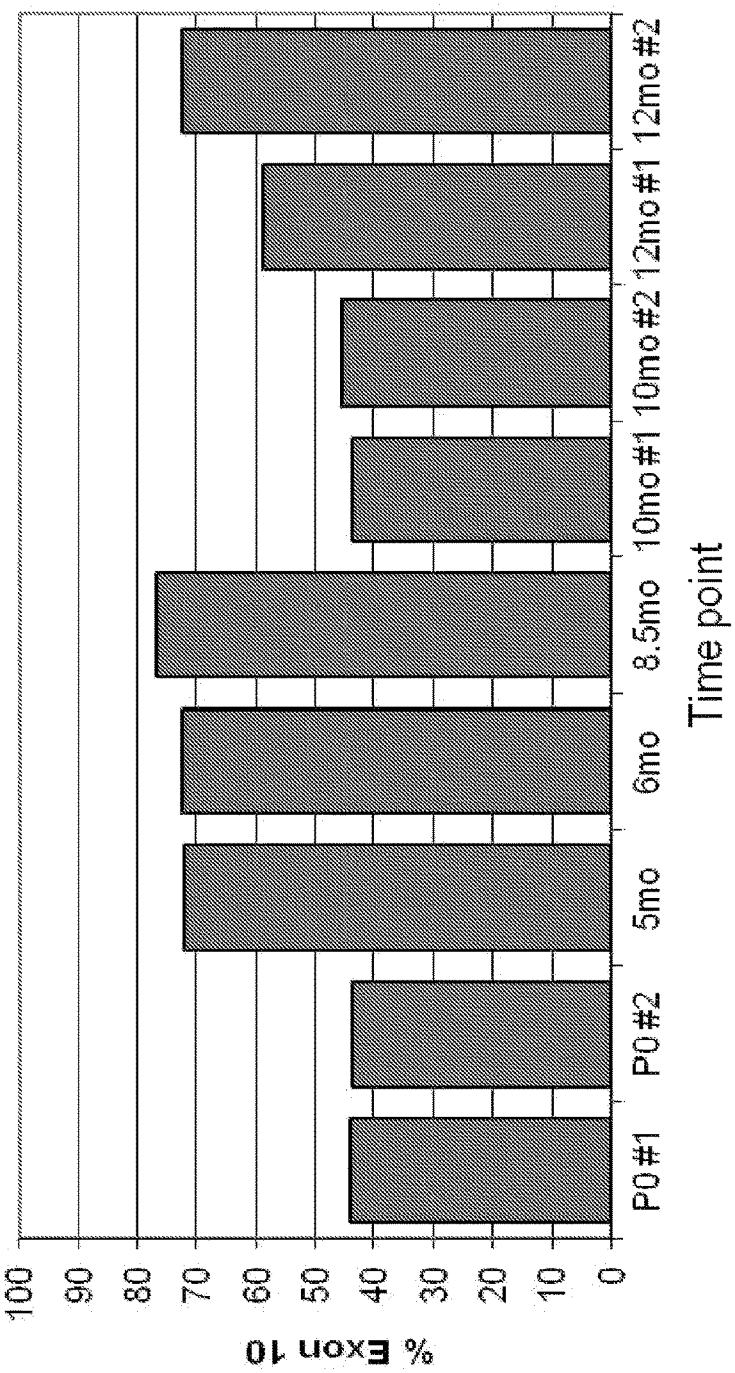
Figure 19:
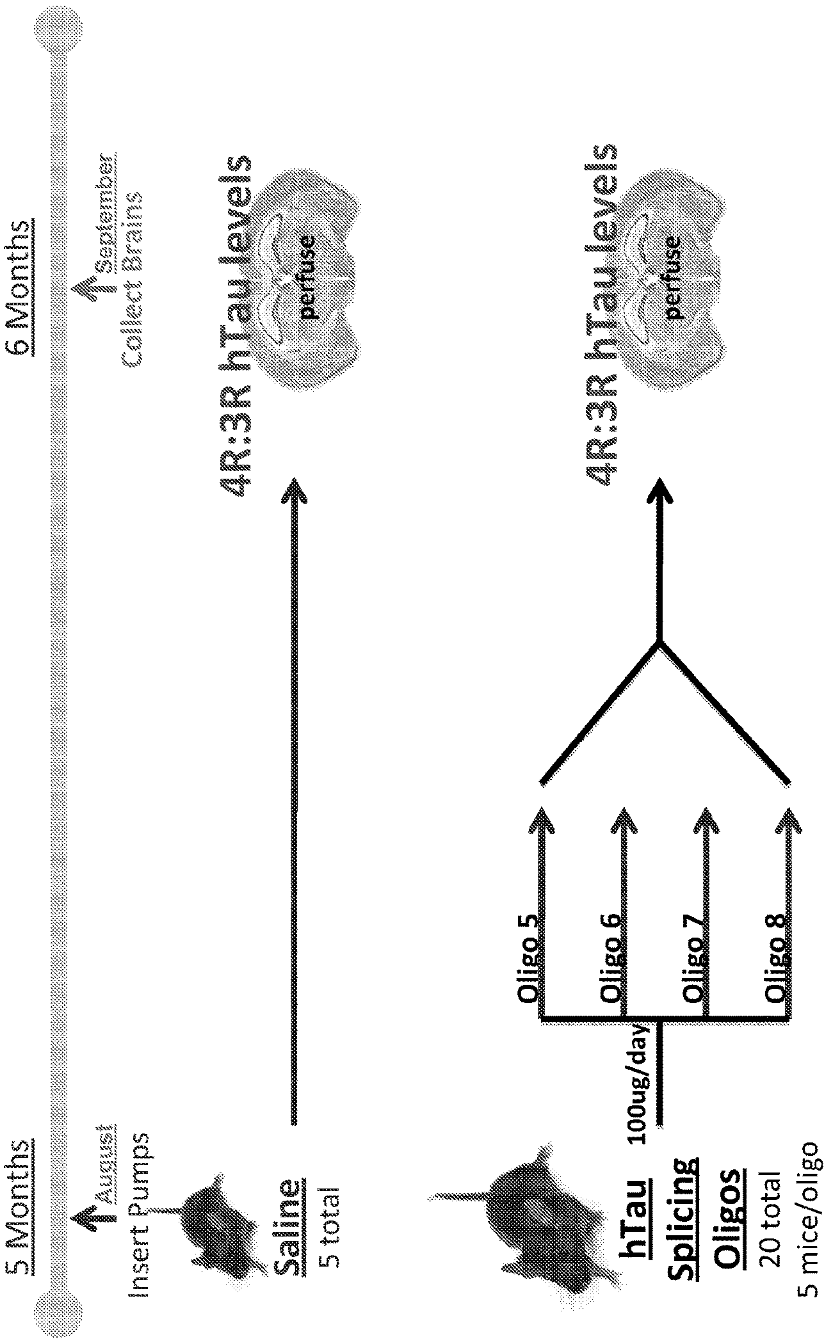
FIG. 19 depicts hTau splicing oligo screening in N279K mice.

Human tau levels and mouse tau mRNA levels were measured and were found to be decreased (FIGS. 15 and 16). Relative GFAP expression was also measured as a measure of toxicity (FIG. 17).

Example 10: Effect Antisense Inhibition of Tau on Treating Seizures Induced by Pentelenetetrazoll (PTZ) was Evaluated Groups of 3 month old C57/BL6 males were infused for 28 days with the Alzet pump at 25 µg/day of ASO. The pumps were removed, and the animals were rested for 3 weeks post-pump removal. Seizures were induced using 55 mg/kg of PTZ by intraperitoneal injection. The mice are videotaped for 15 minutes and scored later in a blinded fashion.

The results show that the knockdown and the splicing oligos (i.e., ISIS 415883) were capable of protection mice against PTZ induced seizures (FIG. 12).

Example Set 3

Example 1: In Vitro Dose-Dependent Inhibition of Tau in Human SH-SY5Y Cells with Gapmer Antisense Oligonucleotides Antisense oligonucleotides (ASO A and ASO B) were designed targeting a Tau nucleic acid (SEQ ID NO: 1) and were tested for their effects on Tau mRNA in vitro. The chimeric antisense oligonucleotides were designed as 5-10-5 MOE gapmers. The gapmers are 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P═S) linkages. All cytosine residues throughout each gapmer are 5-methylcytosines. Each gapmer is targeted to the human Tau genomic sequence, designated herein as SEQ ID NO: 1 (GENBANK Accession No. NT_010783.14 truncated from nucleotides 2624000 to 2761000), as presented in Table 2.

TABLE 2

| Antisense oligonucleotides targeting SEQ ID NO: 1 | |
|---|---|
| ISIS No | Target Region |
| ASO A | Exon 2 |
| ASO B | Exon 7 |

SH-SY5Y cells were plated at a density of 20,000 cells per well and transfected using electroporation with 1,250 nM, 2,500 nM, 5,000 nM, 10,000 nM, or 20,000 nM concentrations of antisense oligonucleotide. After a treatment period of approximately 16 hours, RNA was isolated from the cells and Tau mRNA levels were measured by quantitative real-time PCR. Tau mRNA levels were adjusted according to total RNA content, as measured by RIBOGREEN®. Tau was reduced in a dose-dependent manner in ASO A and ASO B treated cells, relative to untreated control cells.

Example 2: In Vitro Dose-Dependent Reduction of 4R Isoform in Human A172 Cells with Uniformly Modified Antisense Oligonucleotides Targeting Intron 10 of Human Tau Uniformly modified antisense oligonucleotides were tested in vitro in a dose dependent study. The oligonucleotides, ASO C (also ISIS 549620), ISIS 549595, ISIS 549617, and ISIS 549619, are 18 nucleobase uniformly modified antisense oligonucleotides comprising a 2'-MOE modification on each nucleoside was designed targeting intron 10 of human Tau (i.e., SEQ ID NO: 1). Each internucleoside linkage throughout the oligonucleotide are phosphorothioate (P═S) linkages. All cytosine residues throughout the oligonucleotide are 5-methylcytosines.

The antisense oligonucleotide was tested in vitro. A172 cells were transfected using LipofectAMINE2000® with 0.3 nM, 1.0 nM, 3.0 nM, 10.0 nM, 30.0 nM, or 100.0 nM concentrations of antisense oligonucleotide. After a treatment period of approximately 24 hours, RNA was isolated from the cells and the mRNA levels of the 4R isoform and total Tau mRNA were measured by quantitative real-time PCR using primer probe set hMAPT_LTS00914_MGB (forward sequence CGGGAAGGTGCAGATAATTAATAAG, designated SEQ ID NO: 21; reverse sequence GGACGTGTTTGATATTATCCTTTGAG, designated SEQ ID NO: 22; probe sequence AGCTGGATCTTAGCAACG, designated SEQ ID NO: 23). Tau mRNA levels were adjusted according to total RNA content, as measured by RIBOGREEN®.

The half maximal inhibitory concentration (IC50) of each oligonucleotide is presented in the table below and was calculated by plotting the concentrations of oligonucleotides used versus the percent inhibition of human Tau exon 10 mRNA expression achieved at each concentration, and noting the concentration of oligonucleotide at which 50% inhibition of human Tau exon 10 mRNA expression was achieved compared to the control. The 4R isoform of Tau was reduced in a dose-dependent manner in ASO C (also ISIS 549620), ISIS 549595, ISIS 549617, and ISIS 549619-treated cells, relative to untreated control cells.

TABLE 3

| Percent 4R isoform to total Tau mRNA in A172 cells | | | | | | | |
|---|---|---|---|---|---|---|---|
| | 0.3 nM | 1 nM | 3 nM | 10 nM | 30 nM | 100 nM | $IC_{50}$ (nM) |
| ISIS 549595 | 75 | 57 | 33 | 24 | 16 | 31 | 1.3 |
| ISIS 549617 | 83 | 61 | 46 | 34 | 29 | 26 | 3.4 |
| ISIS 549619 | 82 | 78 | 51 | 39 | 21 | 17 | 4.6 |
| ASO C (ISIS 549620) | 83 | 70 | 55 | 33 | 20 | 23 | 4.0 |

Example 3: Effect of Treatment with Gapmer Antisense Oligonucleotides on Tau mRNA Levels, Tau Protein Levels, and Tau Hyperphosphorylation in P301S Transgenic Mouse Model P301S mice over-express the mutated form of human Tau (Yoshiyama, Y. et al., Neuron. 2007. 53: 337-51). The mice exhibit Tau pathology with accumulation of hyperphosphorylated Tau protein. The effect of treatment on these mice with gapmers targeting human Tau was assessed in this model.

Study 1

Groups of 3-4 P301S mice were administered ASO A and ASO B at 60 g/day for 14 days via an intracerebroventricular pump. A control group of two mice were similarly treated with PBS. Alzet osmotic pumps were used to continuously deliver the antisense oligonucleotide. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. The incision was closed with sutures. Tissue was collected from around the catheter site 4 weeks after pump implantation.

RNA Analysis

RNA was extracted from the cortex region around the catheter site and analyzed by qRT-PCR for expression levels of human and murine Tau. The data is presented in Table 4. The results indicate that oligonucleotides inhibit levels of human Tau mRNA.

TABLE 4

| % inhibition of Tau mRNA compared to the PBS control | | |
|---|---|---|
| ISIS No | human | murine |
| ASO A | 35 | 7 |

TABLE 4-continued

| % inhibition of Tau mRNA compared to the PBS control | | |
|---|---|---|
| ISIS No | human | murine |
| ASO B | 55 | 24 |

Study 2

Groups of five P301S mice each (5 months old) were administered ASO B at 50 g/day for 28 days via an intracerebroventricular pump. A control group of five mice were similarly treated with PBS. Alzet osmotic pumps were used to continuously deliver the antisense oligonucleotide. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. Tissues were collected after 2 months.

RNA Analysis

RNA was extracted from the hippocampal region around the injection site and analyzed by qRT-PCR for expression levels of human and murine Tau. The results indicate that ASO B inhibited levels of human Tau mRNA by 36% and of murine Tau mRNA by 5% one month post-ASO B active infusion.

Protein Analysis

Human Tau protein in the brain was analyzed by ELISA (as previously described by Yamada et al., J. Neurosci. 2011. 31: 13110-117), as well as by western blot analysis using the total tau Tau5E2 antibody. The ELISA results indicate that ASO B inhibited levels of human Tau by 40%. The western blot results were quantified and indicate that ASO B inhibited levels of human Tau by 74%. It should be noted that the ELISA recognizes all forms of Tau, including human and mouse, whereas with the Western Blot, the human Tau can be separated from the mouse Tau by size differences. Thus, the Western Blot human Tau quantification is a more accurate representation of the human Tau specific knockdown levels.

Study 3

Groups of 5 P301S mice each (5 months old) were administered ASO B at 50 g/day for 28 days via an intracerebroventricular pump. Another Group of 5 P301S mice (5 months old) were administered ASO B at 100 g/day for 14 days via an intracerebroventricular pump. A control group of five mice were similarly treated with PBS. Alzet osmotic pumps were used to continuously deliver the antisense oligonucleotide. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. Tissues were collected after 2 months.

Hyperphosphorylated Tau Analysis

Figure 25:
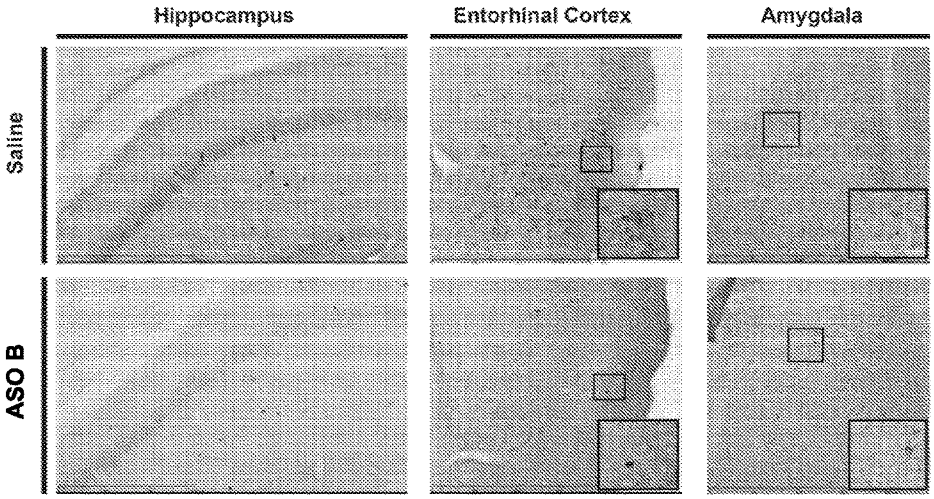
FIG. 25 provides a graphical representation of the percentage of cells stained with the antibody AT8 as a measure of hyperphosphorylated Tau in the P301S transgenic mouse model.

The monoclonal Tau antibody AT8 recognizes Tau protein phosphorylated at both serine 202 and threonine 205 (Goedert, M. et al., Neurosci. Lett. 1995. 189: 167-9) and is therefore is used in a method of detection of hyperphosphorylated Tau. This is also the most commonly used antibody to identify Tau accumulations in human Alzheimer's disease patient brains. Extensive hyperphosphorylated Tau (Ser202 and Thr205) was detected in the entorhinal cortex and the basolateral amygdala by immunohistochemistry using AT8 antibody in P301S brains at 7 months of age. The percentage of cells stained with the antibody is presented in FIG. 25 and Table 5. The results indicate that treatment with ASO B resulted in clearance of hyperphosphorylated Tau.

TABLE 5

| % staining of hyperphosphorylated human Tau | | |
|---|---|---|
| Area | Treatment | % |
| amygdala | PBS | 4.6 |
| | ASO B 50 g | 1.4 |
| | ASO B 100 g | 2.3 |
| entorhinal cortex | PBS | 8.8 |
| | ASO B 50 g | 5.4 |
| | ASO B 100 g | 6.8 |

Example 4: In Vivo Reduction of 4R Isoform in the N279K Transgenic Mouse Model with Uniformly Modified Antisense Oligonucleotides Targeting Intron 10 of Human Tau N279K mice express the human Tau mini-gene with FTD mutation (Dawson, H. N. et al., J. Neurosci. 2007. 27: 9155-68). The N279K mutation promotes the inclusion of exon 10 (4R Tau). The effect of uniformly modified antisense oligonucleotides targeting human Tau on the shifting of the 4R isoform to 3R isoform was assessed in this mouse model.

Groups of 4 N279K mice (5 months of age) were administered ASO C (also ISIS 549620) at 60 g/day for 28 days via an intracerebroventricular pump. A control group of five mice was similarly treated with PBS. Animals were anesthetized with 3% isofluorane and placed in a stereotactic frame. Alzet osmotic pumps were used to continuously deliver the antisense oligonucleotide. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. Tissues around the cannula region were collected on the $29^{th}$ day.

RNA Analysis

RNA was extracted from the cortex around the cannula, and mRNA expression of the 4R and 3R isoforms of human Tau were analyzed by RT-radioactive PCR. Briefly, 1,000 ng of RNA was reverse transcribed with oligo(dT). The cDNA was then amplified in the presence of $\alpha$-$^{32}$P-dCTP. PCR products digested with Hinc II and separated by denaturing PAGE. Exon 10 included and excluded species were detected by autoradiography and quantitated by PhosphorImage analysis. The signal intensity of each cDNA band was normalized according to its G+C content. The results indicate that treatment with ASO C (also ISIS 549620) resulted in a decrease in 4R Tau by 85% of the total Tau mRNA.

Example 5: Effect of Antisense Oligonucleotides Targeting Human Tau on Behavior and Tau Accumulations in the N279K Transgenic Mouse Model The effect of gapmers and uniformly modified antisense oligonucleotides on behavioral assays was analyzed in the N279K transgenic model. ASO A, a gamer, which causes reduction of total Tau mRNA, and ASO C (also ISIS 549620), a uniform MOE oligonucleotide, which causes the shifting of the 4R Tau isoform to 3R Tau isoform, were both used in this assay.

Two groups of 6-8 N279K mice each (3 months of age) were administered ASO A or ASO C (also ISIS 549620) at 25 g/day for 28 days via an intracerebroventricular pump. An N279K transgenic control group of eight mice were similarly treated with PBS. Another control group of eight mice was similarly treated with a scrambled oligonucleotide, ISIS 141923 (CCTTCCCTGAAGGTTCCTCC, 5-10-5 MOE gapmer with no known target (SEQ ID NO: 11)). Another transgenic littermate control group of eight mice were similarly treated with PBS. Animals were anesthetized with 3% isofluorane and placed in a stereotactic frame. Alzet osmotic pumps were used to continuously deliver the antisense oligonucleotide solution. Pumps were assembled and implanted, as per the manufacturer's instructions (Durect Corporation). Animals were anesthetized with 3% isofluorane and placed in a stereotactic frame. After sterilizing the surgical site, a one cm midline incision was made over the bregma. Through the use of stereotaxic guides, a cannula was implanted into the right lateral ventricle and secured. A catheter attached to an Alzet osmotic pump was secured to the cannula and the pump was placed subcutaneously in the midcapsular area. Behavioral studies were performed at 6.5 months of age and mice collected at 7.5 months of age.

Novel Object Recognition Analysis

Novel object recognition is used to determine if the mice can recognize an object that is familiar versus one that is novel (Bevins, R. A. and Besheer, J. Nature Protocols. 2006, 1: 1306-1311). Briefly, the animals are first exposed to two identical objects for 10 minutes; 3 hours later, they are then exposed to this same object (familiar), as well as a new object (novel) for 5 minutes. The mice were videotaped and videos were watched and scored blinded. Non-transgenic mice will spend more time with the novel object compared to the time spent with the familiar object. This is a measure of recall memory in the mice. Human patients affected by a tauopathy, such as Alzheimer's disease, also display deficits in memory recall.

The data are presented in Table 6. The results indicate that mice treated with the uniformly modified antisense oligonucleotide (ASO C also ISIS 549620) spent less time with familiar objects and more time with novel objects compared to the transgenic control.

TABLE 6

Total Percent Time spent with object over a 5 minute period

| | Familiar | Novel |
|---|---|---|
| PBS | 45 | 54 |
| ISIS 141923 | 38 | 62 |
| ASO A | 36 | 64 |
| ASO C (also ISIS 549620) | 25 | 75 |
| Non-Tg mice | 38 | 62 |

Nestlet Building Activity Analysis

As a general measure of mouse performance, nestlet building activity was accessed. Mice instinctually build nests when provided with nestlets. Impaired resting performance indicates either an overall cognitive and/or motor deficit. Human tauopathy patients present with general cognition dysfunction and may also present with motor problems. Nestlet building activity (Deacon, R. M. Nat. Protocol. 2006. 1: 1117-9) was initiated by providing the mice with 3.0 grams of pressed cotton material and leaving the mice overnight to assemble a nest. Male nest building activity was assessed. The mice first shred the tightly packed material, then arrange it into a nest. The nesting activity was scored on a five-point scale with '0' being 'no nest' and '5' being a perfect nest surrounding the mouse. Any untorn material left after a bout of nesting was also weighed and provided a further analysis of nesting behavior. A higher untorn nestlet weight signifies a lower quality nest. The nesting scores and untorn nestlet weights are presented in Table 7. Treatment with both the gapmer antisense oligonucleotide (ASO A) and the uniformly modified antisense oligonucleotide (ASO C also ISIS 549620) led to increase in nesting scores and decrease in untorn material as compared to control, indicating improvement of nesting behavior in the mice.

TABLE 7

Nestlet building activity

| | score | Untorn nestlet weight (g) |
|---|---|---|
| PBS | 1.8 | 2.2 |
| ISIS 141923 | 2.3 | 1.6 |
| ASO A | 2.4 | 1.2 |
| ASO C (also 549620) | 4.4 | 0.8 |
| Non-Tg mice | 4.4 | 0.5 |

Walking Initiation Analysis

The N279K mice display age progressive deficits in walking initiation. Walking initiation in mice may be, in part, equated to the parkinsonism component of FTDP-17. Bradykinesia, or slowed initiation of movement, is a common feature in parkinsonism disorders. To measure walking initiation in mice, the mice were placed in the center of a 21 cm×21 cm square and time taken for all four paws of the mouse to completely leave the square was measured using a stopwatch. The data are presented in Table 8. The results indicate that mice treated with both the gapmer antisense oligonucleotide (ASO A) and the uniformly modified antisense oligonucleotide (ASO C also ISIS 549620) initiated walking at time intervals faster than the N279K PBS and ISIS 141923 controls.

TABLE 8

| Time to leave square (sec) | |
|---|---|
| | (Sec) |
| PBS | 10.8 |
| ISIS 141923 | 10.1 |
| ASO A | 9.7 |
| ASO C (also ISIS 549620) | 7.0 |
| Non-Tg mice | 3.4 |

Hyperphosphorylated Tau Analysis

Figure 26:
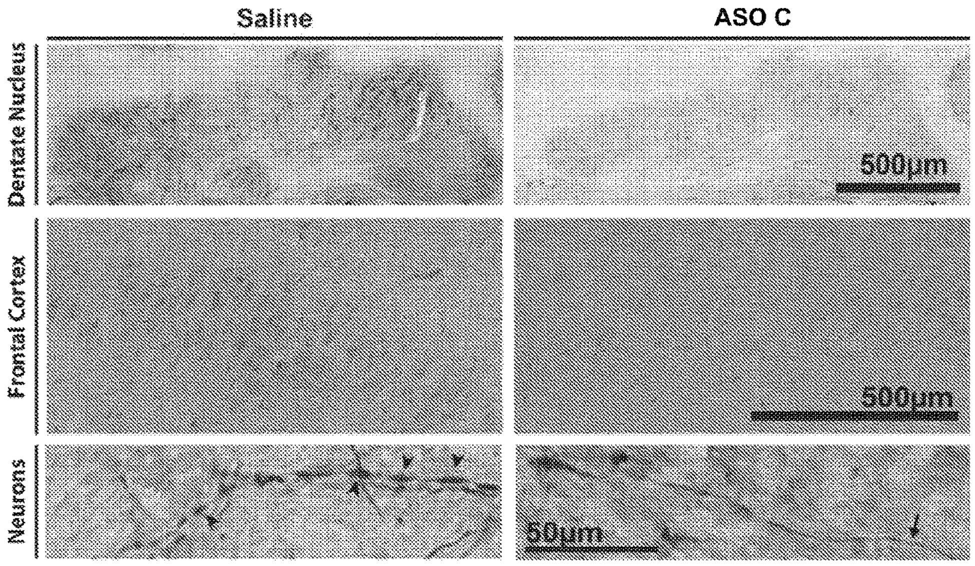
FIG. 26 provides a graphical representation of the percentage of cells stained with the antibody AT8 as a measure of hyperphosphorylated Tau in the N279K transgenic mouse model.

Mice treated with the uniformly modified antisense oligonucleotide (ASO C also ISIS 549620) were euthanized at 7 months of age. The frontal cortex and the dentate nucleus were assessed by immunohistochemistry with the Tau13 antibody, which binds specifically to human Tau protein. The percentage of cells stained with Tau13 somatodendritic accumulations is presented in Table 9 and FIG. 26. The results indicate that mice treated with ASO C (also ISIS 549620) had a decrease in the presence of human Tau inclusions compared to the PBS control. The dentate nucleus is, in part, responsible for the initiation of voluntary movements. So a clearance of Tau deposition in the dentate nucleus may be responsible for the improvement in walking initiation in the ASO C (also ISIS 549620) treated mice as compared to the PBS control.

TABLE 9

| Human Tau inclusions (%) | | |
|---|---|---|
| | PBS | ASO C (also ISIS 549620) |
| Frontal cortex | 16 | 4 |
| Dentate nucleus | 29 | 16 |

Example 6: Effect of Antisense Inhibition of Tau on PTZ Induced Seizures

The effect of antisense inhibition of Tau on treating seizures induced by pentelenetetrazoll (PTZ) was evaluated. The mice were treated with a gapmer antisense oligonucleotide (ASO D) and a uniformly modified antisense oligonucleotide (ISIS 415883). ASO D is a chimeric antisense oligonucleotides 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification (i.e., a 5-10-5 MOE gapmer). The internucleoside linkages throughout each gapmer are phosphorothioate linkages. All cytosine residues throughout each gapmer are 5-methylcytosines. Each gapmer is targeted to the human Tau genomic sequence, designated herein as SEQ ID NO: 1 (GENBANK Accession No. NT_010783.14 truncated from nucleotides 2624000 to 2761000), as presented in Table 1. ISIS 141923, an oligonucleotide with no known target (i.e., a “scrambled oligonucleotide”) and PBS were used as controls.

Groups of 3 month old C57/BL6 males were administered ASO at 25 μg/day for 28 days via an intracerebroventricular pump. A control group of mice were similarly treated with PBS. The pumps were removed, and the animals were rested for 3 weeks post-pump removal. Seizures were induced using 55 mg/kg of PTZ by intraperitoneal injection. The mice are videotaped for 15 minutes and scored later in a blinded fashion. The final stage reached was recorded.

Figure 28:
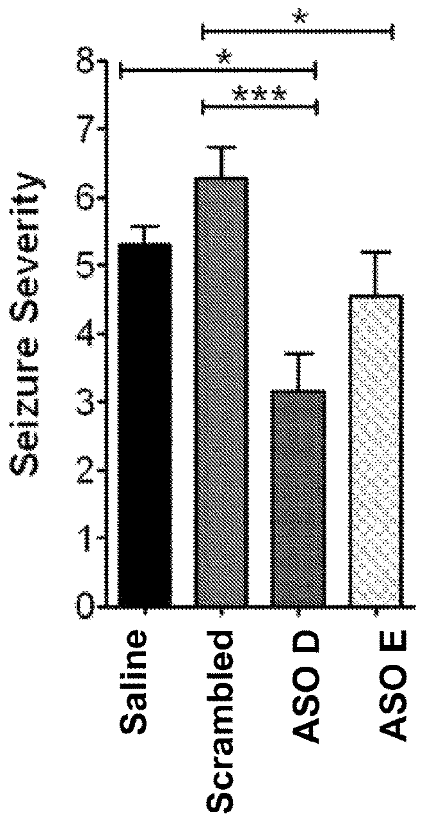
FIG. 28 provides a bar graph showing seizure severity.

Seizure severity was rated on a scale of 0-8 with ‘0’ denoting ‘no seizures’, 1 denoting ‘immobility’, 2 denoting ‘jerk or twitch’, 3 denoting ‘tail extension’, 4 ‘denoting forelimb clonus’, 5 denoting ‘generalized seizure’, 6 denoting ‘running or jumping’, 7 denoting ‘tonic extension’, and ‘8’ denoting ‘death’. The results show that both ASO D and ISIS 415883 were capable of protecting mice against PTZ induced seizures as compared to the scrambled oligonucleotide control (FIG. 28 and Table 10).

Figure 29:
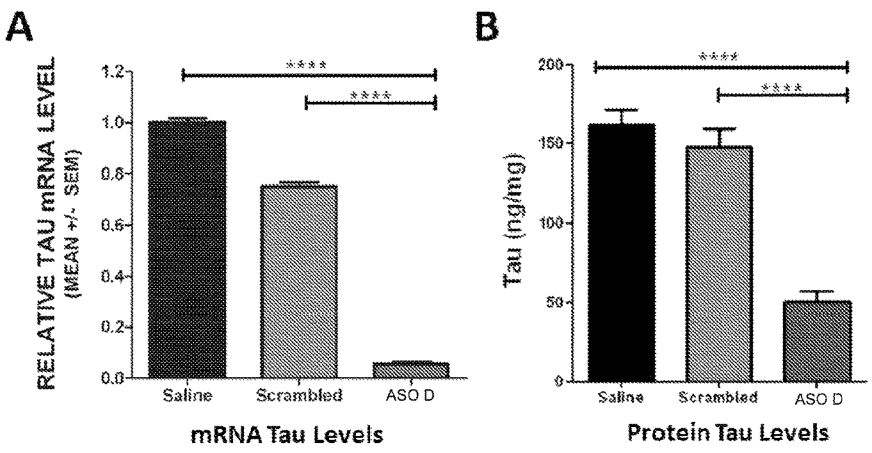
FIG. 29 provides a bar graph showing Tau mRNA (A) and Tau protein (B) levels.

Tau mRNA and protein levels from a 3 mm coronal tissue section around the catheter of the mice treated with ASO D were measured and the data is presented in Table 11 and FIG. 29. The results show that ASO D significantly reduced both mRNA (FIG. 29A) and protein levels (FIG. 29B) of Tau. This correlates well with the decrease in seizure severity of the mice.

Tau isoform of mice treated with ISIS 415883 were measured and the data is presented in Table 12. The results show treatment with ISIS 415883 shifted the Tau isoforms from mainly 4R with some 3R Tau to mostly 3R Tau with some 4R Tau. This is demonstrated with a significant decrease in 4R tau levels while maintaining normal total tau levels.

Figure 30:
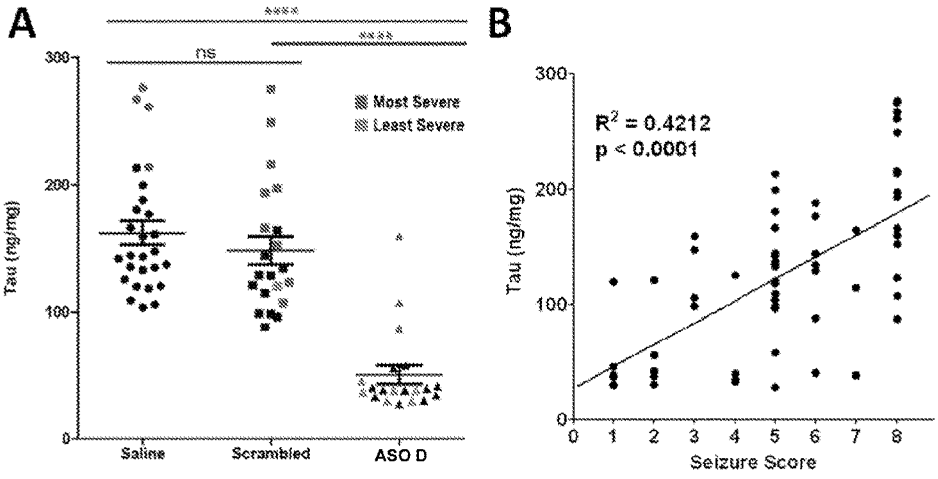
FIG. 30 provides a scatter plot showing seizure severity plotted against Tau levels. (A) shows Tau protein levels in PBS, ISIS 141923-treated, and Tau5-treated groups. (B) shows the correlation of Tau protein levels with seizure score in a linear regression plot.

The levels of Tau protein and corresponding seizure severity of the mice treated with ASO D were analyzed in individual mice. As shown in Table 13 and FIG. 30A, it was noted that those mice that demonstrated higher levels of Tau were also those to experience the most severe seizures (stage 8 or death), while those mice that demonstrated reduced levels of Tau only had first stage or the least severe seizures of the group. Based on this observation, the total Tau level in each mouse of the study was plotted against the final seizure stage that the mouse reached. There is a significant correlation using Spearman’s Correlation ($p<0.0001$) between the total amount of Tau in each mouse and the induced seizure severity, as shown in the linear regression of FIG. 30B. This suggests that inhibition of Tau results in protection against seizure activity in a chemically-induced model.

TABLE 10

| Seizure severity (average in each group) | |
|---|---|
| PBS | 5.4 |
| ISIS 141923 | 6.3 |
| ASO D | 3.4 |
| ISIS 415883 | 4.6 |

TABLE 11

| % inhibition of mRNAand protein levels in mice treated with knockdown oligo (ASO D) | | |
|---|---|---|
| | mRNA | Protein |
| ISIS 141923 | 25 | 8 |
| ASO D | 95 | 70 |

TABLE 12

% Tau 4R Tau isoform and total Tau in mice treated with splicing oligo (ISIS 415883)

| | 4R isoform | Total Tau |
|---|---|---|
| ISIS 141923 | N/A | 25 |
| ISIS 415883 | 90 | 26 |

TABLE 13

Tau protein levels and seizure severity in mice treated with knockdown oligo (ASO D)

| Mouse # | Tau (ng/mg) | Seizure Stage |
|---|---|---|
| PBS 1 | 120 | 5 |
| PBS 2 | 142 | 5 |
| PBS 3 | 177 | 6 |
| PBS 4 | 181 | 5 |
| PBS 5 | 276 | 8 |
| PBS 6 | 267 | 8 |
| PBS 7 | 214 | 8 |
| PBS 8 | 148 | 3 |
| PBS 9 | 144 | 5 |
| PBS 10 | 106 | 3 |
| PBS 11 | 135 | 5 |
| PBS 12 | 118 | 5 |
| PBS 13 | 143 | 6 |
| PBS 14 | 159 | 3 |
| PBS 15 | 167 | 5 |
| PBS 16 | 188 | 6 |
| PBS 17 | 120 | 5 |
| PBS 18 | 200 | 5 |
| PBS 19 | 137 | 5 |
| PBS 20 | 261 | 8 |
| PBS 21 | 213 | 5 |
| PBS 22 | 133 | 5 |
| PBS 23 | 109 | 5 |
| PBS 24 | 104 | 5 |
| PBS 25 | 136 | 5 |
| PBS 26 | 126 | 4 |
| ISIS 141923 1 | 129 | 6 |
| ISIS 141923 2 | 129 | 6 |
| ISIS 141923 3 | 120 | 1 |
| ISIS 141923 4 | 165 | 7 |
| ISIS 141923 5 | 134 | 6 |
| ISIS 141923 6 | 166 | 8 |
| ISIS 141923 7 | 275 | 8 |
| ISIS 141923 8 | 249 | 8 |
| ISIS 141923 9 | 123 | 8 |
| ISIS 141923 10 | 99 | 5 |
| ISIS 141923 11 | 107 | 8 |
| ISIS 141923 12 | 193 | 8 |
| ISIS 141923 13 | 96 | 5 |
| ISIS 141923 14 | 153 | 8 |
| ISIS 141923 15 | 144 | 6 |
| ISIS 141923 16 | 197 | 8 |
| ISIS 141923 17 | 98 | 3 |
| ISIS 141923 18 | 88 | 6 |
| ISIS 141923 19 | 216 | 8 |
| ISIS 141923 20 | 115 | 7 |
| ISIS 141923 21 | 121 | 2 |
| ASO D 1 | 39 | 7 |
| ASO D 2 | 40 | 6 |
| ASO D 3 | 38 | 1 |
| ASO D 4 | 58 | 5 |
| ASO D 5 | 160 | 8 |
| ASO D 6 | 87 | 8 |
| ASO D 7 | 55 | 2 |
| ASO D 8 | 40 | 4 |
| ASO D 9 | 38 | 1 |
| ASO D 10 | 41 | 2 |
| ASO D 11 | 30 | 2 |
| ASO D 12 | 33 | 4 |
| ASO D 13 | 27 | 5 |
| ASO D 14 | 45 | 1 |

TABLE 13-continued

Tau protein levels and seizure severity in mice treated with knockdown oligo (ASO D)

| Mouse # | Tau (ng/mg) | Seizure Stage |
|---|---|---|
| ASO D 15 | 38 | 2 |
| ASO D 16 | 30 | 1 |
| ASO D 17 | 30 | 1 |
| ASO D 18 | 37 | 1 |
| ASO D 19 | 34 | 4 |
| ASO D 20 | 107 | 8 |

Example 7: Evaluation of Oligonucleotide Distribution in P301S Mice

The distribution of oligonucleotide in P301S mice after infusion of ASO D was analyzed.

P301 S mice at 5 months age were administered ASO D at 50 μg/day for 28 days via an intracerebroventricular pump. A control group of P301S mice were similarly treated with PBS. The pumps were removed, and the animals were rested for 28 days post-pump removal. The mice were euthanized and brain tissue and eyes were collected. Brain sections throughout the whole brain were stained with an antibody against the oligonucleotide (developed in-house) and were counterstained with DAPI.

The results show widespread distribution of ASO D throughout the brain sections of the mice. Sections of 50 μm in thickness were taken throughout the entire left hemisphere and stained with the oligonucleotide antibody. For detection, an Alexa-Fluor-546 anti-rabbit secondary antibody was used and a DAPI counter-stain was applied. The presence of a red or pink fluorescence intensity signified the presence of the oligonucleotide. These results demonstrate that ASO D is widely distributed throughout the entire brain following infusion into the right lateral ventricle.

The eyes of the mice were post-fixed, embedded in paraffin, sliced at 6 μm thickness, and mounted onto slides. The sections were stained with an antibody against the oligonucleotide and sections were counterstained with DAPI. The results show significant presence of ASO D in the retinal layers of the eye as well as in the outer layer of the lens in the eye sections of mice treated with ASO D. The same Alexa-Fluor-546 anti-rabbit secondary antibody was used to detect the oligonucleotide antibody. Due to the high level of autofluorescence in the retina because of the retinal pigment epithelium, the green FITC channel was applied to show exactly where the autofluorescence was coming from. Previous studies have shown the presence of hyperphosphorylated Tau in the eyes in patients with Alzheimer's disease and glaucoma (Frost, S. Digital Teleretinal Screen. 2012, 91-100; Ho, W. L. Et al., Molecular Vision, 2012, 18: 2700-2710; Gupta, N. et al., Can. J. Ophthalmol. 2008, 43: 53-60). Hence, this result suggests that an ASO tau treatment can in fact reach the retinal cell layers and may potentially decrease aberrant tau species that may be impeding vision or used as a clinical marker for measuring reduction of tau expression in the CNS.

Example 8: Inhibitory Effect of Uniform 2'-MOE Modified Oligonucleotides on Human Tau Exon 10

Several modified oligonucleotides were evaluated for their effect on inhibiting human Tau exon 10 expression in vitro. ISIS 617782 and 617781 were included in the study for comparison.

"Start site" indicates the 5'-most nucleoside to which the modified oligonucleotide is targeted in the human gene sequence. "Stop site" indicates the 3'-most nucleoside to which the modified oligonucleotide is targeted in the human gene sequence. Each modified oligonucleotide listed in the table below is targeted to the human Tau genomic sequence, designated herein as SEQ ID NO: 1 (GENBANK Accession No NT_010783.15 truncated from nucleotides 9240000 to 9381000).

The half maximal inhibitory concentration (IC50) of each oligonucleotide is presented in the table below and was calculated by plotting the concentrations of oligonucleotides used versus the percent inhibition of human Tau exon 10 mRNA expression achieved at each concentration, and noting the concentration of oligonucleotide at which 50% inhibition of human Tau exon 10 mRNA expression was achieved compared to the control. Results are presented below.

TABLE 14

Inhibitory effect of uniform 2'-MOE modified oligonucleotides on human Tau exon 10 expression

| ISIS NO | Sequence | 0.1 nM | 0.3 nM | 1.0 nM | 3.0 nM | 10 nM | 30 nM | $IC_{50}$ (nM) | SEQ ID NO: X Start Site | SEQ ID NO: X Stop Site | SEQ ID NO |
|---|---|---|---|---|---|---|---|---|---|---|---|
| 617782 | $U_mG_mA_mA_mG_mG_mU_mA_mC_mU_m$ $C_mA_mC_mA_mC_mU_mG_mC_mC_mG_mC_m$ | 100 | 89 | 80 | 55 | 34 | 16 | 4.33 | 121914 | 121934 | 30 |
| 617781 | $U_mA_mU_mC_mU_mG_mC_mA_mC_mC_m$ $U_mU_mU_mG_mG_mU_mA_mG_m$ | 100 | 95 | 79 | 82 | 65 | 41 | 20.25 | 121820 | 121837 | 31 |
| 415883 | TCTTATTAATTATCTGCACC | 77 | 63 | 41 | 28 | 16 | 11 | 0.65 | 121828 | 121847 | 12 |

ISIS 617782 is 21 nucleosides in length, wherein each nucleoside has a 2'-$OCH_3$ modification and is denoted as the subscript "m". Each internucleoside linkage throughout the modified oligonucleotide are phosphorothioate internucleoside linkages (P═S).

ISIS 617781 is 18 nucleosides in length, wherein each nucleoside has a 2'-$OCH_3$ modification and is denoted as the subscript "m". Each internucleoside linkage throughout the modified oligonucleotide are phosphorothioate internucleoside linkages (P═S).

ISIS 415833 is 20 nucleosides in length, wherein each nucleoside has a 2'-MOE modification. Each internucleoside linkage throughout the modified oligonucleotide are phosphorothioate internucleoside linkages (P═S). All cytosine residues throughout the modified oligonucleotides are 5-methylcytosines.

A172 cells were transfected using Lipofectamine2000® with 0, 0.1, 0.3, 1, 3, 10, or 30 nM concentration of modified oligonucleotide as specified in the table below. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels of 617782 and human Tau primer probe set 10_11 was used for ISIS 617781 and 415883.

Human Tau primer probe set 9_10 R5 (forward sequence CACTGAGAACCTGAAGCACC, designated herein as SEQ ID NO: 24; reverse sequence GGACGTTGCTAAGATCCAGCT, designated herein as SEQ ID NO: 25; probe sequence TTAATTATCTGCACCTTCCCGCCTCC, designated herein as SEQ ID NO: 26). Human Tau exon 10 mRNA levels were adjusted according to total RNA content, as measured by RIBOGREEN®.

Human primer probe set 10_11 (forward sequence GGATAATATCAAACACGTCCCG, designated herein as SEQ ID NO: 27; reverse sequence TGCCTAATGAGCCACACTTG, designated herein as SEQ ID NO: 28; probe sequence GTCTACAAACCAGTTGACCTGAGC, designated herein as SEQ ID NO: 29).

Example 9: Effects of Uniform 2'-MOE Modified Oligonucleotides on Human Tau Exon 10

A series of modified oligonucleotides were designed to target exon 10 of human Tau and were screened for their effects in reducing exon 10 inclusion in vitro. They are 18 nucleosides in length, wherein each nucleoside has a 2'-MOE modification. Each internucleoside linkage throughout the modified oligonucleotide are phosphorothioate internucleoside linkages (P═S). All cytosine residues throughout the modified oligonucleotides are 5-methylcytosines.

"Start site" indicates the 5'-most nucleoside to which the modified oligonucleotide is targeted in the human gene sequence. "Stop site" indicates the 3'-most nucleoside to which the modified oligonucleotide is targeted in the human gene sequence. Each modified oligonucleotide listed in the tables below is targeted to the human Tau genomic sequence, designated herein as SEQ ID NO: 32 (GENBANK Accession No NT_010783.15 truncated from nucleotides 9240000 to 9381000).

A172 cells were transfected using Lipofectamine2000® with 5 nM concentration of modified oligonucleotide. After a treatment period of approximately 24 hours, RNA was isolated from the cells and the mRNA levels of Tau transcripts containing exon 10 were measured by quantitative real-time PCR. Human primer probe set 10_11 was used to measure mRNA levels. Tau exon 10 mRNA levels were adjusted according to total RNA content, as measured by RIBOGREEN®. Results are presented as percent of Tau exon 10 mRNA expression, relative to untreated control levels and is denoted as "% UTC."

Human primer probe set 10_11 (forward sequence GGATAATATCAAACACGTCCCG, designated herein as SEQ ID NO: 27; reverse sequence TGCCTAATGAGCCACACTTG, designated herein as SEQ ID NO: 28; probe sequence GTCTACAAACCAGTTGACCTGAGC, designated herein as SEQ ID NO: 29).

TABLE 15

Effects of uniform 2'-MOE modified oligonucleotides on human Tau exon 10 using Primer Probe Set 10_11

| ISIS No. | Sequence | % UTC | SEQ ID NO: 1 Start Site | SEQ ID NO: 1 Stop Site | Mismatches | SEQ ID No. |
|---|---|---|---|---|---|---|
| 549595 | GGACGTGTGAAGGTACTC | 20 | 121924 | 121941 | 0 | 15 |
| 549617 | GCCCAAGAAGGATTTATT | 31.8 | 122012 | 122029 | 0 | 16 |
| 549619 | TCCTGAGAGCCCAAGAAG | 41.7 | 122020 | 122037 | 0 | 17 |
| 549620 | CAGATCCTGAGAGCCCAA | 35.6 | 122024 | 122041 | 0 | 18 |

Example 10: Effects of Uniform 2'-MOE Modified Oligonucleotides on Human Tau Exon 10

A series of modified oligonucleotides were designed to target exon 10 of human Tau and were screened for their effects in reducing exon 10 inclusion in vitro. The modified oligonucleotides are 18 nucleosides in length, wherein each nucleoside has a 2'-MOE modification. Each internucleoside linkage throughout the modified oligonucleotide are phosphorothioate internucleoside linkages (P═S). All cytosine residues throughout the modified oligonucleotides are 5-methylcytosines.

"Start site" indicates the 5'-most nucleoside to which the modified oligonucleotide is targeted in the human gene sequence. "Stop site" indicates the 3'-most nucleoside to which the modified oligonucleotide is targeted in the human gene sequence. Each modified oligonucleotide listed in the tables below is targeted to the human Tau genomic sequence, designated herein as SEQ ID NO: 32 (GENBANK Accession No NT_010783.15 truncated from nucleotides 9240000 to 9381000).

A172 cells were transfected using Lipofectamine2000® with 5 nM concentration of modified oligonucleotide. After a treatment period of approximately 24 hours, RNA was isolated from the cells and the mRNA levels of Tau transcripts containing exon 10 were measured by quantitative real-time PCR. Human Tau primer probe set 9_10 R5 was used to measure mRNA levels. Tau exon 10 mRNA levels were adjusted according to total RNA content, as measured by RIBOGREEN®. Results are presented as percent of Tau exon 10 mRNA expression, relative to untreated control levels and is denoted as "% UTC."

Human Tau primer probe set 9_10 R5 (forward sequence CACTGAGAACCTGAAGCACC, designated herein as SEQ ID NO: 24; reverse sequence GGACGTTGCTAAGATCCAGCT, designated herein as SEQ ID NO: 25; probe sequence TTAATTATCTGCACCTTCCCGCCTCC, designated herein as SEQ ID NO: 26).

TABLE 16

Effects of uniform 2'-MOE modified oligonucleotides on human Tau exon 10 using Human Tau primer probe set 9_10 R5

| ISIS NO | Sequence | % UTC | SEQ ID NO: 1 Start Site | SEQ ID NO . 1 Stop Site. | SEQ ID NO |
|---|---|---|---|---|---|
| 549595 | GGACGTGTGAAGGTACTC | 26 | 121924 | 121941 | 15 |
| 549619 | TCCTGAGAGCCCAAGAAG | 42 | 122020 | 122037 | 17 |
| 549620 | CAGATCCTGAGAGCCCAA | 35 | 122024 | 122041 | 18 |

The invention claimed is:

1. A method of decreasing seizures in a subject with a high 4R:3R tau isoform ratio, the method comprising administering an antisense oligonucleotide to the subject, wherein the method decreases the 4R:3R tau ratio in the central nervous system of the subject, wherein the antisense oligonucleotide comprises a nucleobase sequence of SEQ ID NO:12, wherein the antisense oligonucleotide comprises a non-bicyclic 2'-modified sugar moiety, and wherein the substituent at the 2'-position is 2'-O-methoxyethyl (MOE); wherein the subject has frontotemporal dementia.

2. The method of claim 1, wherein the high 4R:3R tau isoform ratio in the subject is caused by a splicing defect.

3. The method of claim 1, further comprising decreasing the accumulation of aggregated tau in the brain and spinal cord of the subject.

4. The method of claim 1, wherein the oligonucleotide is administered using a single bolus administration.

5. The method of claim 1, wherein the oligonucleotide is administered using a pump.

6. The method of claim 1, wherein the total amount of tau in the central nervous system is not changed.

7. A method of modifying a neurodegenerative syndrome in a subject with a high 4R:3R tau isoform ratio, the method comprising administering an antisense oligonucleotide to the central nervous system of the subject, wherein the antisense oligonucleotide decreases the high 4R:3R tau ratio in the central nervous system of the subject, wherein the antisense oligonucleotide has a nucleobase sequence of SEQ ID NO:12, wherein the antisense oligonucleotide comprises a non-bicyclic 2'-modified sugar moiety, and wherein the substituent at the 2'-position is 2'O-methoxyethyl (MOE); wherein the neurodegenerative syndrome in the subject is frontotemporal dementia.

8. The method of claim 7, wherein the high 4R:3R tau isoform ratio in the subject is caused by a splicing defect.

9. The method of claim 7, wherein the neurodegenerative syndrome is a neurodegenerative syndrome associated with tau.

10. The method of claim 9, wherein the neurodegenerative syndrome associated with tau is associated with tau multimerization.

11. The method of claim 7, wherein modifying a neurodegenerative syndrome improves the behavioral phenotype of the subject.

12. The method of claim 11, wherein the behavioral phenotype of the subject is seizures.

13. The method of claim 7, wherein modifying a neurodegenerative syndrome slows the progression of neurodegenerative disease development in the subject.

14. The method of claim 7, wherein modifying a neurodegenerative syndrome decreases the accumulation of aggregated tau in the brain and spinal cord of the subject.

15. The method of claim 7, wherein the oligonucleotide is administered using a single bolus administration.

16. The method of claim 7, wherein the oligonucleotide is administered using a pump.

17. The method of claim 7, wherein the abnormal 4R:3R tau ratio in the central nervous system is decreased without decreasing the total amount of tau in the central nervous system.

* * * * *

UNITED STATES PATENT AND TRADEMARK OFFICE
CERTIFICATE OF CORRECTION

PATENT NO.        : 10,273,474 B2
APPLICATION NO.   : 14/387853
DATED             : April 30, 2019
INVENTOR(S)       : Timothy M. Miller et al.

Page 1 of 1

It is certified that error appears in the above-identified patent and that said Letters Patent is hereby corrected as shown below:

On the Title Page

(71) and (73) should read:
WASHINGTON UNIVERSITY, St. Louis, MO (US); IONIS PHARMACEUTICALS, INC., Carlsbad, CA (US)

In the Specification

In Column 1, the paragraph under GOVERNMENTAL RIGHTS should read:
This invention was made with government support under AG005681 and NS074194 awarded by the National Institutes of Health. The government has certain rights in the invention.

Signed and Sealed this
Twenty-third Day of July, 2019

Andrei Iancu
*Director of the United States Patent and Trademark Office*